US009624209B2

(12) United States Patent
Frank-Foltyn et al.

(10) Patent No.: US 9,624,209 B2

(45) **Date of Patent: *Apr. 18, 2017**

(54) SUBSTITUTED PHENYLUREAS AND PHENYLAMIDES AS VANILLOID RECEPTOR LIGANDS

(71) Applicant: Gruenenthal GmbH, Aachen (DE)

(72) Inventors: Robert Frank-Foltyn, Aachen (DE); Gregor Bahrenberg, Monschau-Konzen (DE); Thomas Christoph, Aachen (DE); Klaus Schiene, Juechen (DE); Jean De Vry, Stolberg (DE); Nils Damann, Cologne (DE); Sven Frormann, Aachen (DE); Bernhard Lesch, Aachen (DE); Jeewoo Lee, Seoul (KR); Yong-Soo Kim, Gyengnam (KR); Myeong-Seop Kim, Gangw-do (KR); Derek Saunders, Aachen (DE); Hannelore Stockhausen, Huertgenwald (DE)

(73) Assignee: Gruenenthal GmbH, Aachen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/568,592

(22) Filed: Dec. 12, 2014

(65) Prior Publication Data

US 2015/0099728 A1 Apr. 9, 2015

Related U.S. Application Data

(60) Division of application No. 13/292,563, filed on Nov. 9, 2011, now Pat. No. 8,946,204, which is a continuation-in-part of application No. 12/775,235, filed on May 6, 2010, now Pat. No. 8,592,471.

(60) Provisional application No. 61/176,284, filed on May 7, 2009.

(30) Foreign Application Priority Data

May 7, 2009 (EP) .................................... 09006237

(51) Int. Cl.

| | |
|---|---|
| ***A61K 31/415*** | (2006.01) |
| ***C07D 417/12*** | (2006.01) |
| ***C07D 231/12*** | (2006.01) |
| ***C07D 249/08*** | (2006.01) |
| ***C07D 405/12*** | (2006.01) |
| ***A61K 31/4155*** | (2006.01) |
| ***A61K 31/427*** | (2006.01) |
| ***C07D 403/12*** | (2006.01) |

(52) U.S. Cl.

CPC .......... *C07D 417/12* (2013.01); *A61K 31/415* (2013.01); *A61K 31/4155* (2013.01); *A61K 31/427* (2013.01); *C07D 231/12* (2013.01); *C07D 249/08* (2013.01); *C07D 403/12* (2013.01); *C07D 405/12* (2013.01)

(58) Field of Classification Search

USPC ..................................... 514/406, 383, 364.1

See application file for complete search history.

(56) References Cited

U.S. PATENT DOCUMENTS

| | | | | |
|---|---|---|---|---|
| 6,979,686 | B1 | 12/2005 | Naraian | |
| 7,799,782 | B2 | 9/2010 | Munson et al. | |
| 8,334,315 | B2 * | 12/2012 | Frank | C07D 231/12 514/406 |
| 8,592,471 | B2 * | 11/2013 | Frank | C07D 231/12 514/383 |
| 9,120,756 | B2 | 9/2015 | Frank et al. | |
| 2002/0132853 | A1 | 9/2002 | Bakthavatchalam et al. | |
| 2007/0105861 | A1 | 5/2007 | Lee et al. | |
| 2008/0021217 | A1 | 1/2008 | Borchardt et al. | |
| 2009/0018134 | A1 | 1/2009 | Pike et al. | |
| 2009/0118332 | A1 | 5/2009 | Butlin et al. | |
| 2009/0156590 | A1 | 6/2009 | Frank et al. | |
| 2012/0101096 | A1 | 4/2012 | Hedstrom et al. | |

FOREIGN PATENT DOCUMENTS

| | | | |
|---|---|---|---|
| CN | 1443170 | A | 9/2003 |
| CN | 101331124 | A | 12/2008 |
| EP | 1 020 447 | A1 | 7/2000 |
| JP | 2005-526798 | A | 9/2005 |
| JP | 2008-251019 | A | 10/2008 |
| TW | 499295 | B | 8/2002 |
| TW | 200833663 | A | 8/2008 |
| WO | WO 03/080578 | A1 | 10/2003 |
| WO | WO 2005/004810 | A2 | 1/2005 |
| WO | WO 2005/004810 | A3 | 1/2005 |
| WO | WO 2007/045462 | A2 | 4/2007 |
| WO | WO 2007/064872 | A2 | 6/2007 |
| WO | WO 2008/011557 | A2 | 1/2008 |
| WO | WO 2008/011557 | A3 | 1/2008 |
| WO | WO 2008/059370 | A2 | 5/2008 |
| WO | WO 2008/059370 | A3 | 5/2008 |
| WO | WO 2008/059370 | A8 | 5/2008 |
| WO | WO 2008/075064 | A1 | 6/2008 |
| WO | WO 2008/125342 | A2 | 10/2008 |
| WO | WO 2008/137102 | A2 | 11/2008 |
| WO | WO 2008/137102 | A3 | 11/2008 |
| WO | WO 2009/007748 | A2 | 1/2009 |
| WO | WO 2010/108187 | A2 | 9/2010 |
| WO | WO 2010/108187 | A3 | 9/2010 |

OTHER PUBLICATIONS

Gary J. Bennett et al., A peripheral mononeuropathy in rat that produces disorders of pain sensation like those seen in man, Pain, 33, 1988, pp. 87-107.

(Continued)

*Primary Examiner* — Rei-Tsang Shiao

(74) *Attorney, Agent, or Firm* — Crowell & Moring LLP

(57) ABSTRACT

Substituted phenylureas and phenylamides, processes for their preparation, pharmaceutical compositions containing these compounds, and the use of these compounds for preparing pharmaceutical compositions.

12 Claims, No Drawings

(56) References Cited

OTHER PUBLICATIONS

David Dubuisson et al., The Formalin Test A Quantitative Study of the Analgesic Effects of Morphine, Meperidine, and Brain Stem Stimulation in Rats and Cats, Pain 4, 1977, pp. 161-174.
L.C. Hendershot et al., Antagonism of the Frequency of Phenylquinone-Induced Writing in the Mouse by Weak Analgesics and Nonanalgesics, J. Pharmacol Exp Ther , Mar. 1959, pp. 237-240.
Jerry March, Aliphatic Nucleophilic Substitution, Advanced Organic Chemistry, Reactions, Mechanisms, and Structure, $4^{th}$ Edition, 1992, pp. 378-383.
Yung-Chi Cheng et al., Relationship Between the Inhibition Constant ($K_1$) and the Concentration of Inhibitor Which Causes 50 Per Cent Inhibition ($I_{50}$) of and Enzymatic Reaction, Biochemical Pharmacology, 1973, vol. 22, pp. 3099-3108.
Terrance J. Coderre et al., "Contribution of Central Neuroplasticity to Pathological Pain: Review of Clinical and Experimental Evidence", 1993, vol. 52, pp. 259-285.
CID 19292706, Pub Chem Compound, Dec. 5, 2007, pp. 1-3.
CID 19328857, Pub Chem Compound, Dec. 5, 2007, pp. 1-3.
Ambinter, CAS Registry 23, Nov. 25, 2007 (three (3) pages).
Princeton Biomolecular Research Inc., CS Registry, Jul. 19, 2007 (four (4) pages).
Scientific Exchange Inc., CAS Registry, Jul. 16, 2006 (thirty-one (31) pages).
Lizbeth K. Hedstrom et al., "Preparation of Triazoles and Related Compounds as IMPDH Inhibitors for Treating Gastrointestinal Microbial Infection", (2010), CAS 153:431376, Caplus, (two (2) pages).
Allen Borchardt et al., "Preparation of Heteroaryl Compounds, Particularly 1,2,4-triazole Derivatives as Inhibitors of Rho Kinase", (2008), CAS 148:191965, Caplus, (three (3) pages).
Ji et al., "p38 MAPK Activation by NGF in Primary Sensory Neurons after Inflammation Increases TRPV1 Levels and Maintains Heat Hyperalgesia," Neuron, Sep. 26, 2002, pp. 57-68, vol. 36, Cell Press.

* cited by examiner

SUBSTITUTED PHENYLUREAS AND PHENYLAMIDES AS VANILLOID RECEPTOR LIGANDS

CROSS REFERENCE TO RELATED APPLICATIONS

This application is a divisional of U.S. patent application Ser. No. 13/292,563, filed on Nov. 9, 2011, which claims priority under 35 U.S.C. 119(a) to U.S. application Ser. No. 12/775,235, filed May 6, 2010, which claims priority under 35 U.S.C. §119(a) to U.S. Provisional Patent Application No. 61/176,284, filed May 7, 2009, and also claims priority under 35 U.S.C. §119(a) to European Application No. 09 006 237.3, filed May 7, 2009. The contents of all prior applications are hereby incorporated by reference in their entirety.

BACKGROUND OF THE INVENTION

The invention relates to substituted phenylureas and phenylamides, to processes for the preparation thereof, to pharmaceutical compositions containing these compounds and also to the use of these compounds for preparing pharmaceutical compositions.

The treatment of pain, in particular of neuropathic pain, is very important in medicine. There is a worldwide demand for effective pain therapies. The urgent need for action for a patient-focused and target-oriented treatment of chronic and non-chronic states of pain, this being understood to mean the successful and satisfactory treatment of pain for the patient, is also documented in the large number of scientific studies which have recently appeared in the field of applied analgesics or basic research on nociception.

The subtype 1 vanilloid receptor (VR1/TRPV1), which is often also referred to as the capsaicin receptor, is a suitable starting point for the treatment of pain, in particular of pain selected from the group consisting of acute pain, chronic pain, neuropathic pain and visceral pain, particularly preferably of neuropathic pain. This receptor is stimulated inter alia by vanilloids such as capsaicin, heat and protons and plays a central role in the formation of pain. In addition, it is important for a large number of further physiological and pathophysiological processes and is a suitable target for the therapy of a large number of further disorders such as, for example, migraine, depression, neurodegenerative diseases, cognitive disorders, states of anxiety, epilepsy, coughs, diarrhoea, pruritus, inflammations, disorders of the cardiovascular system, eating disorders, medication dependency, misuse of medication and in particular urinary incontinence.

There is a need for further compounds having comparable or better properties, not only with regard to affinity to vanilloid receptors 1 (VR1/TRPV1 receptors) per se (potency, efficacy).

Thus, it may be advantageous to improve the metabolic stability, the solubility in aqueous media or the permeability of the compounds. These factors can have a beneficial effect on oral bioavailability or can alter the PK/PD (pharmacokinetic/pharmacodynamic) profile; this can lead to a more beneficial period of effectiveness, for example.

A weak or non-existent interaction with transporter molecules, which are involved in the ingestion and the excretion of pharmaceutical compositions, is also to be regarded as an indication of improved bioavailability and at most low interactions of pharmaceutical compositions. Furthermore, the interactions with the enzymes involved in the decomposition and the excretion of pharmaceutical compositions should also be as low as possible, as such test results also suggest that at most low interactions, or no interactions at all, of pharmaceutical compositions are to be expected.

SUMMARY OF THE INVENTION

It was therefore an object of the invention to provide new compounds having advantages over the prior-art compounds. The compounds should be suitable in particular as pharmacological active ingredients in pharmaceutical compositions, preferably in pharmaceutical compositions for the treatment and/or inhibition of disorders or diseases which are mediated, at least in part, by vanilloid receptors 1 (VR1/TRPV1 receptors).

This object is achieved by the subject matter described and claimed hereinafter.

Now, it has surprisingly been found that the substituted compounds of general formula (I), as indicated below, display outstanding affinity to the subtype 1 vanilloid receptor (VR1/TRPV1 receptor) and are therefore particularly suitable for the inhibition and/or treatment of disorders or diseases which are mediated, at least in part, by vanilloid receptors 1 (VR1/TRPV1). The substituted compounds of general formula (I), as indicated below, also have anti-inflammatory activity.

The present invention therefore relates to substituted compounds of general formula (I), (I)

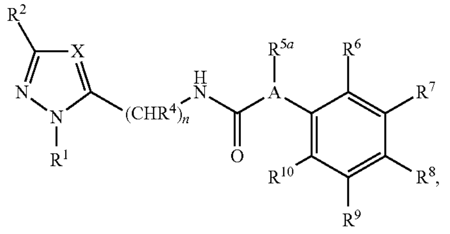

in which

X represents $CR^3$ or N, wherein $R^3$ represents H; $C_{1-10}$ alkyl, saturated or unsaturated, branched or unbranched, unsubstituted or mono- or polysubstituted;

A represents N or $CR^{5b}$, n represents 0, 1, 2, 3 or 4; preferably 1, 2, 3 or 4, $R^0$ represents $C_{1-10}$ alkyl, saturated or unsaturated, branched or unbranched, unsubstituted or mono- or polysubstituted; $C_{3-10}$ cycloalkyl or heterocyclyl, respectively saturated or unsaturated, unsubstituted or mono- or polysubstituted; aryl or heteroaryl, respectively unsubstituted or mono- or polysubstituted; $C_{3-10}$ cycloalkyl or heterocyclyl bridged via $C_{1-8}$ alkyl, respectively saturated or unsaturated, unsubstituted or mono- or polysubstituted, wherein the alkyl chain can be respectively branched or unbranched, saturated or unsaturated, unsubstituted, mono- or polysubstituted; or aryl or heteroaryl bridged via $C_{1-8}$ alkyl, respectively unsubstituted or mono- or polysubstituted, wherein the alkyl chain can be respectively branched or unbranched, saturated or unsaturated, unsubstituted, mono- or polysubstituted;

$R^1$ represents H; $C_{1-10}$ alkyl, saturated or unsaturated, branched or unbranched, unsubstituted or mono- or polysubstituted; $C_{3-10}$ cycloalkyl or heterocyclyl[1], respectively saturated or unsaturated, unsubstituted or mono- or polysubstituted; aryl or heteroaryl, respectively unsubstituted or mono- or polysubstituted; $C_{3-10}$ cycloalkyl[1] or heterocyclyl[1] bridged via $C_{1-8}$ alkyl, respectively saturated or unsaturated, unsubstituted or mono- or polysubstituted, wherein the alkyl chain can be respectively branched or unbranched, saturated or unsaturated, unsubstituted, mono- or polysubstituted; or aryl or heteroaryl bridged via $C_{1-8}$ alkyl, respectively unsubstituted or mono- or polysubstituted, wherein the alkyl chain can be respectively branched or unbranched, saturated or unsaturated, unsubstituted, mono- or polysubstituted; C(═O)—$R^0$; C(═O)—OH; C(═O)—$OR^0$; C(═O)—$NHR^0$; C(═O)—$N(R^0)_2$; OH; O—$R^0$; SH; S—$R^0$; $S(═O)_2$—$R^0$; $S(═O)_2$—$OR^0$; $S(═O)_2$—$NHR^0$; $S(═O)_2$—$N(R^0)_2$; $NH_2$; $NHR^0$; $N(R^0)_2$; NH—$S(═O)_2$—$R^0$; $N(R^0)(S(═O)_2—R^0)$; or $SCl_3$; preferably represents $C_{1-10}$ alkyl, saturated or unsaturated, branched or unbranched, unsubstituted or mono- or polysubstituted; $C_{3-10}$ cycloalkyl[1] or heterocyclyl[1], respectively saturated or unsaturated, unsubstituted or mono- or polysubstituted; aryl or heteroaryl, respectively unsubstituted or mono- or polysubstituted; $C_{3-10}$ cycloalkyl or heterocyclyl[1] bridged via $C_{1-8}$ alkyl, respectively saturated or unsaturated, unsubstituted or mono- or polysubstituted, wherein the alkyl chain can be respectively branched or unbranched, saturated or unsaturated, unsubstituted, mono- or polysubstituted; or aryl or heteroaryl bridged via $C_{1-8}$ alkyl, respectively unsubstituted or mono- or polysubstituted, wherein the alkyl chain can be respectively branched or unbranched, saturated or unsaturated, unsubstituted, mono- or polysubstituted; C(═O)—$R^0$; C(═O)—OH; C(═O)—$OR^0$; C(═O)—$NHR^0$; C(═O)—$N(R^0)_2$; OH; O—$R^0$; SH; S—$R^0$; $S(═O)_2$—$R^0$; $S(═O)_2$—$OR^0$; $S(═O)_2$—$NHR^0$; $S(═O)_2$—$N(R^0)_2$; $NH_2$; $NHR^0$; $N(R^0)_2$; NH—$S(═O)_2$—$R^0$; $N(R^0)(S(═O)_2—R^0)$; or $SCl_3$;

$R^2$ represents H; $R^0$; F; Cl; Br; I; CN; $NO_2$; OH; SH; $CF_3$; $CF_2H$; $CFH_2$; $CF_2Cl$; $CFCl_2$; $CH_2CF_3$; $OCF_3$; $OCF_2H$; $OCFH_2$; $OCF_2Cl$; $OCFCl_2$; $SCF_3$; $SCF_2H$; $SCFH_2$; $SCF_2Cl$; $SCFCl_2$; $S(═O)_2$—$CF_3$; $S(═O)_2$—$CF_2H$; $S(═O)_2$—$CFH_2$; or $SF_5$; preferably represents H; $R^0$; F; I; CN; $NO_2$; OH; SH; $CF_3$; $CF_2H$; $CFH_2$; $CF_2Cl$; $CFCl_2$; $CH_2CF_3$; $OCF_3$; $OCF_2H$; $OCFH_2$; $OCF_2Cl$; $OCFCl_2$; $SCF_3$; $SCF_2H$; $SCFH_2$; $SCF_2Cl$; $SCFCl_2$; $S(═O)_2$—$CF_3$; $S(═O)_2$—$CF_2H$; $S(═O)_2$—$CFH_2$; or $SF_5$;

$R^4$ represents H; F; Cl; Br; I; OH; $C_{1-10}$ alkyl, saturated or unsaturated, branched or unbranched, unsubstituted or mono- or polysubstituted;

$R^{5a}$ represents H; OH; $C_{1-10}$ alkyl, saturated or unsaturated, branched or unbranched, unsubstituted or mono- or polysubstituted;

$R^{5b}$ represents H; or $R^0$; or $R^{5a}$ and $R^{5b}$ form together with the carbon atom connecting them a $C_{3-10}$ cycloalkyl or a heterocyclyl, respectively saturated or unsaturated, unsubstituted or mono- or polysubstituted;

$R^6$, $R^7$, $R^8$, $R^9$ and $R^{10}$ each independently represent H; F; Cl; Br; I; $NO_2$; CN; $CF_3$; $CF_2H$; $CFH_2$; $CF_2Cl$; $CFCl_2$; $R^0$; C(═O)H; C(═O)$R^0$; $CO_2H$; C(═O)$OR^0$; $CONH_2$; C(═O)$NHR^0$; C(═O)$N(R^0)_2$; OH; $OCF_3$; $OCF_2H$; $OCFH_2$; $OCF_2Cl$; $OCFCl_2$; $OR^0$; O—C(═O)—$R^0$; O—C(═O)—O—$R^0$; O—(C═O)—NH—$R^0$; O—C(═O)—$N(R^0)_2$; O—$S(═O)_2$—$R^0$; O—$S(═O)_2OH$; O—$S(═O)_2OR^0$; O—$S(═O)_2NH_2$; O—$S(═O)_2NHR^0$; O—$S(═O)_2N(R^0)_2$; $NH_2$; NH—$R^0$; $N(R^0)_2$; NH—C(═O)—$R^0$; NH—C(═O)—O—$R^0$; NH—C(═O)—$NH_2$; NH—C(═O)—NH—$R^0$; NH—C(═O)—$N(R^0)_2$; $NR^0$—C(═O)—$R^0$; $NR^0$—C(═O)—O—$R^0$; $NR^0$—C(═O)—$NH_2$; $NR^0$—C(═O)—NH—$R^0$; $NR^0$—C(═O)—$N(R^0)_2$; NH—$S(═O)_2OH$; NH—$S(═O)_2R^0$; NH—$S(═O)_2R^0$; NH—$S(═O)_2NH_2$; NH—$S(═O)_2NHR^0$; NH—$S(═O)_2N(R^0)_2$; $NR^0$—$S(═O)_2OH$; $NR^0$—$S(═O)_2R^0$; $NR^0$—$S(═O)_2R^0$; $NR^0$—$S(═O)_2NH_2$; $NR^0$—$S(═O)_2NHR^0$; $NR^0$—$S(═O)_2N(R^0)_2$; SH; $SCF_3$; $SCF_2H$; $SCFH_2$; $SCF_2Cl$; $SCFCl_2$; $SR^0$; S(═O)$R^0$; $S(═O)_2R^0$; $S(═O)_2OH$; $S(═O)_2OR^0$; $S(═O)_2NH_2$; $S(═O)_2NHR^0$; or $S(═O)_2N(R^0)_2$;

preferably $R^6$, $R^7$, $R^9$ and $R^{10}$ each independently represent H; F; Cl; Br; I; $NO_2$; CN; $CF_3$; $CF_2H$; $CFH_2$; $CF_2Cl$; $CFCl_2$; $R^0$; C(═O)H; C(═O)$R^0$; $CO_2H$; C(═O)$OR^0$; $CONH_2$; C(═O)$NHR^0$; C(═O)$N(R^0)_2$; OH; $OCF_3$; $OCF_2H$; $OCFH_2$; $OCF_2Cl$; $OCFCl_2$; $OR^0$; O—C(═O)—$R^0$; O—C(═O)—O—$R^0$; O—(C═O)—NH—$R^0$; O—C(═O)—$N(R^0)_2$; O—$S(═O)_2$—$R^0$; O—$S(═O)_2OH$; O—$S(═O)_2OR^0$; O—$S(═O)_2NH_2$; O—$S(═O)_2NHR^0$; O—$S(═O)_2N(R^0)_2$; $NH_2$; NH—$R^0$; $N(R^0)_2$; NH—C(═O)—$R^0$; NH—C(═O)—O—$R^0$; NH—C(═O)—$NH_2$; NH—C(═O)—NH—$R^0$; NH—C(═O)—$N(R^0)_2$; $NR^0$—C(═O)—$R^0$; $NR^0$—C(═O)—O—$R^0$; $NR^0$—C(═O)—$NH_2$; $NR^0$—C(═O)—NH—$R^0$; $NR^0$—C(═O)—$N(R^0)_2$; NH—$S(═O)_2OH$; NH—$S(═O)_2R^0$; NH—$S(═O)_2OR^0$; NH—$S(═O)_2NH_2$; NH—$S(═O)_2NHR^0$; NH—$S(═O)_2N(R^0)_2$; $NR^0$—$S(═O)_2OH$; $NR^0$—$S(═O)_2R^0$; $NR^0$—$S(═O)_2OR^0$; $NR^0$—$S(═O)_2NH_2$; $NR^0$—$S(═O)_2NHR^0$; $NR^0$—$S(═O)_2N(R^0)_2$; SH; $SCF_3$; $SCF_2H$; $SCFH_2$; $SCF_2Cl$; $SCFCl_2$; $SR^0$; S(═O)$R^0$; $S(═O)_2R^0$; $S(═O)_2OH$; $S(═O)_2OR^0$; $S(═O)_2NH_2$; $S(═O)_2NHR^0$; or $S(═O)_2N(R^0)_2$;

preferably $R^8$ represents H; F; Cl; Br; I; $NO_2$; CN; $CF_3$; $CF_2H$; $CFH_2$; $CF_2Cl$; $CFCl_2$; $R^0$; C(═O)H; C(═O)$R^0$; $CO_2H$; C(═O)$OR^0$; $CONH_2$; C(═O)$NHR^0$; C(═O)$N(R^0)_2$; OH; $OCF_3$; $OCF_2H$; $OCFH_2$; $OCF_2Cl$; $OCFCl_2$; $OR^0$; O—C(═O)—$R^0$; O—C(═O)—O—$R^0$; O—(C═O)—NH—$R^0$; O—C(═O)—$N(R^0)_2$; O—$S(═O)_2$—$R^0$; O—$S(═O)_2OH$; O—$S(═O)_2OR^0$; O—$S(═O)_2NH_2$; O—$S(═O)_2NHR^0$; O—$S(═O)_2N(R^0)_2$; $NH_2$; NH—$R^0$; $N(R^0)_2$; NH—C(═O)—$R^0$; NH—C(═O)—O—$R^0$; NH—C(═O)—$NH_2$; NH—C(═O)—NH—$R^0$; NH—C(═O)—$N(R^0)_2$; $NR^0$—C(═O)—$R^0$; $NR^0$—C(═O)—O—$R^0$; $NR^0$—C(═O)—$NH_2$; $NR^0$—C(═O)—NH—$R^0$; $NR^0$—C(═O)—$N(R^0)_2$; NH—$S(═O)_2OH$; NH—$S(═O)_2R^0$; NH—$S(═O)_2OR^0$; NH—$S(═O)_2NH_2$; NH—$S(═O)_2NHR^0$; NH—$S(═O)_2N(R^0)_2$; $NR^0$—$S(═O)_2OH$; $NR^0$—$S(═O)_2R^0$; $NR^0$—$S(═O)_2OR^0$; $NR^0$—$S(═O)_2NH_2$; $NR^0$—$S(═O)_2NHR^0$; $NR^0$—$S(═O)_2N(R^0)_2$; SH; $SCF_3$; $SCF_2H$; $SCFH_2$; $SCF_2Cl$; $SCFCl_2$; $SR^0$; S(═O)$R^0$; $S(═O)_2R^0$; $S(═O)_2OH$; $S(═O)_2OR^0$; $S(═O)_2NH_2$; $S(═O)_2NHR^0$; or $S(═O)_2N(R^0)_2$; wherein, if $R^8$ denotes $R^0$ and $R^0$ represents heteroaryl, said heteroaryl is selected from the group consisting of benzofuranyl, benzoimidazolyl, benzothienyl, benzothiadiazolyl, benzothiazolyl, benzotriazolyl, benzooxazolyl, benzooxadiazolyl, quinazolinyl, quinoxalinyl, carbazolyl, quinolinyl, dibenzofuranyl, dibenzothienyl, furyl (furanyl), imidazothiazolyl, indazolyl, indolizinyl, indolyl, isoquinolinyl, isoxazoyl, isothiazolyl, indolyl, naphthyridinyl, oxazolyl, oxadiazolyl, phenazinyl, phenothiazinyl, phthalazinyl, pyrazolyl, pyridyl (2-pyridyl, 3-pyridyl, 4-pyridyl), pyrrolyl, pyridazinyl, pyrimidinyl, pyrazinyl, purinyl, phenazinyl, thienyl (thiophenyl), triazolyl, tetrazolyl, thiazolyl, thiadiazolyl and triazinyl;

in which "substituted alkyl", "substituted heterocyclyl" and "substituted cycloalkyl" relate, with respect to the corresponding residues, to the replacement of one or more hydrogen atoms each independently by F; Cl; Br; I; $NO_2$; CN; ═O; ═NH; ═C$(NH_2)_2$; $CF_3$; $CF_2H$; $CFH_2$; $CF_2Cl$; $CFCl_2$; $R^0$; C(═O)H; C(═O)$R^0$; $CO_2H$; C(═O)$OR^0$;

$CONH_2$; C(=O)NHR$^0$; C(=O)N(R$^0$)$_2$; OH; $OCF_3$; $OCF_2H$; $OCFH_2$; $OCF_2Cl$; $OCFCl_2$; OR$^0$; O—C(=O)—R$^0$; O—C(=O)—O—R$^0$; O—(C=O)—NH—R$^0$; O—C(=O)—N(R$^0$)$_2$; O—S(=O)$_2$—R$^0$; O—S(=O)$_2$OH; O—S(=O)$_2$OR$^0$; O—S(=O)$_2$NH$_2$; O—S(=O)$_2$NHR$^0$; O—S(=O)$_2$N(R$^0$)$_2$; NH$_2$; NH—R$^0$; N(R$^0$)$_2$; NH—C(=O)—R$^0$; NH—C(=O)—O—R$^0$; NH—C(=O)—NH$_2$; NH—C(=O)—NH—R$^0$; NH—C(=O)—N(R$^0$)$_2$; NR$^0$—C(=O)—R$^0$; NR$^0$—C(=O)—O—R$^0$; NR$^0$—C(=O)—NH$_2$; NR$^0$—C(=O)—NH—R$^0$; NR$^0$—C(=O)—N(R$^0$)$_2$; NH—S(=O)$_2$OH; NH—S(=O)$_2$R$^0$; NH—S(=O)$_2$OR$^0$; NH—S(=O)$_2$NH$_2$; NH—S(=O)$_2$NHR$^0$; NH—S(=O)$_2$N(R$^0$)$_2$; NR$^0$—S(=O)$_2$OH; NR$^0$—S(=O)$_2$R$^0$; NR$^0$—S(=O)$_2$OR$^0$; NR$^0$—S(=O)$_2$NH$_2$; NR$^0$—S(=O)$_2$NHR$^0$; NR$^0$—S(=O)$_2$N(R$^0$)$_2$; SH; $SCF_3$; $SCF_2H$; $SCFH_2$; $SCF_2Cl$; $SCFCl_2$; SR$^0$; S(=O)R$^0$; S(=O)$_2$R$^0$; S(=O)$_2$OH; S(=O)$_2$OR$^0$; S(=O)$_2$NH$_2$; S(=O)$_2$NHR$^0$; or S(=O)$_2$N(R$^0$)$_2$;

in which "substituted cycloalkyl$^1$" and "substituted heterocyclyl$^1$" relate, with respect to the corresponding residues, to the replacement of one or more hydrogen atoms each independently by F; Cl; Br; I; $NO_2$; CN; =O; =C(NH$_2$)$_2$; $CF_3$; $CF_2H$; $CFH_2$; $CF_2Cl$; $CFCl_2$; R$^0$; C(=O)H; C(=O)R$^0$; $CO_2H$; C(=O)OR$^0$; $CONH_2$; C(=O)NHR$^0$; C(=O)N(R$^0$)$_2$; OH; $OCF_3$; $OCF_2H$; $OCFH_2$; $OCF_2Cl$; $OCFCl_2$; OR$^0$; O—C(=O)—R$^0$; O—C(=O)—O—R$^0$; O—(C=O)—NH—R$^0$; O—C(=O)—N(R$^0$)$_2$; O—S(=O)$_2$—R$^0$; O—S(=O)$_2$OH; O—S(=O)$_2$OR$^0$; O—S(=O)$_2$NH$_2$; —S(=O)$_2$NHR$^0$; O—S(=O)$_2$N(R$^0$)$_2$; SH; $SCF_3$; $SCF_2H$; $SCFH_2$; $SCF_2Cl$; $SCFCl_2$; SR$^0$; S(=O)R$^0$; S(=O)$_2$R$^0$; S(=O)$_2$OH; S(=O)$_2$OR$^0$; S(=O)$_2$NH$_2$; S(=O)$_2$NHR$^0$; or S(=O)$_2$N(R$^0$)$_2$;

in which "substituted aryl" and "substituted heteroaryl" relate, with respect to the corresponding residues, to the replacement of one or more hydrogen atoms each independently by F; Cl; Br; I; $NO_2$; CN; $CF_3$; $CF_2H$; $CFH_2$; $CF_2Cl$; $CFCl_2$; R$^0$; C(=O)H; C(=O)R$^0$; $CO_2H$; C(=O)OR$^0$; $CONH_2$; C(=O)NHR$^0$; C(=O)N(R$^0$)$_2$; OH; $OCF_3$; $OCF_2H$; $OCFH_2$; $OCF_2Cl$; $OCFCl_2$; OR$^0$; O—C(=O)—R$^0$; O—C(=O)—O—R$^0$; O—(C=O)—NH—R$^0$; O—C(=O)—N(R$^0$)$_2$; O—S(=O)$_2$—R$^0$; O—S(=O)$_2$OH; O—S(=O)$_2$OR$^0$; O—S(=O)$_2$NH$_2$; O—S(=O)$_2$NHR$^0$; O—S(=O)$_2$N(R$^0$)$_2$; NH$_2$; NH—R$^0$; N(R$^0$)$_2$; NH—C(=O)—R$^0$; NH—C(=O)—O—R$^0$; NH—C(=O)—NH$_2$; NH—C(=O)—NH—R$^0$; NH—C(=O)—N(R$^0$)$_2$; NR$^0$—C(=O)—R$^0$; NR$^0$—C(=O)—O—R$^0$; NR$^0$—C(=O)—NH$_2$; NR$^0$—C(=O)—NH—R$^0$; NR$^0$—C(=O)—N(R$^0$)$_2$; NH—S(=O)$_2$OH; NH—S(=O)$_2$R$^0$; NH—S(=O)$_2$OR$^0$; NH—S(=O)$_2$NH$_2$; NH—S(=O)$_2$NHR$^0$; NH—S(=O)$_2$N(R$^0$)$_2$; NR$^0$—S(=O)$_2$OH; NR$^0$—S(=O)$_2$R$^0$; NR$^0$—S(=O)$_2$OR$^0$; NR$^0$—S(=O)$_2$NH$_2$; NR$^0$—S(=O)$_2$NHR$^0$; NR$^0$—S(=O)$_2$N(R$^0$)$_2$; SH; $SCF_3$; $SCF_2H$; $SCFH_2$; $SCF_2Cl$; $SCFCl_2$; SR$^0$; S(=O)R$^0$; S(=O)$_2$R$^0$; S(=O)$_2$OH; S(=O)$_2$OR$^0$; S(=O)$_2$NH$_2$; S(=O)$_2$NHR$^0$; or S(=O)$_2$N(R$^0$)$_2$;

preferably in which "substituted aryl" relates, with respect to the corresponding residues, to the replacement of one or more hydrogen atoms each independently by F; Cl; Br; I; $NO_2$; $CF_3$; $CF_2H$; $CFH_2$; $CF_2Cl$; $CFCl_2$; R$^0$; C(=O)H; C(=O)R$^0$; $CO_2H$; C(=O)OR$^0$; $CONH_2$; C(=O)NHR$^0$; C(=O)N(R$^0$)$_2$; OH; $OCF_3$; $OCF_2H$; $OCFH_2$; $OCF_2Cl$; $OCFCl_2$; OR$^0$; O—C(=O)—R$^0$; O—C(=O)—O—R$^0$; O—(C=O)—NH—R$^0$; O—C(=O)—N(R$^0$)$_2$; O—S(=O)$_2$—R$^0$; O—S(=O)$_2$OH; O—S(=O)$_2$OR$^0$; O—S(=O)$_2$NH$_2$; O—S(=O)$_2$NHR$^0$; O—S(=O)$_2$N(R$^0$)$_2$; NH$_2$; NH—R$^0$; N(R$^0$)$_2$; NH—C(=O)—R$^0$; NH—C(=O)—O—R$^0$; NH—C(=O)—NH$_2$; NH—C(=O)—NH—R$^0$; NH—C(=O)—N(R$^0$)$_2$; NR$^0$—C(=O)—R$^0$; NR$^0$—C(=O)—O—R$^0$; NR$^0$—C(=O)—NH$_2$; NR$^0$—C(=O)—NH—R$^0$; NR$^0$—C(=O)—N(R$^0$)$_2$; NH—S(=O)$_2$OH; NH—S(=O)$_2$R$^0$; NH—S(=O)$_2$OR$^0$; NH—S(=O)$_2$NH$_2$; NH—S(=O)$_2$NHR$^0$; NH—S(=O)$_2$N(R$^0$)$_2$; NR$^0$—S(=O)$_2$OH; NR$^0$—S(=O)$_2$R$^0$; NR$^0$—S(=O)$_2$OR$^0$; NR$^0$—S(=O)$_2$NH$_2$; NR$^0$—S(=O)$_2$NHR$^0$; NR$^0$—S(=O)$_2$N(R$^0$)$_2$; SH; $SCF_3$; $SCF_2H$; $SCFH_2$; $SCF_2Cl$; $SCFCl_2$; SR$^0$; S(=O)R$^0$; S(=O)$_2$R$^0$; S(=O)$_2$OH; S(=O)$_2$OR$^0$; S(=O)$_2$NH$_2$; S(=O)$_2$NHR$^0$; or S(=O)$_2$N(R$^0$)$_2$;

preferably in which "substituted heteroaryl" relates, with respect to the corresponding residues, to the replacement of one or more hydrogen atoms each independently by F; Cl; Br; I; $NO_2$; CN; $CF_3$; $CF_2H$; $CFH_2$; $CF_2Cl$; $CFCl_2$; R$^0$; C(=O)H; C(=O)R$^0$; $CO_2H$; C(=O)OR$^0$; $CONH_2$; C(=O)NHR$^0$; C(=O)N(R$^0$)$_2$; OH; $OCF_3$; $OCF_2H$; $OCFH_2$; $OCF_2Cl$; $OCFCl_2$; OR$^0$; O—C(=O)—R$^0$; O—C(=O)—O—R$^0$; O—(C=O)—NH—R$^0$; O—C(=O)—N(R$^0$)$_2$; O—S(=O)$_2$—R$^0$; O—S(=O)$_2$OH; O—S(=O)$_2$OR$^0$; O—S(=O)$_2$NH$_2$; O—S(=O)$_2$NHR$^0$; O—S(=O)$_2$N(R$^0$)$_2$; NH$_2$; NH—R$^0$; N(R$^0$)$_2$; NH—C(=O)—R$^0$; NH—C(=O)—O—R$^0$; NH—C(=O)—NH$_2$; NH—C(=O)—NH—R$^0$; NH—C(=O)—N(R$^0$)$_2$; NR$^0$—C(=O)—R$^0$; NR$^0$—C(=O)—O—R$^0$; NR$^0$—C(=O)—NH$_2$; NR$^0$—C(=O)—NH—R$^0$; NR$^0$—C(=O)—N(R$^0$)$_2$; NH—S(=O)$_2$OH; NH—S(=O)$_2$R$^0$; NH—S(=O)$_2$OR$^0$; NH—S(=O)$_2$NH$_2$; NH—S(=O)$_2$NHR$^0$; NH—S(=O)$_2$N(R$^0$)$_2$; NR$^0$—S(=O)$_2$OH; NR$^0$—S(=O)$_2$R$^0$; NR$^0$—S(=O)$_2$OR$^0$; NR$^0$—S(=O)$_2$NH$_2$; NR$^0$—S(=O)$_2$NHR$^0$; NR$^0$—S(=O)$_2$N(R$^0$)$_2$; SH; $SCF_3$; $SCF_2H$; $SCFH_2$; $SCF_2Cl$; $SCFCl_2$; SR$^0$; S(=O)R$^0$; S(=O)$_2$R$^0$; S(=O)$_2$OH; S(=O)$_2$OR$^0$; S(=O)$_2$NH$_2$; S(=O)$_2$NHR$^0$; or S(=O)$_2$N(R$^0$)$_2$;

in the form of the free compounds; the tautomers; the N-oxides; the racemate; the enantiomers, diastereomers, mixtures of the enantiomers or diastereomers or of an individual enantiomer or diastereomer; or in the form of the salts of physiologically compatible acids or bases; or if appropriate in the form of solvates.

The term "single stereoisomer" preferably means in the sense of the present invention an individual enantiomer or diastereomer. The term "mixture of stereoisomers" means in the sense of this invention the racemate and mixtures of enantiomers and/or diastereomers in any mixing ratio. The term "isolated" used with respect to a stereoisomer means substantially separated from the opposite stereoisomer, but not necessarily from other substances.

The term "physiologically acceptable salt" preferably comprises in the sense of this invention a salt of at least one compound according to the present invention and at least one physiologically acceptable acid or base.

A physiologically acceptable salt of at least one compound according to the present invention and at least one physiologically acceptable acid preferably refers in the sense of this invention to a salt of at least one compound according to the present invention with at least one inorganic or organic acid which is physiologically acceptable—in particular when used in human beings and/or other mammals. Examples of physiologically acceptable acids are: hydrochloric acid, hydrobromic acid, sulfuric acid, methanesulfonic acid, p-toluenesulfonic acid, carbonic acid, formic acid, acetic acid, oxalic acid, succinic acid, tartaric acid, mandelic acid, fumaric acid, maleic acid, lactic acid, citric acid, glutamic acid, saccharic acid, monomethylsebacic acid, 5-oxoproline, hexane-1-sulfonic acid, nicotinic acid, 2, 3 or 4-aminobenzoic acid, 2,4,6-trimethylbenzoic acid, α-lipoic acid, acetyl glycine, hippuric acid, phosphoric acid, aspartic acid. Citric acid and hydrochloric acid are particularly preferred. Hydrochloride salts and citrate salts are therefore particularly preferred salts.

A physiologically acceptable salt of at least one compound according to the present invention and at least one physiologically acceptable base preferably refers in the sense of this invention to a salt of at least one compound according to the present invention as an anion with at least one preferably inorganic cation, which is physiologically acceptable—in particular when used in human beings and/or other mammals. Particularly preferred are the salts of the alkali and alkaline earth metals but also ammonium salts $[NH_xR_{4-x}]^+$, in which x=0, 1, 2, 3 or 4 and R represents a branched or unbranched $C_{1-4}$ alkyl residue, in particular (mono-) or (di)sodium, (mono-) or (di)potassium, magnesium or calcium salts.

The terms "alkyl" or "$C_{1-10}$ alkyl", "$C_{1-8}$ alkyl", "$C_{1-6}$ alkyl", "$C_{1-4}$ alkyl" comprise in the sense of this invention acyclic saturated or unsaturated aliphatic hydrocarbon residues, i.e. $C_{1-10}$ aliphatic residues, $C_{1-8}$ aliphatic residues, $C_{1-6}$ aliphatic residues and $C_{1-4}$ aliphatic residues, which can be respectively branched or unbranched and also unsubstituted or mono- or polysubstituted, containing 1 to 10 or 1 to 8 or 1 to 6 or 1 to 4 carbon atoms, i.e. $C_{1-10}$ alkanyls, $C_{2-10}$ alkenyls and $C_{2-10}$ alkinyls or $C_{2-8}$ alkanyls, $C_{2-8}$ alkenyls and $C_{2-8}$ alkinyls or $C_{1-6}$ alkanyls, $C_{2-6}$ alkenyls and $C_{2-6}$ alkinyls or $C_{1-4}$ alkanyls, $C_{2-4}$ alkenyls and $C_{2-4}$ alkinyls. In this case, alkenyls comprise at least one C—C double bond and alkinyls comprise at least one C—C triple bond. Preferably, alkyl is selected from the group comprising methyl, ethyl, n-propyl, 2-propyl, n-butyl, isobutyl, sec.-butyl, tert.-butyl, n-pentyl, isopentyl, neopentyl, n-hexyl, n-heptyl, n-octyl, n-nonyl, n-decyl, ethenyl (vinyl), ethinyl, propenyl ($—CH_2CH{=}CH_2$, $—CH{=}CH—CH_3$, $—C({=}CH_2)—CH_3$), propinyl ($—CH—C{\equiv}CH$, $—C{\equiv}C—CH_3$), butenyl, butinyl, pentenyl, pentinyl, hexenyl and hexinyl, heptenyl, heptinyl, octenyl, octinyl, nonenyl, noninyl, decenyl and decinyl.

The terms "cycloalkyl" or "$C_{3-10}$ cycloalkyl" and "cycloalkyl[1]" or "$C_{3-10}$ cycloalkyl" mean for the purposes of this invention cyclic aliphatic (cycloaliphatic) hydrocarbons containing 3, 4, 5, 6, 7, 8, 9 or 10 carbon atoms, i.e. $C_{3-10}$ cycloaliphatic residues, wherein the hydrocarbons can be saturated or unsaturated (but not aromatic), unsubstituted or mono- or polysubstituted. The cycloalkyl can be bound to the respective superordinate general structure via any desired and possible ring member of the cycloalkyl residue. The cycloalkyl residues can also be condensed with further saturated, (partially) unsaturated, (hetero)cyclic, aromatic or heteroaromatic ring systems, i.e. with cycloalkyl, heterocyclyl, aryl or heteroaryl which can in turn be unsubstituted or mono- or polysubstituted. The cycloalkyl residues can furthermore be singly or multiply bridged such as, for example, in the case of adamantyl, bicyclo[2.2.1]heptyl or bicyclo [2.2.2]octyl. Preferably, cycloalkyl is selected from the group comprising cyclopropyl, cyclobutyl, cyclopentyl, cyclohexyl, cycloheptyl, cyclooctyl, cyclononyl, cyclodecyl, adamantyl,

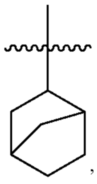,
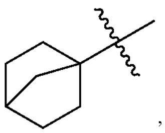,
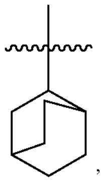,
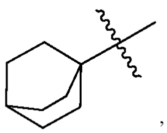, cyclopentenyl, cyclohexenyl, cycloheptenyl and cyclooctenyl.

The terms "heterocyclyl" or "heterocycloalkyl" and "heterocyclyl[1]" or "heterocycloalkyl[1]" comprise aliphatic saturated or unsaturated (but not aromatic) cycloalkyls having three to ten, i.e. 3, 4, 5, 6, 7, 8, 9 or 10, ring members, in which at least one, if appropriate also two or three carbon atoms are replaced by a heteroatom or a heteroatom group independently selected from the group consisting of O, S, $S({=}O)_2$, N, NH and N($C_{1-8}$ alkyl), preferably $N(CH_3)$, wherein the ring members can be unsubstituted or mono- or polysubstituted. Heterocyclyls are thus heterocycloaliphatic residues. The heterocyclyl can be bound to the superordinate general structure via any desired and possible ring member of the heterocyclyl residue. The heterocyclyl residues can therefore be condensed with further saturated, (partially) unsaturated (hetero)cyclic or aromatic or heteroaromatic ring systems, i.e. with cycloalkyl, heterocyclyl, aryl or heteroaryl which can in turn be unsubstituted or mono- or polysubstituted. Heterocyclyl residues from the group comprising azetidinyl, aziridinyl, azepanyl, azocanyl, diazepanyl, dithiolanyl, dihydroquinolinyl, dihydropyrrolyl, dioxanyl, dioxolanyl, dioxepanyl, dihydroindenyl, dihydropyridinyl, dihydrofuranyl, dihydroisoquinolinyl, dihydroindolinyl, dihydroisoindolyl, imidazolidinyl, isoxazolidinyl, morpholinyl, oxiranyl, oxetanyl, pyrrolidinyl, piperazinyl, 4-methylpiperazinyl, piperidinyl, pyrazolidinyl, pyranyl, tetrahydropyrrolyl, tetrahydropyranyl, tetrahydroquinolinyl, tetrahydroisoquinolinyl, tetrahydroindolinyl, tetrahydrofuranyl, tetrahydropyridinyl, tetrahydrothiophenyl, tetrahydropyridoindolyl, tetrahydronaphthyl, tetrahydrocarbolinyl, tetrahydroisoxazolopyridinyl, thiazolidinyl and thiomorpholinyl are preferred.

The term "aryl" means in the sense of this invention aromatic hydrocarbons having up to 14 ring members, including phenyls and naphthyls. Each aryl residue can be unsubstituted or mono- or polysubstituted, wherein the aryl substituents can be the same or different and in any desired and possible position of the aryl. The aryl can be bound to the superordinate general structure via any desired and possible ring member of the aryl residue. The aryl residues can also be condensed with further saturated, (partially) unsaturated, (hetero)cyclic, aromatic or heteroaromatic ring systems, i.e. with cycloalkyl, heterocyclyl, aryl or heteroaryl which can in turn be unsubstituted or mono- or polysubstituted. Examples of condensed aryl residues are benzodioxolanyl and benzodioxanyl. Preferably, aryl is selected from the group containing phenyl, 1-naphthyl and 2-naphthyl which can be respectively unsubstituted or mono- or polysubstituted. A particularly preferred aryl is phenyl, unsubstituted or mono- or polysubstituted.

The term "heteroaryl" represents a 5 or 6-membered cyclic aromatic residue containing at least 1, if appropriate also 2, 3, 4 or 5 heteroatoms, wherein the heteroatoms are each selected independently from the group S, N and O and the heteroaryl residue can be unsubstituted or mono- or polysubstituted; in the case of substitution on the heteroaryl, the substituents can be the same or different and be in any desired and possible position of the heteroaryl. The binding to the superordinate general structure can be carried out via any desired and possible ring member of the heteroaryl residue. The heteroaryl can also be part of a bi- or polycyclic system having up to 14 ring members, wherein the ring system can be formed with further saturated, (partially) unsaturated, (hetero)cyclic or aromatic or heteroaromatic rings, i.e. with cycloalkyl, heterocyclyl, aryl or heteroaryl which can in turn be unsubstituted or mono- or polysubstituted. It is preferable for the heteroaryl residue to be selected from the group comprising benzofuranyl, benzoimidazolyl, benzothienyl, benzothiadiazolyl, benzothiazolyl, benzotriazolyl, benzooxazolyl, benzooxadiazolyl, quinazolinyl, quinoxalinyl, carbazolyl, quinolinyl, dibenzofuranyl, dibenzothienyl, furyl (furanyl), imidazolyl, imidazothiazolyl, indazolyl, indolizinyl, indolyl, isoquinolinyl, isoxazoyl, isothiazolyl, indolyl, naphthyridinyl, oxazolyl, oxadiazolyl, phenazinyl, phenothiazinyl, phthalazinyl, pyrazolyl, pyridyl (2-pyridyl, 3-pyridyl, 4-pyridyl), pyrrolyl, pyridazinyl, pyrimidinyl, pyrazinyl, purinyl, phenazinyl, thienyl (thiophenyl), triazolyl, tetrazolyl, thiazolyl, thiadiazolyl or triazinyl. Furyl, pyridyl and thienyl are particularly preferred.

The terms "aryl, heteroaryl, heterocyclyl, cycloalkyl, heterocyclyl$^1$ or cycloalkyl$^1$ bridged via $C_{1-4}$ alkyl or $C_{1-8}$ alkyl" mean in the sense of the invention that $C_{1-4}$ alkyl or $C_{1-8}$ alkyl and aryl or heteroaryl or heterocyclyl or cycloalkyl or heterocyclyl$^1$ or cycloalkyl$^1$ have the above-defined meanings and the aryl or heteroaryl or heterocyclyl or cycloalkyl or heterocyclyl$^1$ or cycloalkyl$^1$ residue is bound to the respective superordinate general structure via a $C_{1-4}$ alkyl or a $C_{1-8}$ alkyl group. The alkyl chain of the alkyl group can in all cases be branched or unbranched, unsubstituted or mono- or polysubstituted. The alkyl chain of the alkyl group can furthermore be in all cases saturated or unsaturated, i.e. can be an alkylene group, i.e. a $C_{1-4}$ alkylene group or a $C_{1-8}$ alkylene group, an alkenylene group, i.e. a $C_{2-4}$ alkenylene group or a $C_{2-8}$ alkenylene group, or an alkinylene group, i.e. a $C_{2-4}$ alkinylene group or a $C_{2-8}$ alkinylene group. Preferably, $C_{1-4}$ alkyl is selected from the group comprising $—CH_2—$, $—CH_2—CH_2—$, $—CH(CH_3)—$, $—CH_2—CH_2—CH_2—$, $—CH(CH_3)—CH_2—$, $—CH(CH_2CH_3)—$, $—CH_2—(CH_2)_2—CH_2—$, $—CH(CH_3)—CH_2—CH_2—$, $—CH_2—CH(CH_3)—CH_2—$, $—CH(CH_3)—CH(CH_3)—$, $—CH(CH_2CH_3)—CH_2—$, $—C(CH_3)_2—CH_2—$, $—CH(CH_2CH_2CH_3)—$, $—C(CH_3)(CH_2CH_3)—$, $—CH{=}CH—$, $—CH{=}CH—CH_2—$, $—C(CH_3){=}CH_2—$, $—CH{=}CH—CH_2—CH_2—$, $—CH_2—CH{=}CH—CH_2—$, $—CH{=}CH—CH{=}CH—$, $—C(CH_3){=}CH—CH_2—$, $—CH{=}C(CH_3)—CH_2—$, $—C(CH_3){=}C(CH_3)—$, $—C(CH_2CH_3){=}CH—$, $—C{\equiv}C—$, $—C{\equiv}C—CH_2—$, $—C{\equiv}C—CH_2—CH_2—$, $—C{\equiv}C—CH(CH_3)—$, $—CH_2—C{\equiv}C—CH_2—$ and $—C{\equiv}C—C{\equiv}C—$ and $C_{1-8}$ alkyl is selected from the group comprising $—CH_2—$, $—CH_2—CH_2—$, $—CH(CH_3)—$, $—CH_2—CH_2—CH_2—$, $—CH(CH_3)—CH_2—$, $—CH(CH_2CH_3)—$, $—CH_2—(CH_2)_2—CH_2—$, $—CH(CH_3)—CH_2—CH_2—$, $—CH_2—CH(CH_3)—CH_2—$, $—CH(CH_3)—CH(CH_3)—$, $—CH(CH_2CH_3)—CH_2—$, $—C(CH_3)_2—CH_2—$, $—CH(CH_2CH_2CH_3)—$, $—C(CH_3)(CH_2CH_3)—$, $—CH_2—(CH_2)_3—CH_2—$, $—CH(CH_3)—CH_2—CH_2—CH_2—$, $—CH_2—CH(CH_3)—CH_2—CH_2—$, $—CH(CH_3)—CH_2—CH(CH_3)—$, $—CH(CH_3)—CH(CH_3)—CH_2—$, $—C(CH_3)_2—CH_2—CH_2—$, $—CH_2—C(CH_3)_2—CH_2—$, $—CH(CH_2CH_3)—CH_2—CH_2—$, $—CH_2—CH(CH_2CH_3)—CH_2—$, $—C(CH_3)_2—CH(CH_3)—$, $—CH(CH_2CH_3)—CH(CH_3)—$, $—C(CH_3)(CH_2CH_3)—CH_2—$, $—CH(CH_2CH_2CH_3)—CH_2—$, $—C(CH_2CH_2CH_3)—CH_2—$, $—CH(CH_2CH_2CH_2CH_3)—$, $—C(CH_3)(CH_2CH_2CH_3)—$, $—C(CH_2CH_3)_2—$, $—CH_2—(CH_2)_4—CH_2—$, $—CH{=}CH—$, $—CH{=}CH—CH_2—$, $—C(CH_3){=}CH_2—$, $—CH{=}CH—CH_2—CH_2—$, $—CH_2—CH{=}CH—CH_2—$, $—CH{=}CH—CH{=}CH—$, $—C(CH_3){=}CH—CH_2—$, $—CH{=}C(CH_3)—CH_2—$, $—C(CH_3){=}C(CH_3)—$, $—C(CH_2CH_3){=}CH—$, $—CH{=}CH—CH_2—CH_2—CH_2—$, $—CH_2—CH{=}CH_2—CH_2—CH_2—$, $—CH{=}CH{=}CH—CH_2—CH_2—$, $—CH{=}CH_2—CH—CH{=}CH_2—$, $—C{\equiv}C—$, $—C{\equiv}C—CH_2—$, $—C{\equiv}C—CH_2—CH_2—$, $—C{\equiv}C—CH(CH_3)—$, $—CH_2—C{\equiv}C—CH_2—$, $—C{\equiv}C—C{\equiv}C—$, $—C{\equiv}C—C(CH_3)_2—$, $—C{\equiv}C—CH_2—CH_2—CH_2—$, $—CH_2—C{\equiv}C—CH_2—CH_2—$, $—C{\equiv}C—C{\equiv}C—CH_2—$ and $—C{\equiv}C—CH_2—C{\equiv}C—$.

In relation to "alkyl", "heterocyclyl" and "cycloalkyl", the term "mono- or polysubstituted" refers in the sense of this invention to the single or multiple, for example double, triple or quadruple, replacement of one or more hydrogen atoms each independently by substituents selected from the group of F; Cl; Br; I; $NO_2$; CN; =O; =NH; $=C(NH_2)_2$; $CF_3$; $CF_2H$; $CFH_2$; $CF_2Cl$; $CFCl_2$; $R^0$; C(=O)H; C(=O)$R^0$; $CO_2H$; C(=O)O$R^0$; $CONH_2$; C(=O)NH$R^0$; C(=O)N$(R^0)_2$; OH; $OCF_3$; $OCF_2H$; $OCFH_2$; $OCF_2Cl$; $OCFCl_2$; O$R^0$; O—C(=O)—$R^0$; O—C(=O)—O—$R^0$; O—(C=O)—NH—$R^0$; O—C(=O)—N$(R^0)_2$; O—S$(=O)_2$—$R^0$; O—S$(=O)_2$OH; O—S$(=O)_2$O$R^0$; O—S$(=O)_2NH_2$; O—S$(=O)_2$NH$R^0$; O—S$(=O)_2$N$(R^0)_2$; $NH_2$; NH—$R^0$; N$(R^0)_2$; NH—C(=O)—$R^0$; NH—C(=O)—O—$R^0$; NH—C(=O)—$NH_2$; NH—C(=O)—NH—$R^0$; NH—C(=O)—N$(R^0)_2$; N$R^0$—C(=O)—$R^0$; N$R^0$—C(=O)—O—$R^0$; N$R^0$—C(=O)—$NH_2$; N$R^0$—C(=O)—NH—$R^0$; N$R^0$—C(=O)—N$(R^0)_2$; NH—S$(=O)_2$OH; NH—S$(=O)_2R^0$; NH—S$(=O)_2$O$R^0$; NH—S$(=O)_2NH_2$; NH—S$(=O)_2$NH$R^0$; NH—S$(=O)_2$N$(R^0)_2$; N$R^0$—S$(=O)_2$OH; N$R^0$—S$(=O)_2R^0$; N$R^0$—S$(=O)_2$O$R^0$; N$R^0$—S$(=O)_2NH_2$; N$R^0$—S$(=O)_2$NH$R^0$; N$R^0$—S$(=O)_2$N$(R^0)_2$; SH; $SCF_3$; $SCF_2H$; $SCFH_2$; $SCF_2Cl$; $SCFCl_2$; S$R^0$; S(=O)$R^0$; S$(=O)_2R^0$; S$(=O)_2$OH; S$(=O)_2$O$R^0$; S$(=O)_2NH_2$; S$(=O)_2$NH$R^0$; or S$(=O)_2$N$(R^0)_2$; wherein the term "polysubstituted residues" refers to residues of the type that are polysubstituted, for example di-, tri- or tetrasubstituted, either on different or on the same atoms, for example trisubstituted on the same C atom, as in the case of $CF_3$ or $CH_2CF_3$, or at various points, as in the case of CH(OH)—CH=CH—$CHCl_2$. A substituent can if appropriate for its part in turn be mono- or polysubstituted. The multiple substitution can be carried out using the same or using different substituents.

In relation to "cycloalkyl$^1$" and "heterocyclyl$^1$", the term "mono- or polysubstituted" refers in the sense of this invention to the single or multiple, for example double, triple or quadruple, replacement of one or more hydrogen atoms each independently by substituents selected from the group of F; Cl; Br; I; $NO_2$; CN; =O; $=C(NH_2)_2$; $CF_3$; $CF_2H$; $CFH_2$; $CF_2Cl$; $CFCl_2$; $R^0$; C(=O)H; C(=O)$R^0$; $CO_2H$; C(=O)O$R^0$; $CONH_2$; C(=O)NH$R^0$; C(=O)N$(R^0)_2$; OH; $OCF_3$; $OCF_2H$; $OCFH_2$; $OCF_2Cl$; $OCFCl_2$; O$R^0$; O—C(=O)—$R^0$; O—C(=O)—O—$R^0$; O—(C=O)—NH—$R^0$; O—C(=O)—N$(R^0)_2$; O—S$(=O)_2$—$R^0$; O—S$(=O)_2$OH; O—S$(=O)_2$O$R^0$; O—S$(=O)_2NH_2$; O—S$(=O)_2$NH$R^0$; O—S$(=O)_2$N$(R^0)_2$; SH; $SCF_3$; $SCF_2H$; $SCFH_2$; $SCF_2Cl$; $SCFCl_2$; S$R^0$; S(=O)$R^0$; S$(=O)_2R^0$; S$(=O)_2$OH; S$(=O)_2$O$R^0$; S$(=O)_2NH_2$; S$(=O)_2$NH$R^0$; or S$(=O)_2$N$(R^0)_2$; wherein the term "polysubstituted residues" refers to residues of the type that are multiply, for example di-, tri- or tetrasubstituted, either on different or on the same atoms, for example trisubstituted on the same C atom, as in the case of 1,1-difluorocyclohexyl, or at various points, as in the case of 1,2-difluorocyclohexyl. A substituent can if appropriate for its part in turn be mono- or polysubstituted. The multiple substitution can be carried out using the same or using different substituents.

Preferred "alkyl", "heterocyclyl" and "cycloalkyl" substituents are selected from the group of F; Cl; Br; I; $NO_2$; $CF_3$; CN; =O; =NH; $R^0$; C(=O)($R^0$ or H); C(=O)O($R^0$ or H); C(=O)N($R^0$ or H)$_2$; OH; O$R^0$; O—C(=O)—$R^0$; O—($C_{1-8}$ alkyl)-OH; O—($C_{1-8}$ alkyl)-O—$C_{1-8}$ alkyl; $OCF_3$; N(R or H)$_2$; N($R^0$ or H)—C(=O)—$R^0$; N($R^0$ or H)—C(=O)—N($R^0$ or H)$_2$; SH; $SCF_3$; S$R^0$; S(=O)$_2R^0$; S(=O)$_2$O($R^0$ or H) and S(=O)$_2$—N($R^0$ or H)$_2$.

Particularly preferred "alkyl", "heterocyclyl" and "cycloalkyl" substituents are selected from the group consisting of F; Cl; Br; I; $NO_2$; $CF_3$; CN; =O; $C_{1-8}$ alkyl; aryl; heteroaryl; $C_{3-10}$ cycloalkyl; heterocyclyl; aryl, heteroaryl, $C_{3-10}$ cycloalkyl or heterocyclyl bridged via $C_{1-8}$ alkyl; CHO; C(=O)$C_{1-8}$ alkyl; C(=O)aryl; C(=O)heteroaryl; $CO_2H$; C(=O)O—$C_{1-8}$ alkyl; C(=O)O-aryl; C(=O)O-heteroaryl; $CONH_2$; C(=O)NH—$C_{1-8}$ alkyl; C(=O)N($C_{1-8}$ alkyl)$_2$; C(=O)NH-aryl; C(=O)N(aryl)$_2$; C(=O)NH-heteroaryl; C(=O)N(heteroaryl)$_2$; C(=O)N($C_{1-8}$ alkyl)(aryl); C(=O)N($C_{1-8}$ alkyl)(heteroaryl); C(=O)N(heteroaryl)(aryl); OH; O—$C_{1-8}$ alkyl; $OCF_3$; O—($C_{1-8}$ alkyl)-OH; O—($C_{1-8}$ alkyl)-O—$C_{1-8}$ alkyl; O-benzyl; O-aryl; O-heteroaryl; O—C(=O)$C_{1-8}$ alkyl; O—C(=O)aryl; O—C(=O)heteroaryl; $NH_2$; NH—$C_{1-8}$ alkyl; N($C_{1-8}$ alkyl)$_2$; NH—C(=O)$C_{1-8}$ alkyl; NH—C(=O)-aryl; NH—C(=O)-heteroaryl; SH; S—$C_{1-6}$ alkyl; $SCF_3$; S-benzyl; S-aryl; S-heteroaryl; S(=O)$_2$Cl$_{1-8}$ alkyl; S(=O)$_2$ aryl; S(=O)$_2$ heteroaryl; S(=O)$_2$OH; S(=O)$_2$O—$C_{1-8}$ alkyl; S(=O)$_2$O-aryl; S(=O)$_2$O-heteroaryl; S(=O)$_2$—NH—$C_{1-8}$ alkyl; S(=O)$_2$—NH-aryl; and S(=O)$_2$—NH—$C_{1-8}$ heteroaryl.

Preferred "cycloalkyl$^1$" and "heterocyclyl$^1$" substituents are selected from the group of F; Cl; Br; I; $NO_2$; $CF_3$; CN; =O; $R^0$; C(=O)(R or H); C(=O)O($R^0$ or H); C(=O)N($R^0$ or H)$_2$; OH; O$R^0$; O—C(=O)—$R^0$; O—($C_{1-8}$ alkyl)-OH; O—($C_{1-8}$ alkyl)-O—$C_{1-8}$ alkyl; $OCF_3$; SH; $SCF_3$; S$R^0$; S(=O)$_2R^0$; S(=O)$_2$O($R^0$ or H) and S(=O)$_2$—N($R^0$ or H)$_2$.

Particularly preferred "cycloalkyl$^1$" and "heterocyclyl$^1$" substituents are selected from the group consisting of F; Cl; Br; I; $NO_2$; $CF_3$; CN; =O; $C_{1-8}$ alkyl; aryl; heteroaryl; $C_{3-10}$ cycloalkyl; heterocyclyl; aryl, heteroaryl, $C_{3-10}$ cycloalkyl or heterocyclyl bridged via $C_{1-8}$ alkyl; CHO; C(=O)$C_{1-8}$ alkyl; C(=O)aryl; C(=O)heteroaryl; $CO_2H$; C(=O)O—$C_{1-8}$ alkyl; C(=O)O-aryl; C(=O)O-heteroaryl; $CONH_2$; C(=O)NH—$C_{1-8}$ alkyl; C(=O)N($C_{1-8}$ alkyl)$_2$; C(=O)NH-aryl; C(=O)N(aryl)$_2$; C(=O)NH-heteroaryl; C(=O)N(heteroaryl)$_2$; C(=O)N(Cl$_{1-8}$ alkyl)(aryl); C(=O)N($C_{1-8}$ alkyl)(heteroaryl); C(=O)N(heteroaryl)(aryl); OH; O—$C_{1-8}$ alkyl; $OCF_3$; O—($C_{1-8}$ alkyl)-OH; O—($C_{1-8}$ alkyl)-O—Cl_alkyl; O-benzyl; O-aryl; O-heteroaryl; O—C(=O)$C_{1-8}$ alkyl; O—C(=O)aryl; O—C(=O)heteroaryl; SH; S—$C_{1-8}$ alkyl; $SCF_3$; S-benzyl; S-aryl; S-heteroaryl; S(=O)$_2C_{1-8}$ alkyl; S(=O)$_2$aryl; S(=O)$_2$ heteroaryl; S(=O)$_2$OH; S(=O)$_2$O—$C_{1-8}$ alkyl; S(=O)$_2$O-aryl; S(=O)$_2$O-heteroaryl; S(=O)$_2$—NH—$C_{1-8}$ alkyl; S(=O)$_2$—NH-aryl; and S(=O)$_2$—NH—$C_{1-8}$ heteroaryl.

In relation to "aryl" and "heteroaryl", the term "mono- or polysubstituted" refers in the sense of this invention to the single or multiple, for example double, triple or quadruple, replacement of one or more hydrogen atoms of the ring system each independently by substituents selected from the group of F; Cl; Br; I; $NO_2$; CN; $CF_3$; $CF_2H$; $CFH_2$; $CF_2Cl$; $CFCl_2$; $R^0$; C(=O)H; C(=O)$R^0$; $CO_2H$; C(=O)O$R^0$; $CONH_2$; C(=O)NH$R^0$; C(=O)N($R^0$)$_2$; OH; $OCF_3$; $OCF_2H$; $OCFH_2$; $OCF_2Cl$; $OCFCl_2$; O$R^0$; O—C(=O)—$R^0$; O—C(=O)—O—$R^0$; O—(C=O)—NH—$R^0$; O—C(=O)—N($R^0$)$_2$; O—S(=O)$_2$—$R^0$; O—S(=O)$_2$OH; O—S(=O)$_2$O$R^0$; O—S(=O)$_2$NH$_2$; O—S(=O)$_2$NH$R^0$; O—S(=O)$_2$N($R^0$)$_2$; $NH_2$; NH—$R^0$; N($R^0$)$_2$; NH—C(=O)—$R^0$; NH—C(=O)—O—$R^0$; NH—C(=O)—$NH_2$; NH—C(=O)—NH—$R^0$; NH—C(=O)—N($R^0$)$_2$; N$R^0$—C(=O)—$R^0$; N$R^0$—C(=O)—O—$R^0$; N$R^0$—C(=O)—$NH_2$; N$R^0$—C(=O)—NH—$R^0$; N$R^0$—C(=O)—N($R^0$)$_2$; NH—S(=O)$_2$OH; NH—S(=O)$_2R^0$; NH—S(=O)$_2$O$R^0$; NH—S(=O)$_2$NH$_2$; NH—S(=O)$_2$NH$R^0$; NH—S(=O)$_2$N($R^0$)$_2$; N$R^0$—S(=O)$_2$OH; N$R^0$—S(=O)$_2R^0$; N$R^0$—S(=O)$_2$O$R^0$; N$R^0$—S(=O)$_2$NH$_2$; N$R^0$—S(=O)$_2$NH$R^0$; N$R^0$—S(=O)$_2$N($R^0$)$_2$; SH; $SCF_3$; $SCF_2H$; $SCFH_2$; $SCF_2Cl$; $SCFCl_2$; S$R^0$; S(=O)$R^0$; S(=O)$_2R^0$; S(=O)$_2$OH; S(=O)$_2$O$R^0$; S(=O)$_2$NH$_2$; S(=O)$_2$NH$R^0$; or S(=O)$_2$N($R^0$)$_2$, on one or if appropriate different atoms, wherein a substituent can if appropriate for its part in turn be mono- or polysubstituted. The multiple substitution is carried out using the same or using different substituents.

In a particular preferred embodiment "aryl" substituents are ≠CN. Preferred "aryl" and "heteroaryl" substituents are F; Cl; Br; I; $NO_2$; $CF_3$; CN; $R^0$; C(=O)($R^0$ or H); C(=O)O($R^0$ or H); C(=O)N($R^0$ or H)$_2$; OH; O$R^0$; O—C(=O)—$R^0$; O—($C_{1-8}$ alkyl)-O—$C_{1-8}$ alkyl; $OCF_3$; N($R^0$ or H)$_2$; N($R^0$ or H)—C(=O)—$R^0$; N($R^0$ or H)—C(=O)—N($R^0$ or H)$_2$; SH; $SCF_3$; S$R^0$; S(=O)$_2R^0$; S(=O)$_2$O($R^0$ or H); S(=O)$_2$—N($R^0$ or H)$_2$.

Particularly preferred "aryl" and "heteroaryl" substituents are selected from the group consisting of F; Cl; Br; I; $NO_2$; $CF_3$; CN; $C_{1-8}$ alkyl; aryl; heteroaryl; $C_{3-10}$ cycloalkyl; heterocyclyl; aryl, heteroaryl, $C_{3-10}$ cycloalkyl or heterocyclyl bridged via $C_{1-8}$ alkyl; CHO; C(=O)$C_{1-8}$ alkyl; C(=O)aryl; C(=O)heteroaryl; $CO_2H$; C(=O)O—$C_{1-8}$ alkyl; C(=O)O-aryl; C(=O)O-heteroaryl; $CONH_2$; C(=O)NH—$C_{1-8}$ alkyl; C(=O)N($C_{1-8}$ alkyl)$_2$; C(=O)NH-aryl; C(=O)N(aryl)$_2$; C(=O)NH-heteroaryl; C(=O)N(heteroaryl)$_2$; C(=O)N($C_{1-8}$ alkyl)(aryl); C(=O)N($C_{1-8}$ alkyl)(heteroaryl); C(=O)N(heteroaryl)(aryl); OH; O—$C_{1-8}$ alkyl; $OCF_3$; O—($C_{1-8}$ alkyl)-OH; O—($C_{1-8}$ alkyl)-O—$C_{1-8}$ alkyl; O-benzyl; O-aryl; O-heteroaryl; O—C(=O)$C_{1-8}$ alkyl; O—C(=O)aryl; O—C(=O)heteroaryl; $NH_2$; NH—$C_{1-8}$ alkyl; N($C_{1-8}$ alkyl)$_2$; NH—C(=O)C_, alkyl; NH—C(=O)-aryl; NH—C(=O)-heteroaryl; SH; S—$C_{1-8}$ alkyl; $SCF_3$; S-benzyl; S-aryl; S-heteroaryl; S(=O)$_2C_{1-8}$ alkyl; S(=O)$_2$aryl; S(=O)$_2$ heteroaryl; S(=O)$_2$OH; S(=O)$_2$O—$C_{1-8}$ alkyl; S(=O)$_2$O-aryl; S(=O)$_2$O-heteroaryl; S(=O)$_2$—NH—$C_{1-8}$ alkyl; S(=O)$_2$—NH-aryl; S(=O)$_2$—NH—$C_{1-8}$ heteroaryl.

The compounds according to the invention are defined by substituents, for example by $R^1$, $R^2$ and $R^3$ (1$^{st}$ generation substituents) which are for their part if appropriate substituted (2$^{nd}$ generation substituents). Depending on the definition, these substituents of the substituents can for their part be resubstituted (3$^{rd}$ generation substituents). If, for example, $R^1$=aryl (1$^{st}$ generation substituent), then aryl can for its part be substituted, for example with $C_{1-8}$ alkyl (2$^{nd}$ generation substituent). This produces the functional group aryl-$C_{1-8}$ alkyl $C_{1-8}$ alkyl can then for its part be resubstituted, for example with Cl (3$^{rd}$ generation substituent). Overall, this then produces the functional group aryl-$C_{1-8}$ alkyl-CI. However, in a preferred embodiment, the 3$^{rd}$ generation substituents may not be resubstituted, i.e. there are then no 4$^{th}$ generation substituents.

In another preferred embodiment, the 2$^{nd}$ generation substituents may not be resubstituted, i.e. there are then not even any 3$^{rd}$ generation substituents. In other words, in this embodiment, in the case of general formula (I), for example, the functional groups for $R^1$ to $R^{10}$ can each if appropriate be substituted; however, the respective substituents may then for their part not be resubstituted.

In some cases, the compounds according to the invention are defined by substituents which are or carry an aryl or heteroaryl residue, respectively unsubstituted or mono- or polysubstituted, or which form together with the carbon atom(s) or heteroatom(s) connecting them, as the ring member or as the ring members, a ring, for example an aryl or heteroaryl, respectively unsubstituted or mono- or polysubstituted. Both these aryl or heteroaryl residues and the aromatic ring systems formed in this way can if appropriate be condensed with $C_{3-10}$ cycloalkyl or heterocyclyl, respectively saturated or unsaturated, or with aryl or heteroaryl, i.e. with a $C_{3-10}$ cycloalkyl such as cyclopentyl or a heterocyclyl such as morpholinyl, or an aryl such as phenyl or a heteroaryl such as pyridyl, wherein the $C_{3-10}$ cycloalkyl or heterocyclyl residues, aryl or heteroaryl residues condensed in this way can for their part be respectively unsubstituted or mono- or polysubstituted.

In some cases, the compounds according to the invention are defined by substituents which are or carry a $C_{3-10}$ cycloalkyl or heterocyclyl residue, respectively unsubstituted or mono- or polysubstituted, or which form together with the carbon atom(s) or heteroatom(s) connecting them, as the ring member or as the ring members, a ring, for example a $C_{3-10}$ cycloalkyl or heterocyclyl, respectively unsubstituted or mono- or polysubstituted. Both these $C_{3-10}$ cycloalkyl or heterocyclyl residues and the aliphatic ring systems formed can if appropriate be condensed with aryl or heteroaryl or with $C_{3-10}$ cycloalkyl or heterocyclyl, i.e. with an aryl such as phenyl or a heteroaryl such as pyridyl or a $C_{3-10}$ cycloalkyl such as cyclohexyl or a heterocyclyl such as morpholinyl, wherein the aryl or heteroaryl residues or $C_{3-10}$ cycloalkyl or heterocyclyl residues condensed in this way can for their part be respectively unsubstituted or mono- or polysubstituted.

Within the scope of the present invention, the symbol

used in the formulae denotes a link of a corresponding residue to the respective superordinate general structure.

The term "($R^0$ or H)" within a residue means that $R^0$ and H can occur within this residue in any possible combination. Thus, for example, the residue "N($R^0$ or H)$_2$" can represent "$NH_2$", "$NHR^0$" and "$N(R^0)_2$". If, as in the case of "$N(R^0)_2$", $R^0$ occurs multiply within a residue, then $R^0$ can respectively have the same or different meanings: in the present example of "$N(R^0)_2$", $R^0$ can for example represent aryl twice, thus producing the functional group "N(aryl)$_2$", or $R^0$ can represent once aryl and once $C_{1-10}$ alkyl, thus producing the functional group "N(aryl)($C_{1-10}$ alkyl)".

If a residue occurs more than once within a molecule, such as for example the residue $R^0$, then this residue can have respectively different meanings for various substituents: if, for example, both $R^1$=$R^0$ and $R^2$=$R^0$, then $R^0$ can represent $R^1$=aryl and $R^0$ can represent $R^2$=$C_{1-10}$ alkyl.

The term "salt formed with a physiologically compatible acid" refers in the sense of this invention to salts of the respective active ingredient with inorganic or organic acids which are physiologically compatible—in particular when used in human beings and/or other mammals. Hydrochloride is particularly preferred. Examples of physiologically compatible acids are: hydrochloric acid, hydrobromic acid, sulfuric acid, methanesulfonic acid, p-toluenesulfonic acid, carbonic acid, formic acid, acetic acid, oxalic acid, succinic acid, tartaric acid, mandelic acid, fumaric acid, maleic acid, lactic acid, citric acid, glutamic acid, saccharic acid, monomethylsebacic acid, 5-oxoproline, hexane-1-sulfonic acid, nicotinic acid, 2, 3 or 4-aminobenzoic acid, 2,4,6-trimethylbenzoic acid, α-lipoic acid, acetyl glycine, hippuric acid, phosphoric acid, aspartic acid. Citric acid and hydrochloric acid are particularly preferred.

Physiologically compatible salts with cations or bases are salts of the respective compound—as an anion with at least one, preferably inorganic, cation—which are physiologically compatible—in particular when used in human beings and/or other mammals.

Particularly preferred are the salts of the alkali and alkaline earth metals but also ammonium salts $[NH_xR_{4-x}]^+$, in which x=0, 1, 2, 3 or 4 and R represents a branched or unbranched $C_{1-4}$ alkyl residue, in particular (mono-) or (di)sodium, (mono-) or (di)potassium, magnesium or calcium salts.

In preferred embodiments of the compounds according to the invention of general formula (I), n represents 1, 2, 3 or 4, preferably 1, 2 or 3, particularly preferably 1 or 2, most particularly preferably 1.

Further preferred embodiments of the compounds according to the invention of general formula (I) have general formula (Ia), (Ib), (Ic) or (Id):

(Ia)

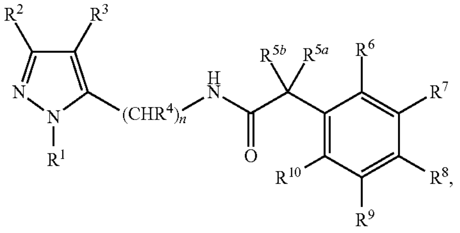

(Ib)

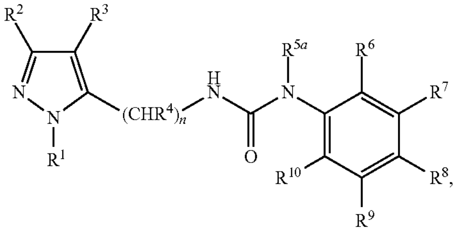

(Ic)

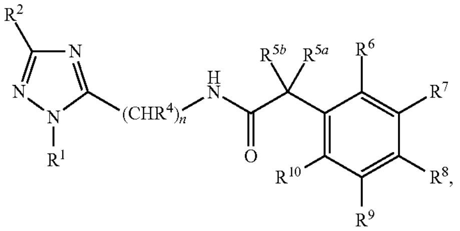

(Id)

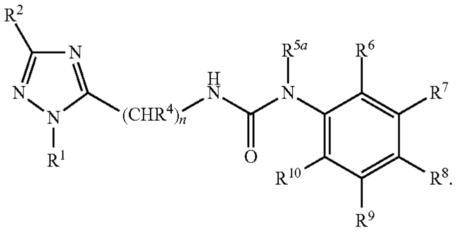

Compounds of general formulas (Ia) and (Ib) are most particularly preferred. In a particular preferred embodiment of the present invention $R^1$ is not H.

In a further preferred embodiment of the compounds according to the invention of general formula (I), the residue $R^1$ represents H; $C_{1-10}$ alkyl, C(═O)—$C_{1-10}$ alkyl, C(═O)—NH—$C_{1-10}$ alkyl, C(═O)—N($C_{1-10}$ alkyl)$_2$, O—$C_{1-10}$ alkyl, S—$C_{1-10}$ alkyl, NH($C_{1-10}$ alkyl), N($C_{1-10}$ alkyl)$_2$, NH—C(═O)—$C_{1-10}$ alkyl, NH—S(═O)$_2$—$C_{1-10}$ alkyl, N($C_{1-10}$ alkyl)-S(═O)$_2$—$C_{1-10}$ alkyl, S(═O)$_2$—$C_{1-10}$ alkyl, S(═O)$_2$—NH—$C_{1-10}$ alkyl, S(═O)$_2$—N($C_{1-10}$ alkyl)$_2$, in which $C_{1-10}$ alkyl can be respectively saturated or unsaturated, branched or unbranched, unsubstituted or mono- or polysubstituted with one or more substituents each selected independently from the group consisting of F, Cl, Br, I, $NO_2$, CN, OH, ═O, O—$C_{1-4}$ alkyl, $OCF_3$, $CF_3$, $NH_2$, NH($C_{1-4}$ alkyl), N($C_{1-4}$ alkyl)$_2$, SH, S—$C_{1-4}$ alkyl, $SCF_3$, phenyl and pyridyl, wherein phenyl or pyridyl are respectively unsubstituted or mono- or polysubstituted with one or more substituents each selected independently from the group consisting of F, Cl, Br, I, $NO_2$, CN, OH, O—$C_{1-4}$ alkyl, $OCF_3$, $C_{1-4}$ alkyl, C(═O)—OH, $CF_3$, $NH_2$, NH($C_{1-4}$ alkyl), N($C_{1-4}$ alkyl)$_2$, SH, S—$C_{1-4}$ alkyl, $SCF_3$ and S(═O)$_2$OH; or $C_{3-10}$ cycloalkyl or heterocyclyl$^1$, respectively saturated or unsaturated, unsubstituted or mono- or polysubstituted with one or more substituents each selected independently from the group consisting of F, Cl, Br, I, $NO_2$, CN, OH, ═O, O—$C_{1-4}$ alkyl, $OCF_3$, $CF_3$, SH, S—$C_{1-4}$ alkyl, $SCF_3$, phenyl and pyridyl, wherein phenyl or pyridyl are respectively unsubstituted or mono- or polysubstituted with one or more substituents each selected independently from the group consisting of F, Cl, Br, I, $NO_2$, CN, OH, O—$C_{1-4}$ alkyl, $OCF_3$, $C_{1-4}$ alkyl, C(═O)—OH, $CF_3$, $NH_2$, NH($C_{1-4}$ alkyl), N($C_{1-4}$ alkyl)$_2$, SH, S—$C_{1-4}$ alkyl, $SCF_3$ and S(═O)$_2$OH; or $C_{3-10}$ cycloalkyl$^1$ or heterocyclyl$^1$ bridged via $C_{1-8}$ alkyl, respectively saturated or unsaturated, unsubstituted or mono- or polysubstituted with one or more substituents each selected independently from the group consisting of F, Cl, Br, I, $NO_2$, CN, OH, ═O, O—$C_{1-4}$ alkyl, $OCF_3$, $CF_3$, SH, S—$C_{1-4}$ alkyl, $SCF_3$, phenyl and pyridyl, wherein phenyl or pyridyl are respectively unsubstituted or mono- or polysubstituted with one or more substituents each selected independently from the group consisting of F, Cl, Br, I, $NO_2$, CN, OH, O—$C_{1-4}$ alkyl, $OCF_3$, $C_{1-4}$ alkyl, C(═O)—OH, $CF_3$, $NH_2$, NH($C_{1-4}$ alkyl), N($C_{1-4}$ alkyl)$_2$, SH, S—$C_{1-4}$ alkyl, $SCF_3$ and S(═O)$_2$OH; wherein the alkyl chain can be respectively branched or unbranched, saturated or unsaturated, unsubstituted, mono- or polysubstituted with one or more substituents each selected independently from the group consisting of F, Cl, Br; I, OH and O—$C_{1-4}$ alkyl; or C(═O)—$C_{3-10}$ cycloalkyl, O—$C_{3-10}$ cycloalkyl, S—$C_{3-10}$ cycloalkyl, respectively saturated or unsaturated, unsubstituted or mono- or polysubstituted with one or more substituents each selected independently from the group consisting of F, Cl, Br, I, $NO_2$, CN, OH, ═O, O—$C_{1-4}$ alkyl, $OCF_3$, $CF_3$, $NH_2$, NH($C_{1-4}$ alkyl), N($C_{1-4}$ alkyl)$_2$, SH, S—$C_{1-4}$ alkyl, $SCF_3$, phenyl and pyridyl, wherein phenyl or pyridyl are respectively unsubstituted or mono- or polysubstituted with one or more substituents each selected independently from the group consisting of F, Cl, Br, I, $NO_2$, CN, OH, O—$C_{1-4}$ alkyl, $OCF_3$, $C_{1-4}$ alkyl, C(═O)—OH, $CF_3$, $NH_2$, NH($C_{1-4}$ alkyl), N($C_{1-4}$ alkyl)$_2$, SH, S—$C_{1-4}$ alkyl, $SCF_3$ and S(═O)$_2$OH; or aryl, heteroaryl, C(═O)-aryl, C(═O)-heteroaryl, O-aryl, O-heteroaryl, NH(aryl), N(aryl)$_2$, NH(heteroaryl), N(heteroaryl)$_2$, NH—C(═O)-aryl, NH—C(═O)-heteroaryl, NH—S(═O)$_2$-aryl, NH—S(═O)$_2$-heteroaryl, S(═O)$_2$-aryl, S(═O)$_2$-heteroaryl or aryl or heteroaryl bridged via $C_{1-8}$ alkyl, can be respectively unsubstituted or mono- or polysubstituted with one or more substituents each selected independently from the group consisting of F, Cl, Br, I, $NO_2$, CN, OH, ═O, O—$C_{1-4}$ alkyl, $OCF_3$, $CF_3$, $NH_2$, NH($C_{1-4}$ alkyl), N($C_{1-4}$ alkyl)$_2$, SH, S—$C_{1-4}$ alkyl, $SCF_3$, S(═O)$_2$OH and NH—S(═O)$_2$—$C_{1-4}$ alkyl, and wherein if appropriate the alkyl chain can be respectively branched or unbranched, saturated or unsaturated, unsubstituted, mono- or polysubstituted with one or more substituents each selected independently from the group consisting of F, Cl, Br, I, OH and O—$C_{1-4}$ alkyl.

In another preferred embodiment of the compounds according to the invention of general formula (I), the residue $R^1$ represents substructure (T1)

(T1)

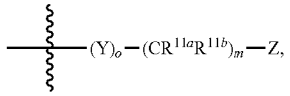

in which

Y represents C(═O), O, S, S(═O)$_2$, NH—C(═O) or $NR^{12}$,
wherein $R^{12}$ represents H; $C_{1-8}$ alkyl or S(═O)$_2$—$C_{1-8}$ alkyl, in which $C_{1-8}$ alkyl can be respectively saturated or unsaturated, branched or unbranched, unsubstituted or mono- or polysubstituted with one or more substituents each selected independently from the group consisting of F, Cl, Br, I, OH, O—$C_{1-4}$ alkyl, $OCF_3$, $NH_2$, NH—$C_{1-4}$ alkyl and N($C_{1-4}$ alkyl)$_2$;

o represents 0 or 1, $R^{11a}$ and $R^{11b}$ each independently represent H; F; Cl; Br; I; $NO_2$; $CF_3$; CN; OH; $OCF_3$; $NH_2$; $C_{1-4}$ alkyl, O—$C_{1-4}$ alkyl, NH—$C_{1-4}$ alkyl, N($C_{1-4}$ alkyl)$_2$, in which $C_{1-4}$ alkyl can be respectively saturated or unsaturated, branched or unbranched, unsubstituted or mono- or polysubstituted with one or more substituents each selected independently from the group consisting of F, Cl, Br, I, O—$C_{1-4}$ alkyl, OH and $OCF_3$;
with the proviso that if $R^{11a}$ and $R^{11b}$ are bound to the same carbon atom, only one of the substituents $R^{11a}$ and $R^{11b}$ can represent OH, $OCF_3$, $NH_2$, O—$C_{1-4}$ alkyl, NH—$C_{1-4}$ alkyl or N($C_{1-4}$ alkyl)$_2$;

m represents 0, 1, 2, 3 or 4;

Z represents $C_{1-4}$ alkyl, saturated or unsaturated, branched or unbranched, unsubstituted or mono- or polysubstituted with one or more substituents each selected independently from the group consisting of F, Cl, Br, I, $NO_2$, CN, OH, ═O, O—$C_{1-4}$ alkyl, $OCF_3$, C(═O)—OH, $CF_3$, $NH_2$, NH($C_{1-4}$ alkyl), N($C_{1-4}$ alkyl)$_2$, SH, S—$C_{1-4}$ alkyl, $SCF_3$ and S(═O)$_2$OH; $C_{3-10}$ cycloalkyl$^1$ or heterocyclyl$^1$, respectively saturated or unsaturated, unsubstituted or mono- or polysubstituted with one or more substituents each selected independently from the group consisting of F, Cl, Br, I, $NO_2$, CN, OH, O—$C_{1-4}$ alkyl, $OCF_3$, $C_{1-4}$ alkyl, C(═O)—OH, $CF_3$, SH, S—$C_{1-4}$ alkyl, $SCF_3$, S(═O)$_2$OH, benzyl, phenyl, pyridyl and thienyl, wherein benzyl, phenyl, pyridyl, thienyl can be respectively unsubstituted or mono- or polysubstituted with one or more substituents selected independently from the group consisting of F, Cl, Br, I, $NO_2$, CN, OH, O—$C_{1-4}$ alkyl, $OCF_3$, $C_{1-4}$ alkyl, C(═O)—OH, $CF_3$, $NH_2$, NH($C_{1-4}$ alkyl), N($C_{1-4}$ alkyl)$_2$, SH, S—$C_{1-4}$ alkyl, $SCF_3$ and S(═O)$_2$OH; aryl or heteroaryl, respectively unsubstituted or mono- or polysubstituted with one or more substituents each selected independently from the group consisting of F, Cl, Br, I, $NO_2$, CN, OH, O—$C_{1-4}$ alkyl, $OCF_3$, $C_{1-4}$ alkyl, C(═O)—OH, $CF_3$, $NH_2$, NH($C_{1-4}$ alkyl), N($C_{1-4}$ alkyl)$_2$, SH, S—$C_{1-4}$ alkyl, $SCF_3$, S(═O)$_2$OH, benzyl, phenyl, pyridyl and thienyl, wherein benzyl, phenyl, pyridyl, thienyl can be respectively unsubstituted or mono- or polysubstituted with one or more substituents selected independently from the group consisting of F, Cl, Br, I, $NO_2$, CN, OH, O—$C_{1-8}$ alkyl, $OCF_3$, $C_{1-4}$ alkyl, C(═O)—OH, $CF_3$, $NH_2$, NH($C_{1-4}$ alkyl), N($C_{1-4}$ alkyl)$_2$, SH, S—$C_{1-4}$ alkyl, $SCF_3$ and S(═O)$_2$OH.

If m is not 0, then the residues $R^{11a}$ and $R^{11b}$ can, taking account of the foregoing condition, both on the same carbon atom and on different carbon atoms, each independently represent H; F; Cl; Br; I; $NO_2$; $CF_3$; CN; OH; $OCF_3$; $NH_2$; $C_{1-4}$ alkyl, O—$C_{1-4}$ alkyl, NH—$C_{1-4}$ alkyl, N($C_{1-4}$ alkyl)$_2$, in which $C_{1-4}$ alkyl can be respectively saturated or unsaturated, branched or unbranched, unsubstituted or mono- or polysubstituted with one or more substituents each selected independently from the group consisting of F, Cl, Br, I, O—$C_{1-4}$ alkyl, OH and $OCF_3$.

Preferably, the residue $R^1$ represents substructure (T1) in which

Y represents C(═O), O, S, S(═O)$_2$, NH—C(═O) or $NR^{12}$, wherein $R^{12}$ represents H; methyl; ethyl; n-propyl; isopropyl; n-butyl; sec.-butyl; tert.-butyl; S(═O)$_2$-methyl; S(═O)$_2$-ethyl;

o represents 0 or 1;

$R^{11a}$ and $R^{11b}$ each independently represent H; F; Cl; Br; I; $NO_2$; $CF_3$; CN; methyl; ethyl; n-propyl; isopropyl; n-butyl; sec.-butyl; tert.-butyl; $CH_2CF_3$; OH; O-methyl; O-ethyl; O—$(CH_2)_2$—O—$CH_3$; O—$(CH_2)_2$—OH; $OCF_3$; $NH_2$; NH-methyl; N(methyl)$_2$; NH-ethyl; N(ethyl)$_2$; or N(methyl)(ethyl);

with the proviso that if $R^{11a}$ and $R^{11b}$ are bound to the same carbon atom, only one of the substituents $R^{11a}$ and $R^{11b}$ can represent OH; $OCF_3$; O-methyl; O-ethyl; O—$(CH_2)_2$—O—$CH_3$; O—$(CH_2)_2$—OH; $NH_2$; NH-methyl; N(methyl)$_2$; NH-ethyl; N(ethyl)$_2$; or N(methyl)(ethyl);

m represents 0, 1 or 2;

Z represents $C_{1-4}$ alkyl, saturated or unsaturated, branched or unbranched, unsubstituted or mono- or polysubstituted with one or more substituents each selected independently from the group consisting of F, Cl, Br, I, OH, ═O, O—$C_{1-4}$ alkyl, $OCF_3$, C(═O)—OH and $CF_3$; phenyl, naphthyl, furyl, pyridyl or thienyl, respectively unsubstituted or mono- or polysubstituted with one or more substituents each selected independently from the group consisting of F, Cl, Br, I, CN, OH, O—$C_{1-4}$ alkyl, $OCF_3$, $C_{1-4}$ alkyl, $CF_3$, $NH_2$, NH($C_{1-4}$ alkyl), N($C_{1-4}$ alkyl)$_2$, SH, S—$C_{1-8}$ alkyl, $SCF_3$, benzyl and phenyl, wherein benzyl and phenyl can be respectively unsubstituted or mono- or polysubstituted with one or more substituents selected independently from the group consisting of F, Cl, Br, I, CN, OH, O—$C_{1-4}$ alkyl, $OCF_3$, $C_{1-4}$ alkyl, $CF_3$, $NH_2$, NH($C_{1-4}$ alkyl), N($C_{1-4}$ alkyl)$_2$, SH, S—$C_{1-4}$ alkyl and $SCF_3$; $C_{3-10}$ cycloalkyl[1] or heterocyclyl[1], respectively saturated or unsaturated, unsubstituted or mono- or polysubstituted with one or more substituents each selected independently from the group consisting of F, Cl, Br, I, CN, OH, O—$C_{1-4}$ alkyl, $OCF_3$, $CO_4$ alkyl, $CF_3$, benzyl, phenyl and pyridyl, wherein benzyl, phenyl and pyridyl can be respectively unsubstituted or mono- or polysubstituted with one or more substituents selected independently from the group consisting of F, Cl, Br, I, CN, OH, O—$C_{1-4}$ alkyl, $OCF_3$, $C_{1-4}$ alkyl, $CF_3$, $NH_2$, NH($C_{1-4}$ alkyl), N($C_{1-4}$ alkyl)$_2$, SH, S—$C_{1-4}$ alkyl and $SCF_3$.

If m≠0, then the residues $R^{11a}$ and $R^{11b}$ can, taking account of the foregoing condition, both on the same carbon atom and on different carbon atoms, each independently represent H; F; Cl; Br; I; $NO_2$; $CF_3$; CN; methyl; ethyl; n-propyl; isopropyl; n-butyl; sec.-butyl; tert.-butyl; $CH_2CF_3$; OH; O-methyl; O-ethyl; O—$(CH_2)_2$—O—$CH_3$; O—$(CH_2)_2$—OH; $OCF_3$; $NH_2$; NH-methyl; N(methyl)$_2$; NH-ethyl; N(ethyl)$_2$; or N(methyl)(ethyl).

Particularly preferably, the residue $R^1$ represents substructure (T1) in which Y represents C(═O), O, S, S(═O)$_2$, NH—C(═O) or $NR^{12}$, wherein $R^{12}$ represents H; methyl; ethyl; n-propyl; isopropyl; n-butyl; sec.-butyl; tert.-butyl; S(═O)$_2$-methyl; S(═O)$_2$-ethyl;

o represents 0 or 1;

$R^{11a}$ and $R^{11b}$ each independently represent H; F; Cl; Br; I; methyl; ethyl; n-propyl; isopropyl; n-butyl; sec.-butyl; tert.-butyl; OH; O-methyl; O-ethyl;

with the proviso that if $R^{11a}$ and $R^{11b}$ are bound to the same carbon atom, only one of the substituents $R^{11a}$ and $R^{11b}$ can represent OH; O-methyl; O-ethyl;

m represents 0, 1 or 2;

Z represents $C_{1-4}$ alkyl, saturated or unsaturated, branched or unbranched, unsubstituted or mono- or polysubstituted with one or more substituents each selected independently from the group consisting of F, Cl, Br, I, OH, O—$C_{1-4}$ alkyl, $OCF_3$, and $CF_3$; $C_{3-10}$ cycloalkyl[1], saturated or unsaturated, unsubstituted or mono- or polysubstituted with one or more substituents each selected independently from the group consisting of F, Cl, Br, I, OH, O—$C_{1-4}$ alkyl, $OCF_3$, $C_{1-4}$ alkyl, $CF_3$, benzyl and phenyl, wherein benzyl and phenyl can be respectively unsubstituted or mono- or polysubstituted with one or more substituents selected independently from the group consisting of F, Cl, Br, I, OH, O—$C_{1-4}$ alkyl, $OCF_3$, $C_{1-4}$ alkyl, $CF_3$, and $SCF_3$; morpholinyl, thiomorpholinyl, piperidinyl, pyrrolidinyl, 4-methylpiperazinyl, piperazinyl, respectively unsubstituted or mono- or polysubstituted with one or more substituents each selected independently from the group consisting of F, Cl, Br, I, OH, O—$C_{1-4}$ alkyl, $OCF_3$, $C_{1-4}$ alkyl, $CF_3$, benzyl and phenyl, wherein benzyl and phenyl can be respectively unsubstituted or mono- or polysubstituted with one or more substituents selected independently from the group consisting of F, Cl, Br, I, OH, O—$C_4$ alkyl, $OCF_3$, $C_{1-4}$ alkyl, $CF_3$ and $SCF_3$; phenyl, naphthyl, pyridyl or thienyl, respectively unsubstituted or mono- or polysubstituted with one or more substituents each selected independently from the group consisting of F, Cl, Br, I, CN, OH, O—$C_{1-4}$ alkyl, $OCF_3$, $C_{1-4}$ alkyl, $CF_3$, SH, S—$C_{1-4}$ alkyl, $SCF_3$, benzyl and phenyl, wherein benzyl and phenyl can be respectively unsubstituted or mono- or polysubstituted with one or more substituents selected independently from the group consisting of F, Cl, Br, I, OH, O—$C_{1-4}$ alkyl, $OCF_3$, $C_{1-4}$ alkyl, $CF_3$ and $SCF_3$.

If m≠0, then the residues $R^{11a}$ and $R^{11b}$ can, taking account of the foregoing condition, both on the same carbon atom and on different carbon atoms, each independently represent H; F; Cl; Br; I; methyl; ethyl; n-propyl; isopropyl; n-butyl; sec.-butyl; tert.-butyl; OH; O-methyl; O-ethyl.

Most particularly preferably, the residue $R^1$ represents substructure (T1) in which Y represents C(=O), O, S, $S(=O)_2$, NH—C(=O) or $NR^{12}$, wherein $R^{12}$ represents H; methyl; ethyl; n-propyl; isopropyl; n-butyl; sec.-butyl; tert.-butyl; $S(=O)_2$-methyl;

o represents 0 or 1;

$R^{11a}$ and $R^{11b}$ each independently represent H; methyl; ethyl; n-propyl; isopropyl; n-butyl; sec.-butyl; tert.-butyl;

m represents 0, 1 or 2;

Z represents $C_{1-4}$ alkyl, saturated or unsaturated, branched or unbranched, unsubstituted or mono- or polysubstituted with one or more substituents each selected independently from the group consisting of F, Cl, Br, I, OH, O—$C_{1-4}$ alkyl; $C_{3-10}$ cycloalkyl[1], saturated or unsaturated, morpholinyl, piperidinyl, 4-methylpiperazinyl, piperazinyl, respectively unsubstituted or mono- or polysubstituted with one or more substituents each selected independently from the group consisting of F, Cl, Br, I, OH, O—$C_{1-4}$ alkyl and $C_{1-4}$ alkyl; phenyl or pyridyl, respectively unsubstituted or mono- or polysubstituted with one or more substituents each selected independently from the group consisting of F, Cl, Br, I, CN, OH, O—$C_{1-4}$ alkyl, $OCF_3$, $C_{1-4}$ alkyl, $CF_3$, SH, S—$C_{1-4}$ alkyl, $SCF_3$.

If m≠0, then the residues $R^{11a}$ and $R^{11b}$ can, both on the same carbon atom and on different carbon atoms, each independently represent H; methyl; ethyl; n-propyl; isopropyl; n-butyl; sec.-butyl; tert.-butyl.

In a particular preferred embodiment of the present invention $R^2$ is ≠Br and ≠Cl.

In a further preferred embodiment of the compounds according to the invention of general formula (I), the residue $R^2$ represents H; F; Cl; Br; I; CN; $NO_2$; $CF_3$; $CF_2H$; $CFH_2$; $CF_2Cl$; $CFCl_2$; OH; $OCF_3$; $OCF_2H$; $OCFH_2$; $OCF_2Cl$; $OCFCl_2$; SH; $SCF_3$; $SCF_2H$; $SCFH_2$; $SCF_2Cl$; $SCFCl_2$; $C_{1-10}$ alkyl, saturated or unsaturated, branched or unbranched, unsubstituted or mono- or polysubstituted with one or more substituents each selected independently from the group consisting of F, Cl, Br, I, $NO_2$, CN, OH, =O, O—$C_{1-4}$ alkyl, $OCF_3$, C(=O)—OH, $CF_3$, $NH_2$, NH($C_{1-4}$ alkyl), N($C_{1-4}$ alkyl)$_2$, SH, S—$C_{1-4}$ alkyl, $SCF_3$S(=O)$_2$OH, benzyl, phenyl, pyridyl and thienyl, wherein benzyl, phenyl, pyridyl, thienyl can be respectively unsubstituted or mono- or polysubstituted with one or more substituents selected independently from the group consisting of F, Cl, Br, I, $NO_2$, CN, OH, O—$C_{1-4}$ alkyl, $OCF_3$, $C_{1-4}$ alkyl, C(=O)—OH, $CF_3$, $NH_2$, NH($C_{1-4}$ alkyl), N($CO_{14}$ alkyl)$_2$, SH, S—$C_{1-4}$ alkyl, $SCF_3$ and S(=O)$_2$OH; $C_{3-10}$ cycloalkyl or heterocyclyl, respectively saturated or unsaturated, unsubstituted or mono- or polysubstituted with one or more substituents selected independently from the group consisting of F, Cl, Br, I, OH, =O, $C_{1-4}$ alkyl, O—$C_{1-4}$ alkyl, $OCF_3$, C(=O)—OH and $CF_3$; or $C_{3-10}$ cycloalkyl or heterocyclyl bridged via $C_{1-8}$ alkyl, respectively saturated or unsaturated, unsubstituted or mono- or polysubstituted with one or more substituents each selected independently from the group consisting of F, Cl, Br, I, OH, =O, $C_{1-4}$ alkyl, O—$C_{1-4}$ alkyl, $OCF_3$, C(=O)—OH and $CF_3$, wherein the alkyl chain can be respectively branched or unbranched, saturated or unsaturated, unsubstituted, mono- or polysubstituted with one or more substituents each selected independently from the group consisting of F, Cl, Br, I, OH, =O and O—$C_{1-4}$ alkyl; aryl or heteroaryl, respectively unsubstituted or mono- or polysubstituted with one or more substituents each selected independently from the group consisting of F, Cl, Br, I, $NO_2$, CN, OH, O—$C_{1-4}$ alkyl, $OCF_3$, $C_{1-4}$ alkyl, C(=O)—OH, $CF_3$, $NH_2$, NH($C_{1-4}$ alkyl), N($C_{1-4}$ alkyl)$_2$, SH, S—$C_{1-8}$ alkyl, $SCF_3$, S(=O)$_2$OH, benzyl, phenyl, pyridyl and thienyl, wherein benzyl, phenyl, pyridyl, thienyl can be respectively unsubstituted or mono- or polysubstituted with one or more substituents selected independently from the group consisting of F, Cl, Br, I, $NO_2$, CN, OH, O—$C_{1-8}$ alkyl, $OCF_3$, $C_{1-4}$ alkyl, C(=O)—OH, $CF_3$, $NH_2$, NH($C_{1-4}$ alkyl), N($C_{1-4}$ alkyl)$_2$, SH, S—$C_{1-4}$ alkyl, $SCF_3$ and S(=O)$_2$OH; or aryl or heteroaryl bridged via $C_{1-8}$ alkyl, respectively unsubstituted or mono- or polysubstituted with one or more substituents each selected independently from the group consisting of F, Cl, Br, I, $NO_2$, CN, OH, O—$C_{1-4}$ alkyl, $OCF_3$, $C_{1-4}$ alkyl, C(=O)—OH, $CF_3$, $NH_2$, NH($C_{1-4}$ alkyl), N($C_{1-4}$ alkyl)$_2$, SH, S—$C_{1-8}$ alkyl, $SCF_3$, S(=O)$_2$OH, benzyl, phenyl, pyridyl and thienyl, wherein benzyl, phenyl, pyridyl, thienyl can be respectively unsubstituted or mono- or polysubstituted with one or more substituents selected independently from the group consisting of F, Cl, Br, I, $NO_2$, CN, OH, O—$C_{1-8}$ alkyl, $OCF_3$, $C_{1-4}$ alkyl, C(=O)—OH, $CF_3$, $NH_2$, NH($C_{1-4}$ alkyl), N($C_{1-4}$ alkyl)$_2$, SH, S—$C_{1-4}$ alkyl, $SCF_3$ and S(=O)$_2$OH, wherein the alkyl chain can be respectively branched or unbranched, saturated or unsaturated, unsubstituted, mono- or polysubstituted with one or more substituents each selected independently from the group consisting of F, Cl, Br, I, OH, =O and O—$C_{1-4}$ alkyl.

Preferably, the residue $R^2$ represents H; F; Cl; Br; I; CN; $CF_3$; $CF_2H$; $CFH_2$; $CF_2Cl$; $CFCl_2$; OH; $OCF_3$; $OCF_2H$; $OCFH_2$; $OCF_2Cl$; $OCFCl_2$; SH; $SCF_3$; $SCF_2H$; $SCFH_2$; $SCF_2Cl$; $SCFCl_2$; $C_{1-10}$ alkyl, saturated or unsaturated, branched or unbranched, unsubstituted or mono- or polysubstituted with one or more substituents each selected independently from the group consisting of F, Cl, Br, I, CN, OH, =O, O—$C_{1-4}$ alkyl, $OCF_3$, $CF_3$, $NH_2$, NH($C_{1-4}$ alkyl), N($C_{1-4}$ alkyl)$_2$, SH, S—$C_{1-4}$ alkyl, $SCF_3$; $C_{3-10}$ cycloalkyl, saturated or unsaturated, unsubstituted or mono- or polysubstituted with one or more substituents selected independently from the group consisting of F, Cl, Br, I, OH, =O, $C_{1-4}$ alkyl, O—$C_{1-4}$ alkyl, $OCF_3$ and $CF_3$; or $C_{3-10}$ cycloalkyl bridged via $C_{1-8}$ alkyl, saturated or unsaturated, unsubstituted or mono- or polysubstituted with one or more substituents selected independently from the group consisting of F, Cl, Br, I, OH, =O, $C_{1-4}$ alkyl, O—$C_{1-4}$ alkyl, $OCF_3$ and $CF_3$, wherein the alkyl chain can be respectively branched or unbranched, saturated or unsaturated, unsubstituted; aryl or heteroaryl, respectively unsubstituted or mono- or polysubstituted with one or more substituents each selected independently from the group consisting of F, Cl, Br, I, CN, OH, O—$C_{1-4}$ alkyl, $OCF_3$, $C_{1-4}$ alkyl, $CF_3$, $NH_2$, NH($C_{1-4}$ alkyl), N($C_{1-4}$ alkyl)$_2$, SH, S—$C_{1-8}$ alkyl, $SCF_3$, benzyl, phenyl, pyridyl and thienyl, wherein benzyl, phenyl, pyridyl, thienyl can be respectively unsubstituted or mono- or polysubstituted with one or more substituents selected independently from the group consisting of F, Cl, Br, I, CN, OH, O—$C_{1-8}$ alkyl, $OCF_3$, $C_{1-4}$ alkyl, C(=O)—OH, $CF_3$, $NH_2$, NH($C_{1-4}$ alkyl), N($C_{1-4}$ alkyl)$_2$, SH, S—$C_{1-4}$ alkyl, $SCF_3$ and S(=O)$_2$OH; or aryl or heteroaryl bridged via $C_{1-8}$ alkyl, respectively unsubstituted or mono- or polysubstituted with one or more substituents each selected independently from the group consisting of F, Cl, Br, I, CN, OH, O—$C_{1-4}$ alkyl, $OCF_3$, $C_{1-4}$ alkyl, $CF_3$, $NH_2$, NH($C_{1-4}$ alkyl), N($C_{1-4}$ alkyl)$_2$, SH, S—$C_{1-8}$ alkyl, $SCF_3$, benzyl, phenyl, pyridyl and thienyl, wherein benzyl, phenyl, pyridyl, thienyl can be respectively unsubstituted or mono- or polysubstituted with one or more substituents selected independently from the group consisting of F, Cl, Br, I, CN, OH, O—$C_{1-8}$ alkyl, $OCF_3$, $C_{1-4}$ alkyl, C(=O)—OH, $CF_3$, $NH_2$, NH($C_{1-4}$ alkyl), $N(C_{1-4}$ alkyl$)_2$, SH, S—$C_{1-4}$ alkyl, $SCF_3$ and $S(=O)_2OH$, wherein the alkyl chain can be respectively branched or unbranched, saturated or unsaturated, unsubstituted.

Particularly preferably, $R^2$ represents H; F; Cl; Br; I; CN; $C_{1-10}$ alkyl, saturated or unsaturated, branched or unbranched, unsubstituted or mono- or polysubstituted with one or more substituents selected independently from the group consisting of F, Cl, Br, I and OH; $C_{3-10}$ cycloalkyl, saturated or unsaturated, unsubstituted; or $C_{3-10}$ cycloalkyl bridged via $C_{1-4}$ alkyl, saturated or unsaturated, unsubstituted, wherein the alkyl chain can be branched or unbranched, saturated or unsaturated, unsubstituted; or phenyl, pyridyl, thienyl, respectively unsubstituted or mono- or polysubstituted with one or more substituents selected independently from the group consisting of $C_{1-4}$ alkyl, O—$C_{1-4}$ alkyl, F, Cl, Br, I, $CF_3$, $OCF_3$, OH, SH and $SCF_3$; or phenyl, pyridyl or thienyl bridged via $C_{1-4}$ alkyl, respectively unsubstituted or mono- or polysubstituted with one or more substituents selected independently from the group consisting of $C_{1-4}$ alkyl, O—$C_{1-4}$ alkyl, F, Cl, Br, I, $CF_3$, $OCF_3$, OH, SH and $SCF_3$, wherein the alkyl chain can be branched or unbranched, saturated or unsaturated, unsubstituted.

Most particularly preferably, the substituent $R^2$ is selected from the group consisting of H; F; Cl; Br; I; CN; cyclopropyl; cyclobutyl; $C_{1-10}$ alkyl, saturated or unsaturated, branched or unbranched, unsubstituted, or mono- or polysubstituted with one or more substituents selected independently from the group consisting of F, Cl, Br; phenyl, unsubstituted or mono- or polysubstituted with one or more substituents selected independently from the group consisting of $C_{1-4}$ alkyl, O—$C_{1-4}$ alkyl, F, Cl, Br, I, $CF_3$ and $OCF_3$.

Particularly preferably, the substituent $R^2$ represents H; F; Cl; Br; 1; $CF_3$; CN; methyl; ethyl; n-propyl; isopropyl; n-butyl; sec.-butyl; tert.-butyl; cyclopropyl; cyclobutyl; phenyl, unsubstituted or mono- or polysubstituted with one or more substituents selected independently from the group consisting of $C_{1-4}$ alkyl, O—$C_{1-4}$ alkyl, F, Cl, Br, F, $CF_3$ and $OCF_3$. Especially particularly preferably, $R^2$ represents tert.-butyl or $CF_3$.

In a further preferred embodiment of the compounds according to the invention of general formula (I), X represents $CR^3$ or N, preferably $CR^3$, wherein $R^3$ represents H; $C_{1-10}$ alkyl, saturated or unsaturated, branched or unbranched, unsubstituted, mono- or polysubstituted with one or more substituents each selected independently from the group consisting of F, Cl, Br, I and OH;

Preferably,

X represents $CR^3$ or N, preferably $CR^3$, wherein $R^3$ represents H; $C_{1-10}$ alkyl, saturated or unsaturated, branched or unbranched, unsubstituted; or $CF_3$.

Particularly preferably,

X represents $CR^3$ or N, preferably $CR^3$, wherein $R^3$ represents H; methyl; ethyl; n-propyl; isopropyl; n-butyl; sec.-butyl; tert.-butyl; or $CF_3$.

Most particularly preferably,

X represents $CR^3$ or N, preferably $CR^3$, wherein $R^3$ represents H or $CH_3$, most preferred H.

In a further preferred embodiment of the compounds according to the invention of general formula (I), the residue $R^4$ represents H; $C_{1-10}$ alkyl, saturated or unsaturated, branched or unbranched, unsubstituted or mono- or polysubstituted with one or more substituents each selected independently from the group consisting of F, Cl, Br; I, OH and O—$C_{1-4}$ alkyl;

A represents N or $CR^{5b}$;

$R^{5a}$ represents H; OH; $C_{1-10}$ alkyl, saturated or unsaturated, branched or unbranched, unsubstituted or mono- or polysubstituted with one or more substituents each selected independently from the group consisting of F, Cl, Br; I, OH and O—$C_{1-4}$ alkyl;

$R^{5b}$ represents H; $C_{1-10}$ alkyl, saturated or unsaturated, branched or unbranched, unsubstituted or mono- or polysubstituted with one or more substituents each selected independently from the group consisting of F, Cl, Br; I, OH and O—$C_{1-4}$ alkyl; $C_{3-10}$ cycloalkyl or heterocyclyl, respectively saturated or unsaturated, unsubstituted or mono- or polysubstituted with one or more substituents each selected independently from the group consisting of F, Cl, Br; I, OH, =O and O—$C_{1-4}$ alkyl; or $C_{3-10}$ cycloalkyl or heterocyclyl bridged via $C_{1-8}$ alkyl, respectively saturated or unsaturated, unsubstituted or mono- or polysubstituted with one or more substituents each selected independently from the group consisting of F, Cl, Br; I, OH, =O and O—$C_{1-4}$ alkyl, wherein the alkyl chain can be respectively branched or unbranched, saturated or unsaturated, unsubstituted, mono- or polysubstituted with one or more substituents each selected independently from the group consisting of F, Cl, Br; I, OH, =O and O—$C_{1-4}$ alkyl; or aryl, heteroaryl, respectively unsubstituted or mono- or polysubstituted with one or more substituents each selected independently from the group consisting of F, Cl, Br, I, $NO_2$, CN, OH, O—$C_{1-4}$ alkyl, $OCF_3$, $C_{1-4}$ alkyl, C(=O)—OH, $CF_3$, $NH_2$, $NH(C_{1-4}$ alkyl), $N(C_{1-4}$ alkyl$)_2$, SH, S—$C_{1-4}$ alkyl, $SCF_3$, $S(=O)_2OH$ and NH—$S(=O)_2$—$C_{1-4}$ alkyl; or aryl or heteroaryl bridged via $C_{1-8}$ alkyl, respectively unsubstituted or mono- or polysubstituted with one or more substituents each selected independently from the group consisting of F, Cl, Br, I, $NO_2$, CN, OH, O—$C_{1-4}$ alkyl, $OCF_3$, $C_{1-4}$ alkyl, C(=O)—OH, $CF_3$, $NH_2$, $NH(C_{1-4}$ alkyl), $N(C_{1-4}$ alkyl$)_2$, SH, S—$C_{1-4}$ alkyl, $SCF_3$, $S(=O)_2OH$ and NH—$S(=O)_2$—$C_{1-4}$ alkyl, wherein the alkyl chain can be respectively branched or unbranched, saturated or unsaturated, unsubstituted, mono- or polysubstituted with one or more substituents each selected independently from the group consisting of F, Cl, Br; I, OH, =O and O—$C_{1-4}$ alkyl; or $R^{5a}$ and $R^{5b}$ form together with the carbon atom connecting them a $C_{3-10}$ cycloalkyl or a heterocyclyl, respectively saturated or unsaturated, unsubstituted or mono- or polysubstituted with one or more substituents each selected independently from the group consisting of F, Cl, Br; I, OH, =O and O—$C_{1-4}$ alkyl.

Preferably, the residue $R^4$ represents H; or $C_{1-10}$ alkyl, saturated or unsaturated, branched or unbranched, unsubstituted;

A represents N or $CR^{5b}$;

$R^{5a}$ represents H; or $C_{1-10}$ alkyl, saturated or unsaturated, branched or unbranched, unsubstituted;

$R^{5b}$ represents H; $C_{1-10}$ alkyl, saturated or unsaturated, branched or unbranched, unsubstituted or mono- or polysubstituted with one or more substituents each selected independently from the group consisting of F, Cl, Br, I, OH and O—$C_{1-4}$ alkyl; $C_{3-10}$ cycloalkyl, saturated or unsaturated, unsubstituted or mono- or polysubstituted with one or more substituents each selected independently from the group consisting of F, Cl, Br, I and $C_{1-4}$ alkyl; or $C_{3-10}$ cycloalkyl bridged via $C_{1-4}$ alkyl, saturated or unsaturated, unsubstituted or mono- or polysubstituted with one or more substituents each selected independently from the group consisting of F, Cl, Br, I and $C_{1-4}$ alkyl, wherein the alkyl chain can be respectively branched or unbranched, saturated or unsaturated, unsubstituted; or phenyl or pyridyl, respectively unsubstituted or mono- or polysubstituted with one or more substituents each selected independently from the group consisting of F, Cl, Br, I, OH, O—$C_{1-4}$ alkyl, $OCF_3$, $C_{1-4}$ alkyl, $CF_3$, $NH_2$, NH($C_{1-4}$ alkyl), N($C_{1-4}$ alkyl)$_2$, SH, S—$C_{1-4}$ alkyl, $SCF_3$ and NH—S(═O)$_2$—$C_{1-4}$ alkyl; or phenyl or pyridyl bridged via $C_{1-4}$ alkyl, respectively unsubstituted or mono- or polysubstituted with one or more substituents each selected independently from the group consisting of F, Cl, Br, I, OH, O—$C_{1-4}$ alkyl, $OCF_3$, $C_{1-4}$ alkyl, $CF_3$, $NH_2$, NH($C_{1-4}$ alkyl), N($C_{1-4}$ alkyl)$_2$, SH, S—$C_{1-4}$ alkyl, $SCF_3$ and NH—S(═O)$_2$—$C_{1-4}$ alkyl, wherein the alkyl chain can be respectively branched or unbranched, saturated or unsaturated, unsubstituted, or $R^{5a}$ and $R^{5b}$ form together with the carbon atom connecting them a $C_{3-10}$ cycloalkyl or a heterocyclyl, respectively saturated or unsaturated, unsubstituted or mono- or polysubstituted with one or more substituents each selected independently from the group consisting of F, Cl, Br; I, OH, ═O and O—$C_{1-4}$ alkyl.

Particularly preferably, the residue $R^4$ represents H; methyl; ethyl; n-propyl; or isopropyl;

A represents N or $CR^{5b}$;

$R^{5a}$ represents H or $CH_3$, preferably H, if A represents N; or $R^{5a}$ represents H or $CH_3$, preferably H, if A represents $CR^{5b}$, wherein $R^{5b}$ represents H; or $C_{1-4}$ alkyl, saturated or unsaturated, branched or unbranched, unsubstituted; $C_{3-10}$ cycloalkyl, saturated or unsaturated, unsubstituted; or phenyl or benzyl, in each case unsubstituted or mono- or polysubstituted with one or more substituents each selected independently from the group consisting of F, Cl, Br, I, $CF_3$, O—$C_{1-4}$ alkyl, $OCF_3$ and $C_{1-4}$ alkyl, or $R^{5a}$ and $R^{5b}$ form together with the carbon atom connecting them a $C_{3-10}$ cycloalkyl, saturated or unsaturated, preferably saturated, unsubstituted or mono- or polysubstituted with one or more substituents each selected independently from the group consisting of F, Cl, Br; I, OH, ═O and O—$C_{1-4}$ alkyl, preferably unsubstituted.

Most particularly preferably, the residue

A represents N or $CR^{5b}$;

$R^4$ represents H;

$R^{5a}$ represents H;

$R^{5b}$ represents H; or $C_{1-4}$ alkyl, saturated or unsaturated, branched or unbranched, unsubstituted; cyclohexyl, unsubstituted; or phenyl or benzyl, in each case unsubstituted or mono- or polysubstituted with one or more substituents each selected independently from the group consisting of F, Cl, Br, I, O—$C_{1-4}$ alkyl, $CF_3$, $OCF_3$ and $C_{1-4}$ alkyl, or $R^{5a}$ and $R^{5b}$ form together with the carbon atom connecting them a $C_{3-10}$ cycloalkyl, saturated or unsaturated, unsubstituted.

In a further preferred embodiment of the compounds according to the invention of general formula (I), the residues $R^6$, $R^7$, $R^8$, $R^9$ and $R^{10}$ are each selected independently from the group consisting of H; F; Cl; Br; I; CN; $NO_2$; $CF_3$; $CF_2H$; $CFH_2$; $CF_2Cl$; $CFCl_2$; OH; $OCF_3$; $OCF_2H$; $OCFH_2$; $OCF_2Cl$; $OCFCl_2$; SH; $SCF_3$; $SCF_2H$; $SCFH_2$; $SCF_2Cl$; $SCFCl_2$; $NH_2$; C(═O)—$NH_2$; $C_{1-10}$ alkyl, $C_{1-10}$ alkyl-O—$C_{1-10}$ alkyl, C(═O)—NH—$C_{1-10}$ alkyl, O—$C_{1-10}$ alkyl, NH($C_{1-10}$ alkyl), N($C_{1-10}$ alkyl)$_2$, NH—C(═O)—$C_{1-10}$ alkyl, N($C_{1-10}$ alkyl)-C(═O)—$C_{1-10}$ alkyl, NH—S(═O)$_2$—$C_{1-10}$ alkyl, S—$C_{1-10}$ alkyl, $SO_2$—$C_{1-10}$ alkyl, $SO_2$—NH($C_{1-10}$ alkyl), $SO_2$—N($C_{1-10}$ alkyl)$_2$, in which $C_{1-10}$ alkyl can be respectively saturated or unsaturated, branched or unbranched, unsubstituted or mono- or polysubstituted with one or more substituents selected independently from the group consisting of F, Cl, Br, I, $NO_2$, CN, OH, O—$C_{1-4}$ alkyl, $OCF_3$, $CF_3$, $NH_2$, NH($C_{1-4}$ alkyl), N($C_{1-4}$ alkyl)$_2$, NH—S(═O)$_2$—$C_{1-4}$ alkyl, N($C_{1-4}$ alkyl)-S(═O)$_2$—$C_{1-4}$ alkyl, SH, S—$C_{1-4}$ alkyl, S(═O)$_2$—$C_{1-4}$ alkyl and $SCF_3$; $C_{3-10}$ cycloalkyl, heterocyclyl or $C_{3-10}$ cycloalkyl or heterocyclyl bridged via $C_{1-8}$ alkyl, respectively saturated or unsaturated, unsubstituted or mono- or polysubstituted with one or more substituents selected independently from the group consisting of F, Cl, Br, I, $NO_2$, CN, OH, O—$C_{1-4}$ alkyl, $OCF_3$, $CF_3$, $C_{1-4}$ alkyl, $NH_2$, NH($C_{1-4}$ alkyl), N($C_{1-4}$ alkyl)$_2$, NH—S(═O)$_2$—$C_{1-4}$ alkyl, N($C_{1-4}$ alkyl)-S(═O)$_2$—$C_{1-4}$ alkyl, SH, S—$C_{1-4}$ alkyl, S(═O)$_2$—$C_{1-4}$ alkyl and $SCF_3$, and wherein if appropriate the alkyl chain can be respectively branched or unbranched, saturated or unsaturated, unsubstituted, mono- or polysubstituted with one or more substituents each selected independently from the group consisting of F, Cl, Br; I, OH and O—$C_{1-4}$ alkyl; aryl, heteroaryl, C(═O)—NH-aryl, C(═O)—NH-heteroaryl, NH—C(═O)-aryl, NH(C═O)-heteroaryl, NH(aryl), NH(heteroaryl), N(aryl)$_2$, N(heteroaryl)$_2$ or aryl or heteroaryl bridged via $C_{1-8}$ alkyl, respectively unsubstituted or mono- or polysubstituted with one or more substituents selected independently from the group consisting of F, Cl, Br, I, CN, OH, O—$C_{1-4}$ alkyl, $OCF_3$, $C_{1-4}$ alkyl, $CF_3$, $NH_2$, NH($C_{1-4}$ alkyl), N($C_{1-4}$ alkyl)$_2$, SH, S—$C_{1-4}$ alkyl and $SCF_3$, and wherein if appropriate the alkyl chain can be respectively branched or unbranched, saturated or unsaturated, unsubstituted, mono- or polysubstituted with one or more substituents each selected independently from the group consisting of F, Cl, Br; I, OH and O—$C_{1-4}$ alkyl.

In another preferred embodiment of the compounds according to the invention of general formula (I), the residues $R^6$ and $R^{10}$ each represent H.

In a further preferred embodiment of the compounds according to the invention of general formula (I), the residues $R^6$ and $R^{10}$ are each selected independently from the group consisting of H; F; Cl; Br; I; CN; $CF_3$; OH; $OCF_3$; SH; $SCF_3$; $C_{1-4}$ alkyl, O—$C_{1-4}$ alkyl and NH—S(═O)$_2$—$C_{1-4}$ alkyl, in which $C_{1-4}$ alkyl can be respectively saturated or unsaturated, branched or unbranched, unsubstituted; and the residues $R^7$, $R^8$ and $R^9$ are each selected independently from the group consisting of H; F; Cl; Br; I; CN; $NO_2$; $CF_3$; OH; $OCF_3$; SH; $SCF_3$; $NH_2$; C(═O)—$NH_2$; $C_{1-4}$ alkyl, $C_{1-4}$ alkyl-O—$C_{1-4}$ alkyl, C(═O)—NH—$C_{1-4}$ alkyl, O—$C_{1-4}$ alkyl, NH($C_{1-4}$ alkyl), N($C_{1-4}$ alkyl)$_2$, NH—C(═O)—$C_{1-4}$ alkyl, NH—S(═O)$_2$—$C_{1-4}$ alkyl, S—$C_{1-4}$ alkyl, $SO_2$—$C_{1-4}$ alkyl, $SO_2$—NH($C_{1-4}$ alkyl), $SO_2$—N($C_{1-4}$ alkyl)$_2$, in which $C_{1-4}$ alkyl can be respectively saturated or unsaturated, branched or unbranched, unsubstituted or mono- or polysubstituted with one or more substituents selected independently from the group consisting of F, Cl, Br, I, OH, O—$C_{1-4}$ alkyl, $OCF_3$, $CF_3$, NH—S(═O)$_2$—$C_{1-4}$ alkyl, SH, S—$C_{1-4}$ alkyl, S(═O)$_2$—$C_{1-4}$ alkyl and $SCF_3$; $C_{3-10}$ cycloalkyl, heterocyclyl or $C_{3-10}$ cycloalkyl or heterocyclyl bridged via $C_{1-8}$ alkyl, respectively saturated or unsaturated, unsubstituted or mono- or polysubstituted with one or more substituents selected independently from the group consisting of F, Cl, Br, I, $NO_2$, CN, OH, O—$C_{1-4}$ alkyl, $OCF_3$, $C_{1-4}$ alkyl, $CF_3$, $NH_2$, NH($C_{1-4}$ alkyl), N($C_{1-4}$ alkyl)$_2$, NH—S(═O)$_2$—$C_{1-4}$ alkyl, N($C_{1-4}$ alkyl)-S(═O)$_2$—$C_{1-4}$ alkyl, SH, S—$C_{1-4}$ alkyl, S(═O)$_2$—$C_{1-4}$ alkyl and $SCF_3$, and wherein if appropriate the alkyl chain can be respectively branched or unbranched, saturated or unsaturated, unsubstituted, mono- or polysubstituted with one or more substituents each selected independently from the group consisting of F, Cl, Br; I, OH and O—$C_{1-4}$ alkyl; phenyl, pyridyl, furyl, thienyl, C(═O)—NH-phenyl, NH—C(═O)-phenyl, NH(phenyl), C(═O)—NH-pyridyl, NH—C(═O)-pyridyl, NH(pyridyl) or phenyl or pyridyl bridged via $C_{1-8}$ alkyl, wherein phenyl, pyridyl, furyl or thienyl are respectively unsubstituted or mono- or polysubstituted with one or more substituents selected independently from the group consisting of F, Cl, Br, I, CN, OH, O—$C_{1-4}$ alkyl, $OCF_3$, $C_{1-4}$ alkyl, $CF_3$, SH, S—$C_{1-4}$ alkyl and $SCF_3$, and wherein if appropriate the alkyl chain can be respectively branched or unbranched, saturated or unsaturated, unsubstituted, mono- or polysubstituted with one or more substituents each selected independently from the group consisting of F, Cl, Br; I, OH and O—$C_{1-4}$ alkyl.

Preferably, $R^6$, $R^7$, $R^9$ and $R^{10}$ are each selected independently from the group consisting of H; F; Cl; Br; I; $CF_3$; $OCF_3$; $SCF_3$; $C_{1-4}$ alkyl, O—$C_{1-4}$ alkyl and NH—S(═O)$_2$—$C_{1-4}$ alkyl, in which $C_{1-4}$ alkyl can be respectively saturated or unsaturated, branched or unbranched, unsubstituted; and $R^8$ is selected from the group consisting of H; F; Cl; Br; I; CN; $NO_2$; $CF_3$; OH; $OCF_3$; SH; $SCF_3$; $NH_2$; C(═O)—$NH_2$; $C_{1-4}$ alkyl, $C_{1-4}$ alkyl-O—$C_{1-4}$ alkyl, C(═O)—NH—$C_{1-4}$ alkyl, O—$C_{1-4}$ alkyl, NH($C_{1-4}$ alkyl), N($C_{1-4}$ alkyl)$_2$, NH—C(═O)—$C_{1-4}$ alkyl, NH—S(═O)$_2$—$C_{1-4}$ alkyl, S—$C_{1-4}$ alkyl, $SO_2$—$C_{1-4}$ alkyl, $SO_2$—NH($C_4$ alkyl), $SO_2$—N($C_{1-4}$ alkyl)$_2$, in which $C_{1-4}$ alkyl can be respectively saturated or unsaturated, branched or unbranched, unsubstituted or mono- or polysubstituted with one or more substituents selected independently from the group consisting of F, Cl, Br, I, OH, O—$C_{1-4}$ alkyl, $OCF_3$, $CF_3$, NH—S(═O)$_2$—$C_{1-4}$ alkyl, SH, S—$C_{1-4}$ alkyl, S(═O)$_2$—$C_{1-4}$ alkyl and $SCF_3$; $C_{3-10}$ cycloalkyl, heterocyclyl or $C_{3-10}$ cycloalkyl or heterocyclyl bridged via $C_{1-8}$ alkyl, respectively saturated or unsaturated, unsubstituted or mono- or polysubstituted with one or more substituents selected independently from the group consisting of F, Cl, Br, I, $NO_2$, CN, OH, O—$C_{1-4}$ alkyl, $OCF_3$, $C_{1-4}$ alkyl, $CF_3$, $NH_2$, NH($C_{1-4}$ alkyl), N($C_{1-4}$ alkyl)$_2$, NH—S(═O)$_2$—$C_{1-4}$ alkyl, N($C_{1-4}$ alkyl)-S(═O)$_2$—$C_{1-4}$ alkyl, SH, S—$C_{1-4}$ alkyl, S(═O)$_2$—$C_{1-4}$ alkyl and $SCF_3$, and wherein if appropriate the alkyl chain can be respectively branched or unbranched, saturated or unsaturated, unsubstituted, mono- or polysubstituted with one or more substituents each selected independently from the group consisting of F, Cl, Br; I, OH and O—$C_{1-4}$ alkyl; phenyl, pyridyl, furyl, thienyl, C(═O)—NH-phenyl, NH—C(═O)-phenyl, NH(phenyl), C(═O)—NH-pyridyl, NH—C(═O)-pyridyl, NH(pyridyl) or phenyl or pyridyl bridged via $C_{1-8}$ alkyl, wherein phenyl, pyridyl, furyl or thienyl are respectively unsubstituted or mono- or polysubstituted with one or more substituents selected independently from the group consisting of F, Cl, Br, I, CN, OH, O—$C_{1-4}$ alkyl, $OCF_3$, $C_{1-4}$ alkyl, $CF_3$, SH, S—$C_{1-4}$ alkyl and $SCF_3$, and wherein if appropriate the alkyl chain can be respectively branched or unbranched, saturated or unsaturated, unsubstituted, mono- or polysubstituted with one or more substituents each selected independently from the group consisting of F, Cl, Br; I, OH and O—$C_{1-4}$ alkyl.

Particularly preferably, $R^6$ and $R^{10}$ each represent H;

$R^7$ and $R^9$ each independently represent H; F; Cl; Br; I; $C_{1-4}$ alkyl, O—$C_{1-4}$ alkyl;

$R^8$ represents H; F; Cl; Br; I; CN; $NO_2$; $CF_3$; OH; $OCF_3$; SH; $SCF_3$; $NH_2$; C(═O)—$NH_2$; C(═O)—NH(methyl); C(═O)—NH(ethyl); C(═O)—N(methyl)$_2$; C(═O)—N(ethyl)$_2$; $C_{1-4}$ alkyl, saturated or unsaturated, branched or unbranched, unsubstituted or mono- or disubstituted with OH; NH—C(═O)-methyl; NH—C(═O)-ethyl; $CH_2$—NH—S(═O)$_2$-methyl; $CH_2$—NH—S(═O)$_2$-ethyl; NH—S(═O)$_2$-methyl; NH—S(═O)$_2$-ethyl; S-methyl; S-ethyl; S(═O)$_2$-methyl; S(═O)$_2$-ethyl; S(═O)$_2$—NH-methyl; S(═O)$_2$—NH-ethyl; S(═O)$_2$—N(methyl)$_2$; S(═O)$_2$—N(ethyl)$_2$; $CH_2$—S(═O)$_2$-(methyl); $CH_2$—S(═O)$_2$-ethyl); O—$C_{1-4}$ alkyl, saturated or unsaturated, branched or unbranched, unsubstituted; $C_{1-4}$ alkyl-O—$C_{1-4}$ alkyl-O—$C_{1-4}$ alkyl, $C_{3-10}$ cycloalkyl or $C_{3-10}$ cycloalkyl bridged via $C_{1-8}$ alkyl, respectively saturated or unsaturated, unsubstituted, and wherein if appropriate the alkyl chain can be respectively branched or unbranched, saturated or unsaturated, unsubstituted; piperidinyl; piperazinyl; 4-methylpiperazinyl; morpholinyl; dioxidoisothiazolidinyl; phenyl, pyridyl, furyl, thienyl, C(═O)—NH-phenyl, NH—C(═O)-phenyl, NH(phenyl), C(═O)—NH-pyridyl, NH—C(═O)-pyridyl, NH(pyridyl), wherein phenyl, pyridyl, thienyl or furyl are respectively unsubstituted or mono- or polysubstituted with one or more substituents selected independently from the group consisting of F, Cl, Br, I, CN, OH, O—$C_{1-4}$ alkyl, $OCF_3$, $C_1$, alkyl, $CF_3$, SH, S—$C_{1-4}$ alkyl and $SCF_3$.

In a further, particularly preferred embodiment, the compounds according to the invention of general formula (I) have general formula (If)

(If)

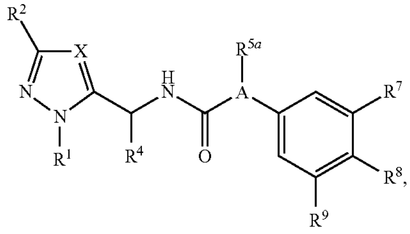

in which

X represents $CR^3$ or N, wherein $R^3$ represents H; methyl; ethyl; n-propyl; isopropyl; n-butyl; sec.-butyl; tert.-butyl; or $CF_3$;

A represents N or $CR^{5b}$;

$R^1$ represents substructure (T1)

(T1)

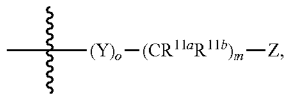

in which

Y represents C(═O), O, S, S(═O)$_2$, NH—C(═O) or $NR^{12}$, wherein $R^{12}$ represents H; methyl; ethyl; n-propyl; isopropyl; n-butyl; sec.-butyl; tert.-butyl; S(═O)$_2$-methyl;

O represents 0 or 1;

$R^{11a}$ and $R^{11b}$ each independently represent H; methyl; ethyl; n-propyl; isopropyl; n-butyl; sec.-butyl; tert.-butyl;

m represents 0, 1 or 2;

Z represents $C_{1-4}$ alkyl, saturated or unsaturated, branched or unbranched, unsubstituted or mono- or polysubstituted with one or more substituents each selected independently from the group consisting of F, Cl, Br, I, OH, O—$C_{1-4}$ alkyl; $C_{3-10}$ cycloalkyl[1], saturated or unsaturated, morpholinyl, tetrahydropyranyl, piperidinyl, 4-methylpiperazinyl, piperazinyl, respectively unsubstituted or mono- or polysubstituted with one or more substituents each selected independently from the group consisting of F, Cl, Br, I, OH, O—$C_{1-4}$ alkyl and $C_{1-4}$ alkyl; phenyl or pyridyl, respectively unsubstituted or mono- or polysubstituted with one or more substituents each selected independently from the group consisting of F, Cl, Br, I, CN, OH, O—$C_{1-4}$ alkyl, $OCF_3$, $C_{1-4}$ alkyl, $CF_3$, SH, S—$C_{1-4}$ alkyl, $SCF_3$;

$R^2$ represents H; F; Cl; Br; I; $CF_3$; CN; methyl; ethyl; n-propyl; isopropyl; n-butyl; sec.-butyl; tert.-butyl; cyclopropyl; cyclobutyl; phenyl, unsubstituted or mono- or polysubstituted with one or more substituents selected independently from the group consisting of $C_{1-4}$ alkyl, O—$C_{1-4}$ alkyl, F, Cl, Br, I, $CF_3$ and $OCF_3$;

$R^4$ represents H; methyl; ethyl; n-propyl; or isopropyl;

$R^{5a}$ represents H or $CH_3$ if A represents N; or represents H; methyl; ethyl; n-propyl; isopropyl if A represents $CR^{5b}$;

$R^{5b}$ represents H; methyl; ethyl; n-propyl; isopropyl; cyclopentyl; cyclohexyl; or phenyl or benzyl, in each case unsubstituted or mono-, di- or trisubstituted with one, two or three substituents each selected independently from the group consisting of $C_{1-4}$ alkyl, O—$C_{1-4}$ alkyl, F, Cl, Br, I, $CF_3$ and $OCF_3$; or $R^{5a}$ and $R^{5b}$ form together with the carbon atom connecting them a $C_{3-10}$ cycloalkyl, saturated or unsaturated, unsubstituted, $R^7$ and $R^9$ each independently represent H; F; Cl; Br; I; $C_{1-4}$ alkyl, O—$C_{1-4}$ alkyl; F; Cl; Br; I; and $R^8$ represents H; F; Cl; Br; I; CN; $NO_2$; $CF_3$; OH; $OCF_3$; SH; $SCF_3$; $NH_2$; C(═O)—$NH_2$; C(═O)—NH(methyl); C(═O)—NH(ethyl); C(═O)—N(methyl)$_2$; C(═O)—N (ethyl)$_2$; $C_{1-4}$ alkyl, saturated or unsaturated, branched or unbranched, unsubstituted or mono- or disubstituted with OH; NH—C(═O)-methyl; NH—C(═O)-ethyl; $CH_2$—NH—S(═O)$_2$-methyl; $CH_2$—NH—S(═O)$_2$-ethyl; NH—S(═O)$_2$-methyl; NH—S(═O)$_2$-ethyl; S-methyl; S-ethyl; S(═O)$_2$-methyl; S(═O)$_2$-ethyl; S(═O)$_2$—NH-methyl; S(═O)$_2$—NH-ethyl; S(═O)$_2$—N(methyl)$_2$; S(═O)$_2$—N(ethyl)$_2$; $CH_2$—S(═O)$_2$-methyl; $CH_2$—S (═O)$_2$-ethyl; $OC_{1-4}$ alkyl, saturated or unsaturated, branched or unbranched, unsubstituted; $C_{1-4}$ alkyl-O—$C_{1-4}$ alkyl-O—$C_{1-4}$ alkyl, $C_{3-10}$ cycloalkyl, or $C_{3-10}$ cycloalkyl bridged via $C_{1-8}$ alkyl, respectively saturated or unsaturated, unsubstituted, and wherein if appropriate the alkyl chain can be respectively branched or unbranched, saturated or unsaturated, unsubstituted; piperidinyl; piperazinyl; 4-methylpiperazinyl; morpholinyl; dioxidoisothiazolidinyl; phenyl, pyridyl, furyl, thienyl, C(═O)—NH-phenyl, NH—C(═O)-phenyl, NH(phenyl), C(═O)—NH-pyridyl, NH—C(═O)-pyridyl, NH(pyridyl), wherein phenyl, pyridyl, thienyl or furyl are respectively unsubstituted or mono- or polysubstituted with one or more substituents selected independently from the group consisting of F, Cl, Br, I, CN, OH, O—$C_{1-4}$ alkyl, $OCF_3$, $C_{1-4}$ alkyl, $CF_3$, SH, S—$C_{1-4}$ alkyl and $SCF_3$.

A preferred group of compounds according to the invention comprises compounds selected from the group consisting of:

1 N-((3-tert-butyl-1H-pyrazol-5-yl)methyl)-2-(3-fluoro-4-(methylsulfonamido)phenyl)propanamide;

2 (S)—N-((3-tert-butyl-1H-pyrazol-5-yl)methyl)-2-(3-fluoro-4-(methylsulfonamido)phenyl)propanamide;

3 N-((3-tert-butyl-1-methyl-1H-pyrazol-5-yl)methyl)-2-(3-fluoro-4-(methylsulfonamido)phenyl)propanamide;

4 (S)—N-((3-tert-butyl-1-methyl-1H-pyrazol-5-yl)methyl)-2-(3-fluoro-4-(methylsulfonamido)phenyl)propanamide;

5 N-((3-tert-butyl-1-hexyl-1H-pyrazol-5-yl)methyl)-2-(3-fluoro-4-(methylsulfonamido)phenyl)propanamide;

6 (S)—N-((3-tert-butyl-1-hexyl-1H-pyrazol-5-yl)methyl)-2-(3-fluoro-4-(methylsulfonamido)phenyl)propanamide;

7 N-((3-tert-butyl-1-cyclohexyl-1H-pyrazol-5-yl)methyl)-2-(3-fluoro-4-(methylsulfonamido)phenyl)propanamide;

8 (S)—N-((3-tert-butyl-1-cyclohexenyl-1H-pyrazol-5-yl) methyl)-2-(3-fluoro-4-(methylsulfonamido)phenyl)propanamide;

9 2-(3-fluoro-4-(methylsulfonamido)phenyl)-N-((3-methyl-1-phenyl-1H-pyrazol-5-yl)methyl)propanamide;

10 N-((3-chloro-1-phenyl-1H-pyrazol-5-yl)methyl)-2-(3-fluoro-4-(methylsulfonamido)phenyl)propanamide;

11 2-(3-fluoro-4-(methylsulfonamido)phenyl)-N-((3-(4-fluorophenyl)-1-phenyl-1H-pyrazol-5-yl)methyl)propanamide;

12 N-((3-tert-butyl-1-p-tolyl-1H-pyrazol-5-yl)methyl)-2-(3-fluoro-4-(methylsulfonamido)phenyl)propanamide;

13 N-((3-tert-butyl-1-(4-tert-butylphenyl)-1H-pyrazol-5-yl) methyl)-2-(3-fluoro-4-(methylsulfonamido)phenyl)propanamide;

14 N-((3-tert-butyl-1-(4-chlorophenyl)-1H-pyrazol-5-yl) methyl)-2-(3-fluoro-4-(methylsulfonamido)phenyl)propanamide;

15 (S)—N-((3-tert-butyl-1-(4-chlorophenyl)-1H-pyrazol-5-yl)methyl)-2-(3-fluoro-4-(methylsulfonamido)phenyl) propanamide;

16 N-((3-tert-butyl-1-(3-chlorophenyl)-1H-pyrazol-5-yl) methyl)-2-(3-fluoro-4-(methylsulfonamido)phenyl)propanamide;

17 (S)—N-((3-tert-butyl-1-(3-chlorophenyl)-1H-pyrazol-5-yl)methyl)-2-(3-fluoro-4-(methylsulfonamido)phenyl) propanamide;

18 N-((3-tert-butyl-1-(3-chloro-4-fluorophenyl)-1H-pyrazol-5-yl)methyl)-2-(3-fluoro-4-(methylsulfonamido)phenyl)propanamide;

19 (E)-N-((3-tert-butyl-1-(4-methylstyryl)-1H-pyrazol-5-yl) methyl)-2-(3-fluoro-4-(methylsulfonamido)phenyl)propanamide;

20 N-((3-tert-butyl-1-(4-m ethoxyphenyl)-1H-pyrazol-5-yl) methyl)-2-(3-fluoro-4-(methylsulfonamido)phenyl)propanamide;

21 N-((1-(4-chlorophenyl)-3-(trifluoromethyl)-1H-pyrazol-5-yl)methyl)-2-(3-fluoro-4-(methylsulfonamido)phenyl) propanamide;

22 (R)—N-((1-(4-chlorophenyl)-3-(trifluoromethyl)-1H-pyrazol-5-yl)methyl)-2-(3-fluoro-4-(methylsulfonamido) phenyl)propanamide;

23 (S)—N-((1-(4-chlorophenyl)-3-(trifluoromethyl)-1H-pyrazol-5-yl)methyl)-2-(3-fluoro-4-(methylsulfonamido) phenyl)propanamide;

24 N-((1-(3-chlorophenyl)-3-(trifluoromethyl)-1H-pyrazol-5-yl)methyl)-2-(3-fluoro-4-(methylsulfonamido)phenyl) propanamide;

25 (R)—N-((1-(3-chlorophenyl)-3-(trifluoromethyl)-1H-pyrazol-5-yl)methyl)-2-(3-fluoro-4-(methylsulfonamido)phenyl)propanamide;

26 (S)—N-((1-(3-chlorophenyl)-3-(trifluoromethyl)-1H-pyrazol-5-yl)methyl)-2-(3-fluoro-4-(methylsulfonamido)phenyl)propanamide;

27 N-((3-tert-butyl-1-(3-chlorophenyl)-1H-pyrazol-5-yl)methyl)-2-(3-methoxy-4-(methylsulfonamido)phenyl)propanamide;

28 N-((1-(3-chlorophenyl)-3-(trifluoromethyl)-1H-pyrazol-5-yl)methyl)-2-(3-methoxy-4-(methylsulfonamido)phenyl)propanamide;

29 N-((3-tert-butyl-1-(3-chlorophenyl)-1H-pyrazol-5-yl)methyl)-2-(3,5-difluoro-4-(methylsulfonamido)phenyl)propanamide;

30 N-((1-(3-chlorophenyl)-3-(trifluoromethyl)-1H-pyrazol-5-yl)methyl)-2-(3,5-difluorophenyl)propanamide;

31 2-(4-bromo-3-fluorophenyl)-N-((1-(3-chlorophenyl)-3-(trifluoromethyl)-1H-pyrazol-5-yl)methyl)propanamide;

32 N-((3-tert-butyl-1-(3-chlorophenyl)-1H-pyrazol-5-yl)methyl)-2-(4-isobutylphenyl)propanamide;

33 N-((3-tert-butyl-1-(3-chlorophenyl)-1H-pyrazol-5-yl)methyl)-2-(3-fluoro-4-(methylsulfonamidomethyl)phenyl)propanamide;

34 N-((1-(3-chlorophenyl)-3-(trifluoromethyl)-1H-pyrazol-5-yl)methyl)-2-(3-fluoro-4-(furan-3-yl)phenyl)propanamide;

35 N-((3-tert-butyl-1-(3-chlorophenyl)-1H-pyrazol-5-yl)methyl)-2-(2-fluorobiphenyl-4-yl)propanamide;

36 N-((1-(3-chlorophenyl)-3-(trifluoromethyl)-1H-pyrazol-5-yl)methyl)-2-(4-(1,2-dihydroxyethyl)-3-fluorophenyl)propanamide;

37 4-(1-((1-(3-chlorophenyl)-3-(trifluoromethyl)-1H-pyrazol-5-yl)methylamino)-1-oxopropan-2-yl)-2-fluorobenzamide;

38 4-(1-((1-(3-chlorophenyl)-3-(trifluoromethyl)-1H-pyrazol-5-yl)methylamino)-1-oxopropan-2-yl)-N-ethylbenzamide;

39 4-(1-((1-(3-chlorophenyl)-3-(trifluoromethyl)-1H-pyrazol-5-yl)methylamino)-1-oxopropan-2-yl)-2-fluoro-N-phenylbenzamide;

40 4-(1-((1-(3-chlorophenyl)-3-(trifluoromethyl)-1H-pyrazol-5-yl)methylamino)-1-oxopropan-2-yl)-N-(4-fluorophenyl)benzamide;

41 4-(1-((1-(3-chlorophenyl)-3-(trifluoromethyl)-1H-pyrazol-5-yl)methylamino)-1-oxopropan-2-yl)-N-(4-(trifluoromethyl)phenyl)benzamide;

42 4-(1-((1-(3-chlorophenyl)-3-(trifluoromethyl)-1H-pyrazol-5-yl)methylamino)-1-oxopropan-2-yl)-N-(pyridin-4-yl)benzamide;

43 N-((1-(3-chlorophenyl)-3-(trifluoromethyl)-1H-pyrazol-5-yl)methyl)-2-(4-(trifluoromethoxy)phenyl)propanamide;

44 N-((1-(3-chlorophenyl)-3-(trifluoromethyl)-1H-pyrazol-5-yl)methyl)-2-(3,5-dibromo-4-hydroxyphenyl)acetamide;

45 N-((1-(3-chlorophenyl)-3-(trifluoromethyl)-1H-pyrazol-5-yl)methyl)-2-(3,5-dibromo-4-hydroxyphenyl)propanamide;

46 N-((3-tert-butyl-1-(3-chlorophenyl)-1H-pyrazol-5-yl)methyl)-2-(3,5-difluoro-4-hydroxyphenyl)propanamide;

47 N-((1-(3-chlorophenyl)-3-(trifluoromethyl)-1H-pyrazol-5-yl)methyl)-2-(3,5-difluoro-4-methoxyphenyl)propanamide;

48 N-((3-tert-butyl-1-(3-chlorophenyl)-1H-pyrazol-5-yl)methyl)-2-(4-methoxy-3,5-dimethylphenyl)acetamide;

49 N-((3-tert-butyl-1-(3-chlorophenyl)-1H-pyrazol-5-yl)methyl)-2-(4-(N,N-dimethylsulfamoyl)-3-fluorophenyl)propanamide;

50 N-((1-(3-chlorophenyl)-3-(trifluoromethyl)-1H-pyrazol-5-yl)methyl)-2-(4-(4-chlorophenylamino)phenyl)propanamide;

51 N-((1-(3-chlorophenyl)-3-(trifluoromethyl)-1H-pyrazol-5-yl)methyl)-2-(4-(4-methoxyphenylamino)phenyl)propanamide;

52 2-(4-amino-3,5-difluorophenyl)-N-((1-(3-chlorophenyl)-3-(trifluoromethyl)-1H-pyrazol-5-yl)methyl)propanamide;

53 2-(4-acetamido-3-fluorophenyl)-N-((1-(3-chlorophenyl)-3-(trifluoromethyl)-1H-pyrazol-5-yl)methyl)propanamide;

54 N-(4-(1-((1-(3-chlorophenyl)-3-(trifluoromethyl)-1H-pyrazol-5-yl)methylamino)-1-oxopropan-2-yl)-2-fluorophenyl)benzamide;

55 N-((3-tert-butyl-1-(3-chlorophenyl)-1H-pyrazol-5-yl)methyl)-2-[4-(1,1-dioxidoisothiazolidin-2-yl)-3-fluorophenyl]propanamide;

56 N-((3-tert-butyl-1-(3-chlorophenyl)-1H-pyrazol-5-yl)methyl)-2-(4-(N,N-dimethylsulfamoyl)-3-fluorophenyl)propanamide;

57 1-((3-tert-butyl-1-(3-chlorophenyl)-1H-pyrazol-5-yl)methyl)-3-(3,5-difluorophenyl)urea;

58 1-(4-bromo-3-fluorophenyl)-3-((3-tert-butyl-1-(3-chlorophenyl)-1H-pyrazol-5-yl)methyl)urea;

59 1-((3-tert-butyl-1-(3-chlorophenyl)-1H-pyrazol-5-yl)methyl)-3-(4-(trifluoromethyl)phenyl)urea;

60 1-((3-tert-butyl-1-(3-chlorophenyl)-1H-pyrazol-5-yl)methyl)-3-(4-(difluoromethoxy)phenyl)urea;

61 1-((3-tert-butyl-1-(3-chlorophenyl)-1H-pyrazol-5-yl)methyl)-3-(3,5-difluoro-4-methoxyphenyl)urea;

62 1-((3-tert-butyl-1-(3-chlorophenyl)-1H-pyrazol-5-yl)methyl)-3-(4-methoxy-3,5-dimethylphenyl)urea;

63 1-((3-tert-butyl-1-(3-chlorophenyl)-1H-pyrazol-5-yl)methyl)-3-(3-fluoro-4-(methylsulfonyl)phenyl)urea;

64 1-((3-tert-butyl-1-(3-chlorophenyl)-1H-pyrazol-5-yl)methyl)-3-(4-(phenylamino)phenyl)urea;

65 4-(3-((3-tert-butyl-1-(3-chlorophenyl)-1H-pyrazol-5-yl)methyl)ureido)-N-(4-fluorophenyl)benzamide;

66 N-((3-tert-butyl-1-(3-chlorophenyl)-1H-pyrazol-5-yl)methyl)-2-(3-fluoro-4-(methylsulfonamido)phenyl)-2-(3-fluorophenyl)acetamide;

67 N-((3-tert-butyl-1-(3-chlorophenyl)-1H-pyrazol-5-yl)methyl)-2-cyclohexyl-2-(3-fluoro-4-(methylsulfonamido)phenyl)acetamide;

68 N-((3-tert-butyl-1-(3-chlorophenyl)-1H-pyrazol-5-yl)methyl)-2-(3-fluoro-4-(methylsulfonamido)phenyl)-2-p-tolylacetamide;

69 N-((3-tert-butyl-1-(3-chlorophenyl)-1H-pyrazol-5-yl)methyl)-2-(3-chloro-4-(methylthio)phenyl)propanamide;

70 N-((3-tert-butyl-1-(3-chlorophenyl)-1H-pyrazol-5-yl)methyl)-2-(3-chloro-4-(methylsulfonyl)phenyl)propanamide;

71 N-((3-tert-butyl-1-(3-chlorophenyl)-1H-pyrazol-5-yl)methyl)-2-(3-fluoro-4-(methylthio)phenyl)propanamide;

72 N-((3-tert-butyl-1-(3-chlorophenyl)-1H-pyrazol-5-yl)methyl)-2-(3-fluoro-4-(methylsulfonyl)phenyl)propanamide;

73 N-((3-tert-butyl-1-(3-chlorophenyl)-1H-pyrazol-5-yl)methyl)-2-(3-fluorophenyl)acetamide;

74 N-((1-(3-chlorophenyl)-3-(trifluoromethyl)-1H-pyrazol-5-yl)methyl)-2-(3-fluorophenyl)acetamide;

75 N-[[5-tert-butyl-2-(3-chlorophenyl)-2H-[1,2,4]triazol-3-yl]-methyl]-2-[3-fluoro-4-(methanesulfonamido)phenyl]propionamide;

76 N-[[2-(3-chlorophenyl)-5-(trifluoromethyl)-2H-[1,2,4]triazol-3-yl]-methyl]-2-[3-fluoro-4-(methanesulfonamido)phenyl]propionamide;

77 N-[(5-tert-butyl-2-cyclohexyl-2H-[1,2,4]triazol-3-yl)-methyl]-2-[3-fluoro-4-(methanesulfonamido)phenyl]propionamide;

78 N-[[2-cyclohexyl-5-(trifluoromethyl)-2H-[1,2,4]triazol-3-yl]-methyl]-2-[3-fluoro-4-(methanesulfonamido)phenyl]propionamide;

79 N-[(5-tert-butyl-2-pyridin-3-yl-2H-[1,2,4]triazol-3-yl)-methyl]-2-[3-fluoro-4-(methanesulfonamido)phenyl]propionamide;

80 2-[3-fluoro-4-(methanesulfonamido)phenyl]-N-[[2-pyridin-3-yl-5-(trifluoromethyl)-2H-[1,2,4]triazol-3-yl]-methyl]propionamide;

81 N-[[5-tert-butyl-2-(6-chloropyridin-2-yl)-2H-pyrazol-3-yl]-methyl]-2-[3-fluoro-4-(methanesulfonamido)phenyl]propionamide;

82 N-[[5-tert-butyl-2-(3,3-difluorocyclobutanecarbonyl)-2H-pyrazol-3-yl]-methyl]-2-[3-fluoro-4-(methanesulfonamido)phenyl]propionamide;

83 N-[[2-(3-chlorophenyl)-4-methyl-5-(trifluoromethyl)-2H-pyrazol-3-yl]-methyl]-2-[3-fluoro-4-(methanesulfonamido)phenyl]propionamide;

84 N-[[2-(dipropylamino)-5-(trifluoromethyl)-2H-pyrazol-3-yl]-methyl]-2-[4-(methanesulfonamido)-3-methoxyphenyl]propionamide;

85 N-[[2-(dipropylamino)-5-(trifluoromethyl)-2H-pyrazol-3-yl]-methyl]-2-[3-fluoro-4-(hydroxymethyl)phenyl]propionamide;

86 N-[[2-(dipropylamino)-5-(trifluoromethyl)-2H-pyrazol-3-yl]-methyl]-2-[3-fluoro-4-(methanesulfonamido)phenyl]propionamide;

87 N-[[2-(dipropylamino)-5-(trifluoromethyl)-2H-pyrazol-3-yl]-methyl]-2-(3-fluorophenyl)acetamide;

88 4-[1-[[2-(dipropylamino)-5-(trifluoromethyl)-2H-pyrazol-3-yl]-methylcarbamoyl]ethyl]-2-fluorobenzamide;

89 4-[1-[[2-(dipropylamino)-5-(trifluoromethyl)-2H-pyrazol-3-yl]-methylcarbamoyl]ethyl]-N-pyridin-2-yl-benzamide;

90 2-[3-fluoro-4-(hydroxymethyl)phenyl]-N-[[2-piperidin-1-yl-5-(trifluoromethyl)-2H-pyrazol-3-yl]-methyl]propionamide;

91 2-[3-fluoro-4-(2-hydroxyethyl)phenyl]-N-[[2-piperidin-1-yl-5-(trifluoromethyl)-2H-pyrazol-3-yl]-methyl]propionamide;

92 2-[3-fluoro-4-(methanesulfonamido)phenyl]-N-[[2-piperidin-1-yl-5-(trifluoromethyl)-2H-pyrazol-3-yl]-methyl]propionamide;

93 2-[4-(methanesulfonamido)-3-methoxyphenyl]-N-[[2-piperidin-1-yl-5-(trifluoromethyl)-2H-pyrazol-3-yl]-methyl]propionamide;

94 2-[4-(1,2-dihydroxyethyl)-3-fluorophenyl]-N-[[2-piperidin-1-yl-5-(trifluoromethyl)-2H-pyrazol-3-yl]-methyl]propionamide;

95 2-(3-fluorophenyl)-N-[[2-piperidin-1-yl-5-(trifluoromethyl)-2H-pyrazol-3-yl]-methyl]acetamide;

96 2-fluoro-4-[1-[[2-piperidin-1-yl-5-(trifluoromethyl)-2H-pyrazol-3-yl]-methylcarbamoyl]ethyl]benzamide;

97 2-[3-fluoro-4-(methanesulfonamido)phenyl]-N-[[2-[(4-fluorophenyl)methylmethylamino]-5-(trifluoromethyl)-2H-pyrazol-3-yl]-methyl]propionamide;

98 N-[[5-tert-butyl-2-(2,2,2-trifluoroethylamino)-2H-pyrazol-3-yl]-methyl]-2-[3-fluoro-4-(methanesulfonamido)phenyl]propionamide;

99 N-[[2-butoxy-5-(trifluoromethyl)-2H-pyrazol-3-yl]-methyl]-2-[3-fluoro-4-(hydroxymethyl)phenyl]propionamide;

100 N-[[2-butoxy-5-(trifluoromethyl)-2H-pyrazol-3-yl]-methyl]-2-[3-fluoro-4-(methanesulfonamido)phenyl]propionamide;

101 N-[[2-butoxy-5-(trifluoromethyl)-2H-pyrazol-3-yl]-methyl]-2-[4-(methanesulfonamido)-3-methoxyphenyl]propionamide;

102 N-[(2-butoxy-5-tert-butyl-2H-pyrazol-3-yl)-methyl]-2-(3-fluorophenyl)acetamide;

103 N-[[2-cyclopentyloxy-5-(trifluoromethyl)-2H-pyrazol-3-yl]-methyl]-2-[3-fluoro-4-(methanesulfonamido)phenyl]propionamide;

104 N-[[2-cyclopentyloxy-5-(trifluoromethyl)-2H-pyrazol-3-yl]-methyl]-2-[4-(methanesulfonamido)-3-methoxyphenyl]propionamide;

105 2-(3-fluorophenyl)-N-[[2-[(4-methoxyphenyl)methoxy]-5-(trifluoromethyl)-2H-pyrazol-3-yl]-methyl]acetamide;

106 N-[[5-tert-butyl-2-(3-cyano-5-fluorophenoxy)-2H-pyrazol-3-yl]-methyl]-2-(3-fluorophenyl)acetamide;

107 N-[[2-(cyclohexylsulfanyl)-5-(trifluoromethyl)-2H-pyrazol-3-yl]-methyl]-2-[3-fluoro-4-(methanesulfonamido)phenyl]propionamide;

108 N-[[2-(benzenesulfonyl)-5-tert-butyl-2H-pyrazol-3-yl]-methyl]-2-(3-fluorophenyl)acetamide;

109 N-[[2-cyclohexyl-5-(trifluoromethyl)-2H-[1,2,4]triazol-3-yl]-methyl]-2-[4-(methanesulfonamido)-3-methoxyphenyl]propionamide;

110 N-[[2-cyclohexyl-5-(trifluoromethyl)-2H-[1,2,4]triazol-3-yl]-methyl]-2-(3-fluorophenyl)acetamide;

111 4-[1-[[2-cyclohexyl-5-(trifluoromethyl)-2H-[1,2,4]triazol-3-yl]-methylcarbamoyl]ethyl]-2-fluorobenzamide;

112 2-[3-fluoro-4-(hydroxymethyl)phenyl]-N-[[2-hexyl-5-(trifluoromethyl)-2H-[1,2,4]triazol-3-yl]-methyl]propionamide;

113 4-[1-[[2-cyclobutyl-5-(trifluoromethyl)-2H-[1,2,4]triazol-3-yl]-methylcarbamoyl]ethyl]-2-fluorobenzamide;

114 N-[[5-tert-butyl-2-(3,3-difluorocyclobutanecarbonyl)-2H-[1,2,4]triazol-3-yl]-methyl]-2-[3-fluoro-4-(methanesulfonamido)phenyl]propionamide;

115 N-[[5-tert-butyl-2-(3-cyano-5-fluorophenoxy)-2H-[1,2,4]triazol-3-yl]-methyl]-2-(3-fluorophenyl)acetamide;

116 N-[[2-(benzenesulfonyl)-5-tert-butyl-2H-[1,2,4]triazol-3-yl]-methyl]-2-(3-fluorophenyl)acetamide;

117 N-((1-(3-chlorophenyl)-3-(trifluromethyl)-1H-pyrazol-5-yl)methyl)-2-(3-fluorophenyl)-2-methylpropanamide;

118 N-((3-tert-butyl-1-(3-chlorophenyl)-1H-pyrazol-5-yl)methyl)-1-(3-fluorophenyl)cyclopropancarboxamide;

119 N-((1-(3-chlorophenyl)-3-(trifluoromethyl)-1H-pyrazol-5-yl)methyl)-1-(3-fluorophenyl)cyclobutanecarboxamide;

120 N-((1-(3-chlorophenyl)-3-(trifluoromethyl)-1H-pyrazol-5-yl)methyl)-1-(3-fluorophenyl)cyclopentancarboxamide;

121 N-((1-(3-chlorophenyl)-3-(trifluoromethyl)-1H-pyrazol-5-yl)methyl)-1-(3-fluorophenyl)cyclohexanecarboxamide;

122 1-((3-tert-butyl-1-(4-fluorophenyl)-1H-pyrazol-5-yl)methyl)-3-(3-fluorophenyl)urea;

123 3-((1-(3-chlorophenyl)-3-(trifluoromethyl)-1H-pyrazol-5-yl)methyl)-1-(3-fluorophenyl)-1-methylurea;

124 N-((1-(3-chloro-4-fluorophenyl)-3-(trifluoromethyl)-1H-pyrazol-5-yl)methyl)-2-(3-fluoro-4-(methylsulfonylmethyl)phenyl)propanamide;

125 N-((3-tert-butyl-1-(3-chlorophenyl)-1H-pyrazol-5-yl)methyl)-2-(4-cyclopropyl-3-fluorophenyl)propanamide;

126 1-((1-(3-chlorophenyl)-3-(trifluoromethyl)-1H-pyrazol-5-yl)methyl)-3-(4-cyclopropyl-3-fluorophenyl)urea;

127 N-((3-tert-butyl-1-(pyridin-2-yl)-1H-pyrazol-5-yl)methyl)-2-(3-fluoro-4-(methylsulfonamiomethyl)phenyl)propanamide;

128 N-((1-(3-chlorophenyl)-3-cyclopropyl-1H-pyrazol-5-yl)methyl)-2-(3-fluoro-4-(methylsulfonylmethyl)phenyl)propanamide;

129 2-(3-fluoro-4-(methylsulfonamidoethyl)phenyl)-N-((1-(pyridin-2-ylmethylamino)-3-(trifluoromethyl)-1H-pyrazol-5-yl)methyl)propanamide;

130 N-((1-(3-chlorophenyl)-4-methyl-3-(trifluoromethyl)-1H-pyrazol-5-yl)methyl)-2-(3-fluorophenyl)acetamide;

131 2-(3-fluorophenyl)-N-((1-pentyl-3-(trifluoromethyl)-1H-pyrazol-5-yl)methyl)acetamide;

132 2-(3-fluorophenyl)-N-((1-(4-methoxybenzyl)-3-(trifluoromethyl)-1H-pyrazol-5-yl)methyl)acetamide;

133 N-((3-tert-butyl-1-(2,2,2-trifluoroethylamino)-1H-pyrazol-5-yl)methyl)-2-(3-fluorophenyl)acetamide;

134 N-((1-(3-chlorophenyl)-4-methyl-3-(trifluoromethyl)-1H-pyrazol-5-yl)methyl)-2-(3-fluoro-4-(methylsulfonamidoethyl)phenyl)propanamide;

135 N-((3-tert-butyl-1-(3-chlorophenyl)-1H-1,2,4-triazol-5-yl)methyl)-2-(3-fluorophenyl)acetamide;

136 2-(3-fluorophenyl)-N-((1-(pyridin-3-yl)-3-(trifluoromethyl)-1H-pyrazol-5-yl)methyl)acetamide;

137 N-((1-cyclohexyl-3-(trifluoromethyl)-1H-pyrazol-5-yl)methyl)-2-(3-fluoro-4-(methylsulfonamidoethyl)phenyl)propanamide;

138 2-(3-fluoro-4-(methylsulfonamidoethyl)phenyl)-N-((1-(tetrahydro-2H-pyran-4-yl)-3-(trifluoromethyl)-1H-pyrazol-5-yl)methyl)propanamide;

139 1-((1-(3-chlorophenyl)-3-(trifluoromethyl)-1H-pyrazol-5-yl)methyl)-3-(4-(cyclopropylethynyl)-3-fluorophenyl)urea;

140 N-((1-(3-chlorophenyl)-3-(trifluoromethyl)-1H-pyrazol-5-yl)methyl)-2-(3-fluoro-4-(trifluoromethyl)phenyl)acetamide;

141 N-((1-(3-chlorophenyl)-3-(trifluoromethyl)-1H-pyrazol-5-yl)methyl)-2-(3-fluoro-4-(trifluoromethyl)phenyl)propanamide;

142 N-((3-tert-butyl-1-(3-chlorophenyl)-1H-pyrazol-5-yl)methyl)-2-(3-fluoro-4-((2-methoxyethoxy)methyl)phenyl)propanamide;

143 4-(1-((1-(3-chlorophenyl)-3-(trifluoromethyl)-1H-pyrazol-5-yl)methylamino)-1-oxopropan-2-yl)-N-phenylbenzamide;

144 1-((3-tert-butyl-1-(3-chlorophenyl)-1H-pyrazol-5-yl)methyl)-3-(3-fluoro-4-morpholinphenyl)urea;

145 N-((1-(3-chlorophenyl)-3-(trifluoromethyl)-1H-pyrazol-5-yl)methyl)-2-(3-fluoro-4-(methylsulfonamide)phenyl)-3-phenylpropanamide;

146 N-(5-((2-(3-fluorophenyl)acetamide)methyl)-3-(trifluoromethyl)-1H-pyrazol-1-yl)benzamide;

147 N-((1-(3-chlorophenyl)-3-(trifluoromethyl)-1H-pyrazol-5-yl)methyl)-2-(3,5-difluoro-4-hydroxyphenyl)acetamide;

respectively in the form of the free compounds; the racemate; the enantiomers, diastereomers, mixtures of the enantiomers or diastereomers or of an individual enantiomer or diastereomer; or in the form of the salts of physiologically compatible acids or bases; or in the form of solvates.

One particularly preferred subgroup of the compounds of the invention comprises compounds corresponding to the formula (Q)

(Q)

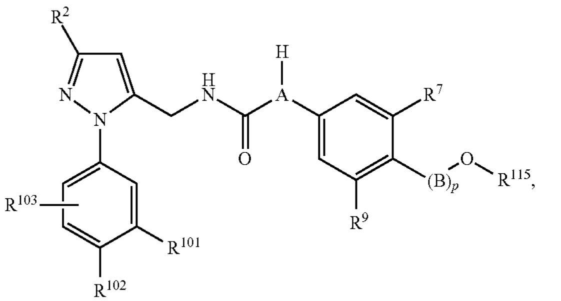

wherein $R^{101}$, $R^{102}$ and $R^{103}$ are each independently selected from the group consisting of H, F, Cl, Br, $CFH_2$, $CF_2H$, $CF_3$, CN, $CH_2$—OH, $CH_2CH_2$—OH, $CH_2$—$OCH_3$, $CH_2CH_2$—$OCH_3$, $OCFH_2$, $OCF_2H$, $OCF_3$, OH, $NH_2$, a $C_{1-4}$ alkyl, an O—$C_{1-4}$ alkyl, a NH—$C_{1-4}$ alkyl, and a $N(C_{1-4}$ alkyl$)_2$, wherein the $C_{1-4}$ alkyl is in each case unsubstituted;

$R^2$ represents $CF_3$, an unsubstituted $C_{1-4}$ alkyl or an unsubstituted $C_{3-6}$ cycloalkyl;

$R^7$ and $R^9$ are each independently selected from the group consisting of H, F, Cl, Br, $CFH_2$, $CF_2H$, $CF_3$, CN, OH, $OCF_3$, $C_{1-4}$ alkyl, and O—$C_{1-4}$ alkyl, wherein the $C_{1-4}$ alkyl is in each case unsubstituted;

A denotes N, CH or $C(CH_3)$;

p denotes 0 or 1;

$R^{115}$ represents H or a $C_{1-6}$ alkyl, which is unsubstituted or mono-, di- or trisubstituted with 1, 2 or 3 substituents independently selected from the group consisting of OH and $OCH_3$;

B denotes $C(R^{116a})(R^{116b})$, wherein $R^{116a}$ is selected from the group consisting of H, $CH_3$, $CH_2OH$ and OH, and $R^{116b}$ is selected from the group consisting of H, $CH_3$ and $CH_2OH$, with the proviso that $R^{116a}$ is not OH, when $R^{115}$ represents H; or $R^{116a}$ and $R^{116b}$ together with the carbon atom connecting them form an unsubstituted $C_{3-6}$ cycloalkyl or an unsubstituted 3 to 6 membered heterocyclyl, wherein at least one ring member of the heterocyclyl is selected from the group consisting of O, S, N, NH and $N(C_{1-4}$ alkyl); or B denotes $C(R^{116c})(R^{116d})$—$C(R^{117a})(R^{117b})$, wherein $R^{116c}$ is selected from the group consisting of H, $CH_3$, $CH_2OH$ and OH, and $R^{116d}$ is selected from the group consisting of H, $CH_3$ and $CH_2OH$; or $R^{116c}$ and $R^{116d}$ together with the carbon atom connecting them form an unsubstituted $C_{3-6}$ cycloalkyl or an unsubstituted 3 to 6 membered heterocyclyl, wherein at least one ring member of the heterocyclyl is selected from the group consisting of O, S, N, NH and $N(C_{1-4}$ alkyl);

$R^{117a}$ is selected from the group consisting of H, $CH_3$, $CH_2OH$ and OH, and $R^{117b}$ is selected from the group consisting of H, $CH_3$ and $CH_2OH$, with the proviso that $R^{117a}$ is not OH, when $R^{115}$ represents H; or $R^{117a}$ and $R^{117b}$ together with the carbon atom connecting them form an unsubstituted $C_{3-6}$ cycloalkyl or an unsubstituted 3 to 6 membered heterocyclyl, wherein at least one ring member of the heterocyclyl is selected from the group consisting of O, S, N, NH and N($C_{1-4}$ alkyl);

optionally in the form of a single stereoisomer or a mixture of stereoisomers, in the form of the free compound and/or a physiologically acceptable salt and/or a physiologically acceptable solvate thereof.

In a preferred embodiment of the compounds of formula (Q) $R^{101}$, $R^{102}$ and $R^{103}$ are each independently selected from the group consisting of H, F, Cl, Br, $CFH_2$, $CF_2H$, $CF_3$, CN, $CH_2$—OH, $CH_2$—$OCH_3$, $OCF_3$, OH, $CH_3$, $CH_2CH_3$, $CH(CH_3)_2$, O—$CH_3$, O—$CH_2CH_3$, $NH_2$, $NH(CH_3)$, and $N(CH_3)_2$.

Preferably, $R^{101}$, $R^{102}$ and $R^{103}$ are each independently selected from the group consisting of H, F, Cl, Br, $CFH_2$, $CF_2H$, $CF_3$, CN, $CH_2$—OH, $CH_2$—$OCH_3$, $OCF_3$, OH, $CH_3$, O—$CH_3$, O—$CH_2CH_3$, $NH_2$, $NH(CH_3)$, and $N(CH_3)_2$.

More preferably, $R^{101}$, $R^{102}$ and $R^{103}$ are each independently selected from the group consisting of H, F, Cl, $CFH_2$, $CF_2H$, $CF_3$, CN, $CH_2$—$OCH_3$, $OCF_3$, $CH_3$, O—$CH_3$, O—$CH_2CH_3$ and $N(CH_3)_2$.

Even more preferably, $R^{101}$, $R^{102}$ and $R^{103}$ are each independently selected from the group consisting of H, F, Cl, $CFH_2$, $CF_2H$, $CF_3$, $OCF_3$, $CH_3$, O—$CH_3$, and O—$CH_2CH_3$.

Still more preferably, $R^{101}$, $R^{102}$ and $R^{103}$ are each independently selected from the group consisting of H, F, Cl, $CF_3$, $OCF_3$, $CH_3$ and O—$CH_3$.

Particularly, $R^{101}$, $R^{102}$ and $R^{103}$ are each independently selected from the group consisting of H, F, Cl, $CF_3$ and O—$CH_3$.

Even more particularly preferred $R^{101}$, $R^{102}$ and $R^{103}$ are each independently selected from the group consisting of H, F, Cl and O—$CH_3$.

In a preferred embodiment of the compound of formula (Q), at least one of $R^{101}$, $R^{102}$ and $R^{103}$ is not H.

In another preferred embodiment of the compound of formula (Q), one or two of $R^{101}$, $R^{102}$ and $R^{103}$, preferably $R^{102}$ and/or $R^{103}$, denote(s) H.

In another preferred embodiment of the compound of formula (Q), one of $R^{101}$, $R^{102}$ and $R^{103}$ represents H. Preferably $R^{103}$ represents H.

In another preferred embodiment of the compound of formula (Q), $R^{101}$ and $R^{102}$ are each independently selected from the group consisting of H, F, Cl, Br, $CFH_2$, $CF_2H$, $CF_3$, CN, $CH_2$—OH, $CH_2$—$OCH_3$, $OCF_3$, OH, $CH_3$, $CH_2CH_3$, $CH(CH_3)_2$, O—$CH_3$, O—$CH_2CH_3$, $NH_2$, $NH(CH_3)$, and $N(CH_3)_2$, and $R^{103}$ represents H.

Preferably, $R^{101}$ and $R^{102}$ are each independently selected from the group consisting of H, F, Cl, Br, $CFH_2$, $CF_2H$, $CF_3$, CN, $CH_2$—OH, $CH_2$—$OCH_3$, $OCF_3$, OH, $CH_3$, O—$CH_3$, O—$CH_2CH_3$, $NH_2$, $NH(CH_3)$, and $N(CH_3)_2$, more preferably are each independently selected from the group consisting of H, F, Cl, $CFH_2$, $CF_2H$, $CF_3$, CN, $CH_2$—$OCH_3$, $OCF_3$, $CH_3$, O—$CH_3$, O—$CH_2CH_3$ and $N(CH_3)_2$, even more preferably are each independently selected from the group consisting of H, F, Cl, $CFH_2$, $CF_2H$, $CF_3$, $OCF_3$, $CH_3$, O—$CH_3$, and O—$CH_2CH_3$, still more preferably are each independently selected from the group consisting of H, F, Cl, $CF_3$, $OCF_3$, $CH_3$ and O—$CH_3$, in particular are each independently selected from the group consisting of H, F, Cl, $CF_3$ and 0-$CH_3$, and even more particularly preferably are each independently selected from the group consisting of H, F, Cl, and O—$CH_3$, and $R^{103}$ represents H.

In yet another preferred embodiment of the compound of formula (Q), $R^{101}$ is selected from the group consisting of F, Cl, Br, $CFH_2$, $CF_2H$, $CF_3$, CN, $CH_2$—OH, $CH_2$—$OCH_3$, $OCF_3$, OH, $CH_3$, $CH_2CH_3$, $CH(CH_3)_2$, O—$CH_3$, O—$CH_2CH_3$, $NH_2$, $NH(CH_3)$, and $N(CH_3)_2$, and both $R^{102}$ and $R^{103}$ represent H.

Preferably, $R^{101}$ is selected from the group consisting of F, Cl, Br, $CFH_2$, $CF_2H$, $CF_3$, CN, $CH_2$—OH, $CH_2$—$OCH_3$, $OCF_3$, OH, $CH_3$, O—$CH_3$, O—$CH_2CH_3$, $NH_2$, $NH(CH_3)$, and $N(CH_3)_2$, more preferably is selected from the group consisting of F, Cl, $CFH_2$, $CF_2H$, $CF_3$, CN, $CH_2$—$OCH_3$, $OCF_3$, $CH_3$, O—$CH_3$, O—$CH_2CH_3$ and $N(CH_3)_2$, even more preferably is selected from the group consisting of F, Cl, $CFH_2$, $CF_2H$, $CF_3$, $OCF_3$, $CH_3$, O—$CH_3$, and O—$CH_2CH_3$, still more preferably is selected from the group consisting of F, Cl, $CF_3$, $OCF_3$, $CH_3$ and O—$CH_3$, in particular is selected from the group consisting of F, Cl, $CF_3$ and O—$CH_3$, even more particularly preferred is selected from the group consisting of F, Cl, and O—$CH_3$, and both $R^{102}$ and $R^{103}$ represent H.

In still another preferred embodiment of the compound of formula (Q), $R^{102}$ is selected from the group consisting of F, Cl, Br, $CFH_2$, $CF_2H$, $CF_3$, CN, $CH_2$—OH, $CH_2$—$OCH_3$, $OCF_3$, OH, $CH_3$, $CH_2CH_3$, $CH(CH_3)_2$, O—$CH_3$, O—$CH_2CH_3$, $NH_2$, $NH(CH_3)$, and $N(CH_3)_2$, and both $R^{101}$ and $R^{103}$ represent H.

Preferably, $R^2$ is selected from the group consisting of F, Cl, Br, $CFH_2$, $CF_2H$, $CF_3$, CN, $CH_2$—OH, $CH_2$—$OCH_3$, $OCF_3$, OH, $CH_3$, O—$CH_3$, O—$CH_2CH_3$, $NH_2$, $NH(CH_3)$, and $N(CH_3)_2$, more preferably is selected from the group consisting of F, Cl, $CFH_2$, $CF_2H$, $CF_3$, CN, $CH_2$—$OCH_3$, $OCF_3$, $CH_3$, O—$CH_3$, O—$CH_2CH_3$ and $N(CH_3)_2$, even more preferably is selected from the group consisting of F, Cl, $CFH_2$, $CF_2H$, $CF_3$, $OCF_3$, $CH_3$, O—$CH_3$, and O—$CH_2CH_3$, still more preferably is selected from the group consisting of F, Cl, $CF_3$, $OCF_3$, $CH_3$ and O—$CH_3$, in particular is selected from the group consisting of F, Cl, $CF_3$ and O—$CH_3$, even more particularly preferred is selected from the group consisting of F, Cl, and O—$CH_3$, and both $R^{101}$ and $R^{103}$ represent H.

In yet a further preferred embodiment of the compound of formula (Q), $R^{101}$ is selected from the group consisting of F, Cl, Br, $CFH_2$, $CF_2H$, $CF_3$, CN, $CH_2$—OH, $CH_2$—$OCH_3$, $OCF_3$, OH, $CH_3$, $CH_2CH_3$, $CH(CH_3)_2$, O—$CH_3$, O—$CH_2CH_3$, $NH_2$, $NH(CH_3)$, and $N(CH_3)_2$;

$R^{102}$ is selected from the group consisting of H, F, Cl, Br, $CFH_2$, $CF_2H$, $CF_3$, CN, $CH_2$—OH, $CH_2$—$OCH_3$, $OCF_3$, OH, $CH_3$, $CH_2CH_3$, $CH(CH_3)_2$, O—$CH_3$, O—$CH_2CH_3$, $NH_2$, $NH(CH_3)$, and $N(CH_3)_2$; and $R^{103}$ represents H.

Preferably, $R^{101}$ is selected from the group consisting of F, Cl, Br, $CFH_2$, $CF_2H$, $CF_3$, CN, $CH_2$—OH, $CH_2$—$OCH_3$, $OCF_3$, OH, $CH_3$, O—$CH_3$, O—$CH_2CH_3$, $NH_2$, $NH(CH_3)$, and $N(CH_3)_2$, more preferably is selected from the group consisting of F, Cl, $CFH_2$, $CF_2H$, $CF_3$; CN, $CH_2$—$OCH_3$, $OCF_3$, $CH_3$, O—$CH_3$, O—$CH_2CH_3$ and $N(CH_3)_2$, even more preferably is selected from the group consisting of F, Cl, $CFH_2$, $CF_2H$, $CF_3$, $OCF_3$, $CH_3$, O—$CH_3$, and O—$CH_2CH_3$, still more preferably is selected from the group consisting of F, Cl, $CF_3$, $OCF_3$, $CH_3$ and O—$CH_3$, in particular is selected from the group consisting of F, Cl, $CF_3$ and O—$CH_3$, even more particularly preferred is selected from the group consisting of F, Cl, and O—$CH_3$;

$R^{102}$ is selected from the group consisting of H, F, Cl, Br, $CFH_2$, $CF_2H$, $CF_3$, CN, $CH_2$—OH, $CH_2$—$OCH_3$, $OCF_3$, OH, $CH_3$, O—$CH_3$, O—$CH_2CH_3$, $NH_2$, $NH(CH_3)$, and $N(CH_3)_2$, more preferably is selected from the group consisting of H, F, Cl, $CFH_2$, $CF_2H$, $CF_3$, CN, $CH_2$—$OCH_3$, $OCF_3$, $CH_3$, O—$CH_3$, O—$CH_2CH_3$ and $N(CH_3)_2$, even more preferably is selected from the group consisting of H, F, Cl, $CFH_2$, $CF_2H$, $CF_3$, $OCF_3$, $CH_3$, O—$CH_3$, and O—$CH_2CH_3$, still more preferably is selected from the group consisting of H, F, Cl, $CF_3$, $OCF_3$, $CH_3$ and O—$CH_3$, in particular is selected from the group consisting of H, F, Cl, $CF_3$ and O—$CH_3$, even more particularly preferred is selected from the group consisting of H, F, Cl, and O—$CH_3$, and $R^{103}$ represents H.

In another particularly preferred embodiment of the compound of formula (Q) the partial structure (QS2)

(QS2)

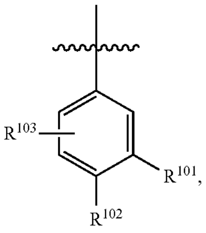

is selected from the group consisting of:

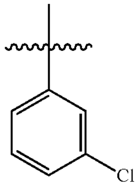 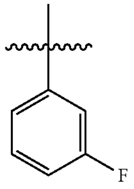 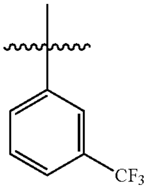

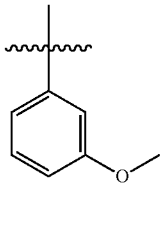 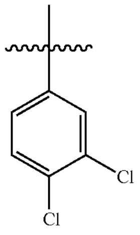 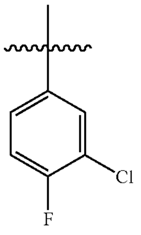

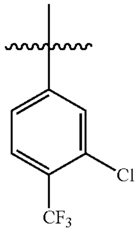 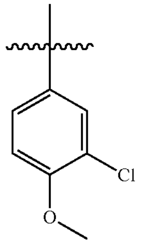 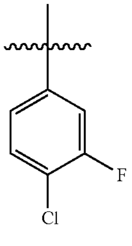

-continued

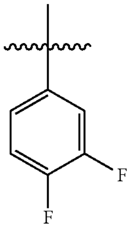 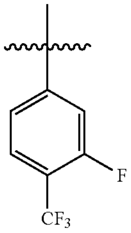 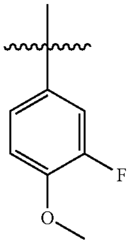

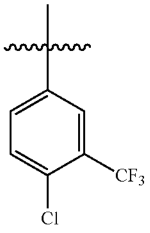 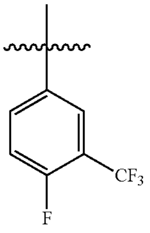 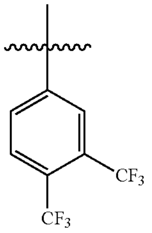

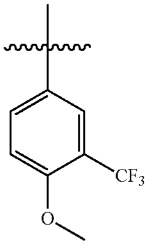 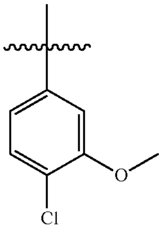 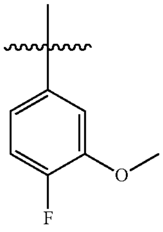

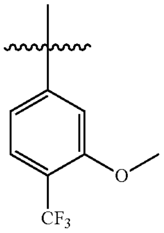 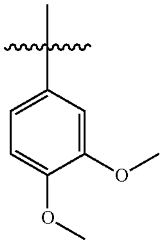 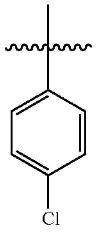

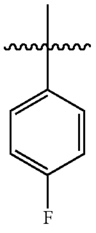 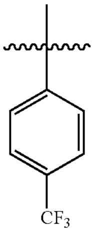 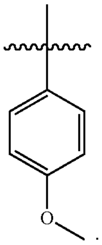 .

Even more particularly preferred, the partial structure (QS2) is selected from the group consisting of:

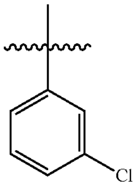 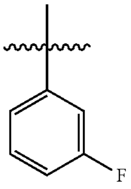 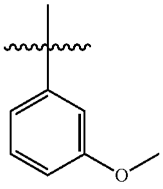

-continued

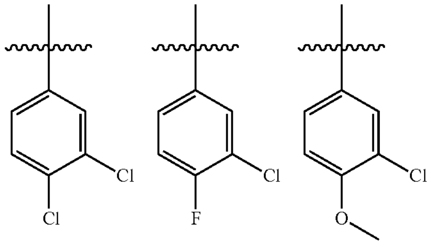

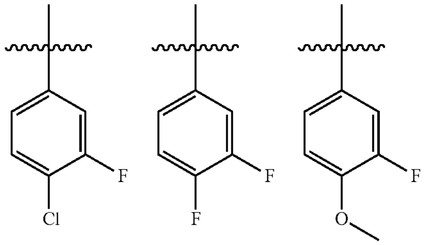

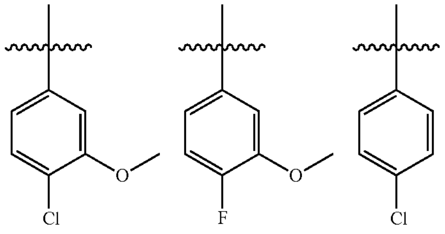

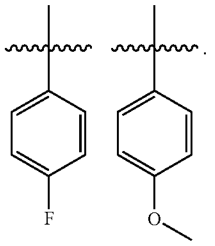

Most preferred, the partial structure (QS2) is selected from the group consisting of:

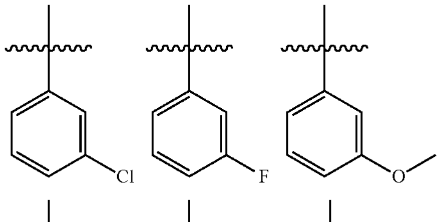

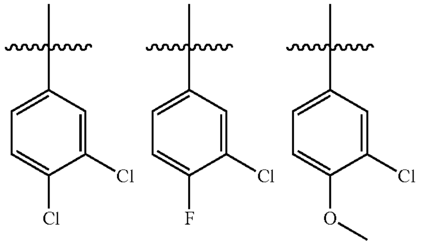

-continued

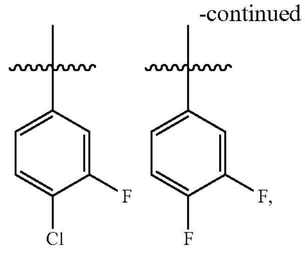

especially preferably from the group consisting of:

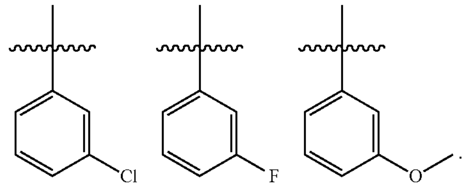

In another preferred embodiment of the compound of formula (Q), $R^2$ represents $CF_3$, methyl, ethyl, n-propyl, 2-propyl, n-butyl, iso-butyl, sec.-butyl, tert.-butyl, cyclopropyl, cyclobutyl, cyclopentyl or cyclohexyl. Preferably, $R^2$ represents $CF_3$, 2-propyl, n-butyl, iso-butyl, sec.-butyl, tert.-butyl, cyclopropyl, or cyclobutyl. More preferably, $R^2$ represents $CF_3$, tert.-butyl or cyclopropyl. In one particularly preferred embodiment of the compound of formula (Q), $R^2$ represents $CF_3$. In another particularly preferred embodiment of the compound of formula (Q), $R^2$ represents tert.-butyl. In yet another particularly preferred embodiment of the compound of formula (Q), $R^2$ represents cyclopropyl.

In a further preferred embodiment of the compound of formula (Q), $R^7$ and $R^9$ are each independently selected from the group consisting of H, F, Cl, Br, $CF_3$, CN, OH, $OCF_3$, $CH_3$, $CH_2CH_3$, $CH(CH_3)_2$, O—$CH_3$, and O—$CH_2CH_3$. Preferably, $R^7$ and $R^9$ are independently selected from the group consisting of H, F, Cl, $CF_3$, CN, OH, $OCF_3$, $CH_3$, O—$CH_3$, and O—$CH_2CH_3$. More preferably, $R^7$ and $R^9$ are each independently selected from the group consisting of H, F, Cl, $CF_3$, OH, O—$CH_3$, and O—$CH_2CH_3$. Even more preferably, $R^7$ and $R^9$ are each independently selected from the group consisting of H, F, Cl, and O—$CH_3$, and still more preferably independently selected from the group consisting of H, F and Cl.

In yet a further preferred embodiment of the compound of formula (Q), at least one of $R^7$ and $R^9$ is not H.

In a further preferred embodiment of the compound of formula (Q), $R^9$ denotes H.

In yet another preferred embodiment of the compound of formula (Q), $R^7$ is selected from the group consisting of F, Cl, Br, $CF_3$, CN, OH, $OCF_3$, $CH_3$, $CH_2CH_3$, $CH(CH_3)_2$, O—$CH_3$, and O—$CH_2CH_3$, preferably is selected from the group consisting of F, Cl, $CF_3$, CN, OH, $OCF_3$, $CH_3$, O—$CH_3$, and O—$CH_2CH_3$, more preferably is selected from the group consisting of F, Cl, $CF_3$, O—$CH_3$, and O—$CH_2CH_3$, even more preferably is selected from the group consisting of F, Cl, and O—$CH_3$, and still more preferably is selected from the group consisting of F and Cl, and $R^9$ represents H.

In another preferred embodiment of the compound of formula (Q), A denotes N or $C(CH_3)$. In one particularly preferred embodiment of the compound of formula (Q), A denotes N. In another particularly preferred embodiment of the compound of formula (Q), A denotes $C(CH_3)$.

In another preferred embodiment of the compound of formula (Q), the partial structure (QS1)

(QS1)

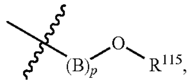

represents (a) partial structure (PQ1)

(PQ1)

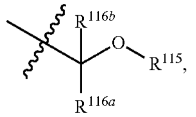

wherein $R^{115}$ represents H, $CH_3$, $CH_2OH$, $CH_2OCH_3$, $CH_2CH_3$, $CH(OH)CH_3$, $CH_2CH_2OH$, $CH(OH)CH_2OH$, $CH(OCH_3)CH_2OH$, $CH(OH)CH_2OCH_3$, or $CH_2CH_2OCH_3$;

$R^{116a}$ is selected from the group consisting of H, $CH_3$, $CH_2OH$ and OH, and $R^{116b}$ is selected from the group consisting of H, $CH_3$ and $CH_2OH$, with the proviso that $R^{116a}$ is not OH, when $R^{115}$ represents H, or $R^{116a}$ and $R^{116b}$ together with the carbon atom connecting them form an unsubstituted $C_{3-6}$ cycloalkyl or an unsubstituted 3 to 6 membered heterocyclyl, wherein at least one ring member of the heterocyclyl is selected from the group consisting of O, S, N, NH and N($C_{1-4}$ alkyl), and preferably one ring member of the heterocyclyl is O, or (b) partial structure (PQ2)

(PQ2)

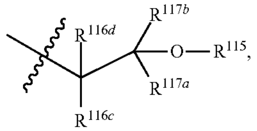

wherein $R^{115}$ represents H, $CH_3$, $CH_2OH$, $CH_2OCH_3$, $CH_2CH_3$, $CH(OH)CH_3$, $CH_2CH_2OH$, $CH(OH)CH_2OH$, $CH(OCH_3)CH_2OH$, $CH(OH)CH_2OCH_3$, or $CH_2CH_2OCH_3$;

$R^{116c}$ is selected from the group consisting of H, $CH_3$, $CH_2OH$ and OH, and $R^{116d}$ is selected from the group consisting of H, $CH_3$ and $CH_2OH$; or $R^{116c}$ and $R^{116d}$ together with the carbon atom connecting them form an unsubstituted $C_{3-6}$ cycloalkyl or an unsubstituted 3 to 6 membered heterocyclyl, wherein at least one ring member of the heterocyclyl is selected from the group consisting of O, S, N, NH and N($C_{1-4}$ alkyl), and preferably one ring member of the heterocyclyl is O;

$R^{117a}$ is selected from the group consisting of H, $CH_3$, $CH_2OH$ and OH, and $R^{117b}$ is selected from the group consisting of H, $CH_3$ and $CH_2OH$, with the proviso that $R^{117a}$ is not OH, when $R^{115}$ represents H; or $R^{117a}$ and $R^{117b}$ together with the carbon atom connecting them form an unsubstituted $C_{3-6}$ cycloalkyl or an unsubstituted 3 to 6 membered heterocyclyl, wherein at least one ring member of the heterocyclyl is selected from the group consisting of O, S, N, NH and N($C_{1-4}$ alkyl), and preferably one ring member of the heterocyclyl is O;

or, if p is 0, (c) OH, $OCH_3$, $OCH_2CH_3$, or partial structure (PQ3), preferably partial structure (PQ3), (PQ3)

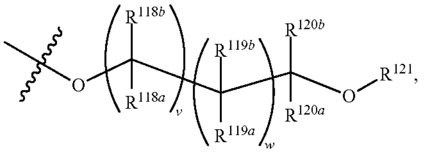

wherein v denotes 0 or 1, w denotes 0 or 1, $R^{118a}$ is selected from the group consisting of H and OH, and $R^{118b}$ is selected from the group consisting of H and $CH_3$;

$R^{119a}$ is selected from the group consisting of H and OH, and $R^{119b}$ is selected from the group consisting of H and $CH_3$;

$R^{120a}$ is selected from the group consisting of H and OH, and $R^{120b}$ is selected from the group consisting of H and $CH_3$;

$R^{121}$ represents H or $CH_3$, with the proviso that $R^{120a}$ is not OH, when $R^{121}$ represents H.

Preferably, the partial structure (QS1) represents (a) partial structure (PQ1)

(PQ1)

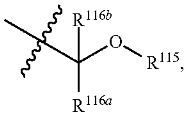

wherein $R^{115}$ represents H, $CH_2OH$, $CH_2CH_2OH$, $CH(OH)CH_2OH$, $CH(OCH_3)CH_2OH$;

$R^{116a}$ is selected from the group consisting of H, $CH_3$, and OH, and $R^{116b}$ is selected from the group consisting of H, and $CH_3$, with the proviso that $R^{116a}$ is not OH, when $R^{115}$ represents H; or $R^{116a}$ and $R^{116b}$ together with the carbon atom connecting them form an unsubstituted moiety selected from the group consisting of cyclopropyl, cyclobutyl, oxiranyl and oxetanyl, or (b) partial structure (PQ2)

(PQ2)

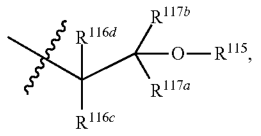

wherein $R^{115}$ represents H, $CH_3$, $CH_2OH$, $CH_2OCH_3$, $CH_2CH_3$, $CH(OH)CH_3$, $CH_2CH_2OH$, $CH(OH)CH_2OH$, $CH(OCH_3)CH_2OH$, $CH(OH)CH_2OCH_3$, or $CH_2CH_2OCH_3$;

$R^{116c}$ is selected from the group consisting of H, $CH_3$, and $CH_2OH$, and $R^{116d}$ is selected from the group consisting of H, $CH_3$ and $CH_2OH$;

$R^{117a}$ is selected from the group consisting of H, $CH_3$, $CH_2OH$ and OH, and $R^{117b}$ is selected from the group consisting of H, $CH_3$ and $CH_2OH$, with the proviso that $R^{117a}$ is not OH, when $R^{115}$ represents H;

or, if p is 0, (c) partial structure (PQ3)

(PQ3)

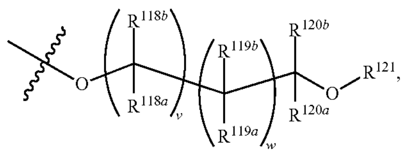

wherein v denotes 0 or 1;

w denotes 0 or 1;

$R^{118a}$ is selected from the group consisting of H and OH, and $R^{118b}$ is selected from the group consisting of H and $CH_3$;

$R^{119a}$ is selected from the group consisting of H and OH, and $R^{119b}$ is selected from the group consisting of H and $CH_3$;

$R^{120a}$ is selected from the group consisting of H and OH, and $R^{120b}$ is selected from the group consisting of H and $CH_3$;

$R^{121}$ represents H or $CH_3$, with the proviso that $R^{120a}$ is not OH, when $R^{121}$ represents H.

More preferably, the partial structure (QS1) represents (a) partial structure (PQ1)

(PQ1)

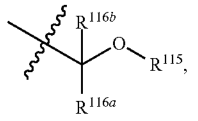

wherein $R^{115}$ represents H, $CH_2OH$, or $CH_2CH_2OH$;

$R^{116a}$ is selected from the group consisting of H, $CH_3$, and OH, and $R^{116b}$ is selected from the group consisting of H, and $CH_3$, with the proviso that $R^{116a}$ is not OH, when $R^{115}$ represents H; or $R^{116a}$ and $R^{116b}$ together with the carbon atom connecting them form an unsubstituted moiety selected from the group consisting of cyclopropyl, cyclobutyl, oxiranyl and oxetanyl;

or (b) partial structure (PQ2)

(PQ2)

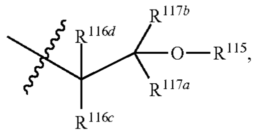

wherein $R^{115}$ represents H, $CH_2OH$, $CH_2CH_2OH$, or $CH(OH)CH_2OH$;

$R^{116c}$ is selected from the group consisting of H, $CH_3$, and $CH_2OH$, and $R^{116d}$ is selected from the group consisting of H, $CH_3$ and $CH_2OH$;

$R^{117a}$ is selected from the group consisting of H, $CH_3$, $CH_2OH$ and OH, and $R^{117b}$ is selected from the group consisting of H, $CH_3$ and $CH_2OH$, with the proviso that $R^{117a}$ is not OH, when $R^{115}$ represents H;

or, if p is 0, (c) partial structure (PQ3)

(PQ3)

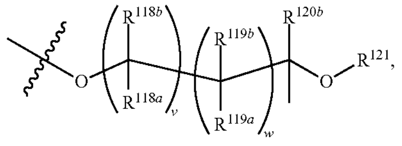

wherein v denotes 0 or 1;

w denotes 0 or 1;

$R^{118a}$ is selected from the group consisting of H and OH, and $R^{118b}$ is selected from the group consisting of H and $CH_3$;

$R^{119a}$ is selected from the group consisting of H and OH, and $R^{119b}$ is selected from the group consisting of H and $CH_3$;

$R^{120a}$ is selected from the group consisting of H and OH, and $R^{120b}$ is selected from the group consisting of H and $CH_3$;

$R^{121}$ represents H or $CH_3$, with the proviso that $R^{120a}$ is not OH, when $R^{121}$ represents H.

Even more preferably, partial structure (QS1) represents (a) partial structure (PQ1)

(PQ1-a)

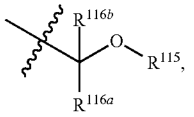

wherein $R^{115}$ represents H, $CH_2OH$, or $CH_2CH_2OH$, preferably H or $CH_2CH_2OH$;

$R^{116a}$ is selected from the group consisting of H, $CH_3$ and OH, and $R^{116b}$ is selected from the group consisting of H and $CH_3$, with the proviso that $R^{116a}$ is not OH, when $R^{115}$ represents H; or $R^{116a}$ and $R^{116b}$ together with the carbon atom connecting them form an unsubstituted cyclopropyl or an unsubstituted oxetanyl, or (b) partial structure (PQ2)

(PQ2)

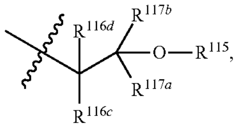

wherein $R^{115}$ represents H, $CH_2OH$, or $CH_2CH_2OH$, preferably H;

$R^{116c}$ is selected from the group consisting of H, $CH_3$ and $CH_2OH$, and $R^{116d}$ is selected from the group consisting of H, $CH_3$ and $CH_2OH$;

$R^{117a}$ is selected from the group consisting of H, $CH_3$, $CH_2OH$ and OH, and $R^{117b}$ is selected from the group consisting of H, $CH_3$ and $CH_2OH$, with the proviso that $R^{117a}$ is not OH, when $R^{15}$ represents H;

or, if p is 0, (c) partial structure (PQ3)

(PQ3)

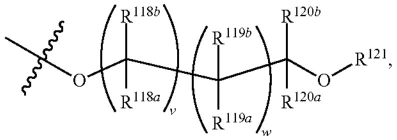

wherein v denotes 0 or 1;

w denotes 0 or 1;

$R^{118a}$ is selected from the group consisting of H and OH, and $R^{118b}$ is selected from the group consisting of H and $CH_3$;

$R^{119a}$ is selected from the group consisting of H and OH, and $R^{119b}$ is selected from the group consisting of H and $CH_3$;

$R^{120a}$ is selected from the group consisting of H and OH, and $R^{120b}$ is selected from the group consisting of H and $CH_3$;

$R^{121}$ represents H, with the proviso that $R^{120a}$ is not OH, when $R^{121}$ represents H.

Still more preferably, the partial structure (QS1) represents (a) partial structure (PQ1-1)

(PQ1-1)

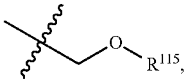

wherein $R^{115}$ represents H, $CH_2OH$, or $CH_2CH_2OH$, preferably H or $CH_2CH_2OH$;

or (b) partial structure (PQ2-1)

(PQ2-1)

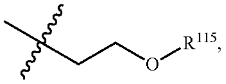

wherein $R^{115}$ represents H, $CH_2OH$, or $CH_2CH_2OH$, preferably H;

or, if p is 0, (c) partial structure (PQ3-1)

(PQ3-1)

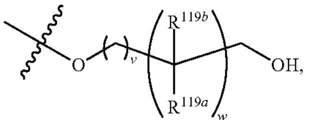

wherein v denotes 0 or 1;

w denotes 0 or 1;

$R^{119a}$ is selected from the group consisting of H and OH, and $R^{119b}$ is selected from the group consisting of H and $CH_3$.

In particular, the partial structure (QS1) represents (a) partial structure (PQ1-2) or partial structure (PQ1-3)

(PQ1-2)

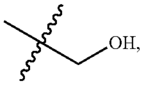

(PQ1-3)

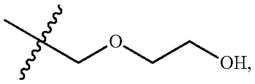

(b) partial structure (PQ2-1)

(PQ2-1)

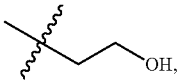

or, if p is 0, (c) partial structure (PQ3-2)

(PQ3-2)

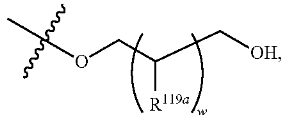

wherein w denotes 1, and $R^{119a}$ represents OH, or w denotes 0.

In a particularly preferred embodiment of the compound of formula (Q)

$R^{101}$, $R^{102}$ and $R^{103}$ are each independently selected from the group consisting of H, F, Cl, Br, $CFH_2$, $CF_2H$, $CF_3$, CN, $CH_2$—OH, $CH_2$—$OCH_3$, $OCF_3$, OH, $CH_3$, $CH_2CH_3$, $CH(CH_3)_2$, O—$CH_3$, O—$CH_2CH_3$, $NH_2$, $NH(CH_3)$, and $N(CH_3)_2$, preferably, wherein at least one of $R^{101}$, $R^{102}$ and $R^{103}$ is not H;

$R^2$ represents $CF_3$, tert.-butyl or cyclopropyl;

$R^7$ and $R^9$ are each independently selected from the group consisting of H, F, Cl, Br, $CF_3$, CN, $OCF_3$, $CH_3$, $CH_2CH_3$, $CH(CH_3)_2$, O—$CH_3$, and O—$CH_2CH_3$, preferably, wherein at least one of $R^7$ and $R^9$ is not H;

A denotes N, CH or $C(CH_3)$, and the partial structure (QS1) represents (a) $CH_2OH$ or $CH_2O$—$CH_2CH_2OH$, (b) $CH_2CH_2OH$, or (c) O—$CH_2CH_2OH$ or O—CH—CH(OH)—$CH_2OH$.

Preferred embodiments of the compound of formula (Q) have the formula (Q0-a) or (Q0-b):

(Q0-a)

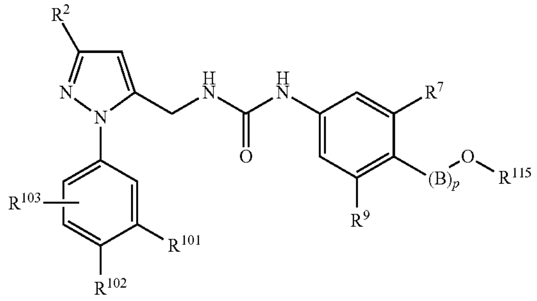

(Q0-b)

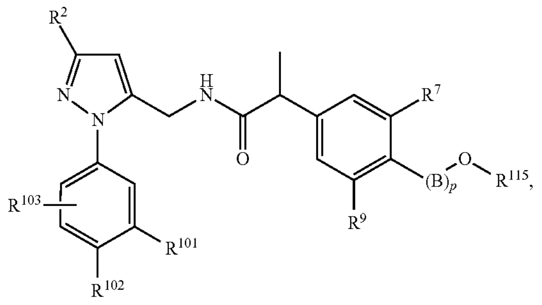

wherein the respective substituents, variables and indices have the meanings described above.

Further preferred embodiments of the compound of formula (Q) have the formula (Q1-a), (Q1-a-1) or (Q1-a-2):

(Q1-a)

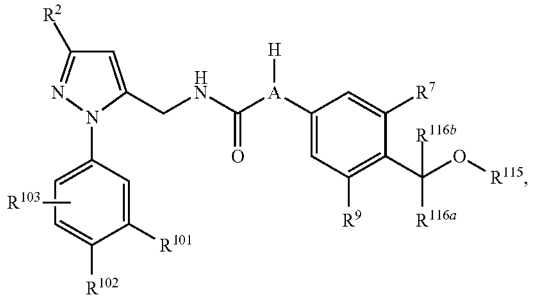

(Q1-a-1)

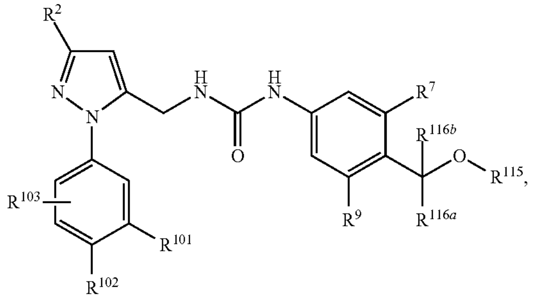

(Q1-a-2)

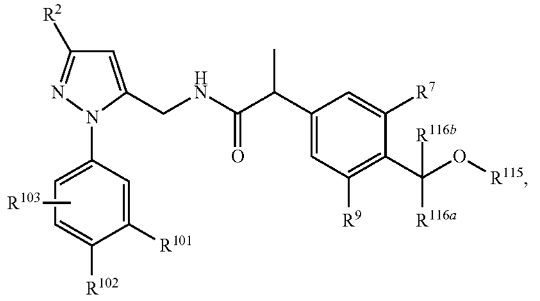

wherein the respective substituents, variables and indices have the meanings described above.

Moreover, preferred embodiments of the compound of formula (Q) have the formula (Q1-b), (Q1-b-1) or (Q1-b-2):

(Q1-b)

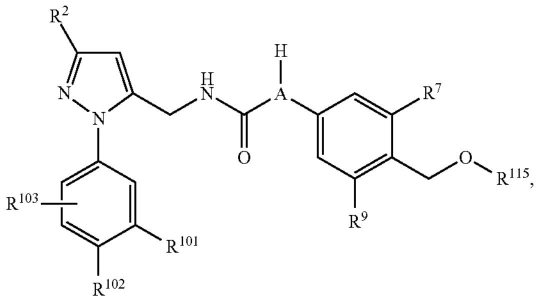

-continued (Q1-b-1)

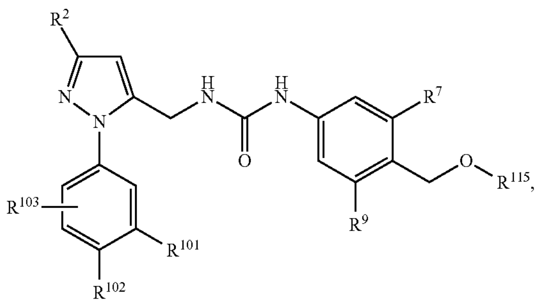

(Q1-b-2)

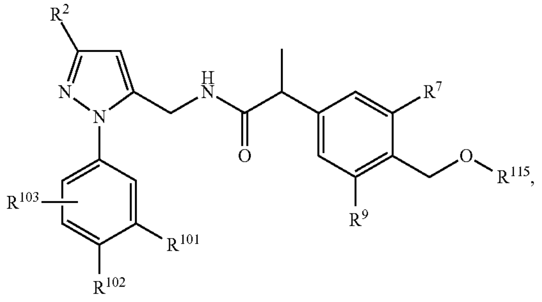

wherein the respective substituents, variables and indices have the meanings described above.

In addition, preferred embodiments of the compound of formula (Q) have the formula (Q1-c), (Q1-c-1) or (Q1-c-2):

(Q1-c)

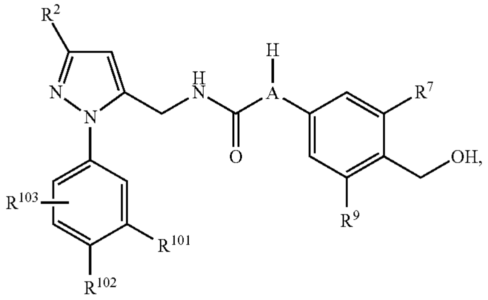

(Q1-c-1)

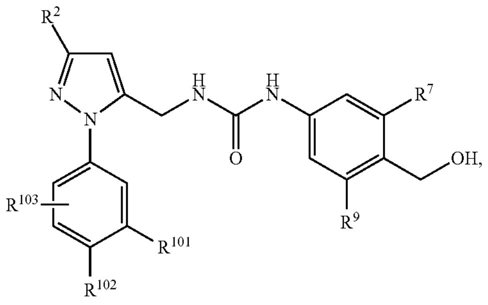

-continued (Q1-c-2)

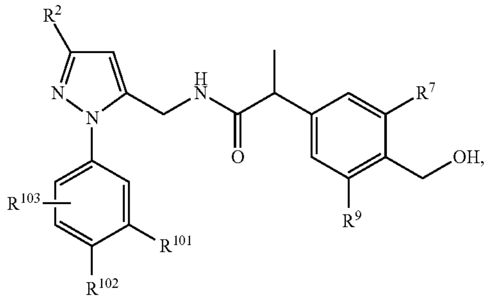

wherein the respective substituents, variables and indices have the meanings described above.

Yet further preferred embodiments of the compound of formula (Q) have the formula (Q1-d), (Q1-d-1) or (Q1-d-2):

(Q1-d)

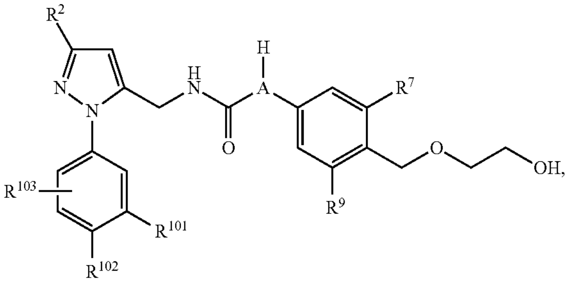

(Q1-d-1)

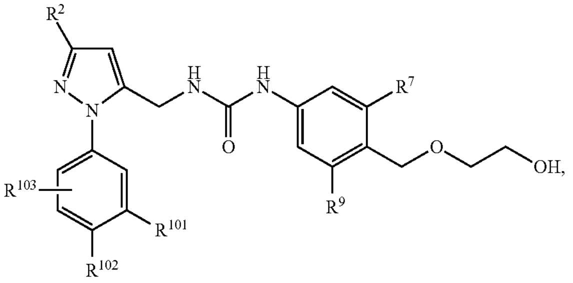

(Q1-d-2)

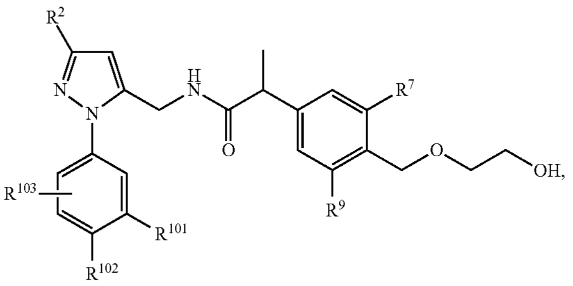

wherein the respective substituents, variables and indices have the meanings described above.

Further preferred embodiments of the compound of formula (Q) have the formula (Q2-a), (Q2-a-1) or (Q2-a-2):

(Q2-a)

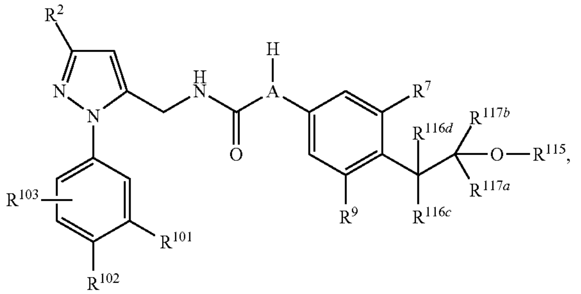

(Q2-a-1)

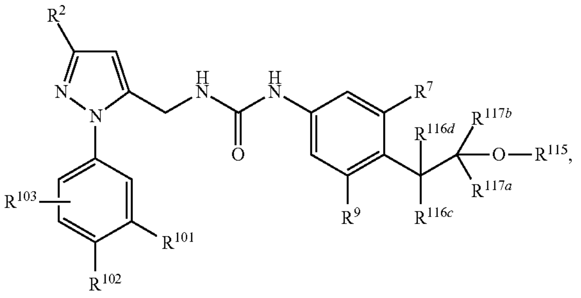

(Q2-a-2)

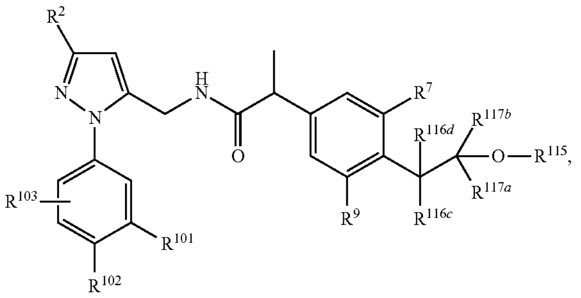

wherein the respective substituents, variables and indices have the meanings described above.

Moreover, preferred embodiments of the compound of formula (Q) have the formula (Q2-b), (Q2-b-1) or (Q2-b-2):

(Q2-b)

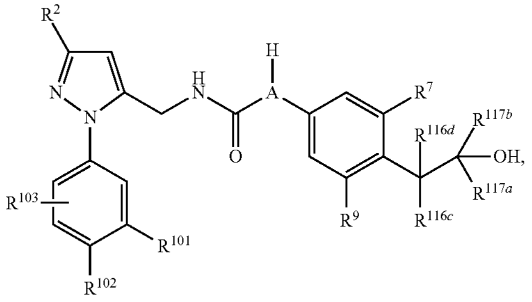

-continued (Q2-b-1)

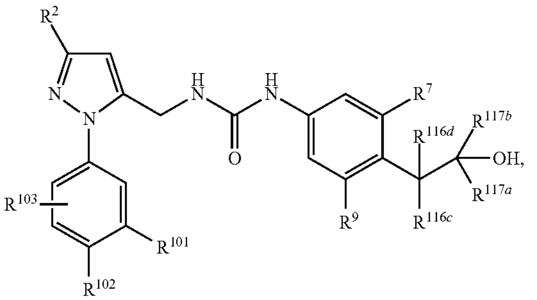

(Q2-b-2)

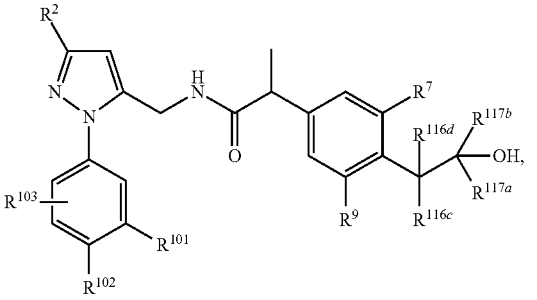

wherein the respective substituents, variables and indices have the meanings described above.

Yet further preferred embodiments of the compound of formula (Q) have the formula (Q2-c), (Q2-c-1) or (Q2-c-2):

(Q2-c)

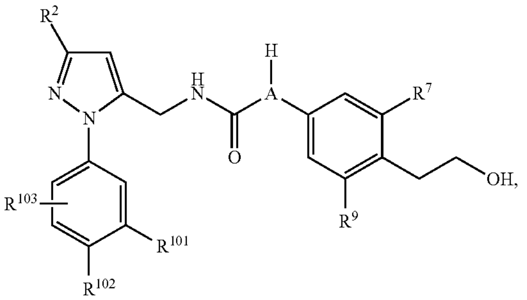

(Q2-c-1)

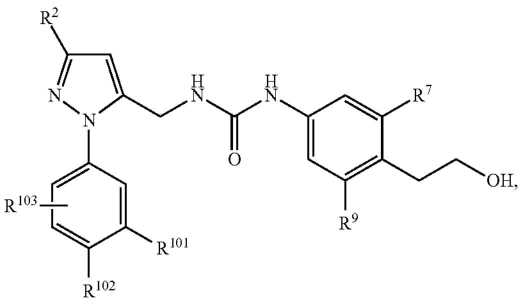

-continued (Q2-c-2)

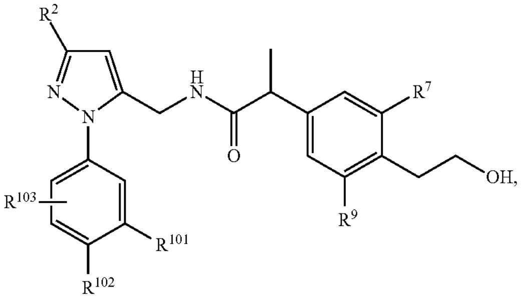

wherein the respective substituents, variables and indices have the meanings described above.

Further preferred embodiments of the compound of formula (Q) have the formula (Q3-a), (Q3-a-1) or (Q3-a-2):

(Q3-a)

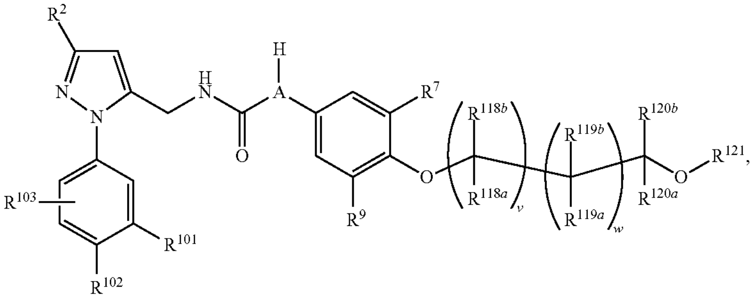

(Q3-a-1)

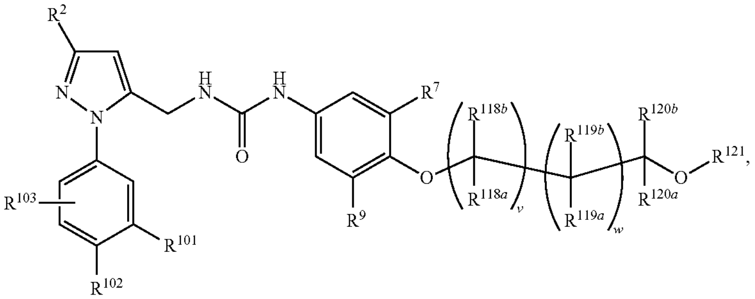

(Q3-a-2)

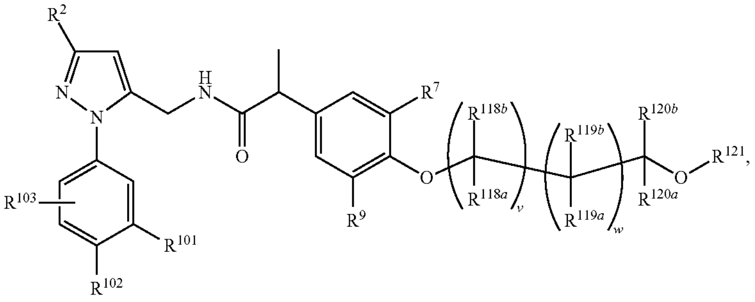

wherein the respective substituents, variables and indices have the meanings described above.

Moreover, preferred embodiments of the compound of formula (Q) have the formula (Q3-b), (Q3-b-1) or (Q3-b-2):

(Q3-b)

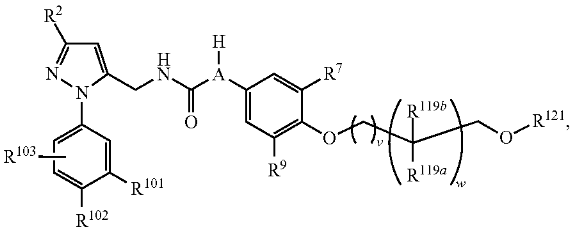

-continued (Q3-b-1)

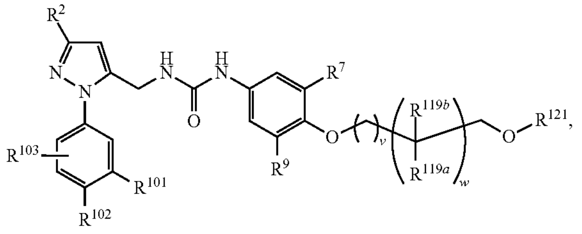

(Q3-b-2)

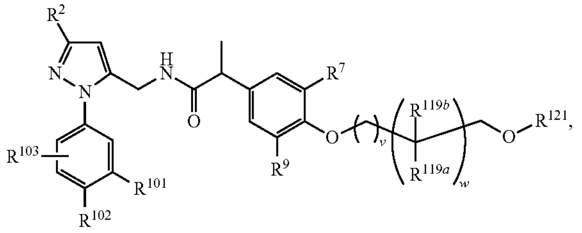

wherein the respective substituents, variable and indices have the meanings described above.

In addition, preferred embodiments of the compound of formula (Q) have the formula (Q3-c), (Q3-c-1) or (Q3-c-2):

(Q3-c)

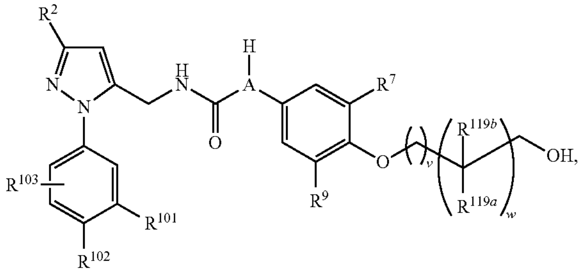

(Q3-c-1)

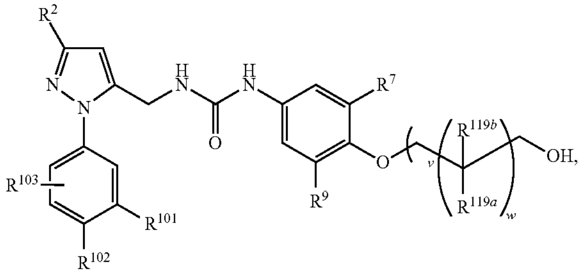

(Q3-c-2)

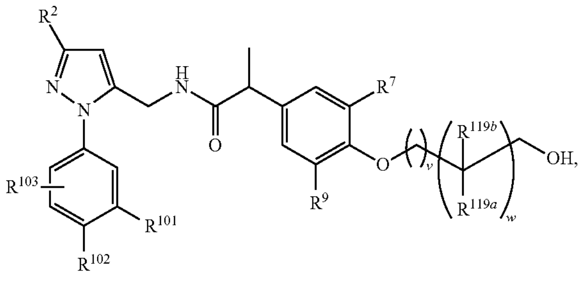

wherein the respective substituents, variables and indices have the meanings described above.

Yet further preferred embodiments of the compound of formula (Q) have the formula (Q3-d), (Q3-d-1) or (Q3-d-2):

(Q3-d)

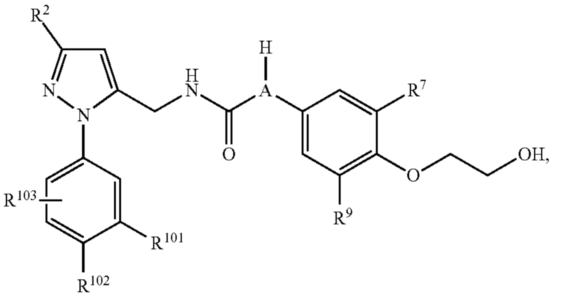

(Q3-d-1)

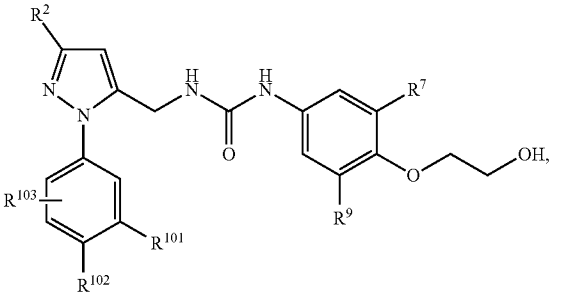

(Q3-d-2)

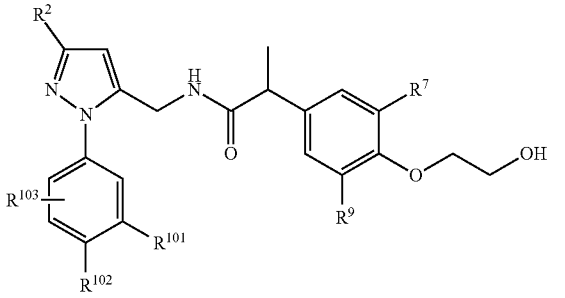

wherein the respective substituents, variables and indices have the meanings described above.

Still further preferred embodiments of the compound of formula (Q) have the formula (Q3-e), (Q3-e-1) or (Q3-e-2):

(Q3-e)

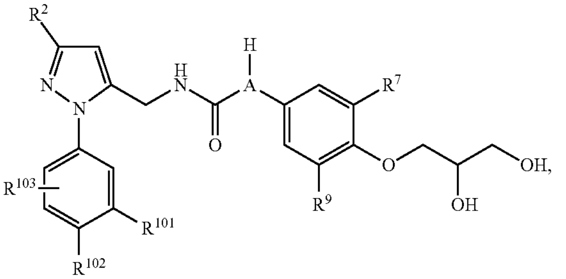

-continued (Q3-e-1)

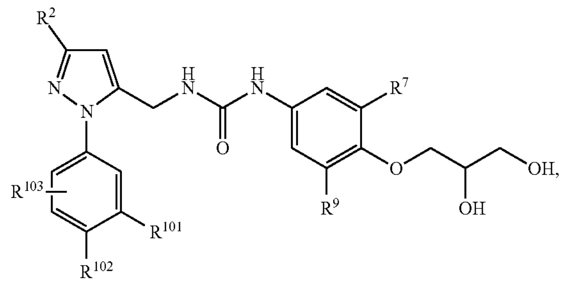

(Q3-e-2)

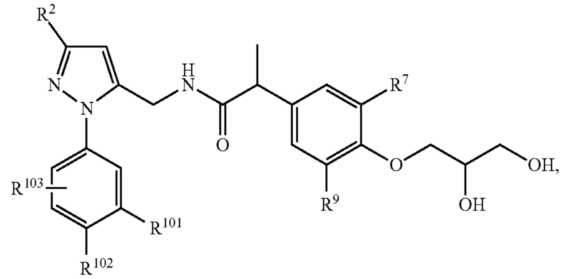

wherein the respective substituents, variables and indices have the meanings described above.

Especially preferred embodiments of the compound of formula (Q) have formula (Q1-c), (Q1-c-1), (Q1-c-2), (Q1-d), (Q1-d-1), (Q1-d-2), (Q3-d), (Q3-d-1), (Q3-d-2) (Q3-e), (Q3-e-1) or (Q3-e-2), wherein the respective substituents, variables and indices have the meanings described above.

In particularly preferred embodiments of the compound of formula (Q), $R^{101}$ in formula (Q0-a), (Q0-b), (Q1-a), (Q1-a-1), (Q1-a-2), (Q1-b), (Q1-b-1), (Q1-b-2), (Q1-c), (Q1-c-1), (Q1-c-2), (Q1-d), (Q1-d-1), (Q1-d-2), (Q2-a), (Q2-a-1), (Q2-a-2), (Q2-b), (Q2-b-1), (Q2-b-2), (Q2-c), (Q2-c-1), (Q2-c-2), (Q3-a), (Q3-a-1), (Q3-a-2), (Q3-b), (Q3-b-1), (Q3-b-2), (Q3-c), (Q3-c-1), (Q3-c-2), (Q3-d), (Q3-d-1), (Q3-d-2), (Q3-e), (Q3-e-1) or (Q3-e-2) represents F, Cl, $CF_3$ or O—$CH_3$, preferably F or Cl, most preferably Cl—preferably when $R^{103}$ is H and $R^{102}$ represents H, F, Cl, $CF_3$ or $OCH_3$, more preferably when $R^{103}$ is H and $R^{102}$ represents H, F or Cl, even more preferably when both $R^{102}$ and $R^{103}$ denote H—, and the remaining substituents, variables and indices have the meanings described above.

In further particularly preferred embodiments of the compound of formula (Q), in a compound of formula (Q1-b), (Q1-b-1) or (Q1-b-2),
A denotes N or $C(CH_3)$,
$R^{101}$ denotes F, Cl or $OCH_3$,
$R^{102}$ denotes H or F,
$R^{103}$ denotes H,
$R^2$ represents $CF_3$, tert.-butyl, or cyclopropyl,
$R^7$ denotes H or F,
$R^9$ represents H, and
$R^{115}$ denotes H or $CH_2CH_2OH$.

In further particularly preferred embodiments of the compound of formula (Q), in a compound of formula (Q3-b), (Q3-b-1) or (Q3-b-2),
A denotes N or $C(CH_3)$,
$R^{101}$ denotes F, Cl or $OCH_3$,
$R^{102}$ denotes H or F,
$R^{103}$ denotes H,
$R^2$ represents $CF_3$, tert.-butyl, or cyclopropyl,
$R^7$ denotes H or F,
$R^9$ represents H,
$R^{119a}$ denotes H or OH
$R^{119b}$ denotes H,
v denotes 0 or 1,
w denotes 0 or 1, and
$R^{121}$ denotes H.

Particularly preferred compounds of formula (Q) are selected from the group consisting of:

A1 N-[[5-tert-Butyl-2-(3-chlorophenyl)-2H-pyrazol-3-yl]-methyl]-2-(3,5-difluoro-4-methoxy-phenyl)-acetamide;
A2 N-[[2-(3-Chlorophenyl)-5-(trifluoromethyl)-2H-pyrazol-3-yl]-methyl]-2-(3,5-difluoro-4-methoxy-phenyl)-acetamide;
A3 N-[[2-(3-Chlorophenyl)-5-cyclopropyl-2H-pyrazol-3-yl]-methyl]-2-(3,5-difluoro-4-methoxy-phenyl)-propionamide;
A4 N-[[5-tert-Butyl-2-(3-chlorophenyl)-2H-pyrazol-3-yl]-methyl]-2-(3,5-difluoro-4-methoxy-phenyl)-propionamide;
A5 N-[[5-tert-Butyl-2-(3-chloro-4-fluoro-phenyl)-2H-pyrazol-3-yl]-methyl]-2-(3,5-difluoro-4-methoxy-phenyl)-propionamide;
A6 N-[[5-tert-Butyl-2-(3-chloro-4-fluoro-phenyl)-2H-pyrazol-3-yl]-methyl]-2-(3,5-difluoro-4-methoxy-phenyl)-acetamide;
A7 N-[[2-(3-Chloro-4-fluoro-phenyl)-5-(trifluoromethyl)-2H-pyrazol-3-yl]-methyl]-2-(3,5-difluoro-4-methoxy-phenyl)-acetamide;
A8 1-[[2-(3-Chlorophenyl)-5-(trifluoromethyl)-2H-pyrazol-3-yl]-methyl]-3-(3,5-difluoro-4-methoxy-phenyl)-urea;
A9 N-[[2-(3-Chloro-4-fluoro-phenyl)-5-(trifluoromethyl)-2H-pyrazol-3-yl]-methyl]-2-(3,5-difluoro-4-methoxy-phenyl)-propionamide;
A10 N-[[2-(3-Chlorophenyl)-5-(trifluoromethyl)-2H-pyrazol-3-yl]-methyl]-2-(3,5-difluoro-4-hydroxy-phenyl)-propionamide;
A11 1-[[5-tert-Butyl-2-(3-chlorophenyl)-2H-pyrazol-3-yl]-methyl]-3-(3,5-difluoro-4-hydroxy-phenyl)-urea;
A12 1-[[2-(3-Chlorophenyl)-5-(trifluoromethyl)-2H-pyrazol-3-yl]-methyl]-3-(3,5-difluoro-4-hydroxy-phenyl)-urea;
A13 1-[[5-tert-Butyl-2-(3-chlorophenyl)-2H-pyrazol-3-yl]-methyl]-3-(3,4-dim ethoxyphenyl)-urea;
A14 1-[[2-(3-Chlorophenyl)-5-(trifluoromethyl)-2H-pyrazol-3-yl]-methyl]-3-(3,4-dimethoxyphenyl)-urea;
A15 1-[[2-(3-Chlorophenyl)-5-(trifluoromethyl)-2H-pyrazol-3-yl]-methyl]-3-(4-hydroxy-3-methoxy-phenyl)-urea;
A16 1-[[2-(3-Chlorophenyl)-5-(trifluoromethyl)-2H-pyrazol-3-yl]-methyl]-3-(3-hydroxy-4-methoxy-phenyl)-urea;
A17 1-[[5-tert-Butyl-2-(3-chlorophenyl)-2H-pyrazol-3-yl]-methyl]-3-[3-fluoro-4-(2-methoxy-ethoxy)-phenyl]-urea;
A18 1-[[2-(3-Chlorophenyl)-5-(trifluoromethyl)-2H-pyrazol-3-yl]-methyl]-3-[3-fluoro-4-(2-methoxy-ethoxy)-phenyl]-urea;
A19 1-[[5-tert-Butyl-2-(3-chlorophenyl)-2H-pyrazol-3-yl]-methyl]-3-[3-fluoro-4-(2-hydroxy-ethoxy)-phenyl]-urea;
A20 1-[[2-(3-Chlorophenyl)-5-(trifluoromethyl)-2H-pyrazol-3-yl]-methyl]-3-[3-fluoro-4-(2-hydroxy-ethoxy)-phenyl]-urea;
A21 1-[3-Fluoro-4-(2-hydroxy-ethoxy)-phenyl]-3-[[2-(3-fluorophenyl)-5-(trifluoromethyl)-2H-pyrazol-3-yl]-methyl]-urea;
A22 1-[[2-(3-Chloro-4-fluoro-phenyl)-5-(trifluoromethyl)-2H-pyrazol-3-yl]-methyl]-3-[3-fluoro-4-(2-hydroxy-ethoxy)-phenyl]-urea;

A23 1-[[2-(3-Chlorophenyl)-5-(trifluoromethyl)-2H-pyrazol-3-yl]-methyl]-3-[4-(2,3-dihydroxy-propoxy)-phenyl]-urea;

A24 1-[[5-tert-Butyl-2-(3-chlorophenyl)-2H-pyrazol-3-yl]-methyl]-3-[4-(2,3-dihydroxy-propoxy)-3-fluoro-phenyl]-urea;

A25 1-[[2-(3-Chlorophenyl)-5-(trifluoromethyl)-2H-pyrazol-3-yl]-methyl]-3-[4-(2,3-dihydroxy-propoxy)-3-fluoro-phenyl]-urea;

A26 1-[4-(2,3-Dihydroxy-propoxy)-phenyl]-3-[[2-(3-fluorophenyl)-5-(trifluoromethyl)-2H-pyrazol-3-yl]-methyl]-urea;

A27 1-[[5-tert-Butyl-2-(3-chlorophenyl)-2H-pyrazol-3-yl]-methyl]-3-[4-(hydroxymethyl)-phenyl]-urea;

A28 1-[[2-(3-Chlorophenyl)-5-(trifluoromethyl)-2H-pyrazol-3-yl]-methyl]-3-[4-(hydroxymethyl)-phenyl]-urea;

A29 N-[[5-tert-Butyl-2-(3-chlorophenyl)-2H-pyrazol-3-yl]-methyl]-2-[3-fluoro-4-(hydroxymethyl)-phenyl]-acetamide;

A30 N-[[2-(3-Chlorophenyl)-5-(trifluoromethyl)-2H-pyrazol-3-yl]-methyl]-2-[3-fluoro-4-(hydroxymethyl)-phenyl]-acetamide A31 N-[[2-(3-Chlorophenyl)-5-cyclopropyl-2H-pyrazol-3-yl]-methyl]-2-[3-fluoro-4-(hydroxymethyl)-phenyl]-propionamide;

A32 N-[[5-tert-Butyl-2-(3-chlorophenyl)-2H-pyrazol-3-yl]-methyl]-2-[3-fluoro-4-(hydroxymethyl)-phenyl]-propionamide;

A33 N-[[2-(3-Chlorophenyl)-5-(trifluoromethyl)-2H-pyrazol-3-yl]-methyl]-2-[3-fluoro-4-(hydroxymethyl)-phenyl]-propionamide;

A34 (2S)—N-[[2-(3-Chlorophenyl)-5-(trifluoromethyl)-2H-pyrazol-3-yl]-methyl]-2-[3-fluoro-4-(hydroxymethyl)-phenyl]-propionamide;

A35 (2R)—N-[[2-(3-Chlorophenyl)-5-(trifluoromethyl)-2H-pyrazol-3-yl]-methyl]-2-[3-fluoro-4-(hydroxymethyl)-phenyl]-propionamide;

A36 2-[3-Chloro-4-(hydroxymethyl)-phenyl]-N-[[2-(3-chlorophenyl)-5-(trifluoromethyl)-2H-pyrazol-3-yl]-methyl]-propionamide;

A37 N-[[5-tert-Butyl-2-(3-fluorophenyl)-2H-pyrazol-3-yl]-methyl]-2-[3-fluoro-4-(hydroxymethyl)-phenyl]-propionamide;

A38 2-[3-Fluoro-4-(hydroxymethyl)-phenyl]-N-[[2-(3-fluorophenyl)-5-(trifluoromethyl)-2H-pyrazol-3-yl]-methyl]-propionamide;

A39 N-[[5-tert-Butyl-2-(3,4-difluoro-phenyl)-2H-pyrazol-3-yl]-methyl]-2-[3-fluoro-4-(hydroxymethyl)-phenyl]-propionamide;

A40 N-[[2-(3,4-Difluoro-phenyl)-5-(trifluoromethyl)-2H-pyrazol-3-yl]-methyl]-2-[3-fluoro-4-(hydroxymethyl)-phenyl]-propionamide;

A41 N-[[5-tert-Butyl-2-(3-chloro-4-fluoro-phenyl)-2H-pyrazol-3-yl]-methyl]-2-[3-fluoro-4-(hydroxymethyl)-phenyl]-propionamide;

A42 N-[[2-(3-Chloro-4-fluoro-phenyl)-5-(trifluoromethyl)-2H-pyrazol-3-yl]-methyl]-2-[3-fluoro-4-(hydroxymethyl)-phenyl]-propionamide;

A43 2-[3-Fluoro-4-(hydroxymethyl)-phenyl]-N-[[2-(3-methoxyphenyl)-5-(trifluoromethyl)-2H-pyrazol-3-yl]-methyl]-propionamide;

A44 2-[3-Fluoro-4-(hydroxymethyl)-phenyl]-N-[[2-(3-isopropyl-phenyl)-5-(trifluoromethyl)-2H-pyrazol-3-yl]-methyl]-propionamide;

A45 N-[[5-tert-Butyl-2-(4-fluorophenyl)-2H-pyrazol-3-yl]-methyl]-2-[3-fluoro-4-(hydroxymethyl)-phenyl]-propionamide;

A46 2-[3-Fluoro-4-(hydroxymethyl)-phenyl]-N-[[2-(4-fluorophenyl)-5-(trifluoromethyl)-2H-pyrazol-3-yl]-methyl]-propionamide;

A47 N-[[5-tert-Butyl-2-[3-(trifluoromethyl)phenyl]-2H-pyrazol-3-yl]-methyl]-2-[3-fluoro-4-(hydroxymethyl)-phenyl]-propionamide;

A48 2-[3-Fluoro-4-(hydroxymethyl)-phenyl]-N-[[5-(trifluoromethyl)-2-[3-(trifluoromethyl)phenyl]-2H-pyrazol-3-yl]-methyl]-propionamide;

A49 N-[[5-tert-Butyl-2-(3-chlorophenyl)-2H-pyrazol-3-yl]-methyl]-2-[4-(hydroxymethyl)-3-methoxy-phenyl]-propionamide;

A50 N-[[2-(3-Chlorophenyl)-5-(trifluoromethyl)-2H-pyrazol-3-yl]-methyl]-2-[4-(hydroxymethyl)-3-methoxy-phenyl]-propionamide;

A51 N-[[5-tert-Butyl-2-(3-chlorophenyl)-2H-pyrazol-3-yl]-methyl]-2-[3-chloro-4-(hydroxymethyl)-phenyl]-propionamide;

A52 N-[[2-(3-Chlorophenyl)-5-(trifluoromethyl)-2H-pyrazol-3-yl]-methyl]-2-[3,5-difluoro-4-(hydroxymethyl)-phenyl]-propionamide;

A53 1-[[2-(3-Chlorophenyl)-5-cyclopropyl-2H-pyrazol-3-yl]-methyl]-3-[3-fluoro-4-(hydroxymethyl)-phenyl]-urea;

A54 1-[[5-tert-Butyl-2-(3-fluorophenyl)-2H-pyrazol-3-yl]-methyl]-3-[3-fluoro-4-(hydroxymethyl)-phenyl]-urea;

A55 1-[[5-tert-Butyl-2-(3-chlorophenyl)-2H-pyrazol-3-yl]-methyl]-3-[3-fluoro-4-(hydroxymethyl)-phenyl]-urea;

A56 1-[[5-tert-Butyl-2-(m-tolyl)-2H-pyrazol-3-yl]-methyl]-3-[3-fluoro-4-(hydroxymethyl)-phenyl]-urea;

A57 1-[[5-tert-Butyl-2-(3,4-difluoro-phenyl)-2H-pyrazol-3-yl]-methyl]-3-[3-fluoro-4-(hydroxymethyl)-phenyl]-urea;

A58 1-[3-Fluoro-4-(hydroxymethyl)-phenyl]-3-[[2-phenyl-5-(trifluoromethyl)-2H-pyrazol-3-yl]-methyl]-urea;

A59 1-[[2-(3-Chlorophenyl)-5-(trifluoromethyl)-2H-pyrazol-3-yl]-methyl]-3-[3-fluoro-4-(hydroxymethyl)-phenyl]-urea;

A60 1-[[2-(4-Chlorophenyl)-5-(trifluoromethyl)-2H-pyrazol-3-yl]-methyl]-3-[3-fluoro-4-(hydroxymethyl)-phenyl]-urea;

A61 1-[3-Fluoro-4-(hydroxymethyl)-phenyl]-3-[[2-(2-fluorophenyl)-5-(trifluoromethyl)-2H-pyrazol-3-yl]-methyl]-urea;

A62 1-[3-Fluoro-4-(hydroxymethyl)-phenyl]-3-[[2-(3-fluorophenyl)-5-(trifluoromethyl)-2H-pyrazol-3-yl]-methyl]-urea;

A63 1-[3-Fluoro-4-(hydroxymethyl)-phenyl]-3-[[2-(4-fluorophenyl)-5-(trifluoromethyl)-2H-pyrazol-3-yl]-methyl]-urea;

A64 1-[[2-(3,4-Difluoro-phenyl)-5-(trifluoromethyl)-2H-pyrazol-3-yl]-methyl]-3-[3-fluoro-4-(hydroxymethyl)-phenyl]-urea;

A65 1-[[2-(3-Chloro-4-fluoro-phenyl)-5-(trifluoromethyl)-2H-pyrazol-3-yl]-methyl]-3-[3-fluoro-4-(hydroxymethyl)-phenyl]-urea;

A66 1-[[2-(3,5-Difluoro-phenyl)-5-(trifluoromethyl)-2H-pyrazol-3-yl]-methyl]-3-[3-fluoro-4-(hydroxymethyl)-phenyl]-urea;

A67 1-[3-Fluoro-4-(hydroxymethyl)-phenyl]-3-[[2-(3-methoxyphenyl)-5-(trifluoromethyl)-2H-pyrazol-3-yl]-methyl]-urea;

A68 1-[3-Fluoro-4-(hydroxymethyl)-phenyl]-3-[[2-(4-methoxyphenyl)-5-(trifluoromethyl)-2H-pyrazol-3-yl]-methyl]-urea;

A69 1-[3-Fluoro-4-(hydroxymethyl)-phenyl]-3-[[2-(o-tolyl)-5-(trifluoromethyl)-2H-pyrazol-3-yl]-methyl]-urea;

A70 1-[3-Fluoro-4-(hydroxymethyl)-phenyl]-3-[[2-(m-tolyl)-5-(trifluoromethyl)-2H-pyrazol-3-yl]-methyl]-urea;

A71 1-[3-Fluoro-4-(hydroxymethyl)-phenyl]-3-[[2-(p-tolyl)-5-(trifluoromethyl)-2H-pyrazol-3-yl]-methyl]-urea;

A72 1-[[2-(2,3-Dimethyl-phenyl)-5-(trifluoromethyl)-2H-pyrazol-3-yl]-methyl]-3-[3-fluoro-4-(hydroxymethyl)-phenyl]-urea;

A73 1-[[2-(3,5-Dimethyl-phenyl)-5-(trifluoromethyl)-2H-pyrazol-3-yl]-methyl]-3-[3-fluoro-4-(hydroxymethyl)-phenyl]-urea;

A74 1-[[2-(2,5-Dimethyl-phenyl)-5-(trifluoromethyl)-2H-pyrazol-3-yl]-methyl]-3-[3-fluoro-4-(hydroxymethyl)-phenyl]-urea;

A75 1-[[2-(3,4-Dimethyl-phenyl)-5-(trifluoromethyl)-2H-pyrazol-3-yl]-methyl]-3-[3-fluoro-4-(hydroxymethyl)-phenyl]-urea;

A76 1-[3-Fluoro-4-(hydroxymethyl)-phenyl]-3-[[2-(2-fluoro-3-methyl-phenyl)-5-(trifluoromethyl)-2H-pyrazol-3-yl]-methyl]-urea;

A77 1-[3-Fluoro-4-(hydroxymethyl)-phenyl]-3-[[2-(3-fluoro-5-methyl-phenyl)-5-(trifluoromethyl)-2H-pyrazol-3-yl]-methyl]-urea;

A78 1-[[2-(4-Chloro-3-methyl-phenyl)-5-(trifluoromethyl)-2H-pyrazol-3-yl]-methyl]-3-[3-fluoro-4-(hydroxymethyl)-phenyl]-urea;

A79 1-[[2-(4-Ethoxy-3-methyl-phenyl)-5-(trifluoromethyl)-2H-pyrazol-3-yl]-methyl]-3-[3-fluoro-4-(hydroxymethyl)-phenyl]-urea;

A80 1-[3-Fluoro-4-(hydroxymethyl)-phenyl]-3-[[2-(4-fluoro-3-methyl-phenyl)-5-(trifluoromethyl)-2H-pyrazol-3-yl]-methyl]-urea;

A81 1-[[2-(4-Cyano-3-methyl-phenyl)-5-(trifluoromethyl)-2H-pyrazol-3-yl]-methyl]-3-[3-fluoro-4-(hydroxymethyl)-phenyl]-urea;

A82 1-[3-Fluoro-4-(hydroxymethyl)-phenyl]-3-[[2-(3-isopropyl-phenyl)-5-(trifluoromethyl)-2H-pyrazol-3-yl]-methyl]-urea;

A83 1-[[2-[3-(Difluoro-methyl)-phenyl]-5-(trifluoromethyl)-2H-pyrazol-3-yl]-methyl]-3-[3-fluoro-4-(hydroxymethyl)-phenyl]-urea;

A84 1-[3-Fluoro-4-(hydroxymethyl)-phenyl]-3-[[2-[3-(methoxymethyl)-phenyl]-5-(trifluoromethyl)-2H-pyrazol-3-yl]-methyl]-urea;

A85 1-[[2-(3-Cyano-phenyl)-5-(trifluoromethyl)-2H-pyrazol-3-yl]-methyl]-3-[3-fluoro-4-(hydroxymethyl)-phenyl]-urea;

A86 1-[[2-(3-Dimethylamino-phenyl)-5-(trifluoromethyl)-2H-pyrazol-3-yl]-methyl]-3-[3-fluoro-4-(hydroxymethyl)-phenyl]-urea;

A87 1-[3-Fluoro-4-(hydroxymethyl)-phenyl]-3-[[2-(4-methoxy-3-methyl-phenyl)-5-(trifluoromethyl)-2H-pyrazol-3-yl]-methyl]-urea;

A88 1-[[2-(2-Ethoxy-5-methyl-phenyl)-5-(trifluoromethyl)-2H-pyrazol-3-yl]-methyl]-3-[3-fluoro-4-(hydroxymethyl)-phenyl]-urea;

A89 1-[[2-(2,3-Dichloro-phenyl)-5-(trifluoromethyl)-2H-pyrazol-3-yl]-methyl]-3-[3-fluoro-4-(hydroxymethyl)-phenyl]-urea;

A90 1-[[2-(3-Chloro-2-methoxy-phenyl)-5-(trifluoromethyl)-2H-pyrazol-3-yl]-methyl]-3-[3-fluoro-4-(hydroxymethyl)-phenyl]-urea;

A91 1-[[2-(5-Chloro-2-methoxy-phenyl)-5-(trifluoromethyl)-2H-pyrazol-3-yl]-methyl]-3-[3-fluoro-4-(hydroxymethyl)-phenyl]-urea;

A92 1-[3-Fluoro-4-(hydroxymethyl)-phenyl]-3-[[2-(3-m ethoxy-5-methyl-phenyl)-5-(trifluoromethyl)-2H-pyrazol-3-yl]-methyl]-urea;

A93 1-[[2-(3-Ethoxy-5-methyl-phenyl)-5-(trifluoromethyl)-2H-pyrazol-3-yl]-methyl]-3-[3-fluoro-4-(hydroxymethyl)-phenyl]-urea;

A94 1-[3-Fluoro-4-(hydroxymethyl)-phenyl]-3-[[2-(2-methoxy-3-methyl-phenyl)-5-(trifluoromethyl)-2H-pyrazol-3-yl]-methyl]-urea;

A95 1-[3-Fluoro-4-(hydroxymethyl)-phenyl]-3-[[2-(3-fluoro-4-m ethoxy-phenyl)-5-(trifluoromethyl)-2H-pyrazol-3-yl]-methyl]-urea;

A96 1-[[5-tert-Butyl-2-(3-chlorophenyl)-2H-pyrazol-3-yl]-methyl]-3-[3-chloro-4-(hydroxymethyl)-phenyl]-urea;

A97 1-[3-Chloro-4-(hydroxymethyl)-phenyl]-3-[[2-(3-chlorophenyl)-5-(trifluoromethyl)-2H-pyrazol-3-yl]-methyl]-urea;

A98 N-[[5-tert-Butyl-2-(3-chlorophenyl)-2H-pyrazol-3-yl]-methyl]-2-[3-fluoro-4-(1-hydroxy-ethyl)-phenyl]-propionamide;

A99 N-[[2-(3-Chlorophenyl)-5-(trifluoromethyl)-2H-pyrazol-3-yl]-methyl]-2-[3-fluoro-4-(1-hydroxy-ethyl)-phenyl]-propionamide;

A100 N-[[5-tert-Butyl-2-(3-chlorophenyl)-2H-pyrazol-3-yl]-methyl]-2-[3-fluoro-4-(1-hydroxy-cyclopropyl)-phenyl]-propionamide;

A101 N-[[2-(3-Chlorophenyl)-5-(trifluoromethyl)-2H-pyrazol-3-yl]-methyl]-2-[3-fluoro-4-(1-hydroxy-cyclopropyl)-phenyl]-propionamide;

A102 2-[3-Fluoro-4-(1-hydroxy-cyclopropyl)-phenyl]-N-[[2-(3-fluorophenyl)-5-(trifluoromethyl)-2H-pyrazol-3-yl]-methyl]-propionamide;

A103 2-[3-Fluoro-4-(1-hydroxy-cyclopropyl)-phenyl]-N-[[2-(3-methoxyphenyl)-5-(trifluoromethyl)-2H-pyrazol-3-yl]-methyl]-propionamide;

A104 N-[[2-(3,4-Difluoro-phenyl)-5-(trifluoromethyl)-2H-pyrazol-3-yl]-methyl]-2-[3-fluoro-4-(1-hydroxy-cyclopropyl)-phenyl]-propionamide;

A105 1-[[5-tert-Butyl-2-(3-chlorophenyl)-2H-pyrazol-3-yl]-methyl]-3-[3-fluoro-4-(1-hydroxy-cyclopropyl)-phenyl]-urea;

A106 1-[[2-(3-Chlorophenyl)-5-(trifluoromethyl)-2H-pyrazol-3-yl]-methyl]-3-[3-fluoro-4-(1-hydroxy-cyclopropyl)-phenyl]-urea;

A107 1-[[5-tert-Butyl-2-(3-chlorophenyl)-2H-pyrazol-3-yl]-methyl]-3-[4-(3-hydroxy-oxetan-3-yl)-phenyl]-urea;

A108 1-[[2-(3-Chlorophenyl)-5-(trifluoromethyl)-2H-pyrazol-3-yl]-methyl]-3-[4-(3-hydroxy-oxetan-3-yl)-phenyl]-urea;

A109 1-[[5-tert-Butyl-2-(3-chlorophenyl)-2H-pyrazol-3-yl]-methyl]-3-[3-fluoro-4-(3-hydroxy-oxetan-3-yl)-phenyl]-urea;

A110 1-[[2-(3-Chlorophenyl)-5-(trifluoromethyl)-2H-pyrazol-3-yl]-methyl]-3-[3-fluoro-4-(3-hydroxy-oxetan-3-yl)-phenyl]-urea;

A111 N-[[2-(3-Chlorophenyl)-5-(trifluoromethyl)-2H-pyrazol-3-yl]-methyl]-2-[3-fluoro-4-(2-methoxy-ethoxy-methyl)-phenyl]-propionamide;

A112 N-[[2-(3-Chloro-4-fluoro-phenyl)-5-(trifluoromethyl)-2H-pyrazol-3-yl]-methyl]-2-[3-fluoro-4-(2-methoxy-ethoxy-methyl)-phenyl]-propionamide;

A113 N-[[2-(3-Chlorophenyl)-5-(trifluoromethyl)-2H-pyrazol-3-yl]-methyl]-2-[3-fluoro-4-(2-hydroxy-ethoxy-methyl)-phenyl]-acetamide;

A114 2-[3-Fluoro-4-(2-hydroxy-ethoxy-methyl)-phenyl]-N-[[2-(3-methoxyphenyl)-5-(trifluoromethyl)-2H-pyrazol-3-yl]-methyl]-propionamide;

A115 2-[3-Fluoro-4-(2-hydroxy-ethoxy-methyl)-phenyl]-N-[[2-(3-isopropyl-phenyl)-5-(trifluoromethyl)-2H-pyrazol-3-yl]-methyl]-propionamide;

A116 N-[[5-tert-Butyl-2-(3-fluorophenyl)-2H-pyrazol-3-yl]-methyl]-2-[3-fluoro-4-(2-hydroxy-ethoxy-methyl)-phenyl]-propionamide;

A117 N-[[5-tert-Butyl-2-(3-chlorophenyl)-2H-pyrazol-3-yl]-methyl]-2-[3-fluoro-4-(2-hydroxy-ethoxy-methyl)-phenyl]-propionamide;

A118 N-[[2-(3-Chlorophenyl)-5-(trifluoromethyl)-2H-pyrazol-3-yl]-methyl]-2-[3-fluoro-4-(2-hydroxy-ethoxy-methyl)-phenyl]-propionamide;

A119 (2S)—N-[[2-(3-Chlorophenyl)-5-(trifluoromethyl)-2H-pyrazol-3-yl]-methyl]-2-[3-fluoro-4-(2-hydroxy-ethoxy-methyl)-phenyl]-propionamide;

A120 (2R)—N-[[2-(3-Chlorophenyl)-5-(trifluoromethyl)-2H-pyrazol-3-yl]-methyl]-2-[3-fluoro-4-(2-hydroxy-ethoxy-methyl)-phenyl]-propionamide;

A121 N-[[2-(3-Chloro-4-fluoro-phenyl)-5-(trifluoromethyl)-2H-pyrazol-3-yl]-methyl]-2-[3-fluoro-4-(2-hydroxy-ethoxy-methyl)-phenyl]-propionamide;

A122 2-[3-Fluoro-4-(2-hydroxy-ethoxy-methyl)-phenyl]-N-[[2-(3-fluorophenyl)-5-(trifluoromethyl)-2H-pyrazol-3-yl]-methyl]-propionamide;

A123 2-[3-Fluoro-4-(2-hydroxy-ethoxy-methyl)-phenyl]-N-[[2-(m-tolyl)-5-(trifluoromethyl)-2H-pyrazol-3-yl]-methyl]-propionamide;

A124 N-[[5-tert-Butyl-2-(4-fluorophenyl)-2H-pyrazol-3-yl]-methyl]-2-[3-fluoro-4-(2-hydroxy-ethoxy-methyl)-phenyl]-propionamide;

A125 N-[[5-tert-Butyl-2-[3-(trifluoromethyloxy)-phenyl]-2H-pyrazol-3-yl]-methyl]-2-[3-fluoro-4-(2-hydroxy-ethoxy-methyl)-phenyl]-propionamide;

A126 N-[[2-(3,5-Difluoro-phenyl)-5-(trifluoromethyl)-2H-pyrazol-3-yl]-methyl]-2-[3-fluoro-4-(2-hydroxy-ethoxy-methyl)-phenyl]-propionamide;

A127 1-[[2-(3-Chlorophenyl)-5-(trifluoromethyl)-2H-pyrazol-3-yl]-methyl]-3-[3-fluoro-4-(2-hydroxy-ethoxy-methyl)-phenyl]-urea;

A128 1-[[2-(3-Chlorophenyl)-5-(trifluoromethyl)-2H-pyrazol-3-yl]-methyl]-3-[3-fluoro-4-(2-methoxy-ethoxy-methyl)-phenyl]-urea;

A129 1-[[5-tert-Butyl-2-(3-chlorophenyl)-2H-pyrazol-3-yl]-methyl]-3-[3-fluoro-4-(2-hydroxy-ethoxy-methyl)-phenyl]-urea;

A130 1-[[2-(3-Chloro-4-fluoro-phenyl)-5-(trifluoromethyl)-2H-pyrazol-3-yl]-methyl]-3-[3-fluoro-4-(2-hydroxy-ethoxy-methyl)-phenyl]-urea;

A131 1-[3-Fluoro-4-(2-hydroxy-ethoxy-methyl)-phenyl]-3-[[2-(3-fluorophenyl)-5-(trifluoromethyl)-2H-pyrazol-3-yl]-methyl]-urea;

A132 1-[[2-(3,4-Difluoro-phenyl)-5-(trifluoromethyl)-2H-pyrazol-3-yl]-methyl]-3-[3-fluoro-4-(2-hydroxy-ethoxy-methyl)-phenyl]-urea;

A133 1-[[2-(2,3-Dichloro-phenyl)-5-(trifluoromethyl)-2H-pyrazol-3-yl]-methyl]-3-[3-fluoro-4-(2-hydroxy-ethoxy-methyl)-phenyl]-urea;

A134 1-[[5-tert-Butyl-2-(4-fluorophenyl)-2H-pyrazol-3-yl]-methyl]-3-[3-fluoro-4-(2-hydroxy-ethoxy-methyl)-phenyl]-urea;

A135 1-[[2-(3-Ethoxy-5-methyl-phenyl)-5-(trifluoromethyl)-2H-pyrazol-3-yl]-methyl]-3-[3-fluoro-4-(2-hydroxy-ethoxy-methyl)-phenyl]-urea;

A136 2-[3-Fluoro-4-(2-hydroxy-ethyl)-phenyl]-N-[[2-(3-fluorophenyl)-5-(trifluoromethyl)-2H-pyrazol-3-yl]-methyl]-propionamide;

A137 2-[3-Fluoro-4-(2-hydroxy-ethyl)-phenyl]-N-[[2-(3-isopropyl-phenyl)-5-(trifluoromethyl)-2H-pyrazol-3-yl]-methyl]-propionamide;

A138 N-[[2-(3-Chlorophenyl)-5-(trifluoromethyl)-2H-pyrazol-3-yl]-methyl]-2-[3-fluoro-4-(2-hydroxy-ethyl)-phenyl]-propionamide;

A139 N-[[5-tert-Butyl-2-(3-chlorophenyl)-2H-pyrazol-3-yl]-methyl]-2-[3-fluoro-4-(2-hydroxy-ethyl)-phenyl]-propionamide;

A140 1-[[5-tert-Butyl-2-(3-chlorophenyl)-2H-pyrazol-3-yl]-methyl]-3-[3-fluoro-4-(2-hydroxy-ethyl)-phenyl]-urea;

A141 1-[[2-(3-Chlorophenyl)-5-(trifluoromethyl)-2H-pyrazol-3-yl]-methyl]-3-[3-fluoro-4-(2-hydroxy-ethyl)-phenyl]-urea;

A142 1-[3-Fluoro-4-(2-hydroxy-ethyl)-phenyl]-3-[[2-(3-fluorophenyl)-5-(trifluoromethyl)-2H-pyrazol-3-yl]-methyl]-urea;

A143 1-[3-Fluoro-4-(2-hydroxy-ethyl)-phenyl]-3-[[2-(3-methoxyphenyl)-5-(trifluoromethyl)-2H-pyrazol-3-yl]-methyl]-urea;

A144 1-[3-Fluoro-4-(2-hydroxy-ethyl)-phenyl]-3-[[2-(m-tolyl)-5-(trifluoromethyl)-2H-pyrazol-3-yl]-methyl]-urea;

A145 N-[[5-tert-Butyl-2-(3-chlorophenyl)-2H-pyrazol-3-yl]-methyl]-2-[4-(1,2-dihydroxy-ethyl)-3-fluoro-phenyl]-propionamide;

A146 N-[[2-(3-Chlorophenyl)-5-(trifluoromethyl)-2H-pyrazol-3-yl]-methyl]-2-[4-(1,2-dihydroxy-ethyl)-phenyl]-propionamide;

A147 N-[[5-tert-Butyl-2-(3-chlorophenyl)-2H-pyrazol-3-yl]-methyl]-2-[4-(1,2-dihydroxy-ethyl)-phenyl]-propionamide;

A148 N-[[2-(3-Chlorophenyl)-5-(trifluoromethyl)-2H-pyrazol-3-yl]-methyl]-2-[4-(1,2-dihydroxy-ethyl)-3-fluoro-phenyl]-propionamide;

A149 2-[4-(1,2-Dihydroxy-ethyl)-3-fluoro-phenyl]-N-[[2-(3-fluorophenyl)-5-(trifluoromethyl)-2H-pyrazol-3-yl]-methyl]-propionamide;

A150 1-[[5-tert-Butyl-2-(3-chlorophenyl)-2H-pyrazol-3-yl]-methyl]-3-[4-(1,2-dihydroxy-ethyl)-3-fluoro-phenyl]-urea;

A151 1-[[2-(3-Chlorophenyl)-5-(trifluoromethyl)-2H-pyrazol-3-yl]-methyl]-3-[4-(1,2-dihydroxy-ethyl)-3-fluoro-phenyl]-urea;

A152 1-[[5-tert-Butyl-2-(3-chlorophenyl)-2H-pyrazol-3-yl]-methyl]-3-[3-fluoro-4-[2-hydroxy-1-(hydroxymethyl)-ethyl]-phenyl]-urea;

A153 1-[[2-(3-Chlorophenyl)-5-(trifluoromethyl)-2H-pyrazol-3-yl]-methyl]-3-[3-fluoro-4-[2-hydroxy-1-(hydroxymethyl)-ethyl]-phenyl]-urea;

A154 1-[[2-(3-Chlorophenyl)-5-(trifluromethyl)-2H-pyrazol-3-yl]-methyl]-3-[3-fluoro-4-[2-hydroxy-1-(hydroxymethyl)-1-methyl-ethyl]-phenyl]-urea;

A155 1-[[2-(3-Chlorophenyl)-5-(trifluoromethyl)-2H-pyrazol-3-yl]-methyl]-3-[4-[2-hydroxy-1-(hydroxymethyl)-1-methyl-ethyl]-phenyl]-urea;

A156 1-[[5-tert-Butyl-2-(3-chlorophenyl)-2H-pyrazol-3-yl]-methyl]-3-[3-fluoro-4-[2-hydroxy-1-(hydroxymethyl)-1-methyl-ethyl]-phenyl]-urea;

A157 1-[[5-tert-Butyl-2-(3-chlorophenyl)-2H-pyrazol-3-yl]-methyl]-3-[4-[2-hydroxy-1-(hydroxymethyl)-1-methyl-ethyl]-phenyl]-urea;

A158 1-[[2-(3-Chlorophenyl)-5-(trifluoromethyl)-2H-pyrazol-3-yl]-methyl]-3-[4-[1,2-dihydroxy-1-(hydroxymethyl)-ethyl]-phenyl]-urea; and A159 1-[[5-tert-Butyl-2-(3-chlorophenyl)-2H-pyrazol-3-yl]-methyl]-3-[4-[1,2-dihydroxy-1-(hydroxymethyl)-ethyl]-phenyl]-urea;

optionally in the form of an individual stereoisomer or a mixture of stereoisomers, in the form of the free compound and/or a physiologically acceptable salt thereof.

Another particularly preferred subgroup of the compounds of the invention relates to compounds corresponding to the formula (R)

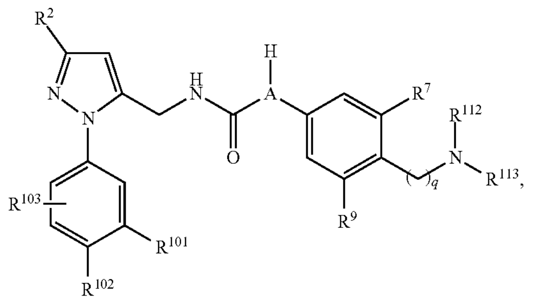

(R)

wherein $R^{101}$, $R^{102}$ and $R^{103}$ are each independently selected from the group consisting of H, F, Cl, Br, $CFH_2$, $CF_2H$, $CF_3$, CN, $CH_2$—OH, $CH_2CH_2$—OH, $CH_2$—$OCH_3$, $CH_2CH_2$—$OCH_3$, $OCFH_2$, $OCF_2H$, $OCF_3$, OH, $NH_2$, a $C_{1-4}$ alkyl, an O—$C_{1-4}$ alkyl, a NH—$C_{1-4}$ alkyl, and a $N(C_{1-4}$ alkyl$)_2$, wherein the $C_{1-4}$ alkyl is in each case unsubstituted;

$R^2$ represents $CF_3$, an unsubstituted $C_{1-4}$ alkyl or an unsubstituted $C_{3-6}$ cycloalkyl;

$R^7$ and $R^9$ are each independently selected from the group consisting of H, F, Cl, Br, $CFH_2$, $CF_2H$, $CF_3$, CN, OH, $OCF_3$, a $C_{1-4}$ alkyl, and an O—$C_{1-4}$ alkyl, wherein the $C_{1-4}$ alkyl is in each case unsubstituted;

A denotes N, CH or $C(CH_3)$;

q denotes 0, 1 or 2;

$R^{112}$ represents H or a $C_{1-4}$ alkyl, which is unsubstituted or mono-, di- or trisubstituted with 1, 2 or 3 substituents selected from the group consisting of F, Cl, Br, OH, =O and $OCH_3$;

$R^{113}$ represents a H, $S(=O)_2$—$NH_2$, a $C_{1-4}$ alkyl or a $S(=O)_2$—$C_{1-4}$ alkyl, wherein the $C_{1-4}$ alkyl is in each case unsubstituted or mono-, di- or trisubstituted with 1, 2 or 3 substituents selected from the group consisting of F, Cl, Br, OH, =O and $OCH_3$;

or, if q is not 0, then $R^{112}$ and $R^{113}$ together with the nitrogen atom connecting them form a 3 to 6 membered heterocyclyl, which is unsubstituted or mono-, di- or trisubstituted with 1, 2 or 3 substituents independently selected from the group consisting of F, Cl, Br, CN, $CF_3$, $CH_3$, $CH_2CH_3$, $CH(CH_3)_2$, tert.-butyl, cyclopropyl, OH, =O, $OCH_3$, $OCF_3$, $NH_2$, $NH(CH_3)$ and $N(CH_3)_2$;

in the form of a single stereoisomer or a mixture of stereoisomers, and in the form of a free compound or a physiologically acceptable salt or a physiologically acceptable solvate thereof.

In one preferred embodiment of the compound of formula (R), $R^{101}$, $R^{102}$ and $R^{103}$ are each independently selected from the group consisting of H, F, Cl, Br, $CFH_2$, $CF_2H$, $CF_3$, CN, $CH_2$—OH, $CH_2$—$OCH_3$, $OCF_3$, OH, $CH_3$, $CH_2CH_3$, $CH(CH_3)_2$, O—$CH_3$, O—$CH_2CH_3$, $NH_2$, $NH(CH_3)$, and $N(CH_3)_2$. Preferably, $R^{101}$, $R^{102}$ and $R^{103}$ are each independently selected from the group consisting of H, F, Cl, Br, $CFH_2$, $CF_2H$, $CF_3$, CN, $CH_2$—OH, $CH_2$—$OCH_3$, $OCF_3$, OH, $CH_3$, O—$CH_3$, O—$CH_2CH_3$, $NH_2$, $NH(CH_3)$, and $N(CH_3)_2$. More preferably, $R^{101}$, $R^{102}$ and $R^{103}$ are each independently selected from the group consisting of H, F, Cl, $CFH_2$, $CF_2H$, $CF_3$, CN, $CH_2$—$OCH_3$, $OCF_3$, $CH_3$, O—$CH_3$, O—$CH_2CH_3$ and $N(CH_3)_2$. Even more preferably, $R^{101}$, $R^{102}$ and $R^{103}$ are each independently selected from the group consisting of H, F, Cl, $CFH_2$, $CF_2H$, $CF_3$, $OCF_3$, $CH_3$, O—$CH_3$, and O—$CH_2CH_3$. Still more preferably, $R^{101}$, $R^{102}$ and $R^{103}$ are each independently selected from the group consisting of H, F, Cl, $CF_3$, $OCF_3$, $CH_3$ and O—$CH_3$. Particularly, $R^{101}$, $R^{102}$ and $R^{103}$ are each independently selected from the group consisting of H, F, Cl, $CF_3$ and O—$CH_3$. Even more particularly preferred, $R^{101}$, $R^{102}$ and $R^{103}$ are each independently selected from the group consisting of H, F, Cl and O—$CH_3$.

In a preferred embodiment of the compound of formula (R) at least one of $R^{101}$, $R^{102}$ and $R^{103}$ is not H.

In another preferred embodiment of the compound of formula (R) one or two of $R^{101}$, $R^{102}$ and $R^{103}$, preferably $R^{102}$ and/or $R^{103}$, denote(s) H.

In another preferred embodiment of the compound of formula (R) one of $R^{101}$, $R^{102}$ and $R^{103}$ represents H, preferably $R^{103}$ represents H.

In another preferred embodiment of the compound of formula (R), $R^{101}$ and $R^{102}$ are each independently selected from the group consisting of H, F, Cl, Br, $CFH_2$, $CF_2H$, $CF_3$, CN, $CH_2$—OH, $CH_2$—$OCH_3$, $OCF_3$, OH, $CH_3$, $CH_2CH_3$, $CH(CH_3)_2$, O—$CH_3$, O—$CH_2CH_3$, $NH_2$, $NH(CH_3)$, and $N(CH_3)_2$, and $R^{103}$ represents H.

Preferably, $R^{101}$ and $R^{102}$ are each independently selected from the group consisting of H, F, Cl, Br, $CFH_2$, $CF_2H$, $CF_3$, CN, $CH_2$—OH, $CH_2$—$OCH_3$, $OCF_3$, OH, $CH_3$, O—$CH_3$, O—$CH_2CH_3$, $NH_2$, $NH(CH_3)$, and $N(CH_3)_2$, more preferably each independently selected from the group consisting of H, F, Cl, $CFH_2$, $CF_2H$, $CF_3$, CN, $CH_2$—$OCH_3$, $OCF_3$, $CH_3$, O—$CH_3$, O—$CH_2CH_3$ and $N(CH_3)_2$, even more preferably each independently selected from the group consisting of H, F, Cl, $CFH_2$, $CF_2H$, $CF_3$, $OCF_3$, $CH_3$, O—$CH_3$, and O—$CH_2CH_3$, still more preferably each independently selected from the group consisting of H, F, Cl, $CF_3$, $OCF_3$, $CH_3$ and O—$CH_3$, in particular each independently selected from the group consisting of H, F, Cl, $CF_3$ and O—$CH_3$, and even more particularly preferably each independently selected from the group consisting of H, F, Cl, and O—$CH_3$, and $R^{103}$ represents H.

In yet another preferred embodiment of the compound of formula (R), $R^{101}$ is selected from the group consisting of F, Cl, Br, $CFH_2$, $CF_2H$, $CF_3$, CN, $CH_2$—OH, $CH_2$—$OCH_3$, $OCF_3$, OH, $CH_3$, $CH_2CH_3$, $CH(CH_3)_2$, O—$CH_3$, O—$CH_2CH_3$, $NH_2$, $NH(CH_3)$, and $N(CH_3)_2$, and both $R^{102}$ and $R^{103}$ represent H.

Preferably, $R^{101}$ is selected from the group consisting of F, Cl, Br, $CFH_2$, $CF_2H$, $CF_3$, CN, $CH_2$—OH, $CH_2$—$OCH_3$, $OCF_3$, OH, $CH_3$, O—$CH_3$, O—$CH_2CH_3$, $NH_2$, $NH(CH_3)$, and $N(CH_3)_2$, more preferably is selected from the group consisting of F, Cl, $CFH_2$, $CF_2H$, $CF_3$, CN, $CH_2$—$OCH_3$, $OCF_3$, $CH_3$, O—$CH_3$, O—$CH_2CH_3$ and $N(CH_3)_2$, even more preferably is selected from the group consisting of F, Cl, $CFH_2$, $CF_2H$, $CF_3$, $OCF_3$, $CH_3$, O—$CH_3$, and O—$CH_2CH_3$, still more preferably is selected from the group consisting of F, Cl, $CF_3$, $OCF_3$, $CH_3$ and O—$CH_3$, in particular is selected from the group consisting of F, Cl, $CF_3$ and O—$CH_3$, even more particularly preferably is selected from the group consisting of F, Cl, and O—$CH_3$, and both $R^{102}$ and $R^{103}$ represent H.

In still another preferred embodiment of the compound of formula (R), $R^{102}$ is selected from the group consisting of F, Cl, Br, $CFH_2$, $CF_2H$, $CF_3$, CN, $CH_2$—OH, $CH_2$—$OCH_3$, $OCF_3$, OH, $CH_3$, $CH_2CH_3$, $CH(CH_3)_2$, O—$CH_3$, O—$CH_2CH_3$, $NH_2$, $NH(CH_3)$, and $N(CH_3)_2$, and both $R^{01}$ and $R^{103}$ represent H.

Preferably, $R^{102}$ is selected from the group consisting of F, Cl, Br, $CFH_2$, $CF_2H$, $CF_3$, CN, $CH_2$—OH, $CH_2$—$OCH_3$, $OCF_3$, OH, $CH_3$, O—$CH_3$, O—$CH_2CH_3$, $NH_2$, $NH(CH_3)$, and $N(CH_3)_2$, more preferably is selected from the group consisting of F, Cl, $CFH_2$, $CF_2H$, $CF_3$, CN, $CH_2$—$OCH_3$, $OCF_3$, $CH_3$, O—$CH_3$, O—$CH_2CH_3$ and $N(CH_3)_2$, even more preferably is selected from the group consisting of F, Cl, $CFH_2$, $CF_2H$, $CF_3$, $OCF_3$, $CH_3$, O—$CH_3$, and O—$CH_2CH_3$, still more preferably is selected from the group consisting of F, Cl, $CF_3$, $OCF_3$, $CH_3$ and O—$CH_3$, in particular is selected from the group consisting of F, Cl, $CF_3$ and O—$CH_3$, and even more particularly preferably is selected from the group consisting of F, Cl, and O—$CH_3$, and both $R^{101}$ and $R^{103}$ represent H.

In yet a further preferred embodiment of the compound of formula (R), $R^{101}$ is selected from the group consisting of F, Cl, Br, $CFH_2$, $CF_2H$, $CF_3$, CN, $CH_2$—OH, $CH_2$—$OCH_3$, $OCF_3$, OH, $CH_3$, $CH_2CH_3$, $CH(CH_3)_2$, O—$CH_3$, O—$CH_2CH_3$, $NH_2$, $NH(CH_3)$, and $N(CH_3)_2$;

$R^{102}$ is selected from the group consisting of H, F, Cl, Br, $CFH_2$, $CF_2H$, $CF_3$, CN, $CH_2$—OH, $CH_2$—$OCH_3$, $OCF_3$, OH, $CH_3$, $CH_2CH_3$, $CH(CH_3)_2$, O—$CH_3$, O—$CH_2CH_3$, $NH_2$, $NH(CH_3)$, and $N(CH_3)_2$; and $R^{103}$ represents H.

Preferably, $R^{101}$ is selected from the group consisting of F, Cl, Br, $CFH_2$, $CF_2H$, $CF_3$, CN, $CH_2$—OH, $CH_2$—$OCH_3$, $OCF_3$, OH, $CH_3$, O—$CH_3$, O—$CH_2CH_3$, $NH_2$, $NH(CH_3)$, and $N(CH_3)_2$, more preferably is selected from the group consisting of F, Cl, $CFH_2$, $CF_2H$, $CF_3$, CN, $CH_2$—$OCH_3$, $OCF_3$, $CH_3$, O—$CH_3$, O—$CH_2CH_3$ and $N(CH_3)_2$, even more preferably is selected from the group consisting of F, Cl, $CFH_2$, $CF_2H$, $CF_3$, $OCF_3$, $CH_3$, O—$CH_3$, and O—$CH_2CH_3$, still more preferably is selected from the group consisting of F, Cl, $CF_3$, $OCF_3$, $CH_3$ and O—$CH_3$, in particular is selected from the group consisting of F, Cl, $CF_3$ and O—$CH_3$, and even more particularly preferably is selected from the group consisting of F, Cl, and O—$CH_3$;

$R^{102}$ is selected from the group consisting of H, F, Cl, Br, $CFH_2$, $CF_2H$, $CF_3$, CN, $CH_2$—OH, $CH_2$—$OCH_3$, $OCF_3$, OH, $CH_3$, O—$CH_3$, O—$CH_2CH_3$, $NH_2$, $NH(CH_3)$, and $N(CH_3)_2$, more preferably is selected from the group consisting of H, F, Cl, $CFH_2$, $CF_2H$, $CF_3$, CN, $CH_2$—$OCH_3$, $OCF_3$, $CH_3$, O—$CH_3$, O—$CH_2CH_3$ and $N(CH_3)_2$, even more preferably is selected from the group consisting of H, F, Cl, $CFH_2$, $CF_2H$, $CF_3$, $OCF_3$, $CH_3$, O—$CH_3$, and O—$CH_2CH_3$, still more preferably is selected from the group consisting of H, F, Cl, $CF_3$, $OCF_3$, $CH_3$ and O—$CH_3$, in particular is selected from the group consisting of H, F, Cl, $CF_3$ and O—$CH_3$, and even more particularly preferably is selected from the group consisting of H, F, Cl, and O—$CH_3$, and $R^{103}$ represents H.

In yet another further preferred embodiment of the compound of formula (R)

$R^{101}$ is selected from the group consisting of F, Br, $CFH_2$, $CF_2H$, $CF_3$, CN, $CH_2$—OH, $CH_2$—$OCH_3$, $OCF_3$, OH, $CH_3$, O—$CH_3$, O—$CH_2CH_3$, $NH_2$, $NH(CH_3)$, and $N(CH_3)_2$, more preferably is selected from the group consisting of F, $CFH_2$, $CF_2H$, $CF_3$, CN, $CH_2$—$OCH_3$, $OCF_3$, $CH_3$, O—$CH_3$, O—$CH_2CH_3$ and $N(CH_3)_2$, even more preferably is selected from the group consisting of F, $CFH_2$, $CF_2H$, $CF_3$, $OCF_3$, $CH_3$, O—$CH_3$, and O—$CH_2CH_3$, still more preferably is selected from the group consisting of F, $CF_3$, $OCF_3$, $CH_3$ and O—$CH_3$, in particular is selected from the group consisting of F, $CF_3$ and O—$CH_3$, and even more particularly preferred is selected from the group consisting of F and O—$CH_3$; and $R^{102}$ and $R^{103}$ each represent H.

In still another further preferred embodiment of the compound of formula (R), $R^{101}$ is selected from the group consisting of F, Br, $CFH_2$, $CF_2H$, $CF_3$, CN, $CH_2$—OH, $CH_2$—$OCH_3$, $OCF_3$, OH, $CH_3$, $CH_2CH_3$, $CH(CH_3)_2$, O—$CH_3$, O—$CH_2CH_3$, $NH_2$, $NH(CH_3)$, and $N(CH_3)_2$;

$R^{102}$ is selected from the group consisting of H, F, Cl, Br, $CFH_2$, $CF_2H$, $CF_3$, CN, $CH_2$—OH, $CH_2$—$OCH_3$, $OCF_3$, OH, $CH_3$, $CH_2CH_3$, $CH(CH_3)_2$, O—$CH_3$, O—$CH_2CH_3$, $NH_2$, $NH(CH_3)$, and $N(CH_3)_2$; and $R^{103}$ represents H.

Preferably, $R^{101}$ is selected from the group consisting of F, Br, $CFH_2$, $CF_2H$, $CF_3$, CN, $CH_2$—OH, $CH_2$—$OCH_3$, $OCF_3$, OH, $CH_3$, O—$CH_3$, O—$CH_2CH_3$, $NH_2$, $NH(CH_3)$, and $N(CH_3)_2$, more preferably is selected from the group consisting of F, $CFH_2$, $CF_2H$, $CF_3$, CN, $CH_2$—$OCH_3$, $OCF_3$, $CH_3$, O—$CH_3$, O—$CH_2CH_3$ and $N(CH_3)_2$, even more preferably is selected from the group consisting of F, $CFH_2$, $CF_2H$, $CF_3$, $OCF_3$, $CH_3$, O—$CH_3$, and O—$CH_2CH_3$, still more preferably is selected from the group consisting of F, $CF_3$, $OCF_3$, $CH_3$ and O—$CH_3$, in particular is selected from the group consisting of F, $CF_3$ and O—$CH_3$, and even more particularly preferably is selected from the group consisting of F and O—$CH_3$; and $R^{102}$ is selected from the group consisting of H, F, Cl, Br, $CFH_2$, $CF_2H$, $CF_3$, CN, $CH_2$—OH, $CH_2$—$OCH_3$, $OCF_3$, OH, $CH_3$, O—$CH_3$, O—$CH_2CH_3$, $NH_2$, $NH(CH_3)$, and $N(CH_3)_2$, more preferably is selected from the group consisting of H, F, Cl, $CFH_2$, $CF_2H$, $CF_3$, CN, $CH_2$—$OCH_3$, $OCF_3$, $CH_3$, O—$CH_3$, O—$CH_2CH_3$ and $N(CH_3)_2$, even more preferably is selected from the group consisting of H, F, Cl, $CFH_2$, $CF_2H$, $CF_3$, $OCF_3$, $CH_3$, O—$CH_3$, and O—$CH_2CH_3$, still more preferably is selected from the group consisting of H, F, Cl, $CF_3$, $OCF_3$, $CH_3$ and O—$CH_3$, in particular is selected from the group consisting of H, F, Cl, $CF_3$ and O—$CH_3$, and even more particularly preferably is selected from the group consisting of H, F, Cl, and O—$CH_3$.

In another particularly preferred embodiment of the compound of formula (R), the partial structure (RS2)

(RS2)

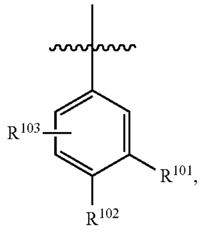

is selected from the group consisting of:
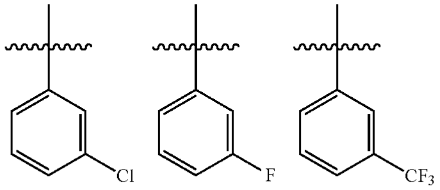
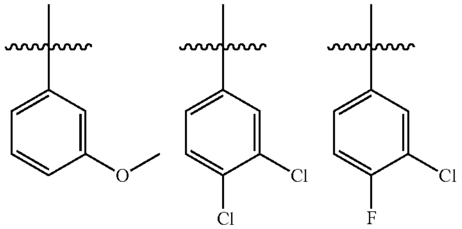
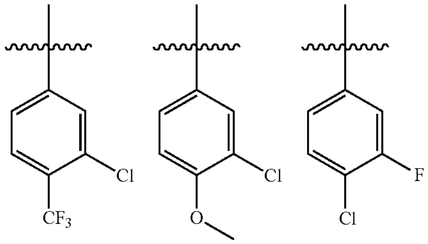
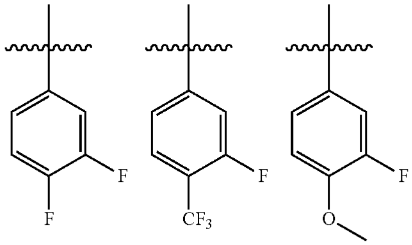
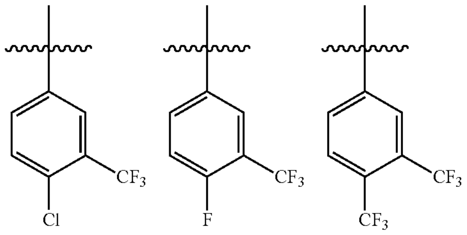
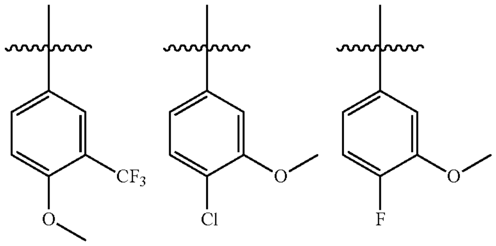
-continued
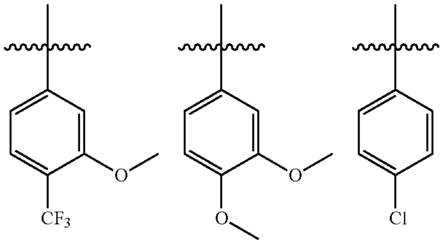
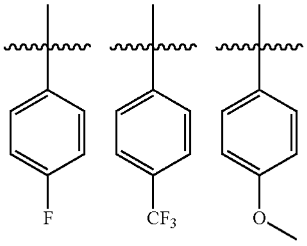
,
in particular when q denotes 0, 1 or 2, and A denotes N.
Even more particularly preferred, the partial structure (RS2) is selected from the group consisting of:
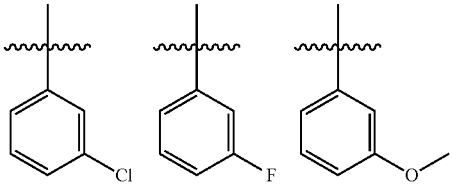
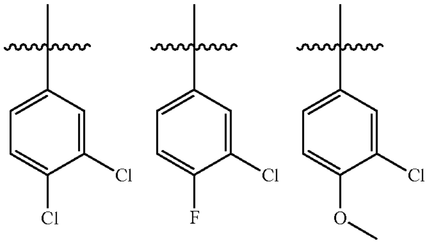
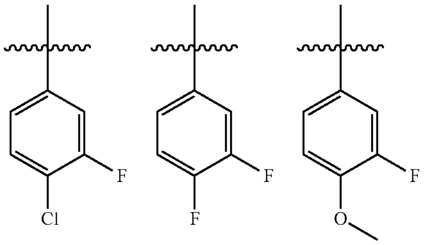
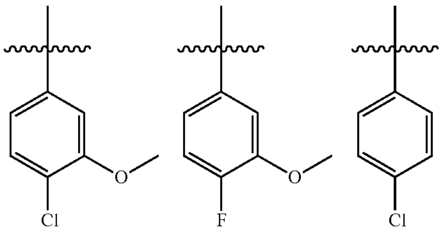

-continued

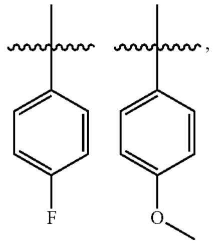

in particular when q denotes 0, 1 or 2, and A denotes N.

Most preferred, the partial structure (RS2) is selected from the group consisting of:

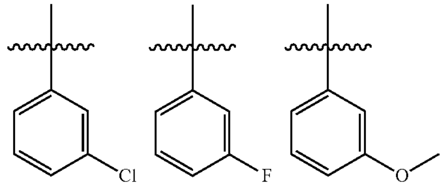

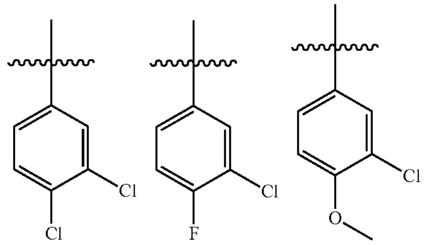

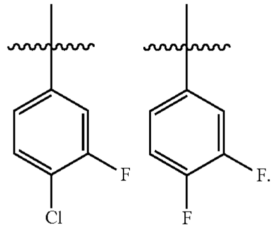

in particular when q denotes 0, 1 or 2, and A denotes N.

Preferably the partial structure (RS2) is selected from the group consisting of:

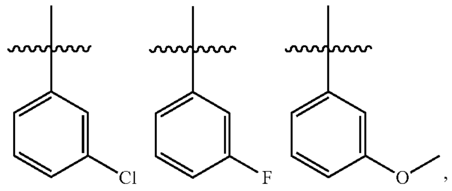

in particular when q denotes 0, 1 or 2, and A denotes N.

In another particularly preferred embodiment of formula (R) the partial structure (RS2) is selected from the group consisting of:

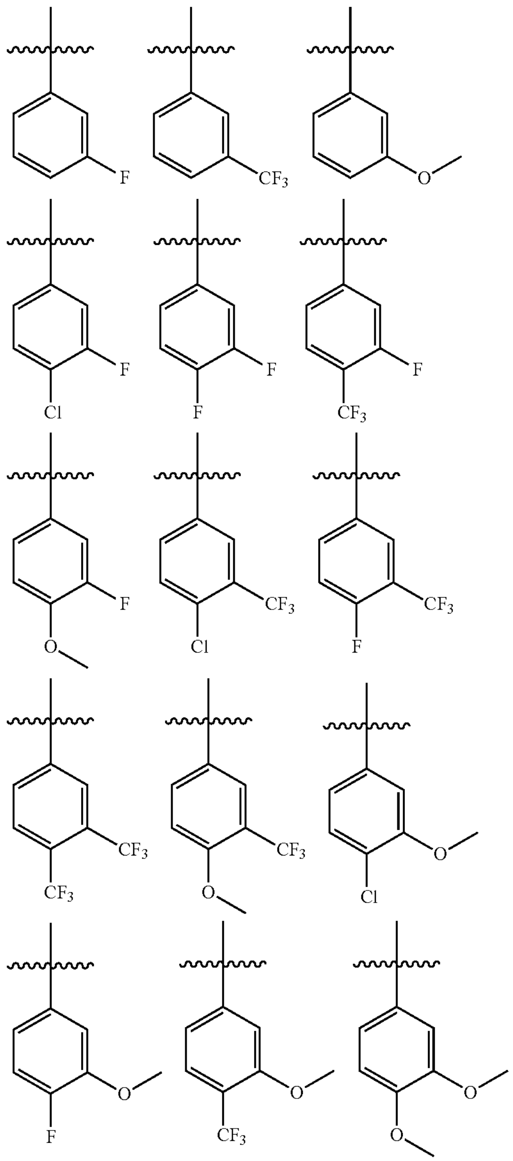

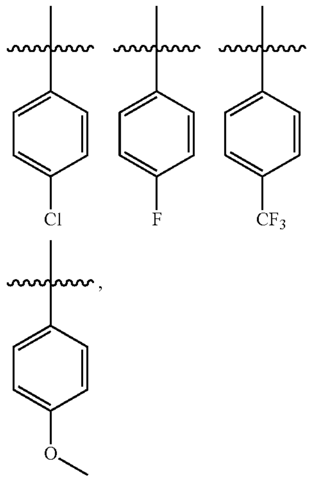

in particular when q denotes 1 or 2, and A denotes CH or $C(CH_3)$.

Even more particularly preferred, the partial structure (RS2) is selected from the group consisting of:

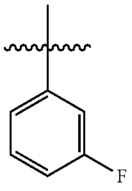
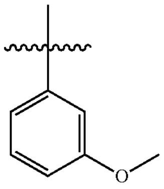
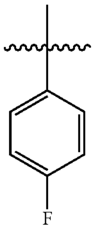

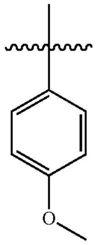
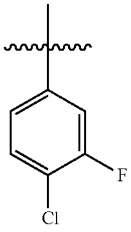
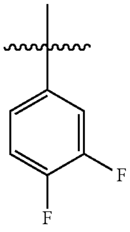

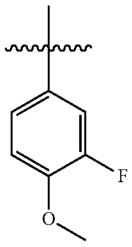
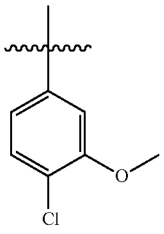
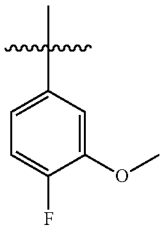

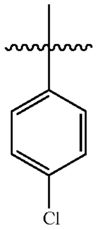
, in particular when q denotes 1 or 2, and A denotes CH or $C(CH_3)$.

Most preferred, the partial structure (RS2) is selected from the group consisting of:

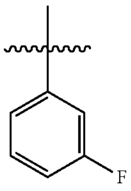
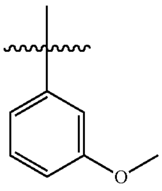
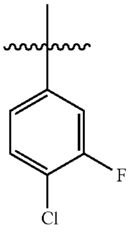

-continued

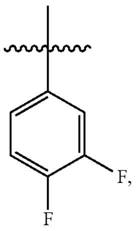

in particular when q denotes 1 or 2, and A denotes CH or $C(CH_3)$.

Preferably the partial structure (RS2) is selected from the group consisting of:

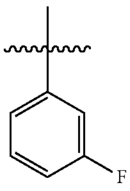
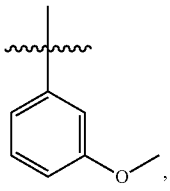
, in particular when q denotes 1 or 2, and A denotes CH or $C(CH_3)$.

In another preferred embodiment of the compound of formula (R), $R^2$ represents $CF_3$, methyl, ethyl, n-propyl, 2-propyl, n-butyl, iso-butyl, sec.-butyl, tert.-butyl, cyclopropyl, cyclobutyl, cyclopentyl or cyclohexyl. Preferably, $R^2$ represents $CF_3$, 2-propyl, n-butyl, iso-butyl, sec.-butyl, tert.-butyl, cyclopropyl, or cyclobutyl. More preferably, $R^2$ represents $CF_3$, tert.-butyl or cyclopropyl.

In one particularly preferred embodiment of the compound of formula (R), $R^2$ represents $CF_3$.

In another particularly preferred embodiment of the compound of formula (R), $R^2$ represents tert.-butyl.

In yet another particularly preferred embodiment of the compound of formula (R), $R^2$ represents cyclopropyl.

In a further preferred embodiment of the compound of formula (R), $R^7$ and $R^9$ are each independently selected from the group consisting of H, F, Cl, Br, $CF_3$, CN, OH, $OCF_3$, $CH_3$, $CH_2CH_3$, $CH(CH_3)_2$, O—$CH_3$, and O—$CH_2CH_3$. Preferably, $R^7$ and $R^9$ are each independently selected from the group consisting of H, F, Cl, $CF_3$, CN, OH, $OCF_3$, $CH_3$, O—$CH_3$, and O—$CH_2CH_3$. More preferably, $R^7$ and $R^9$ are each independently selected from the group consisting of H, F, Cl, $CF_3$, O—$CH_3$, and O—$CH_2CH_3$. Even more preferably, $R^7$ and $R^9$ are each independently selected from the group consisting of H, F, Cl, and O—$CH_3$. Still more preferably $R^7$ and $R^9$ are each independently selected from the group consisting of H, F and Cl.

In yet a further preferred embodiment of the compound of formula (R), at least one of $R^7$ and $R^9$ is not H.

In a further preferred embodiment of the compound of formula (R), $R^9$ denotes H.

In yet another preferred embodiment of the compound of formula (R), $R^7$ is selected from the group consisting of F, Cl, Br, $CF_3$, CN, OH, $OCF_3$, $CH_3$, $CH_2CH_3$, $CH(CH_3)_2$, O—$CH_3$, and O—$CH_2CH_3$, preferably is selected from the group consisting of F, Cl, $CF_3$, CN, OH, $OCF_3$, $CH_3$, O—$CH_3$, and O—$CH_2CH_3$, more preferably is selected from the group consisting of F, Cl, $CF_3$, O—$CH_3$, and O—$CH_2CH_3$, even more preferably is selected from the group consisting of F, Cl, and O—$CH_3$, and still more preferably is selected from the group consisting of F and Cl, and $R^9$ represents H.

In another preferred embodiment of the compound of formula (R), A denotes N or $C(CH_3)$.

In one particularly preferred embodiment of the compound of formula (R) A denotes N.

In another particularly preferred embodiment of the compound of formula (R), A denotes $C(CH_3)$.

In another preferred embodiment of the compound of formula (R), q denotes 1 or 2, preferably 1.

In a further preferred embodiment of the compound of formula (R),

A denotes N;

$R^{112}$ represents H or a $C_{1-4}$ alkyl, which is unsubstituted or mono-, di- or trisubstituted with 1, 2 or 3 substituents selected from the group consisting of F, Cl, Br, OH, =O and $OCH_3$; preferably H or a $C_{1-4}$ alkyl, which is unsubstituted; and $R^{113}$ represents H, $S(=O)_2$—$NH_2$, a $C_{1-4}$ alkyl or a $S(=O)_2$—$C_{1-4}$ alkyl, wherein the $C_{1-4}$ alkyl is in each case unsubstituted or mono-, di- or trisubstituted with 1, 2 or 3 substituents selected from the group consisting of F, Cl, Br, OH, =O and $OCH_3$, preferably H, $S(=O)_2$—$NH_2$, a $C_{1-4}$ alkyl or a $S(=O)_2$—$C_{1-4}$ alkyl, wherein the $C_{1-4}$ alkyl is in each case unsubstituted;

or, if q is not 0, then $R^{112}$ and $R^{113}$ together with the nitrogen atom connecting them form a 3 to 6 membered heterocyclyl, which is unsubstituted or mono-, di- or trisubstituted with 1, 2 or 3 substituents independently selected from the group consisting of F, Cl, Br, CN, $CF_3$, $CH_3$, $CH_2CH_3$, $CH(CH_3)_2$, tert.-butyl, cyclopropyl, OH, =O, $OCH_3$, $OCF_3$, $NH_2$, $NH(CH_3)$ and $N(CH_3)_2$; preferably a 3 to 6 membered heterocyclyl, which is unsubstituted;

or

A denotes CH or $C(CH_3)$;

$R^{112}$ represents H or a $C_{1-4}$ alkyl, which is unsubstituted or mono-, di- or trisubstituted with 1, 2 or 3 substituents selected from the group consisting of F, Cl, Br, OH, =O and $OCH_3$, preferably H or a $C_{1-4}$ alkyl, which is unsubstituted; and $R^{113}$ represents H, $S(=O)_2$—$NH_2$, a $C_{1-4}$ alkyl, which is unsubstituted or mono-, di- or trisubstituted with 1, 2 or 3 substituents selected from the group consisting of F, Cl, Br, OH, =O and $OCH_3$, preferably H, $S(=O)_2$—$NH_2$, or a $C_{1-4}$ alkyl, which is unsubstituted;

or, if q is not 0, then $R^{112}$ and $R^{113}$ together with the nitrogen atom connecting them form a 3 to 6 membered heterocyclyl, which is unsubstituted or mono-, di- or trisubstituted with 1, 2 or 3 substituents independently selected from the group consisting of F, Cl, Br, CN, $CF_3$, $CH_3$, $CH_2CH_3$, $CH(CH_3)_2$, tert.-butyl, cyclopropyl, OH, =O, $OCH_3$, $OCF_3$, $NH_2$, $NH(CH_3)$ and $N(CH_3)_2$, preferably a 3 to 6 membered heterocyclyl, which is unsubstituted.

In another preferred embodiment of the compound of formula (R)

q denotes 0, 1 or 2, preferably 1 or 2, more preferably 1;

A denotes N;

$R^{101}$ is selected from the group consisting of H, F, Cl, Br, $CFH_2$, $CF_2H$, $CF_3$, CN, $CH_2$—OH, $CH_2$—$OCH_3$, $OCF_3$, OH, $CH_3$, $CH_2CH_3$, $CH(CH_3)_2$, O—$CH_3$, O—$CH_2CH_3$, $NH_2$, $NH(CH_3)$ and $N(CH_3)_2$; preferably from the group consisting of H, F, Cl, $CFH_2$, $CF_2H$, $CF_3$, CN, $CH_2$—$OCH_3$, $OCF_3$, $CH_3$, O—$CH_3$, O—$CH_2CH_3$ and $N(CH_3)_2$; more preferably from the group consisting of H, F, Cl, $CFH_2$, $CF_2H$, $CF_3$, $OCF_3$, $CH_3$, O—$CH_3$, and O—$CH_2CH_3$; even more preferably from the group consisting of H, F, Cl, $CF_3$, $OCF_3$, $CH_3$ and O—$CH_3$; still more preferably from the group consisting of H, F, Cl, $CF_3$ and O—$CH_3$; in particular from the group consisting of H, F, Cl, and O—$CH_3$; and most preferably denotes F or Cl; and $R^{102}$ and $R^{103}$ are each independently selected from the group consisting of H, F, Cl, Br, $CFH_2$, $CF_2H$, $CF_3$, CN, $CH_2$—OH, $CH_2$—$OCH_3$, $OCF_3$, OH, $CH_3$, $CH_2CH_3$, $CH(CH_3)_2$, O—$CH_3$, O—$CH_2CH_3$, $NH_2$, $NH(CH_3)$ and $N(CH_3)_2$; preferably each independently selected from the group consisting of H, F, Cl, $CFH_2$, $CF_2H$, $CF_3$, CN, $CH_2$—$OCH_3$, $OCF_3$, $CH_3$, O—$CH_3$, O—$CH_2CH_3$ and $N(CH_3)_2$; more preferably each independently selected from the group consisting of H, F, Cl, $CFH_2$, $CF_2H$, $CF_3$, $OCF_3$, $CH_3$, O—$CH_3$, and O—$CH_2CH_3$; even more preferably each independently selected from the group consisting of H, F, Cl, $CF_3$, $OCF_3$, $CH_3$ and O—$CH_3$; still more preferably each independently selected from the group consisting of H, F, Cl, $CF_3$ and O—$CH_3$; in particular each independently selected from the group consisting of H, F, Cl, and O—$CH_3$; and most preferably independently denote F or Cl;

or q denotes 1 or 2, preferably 1;

A denotes CH or $C(CH_3)$, preferably $C(CH_3)$;

$R^{101}$ is selected from the group consisting of H, F, Br, $CFH_2$, $CF_2H$, $CF_3$, CN, $CH_2$—OH, $CH_2$—$OCH_3$, $OCF_3$, OH, $CH_3$, $CH_2CH_3$, $CH(CH_3)_2$, O—$CH_3$, O—$CH_2CH_3$, $NH_2$, $NH(CH_3)$ and $N(CH_3)_2$; preferably from the group consisting of H, F, $CFH_2$, $CF_2H$, $CF_3$, CN, $CH_2$—$OCH_3$, $OCF_3$, $CH_3$, O—$CH_3$, O—$CH_2CH_3$ and $N(CH_3)_2$; more preferably from the group consisting of H, F, $CFH_2$, $CF_2H$, $CF_3$, $OCF_3$, $CH_3$, O—$CH_3$, and O—$CH_2CH_3$; even more preferably from the group consisting of H, F, $CF_3$, $OCF_3$, $CH_3$ and O—$CH_3$; still more preferably from the group consisting of H, F, $CF_3$ and O—$CH_3$; in particular from the group consisting of H, F and O—$CH_3$; and most preferably denotes F; and $R^{102}$ and $R^{103}$ are each independently selected from the group consisting of H, F, Cl, Br, $CFH_2$, $CF_2H$, $CF_3$, CN, $CH_2$—OH, $CH_2$—$OCH_3$, $OCF_3$, OH, $CH_3$, $CH_2CH_3$, $CH(CH_3)_2$, O—$CH_3$, O—$CH_2CH_3$, $NH_2$, $NH(CH_3)$ and $N(CH_3)_2$; preferably each independently selected from the group consisting of H, F, Cl, $CFH_2$, $CF_2H$, $CF_3$, CN, $CH_2$—$OCH_3$, $OCF_3$, $CH_3$, O—$CH_3$, O—$CH_2CH_3$ and $N(CH_3)_2$; more preferably each independently selected from the group consisting of H, F, Cl, $CFH_2$, $CF_2H$, $CF_3$, $OCF_3$, $CH_3$, O—$CH_3$, and O—$CH_2CH_3$; even more preferably each independently selected from the group consisting of H, F, Cl, $CF_3$, $OCF_3$, $CH_3$ and O—$CH_3$; still more preferably each independently selected from the group consisting of H, F, Cl, $CF_3$ and O—$CH_3$; in particular each independently selected from the group consisting of H, F, Cl, and O—$CH_3$; and most preferably independently denote F or Cl.

In a further preferred embodiment of the compound of formula (R) the partial structure (RS1)

(RS1)

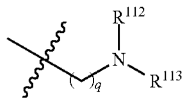

represents the partial structure (PR1)

wherein (PR1)

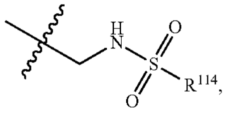

$R^{114}$ represents $NH_2$ or an unsubstituted $C_{1-4}$ alkyl; preferably $NH_2$, $CH_3$ or $CH_2CH_3$, more preferably $NH_2$ or $CH_3$, and in particular $CH_3$;

or represents the partial structure (PR2-a) or (PR2-b)

(PR2-a)

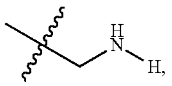

(PR2-b)

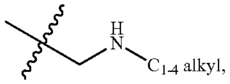

wherein the $C_{1-4}$ alkyl in partial structure (PR2-b) is unsubstituted or monosubstituted with =O or OH, preferably is unsubstituted, and wherein the $C_{1-4}$ alkyl in partial structure (PR2-b) is preferably selected from the group consisting of methyl and ethyl;

or represents one of the following partial structures

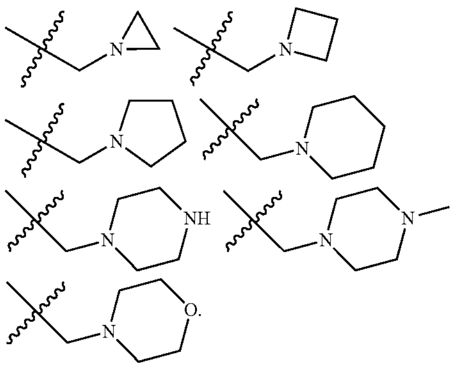

Preferably, the partial structure (RS1) represents the partial structure (PR1)

(PR1)

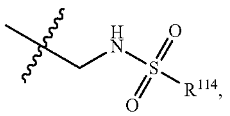

wherein $R^{114}$ represents $NH_2$ or an unsubstituted $C_{1-4}$ alkyl; preferably $NH_2$, $CH_3$ or $CH_2CH_3$, more preferably $NH_2$ or $CH_3$, and in particular $CH_3$.

In a particularly preferred embodiment of the present invention,

A denotes N;

$R^{101}$ is selected from the group consisting of H, F, Cl, Br, $CFH_2$, $CF_2H$, $CF_3$, CN, $CH_2$—OH, $CH_2$—$OCH_3$, $OCF_3$, OH, $CH_3$, $CH_2CH_3$, $CH(CH_3)_2$, O—$CH_3$, O—$CH_2CH_3$, $NH_2$, $NH(CH_3)$ and $N(CH_3)_2$, and $R^{102}$ and $R^{103}$ are each independently selected from the group consisting of H, F, Cl, Br, $CFH_2$, $CF_2H$, $CF_3$, CN, $CH_2$—OH, $CH_2$—$OCH_3$, $OCF_3$, OH, $CH_3$, $CH_2CH_3$, $CH(CH_3)_2$, O—$CH_3$, O—$CH_2CH_3$, $NH_2$, $NH(CH_3)$ and $N(CH_3)_2$, preferably, wherein at least one of $R^{101}$, $R^{102}$ and $R^{103}$ is not H, or A denotes CH or $C(CH_3)$, preferably $C(CH_3)$;

$R^{101}$ is selected from the group consisting of H, F, Br, $CFH_2$, $CF_2H$, $CF_3$, CN, $CH_2$—OH, $CH_2$—$OCH_3$, $OCF_3$, OH, $CH_3$, $CH_2CH_3$, $CH(CH_3)_2$, O—$CH_3$, O—$CH_2CH_3$, $NH_2$, $NH(CH_3)$ and $N(CH_3)_2$, and $R^{102}$ and $R^{103}$ are each independently selected from the group consisting of H, F, Cl, Br, $CFH_2$, $CF_2H$, $CF_3$, CN, CH—OH, $CH_2$—$OCH_3$, $OCF_3$, OH, $CH_3$, $CH_2CH_3$, $CH(CH_3)_2$, O—$CH_3$, O—$CH_2CH_3$, $NH_2$, $NH(CH_3)$ and $N(CH_3)_2$;

preferably, wherein at least one of $R^{101}$, $R^{102}$ and $R^{103}$ is not H;

$R^2$ represents $CF_3$, tert.-butyl or cyclopropyl;

$R^7$ and $R^9$ are each independently selected from the group consisting of H, F, Cl, Br, $CF_3$, CN, OH, $OCF_3$, $CH_3$, $CH_2CH_3$, $CH(CH_3)_2$, O—$CH_3$, and O—$CH_2CH_3$, preferably, wherein at least one of $R^7$ and $R^9$ is not H; and the partial structure (RS1) represents the partial structure (PR1)

(PR1)

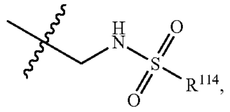

wherein $R^{114}$ represents $NH_2$, $CH_3$ or $CH_2CH_3$.

In another particularly preferred embodiment of the compound of formula (R), $R^{101}$ is selected from the group consisting of H, F, Cl, Br, $CFH_2$, $CF_2H$, $CF_3$, CN, $CH_2$—OH, $CH_2$—$OCH_3$, $OCF_3$, OH, $CH_3$, $CH_2CH_3$, $CH(CH_3)_2$, O—$CH_3$, O—$CH_2CH_3$, $NH_2$, $NH(CH_3)$ and $N(CH_3)_2$;

$R^{102}$ and $R^{103}$ are each independently selected from the group consisting of H, F, Cl, Br, $CFH_2$, $CF_2H$, $CF_3$, CN, $CH_2$—OH, $CH_2$—$OCH_3$, $OCF_3$, OH, $CH_3$, $CH_2CH_3$, $CH(CH_3)_2$, O—$CH_3$, O—$CH_2CH_3$, $NH_2$, $NH(CH_3)$ and $N(CH_3)_2$, preferably, wherein at least one of $R^{101}$, $R^{102}$ and $R^{103}$ is not H;

$R^2$ represents $CF_3$, tert.-butyl or cyclopropyl;

$R^7$ and $R^9$ are each independently selected from the group consisting of H, F, Cl, Br, $CF_3$, CN, OH, $OCF_3$, $CH_3$, $CH_2CH_3$, $CH(CH_3)_2$, O—$CH_3$, and O—$CH_2CH_3$, preferably, wherein at least one of $R^7$ and $R^9$ is not H;

A denotes N;

$R^{112}$ represents H or a $C_{1-4}$ alkyl, which is unsubstituted, preferably H, $CH_3$ or $CH_2CH_3$, more preferably H or $CH_3$, and in particular H;

$R^{113}$ represents H, $S(=O)_2$—$NH_2$, a $C_{1-4}$ alkyl or a $S(=O)_2$—$C_{1-4}$ alkyl, wherein the $C_{1-4}$ alkyl is in each case unsubstituted, preferably $S(=O)_2$—$NH_2$, or an unsubstituted $S(=O)_2-C_{1-4}$ alkyl, more preferably $S(=O)_2-NH_2$, $S(=O)_2-CH_3$ or $S(=O)_2-CH_2CH_3$, even more preferably $S(=O)_2-NH_2$ or $S(=O)_2-CH_3$, and in particular $S(=O)_2-CH_3$;

or

A denotes CH or $C(CH_3)$, preferably $C(CH_3)$;

$R^{112}$ represents H or a $C_4$ alkyl, which is unsubstituted, preferably H, $CH_3$ or $CH_2CH_3$, more preferably H or $CH_3$, and in particular H; and $R^{113}$ represents H, $S(=O)_2-NH_2$, or a $C_{1-4}$ alkyl, which is unsubstituted, preferably $S(=O)_2-NH_2$.

Preferred embodiments of the compound of formula (R) have the formula (R0-a) or (R0-b):

(R0-a)

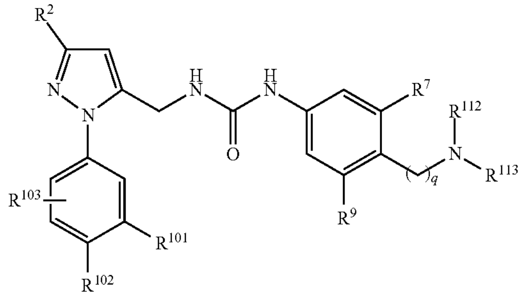

(R0-b)

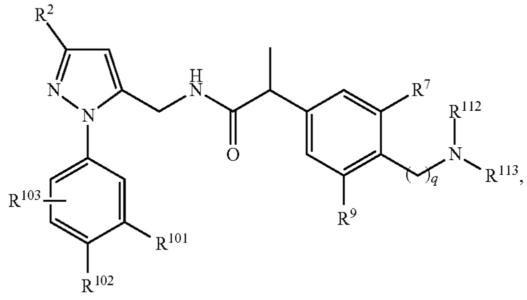

wherein the respective substituents, variables and indices have the meanings described above.

Further preferred embodiments of the compound of formula (R) have the formula (R1-a), (R1-a-1) or (R1-a-2):

(R1-a)

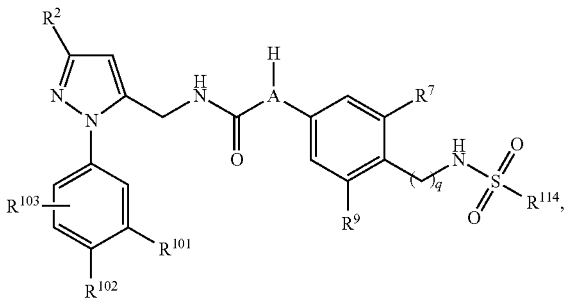

-continued (R1-a-1)

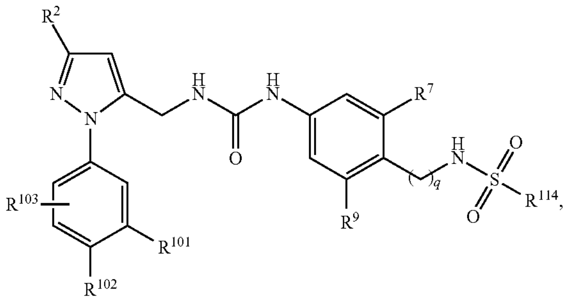

(R1-a-2)

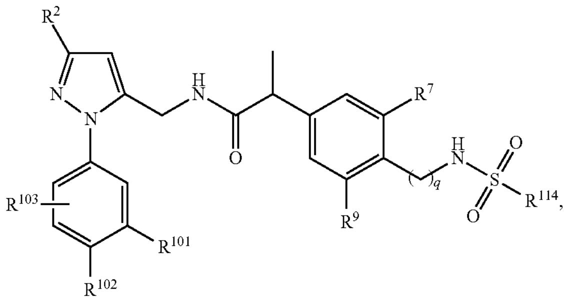

wherein the respective substituents, variables and indices have the meanings described above.

Moreover, preferred embodiments of the compound of formula (R) have the formula (R1-b), (R1-b-1) or (R1-b-2):

(R1-b)

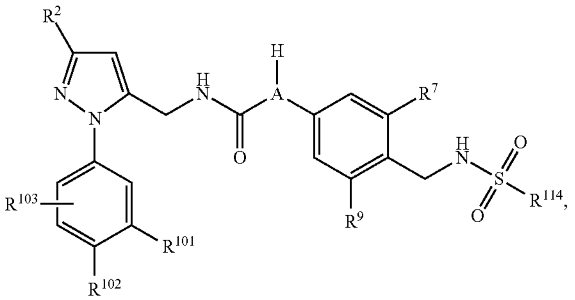

(R1-b-1)

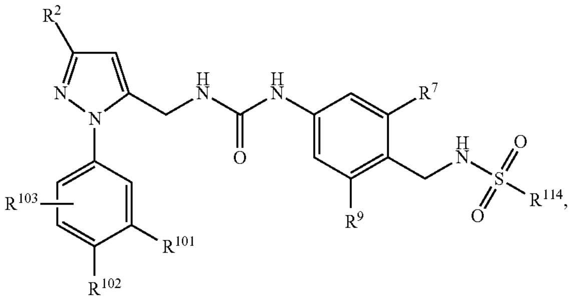

-continued (R1-b-2)

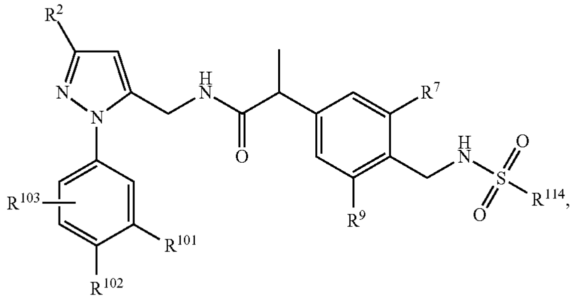

wherein the respective substituents, variables and indices have the meanings described above.

In addition, preferred embodiments of the compound of formula (R) have the formula (R1-c), (R1-c-1) or (R1-c-2):

(R1-c)

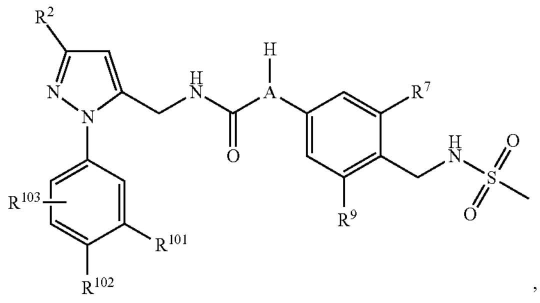

, (R1-c-1)

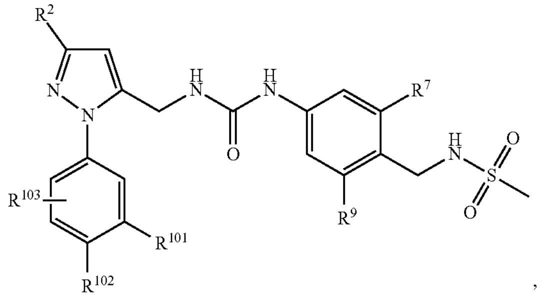

, (R1-c-2)

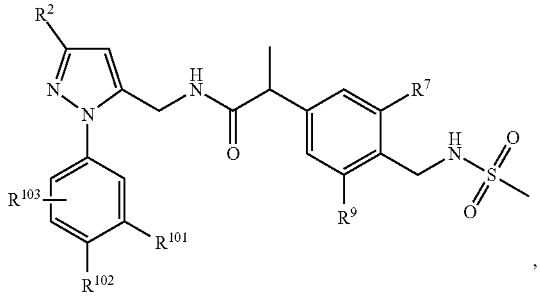

, wherein the respective substituents, variables and indices have the meanings described above.

Yet further preferred embodiments of the compound of formula (R) have the formula (R1-d), (R1-d-1) or (R1-d-2):

(R1-d)

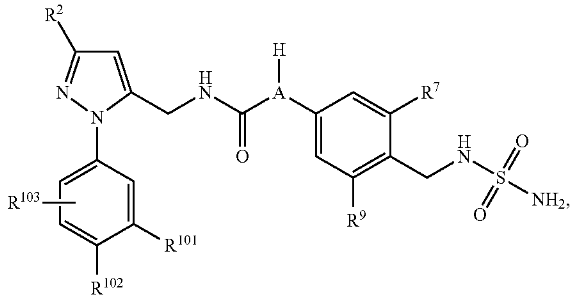

(R1-d-1)

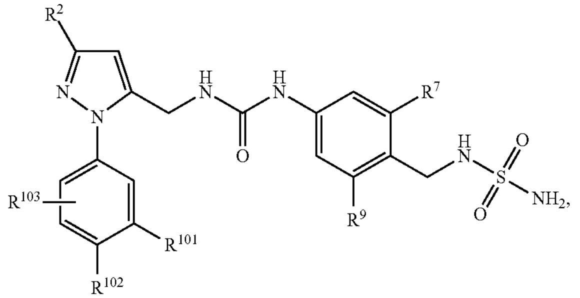

(R1-d-2)

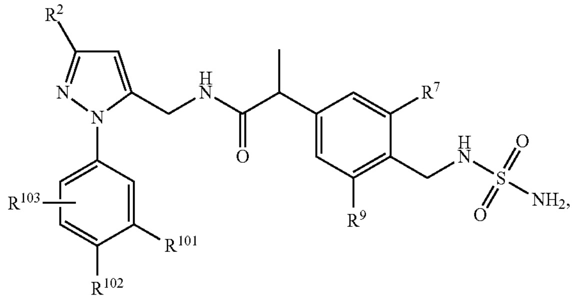

wherein the respective substituents, variables and indices have the meanings described above.

Further preferred embodiments of the compound of formula (R) have the formula (R1-e), (R1-e-1) or (R1-e-2):

(R1-e)

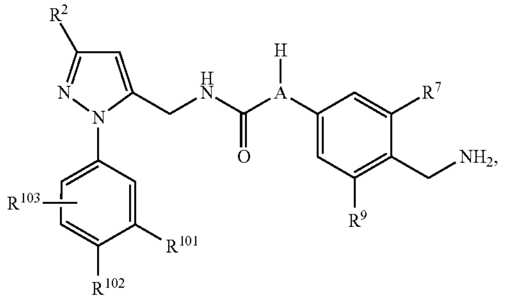

-continued (R1-e-1)

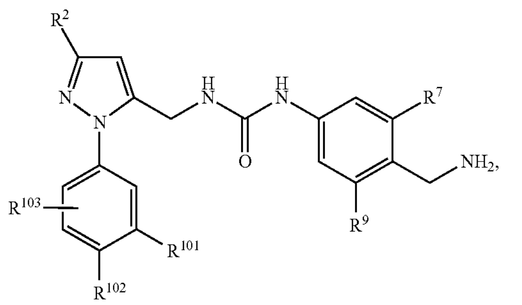

(R1-e-2)

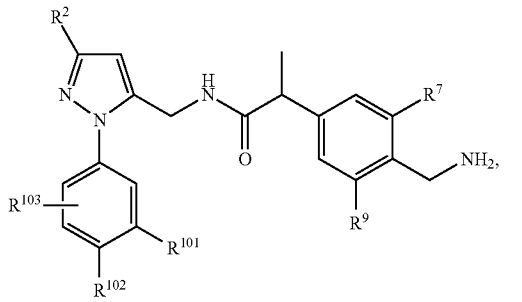

wherein the respective substituents, variables and indices have the meanings described above.

Additionally, preferred embodiments of the compound of formula (R) have the formula (R1-f), (R1-f-1) or (R1-f-2):

(R1-f)

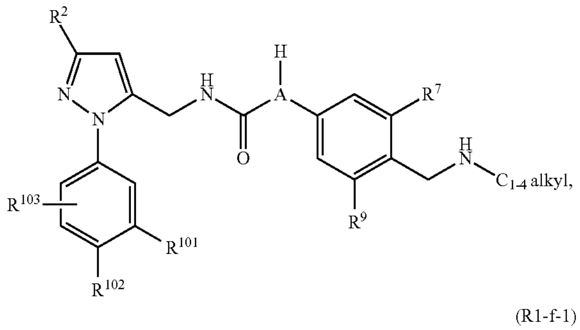

(R1-f-1)

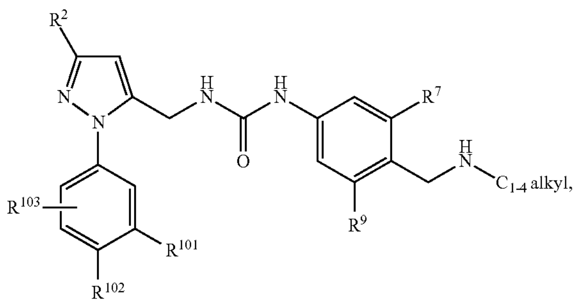

-continued (R1-f-2)

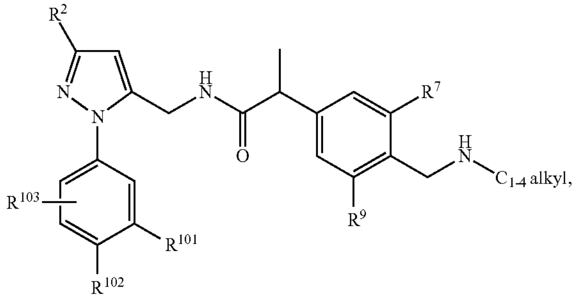

wherein the respective substituents, variables and indices have the meanings described above.

In particularly preferred embodiments of the compound of formula (R), $R^{101}$ in the compound of formula (R), (R1-a), (R1-a-1), (R1-b), (R1-b-1), (R1-c), (R1-c-1), (R1-d), or (R1-d-1) represents F, Cl, $CF_3$ or O—$CH_3$, preferably F or Cl, most preferably Cl—preferably when $R^{103}$ is H and $R^{102}$ represents H, F, Cl, $CF_3$ or $OCH_3$, more preferably when $R^{103}$ is H and $R^{102}$ represents H, F or Cl, even more preferably when both $R^{102}$ and $R^{103}$ denote H, and the remaining respective substituents, variables and indices have the meanings described above.

In particularly preferred embodiments of the compound of formula (R), $R^{101}$ in the compound of formula (R), (R1-a), (R1-a-2), (R1-b), (R1-b-2), (R1-c), (R1-c-2), (R1-d) or (R1-d-2), represents F, $CF_3$ or O—$CH_3$, preferably F or $OCH_3$, most preferably F—preferably when $R^{103}$ is H and $R^{102}$ represents H, F, Cl, $CF_3$ or $OCH_3$, more preferably when $R^{103}$ is H and $R^{102}$ represents H, F or Cl, even more preferably when both $R^{102}$ and $R^{103}$ denote H, and the remaining respective substituents, variables and indices have the meanings described above.

In further particularly preferred embodiments of the compound of formula (R), $R^{101}$ in the compound of formula (R1-e), (R1-e-1), (R1-e-2), (R1-f), (R1-f-1) or (R1-f-2) represents F, Cl, $CF_3$ or O—$CH_3$, preferably F or Cl, most preferably Cl—preferably when $R^{103}$ is H and $R^{102}$ represents H, F, Cl, $CF_3$ or $OCH_3$, more preferably when $R^{103}$ is H and $R^{102}$ represents H, F or Cl, even more preferably when both $R^{102}$ and $R^{103}$ denote H, and the remaining respective substituents, variables and indices have the meanings described above.

Particularly preferred are compounds of formula (R) selected from the group consisting of:

B1 N-[[2-(3-Chlorophenyl)-5-(trifluoromethyl)-2H-pyrazol-3-yl]-methyl]-2-[3-fluoro-4-(methanesulfonamido-methyl)-phenyl]-propionamide;

B2 N-[[2-(3-Chloro-4-fluoro-phenyl)-5-(trifluoromethyl)-2H-pyrazol-3-yl]-methyl]-2-[3-fluoro-4-(methanesulfonamido-methyl)-phenyl]-propionamide;

B3 N-[[5-tert-Butyl-2-(3-chloro-4-fluoro-phenyl)-2H-pyrazol-3-yl]-methyl]-2-[3-fluoro-4-(methanesulfonamido-methyl)-phenyl]-propionamide;

B4 N-[[2-(3-Chlorophenyl)-5-cyclopropyl-2H-pyrazol-3-yl]-methyl]-2-[3-fluoro-4-(methanesulfonamido-methyl)-phenyl]-propionamide;

B5 N-[[2-(3-Chlorophenyl)-5-(trifluoromethyl)-2H-pyrazol-3-yl]-methyl]-2-[4-(methanesulfonamido-methyl)-phenyl]-propionamide;

B6 N-[[5-tert-Butyl-2-(3-chlorophenyl)-2H-pyrazol-3-yl]-methyl]-2-[4-(methanesulfonamido-methyl)-phenyl]-propionamide;

B7 2-[3-Fluoro-4-(methanesulfonamido-methyl)-phenyl]-N-[[2-(3-fluorophenyl)-5-(trifluoromethyl)-2H-pyrazol-3-yl]-methyl]-propionamide;

B8 2-[3-Fluoro-4-(methanesulfonamido-methyl)-phenyl]-N-[[5-(trifluoromethyl)-2-[3-(trifluoromethyl)phenyl]-2H-pyrazol-3-yl]-methyl]-propionamide;

B9 N-[[5-tert-Butyl-2-(3-fluorophenyl)-2H-pyrazol-3-yl]-methyl]-2-[3-fluoro-4-(methanesulfonamido-methyl)-phenyl]-propionamide;

B10 N-[[5-tert-Butyl-2-(3,4-difluoro-phenyl)-2H-pyrazol-3-yl]-methyl]-2-[3-fluoro-4-(methanesulfonamido-methyl)-phenyl]-propionamide;

B11 1-[[5-tert-Butyl-2-(3-chlorophenyl)-2H-pyrazol-3-yl]-methyl]-3-[4-(methanesulfonamido-methyl)-3-methoxy-phenyl]-urea;

B12 1-[[2-(3-Chlorophenyl)-5-(trifluoromethyl)-2H-pyrazol-3-yl]-methyl]-3-[4-(methanesulfonamido-methyl)-3-methoxy-phenyl]-urea;

B13 N-[[5-tert-Butyl-2-(3-chlorophenyl)-2H-pyrazol-3-yl]-methyl]-2-[3-chloro-4-(methanesulfonamido-methyl)-phenyl]-propionamide;

B14 1-[[2-(3-Chlorophenyl)-5-(trifluoromethyl)-2H-pyrazol-3-yl]-methyl]-3-[4-(methylamino-methyl)-phenyl]-urea;

B15 2-[3-Fluoro-4-(methanesulfonamido-methyl)-phenyl]-N-[[2-(3-methoxyphenyl)-5-(trifluoromethyl)-2H-pyrazol-3-yl]-methyl]-propionamide;

B16 N-[[5-tert-Butyl-2-(3-chlorophenyl)-2H-pyrazol-3-yl]-methyl]-2-[4-[[(ethylsulfonyl)amino]-methyl]-3-fluoro-phenyl]-propionamide;

B17 N-[[2-(3-Chlorophenyl)-5-(trifluoromethyl)-2H-pyrazol-3-yl]-methyl]-2-[4-[[(ethylsulfonyl)amino]-methyl]-3-fluoro-phenyl]-propionamide;

B18 N-[[2-(4-Chlorophenyl)-5-(trifluoromethyl)-2H-pyrazol-3-yl]-methyl]-2-[3-fluoro-4-(methanesulfonamido-methyl)-phenyl]-propionamide;

B19 N-[[2-(3,4-Difluoro-phenyl)-5-(trifluoromethyl)-2H-pyrazol-3-yl]-methyl]-2-[3-fluoro-4-(methanesulfonamido-methyl)-phenyl]-propionamide;

B20 N-[[5-tert-Butyl-2-(4-chlorophenyl)-2H-pyrazol-3-yl]-methyl]-2-[3-fluoro-4-(methanesulfonamido-methyl)-phenyl]-propionamide;

B21 N-[[5-tert-Butyl-2-(4-fluorophenyl)-2H-pyrazol-3-yl]-methyl]-2-[3-fluoro-4-(methanesulfonamido-methyl)-phenyl]-propionamide;

B22 2-[3-Chloro-4-(methanesulfonamido-methyl)-phenyl]-N-[[2-(3-chlorophenyl)-5-(trifluoromethyl)-2H-pyrazol-3-yl]-methyl]-propionamide;

B23 N-[[2-(3-Chlorophenyl)-5-(trifluoromethyl)-2H-pyrazol-3-yl]-methyl]-2-[3-fluoro-4-(methanesulfonamido-methyl)-phenyl]-acetamide;

B24 1-[[2-(3-Chlorophenyl)-5-(trifluoromethyl)-2H-pyrazol-3-yl]-methyl]-3-[4-(ethylamino-methyl)-3-fluoro-phenyl]-urea;

B25 1-[[5-tert-Butyl-2-(3-chlorophenyl)-2H-pyrazol-3-yl]-methyl]-3-[4-(ethylamino-methyl)-3-fluoro-phenyl]-urea;

B26 N-[[5-tert-Butyl-2-(3-chlorophenyl)-2H-pyrazol-3-yl]-methyl]-2-[3-fluoro-4-(methanesulfonamido-methyl)-phenyl]-acetamide;

B27 1-[[2-(3-Chlorophenyl)-5-(trifluoromethyl)-2H-pyrazol-3-yl]-methyl]-3-[3,5-difluoro-4-(methanesulfonamido-methyl)-phenyl]-urea;

B28 1-[[5-tert-Butyl-2-(3-chlorophenyl)-2H-pyrazol-3-yl]-methyl]-3-[4-(methanesulfonamido-methyl)-phenyl]-urea;

B29 N-[[2-(3-Chlorophenyl)-5-(trifluoromethyl)-2H-pyrazol-3-yl]-methyl]-2-[3-fluoro-4-[(methyl-methylsulfonyl-amino)-methyl]-phenyl]-propionamide;

B30 N-[[5-tert-Butyl-2-(3-chlorophenyl)-2H-pyrazol-3-yl]-methyl]-2-[3-fluoro-4-[(methyl-methylsulfonyl-amino)-methyl]-phenyl]-propionamide;

B31 1-[[5-tert-Butyl-2-(3-chlorophenyl)-2H-pyrazol-3-yl]-methyl]-3-[3-fluoro-4-(methanesulfonamido-methyl)-phenyl]-urea;

B32 1-[[5-tert-Butyl-2-(3-chlorophenyl)-2H-pyrazol-3-yl]-methyl]-3-[3,5-difluoro-4-(methanesulfonamido-methyl)-phenyl]-urea;

B33 N-[[4-[[[2-(3-Chlorophenyl)-5-(trifluoromethyl)-2H-pyrazol-3-yl]-methyl-carbamoyl]amino]-2-fluoro-phenyl]-methyl]-acetamide;

B34 N-[[4-[[[5-tert-Butyl-2-(3-chlorophenyl)-2H-pyrazol-3-yl]-methyl-carbamoyl]amino]-2-fluoro-phenyl]-methyl]-acetamide;

B35 1-[[2-(3-Chlorophenyl)-5-(trifluoromethyl)-2H-pyrazol-3-yl]-methyl]-3-[4-[(sulfamoylamino)-methyl]-phenyl]-urea;

B36 1-[[5-tert-Butyl-2-(3-chlorophenyl)-2H-pyrazol-3-yl]-methyl]-3-[4-[(sulfamoylamino)-methyl]-phenyl]-urea;

B37 2-[3-Fluoro-4-(methanesulfonamido-methyl)-phenyl]-N-[[2-(3-fluorophenyl)-5-(trifluoromethyl)-2H-pyrazol-3-yl]-methyl]-acetamide;

B38 1-[[2-(3-Chlorophenyl)-5-(trifluoromethyl)-2H-pyrazol-3-yl]-methyl]-3-[4-(dimethylaminomethyl)-3-fluoro-phenyl]-urea;

B39 1-[4-(Aminomethyl)-3-fluoro-phenyl]-3-[[2-(3-chloro-phenyl)-5-(trifluoromethyl)-2H-pyrazol-3-yl]-methyl]-urea;

B40 1-[4-(Aminomethyl)-3-fluoro-phenyl]-3-[[5-tert-butyl-2-(3-chlorophenyl)-2H-pyrazol-3-yl]-methyl]-urea;

B41 1-[[2-(3-Chlorophenyl)-5-(trifluoromethyl)-2H-pyrazol-3-yl]methyl]-3-[3-fluoro-4-[(sulfamoylamino)-methyl]-phenyl]-urea;

B42 2-[4-(Aminomethyl)-3-fluoro-phenyl]-N-[[2-(3-chlorophenyl)-5-(trifluoromethyl)-2H-pyrazol-3-yl]-methyl]-propionamide;

B43 N-[[5-tert-Butyl-2-[3-(trifluoromethyl)phenyl]-2H-pyrazol-3-yl]-methyl]-2-[3-fluoro-4-(methanesulfonamido-methyl)-phenyl]-propionamide;

B44 1-[[2-(3-Fluorophenyl)-5-(trifluoromethyl)-2H-pyrazol-3-yl]-methyl]-3-[4-(methanesulfonamido-methyl)-phenyl]-urea;

B45 1-[[5-tert-Butyl-2-(3-fluorophenyl)-2H-pyrazol-3-yl]-methyl]-3-[4-(methanesulfonamido-methyl)-phenyl]-urea;

B46 1-[[5-tert-Butyl-2-(3-chlorophenyl)-2H-pyrazol-3-yl]-methyl]-3-[3-fluoro-4-[(sulfamoylamino)-methyl]-phenyl]-urea;

B47 2-[4-(Aminomethyl)-3-fluoro-phenyl]-N-[[5-tert-butyl-2-(3-chlorophenyl)-2H-pyrazol-3-yl]-methyl]-propionamide;

B48 1-[3-Fluoro-4-(methanesulfonamido-methyl)-phenyl]-3-[[2-(3-fluorophenyl)-5-(trifluoromethyl)-2H-pyrazol-3-yl]-methyl]-urea;

B49 1-[[2-(3,4-Difluoro-phenyl)-5-(trifluoromethyl)-2H-pyrazol-3-yl]-methyl]-3-[3-fluoro-4-(methanesulfonamido-methyl)-phenyl]-urea;

B50 1-[[5-tert-Butyl-2-(3-fluorophenyl)-2H-pyrazol-3-yl]-methyl]-3-[3-fluoro-4-(methanesulfonamido-methyl)-phenyl]-urea;

B51 1-[[5-tert-Butyl-2-(3-chloro-4-fluoro-phenyl)-2H-pyrazol-3-yl]-methyl]-3-[3-fluoro-4-(methanesulfonamido-methyl)-phenyl]-urea;

B52 1-[[2-(3-Chlorophenyl)-5-(trifluoromethyl)-2H-pyrazol-3-yl]-methyl]-3-[3-fluoro-4-(methanesulfonamido-methyl)-phenyl]-urea;

B53 1-[[5-tert-Butyl-2-(4-fluorophenyl)-2H-pyrazol-3-yl]-methyl]-3-[3-fluoro-4-(methanesulfonamido-methyl)-phenyl]-urea;

B54 1-[[5-tert-Butyl-2-[3-(trifluoromethyl)phenyl]-2H-pyrazol-3-yl]-methyl]-3-[3-fluoro-4-(methanesulfonamido-methyl)-phenyl]-urea;

B55 1-[3-Fluoro-4-(methanesulfonamido-methyl)-phenyl]-3-[[5-(trifluoromethyl)-2-[3-(trifluoromethyl)phenyl]-2H-pyrazol-3-yl]-methyl]-urea;

B56 1-[[5-tert-Butyl-2-(3-fluorophenyl)-2H-pyrazol-3-yl]-methyl]-3-[4-[(sulfamoylamino)-methyl]-phenyl]-urea;

B57 1-[[2-(3,4-Difluoro-phenyl)-5-(trifluoromethyl)-2H-pyrazol-3-yl]-methyl]-3-[4-[(sulfamoylamino)-methyl]-phenyl]-urea;

B58 1-[3-Fluoro-4-(methanesulfonamido-methyl)-phenyl]-3-[[2-(3-methoxyphenyl)-5-(trifluoromethyl)-2H-pyrazol-3-yl]-methyl]-urea;

B59 1-[[5-tert-Butyl-2-(3-fluorophenyl)-2H-pyrazol-3-yl]-methyl]-3-[3-fluoro-4-[(sulfamoylamino)-methyl]-phenyl]-urea;

B60 1-[[2-(3-Fluorophenyl)-5-(trifluoromethyl)-2H-pyrazol-3-yl]-methyl]-3-[3-fluoro-4-[(sulfamoylamino)-methyl]-phenyl]-urea;

B61 1-[[2-(3-Chlorophenyl)-5-cyclopropyl-2H-pyrazol-3-yl]-methyl]-3-[3-fluoro-4-[(sulfamoylamino)-methyl]-phenyl]-urea;

B62 1-[[2-(3,4-Difluoro-phenyl)-5-(trifluoromethyl)-2H-pyrazol-3-yl]-methyl]-3-[3-fluoro-4-[(sulfamoylamino)-methyl]-phenyl]-urea;

B63 N-[[5-tert-Butyl-2-(3-chlorophenyl)-2H-pyrazol-3-yl]-methyl]-2-[3-fluoro-4-(methylamino-methyl)-phenyl]-propionamide;

B64 N-[[5-tert-Butyl-2-(3-chlorophenyl)-2H-pyrazol-3-yl]-methyl]-2-[4-(dimethylaminomethyl)-3-fluoro-phenyl]-propionamide;

B65 N-[[2-(3-Chlorophenyl)-5-(trifluoromethyl)-2H-pyrazol-3-yl]-methyl]-2-[4-(dimethylaminomethyl)-3-fluoro-phenyl]-propionamide;

B66 2-[4-(Acetylamino-methyl)-3-fluoro-phenyl]-N-[[2-(3-chlorophenyl)-5-(trifluoromethyl)-2H-pyrazol-3-yl]-methyl]-propionamide;

B67 2-[4-(Acetylamino-methyl)-3-fluoro-phenyl]-N-[[5-tert-butyl-2-(3-chlorophenyl)-2H-pyrazol-3-yl]-methyl]-propionamide;

B68 2-[3-Fluoro-4-(methanesulfonamido-methyl)-phenyl]-N-[[2-(m-tolyl)-5-(trifluoromethyl)-2H-pyrazol-3-yl]-methyl]-propionamide;

B69 1-[[5-tert-Butyl-2-(3,4-difluoro-phenyl)-2H-pyrazol-3-yl]-methyl]-3-[3-fluoro-4-[(sulfamoylamino)-methyl]-phenyl]-urea;

B70 1-[[2-(3-Chloro-4-fluoro-phenyl)-5-(trifluoromethyl)-2H-pyrazol-3-yl]-methyl]-3-[3-fluoro-4-[(sulfamoylamino)-methyl]-phenyl]-urea;

B71 1-[3-Fluoro-4-[(sulfamoylamino)-methyl]-phenyl]-3-[[2-(3-methoxyphenyl)-5-(trifluoromethyl)-2H-pyrazol-3-yl]-methyl]-urea;

B72 1-[[5-tert-Butyl-2-(3,4-difluoro-phenyl)-2H-pyrazol-3-yl]-methyl]-3-[3-fluoro-4-(methanesulfonamido-methyl)-phenyl]-urea;

B73 1-[3-Fluoro-4-(methanesulfonamido-methyl)-phenyl]-3-[[2-(3-isopropyl-phenyl)-5-(trifluoromethyl)-2H-pyrazol-3-yl]-methyl]-urea;

B74 1-[[5-tert-Butyl-2-(3,4-difluoro-phenyl)-2H-pyrazol-3-yl]-methyl]-3-[4-[(sulfamoylamino)-methyl]-phenyl]-urea;

B75 1-[[2-(3-Chlorophenyl)-5-cyclopropyl-2H-pyrazol-3-yl]-methyl]-3-[4-[(sulfamoylamino)-methyl]-phenyl]-urea;

B76 N-[[2-(3-Chlorophenyl)-5-(trifluoromethyl)-2H-pyrazol-3-yl]-methyl]-2-[4-(methanesulfonamido-methyl)-3-methoxy-phenyl]-propionamide;

B77 1-[[2-(3-Fluorophenyl)-5-(trifluoromethyl)-2H-pyrazol-3-yl]-methyl]-3-[4-[(sulfamoylamino)-methyl]-phenyl]-urea;

B78 1-[[2-(3-Chloro-4-fluoro-phenyl)-5-(trifluoromethyl)-2H-pyrazol-3-yl]-methyl]-3-[4 [(sulfamoylamino)-methyl]-phenyl]-urea;

B79 1-[[2-(3-Isopropyl-phenyl)-5-(trifluoromethyl)-2H-pyrazol-3-yl]-methyl]-3-[4-[(sulfamoylamino)-methyl]-phenyl]-urea;

B80 1-[3-Fluoro-4-[(sulfamoylamino)-methyl]-phenyl]-3-[[2-(3-isopropyl-phenyl)-5-(trifluoromethyl)-2H-pyrazol-3-yl]-methyl]-urea;

B81 1-[[2-(3-Chlorophenyl)-5-(trifluoromethyl)-2H-pyrazol-3-yl]-methyl]-3-[4-(methanesulfonamido-methyl)-phenyl]-urea;

B82 2-[3-Fluoro-4-(methanesulfonamido-methyl)-phenyl]-N-[[2-(3-isopropyl-phenyl)-5-(trifluoromethyl)-2H-pyrazol-3-yl]-methyl]-propionamide;

B83 1-[[2-(3-isopropyl-phenyl)-5-(trifluoromethyl)-2H-pyrazol-3-yl]-methyl]-3-[4-(methanesulfonamido-methyl)-phenyl]-urea;

B84 1-[[2-(3-Chlorophenyl)-5-(trifluoromethyl)-2H-pyrazol-3-yl]-methyl]-3-[4-[[(ethylsulfonyl)amino]-methyl]-phenyl]-urea;

B85 1-[[5-tert-Butyl-2-(3-chlorophenyl)-2H-pyrazol-3-yl]-methyl]-3-[4-[[(ethylsulfonyl)amino]-methyl]-phenyl]-urea;

B86 1-[4-(Methanesulfonamido-methyl)-3-methoxy-phenyl]-3-[[2-(m-tolyl)-5-(trifluoromethyl)-2H-pyrazol-3-yl]-methyl]-urea;

B87 1-[3-Fluoro-4-(m ethanesulfonamido-methyl)-phenyl]-3-[[2-(m-tolyl)-5-(trifluoromethyl)-2H-pyrazol-3-yl]-methyl]-urea;

B88 N-[[5-tert-Butyl-2-(m-tolyl)-2H-pyrazol-3-yl]-methyl]-2-[3-fluoro-4-(methanesulfonamido-methyl)-phenyl]-propionamide;

B89 1-[4-(Methanesulfonamido-methyl)-phenyl]-3-[[2-(m-tolyl)-5-(trifluoromethyl)-2H-pyrazol-3-yl]-methyl]-urea;

B90 1-[[5-tert-Butyl-2-(m-tolyl)-2H-pyrazol-3-yl]-methyl]-3-[4-(methanesulfonamido-methyl)-phenyl]-urea;

B91 1-[4-[[(Ethylsulfonyl)amino]-methyl]-phenyl]-3-[[2-(m-tolyl)-5-(trifluoromethyl)-2H-pyrazol-3-yl]-methyl]-urea;

B92 1-[[5-tert-Butyl-2-(m-tolyl)-2H-pyrazol-3-yl]-methyl]-3-[4-[[(ethylsulfonyl)amino]-methyl]-phenyl]-urea;

B93 N-[[5-tert-Butyl-2-(3-chlorophenyl)-2H-pyrazol-3-yl]-methyl]-2-[3-fluoro-4-[(sulfamoylamino)-methyl]-phenyl]-propionamide;

B94 2-[3-Fluoro-4-[(sulfamoylamino)-methyl]-phenyl]-N-[[2-(3-isopropyl-phenyl)-5-(trifluoromethyl)-2H-pyrazol-3-yl]-methyl]-propionamide;

B95 N-[[2-(3-Chlorophenyl)-5-cyclopropyl-2H-pyrazol-3-yl]-methyl]-2-[3-fluoro-4-[(sulfamoylamino)-methyl]-phenyl]-propionamide;

B96 N-[[5-tert-Butyl-2-(3-chloro-4-fluoro-phenyl)-2H-pyrazol-3-yl]-methyl]-2-[3-fluoro-4-[(sulfamoylamino)-methyl]-phenyl]-propionamide;

B97 N-[[2-(3-Chlorophenyl)-5-(trifluoromethyl)-2H-pyrazol-3-yl]-methyl]-2-[3-fluoro-4-[(sulfamoylamino)-methyl]-phenyl]-propionamide;

B98 N-[[5-tert-Butyl-2-(3-chlorophenyl)-2H-pyrazol-3-yl]-methyl]-2-[4-(methanesulfonamido-methyl)-3-methoxy-phenyl]-propionamide;

B99 1-[[2-(3-Chlorophenyl)-5-(trifluoromethyl)-2H-pyrazol-3-yl]-methyl]-3-[4-(pyrrolidin-1-yl-methyl)-phenyl]-urea;

B100 1-[[2-(3-Chlorophenyl)-5-(trifluoromethyl)-2H-pyrazol-3-yl]-methyl]-3-[3-fluoro-4-(piperidin-1-yl-methyl)-phenyl]-urea;

B101 1-[[5-tert-Butyl-2-(3-chlorophenyl)-2H-pyrazol-3-yl]-methyl]-3-[3-fluoro-4-(pyrrolidin-1-yl-methyl)-phenyl]-urea;

B102 N-[[2-(3-Chlorophenyl)-5-(trifluoromethyl)-2H-pyrazol-3-yl]-methyl]-2-[4-[(sulfamoylamino)-methyl]-phenyl]-propionamide;

B103 N-[[5-tert-Butyl-2-(3-chlorophenyl)-2H-pyrazol-3-yl]-methyl]-2-[4-[(sulfamoylamino)-methyl]-phenyl]-propionamide;

B104 N-[[2-(3-Fluorophenyl)-5-(trifluoromethyl)-2H-pyrazol-3-yl]-methyl]-2-[4-(methanesulfonamido-methyl)-phenyl]-propionamide;

B105 1-[[2-(3-Fluorophenyl)-5-(trifluoromethyl)-2H-pyrazol-3-yl]-methyl]-3-[4-(methanesulfonamido-methyl)-3-methoxy-phenyl]-urea;

B106 N-[[2-(3-Chlorophenyl)-5-(trifluoromethyl)-2H-pyrazol-3-yl]-methyl]-2-[4-(methanesulfonamido-methyl)-3-methyl-phenyl]-propionamide; and B107 N-[[5-tert-Butyl-2-(3-chlorophenyl)-2H-pyrazol-3-yl]-methyl]-2-[4-(methanesulfonamido-methyl)-3-methyl-phenyl]-propionamide;

in the form of an individual stereoisomer or a mixture of stereoisomers, and in the form of a free compound or a physiologically acceptable salt thereof.

A further particularly preferred subgroup of the compounds of the invention relates to compounds corresponding to the formula (S)

(S)

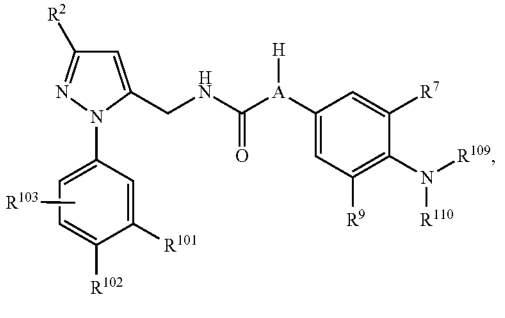

wherein $R^{101}$, $R^{102}$ and $R^{103}$ are each independently selected from the group consisting of H, F, Cl, Br, $CFH_2$, $CF_2H$, $CF_3$, CN, $CH_2$—OH, $CH_2CH_2$—OH, $CH_2$—$OCH_3$, $CH_2CH_2$—$OCH_3$, $OCFH_2$, $OCF_2H$, $OCF_3$, OH, $NH_2$, $C_{1-4}$ alkyl, O—$C_{1-4}$ alkyl, NH—$C_{1-4}$ alkyl, and N($C_{1-4}$ alkyl)$_2$, wherein the $C_{1-4}$ alkyl is in each case unsubstituted;

$R^2$ represents $CF_3$, an unsubstituted $C_{1-4}$ alkyl or an unsubstituted $C_{3-6}$ cycloalkyl;

$R^7$ and $R^9$ are independently selected from the group consisting of H, F, Cl, Br, $CFH_2$, $CF_2H$, $CF_3$, CN, OH, $OCF_3$, $C_{1-4}$ alkyl, and O—$C_{1-4}$ alkyl, wherein the $C_{1-4}$ alkyl is in each case unsubstituted;

A denotes N, CH or C($CH_3$); and $R^{109}$ and $R^{110}$ together with the nitrogen atom connecting them form a 3 to 10 membered heterocyclyl, which is unsubstituted or mono-, di- or trisubstituted with 1, 2 or 3 substituents independently selected from the group consisting of F, Cl, Br, CN, $CF_3$, $CH_2OH$, $CH_2CH_2OH$, $CH_3$, $CH_2CH_3$, $CH(CH_3)_2$, tert.-butyl, cyclopropyl, OH, =O, $OCH_3$, $OCF_3$, $NH_2$, $NH(CH_3)$ and $N(CH_3)_2$;

in the form of an individual stereoisomer or a mixture of stereoisomers, and in the form of a free compound or a physiologically acceptable salt or physiologically acceptable solvate thereof.

In a preferred embodiment of the compound of formula (S), $R^{101}$, $R^{102}$ and $R^{103}$ are each independently selected from the group consisting of H, F, Cl, Br, $CFH_2$, $CF_2H$, $CF_3$, CN, $CH_2$—OH, $CH_2$—$OCH_3$, $OCF_3$, OH, $CH_3$, $CH_2CH_3$, $CH(CH_3)_2$, O—$CH_3$, O—$CH_2CH_3$, $NH_2$, $NH(CH_3)$, and $N(CH_3)_2$. Preferably, $R^{101}$, $R^{102}$ and $R^{103}$ are each independently selected from the group consisting of H, F, Cl, Br, $CFH_2$, $CF_2H$, $CF_3$, CN, $CH_2$—OH, $CH_2$—$OCH_3$, $OCF_3$, OH, $CH_3$, O—$CH_3$, O—$CH_2CH_3$, $NH_2$, $NH(CH_3)$, and $N(CH_3)_2$. More preferably, $R^{101}$, $R^{102}$ and $R^{103}$ are each independently selected from the group consisting of H, F, Cl, $CFH_2$, $CF_2H$, $CF_3$, CN, $CH_2$—$OCH_3$, $OCF_3$, $CH_3$, O—$CH_3$, O—$CH_2CH_3$ and $N(CH_3)_2$. Even more preferably, $R^{101}$, $R^{102}$ and $R^{103}$ are each independently selected from the group consisting of H, F, Cl, $CFH_2$, $CF_2H$, $CF_3$, $OCF_3$, $CH_3$, O—$CH_3$, and O—$CH_2CH_3$. Still more preferably, $R^{101}$, $R^{102}$ and $R^{103}$ are each independently selected from the group consisting of H, F, Cl, $CF_3$, $OCF_3$, $CH_3$ and O—$CH_3$. Particularly, $R^{101}$, $R^{102}$ and $R^{103}$ are each independently selected from the group consisting of H, F, Cl, $CF_3$ and O—$CH_3$. Even more particularly preferably $R^{101}$, $R^{102}$ and $R^{103}$ are each independently selected from the group consisting of H, F, Cl and O—$CH_3$.

In a preferred embodiment of the compound of formula (S) at least one of $R^{101}$, $R^{102}$ and $R^{103}$ is not H.

In another preferred embodiment of the compound of formula (S), one or two of $R^{101}$, $R^{102}$ and $R^{103}$, preferably $R^{102}$ and/or $R^{103}$, denote(s) H.

In another preferred embodiment of the compound of formula (S) one of $R^{101}$, $R^{102}$ and $R^{103}$ represents H, preferably $R^{103}$ represents H.

In another preferred embodiment of the compound of formula (S), $R^{101}$ and $R^{102}$ are each independently selected from the group consisting of H, F, Cl, Br, $CFH_2$, $CF_2H$, $CF_3$, CN, $CH_2$—OH, $CH_2$—$OCH_3$, $OCF_3$, OH, $CH_3$, $CH_2CH_3$, $CH(CH_3)_2$, O—$CH_3$, O—$CH_2CH_3$, $NH_2$, $NH(CH_3)$, and $N(CH_3)_2$, and $R^{103}$ represents H.

Preferably, $R^{101}$ and $R^{102}$ are each independently selected from the group consisting of H, F, Cl, Br, $CFH_2$, $CF_2H$, $CF_3$, CN, $CH_2$—OH, $CH_2$—$OCH_3$, $OCF_3$, OH, $CH_3$, O—$CH_3$, O—$CH_2CH_3$, $NH_2$, $NH(CH_3)$, and $N(CH_3)_2$, more preferably each independently selected from the group consisting of H, F, Cl, $CFH_2$, $CF_2H$, $CF_3$, CN, $CH_2$—$OCH_3$, $OCF_3$, $CH_3$, O—$CH_3$, O—$CH_2CH_3$ and $N(CH_3)_2$, even more preferably each independently selected from the group consisting of H, F, Cl, $CFH_2$, $CF_2H$, $CF_3$, $OCF_3$, $CH_3$, O—$CH_3$, and O—$CH_2CH_3$, still more preferably each independently selected from the group consisting of H, F, Cl, $CF_3$, $OCF_3$, $CH_3$ and O—$CH_3$, in particular each independently selected from the group consisting of H, F, Cl, $CF_3$ and O—$CH_3$, and even more particularly preferably each independently selected from the group consisting of H, F, Cl, and O—$CH_3$, and $R^{103}$ represents H.

In yet another preferred embodiment of the compound of formula (S), $R^{101}$ is selected from the group consisting of F, Cl, Br, $CFH_2$, $CF_2H$, $CF_3$, CN, $CH_2$—OH, $CH_2$—$OCH_3$, $OCF_3$, OH, $CH_3$, $CH_2CH_3$, $CH(CH_3)_2$, O—$CH_3$, O—$CH_2CH_3$, $NH_2$, $NH(CH_3)$, and $N(CH_3)_2$, and $R^{102}$ and $R^{103}$ each represent H.

Preferably, $R^{101}$ is selected from the group consisting of F, Cl, Br, $CFH_2$, $CF_2H$, $CF_3$, CN, $CH_2$—OH, $CH_2$—$OCH_3$, $OCF_3$, OH, $CH_3$, O—$CH_3$, O—$CH_2CH_3$, $NH_2$, $NH(CH_3)$, and $N(CH_3)_2$, more preferably selected from the group consisting of F, Cl, $CFH_2$, $CF_2H$, $CF_3$, CN, $CH_2$—$OCH_3$, $OCF_3$, $CH_3$, O—$CH_3$, O—$CH_2CH_3$ and $N(CH_3)_2$, even more preferably selected from the group consisting of F, Cl, $CFH_2$, $CF_2H$, $CF_3$, $OCF_3$, $CH_3$, O—$CH_3$, and O—$CH_2CH_3$, still more preferably selected from the group consisting of F, Cl, $CF_3$, $OCF_3$, $CH_3$ and O—$CH_3$, in particular selected from the group consisting of F, Cl, $CF_3$ and O—$CH_3$, and even more particularly preferably is selected from the group consisting of F, Cl, and O—$CH_3$, and $R^{102}$ and $R^{103}$ each represent H.

In still another preferred embodiment of the compound of formula (S), $R^{102}$ is selected from the group consisting of F, Cl, Br, $CFH_2$, $CF_2H$, $CF_3$, CN, $CH_2$—OH, $CH_2$—$OCH_3$, $OCF_3$, OH, $CH_3$, $CH_2CH_3$, $CH(CH_3)_2$, O—$CH_3$, O—$CH_2CH_3$, $NH_2$, $NH(CH_3)$, and $N(CH_3)_2$, and $R^{101}$ and $R^{103}$ each represent H.

Preferably, $R^{102}$ is selected from the group consisting of F, Cl, Br, $CFH_2$, $CF_2H$, $CF_3$, CN, $CH_2$—OH, $CH_2$—$OCH_3$, $OCF_3$, OH, $CH_3$, O—$CH_3$, O—$CH_2CH_3$, $NH_2$, $NH(CH_3)$, and $N(CH_3)_2$, more preferably selected from the group consisting of F, Cl, $CFH_2$, $CF_2H$, $CF_3$, CN, $CH_2$—$OCH_3$, $OCF_3$, $CH_3$, O—$CH_3$, O—$CH_2CH_3$ and $N(CH_3)_2$, even more preferably selected from the group consisting of F, Cl, $CFH_2$, $CF_2H$, $CF_3$, $OCF_3$, $CH_3$, O—$CH_3$, and O—$CH_2CH_3$, still more preferably selected from the group consisting of F, Cl, $CF_3$, $OCF_3$, $CH_3$ and O—$CH_3$, in particular selected from the group consisting of F, Cl, $CF_3$ and O—$CH_3$, and even more particularly preferably selected from the group consisting of F, Cl, and O—$CH_3$, and $R^{101}$ and $R^{103}$ each represent H.

In yet a further preferred embodiment of the compound of formula (S), $R^{101}$ is selected from the group consisting of F, Cl, Br, $CFH_2$, $CF_2H$, $CF_3$, CN, $CH_2$—OH, $CH_2$—$OCH_3$, $OCF_3$, OH, $CH_3$, $CH_2CH_3$, $CH(CH_3)_2$, O—$CH_3$, O—$CH_2CH_3$, $NH_2$, $NH(CH_3)$, and $N(CH_3)_2$;

$R^{102}$ is selected from the group consisting of H, F, Cl, Br, $CFH_2$, $CF_2H$, $CF_3$, CN, $CH_2$—OH, $CH_2$—$OCH_3$, $OCF_3$, OH, $CH_3$, $CH_2CH_3$, $CH(CH_3)_2$, O—$CH_3$, O—$CH_2CH_3$, $NH_2$, $NH(CH_3)$, and $N(CH_3)_2$; and $R^{103}$ represents H.

Preferably, $R^{101}$ is selected from the group consisting of F, Cl, Br, $CFH_2$, $CF_2H$, $CF_3$, CN, $CH_2$—OH, $CH_2$—$OCH_3$, $OCF_3$, OH, $CH_3$, O—$CH_3$, O—$CH_2CH_3$, $NH_2$, $NH(CH_3)$, and $N(CH_3)_2$, more preferably selected from the group consisting of F, Cl, $CFH_2$, $CF_2H$, $CF_3$, CN, $CH_2$—$OCH_3$, $OCF_3$, $CH_3$, O—$CH_3$, O—$CH_2CH_3$ and $N(CH_3)_2$, even more preferably selected from the group consisting of F, Cl, $CFH_2$, $CF_2H$, $CF_3$, $OCF_3$, $CH_3$, O—$CH_3$, and O—$CH_2CH_3$, still more preferably selected from the group consisting of F, Cl, $CF_3$, $OCF_3$, $CH_3$ and O—$CH_3$, in particular selected from the group consisting of F, Cl, $CF_3$ and O—$CH_3$, and even more particularly preferably selected from the group consisting of F, Cl, and O—$CH_3$;

$R^{102}$ is selected from the group consisting of H, F, Cl, Br, $CFH_2$, $CF_2H$, $CF_3$, CN, $CH_2$—OH, $CH_2$—$OCH_3$, $OCF_3$, OH, $CH_3$, O—$CH_3$, O—$CH_2CH_3$, $NH_2$, $NH(CH_3)$, and $N(CH_3)_2$, more preferably selected from the group consisting of H, F, Cl, $CFH_2$, $CF_2H$, $CF_3$, CN, $CH_2$—$OCH_3$, $OCF_3$, $CH_3$, O—$CH_3$, O—$CH_2CH_3$ and $N(CH_3)_2$, even more preferably selected from the group consisting of H, F, Cl, $CFH_2$, $CF_2H$, $CF_3$, $OCF_3$, $CH_3$, O—$CH_3$, and O—$CH_2CH_3$, still more preferably selected from the group consisting of H, F, Cl, $CF_3$, $OCF_3$, $CH_3$ and O—$CH_3$, in particular selected from the group consisting of H, F, Cl, $CF_3$ and O—$CH_3$, and even more particularly preferably is selected from the group consisting of H, F, Cl, and O—$CH_3$, and $R^{103}$ represents H.

In another particularly preferred embodiment of formula (S) the partial structure (SS2)

(SS2)

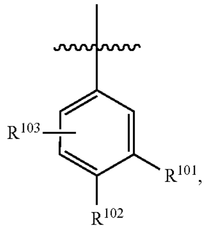

is selected from the group consisting of:

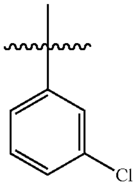
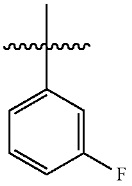
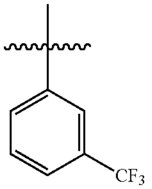

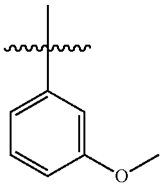
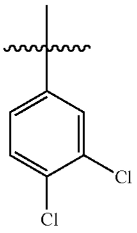
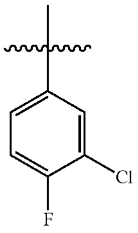

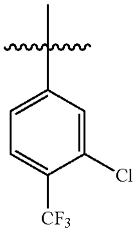
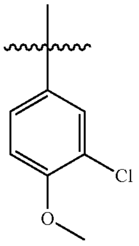
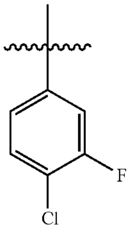

-continued
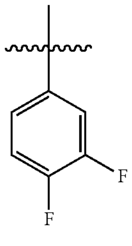 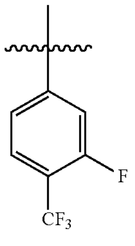 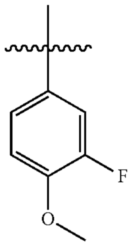
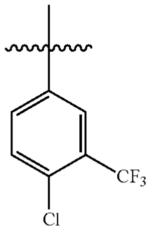 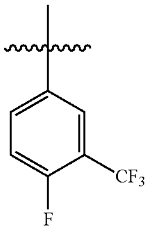 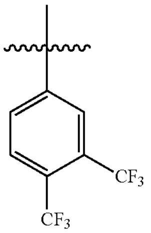
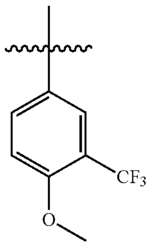 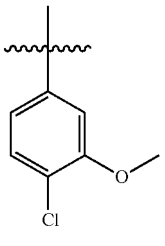 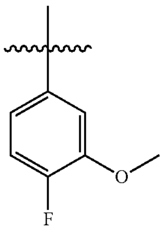
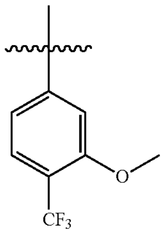 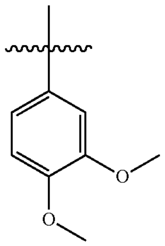 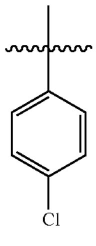
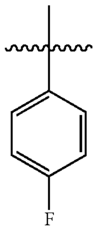 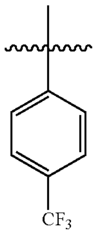 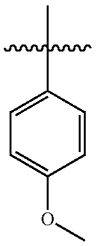 .
Even more particularly preferred, the partial structure (SS2) is selected from the group consisting of:
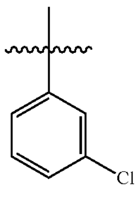 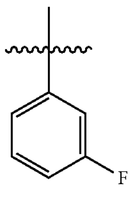 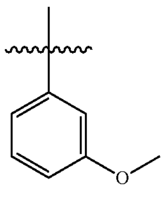
-continued
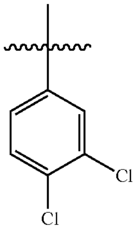 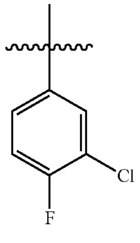 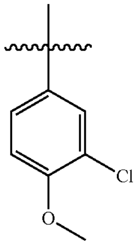
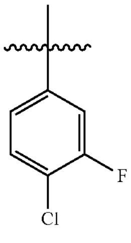 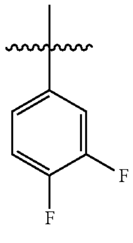 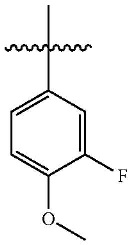
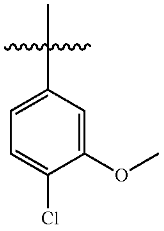 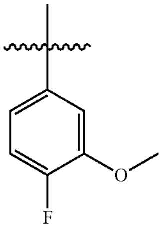 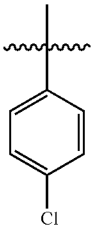
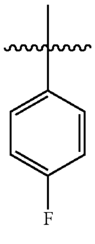 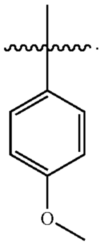 .
Most preferred, the partial structure (SS2) is selected from the group consisting of:
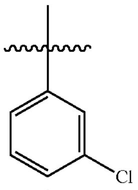 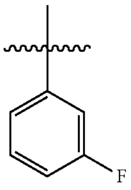 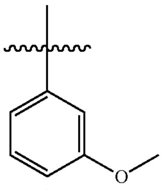
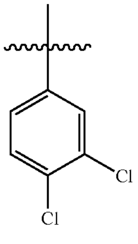 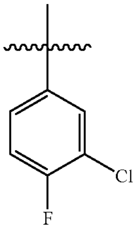 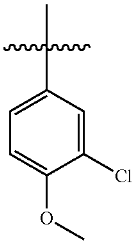

-continued

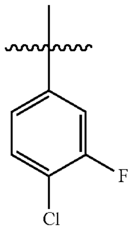

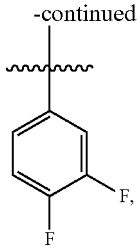, and especially preferably is selected from the group consisting of:

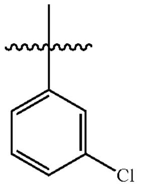

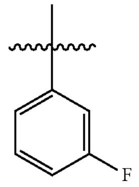

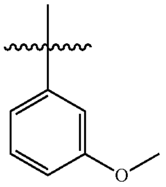.

In another preferred embodiment of the compound of formula (S), $R^2$ represents $CF_3$, methyl, ethyl, n-propyl, 2-propyl, n-butyl, iso-butyl, sec.-butyl, tert.-butyl, cyclopropyl, cyclobutyl, cyclopentyl or cyclohexyl. Preferably, $R^2$ represents $CF_3$, 2-propyl, n-butyl, iso-butyl, sec.-butyl, tert.-butyl, cyclopropyl, or cyclobutyl. More preferably, $R^2$ represents $CF_3$, tert.-butyl or cyclopropyl.

In one particularly preferred embodiment of the compound of formula (S) $R^2$ represents $CF_3$.

In another particularly preferred embodiment of the compound of formula (S) $R^2$ represents tert.-butyl.

In another particularly preferred embodiment of the compound of formula (S) $R^2$ represents cyclopropyl.

In a further preferred embodiment of the compound of formula (S), $R^7$ and $R^9$ are each independently selected from the group consisting of H, F, Cl, Br, $CF_3$, CN, OH, $OCF_3$, $CH_3$, $CH_2CH_3$, $CH(CH_3)_2$, O—$CH_3$, and O—$CH_2CH_3$. Preferably, $R^7$ and $R^9$ are each independently selected from the group consisting of H, F, Cl, $CF_3$, CN, OH, $OCF_3$, $CH_3$, O—$CH_3$, and O—$CH_2CH_3$. More preferably, $R^7$ and $R^9$ are each independently selected from the group consisting of H, F, Cl, $CF_3$, O—$CH_3$, and O—$CH_2CH_3$. Even more preferably, $R^7$ and $R^9$ are each independently selected from the group consisting of H, F, Cl, and O—$CH_3$, and still more preferably each independently selected from the group consisting of H, F and Cl.

In yet a further preferred embodiment of the compound of formula (S) at least one of $R^7$ and $R^9$ is not H.

In a further preferred embodiment of the compound of formula (S) $R^9$ denotes H.

In yet another preferred embodiment of the compound of formula (S), $R^7$ is selected from the group consisting of F, Cl, Br, $CF_3$, CN, OH, $OCF_3$, $CH_3$, $CH_2CH_3$, $CH(CH_3)_2$, O—$CH_3$, and O—$CH_2CH_3$, preferably selected from the group consisting of F, Cl, $CF_3$, CN, OH, $OCF_3$, $CH_3$, O—$CH_3$, and O—$CH_2CH_3$, more preferably selected from the group consisting of F, Cl, $CF_3$, O—$CH_3$, and O—$CH_2CH_3$, even more preferably selected from the group consisting of F, Cl, and O—$CH_3$, and still more preferably selected from the group consisting of F and Cl, and $R^9$ represents H.

In another preferred embodiment of the compound of formula (S), A denotes N or $C(CH_3)$.

In one particularly preferred embodiment of the compound of formula (S) A denotes N.

In another particularly preferred embodiment of the compound of formula (S), A denotes $C(CH_3)$.

In another preferred embodiment of the compound of formula (S), $R^{109}$ and $R^{110}$ together with the nitrogen atom connecting them form the partial structure (SS1)

(SS1)

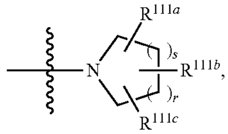

wherein r denotes 0, 1, 2 or 3;

s denotes 0, 1, 2 or 3;

$R^{111a}$, $R^{111b}$ and $R^{111c}$ are each independently selected from the group consisting of H, F, Cl, Br, CN, $CF_3$, $CH_3$, $CH_2OH$, $CH_2CH_2OH$, $CH_2CH_3$, $CH(CH_3)_2$, tert.-butyl, cyclopropyl, OH, $OCH_3$, $OCF_3$, $NH_2$, $NH(CH_3)$ and $N(CH_3)_2$, and preferably from the group consisting of H, F, Cl, $CF_3$, $CH_3$, $CH_2OH$, $CH_2CH_2OH$, $CH_2CH_3$, $CH(CH_3)_2$, OH, $OCH_3$, $NH_2$, $NH(CH_3)$ and $N(CH_3)_2$; or two of $R^{111a}$, $R^{111b}$ and $R^{111c}$ together denote =O, and the remaining residue of $R^{111a}$, $R^{111b}$ and $R^{111c}$ represents H, F, Cl, Br, CN, $CF_3$, $CH_3$, $CH_2OH$, $CH_2CH_2OH$, $CH_2CH_3$, $CH(CH_3)_2$, tert.-butyl, cyclopropyl, OH, $OCH_3$, $OCF_3$, $NH_2$, $NH(CH_3)$ or $N(CH_3)_2$, preferably H, F, Cl, $CF_3$, $CH_3$, $CH_2OH$, $CH_2CH_2OH$, $CH_2CH_3$, $CH(CH_3)_2$, OH, $OCH_3$, $NH_2$, $NH(CH_3)$ or $N(CH_3)_2$, or, if A denotes N, then $R^{109}$ and $R^{110}$ together with the nitrogen atom connecting them form a 3 to 10 membered heterocyclyl, wherein at least one ring member of the heterocyclyl is selected from the group consisting of S, S(=O), $S(=O)_2$, N, NH and $N(C_{1-4}$ alkyl), which is unsubstituted or mono-, di- or trisubstituted with 1, 2 or 3 substituents independently selected from the group consisting of F, Cl, Br, CN, $CF_3$, $CH_3$, $CH_2OH$, $CH_2CH_2OH$, $CH_2CH_3$, $CH(CH_3)_2$, tert.-butyl, cyclopropyl, OH, =O, $OCH_3$, $OCF_3$, $NH_2$, $NH(CH_3)$ and $N(CH_3)_2$, preferably which is unsubstituted or mono-, di- or trisubstituted with 1, 2 or 3 substituents independently selected from the group consisting of F, Cl, CN, $CF_3$, $CH_3$, $CH_2OH$, $CH_2CH_2OH$, $CH_2CH_3$, $CH(CH_3)_2$, OH, =O, $OCH_3$, $NH_2$, $NH(CH_3)$ and $N(CH_3)_2$, more preferably which is unsubstituted or mono-, di- or trisubstituted with 1, 2 or 3 substituents independently selected from the group consisting of F, Cl, $CH_3$, $CH_2OH$, $CH_2CH_2OH$, OH, =O, and $OCH_3$, and even more preferably which is unsubstituted, or, if A denotes CH or $C(CH_3)$, then $R^{109}$ and $R^{110}$ together with the nitrogen atom connecting them form a 3 to 10 membered heterocyclyl, wherein at least one ring member of the heterocyclyl is selected from the group consisting of O, S, N, NH and $N(C_{1-4}$ alkyl), unsubstituted or mono-, di- or trisubstituted with 1, 2 or 3 substituents independently selected from the group consisting of F, Cl, Br, CN, $CF_3$, $CH_3$, $CH_2OH$, $CH_2CH_2OH$, $CH_2CH_3$, $CH(CH_3)_2$, tert.-butyl, cyclopropyl, OH, =O, $OCH_3$, $OCF_3$, $NH_2$, $NH(CH_3)$ and $N(CH_3)_2$, preferably which is unsubstituted or mono-, di- or trisubstituted with 1, 2 or 3 substituents independently selected from the group consisting of F, C, CN, $CF_3$, $CH_3$, $CH_2OH$, $CH_2CH_2OH$, $CH_2CH_3$, $CH(CH_3)_2$, OH, =O, $OCH_3$, $NH_2$, $NH(CH_3)$ and $N(CH_3)_2$, more preferably which is unsubstituted or mono-, di- or trisubstituted with 1, 2 or 3 substituents independently selected from the group consisting of F, Cl, $CH_3$, $CH_2OH$, $CH_2CH_2OH$, OH, =O, and $OCH_3$, and even more preferably which is unsubstituted.

In another preferred embodiment of the compound of formula (S), $R^{109}$ and $R^{110}$ together with the nitrogen atom connecting them form the partial structure (SS1)

(SS1)

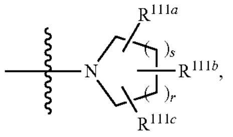

wherein r denotes 0, 1 or 2;

s denotes 0, 1 or 2;

$R^{111a}$, $R^{111b}$ and $R^{111c}$ are each independently selected from the group consisting of H, F, Cl, Br, CN, $CF_3$, $CH_3$, $CH_2OH$, $CH_2CH_2OH$, $CH_2CH_3$, $CH(CH_3)_2$, tert.-butyl, cyclopropyl, OH, $OCH_3$, $OCF_3$, $NH_2$, $NH(CH_3)$ and $N(CH_3)_2$, preferably are each independently selected from the group consisting of H, F, Cl, $CF_3$, $CH_3$, $CH_2OH$, $CH_2CH_2OH$, $CH_2CH_3$, $CH(CH_3)_2$, OH, $OCH_3$, $NH_2$, $NH(CH_3)$ and $N(CH_3)_2$, or two of $R^{111a}$, $R^{111b}$ and $R^{111c}$ together denote =O and the remaining residue of $R^{111a}$, $R^{111b}$ and $R^{111c}$ represents H, F, Cl, Br, CN, $CF_3$, $CH_3$, $CH_2OH$, $CH_2CH_2OH$, $CH_2CH_3$, $CH(CH_3)_2$, tert.-butyl, cyclopropyl, OH, $OCH_3$, $OCF_3$, $NH_2$, $NH(CH_3)$ or $N(CH_3)_2$, preferably H, F, Cl, $CF_3$, $CH_3$, $CH_2OH$, $CH_2CH_2OH$, $CH_2CH_3$, $CH(CH_3)_2$, OH, $OCH_3$, $NH_2$, $NH(CH_3)$ and $N(CH_3)_2$.

Preferably, $R^{109}$ and $R^{110}$ together with the nitrogen atom connecting them form the partial structure (SS1)

(SS1)

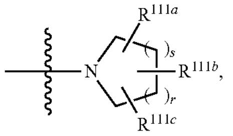

wherein r denotes 0, 1 or 2;

s denotes 0 or 1;

$R^{111a}$ and $R^{111b}$ are each independently selected from the group consisting of H, F, Cl, $CF_3$, $CH_3$, $CH_2OH$, $CH_2CH_2OH$, $CH_2CH_3$, $CH(CH_3)_2$, OH, $OCH_3$, $NH_2$, $NH(CH_3)$ and $N(CH_3)_2$, preferably each independently selected from the group consisting of H, $CH_3$, $CH_2OH$, $CH_2CH_2OH$, $CH_2CH_3$, $CH(CH_3)_2$, OH, $OCH_3$, and even more preferably are each independently selected from the group consisting of H, OH and $OCH_3$, and $R^{111c}$ denotes H; or $R^{111a}$ and $R^{111b}$ together denote =O, and $R^{111c}$ denotes H.

More preferably, $R^{109}$ and $R^{110}$ together with the nitrogen atom connecting them form a partial structure selected from the group consisting of:

(SS1-a)

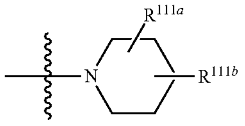

(SS1-b)

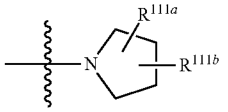

(SS1-c)

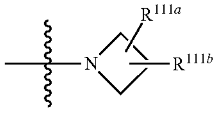

(SS1-d)

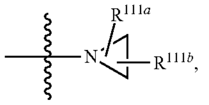

wherein $R^{111a}$ and $R^{111b}$ are each independently selected from the group consisting of H, F, Cl, $CF_3$, $CH_3$, $CH_2OH$, $CH_2CH_2OH$, $CH_2CH_3$, $CH(CH_3)_2$, OH, and $OCH_3$, preferably each independently selected from the group consisting of H, $CH_3$, $CH_2OH$, $CH_2CH_2OH$, $CH_2CH_3$, $CH(CH_3)_2$, OH, $OCH_3$, and even more preferably each independently selected from the group consisting of H, OH and $OCH_3$, or $R^{111a}$ and $R^{111b}$ together denote =O.

Even more preferably, $R^{109}$ and $R^{110}$ together with the nitrogen atom connecting them form a partial structure selected from the group consisting of:

(SS1-a)

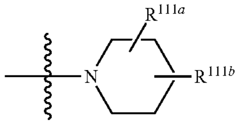

(SS1-b)

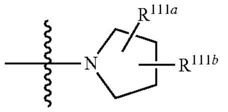

(SS1-c)

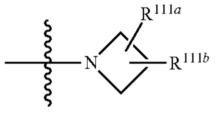

(SS1-d)

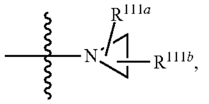

wherein $R^{111a}$ is selected from the group consisting of H, F, Cl, $CF_3$, $CH_3$, $CH_2OH$, $CH_2CH_2OH$, $CH_2CH_3$, $CH(CH_3)_2$, OH, and $OCH_3$, preferably from the group consisting of H, $CH_3$, $CH_2OH$, $CH_2CH_2OH$, $CH_2CH_3$, $CH(CH_3)_2$, OH, $OCH_3$, and even more preferably from the group consisting of H, OH and $OCH_3$, and $R^{111b}$ denotes H.

Particularly, $R^{109}$ and $R^{110}$ together with the nitrogen atom connecting them form a partial structure selected from the group consisting of:

(SS1-b)

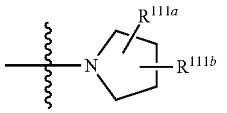

(SS1-c)

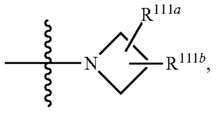

wherein $R^{111a}$ is selected from the group consisting of H, F, Cl, $CF_3$, $CH_3$, $CH_2OH$, $CH_2CH_2OH$, $CH_2CH_3$, $CH(CH_3)_2$, OH, and $OCH_3$, preferably from the group consisting of H, $CH_3$, $CH_2OH$, $CH_2CH_2OH$, $CH_2CH_3$, $CH(CH_3)_2$, OH, $OCH_3$, and even more preferably from the group consisting of H, OH and $OCH_3$, and $R^{111b}$ denotes H.

In a particularly preferred embodiment of the present invention, $R^{101}$, $R^{102}$ and $R^{103}$ are each independently selected from the group consisting of H, F, Cl, Br, $CFH_2$, $CF_2H$, $CF_3$, CN, $CH_2$—OH, $CH_2$—$OCH_3$, $OCF_3$, OH, $CH_3$, $CH_2CH_3$, $CH(CH_3)_2$, O—$CH_3$, O—$CH_2CH_3$, $NH_2$, $NH(CH_3)$, and $N(CH_3)_2$, preferably, wherein at least one of $R^{101}$, $R^{102}$ and $R^{103}$ is not H;

$R^2$ represents $CF_3$, tert.-butyl or cyclopropyl;

$R^7$ and $R^9$ are each independently selected from the group consisting of H, F, Cl, Br, $CF_3$, CN, OH, $OCF_3$, $CH_3$, $CH_2CH_3$, $CH(CH_3)_2$, O—$CH_3$, and O—$CH_2CH_3$, preferably, wherein at least one of $R^7$ and $R^9$ is not H;

A denotes N, CH or $C(CH_3)$, and $R^{109}$ and $R^{110}$ together with the nitrogen atom connecting them form a partial structure selected from the group consisting of:

(SS1-a)

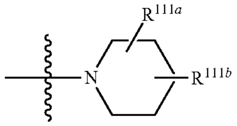

(SS1-b)

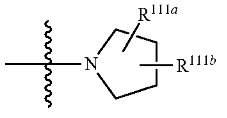

(SS1-c)

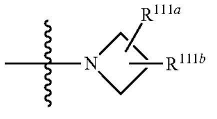

(SS1-d)

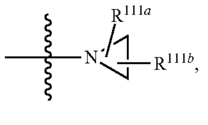

wherein $R^{111a}$ is selected from the group consisting of H, F, Cl, $CF_3$, $CH_3$, $CH_2OH$, $CH_2CH_2OH$, $CH_2CH_3$, $CH(CH_3)_2$, OH, and $OCH_3$, preferably from the group consisting of H, $CH_3$, $CH_2OH$, $CH_2CH_2OH$, $CH_2CH_3$, $CH(CH_3)_2$, OH, $OCH_3$, and even more preferably from the group consisting of H, OH and $OCH_3$; and $R^{111b}$ denotes H; or $R^{111a}$ and $R^{111b}$ together denote =O.

Preferred embodiments of the compound of formula (S) have the formula (S0-a) or (S0-b):

(S0-a)

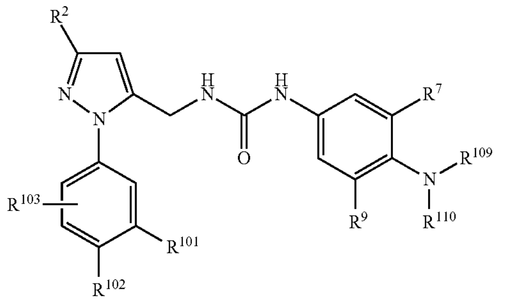

(S0-b)

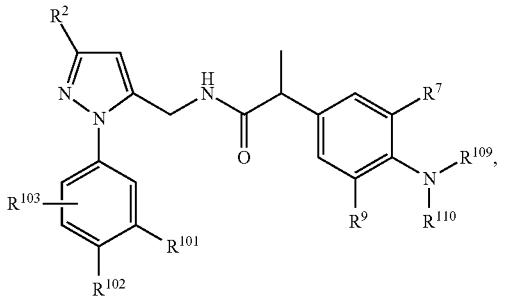

wherein the respective substituents, variables and indices have the meanings described above.

Further preferred embodiments of the compound of formula (S) have the formula (S1-a), (S1-a-1) or (S1-a-2):

(S1-a)

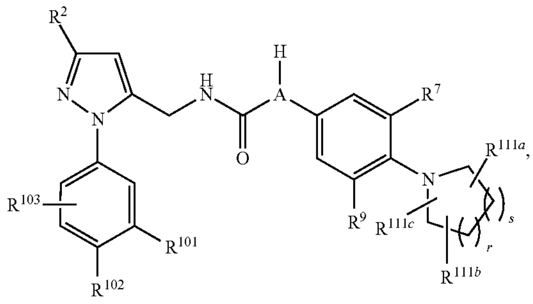

-continued (S1-a-1)

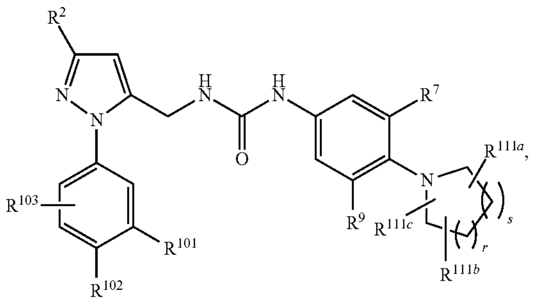

(S1-a-2)

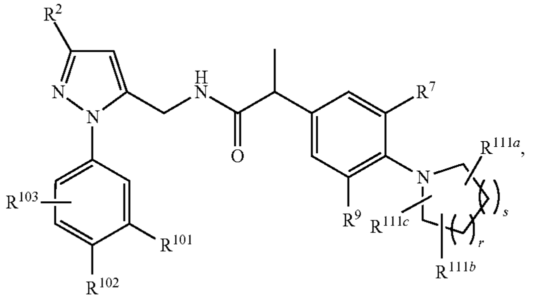

wherein the respective substituents, variables and indices have the meanings described above. Preferably $R^{111a}$ denotes OH; $R^{111b}$ and $R^{111c}$ each denote H, and the remaining substituents, variables and indices have the respective meanings described above.

Moreover, preferred embodiments of the compound of formula (S) have the formula (S1-b), (S1-b-1) or (S1-b-2):

(S1-b)

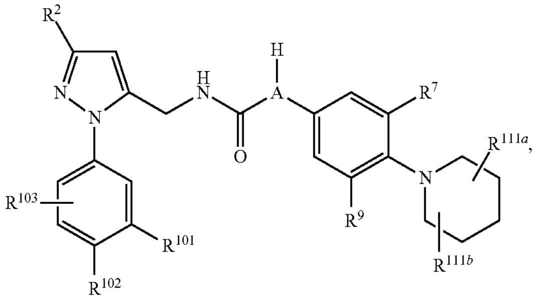

(S1-b-1)

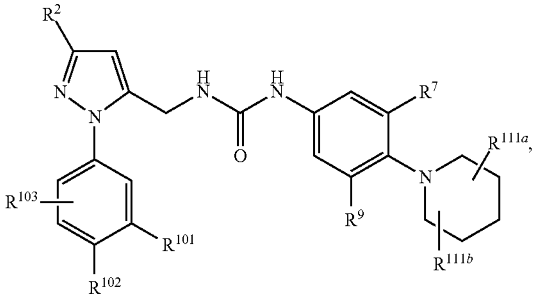

-continued (S1-b-2)

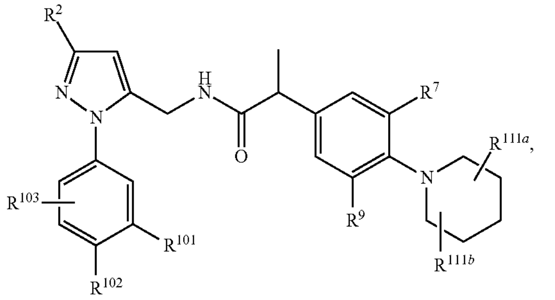

wherein the respective substituents, variables and indices have the meanings described above. Preferably $R^{111a}$ denotes OH; $R^{111b}$ denotes H, and the remaining substituents, variables and indices have the respective meanings described above.

In addition, preferred embodiments of the compound of formula (S) have the formula (S1-c), (S1-c-1) or (S1-c-2):

(S1-c)

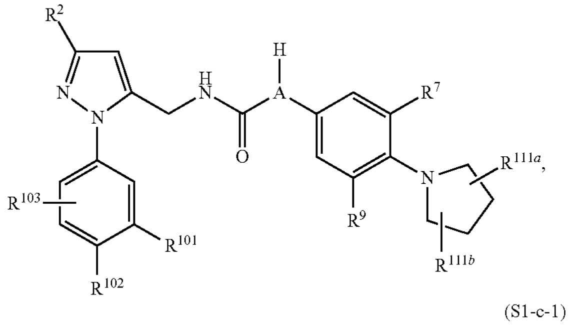

(S1-c-1)

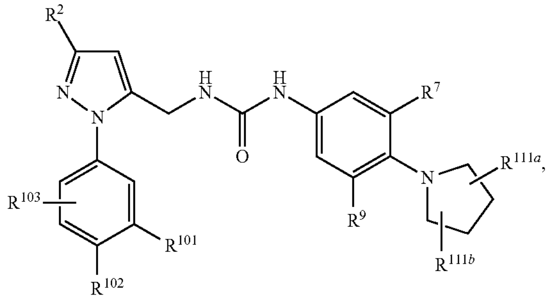

(S1-c-2)

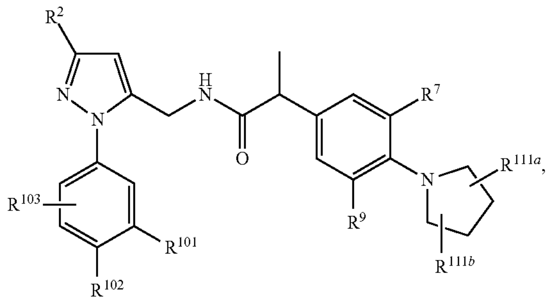

wherein the respective substituents, variables and indices have the meanings described above. Preferably, $R^{111a}$ denotes OH; $R^{111b}$ denotes H, and the remaining substituents, variables and indices have the respective meanings described above.

Yet further preferred embodiments of the compound of formula (S) have the formula (S1-d), (S1-d-1) or (S1-d-2):

(S1-d)

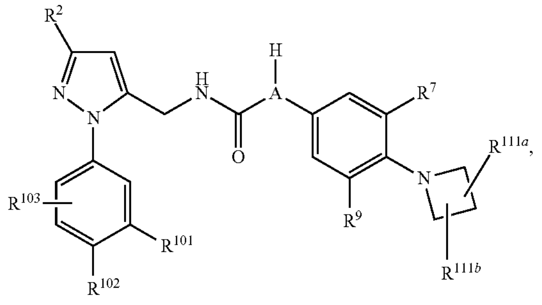

(S1-d-1)

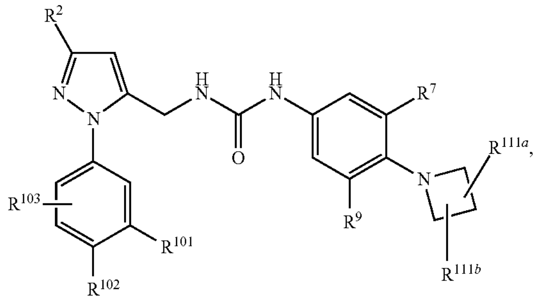

(S1-d-2)

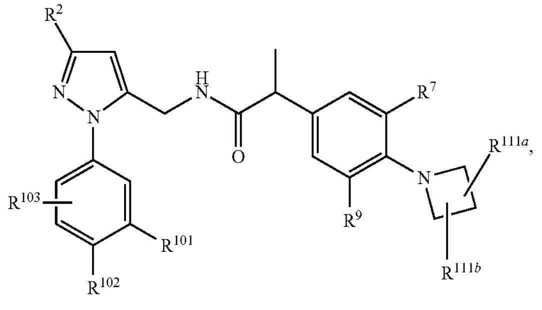

wherein the respective substituents, variables and indices have the meanings described above. Preferably $R^{111a}$ denotes OH; $R^{111b}$ denotes H, and the remaining substituents, variables and indices have the respective meanings described above.

Further preferred embodiments of the compound of formula (S) have the formula (S1-e), (S1-e-1) or (S1-e-2):

(S1-e)

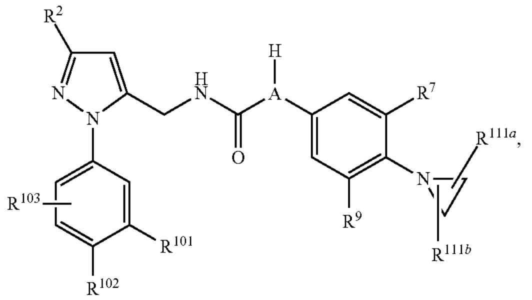

(S1-e-1)

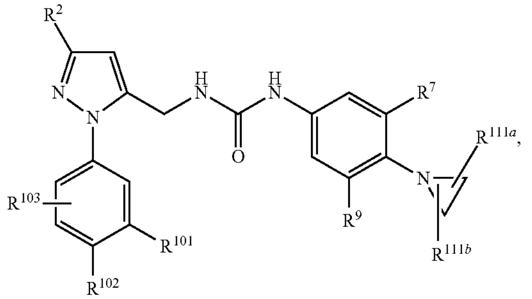

(S1-e-2)

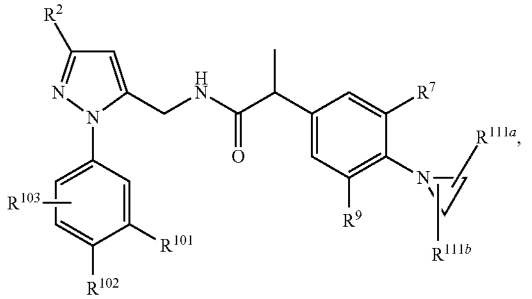

wherein the respective substituents, variables and indices have the meanings described above. Preferably $R^{111a}$ denotes OH; $R^{111b}$ denotes H, and the remaining substituents, variables and indices have the respective meanings described above.

Embodiments of the compound of formula (S) having the formula (S1-d), (S1-d-1) or (S1-d-2) are especially preferred.

In particularly preferred embodiments of the present invention, $R^{101}$ in the compound of general formula (S), (S1-a), (S1-a-1), (S1-a-2), (S1-b), (S1-b-1), (S1-b-2), (S1-c), (S1-c-1), (S1-c-2), (S1-d), (S1-d-1), (S1-d-2), (S1-e), (S1-e-1) and/or (S1-e-2) represents F, Cl, $CF_3$ or O—$CH_3$, preferably F or Cl, most preferably Cl—preferably when $R^{103}$ is H and $R^{102}$ represents H, F, Cl, $CF_3$ or $OCH_3$, more preferably when $R^{103}$ is H and $R^{102}$ represents H, F or Cl, even more preferably when both $R^{102}$ and $R^{103}$ denote H, and the remaining substituents, variables and indices have the respective meanings described above.

Particularly preferred are compounds of formula (S) selected from the group consisting of:

C1 N-[[2-(3-Chlorophenyl)-5-(trifluoromethyl)-2H-pyrazol-3-yl]-methyl]-2-[4-(1,1-dioxo-[1,2]thiazolidin-2-yl)-3-fluoro-phenyl]-propionamide;

C2 N-[[5-tert-Butyl-2-(3-chloro-4-fluoro-phenyl)-2H-pyrazol-3-yl]-methyl]-2-[4-(1,1-dioxo-[1,2]thiazolidin-2-yl)-3-fluoro-phenyl]-propionamide;

C3 N-[[2-(3,4-Difluoro-phenyl)-5-(trifluoromethyl)-2H-pyrazol-3-yl]-methyl]-2-[4-(1,1-dioxo-[1,2]thiazolidin-2-yl)-3-fluoro-phenyl]-propionamide;

C4 1-[[2-(3-Fluorophenyl)-5-(trifluoromethyl)-2H-pyrazol-3-yl]-methyl]-3-(3-fluoro-4-pyrrolidin-1-yl-phenyl)-urea;

C5 1-[[2-(3-Chlorophenyl)-5-(trifluoromethyl)-2H-pyrazol-3-yl]-methyl]-3-(3-fluoro-4-morpholin-4-yl-phenyl)-urea;

C6 1-[[2-(3-Chlorophenyl)-5-(trifluoromethyl)-2H-pyrazol-3-yl]-methyl]-3-[3-fluoro-4-(3-hydroxy-azetidin-1-yl)-phenyl]-urea;

C7 1-[[5-tert-Butyl-2-(3-chlorophenyl)-2H-pyrazol-3-yl]-methyl]-3-[3-fluoro-4-(3-hydroxy-azetidin-1-yl)-phenyl]-urea;

C8 1-[[5-tert-Butyl-2-(3-fluorophenyl)-2H-pyrazol-3-yl]-methyl]-3-[3-fluoro-4-(3-hydroxy-azetidin-1-yl)-phenyl]-urea;

C9 1-[3-Fluoro-4-(3-hydroxy-azetidin-1-yl)-phenyl]-3-[[2-(3-fluorophenyl)-5-(trifluoromethyl)-2H-pyrazol-3-yl]-methyl]-urea;

C10 1-[[2-(3,4-Difluoro-phenyl)-5-(trifluoromethyl)-2H-pyrazol-3-yl]-methyl]-3-[3-fluoro-4-(3-hydroxy-azetidin-1-yl)-phenyl]-urea;

C11 1-[[5-tert-Butyl-2-(3,4-difluoro-phenyl)-2H-pyrazol-3-yl]-methyl]-3-[3-fluoro-4-(3-hydroxy-azetidin-1-yl)-phenyl]-urea;

C12 1-[3-Fluoro-4-(3-hydroxy-azetidin-1-yl)-phenyl]-3-[[2-(m-tolyl)-5-(trifluoromethyl)-2H-pyrazol-3-yl]-methyl]-urea; and C13 1-[[2-(3-Chlorophenyl)-5-cyclopropyl-2H-pyrazol-3-yl]-methyl]-3-[3-fluoro-4-(3-hydroxy-azetidin-1-yl)-phenyl]-urea;

in the form of an individual stereoisomer or a mixture of stereoisomers, and in the form of a free compound or a physiologically acceptable salt thereof.

Yet another particularly preferred subgroup of the compounds of the invention relates to compounds corresponding to the formula (T)

(T)

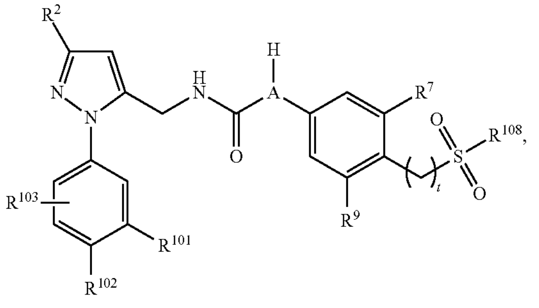

wherein $R^{101}$, $R^{102}$ and $R^{103}$ are each independently selected from the group consisting of H, F, Cl, Br, $CFH_2$, $CF_2H$, $CF_3$, CN, $CH_2$—OH, $CH_2CH_2$—OH, $CH_2$—$OCH_3$, $CH_2CH_2$—$OCH_3$, $OCFH_2$, $OCF_2H$, $OCF_3$, OH, $NH_2$, $C_{1-4}$ alkyl, O—$C_{1-4}$ alkyl, NH—$C_{1-4}$ alkyl, and N($C_{1-4}$ alkyl)$_2$, wherein the $C_{1-4}$ alkyl is in each case unsubstituted;

$R^2$ represents $CF_3$, an unsubstituted $C_{1-4}$ alkyl or an unsubstituted $C_{3-6}$ cycloalkyl;

$R^7$ and $R^9$ are each independently selected from the group consisting of H, F, Cl, Br, $CFH_2$, $CF_2H$, $CF_3$, CN, OH, $OCF_3$, $C_{1-4}$ alkyl, and O—$C_{1-4}$ alkyl, wherein the $C_{1-4}$ alkyl is in each case unsubstituted;

A denotes N, CH or C($CH_3$);

t denotes 0, 1 or 2; and $R^{108}$ represents $C_{1-4}$ alkyl, which is unsubstituted or mono-, di- or trisubstituted with 1, 2 or 3 substituents selected from the group consisting of F, Cl, Br, OH, =O and $OCH_3$;

in the form of an individual stereoisomer or a mixture of stereoisomers, and in the form of a free compound or a physiologically acceptable salt or a physiologically acceptable solvate thereof.

In a preferred embodiment of the compound of formula (T), $R^{101}$, $R^{102}$ and $R^{103}$ are each independently selected from the group consisting of H, F, Cl, Br, $CFH_2$, $CF_2H$, $CF_3$, CN, $CH_2$—OH, $CH_2$—$OCH_3$, $OCF_3$, OH, $CH_3$, $CH_2CH_3$, CH($CH_3$)$_2$, O—$CH_3$, O—$CH_2CH_3$, $NH_2$, NH($CH_3$), and N($CH_3$)$_2$. Preferably, $R^{101}$, $R^{102}$ and $R^{103}$ are each independently selected from the group consisting of H, F, Cl, Br, $CFH_2$, $CF_2H$, $CF_3$, CN, $CH_2$—OH, $CH_2$—$OCH_3$, $OCF_3$, OH, $CH_3$, O—$CH_3$, O—$CH_2CH_3$, $NH_2$, NH($CH_3$), and N($CH_3$)$_2$. More preferably, $R^{101}$, $R^{102}$ and $R^{103}$ are each independently selected from the group consisting of H, F, Cl, $CFH_2$, $CF_2H$, $CF_3$, CN, $CH_2$—$OCH_3$, $OCF_3$, $CH_3$, O—$CH_3$, O—$CH_2CH_3$ and N($CH_3$)$_2$. Even more preferably, $R^{101}$, $R^{102}$ and $R^{103}$ are each independently selected from the group consisting of H, F, Cl, $CFH_2$, $CF_2H$, $CF_3$, $OCF_3$, $CH_3$, O—$CH_3$, and O—$CH_2CH_3$. Still more preferably, $R^{101}$, $R^{102}$ and $R^{103}$ are each independently selected from the group consisting of H, F, Cl, $CF_3$, $OCF_3$, $CH_3$ and O—$CH_3$. Particularly, $R^{101}$, $R^{102}$ and $R^{103}$ are each independently selected from the group consisting of H, F, Cl, $CF_3$ and O—$CH_3$. Even more particularly preferred $R^{101}$, $R^{102}$ and $R^{103}$ are each independently selected from the group consisting of H, F, Cl and O—$CH_3$.

In a preferred embodiment of the compound of formula (T) at least one of $R^{101}$, $R^{102}$ and $R^{103}$ is not H.

In another preferred embodiment of the compound of formula (T) one or two of $R^{101}$, $R^{102}$ and $R^{103}$, preferably $R^{102}$ and/or $R^{103}$, denote(s) H.

In another preferred embodiment of the compound of formula (T) one of $R^{101}$, $R^{102}$ and $R^{103}$ represents H. Preferably $R^{103}$ represents H.

In another preferred embodiment of the compound of formula (T) $R^{101}$ and $R^{102}$ are each independently selected from the group consisting of H, F, Cl, Br, $CFH_2$, $CF_2H$, $CF_3$, CN, $CH_2$—OH, $CH_2$—$OCH_3$, $OCF_3$, OH, $CH_3$, $CH_2CH_3$, CH($CH_3$)$_2$, O—$CH_3$, O—$CH_2CH_3$, $NH_2$, NH($CH_3$), and N($CH_3$)$_2$, and $R^{103}$ represents H.

Preferably, $R^{101}$ and $R^{102}$ are each independently selected from the group consisting of H, F, Cl, Br, $CFH_2$, $CF_2H$, $CF_3$, CN, $CH_2$—OH, $CH_2$—$OCH_3$, $OCF_3$, OH, $CH_3$, O—$CH_3$, O—$CH_2CH_3$, $NH_2$, NH($CH_3$), and N($CH_3$)$_2$, more preferably are each independently selected from the group consisting of H, F, Cl, $CFH_2$, $CF_2H$, $CF_3$, CN, $CH_2$—$OCH_3$, $OCF_3$, $CH_3$, O—$CH_3$, O—$CH_2CH_3$ and N($CH_3$)$_2$, even more preferably are each independently selected from the group consisting of H, F, Cl, $CFH_2$, $CF_2H$, $CF_3$, $OCF_3$, $CH_3$, O—$CH_3$, and O—$CH_2CH_3$, still more preferably are each independently selected from the group consisting of H, F, Cl, $CF_3$, $OCF_3$, $CH_3$ and O—$CH_3$, in particular are each independently selected from the group consisting of H, F, Cl, $CF_3$ and 0-$CH_3$, even more particularly preferred are each independently selected from the group consisting of H, F, Cl, and O—$CH_3$, and $R^{103}$ represents H.

In yet another preferred embodiment of the compound of formula (T) $R^{101}$ is selected from the group consisting of F, Cl, Br, $CFH_2$, $CF_2H$, $CF_3$, CN, $CH_2$—OH, $CH_2$—$OCH_3$, $OCF_3$, OH, $CH_3$, $CH_2CH_3$, $CH(CH_3)_2$, O—$CH_3$, O—$CH_2CH_3$, $NH_2$, $NH(CH_3)$, and $N(CH_3)_2$, and $R^{102}$ and $R^{103}$ each represent H.

Preferably, $R^{101}$ is selected from the group consisting of F, Cl, Br, $CFH_2$, $CF_2H$, $CF_3$, CN, $CH_2$—OH, $CH_2$—$OCH_3$, $OCF_3$, OH, $CH_3$, O—$CH_3$, O—$CH_2CH_3$, $NH_2$, $NH(CH_3)$, and $N(CH_3)_2$, more preferably from the group consisting of F, Cl, $CFH_2$, $CF_2H$, $CF_3$, CN, $CH_2$—$OCH_3$, $OCF_3$, $CH_3$, O—$CH_3$, O—$CH_2CH_3$ and $N(CH_3)_2$, even more preferably from the group consisting of F, Cl, $CFH_2$, $CF_2H$, $CF_3$, $OCF_3$, $CH_3$, O—$CH_3$, and O—$CH_2CH_3$, still more preferably from the group consisting of F, Cl, $CF_3$, $OCF_3$, $CH_3$ and O—$CH_3$, in particular from the group consisting of F, Cl, $CF_3$ and O—$CH_3$, and even more particularly preferably from the group consisting of F, Cl, and O—$CH_3$, and $R^{102}$ and $R^{103}$ each represent H.

In still another preferred embodiment of the compound of formula (T) $R^{102}$ is selected from the group consisting of F, Cl, Br, $CFH_2$, $CF_2H$, $CF_3$, CN, $CH_2$—OH, $CH_2$—$OCH_3$, $OCF_3$, OH, $CH_3$, $CH_2CH_3$, $CH(CH_3)_2$, O—$CH_3$, O—$CH_2CH_3$, $NH_2$, $NH(CH_3)$, and $N(CH_3)_2$, and $R^{10'}$ and $R^{103}$ each represent H.

Preferably, $R^{102}$ is selected from the group consisting of F, Cl, Br, $CFH_2$, $CF_2H$, $CF_3$, CN, $CH_2$—OH, $CH_2$—$OCH_3$, $OCF_3$, OH, $CH_3$, O—$CH_3$, O—$CH_2CH_3$, $NH_2$, $NH(CH_3)$, and $N(CH_3)_2$, more preferably from the group consisting of F, Cl, $CFH_2$, $CF_2H$, $CF_3$, CN, $CH_2$—$OCH_3$, $OCF_3$, $CH_3$, O—$CH_3$, O—$CH_2CH_3$ and $N(CH_3)_2$, even more preferably from the group consisting of F, Cl, $CFH_2$, $CF_2H$, $CF_3$, $OCF_3$, $CH_3$, O—$CH_3$, and O—$CH_2CH_3$, still more preferably from the group consisting of F, Cl, $CF_3$, $OCF_3$, $CH_3$ and O—$CH_3$, in particular from the group consisting of F, Cl, $CF_3$ and O—$CH_3$, and even more particularly preferably from the group consisting of F, Cl, and O—$CH_3$, and $R^{10'}$ and $R^{103}$ each represent H.

In yet a further preferred embodiment of the compound of formula (T)

$R^{101}$ is selected from the group consisting of F, Cl, Br, $CFH_2$, $CF_2H$, $CF_3$, CN, $CH_2$—OH, $CH_2$—$OCH_3$, $OCF_3$, OH, $CH_3$, $CH_2CH_3$, $CH(CH_3)_2$, O—$CH_3$, O—$CH_2CH_3$, $NH_2$, $NH(CH_3)$, and $N(CH_3)_2$;

$R^{102}$ is selected from the group consisting of H, F, Cl, Br, $CFH_2$, $CF_2H$, $CF_3$, CN, $CH_2$—OH, $CH_2$—$OCH_3$, $OCF_3$, OH, $CH_3$, $CH_2CH_3$, $CH(CH_3)_2$, O—$CH_3$, O—$CH_2CH_3$, $NH_2$, $NH(CH_3)$, and $N(CH_3)_2$; and $R^{103}$ represents H.

Preferably, $R^{101}$ is selected from the group consisting of F, Cl, Br, $CFH_2$, $CF_2H$, $CF_3$, CN, $CH_2$—OH, $CH_2$—$OCH_3$, $OCF_3$, OH, $CH_3$, O—$CH_3$, O—$CH_2CH_3$, $NH_2$, $NH(CH_3)$, and $N(CH_3)_2$, more preferably from the group consisting of F, Cl, $CFH_2$, $CF_2H$, $CF_3$, CN, $CH_2$—$OCH_3$, $OCF_3$, $CH_3$, O—$CH_3$, O—$CH_2CH_3$ and $N(CH_3)_2$, even more preferably from the group consisting of F, Cl, $CFH_2$, $CF_2H$, $CF_3$, $OCF_3$, $CH_3$, O—$CH_3$, and O—$CH_2CH_3$, still more preferably from the group consisting of F, Cl, $CF_3$, $OCF_3$, $CH_3$ and O—$CH_3$, in particular from the group consisting of F, Cl, $CF_3$ and O—$CH_3$, and even more particularly preferably from the group consisting of F, Cl, and O—$CH_3$;

$R^{102}$ is selected from the group consisting of H, F, Cl, Br, $CFH_2$, $CF_2H$, $CF_3$, CN, $CH_2$—OH, $CH_2$—$OCH_3$, $OCF_3$, OH, $CH_3$, O—$CH_3$, O—$CH_2CH_3$, $NH_2$, $NH(CH_3)$, and $N(CH_3)_2$, more preferably from the group consisting of H, F, Cl, $CFH_2$, $CF_2H$, $CF_3$, CN, $CH_2$—$OCH_3$, $OCF_3$, $CH_3$, O—$CH_3$, O—$CH_2CH_3$ and $N(CH_3)_2$, even more preferably from the group consisting of H, F, Cl, $CFH_2$, $CF_2H$, $CF_3$, $OCF_3$, $CH_3$, O—$CH_3$, and O—$CH_2CH_3$, still more preferably from the group consisting of H, F, Cl, $CF_3$, $OCF_3$, $CH_3$ and O—$CH_3$, in particular from the group consisting of H, F, Cl, $CF_3$ and O—$CH_3$, and even more particularly preferably from the group consisting of H, F, Cl, and O—$CH_3$; and $R^{103}$ represents H.

In yet another further preferred embodiment of the compound of formula (T), $R^{101}$ is selected from the group consisting of F, Br, $CFH_2$, $CF_2H$, $CF_3$, CN, $CH_2$—OH, $CH_2$—$OCH_3$, $OCF_3$, OH, $CH_3$, O—$CH_3$, O—$CH_2CH_3$, $NH_2$, $NH(CH_3)$, and $N(CH_3)_2$, more preferably from the group consisting of F, $CFH_2$, $CF_2H$, $CF_3$, CN, $CH_2$—$OCH_3$, $OCF_3$, $CH_3$, O—$CH_3$, O—$CH_2CH_3$ and $N(CH_3)_2$, even more preferably from the group consisting of F, $CFH_2$, $CF_2H$, $CF_3$, $OCF_3$, $CH_3$, O—$CH_3$, and O—$CH_2CH_3$, still more preferably from the group consisting of F, $CF_3$, $OCF_3$, $CH_3$ and O—$CH_3$, in particular from the group consisting of F, $CF_3$ and O—$CH_3$, and even more particularly preferably from the group consisting of F and O—$CH_3$, and $R^{102}$ and $R^{103}$ each represent H.

In still another further preferred embodiment of the compound of formula (T), $R^{101}$ is selected from the group consisting of F, Br, $CFH_2$, $CF_2H$, $CF_3$, CN, $CH_2$—OH, $CH_2$—$OCH_3$, $OCF_3$, OH, $CH_3$, $CH_2CH_3$, $CH(CH_3)_2$, O—$CH_3$, O—$CH_2CH_3$, $NH_2$, $NH(CH_3)$, and $N(CH_3)_2$;

$R^{102}$ is selected from the group consisting of H, F, Cl, Br, $CFH_2$, $CF_2H$, $CF_3$, CN, $CH_2$—OH, $CH_2$—$OCH_3$, $OCF_3$, OH, $CH_3$, $CH_2CH_3$, $CH(CH_3)_2$, O—$CH_3$, O—$CH_2CH_3$, $NH_2$, $NH(CH_3)$, and $N(CH_3)_2$; and $R^{103}$ represents H.

Preferably, $R^{101}$ is selected from the group consisting of F, Br, $CFH_2$, $CF_2H$, $CF_3$, CN, $CH_2$—OH, $CH_2$—$OCH_3$, $OCF_3$, OH, $CH_3$, O—$CH_3$, O—$CH_2CH_3$, $NH_2$, $NH(CH_3)$, and $N(CH_3)_2$, more preferably from the group consisting of F, $CFH_2$, $CF_2H$, $CF_3$, CN, $CH_2$—$OCH_3$, $OCF_3$, $CH_3$, O—$CH_3$, O—$CH_2CH_3$ and $N(CH_3)_2$, even more preferably from the group consisting of F, $CFH_2$, $CF_2H$, $CF_3$, $OCF_3$, $CH_3$, O—$CH_3$, and O—$CH_2CH_3$, still more preferably from the group consisting of F, $CF_3$, $OCF_3$, $CH_3$ and O—$CH_3$, in particular from the group consisting of F, $CF_3$ and O—$CH_3$, and even more particularly preferably from the group consisting of F and O—$CH_3$; and $R^{102}$ is selected from the group consisting of H, F, Cl, Br, $CFH_2$, $CF_2H$, $CF_3$, CN, $CH_2$—OH, $CH_2$—$OCH_3$, $OCF_3$, OH, $CH_3$, O—$CH_3$, O—$CH_2CH_3$, $NH_2$, $NH(CH_3)$, and $N(CH_3)_2$, more preferably from the group consisting of H, F, Cl, $CFH_2$, $CF_2H$, $CF_3$, CN, $CH_2$—$OCH_3$, $OCF_3$, $CH_3$, O—$CH_3$, O—$CH_2CH_3$ and $N(CH_3)_2$, even more preferably from the group consisting of H, F, Cl, $CFH_2$, $CF_2H$, $CF_3$, $OCF_3$, $CH_3$, O—$CH_3$, and O—$CH_2CH_3$, still more preferably from the group consisting of H, F, Cl, $CF_3$, $OCF_3$, $CH_3$ and O—$CH_3$, in particular from the group consisting of H, F, Cl, $CF_3$ and O—$CH_3$, and even more particularly preferably from the group consisting of H, F, Cl, and O—$CH_3$.

In another particularly preferred embodiment of formula (T), the partial structure (TS2)

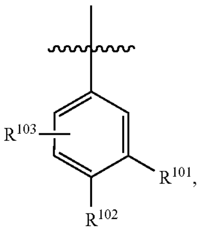
(TS2)
is selected from the group consisting of:
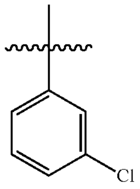 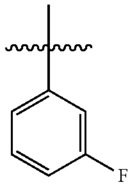 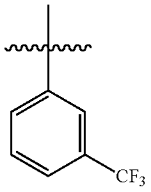
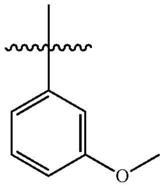 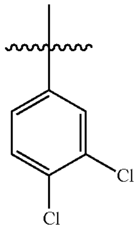 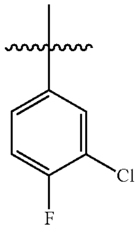
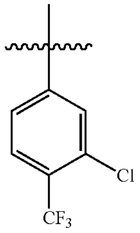 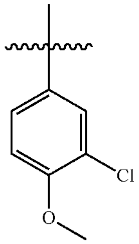 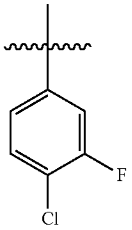
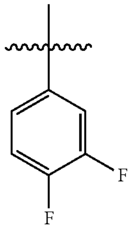 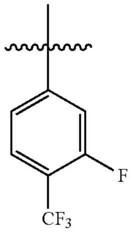 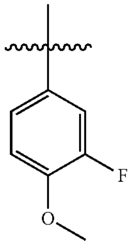
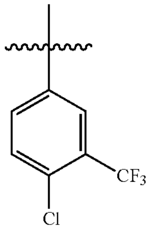 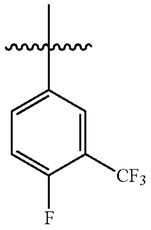 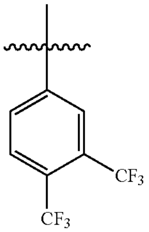
-continued
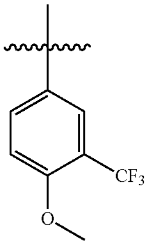 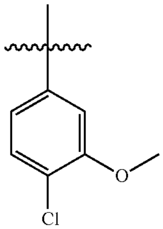 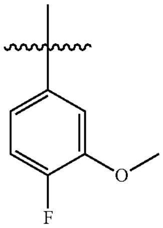
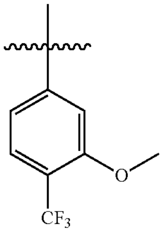 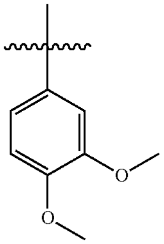 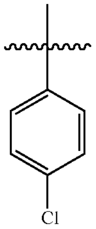
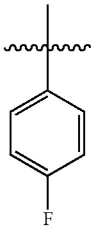 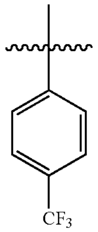 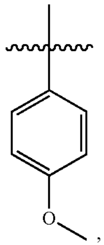 ,
in particular when t denotes 0, 1 or 2, and preferably denotes 1 or 2, and A denotes N.
Even more particularly preferred, the partial structure (TS2) is selected from the group consisting of:
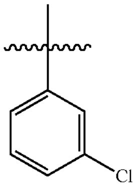 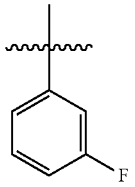 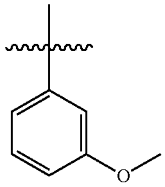
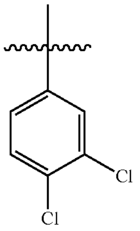 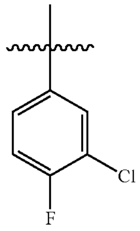 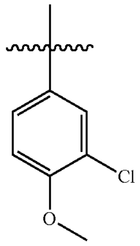
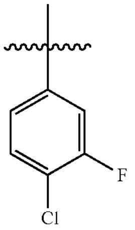 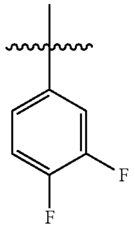 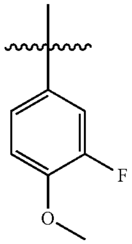

-continued

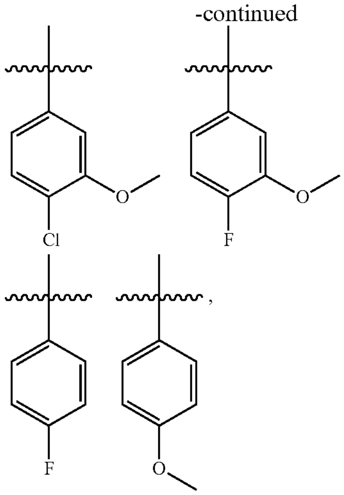

in particular when t denotes 0, 1 or 2, and preferably denotes 1 or 2, and A denotes N.

Most preferred, the partial structure (TS2) is selected from the group consisting of:

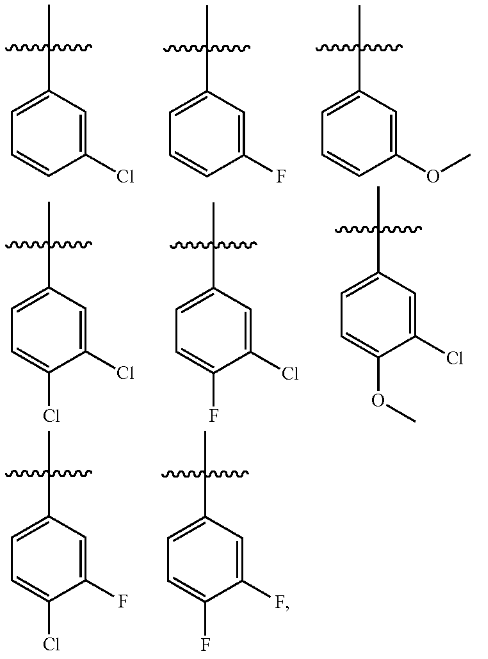

in particular when t denotes 0, 1 or 2, and preferably denotes 1 or 2, and A denotes N.

Especially preferably, partial structure (TS2) is selected from the group consisting of:

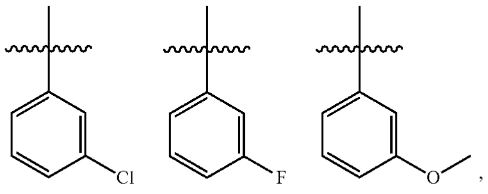

in particular when t denotes 0, 1 or 2, and preferably denotes 1 or 2, and A denotes N.

In another particularly preferred embodiment of formula (T) the partial structure (TS2) is selected from the group consisting of:

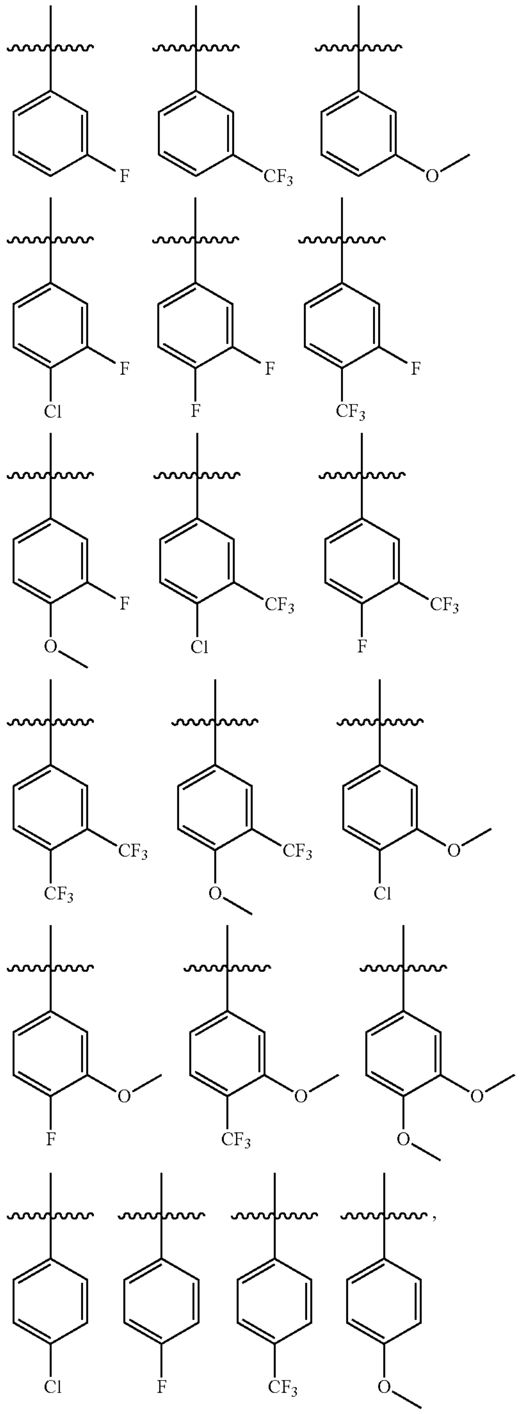

in particular when t denotes 0, 1 or 2, and preferably denotes 1 or 2, and A denotes CH or $C(CH_3)$.

Even more particularly preferred, the partial structure (TS2) is selected from the group consisting of:

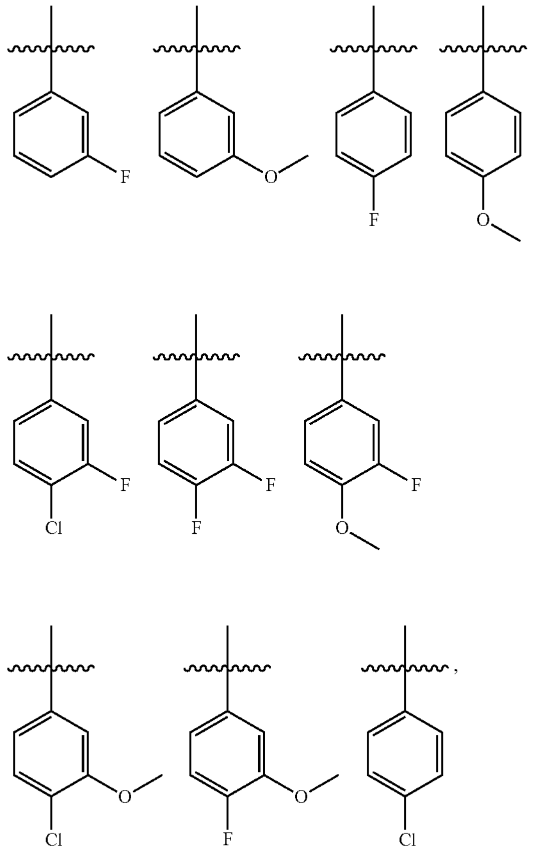

in particular when t denotes 1 or 2, and preferably denotes 1 or 2, and A denotes CH or $C(CH_3)$.

Most preferred, the partial structure (TS2) is selected from the group consisting of:

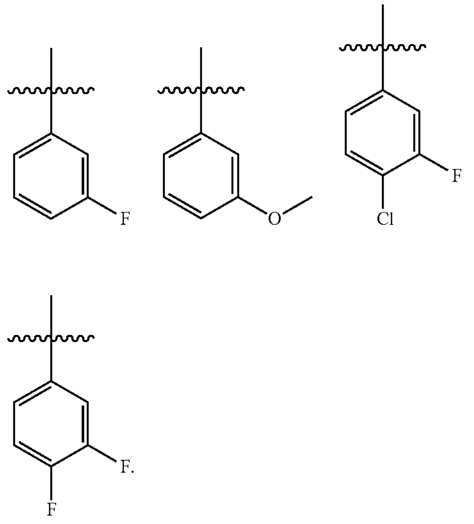

in particular when t denotes 1 or 2, and preferably denotes 1 or 2, and A denotes CH or $C(CH_3)$.

Preferably, partial structure (TS2) is selected from the group consisting of:

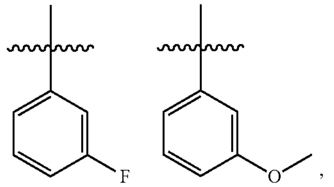

in particular when t denotes 1 or 2, and preferably denotes 1 or 2, and A denotes CH or $C(CH_3)$.

In another preferred embodiment of the compound of formula (T), $R^2$ represents $CF_3$, methyl, ethyl, n-propyl, 2-propyl, n-butyl, iso-butyl, sec.-butyl, tert.-butyl, cyclopropyl, cyclobutyl, cyclopentyl or cyclohexyl. Preferably, $R^2$ represents $CF_3$, 2-propyl, n-butyl, iso-butyl, sec.-butyl, tert.-butyl, cyclopropyl, or cyclobutyl. More preferably, $R^2$ represents $CF_3$, tert.-butyl or cyclopropyl.

In one particularly preferred embodiment of the compound of formula (T) $R^2$ represents $CF_3$.

In another particularly preferred embodiment of the compound of formula (T) $R^2$ represents tert.-butyl.

In still another particularly preferred embodiment of the compound of formula (T) $R^2$ represents cyclopropyl.

In a further preferred embodiment of the compound of formula (T), $R^7$ and $R^9$ are each independently selected from the group consisting of H, F, Cl, Br, $CF_3$, CN, OH, $OCF_3$, $CH_3$, $CH_2CH_3$, $CH(CH_3)_2$, O—$CH_3$, and O—$CH_2CH_3$. Preferably, $R^7$ and $R^9$ are each independently selected from the group consisting of H, F, Cl, $CF_3$, CN, OH, $OCF_3$, $CH_3$, O—$CH_3$, and O—$CH_2CH_3$. More preferably, $R^7$ and $R^9$ are each independently selected from the group consisting of H, F, Cl, $CF_3$, O—$CH_3$, and O—$CH_2CH_3$. Even more preferably, $R^7$ and $R^9$ are each independently selected from the group consisting of H, F, Cl, and O—$CH_3$. Still more preferably $R^7$ and $R^9$ are each independently selected from the group consisting of H, F and Cl.

In yet a further preferred embodiment of the compound of formula (T), at least one of $R^7$ and $R^9$ is not H.

In a further preferred embodiment of the compound of formula (T), $R^9$ denotes H.

In yet another preferred embodiment of the compound of formula (T), $R^7$ is selected from the group consisting of F, Cl, Br, $CF_3$, CN, OH, $OCF_3$, $CH_3$, $CH_2CH_3$, $CH(CH_3)_2$, O—$CH_3$, and O—$CH_2CH_3$, preferably from the group consisting of F, Cl, $CF_3$, CN, OH, $OCF_3$, $CH_3$, O—$CH_3$, and O—$CH_2CH_3$, more preferably from the group consisting of F, Cl, $CF_3$, O—$CH_3$, and 0-$CH_2CH_3$, even more preferably from the group consisting of F, Cl, and O—$CH_3$, and still more preferably from the group consisting of F and Cl, and $R^9$ represents H.

In another preferred embodiment of the compound of formula (T), A denotes N or $C(CH_3)$.

In a particularly preferred embodiment of the compound of formula (T), A denotes N.

In another particularly preferred embodiment of the compound of formula (T), A denotes $C(CH_3)$.

In another preferred embodiment of the compound of formula (T), t denotes 1 or 2.

In one particularly preferred embodiment of the compound of formula (T), t denotes 1.

In another particularly preferred embodiment of the compound of formula (T), t denotes 2.

In a further preferred embodiment of the compound of formula (T), t denotes 1 or 2, preferably 1;

A denotes N;

$R^{101}$ is selected from the group consisting of H, F, Cl, Br, $CFH_2$, $CF_2H$, $CF_3$, CN, $CH_2$—OH, $CH_2$—$OCH_3$, $OCF_3$, OH, $CH_3$, $CH_2CH_3$, $CH(CH_3)_2$, O—$CH_3$, O—$CH_2CH_3$, $NH_2$, $NH(CH_3)$ and $N(CH_3)_2$; preferably from the group consisting of H, F, Cl, $CFH_2$, $CF_2H$, $CF_3$, CN, $CH_2$—$OCH_3$, $OCF_3$, $CH_3$, O—$CH_3$, O—$CH_2CH_3$ and $N(CH_3)_2$; more preferably from the group consisting of H, F, Cl, $CFH_2$, $CF_2H$, $CF_3$, $OCF_3$, $CH_3$, O—$CH_3$, and O—$CH_2CH_3$; even more preferably from the group consisting of H, F, Cl, $CF_3$, $OCF_3$, $CH_3$ and O—$CH_3$; still more preferably from the group consisting of H, F, Cl, $CF_3$ and O—$CH_3$; in particular from the group consisting of H, F, Cl, and O—$CH_3$; and most preferably denotes F or Cl; and $R^{102}$ and $R^{103}$ are each independently selected from the group consisting of H, F, Cl, Br, $CFH_2$, $CF_2H$, $CF_3$, CN, $CH_2$—OH, $CH_2$—$OCH_3$, $OCF_3$, OH, $CH_3$, $CH_2CH_3$, $CH(CH_3)_2$, O—$CH_3$, O—$CH_2CH_3$, $NH_2$, $NH(CH_3)$ and $N(CH_3)_2$; preferably from the group consisting of H, F, Cl, $CFH_2$, $CF_2H$, $CF_3$, CN, $CH_2$—$OCH_3$, $OCF_3$, $CH_3$, O—$CH_3$, O—$CH_2CH_3$ and $N(CH_3)_2$; more preferably from the group consisting of H, F, Cl, $CFH_2$, $CF_2H$, $CF_3$, $OCF_3$, $CH_3$, O—$CH_3$, and O—$CH_2CH_3$; even more preferably from the group consisting of H, F, Cl, $CF_3$, $OCF_3$, $CH_3$ and O—$CH_3$; still more preferably from the group consisting of H, F, Cl, $CF_3$ and O—$CH_3$; in particular from the group consisting of H, F, Cl, and O—$CH_3$; and most preferably independently denote F or Cl;

or t denotes 0, 1 or 2, preferably 1 or 2, more preferably 1;

A denotes CH or $C(CH_3)$, preferably $C(CH_3)$;

$R^{101}$ is selected from the group consisting of H, F, Br, $CFH_2$, $CF_2H$, $CF_3$, CN, $CH_2$—OH, $CH_2$—$OCH_3$, $OCF_3$, OH, $CH_3$, $CH_2CH_3$, $CH(CH_3)_2$, O—$CH_3$, O—$CH_2CH_3$, $NH_2$, $NH(CH_3)$ and $N(CH_3)_2$; preferably from the group consisting of H, F, $CFH_2$, $CF_2H$, $CF_3$, CN, $CH_2$—$OCH_3$, $OCF_3$, $CH_3$, O—$CH_3$, O—$CH_2CH_3$ and $N(CH_3)_2$; more preferably from the group consisting of H, F, $CFH_2$, $CF_2H$, $CF_3$, $OCF_3$, $CH_3$, O—$CH_3$, and O—$CH_2CH_3$; even more preferably from the group consisting of H, F, $CF_3$, $OCF_3$, $CH_3$ and O—$CH_3$; still more preferably from the group consisting of H, F, $CF_3$ and O—$CH_3$; in particular from the group consisting of H, F and O—$CH_3$; and most preferably denotes F; and $R^{102}$ and $R^{103}$ are each independently selected from the group consisting of H, F, Cl, Br, $CFH_2$, $CF_2H$, $CF_3$, CN, $CH_2$—OH, $CH_2$—$OCH_3$, $OCF_3$, OH, $CH_3$, $CH_2CH_3$, $CH(CH_3)_2$, O—$CH_3$, O—$CH_2CH_3$, $NH_2$, $NH(CH_3)$ and $N(CH_3)_2$; preferably from the group consisting of H, F, Cl, $CFH_2$, $CF_2H$, $CF_3$, CN, $CH_2$—$OCH_3$, $OCF_3$, $CH_3$, O—$CH_3$, O—$CH_2CH_3$ and $N(CH_3)_2$; more preferably from the group consisting of H, F, Cl, $CFH_2$, $CF_2H$, $CF_3$, $OCF_3$, $CH_3$, O—$CH_3$, and O—$CH_2CH_3$; even more preferably from the group consisting of H, F, Cl, $CF_3$, $OCF_3$, $CH_3$ and O—$CH_3$; still more preferably from the group consisting of H, F, Cl, $CF_3$ and O—$CH_3$; in particular from the group consisting of H, F, Cl, and O—$CH_3$; and most preferably independently denote F or Cl.

In a further preferred embodiment of the compound of formula (T), the partial structure (TS1)

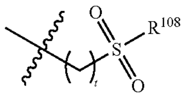

(TS1)

represents the partial structure (PT1), (PT2) or (PT3), (PT1)

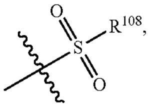

(PT2)

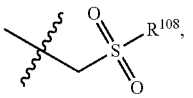

(PT3)

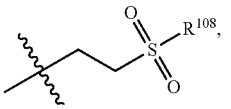

wherein $R^{108}$ represents unsubstituted $C_{1-4}$ alkyl, preferably $CH_3$ or $CH_2CH_3$, more preferably $CH_3$.

Preferably, the partial structure (TS1) represents the partial structure (PT2) or (PT3)

(PT2)

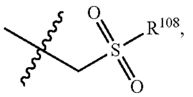

(PT3)

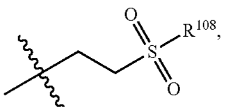

wherein $R^{108}$ represents $CH_3$ or $CH_2CH_3$, preferably $CH_3$.

In a particularly preferred embodiment of the compound of formula (T),

A denotes N;

$R^{101}$ is selected from the group consisting of H, F, Cl, Br, $CFH_2$, $CF_2H$, $CF_3$, CN, $CH_2$—OH, $CH_2$—$OCH_3$, $OCF_3$, OH, $CH_3$, $CH_2CH_3$, $CH(CH_3)_2$, O—$CH_3$, O—$CH_2CH_3$, $NH_2$, $NH(CH_3)$, and $N(CH_3)_2$; and $R^{102}$ and $R^{103}$ are each independently selected from the group consisting of H, F, Cl, Br, $CFH_2$, $CF_2H$, $CF_3$, CN, $CH_2$—OH, $CH_2$—$OCH_3$, $OCF_3$, OH, $CH_3$, $CH_2CH_3$, $CH(CH_3)_2$, O—$CH_3$, O—$CH_2CH_3$, $NH_2$, $NH(CH_3)$, and $N(CH_3)_2$, preferably, wherein at least one of $R^{101}$, $R^{102}$ and $R^{103}$ is not H;

or

A denotes CH or $C(CH_3)$, preferably $C(CH_3)$;

$R^{101}$ is selected from the group consisting of H, F, Br, $CFH_2$, $CF_2H$, $CF_3$, CN, $CH_2$—OH, $CH_2$—$OCH_3$, $OCF_3$, OH, $CH_3$, $CH_2CH_3$, $CH(CH_3)_2$, O—$CH_3$, O—$CH_2CH_3$, $NH_2$, $NH(CH_3)$, and $N(CH_3)_2$; and $R^{102}$ and $R^{103}$ are each independently selected from the group consisting of H, F, Cl, Br, $CFH_2$, $CF_2H$, $CF_3$, CN, $CH_2$—OH, $CH_2$—$OCH_3$, $OCF_3$, OH, $CH_3$, $CH_2CH_3$, $CH(CH_3)_2$, O—$CH_3$, O—$CH_2CH_3$, $NH_2$, $NH(CH_3)$, and $N(CH_3)_2$, preferably, wherein at least one of $R^{101}$, $R^{102}$ and $R^{103}$ is not H;

and $R^2$ represents $CF_3$, tert.-butyl or cyclopropyl;

$R^7$ and $R^9$ are each independently selected from the group consisting of H, F, Cl, Br, $CF_3$, CN, OH, $OCF_3$, $CH_3$, $CH_2CH_3$, $CH(CH_3)_2$, O—$CH_3$, and O—$CH_2CH_3$, preferably, wherein at least one of $R^7$ and $R^9$ is not H; and the partial structure (TS1) represents the partial structure (PT2) or (PT3), (PT2)

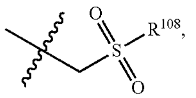

(PT3)

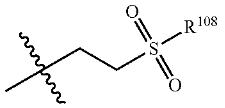

wherein $R^{108}$ represents $CH_3$ or $CH_2CH_3$, preferably $CH_3$.

Preferred embodiments of the compound of formula (T) have the formula (T0-a) or (T0-b)

(T0-a)

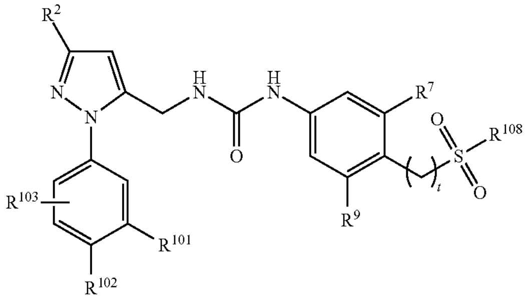

(T0-b)

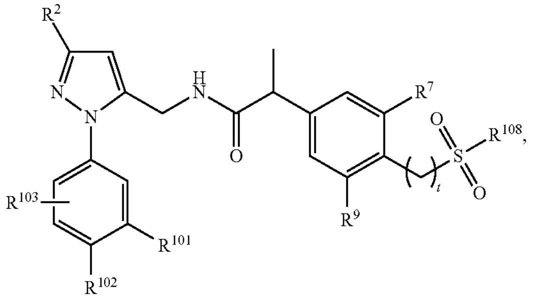

wherein the respective substituents, variables and indices have the meanings described above in connection with the compounds of formula (T) and preferred embodiments thereof.

Further preferred embodiments of the compound of formula (T) have the formula (T1-a), (T1-a-1) or (T1-a-2)

(T1-a)

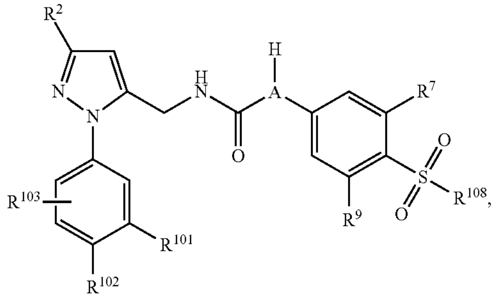

(T1-a-1)

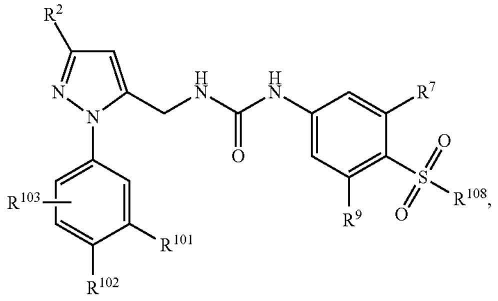

(T1-a-2)

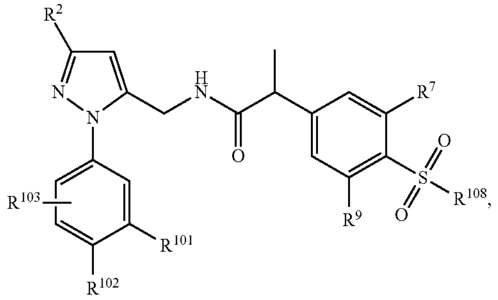

wherein the respective substituents, variables and indices have the meanings described above in connection with the compounds of formula (T) and preferred embodiments thereof.

Moreover, preferred embodiments of the compound of formula (T) have the formula (T1-b), (T1-b-1) or (T1-b-2)

(T1-b)

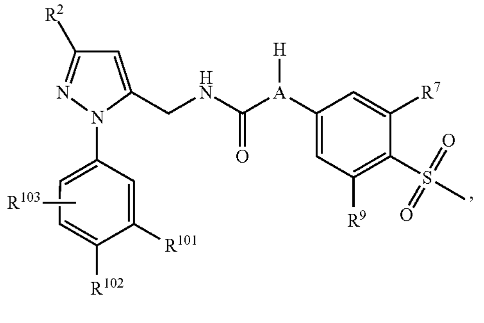

-continued (T1-b-1)

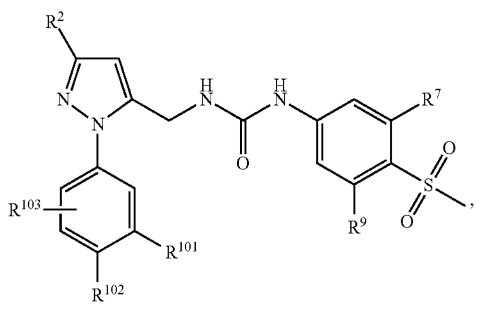

(T1-b-2)

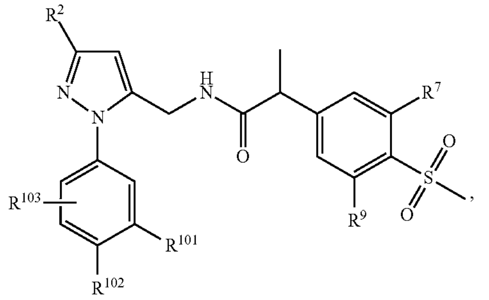

wherein the respective substituents, variables and indices have the meanings described above in connection with the compounds of formula (T) and preferred embodiments thereof.

Further preferred embodiments of the compound of formula (T) have the formula (T2-a), (T2-a-1) or (T2-a-2)

(T2-a)

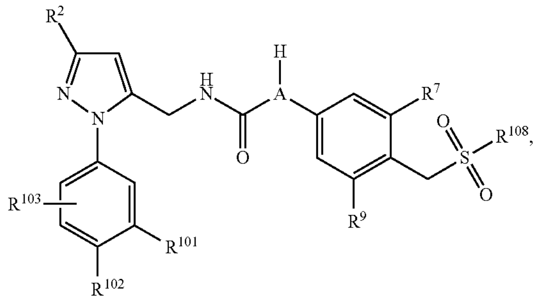

(T2-a-1)

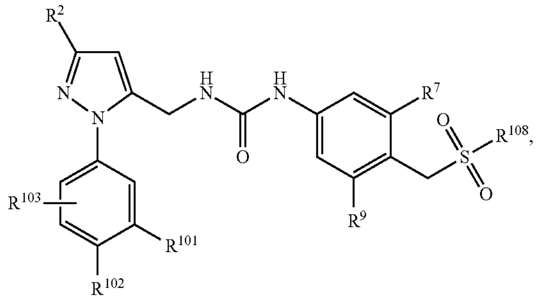

-continued (T2-a-2)

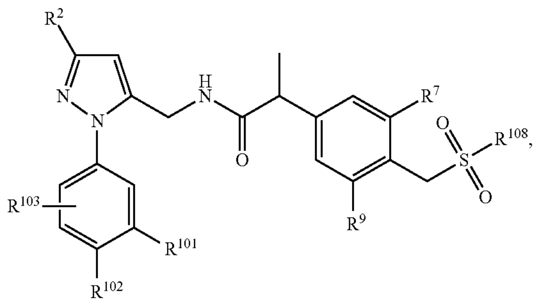

wherein the respective substituents, variables and indices have the meanings described above in connection with the compounds of formula (T) and preferred embodiments thereof.

Moreover, preferred embodiments of the compound of formula (T) have the formula (T2-b), (T2-b-1) or (T2-b-2)

(T2-b)

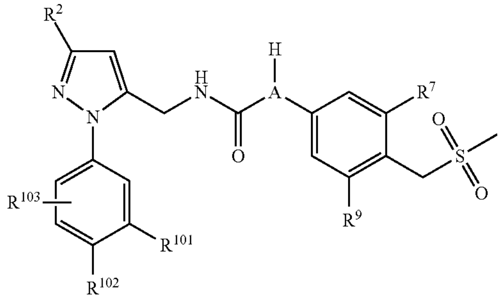

, (T2-b-1)

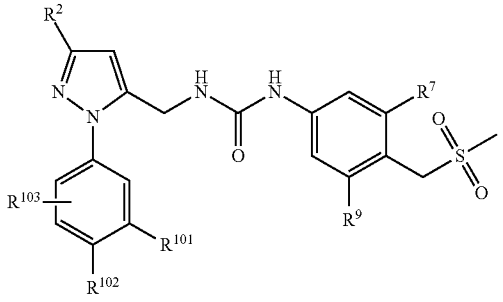

, (T2-b-2)

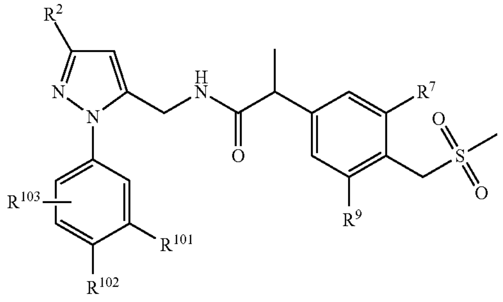

, wherein the respective substituents, variables and indices have the meanings described above in connection with the compounds of formula (T) and preferred embodiments thereof.

Further preferred embodiments of the compound of formula (T) have the formula (T3-a), (T3-a-1) or (T3-a-2)

(T3-a)

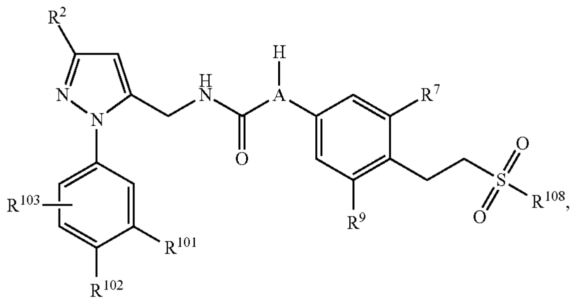

(T3-a-1)

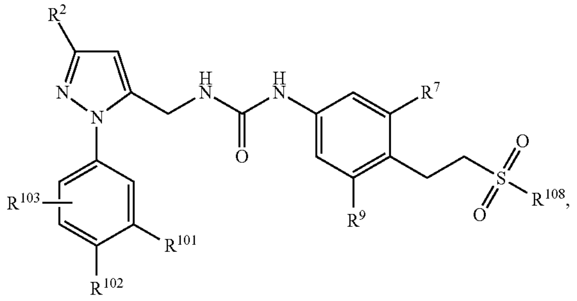

(T3-a-2)

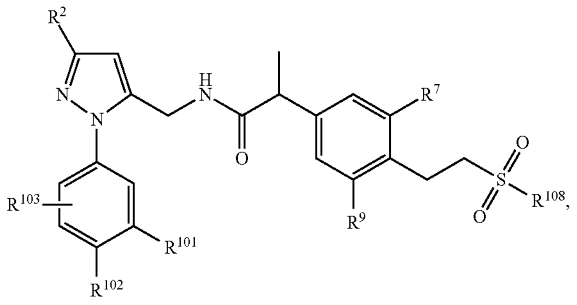

wherein the respective substituents, variables and indices have the meanings described above in connection with the compounds of formula (T) and preferred embodiments thereof.

Moreover, preferred embodiments of the compound of formula (T) have the formula (T3-b), (T3-b-1) or (T3-b-2)

(T3-b)

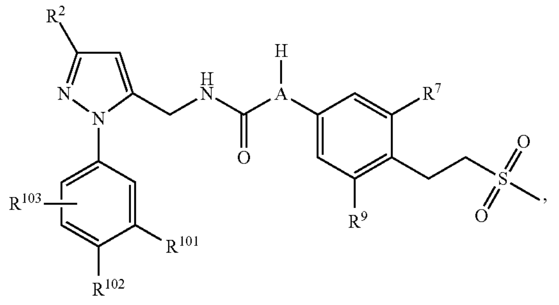

-continued (T3-b-1)

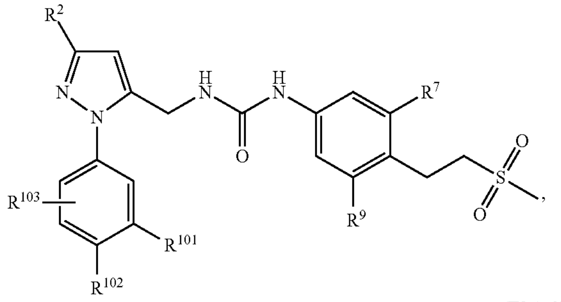

(T3-b-2)

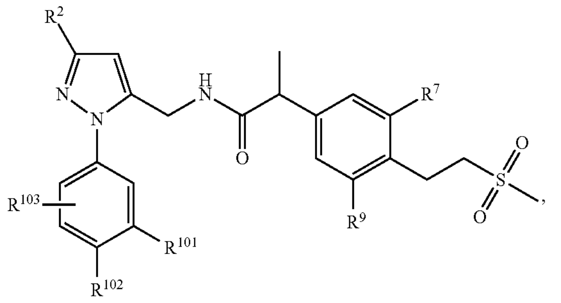

wherein the respective substituents, variables and indices have the meanings described above in connection with the compounds of formula (T) and preferred embodiments thereof.

Especially preferred embodiments of the compound of the present invention have the formula (T2-a), (T2-a-1), (T2-a-2), (T2-b), (T2-b-1) (T2-b-2), (T3-a), (T3-a-1), (T3-a-2), (T3-b), (T3-b-1) or (T3-b-2).

In particularly preferred embodiments of the present invention, $R^{101}$ in the compound of formula (T), (T0-a), (T0-b), (T1-a), (T1-a-1), (T1-a-2), (T1-b), (T1-b-1), (T1-b-2), (T2-a), (T2-a-1), (T2-a-2), (T2-b), (T2-b-1), (T2-b-2), (T3-a), (T3-a-1), (T3-a-2), (T3-b), (T3-b-1), or (T3-b-2), represents F, Cl, $CF_3$ or O—$CH_3$, preferably F or Cl, most preferably Cl—preferably when $R^{103}$ is H and $R^{102}$ represents H, F, Cl, $CF_3$ or $OCH_3$, more preferably when $R^{103}$ is H and $R^{102}$ represents H, F or Cl, even more preferably when both $R^{102}$ and $R^{103}$ denote H—, and the remaining respective substituents, variables and indices have the meanings described above in connection with the compounds of formula (T) and preferred embodiments thereof.

In further particularly preferred embodiments of the present invention, $R^{101}$ in the compound of formula (T), (T1-a), (T1-a-1), (T1-b), (T1-b-1), (T2-a), (T2-a-1), (T2-b), (T2-b-1), (T3-a), (T3-a-1), (T3-b) or (T3-b-1) represents F, Cl, $CF_3$ or O—$CH_3$, preferably F or Cl, most preferably Cl—preferably when $R^{103}$ is H and $R^{102}$ represents H, F, Cl, $CF_3$ or $OCH_3$, more preferably when $R^{103}$ is H and $R^{102}$ represents H, F or Cl, even more preferably when both $R^{102}$ and $R^{103}$ denote H—, and the remaining respective substituents, variables and indices have the meanings described above in connection with the compounds of formula (T) and preferred embodiments thereof.

In further particularly preferred embodiments of the present invention $R^{101}$ in the compound of formula (T), (T1-a), (T1-a-2), (T1-b), (T1-b-2), (T2-a), (T2-a-2), (T2-b), (T2-b-2), (T3-a), (T3-a-2), (T3-b) or (T3-b-2) represents F, $CF_3$ or O—$CH_3$, preferably F—preferably when $R^{103}$ is H and $R^{102}$ represents H, F, Cl, $CF_3$ or $OCH_3$, more preferably when $R^{103}$ is H and $R^{102}$ represents H, F or Cl, even more preferably when both $R^{102}$ and $R^{103}$ denote H—, and the remaining respective substituents, variables and indices have the meanings described above in connection with the compounds of formula (T) and preferred embodiments thereof.

Particularly preferred are compounds of formula (T) selected from the group consisting of:

D1 N-[[5-tert-Butyl-2-(3-chlorophenyl)-2H-pyrazol-3-yl]-methyl]-2-(3-fluoro-4-methylsulfonyl-phenyl)-propionamide;

D2 N-[[2-(3-Chlorophenyl)-5-(trifluoromethyl)-2H-pyrazol-3-yl]-methyl]-2-(3-fluoro-4-methylsulfonyl-phenyl)-propionamide;

D3 2-(3-Fluoro-4-methylsulfonyl-phenyl)-N-[[2-(3-fluoro-phenyl)-5-(trifluoromethyl)-2H-pyrazol-3-yl]-methyl]-propionamide;

D4 N-[[2-(3-Chloro-4-fluoro-phenyl)-5-(trifluoromethyl)-2H-pyrazol-3-yl]-methyl]-2-(3-fluoro-4-methylsulfonyl-phenyl)-propionamide;

D5 2-(3-Chloro-4-methylsulfonyl-phenyl)-N-[[2-(3-chloro-phenyl)-5-(trifluoromethyl)-2H-pyrazol-3-yl]-methyl]-propionamide;

D6 N-[[2-(3-Chlorophenyl)-5-(trifluoromethyl)-2H-pyrazol-3-yl]-methyl]-2-[3-fluoro-4-(methylsulfonyl-methyl)-phenyl]-propionamide;

D7 N-[[5-tert-Butyl-2-(3-chlorophenyl)-2H-pyrazol-3-yl]-methyl]-2-[3-fluoro-4-(methylsulfonyl-methyl)-phenyl]-propionamide;

D8 N-[[5-tert-Butyl-2-(3-chloro-4-fluoro-phenyl)-2H-pyrazol-3-yl]-methyl]-2-[3-fluoro-4-(methylsulfonyl-methyl)-phenyl]-propionamide;

D9 N-[[5-tert-Butyl-2-(3-fluorophenyl)-2H-pyrazol-3-yl]-methyl]-2-[3-fluoro-4-(methylsulfonyl-methyl)-phenyl]-propionamide;

D10 2-[3-Fluoro-4-(methylsulfonyl-methyl)-phenyl]-N-[[2-(3-fluorophenyl)-5-(trifluoromethyl)-2H-pyrazol-3-yl]-methyl]-propionamide;

D11 N-[[5-tert-Butyl-2-(4-fluorophenyl)-2H-pyrazol-3-yl]-methyl]-2-[3-fluoro-4-(methylsulfonyl-methyl)-phenyl]-propionamide;

D12 2-[3-Fluoro-4-(methylsulfonyl-methyl)-phenyl]-N-[[2-(4-fluorophenyl)-5-(trifluoromethyl)-2H-pyrazol-3-yl]-methyl]-propionamide;

D13 N-[[5-tert-Butyl-2-(3,4-difluoro-phenyl)-2H-pyrazol-3-yl]-methyl]-2-[3-fluoro-4-(methylsulfonyl-methyl)-phenyl]-propionamide;

D14 N-[[2-(3,4-Difluoro-phenyl)-5-(trifluoromethyl)-2H-pyrazol-3-yl]-methyl]-2-[3-fluoro-4-(methylsulfonyl-methyl)-phenyl]-propionamide;

D15 N-[[2-(3,5-Difluoro-phenyl)-5-(trifluoromethyl)-2H-pyrazol-3-yl]-methyl]-2-[3-fluoro-4-(methylsulfonyl-methyl)-phenyl]-propionamide;

D16 N-[[5-tert-Butyl-2-[3-(methoxymethyl)-phenyl]-2H-pyrazol-3-yl]-methyl]-2-[3-fluoro-4-(methylsulfonyl-methyl)-phenyl]-propionamide;

D17 N-[[5-tert-Butyl-2-(3-dimethylamino-phenyl)-2H-pyrazol-3-yl]-methyl]-2-[3-fluoro-4-(methylsulfonyl-methyl)-phenyl]-propionamide;

D18 N-[[5-tert-Butyl-2-(3-fluoro-5-methyl-phenyl)-2H-pyrazol-3-yl]-methyl]-2-[3-fluoro-4-(methylsulfonyl-methyl)-phenyl]-propionamide;

D19 N-[[5-tert-Butyl-2-(3-cyano-phenyl)-2H-pyrazol-3-yl]-methyl]-2-[3-fluoro-4-(methylsulfonyl-methyl)-phenyl]-propionamide;

D20 N-[[5-tert-Butyl-2-[3-(difluoro-methyl)-phenyl]-2H-pyrazol-3-yl]-methyl]-2-[3-fluoro-4-(methylsulfonyl-methyl)-phenyl]-propionamide;

D21 N-[[5-tert-Butyl-2-(3-methoxyphenyl)-2H-pyrazol-3-yl]-methyl]-2-[3-fluoro-4-(methylsulfonyl-methyl)-phenyl]-propionamide;

D22 2-[3-Fluoro-4-(methylsulfonyl-methyl)-phenyl]-N-[[2-(3-methoxyphenyl)-5-(trifluoromethyl)-2H-pyrazol-3-yl]-methyl]-propionamide;

D23 N-[[5-tert-Butyl-2-[3-(trifluoromethyl)phenyl]-2H-pyrazol-3-yl]-methyl]-2-[3-fluoro-4-(methylsulfonyl-methyl)-phenyl]-propionamide;

D24 N-[[5-tert-Butyl-2-(m-tolyl)-2H-pyrazol-3-yl]-methyl]-2-[3-fluoro-4-(methylsulfonyl-methyl)-phenyl]-propionamide;

D25 2-[3-Fluoro-4-(methylsulfonyl-methyl)-phenyl]-N-[[2-(4-methoxyphenyl)-5-(trifluoromethyl)-2H-pyrazol-3-yl]-methyl]-propionamide;

D26 1-[[2-(3-Chlorophenyl)-5-cyclopropyl-2H-pyrazol-3-yl]-methyl]-3-[3-fluoro-4-(2-methylsulfonyl-ethyl)-phenyl]-urea;

D27 1-[[2-(3-Chlorophenyl)-5-(trifluoromethyl)-2H-pyrazol-3-yl]-methyl]-3-[3-fluoro-4-(2-methylsulfonyl-ethyl)-phenyl]-urea;

D28 1-[[2-(3-Chloro-4-fluoro-phenyl)-5-(trifluoromethyl)-2H-pyrazol-3-yl]-methyl]-3-[3-fluoro-4-(2-methylsulfonyl-ethyl)-phenyl]-urea;

D29 1-[[5-tert-Butyl-2-(3-chlorophenyl)-2H-pyrazol-3-yl]-methyl]-3-[3-fluoro-4-(2-methylsulfonyl-ethyl)-phenyl]-urea;

D30 1-[[5-tert-Butyl-2-(3-fluorophenyl)-2H-pyrazol-3-yl]-methyl]-3-[3-fluoro-4-(2-methylsulfonyl-ethyl)-phenyl]-urea;

D31 1-[[5-tert-Butyl-2-(3,5-difluoro-phenyl)-2H-pyrazol-3-yl]-methyl]-3-[3-fluoro-4-(2-methylsulfonyl-ethyl)-phenyl]-urea;

D32 1-[3-Fluoro-4-(2-methylsulfonyl-ethyl)-phenyl]-3-[[2-(m-tolyl)-5-(trifluoromethyl)-2H-pyrazol-3-yl]-methyl]-urea; and D33 1-[3-Fluoro-4-(2-methylsulfonyl-ethyl)-phenyl]-3-[[2-(3-isopropyl-phenyl)-5-(trifluoromethyl)-2H-pyrazol-3-yl]-methyl]-urea;

in the form of an individual stereoisomer or a mixture of stereoisomers, and in the form of a free compound or a physiologically acceptable salt thereof.

A still further particularly preferred subgroup of the compounds of the invention relates to compounds corresponding to the formula (U)

(U)

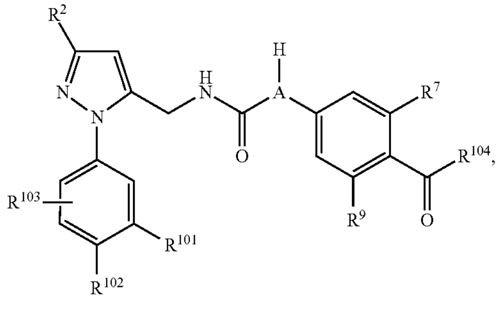

wherein $R^{101}$, $R^{102}$ and $R^{103}$ are each independently selected from the group consisting of H, F, Cl, Br, $CFH_2$, $CF_2H$, $CF_3$, CN, $CH_2$—OH, $CH_2CH_2$—OH, $CH_2$—$OCH_3$, $CH_2CH_2$—$OCH_3$, $OCFH_2$, $OCF_2H$, $OCF_3$, OH, $NH_2$, $C_{1-4}$ alkyl, O—$C_{1-4}$ alkyl, NH—$C_{1-4}$ alkyl, and N($C_{1-4}$ alkyl)$_2$, wherein the $C_{1-4}$ alkyl is in each case unsubstituted;

$R^2$ represents $CF_3$, unsubstituted $C_{1-4}$ alkyl or unsubstituted $C_{3-6}$ cycloalkyl;

$R^7$ and $R^9$ are each independently selected from the group consisting of H, F, Cl, Br, $CFH_2$, $CF_2H$, $CF_3$, CN, OH, $OCF_3$, $C_{1-4}$ alkyl, and O—$C_{1-4}$ alkyl, wherein the $C_{1-4}$ alkyl is in each case unsubstituted;

A denotes N, CH or C($CH_3$); and $R^{104}$ represents

H, a $C_{1-4}$ alkyl, which is unsubstituted or mono-, di- or trisubstituted with 1, 2 or 3 substituents independently selected from the group consisting of F, Cl, Br, $NH_2$, NH($CH_3$), N($CH_3$)$_2$, =O, OH and $OCH_3$, $OR^{105}$, wherein $R^{105}$ represents H or $C_{1-4}$ alkyl, which is unsubstituted or mono-, di- or trisubstituted with 1, 2 or 3 substituents independently selected from the group consisting of F, Cl, Br, $NH_2$, NH($CH_3$), N($CH_3$)$_2$, =O, OH and $OCH_3$, or $NR^{106}R^{107}$, wherein $R^{106}$ represents H or $C_{1-4}$ alkyl, which is unsubstituted or mono-, di- or trisubstituted with 1, 2 or 3 substituents independently selected from the group consisting of F, Cl, Br, $NH_2$, NH($CH_3$), N($CH_3$)$_2$, =O, OH and $OCH_3$; and $R^{107}$ is selected from the group consisting of H, a $C_{1-4}$ alkyl, which is unsubstituted or mono-, di- or trisubstituted with 1, 2 or 3 substituents independently selected from the group consisting of F, Cl, Br, $NH_2$, NH($CH_3$), N($CH_3$)$_2$, =O, OH and $OCH_3$;

$C_{3-6}$ cycloalkyl or 3 to 6 membered heterocyclyl, which in each case is unsubstituted or mono-, di- or trisubstituted with 1, 2 or 3 substituents independently selected from the group consisting of F, Cl, Br, $CF_3$, $CH_3$, $CH_2CH_3$, CH($CH_3$)$_2$, tert.-butyl, cyclopropyl, OH, =O, $OCH_3$, $OCF_3$, $NH_2$, NH($CH_3$) and N($CH_3$)$_2$, and wherein at least one ring member of the heterocyclyl is selected from the group consisting of O, S, N, NH and N($C_{1-4}$ alkyl);

phenyl, which is unsubstituted or mono-, di- or trisubstituted with 1, 2 or 3 substituents independently selected from the group consisting of F, Cl, Br, CN, $CF_3$, $CH_3$, $CH_2CH_3$, CH($CH_3$)$_2$, tert.-butyl, cyclopropyl, $NH_2$, NH($CH_3$), N($CH_3$)$_2$, OH, $OCF_3$ and $OCH_3$; and heteroaryl, which is unsubstituted or mono-, di- or trisubstituted with 1, 2 or 3 substituents independently selected from the group consisting of F, Cl, Br, CN, $CF_3$, $CH_3$, $CH_2CH_3$, CH($CH_3$)$_2$, tert.-butyl, cyclopropyl, $NH_2$, NH($CH_3$), N($CH_3$)$_2$, OH, $OCF_3$ and $OCH_3$;

or wherein $R^{106}$ and $R^{107}$ together with the nitrogen atom connecting them form a 3 to 6 membered heterocyclyl, which is unsubstituted or mono-, di- or trisubstituted with 1, 2 or 3 substituents independently selected from the group consisting of F, Cl, Br, $CF_3$, $CH_3$, $CH_2CH_3$, CH($CH_3$)$_2$, tert.-butyl, cyclopropyl, OH, =O, $OCH_3$, $OCF_3$, $NH_2$, NH($CH_3$) and N($CH_3$)$_2$, in the form of an individual stereoisomer or a mixture of stereoisomers, and in the form of a free compound or a physiologically acceptable salt thereof.

In a preferred embodiment of the compound of formula (U), $R^{101}$, $R^{102}$ and $R^{103}$ are independently selected from the group consisting of H, F, Cl, Br, $CFH_2$, $CF_2H$, $CF_3$, CN, $CH_2$—OH, $CH_2$—$OCH_3$, $OCF_3$, OH, $CH_3$, $CH_2CH_3$, CH($CH_3$)$_2$, O—$CH_3$, O—$CH_2CH_3$, $NH_2$, NH($CH_3$), and N($CH_3$)$_2$. Preferably, $R^{101}$, $R^{102}$ and $R^{103}$ are independently selected from the group consisting of H, F, Cl, Br, $CFH_2$, $CF_2H$, $CF_3$, CN, $CH_2$—OH, $CH_2$—$OCH_3$, $OCF_3$, OH, $CH_3$, O—$CH_3$, O—$CH_2CH_3$, $NH_2$, NH($CH_3$), and N($CH_3$)$_2$. More preferably, $R^{101}$, $R^{102}$ and $R^{103}$ are independently selected from the group consisting of H, F, Cl, $CFH_2$, $CF_2H$, $CF_3$, CN, $CH_2$—$OCH_3$, $OCF_3$, $CH_3$, O—$CH_3$, O—$CH_2CH_3$ and N($CH_3$)$_2$. Even more preferably, $R^{101}$, $R^{102}$ and $R^{103}$ are independently selected from the group consisting of H, F, Cl, $CFH_2$, $CF_2H$, $CF_3$, $OCF_3$, $CH_3$, O—$CH_3$, and 0-$CH_2CH_3$. Still more preferably, $R^{101}$, $R^{102}$ and $R^{103}$ are independently selected from the group consisting of H, F, Cl, $CF_3$, $OCF_3$, $CH_3$ and O—$CH_3$. Particularly, $R^{101}$, $R^{102}$ and $R^{103}$ are independently selected from the group consisting of H, F, Cl, $CF_3$ and O—$CH_3$. Even more particularly preferred $R^{101}$, $R^{102}$ and $R^{103}$ are independently selected from the group consisting of H, F, Cl and O—$CH_3$.

In one preferred embodiment of the compound of formula (U) at least one of $R^{101}$, $R^{102}$ and $R^{103}$ is not H.

In another preferred embodiment of the compound of formula (U) one or two of $R^{101}$, $R^{102}$ and $R^{103}$, preferably $R^{102}$ and/or $R^{103}$, denote(s) H.

In still another preferred embodiment of the compound of formula (U) one of $R^{101}$, $R^{102}$ and $R^{103}$ represents H. Preferably $R^{103}$ represents H.

In another preferred embodiment of the compound of formula (U), $R^{101}$ and $R^{102}$ are independently selected from the group consisting of H, F, Cl, Br, $CFH_2$, $CF_2H$, $CF_3$, CN, $CH_2$—OH, $CH_2$—$OCH_3$, $OCF_3$, OH, $CH_3$, $CH_2CH_3$, CH($CH_3$)$_2$, O—$CH_3$, O—$CH_2CH_3$, $NH_2$, NH($CH_3$), and N($CH_3$)$_2$; and $R^{103}$ represents H.

Preferably, $R^{101}$ and $R^{102}$ are independently selected from the group consisting of H, F, Cl, Br, $CFH_2$, $CF_2H$, $CF_3$, CN, $CH_2$—OH, $CH_2$—$OCH_3$, $OCF_3$, OH, $CH_3$, O—$CH_3$, O—$CH_2CH_3$, $NH_2$, NH($CH_3$), and N($CH_3$)$_2$, more preferably from the group consisting of H, F, Cl, $CFH_2$, $CF_2H$, $CF_3$, CN, $CH_2$—$OCH_3$, $OCF_3$, $CH_3$, O—$CH_3$, O—$CH_2CH_3$ and N($CH_3$)$_2$, even more preferably from the group consisting of H, F, Cl, $CFH_2$, $CF_2H$, $CF_3$, $OCF_3$, $CH_3$, O—$CH_3$, and O—$CH_2CH_3$, still more preferably from the group consisting of H, F, Cl, $CF_3$, $OCF_3$, $CH_3$ and O—$CH_3$, in particular from the group consisting of H, F, Cl, $CF_3$ and O—$CH_3$, and even more particularly preferred from the group consisting of H, F, Cl, and O—$CH_3$; and $R^{103}$ represents H.

In yet another preferred embodiment of the compound of formula (U), $R^{101}$ is selected from the group consisting of F, Cl, Br, $CFH_2$, $CF_2H$, $CF_3$, CN, $CH_2$—OH, $CH_2$—$OCH_3$, $OCF_3$, OH, $CH_3$, $CH_2CH_3$, CH($CH_3$)$_2$, O—$CH_3$, O—$CH_2CH_3$, $NH_2$, NH($CH_3$), and N($CH_3$)$_2$; and $R^{102}$ and $R^{103}$ each represent H.

Preferably, $R^{101}$ is selected from the group consisting of F, Cl, Br, $CFH_2$, $CF_2H$, $CF_3$, CN, $CH_2$—OH, $CH_2$—$OCH_3$, $OCF_3$, OH, $CH_3$, O—$CH_3$, O—$CH_2CH_3$, $NH_2$, $NH(CH_3)$, and $N(CH_3)_2$, more preferably from the group consisting of F, Cl, $CFH_2$, $CF_2H$, $CF_3$, CN, $CH_2$—$OCH_3$, $OCF_3$, $CH_3$, O—$CH_3$, O—$CH_2CH_3$ and $N(CH_3)_2$, even more preferably from the group consisting of F, Cl, $CFH_2$, $CF_2H$, $CF_3$, $OCF_3$, $CH_3$, O—$CH_3$, and O—$CH_2CH_3$, still more preferably from the group consisting of F, Cl, $CF_3$, $OCF_3$, $CH_3$ and O—$CH_3$, in particular from the group consisting of F, Cl, $CF_3$ and O—$CH_3$, and even more particularly preferably from the group consisting of F, Cl, and O—$CH_3$, and $R^{102}$ and $R^{103}$ each represent H.

In still another preferred embodiment of the compound of formula (U), $R^{102}$ is selected from the group consisting of F, Cl, Br, $CFH_2$, $CF_2H$, $CF_3$, CN, $CH_2$—OH, $CH_2$—$OCH_3$, $OCF_3$, OH, $CH_3$, $CH_2CH_3$, $CH(CH_3)_2$, O—$CH_3$, O—$CH_2CH_3$, $NH_2$, $NH(CH_3)$, and $N(CH_3)_2$; and $R^{101}$ and $R^{103}$ each represent H.

Preferably, $R^{102}$ is selected from the group consisting of F, Cl, Br, $CFH_2$, $CF_2H$, $CF_3$, CN, $CH_2$—OH, $CH_2$—$OCH_3$, $OCF_3$, OH, $CH_3$, O—$CH_3$, O—$CH_2CH_3$, $NH_2$, $NH(CH_3)$, and $N(CH_3)_2$, more preferably from the group consisting of F, Cl, $CFH_2$, $CF_2H$, $CF_3$, CN, $CH_2$—$OCH_3$, $OCF_3$, $CH_3$, O—$CH_3$, O—$CH_2CH_3$ and $N(CH_3)_2$, even more preferably from the group consisting of F, Cl, $CFH_2$, $CF_2H$, $CF_3$, $OCF_3$, $CH_3$, O—$CH_3$, and O—$CH_2CH_3$, still more preferably from the group consisting of F, Cl, $CF_3$, $OCF_3$, $CH_3$ and O—$CH_3$, in particular from the group consisting of F, Cl, $CF_3$ and O—$CH_3$, even more particularly preferably from the group consisting of F, Cl, and O—$CH_3$; and $R^{101}$ and $R^{103}$ each represent H.

In yet a further preferred embodiment of the compound of formula (U), $R^{101}$ is selected from the group consisting of F, Cl, Br, $CFH_2$, $CF_2H$, $CF_3$, CN, $CH_2$—OH, $CH_2$—$OCH_3$, $OCF_3$, OH, $CH_3$, $CH_2CH_3$, $CH(CH_3)_2$, O—$CH_3$, O—$CH_2CH_3$, $NH_2$, $NH(CH_3)$, and $N(CH_3)_2$;

$R^{102}$ is selected from the group consisting of H, F, Cl, Br, $CFH_2$, $CF_2H$, $CF_3$, CN, $CH_2$—OH, $CH_2$—$OCH_3$, $OCF_3$, OH, $CH_3$, $CH_2CH_3$, $CH(CH_3)_2$, O—$CH_3$, O—$CH_2CH_3$, $NH_2$, $NH(CH_3)$, and $N(CH_3)_2$; and $R^{103}$ represents H.

Preferably, $R^{101}$ is selected from the group consisting of F, Cl, Br, $CFH_2$, $CF_2H$, $CF_3$, CN, $CH_2$—OH, $CH_2$—$OCH_3$, $OCF_3$, OH, $CH_3$, O—$CH_3$, O—$CH_2CH_3$, $NH_2$, $NH(CH_3)$, and $N(CH_3)_2$, more preferably from the group consisting of F, Cl, $CFH_2$, $CF_2H$, $CF_3$, CN, $CH_2$—$OCH_3$, $OCF_3$, $CH_3$, O—$CH_3$, O—$CH_2CH_3$ and $N(CH_3)_2$, even more preferably from the group consisting of F, Cl, $CFH_2$, $CF_2H$, $CF_3$, $OCF_3$, $CH_3$, O—$CH_3$, and O—$CH_2CH_3$, still more preferably from the group consisting of F, Cl, $CF_3$, $OCF_3$, $CH_3$ and O—$CH_3$, in particular from the group consisting of F, Cl, $CF_3$ and O—$CH_3$, and even more particularly preferably from the group consisting of F, Cl, and O—$CH_3$;

$R^{102}$ is selected from the group consisting of H, F, Cl, Br, $CFH_2$, $CF_2H$, $CF_3$, CN, $CH_2$—OH, $CH_2$—$OCH_3$, $OCF_3$, OH, $CH_3$, O—$CH_3$, O—$CH_2CH_3$, $NH_2$, $NH(CH_3)$, and $N(CH_3)_2$, more preferably from the group consisting of H, F, Cl, $CFH_2$, $CF_2H$, $CF_3$, CN, $CH_2$—$OCH_3$, $OCF_3$, $CH_3$, O—$CH_3$, O—$CH_2CH_3$ and $N(CH_3)_2$, even more preferably from the group consisting of H, F, Cl, $CFH_2$, $CF_2H$, $CF_3$, $OCF_3$, $CH_3$, O—$CH_3$, and O—$CH_2CH_3$, still more preferably from the group consisting of H, F, Cl, $CF_3$, $OCF_3$, $CH_3$ and O—$CH_3$, in particular from the group consisting of H, F, Cl, $CF_3$ and O—$CH_3$, and even more particularly preferably from the group consisting of H, F, Cl, and O—$CH_3$; and $R^{103}$ represents H.

In another particularly preferred embodiment of the compound of formula (U), the partial structure (US2)

(US2)

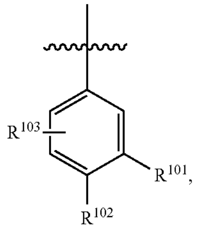

is selected from the group consisting of:

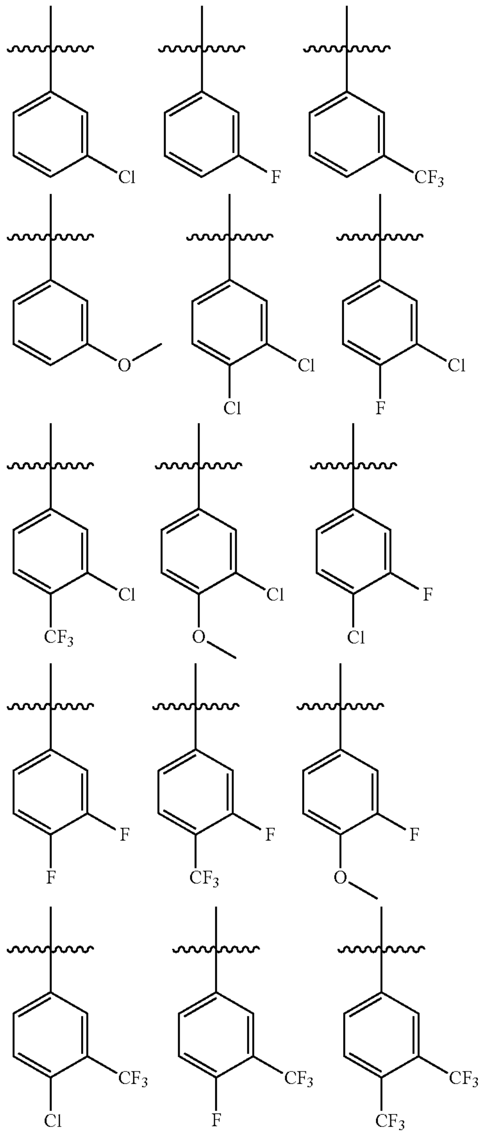

-continued

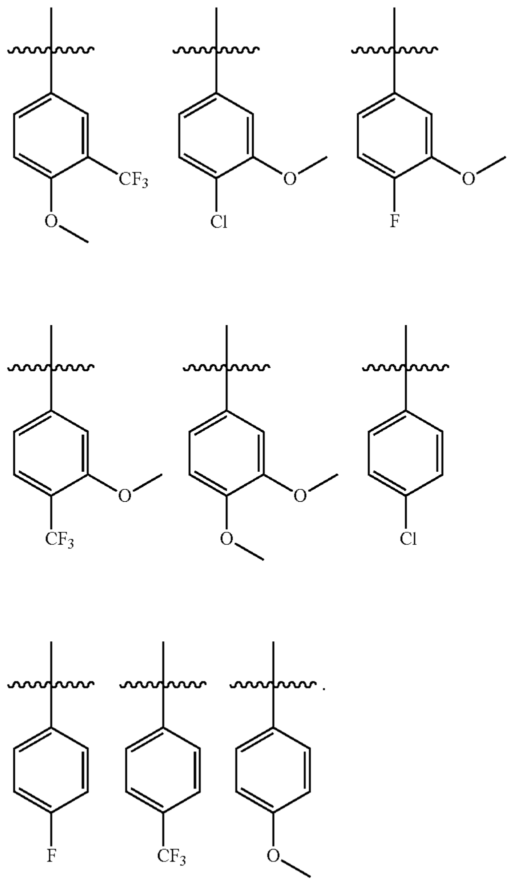

Even more particularly preferred, the partial structure (US2) is selected from the group consisting of:

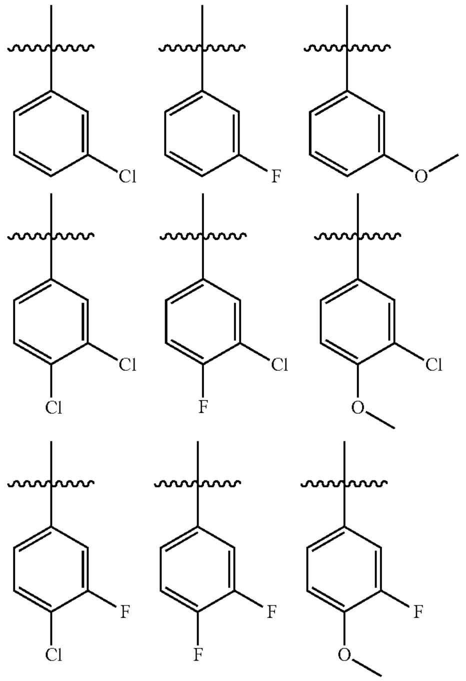

-continued

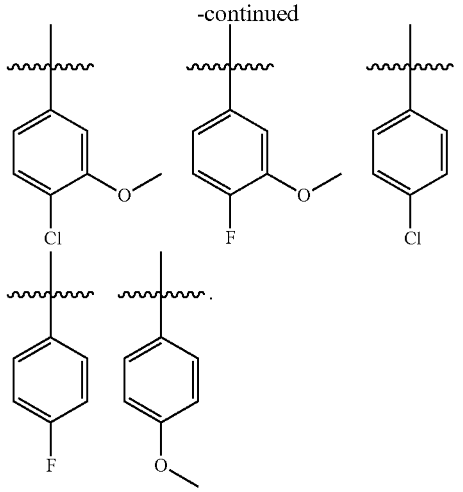

Most preferred, the partial structure (US2) is selected from the group consisting of:

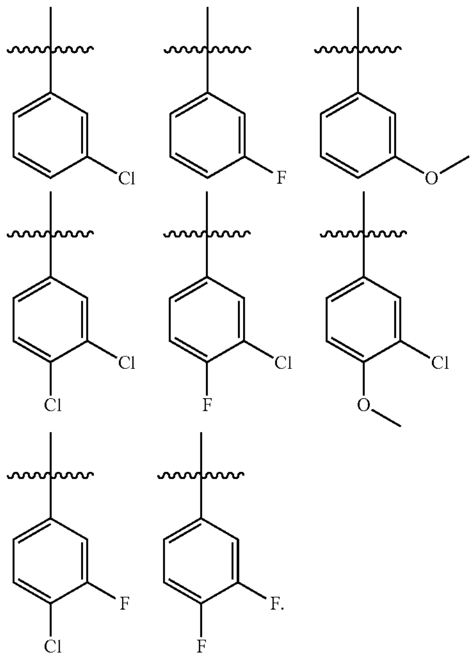

Particularly preferably the partial structure (US2) is selected from the group consisting of:

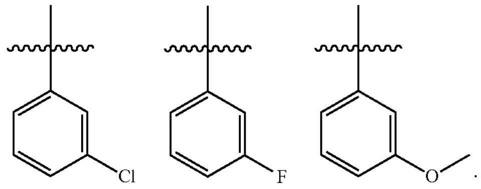

In another preferred embodiment of the compound of formula (U), $R^2$ represents $CF_3$, methyl, ethyl, n-propyl, 2-propyl, n-butyl, iso-butyl, sec.-butyl, tert.-butyl, cyclopropyl, cyclobutyl, cyclopentyl or cyclohexyl. Preferably, $R^2$ represents $CF_3$, 2-propyl, n-butyl, iso-butyl, sec.-butyl, tert.-butyl, cyclopropyl, or cyclobutyl. More preferably, $R^2$ represents $CF_3$, tert.-butyl or cyclopropyl.

In one particularly preferred embodiment of the compound of formula (U), $R^2$ represents $CF_3$.

In another particularly preferred embodiment of the compound of formula (U), $R^2$ represents tert.-butyl.

In another particularly preferred embodiment of the compound of formula (U), $R^2$ represents cyclopropyl.

In a further preferred embodiment of the compound of formula (U), $R^7$ and $R^9$ are each independently selected from the group consisting of H, F, Cl, Br, $CF_3$, CN, OH, $OCF_3$, $CH_3$, $CH_2CH_3$, $CH(CH_3)_2$, O—$CH_3$, and O—$CH_2CH_3$. Preferably, $R^7$ and $R^9$ are independently selected from the group consisting of H, F, Cl, $CF_3$, CN, OH, $OCF_3$, $CH_3$, O—$CH_3$, and O—$CH_2CH_3$. More preferably, $R^7$ and $R^9$ are each independently selected from the group consisting of H, F, Cl, $CF_3$, O—$CH_3$, and O—$CH_2CH_3$. Even more preferably, $R^7$ and $R^9$ are each independently selected from the group consisting of H, F, Cl, and O—$CH_3$, and still more preferably are independently selected from the group consisting of H, F and Cl.

In yet a further preferred embodiment of the compound of formula (U), at least one of $R^7$ and $R^9$ is not H.

In a further preferred embodiment of the compound of formula (U), $R^9$ denotes H.

In yet another preferred embodiment of the compound of formula (U), $R^7$ is selected from the group consisting of F, Cl, Br, $CF_3$, CN, OH, $OCF_3$, $CH_3$, $CH_2CH_3$, $CH(CH_3)_2$, O—$CH_3$, and O—$CH_2CH_3$, preferably from the group consisting of F, Cl, $CF_3$, CN, OH, $OCF_3$, $CH_3$, O—$CH_3$, and O—$CH_2CH_3$, more preferably from the group consisting of F, Cl, $CF_3$, O—$CH_3$, and O—$CH_2CH_3$, even more preferably from the group consisting of F, Cl, and O—$CH_3$, and still more preferably from the group consisting of F and Cl; and $R^9$ represents H.

In another preferred embodiment of the compound of formula (U), A denotes N or $C(CH_3)$.

In one particularly preferred embodiment of the compound of formula (U), A denotes N.

In another particularly preferred embodiment of the compound of formula (U), A denotes $C(CH_3)$.

In another preferred embodiment of the compound of formula (U), $R^{104}$ represents H, $C_{1-4}$ alkyl, which is unsubstituted or mono-, di- or trisubstituted with 1, 2 or 3 substituents independently selected from the group consisting of F, Cl, Br, $NH_2$, $NH(CH_3)$, $N(CH_3)_2$, =O, OH and $OCH_3$; or $OR^{105}$, wherein $R^{105}$ represents H or $C_{1-4}$ alkyl, which is unsubstituted or mono-, di- or trisubstituted with 1, 2 or 3 substituents independently selected from the group consisting of F, Cl, Br, $NH_2$, $NH(CH_3)$, $N(CH_3)_2$, =O, OH and $OCH_3$; or $NR^{106}R^{107}$, wherein $R^{106}$ represents H or $C_{1-4}$ alkyl, which is unsubstituted or mono-, di- or trisubstituted with 1, 2 or 3 substituents independently selected from the group consisting of F, Cl, Br, $NH_2$, $NH(CH_3)$, $N(CH_3)_2$, =O, OH and $OCH_3$, and $R^{107}$ is selected from the group consisting of H, a $C_{1-4}$ alkyl, which is unsubstituted or mono-, di- or trisubstituted with 1, 2 or 3 substituents independently selected from the group consisting of F, Cl, Br, $NH_2$, $NH(CH_3)$, $N(CH_3)_2$, =O, OH and $OCH_3$;

$C_{3-6}$ cycloalkyl or 3 to 6 membered heterocyclyl, which is in each case unsubstituted or mono-, di- or trisubstituted with 1, 2 or 3 substituents independently selected from the group consisting of F, Cl, Br, CN, $CF_3$, $CH_3$, $CH_2CH_3$, $CH(CH_3)_2$, tert.-butyl, cyclopropyl, OH, =O, $OCH_3$, $OCF_3$, $NH_2$, $NH(CH_3)$ and $N(CH_3)_2$;

phenyl, which is mono-, di- or trisubstituted with 1, 2 or 3 substituents, preferably $R^{201}$, $R^{202}$ and/or $R^{203}$, independently selected from the group consisting of F, Cl, Br, CN, $CF_3$, $CH_3$, $CH_2CH_3$, $CH(CH_3)_2$, tert.-butyl, cyclopropyl, $NH_2$, $NH(CH_3)$, $N(CH_3)_2$, OH, $OCF_3$ and $OCH_3$; or heteroaryl, which is unsubstituted or mono-, di- or trisubstituted with 1, 2 or 3 substituents independently selected from the group consisting of F, Cl, Br, $CF_3$, $CH_3$, $CH_2CH_3$, $CH(CH_3)_2$, tert.-butyl, cyclopropyl, $NH_2$, $NH(CH_3)$, $N(CH_3)_2$, OH, $OCF_3$ and $OCH_3$, with the proviso that $R^{107}$ is not H if A represents CH or $C(CH_3)$, or wherein $R^{106}$ and $R^{107}$ together with the nitrogen atom connecting them form a 3 to 6 membered heterocyclyl, which is unsubstituted or mono-, di- or trisubstituted with 1, 2 or 3 substituents independently selected from the group consisting of F, Cl, Br, $CF_3$, $CH_3$, $CH_2CH_3$, $CH(CH_3)_2$, tert.-butyl, cyclopropyl, OH, =O, $OCH_3$, $OCF_3$, $NH_2$, $NH(CH_3)$ and $N(CH_3)_2$.

Preferably, $R^{104}$ represents

H, or $C_{1-4}$ alkyl, which is unsubstituted or mono-, di- or trisubstituted with 1, 2 or 3 substituents independently selected from the group consisting of $NH_2$, $NH(CH_3)$, $N(CH_3)_2$, =O, OH and $OCH_3$; or $OR^{105}$, wherein $R^{105}$ represents H or $C_{1-4}$ alkyl, which is unsubstituted or mono-, di- or trisubstituted with 1, 2 or 3 substituents independently selected from the group consisting of $NH_2$, OH and $OCH_3$; or $NR^{106}R^{107}$, wherein $R^{106}$ represents H or $C_{1-4}$ alkyl, which is unsubstituted or mono-, di- or trisubstituted with 1, 2 or 3 substituents independently selected from the group consisting of $NH_2$, $NH(CH_3)$, $N(CH_3)_2$, =O, OH and $OCH_3$; and $R^{107}$ is selected from the group consisting of H, a $C_{1-4}$ alkyl, which is unsubstituted or mono-, di- or trisubstituted with 1, 2 or 3 substituents independently selected from the group consisting of $NH_2$, $NH(CH_3)$, $N(CH_3)_2$, =O, OH and $OCH_3$;

$C_{3-6}$ cycloalkyl or a 3 to 6 membered heterocyclyl, which is in each case unsubstituted or mono-, di- or trisubstituted with 1, 2 or 3 substituents independently selected from the group consisting of $CF_3$, $CH_3$, $CH_2CH_3$, $CH(CH_3)_2$, tert.-butyl, cyclopropyl, OH, =O, $OCH_3$, $OCF_3$, $NH_2$, $NH(CH_3)$ and $N(CH_3)_2$;

phenyl, which is mono-, di- or trisubstituted with 1, 2 or 3 substituents, preferably $R^{201}$, $R^{202}$ and/or $R^{203}$, independently selected from the group consisting of F, Cl, Br, CN, $CF_3$, $CH_3$, $CH_2CH_3$, $CH(CH_3)_2$, tert.-butyl, cyclopropyl, $NH_2$, $NH(CH_3)$, $N(CH_3)_2$, OH, $OCF_3$ and $OCH_3$; or heteroaryl, which is unsubstituted or mono-, di- or trisubstituted with 1, 2 or 3 substituents independently selected from the group consisting of F, Cl, Br, CN, $CF_3$, $CH_3$, $CH_2CH_3$, $CH(CH_3)_2$, tert.-butyl, cyclopropyl, $NH_2$, $NH(CH_3)$, $N(CH_3)_2$, OH, $OCF_3$ and $OCH_3$;

with the proviso that $R^{107}$ is not H when A represents CH or $C(CH_3)$;

or wherein $R^{106}$ and $R^{107}$ together with the nitrogen atom connecting them form a 3 to 6 membered heterocyclyl, which is unsubstituted or mono-, di- or trisubstituted with 1, 2 or 3 substituents independently selected from the group consisting of $CF_3$, $CH_3$, $CH_2CH_3$, $CH(CH_3)_2$, tert.-butyl, cyclopropyl, OH, =O, $OCH_3$, $OCF_3$, $NH_2$, $NH(CH_3)$ and $N(CH_3)_2$.

More preferably, $R^{104}$ represents

H, or $C_{1-4}$ alkyl, which is unsubstituted or mono-, di- or trisubstituted with 1, 2 or 3 substituents independently selected from the group consisting of OH and $OCH_3$; or $OR^{105}$, wherein $R^{105}$ represents H or $C_{1-4}$ alkyl, which is unsubstituted or mono-, di- or trisubstituted with 1, 2 or 3 substituents independently selected from the group consisting of OH and $OCH_3$; or $NR^{106}R^{107}$, wherein $R^{106}$ represents H or a $C_{1-4}$ alkyl, which is unsubstituted or mono-, di- or trisubstituted with 1, 2 or 3 substituents independently selected from the group consisting of OH and $OCH_3$; and $R^{107}$ is selected from the group consisting of H, a $C_{1-4}$ alkyl, which is unsubstituted or mono-, di- or trisubstituted with 1, 2 or 3 substituents independently selected from the group consisting of OH and $OCH_3$;

$C_{3-6}$ cycloalkyl or a 3 to 6 membered heterocyclyl, which is in each case unsubstituted or mono-, di- or trisubstituted with 1, 2 or 3 substituents independently selected from the group consisting of $CH_3$, $CH_2CH_3$, $CH(CH_3)_2$, OH, and $OCH_3$;

phenyl, which is mono-, di- or trisubstituted with 1, 2 or 3 substituents, preferably $R^{201}$, $R^{202}$ and/or $R^{203}$, independently selected from the group consisting of F, Cl, Br, CN, $CF_3$, $CH_3$, $CH_2CH_3$, $CH(CH_3)_2$, $NH_2$, $NH(CH_3)$, $N(CH_3)_2$, OH, $OCF_3$ and $OCH_3$; and heteroaryl, which is unsubstituted or mono-, di- or trisubstituted with 1, 2 or 3 substituents independently selected from the group consisting of F, Cl, Br, CN, $CF_3$, $CH_3$, $CH_2CH_3$, $NH_2$, $NH(CH_3)$, $N(CH_3)_2$, OH, $OCF_3$ and $OCH_3$;

with the proviso that $R^{107}$ is not H when A represents CH or $C(CH_3)$ or wherein $R^{106}$ and $R^{107}$ together with the nitrogen atom connecting them form a 3 to 6 membered heterocyclyl, which is unsubstituted or mono-, di- or trisubstituted with 1, 2 or 3 substituents independently selected from the group consisting of $CF_3$, $CH_3$, $CH_2CH_3$, $CH(CH_3)_2$, OH, =O, $OCH_3$, $OCF_3$, $NH_2$, $NH(CH_3)$ and $N(CH_3)_2$.

Even more preferably, $R^{104}$ represents

H, or $C_{1-4}$ alkyl, which is unsubstituted or mono-, di- or trisubstituted with 1, 2 or 3 substituents independently selected from the group consisting of OH and $OCH_3$;

$OR^{105}$, wherein $R^{105}$ represents H or $C_{1-4}$ alkyl, which is unsubstituted or mono-, di- or trisubstituted with 1, 2 or 3 substituents independently selected from the group consisting of OH and $OCH_3$; or $NR^{106}R^{107}$, wherein $R^{106}$ represents H or $C_{1-4}$ alkyl, which is unsubstituted or mono-, di- or trisubstituted with 1, 2 or 3 substituents independently selected from the group consisting of OH and $OCH_3$; and $R^{107}$ is selected from the group consisting of:

$C_{1-4}$ alkyl, which is unsubstituted or mono-, di- or trisubstituted with 1, 2 or 3 substituents independently selected from the group consisting of OH and $OCH_3$;

$C_{3-6}$ cycloalkyl or a 3 to 6 membered heterocyclyl, which is in each case unsubstituted or mono-, di- or trisubstituted with 1, 2 or 3 substituents independently selected from the group consisting of $CH_3$, OH, and $OCH_3$;

phenyl, which is mono-, di- or trisubstituted with 1, 2 or 3 substituents, preferably $R^{201}$, $R^{202}$ and/or $R^{203}$, independently selected from the group consisting of F, Cl, $CF_3$, $CH_3$, OH, $OCF_3$ and $OCH_3$; and unsubstituted heteroaryl, or wherein $R^{106}$ and $R^{107}$ together with the nitrogen atom connecting them form a 3 to 6 membered heterocyclyl, which is unsubstituted or mono-, di- or trisubstituted with 1, 2 or 3 substituents independently selected from the group consisting of $CH_3$, OH, and $OCH_3$.

In a particularly preferred embodiment of the present invention, $R^{101}$, $R^{102}$ and $R^{103}$ are independently selected from the group consisting of H, F, Cl, Br, $CF_3$, CN, $CH_2$—OH, $CH_2$—$OCH_3$, $OCF_3$, OH, $CH_3$, $CH_2CH_3$, $CH(CH_3)_2$, O—$CH_3$, O—$CH_2CH_3$, $NH_2$, $NH(CH_3)$, and $N(CH_3)_2$, preferably wherein at least one of $R^{101}$, $R^{102}$ and $R^{103}$ is not H;

$R^2$ represents $CF_3$, tert.-butyl or cyclopropyl;

$R^7$ and $R^9$ are each independently selected from the group consisting of H, F, Cl, Br, $CF_3$, CN, OH, $OCF_3$, $CH_3$, $CH_2CH_3$, $CH(CH_3)_2$, O—$CH_3$, and O—$CH_2CH_3$, wherein at least one of $R^7$ and $R^9$ is not H;

A denotes N, CH or $C(CH_3)$, preferably N or $C(CH_3)$; and $R^{104}$ represents H, or $C_{1-4}$ alkyl, which is unsubstituted or mono-, di- or trisubstituted with 1, 2 or 3 substituents independently selected from the group consisting of OH and $OCH_3$;

$OR^{105}$, wherein $R^{105}$ represents H or $C_{1-4}$ alkyl, which is unsubstituted or mono-, di- or trisubstituted with 1, 2 or 3 substituents independently selected from the group consisting of OH and $OCH_3$; or $NR^{106}R^{107}$, wherein $R^{106}$ represents H or $C_{1-4}$ alkyl, which is unsubstituted or mono-, di- or trisubstituted with 1, 2 or 3 substituents independently selected from the group consisting of OH and $OCH_3$, and $R^{107}$ is selected from the group consisting of:

$C_{1-4}$ alkyl, which is unsubstituted or mono-, di- or trisubstituted with 1, 2 or 3 substituents independently selected from the group consisting of OH and $OCH_3$;

$C_{3-6}$ cycloalkyl or 3 to 6 membered heterocyclyl, which in each case is unsubstituted or mono-, dior trisubstituted with 1, 2 or 3 substituents independently selected from the group consisting of $CH_3$, OH, and $OCH_3$;

phenyl, which is mono-, di- or trisubstituted with 1, 2 or 3 substituents, preferably $R^{201}$, $R^{202}$ and/or $R^{203}$, independently selected from the group consisting of F, Cl, $CF_3$, $CH_3$, OH, $OCF_3$ and $OCH_3$; or unsubstituted heteroaryl, or wherein $R^{106}$ and $R^{107}$ together with the nitrogen atom connecting them form a 3 to 6 membered heterocyclyl, which is unsubstituted or mono-, di- or trisubstituted with 1, 2 or 3 substituents independently selected from the group consisting of $CH_3$, OH, and $OCH_3$.

Preferred embodiments of the compound of formula (U) have the formula (U0-a) or (U0-b):

(U0-a)

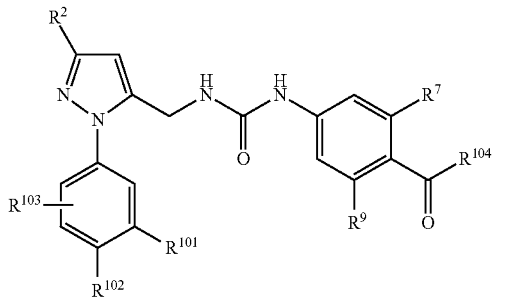

(U0-b)

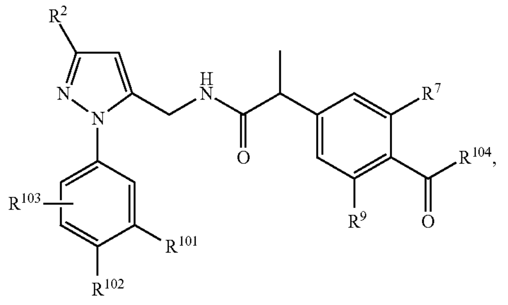

wherein the respective substituents, variables and indices have the meanings described above in connection with the compounds of formula (U) and preferred embodiments thereof.

Further preferred embodiments of the compound of formula (U) have the formula (U1-a), (U1-a-1) or (U1-a-2):

(U1-a)

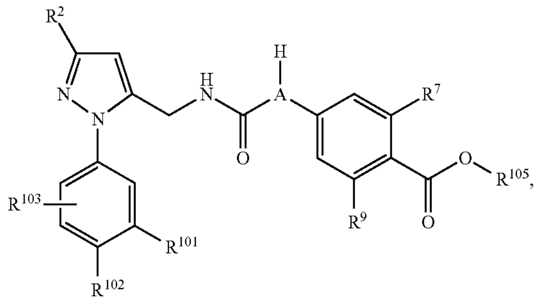

-continued (U1-a-1)

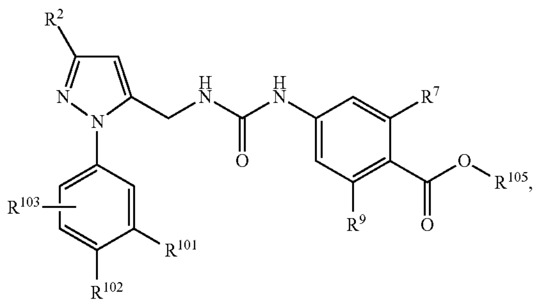

(U1-a-2)

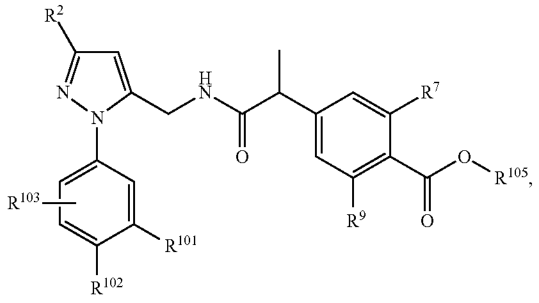

wherein the respective substituents, variables and indices have the meanings described above in connection with the compounds of formula (U) and preferred embodiments thereof.

Moreover, preferred embodiments of the compound of formula (U) have the formula (U1-b), (U1-b-1) or (U1-b-2):

(U1-b)

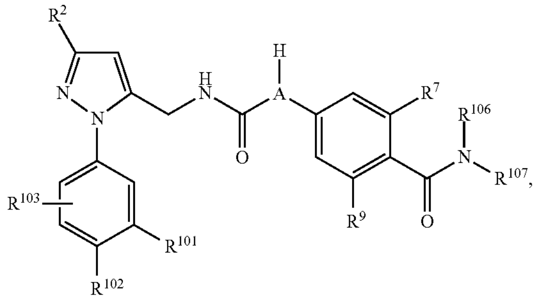

(U1-b-1)

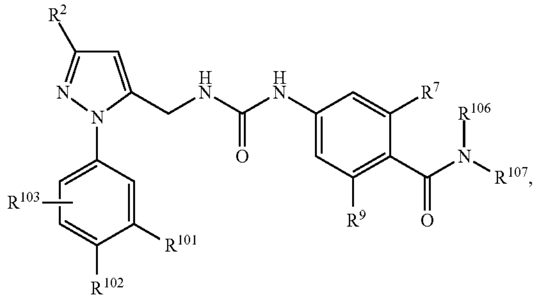

-continued (U1-b-2)

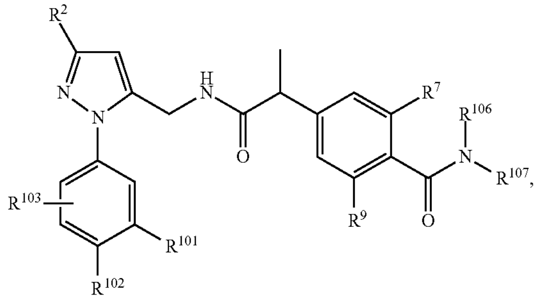

wherein the respective substituents, variables and indices have the meanings described above in connection with the compounds of formula (U) and preferred embodiments thereof.

In addition, preferred embodiments of the compound of formula (U) have the formula (U1-c), (U1-c-1) or (U1-c-2):

(U1-c)

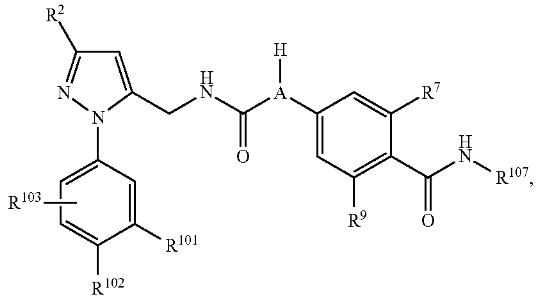

(U1-c-1)

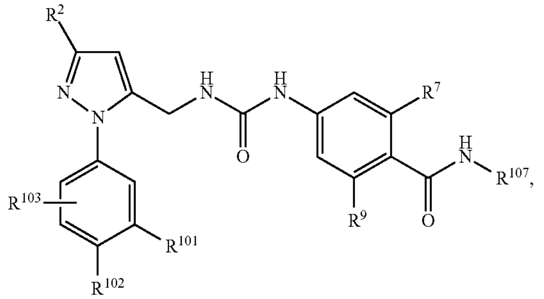

(U1-c-2)

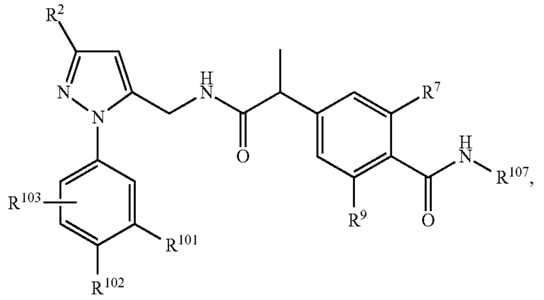

wherein the respective substituents, variables and indices have the meanings described above in connection with the compounds of formula (U) and preferred embodiments thereof.

Yet further preferred embodiments of the compound of formula (U) have the formula (U1-d), (U1-d-1) or (U1-d-2):

(U1-d)

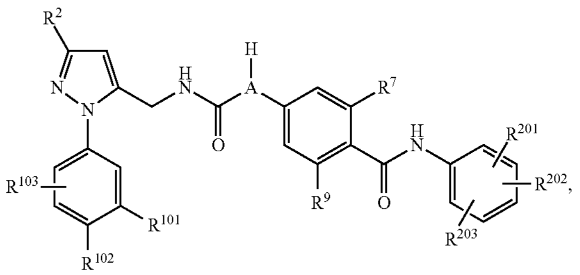

(U1-d-1)

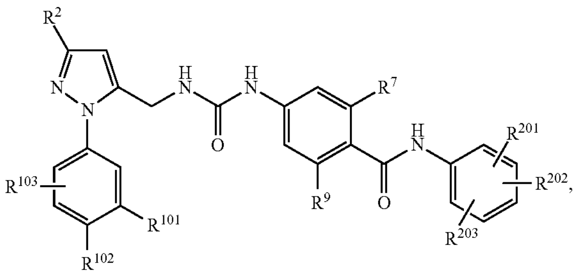

(U1-d-2)

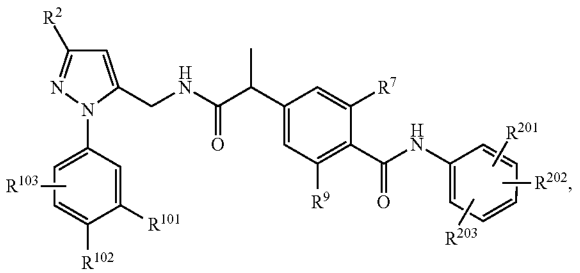

preferably wherein at least one of $R^{201}$, $R^{202}$ and $R^{203}$ in each of the partial structures (U1-d), (U1-d-1) and (U1-d-2) is not H, and wherein the respective substituents, variables and indices have the meanings described above in connection with the compounds of formula (U) and preferred embodiments thereof.

In particularly preferred embodiments of the present invention, $R^{101}$ in the compound of formula (U), (U0-a), (U0-b), (U1-a), (U1-a-1), (U1-a-2), (U1-b), (U1-b-1), (U1-b-2), (U1-c), (U1-c-1), (U1-c-2), (U1-d), (U1-d-1) or (U1-d-2) represents F, Cl, $CF_3$ or O—$CH_3$, preferably F or Cl, most preferably Cl—preferably when $R^{103}$ is H and $R^{102}$ represents H, F, Cl, $CF_3$ or $OCH_3$, more preferably when $R^{103}$ is H and $R^{102}$ represents H, F or Cl, even more preferably when both $R^{102}$ and $R^{103}$ denote H—, and the remaining respective substituents, variables and indices have the meanings described above in connection with the compounds of formula (U) and preferred embodiments thereof.

In particularly preferred embodiments of the present invention in the compound of general formula (U), (U0-a), (U0-b), (U1-a), (U1-a-1), (U1-a-2), (U1-b), (U1-b-1), (U1-b-2), (U1-c), (U1-c-1), (U1-c-2), (U1-d), (U1-d-1) or (U1-d-2), $R^{10'}$ represents F, Cl, $CF_3$ or O—$CH_3$, preferably F or Cl, most preferably Cl—preferably when $R^{103}$ is H and $R^{102}$ represents H, F, Cl, $CF_3$ or $OCH_3$, more preferably when $R^{103}$ is H and $R^{102}$ represents H, F or Cl, even more preferably when both $R^{102}$ and $R^{103}$ denote H—; at least one of $R^7$ and $R^9$ is not H, and $R^7$ and $R^9$ as well as the remaining respective substituents, variables and indices have the meanings described above in connection with the compounds of formula (U) and preferred embodiments thereof.

Particularly preferred compounds of formula (U) are selected from the group consisting of:

E1 N-[[2-(3-Fluorophenyl)-5-(trifluoromethyl)-2H-pyrazol-3-yl]-methyl]-2-(3-fluoro-4-propanoyl-phenyl)-propionamide;

E2 2-(3-Fluoro-4-propanoyl-phenyl)-N-[[2-(3-methoxyphenyl)-5-(trifluoromethyl)-2H-pyrazol-3-yl]-methyl]-propionamide;

E3 N-[[2-(3,4-Difluoro-phenyl)-5-(trifluoromethyl)-2H-pyrazol-3-yl]-methyl]-2-(3-fluoro-4-propanoyl-phenyl)-propionamide;

E4 4-[1-[[2-(3-Chlorophenyl)-5-(trifluoromethyl)-2H-pyrazol-3-yl]-methyl-carbamoyl]-ethyl]-2-fluoro-benzamide;

E5 4-[[[5-tert-Butyl-2-(3-chlorophenyl)-2H-pyrazol-3-yl]-methyl-carbamoyl]amino]-2-fluoro-benzamide;

E6 4-[[[2-(3-Chlorophenyl)-5-(trifluoromethyl)-2H-pyrazol-3-yl]-methyl-carbamoyl]amino]-2-fluoro-benzamide;

E7 4-[[[5-tert-Butyl-2-(3-chlorophenyl)-2H-pyrazol-3-yl]-methyl-carbamoyl]amino]-2-methoxy-benzamide;

E8 4-[[[5-tert-Butyl-2-(3-chlorophenyl)-2H-pyrazol-3-yl]-methyl-carbamoyl]amino]-2-fluoro-N-methyl-benzamide;

E9 4-[[[2-(3-Chlorophenyl)-5-(trifluoromethyl)-2H-pyrazol-3-yl]-methyl-carbamoyl]amino]-2-fluoro-N-methyl-benzamide;

E10 4-[1-[[5-tert-Butyl-2-(3-chlorophenyl)-2H-pyrazol-3-yl]-methyl-carbamoyl]-ethyl]-2-fluoro-N-methyl-benzamide;

E11 4-[1-[[2-(3-Chlorophenyl)-5-(trifluoromethyl)-2H-pyrazol-3-yl]-methyl-carbamoyl]-ethyl]-2-fluoro-N-methyl-benzamide;

E12 4-[[[5-tert-Butyl-2-(3-chlorophenyl)-2H-pyrazol-3-yl]-methyl-carbamoyl]amino]-2-fluoro-N,N-dimethyl-benzamide;

E13 4-[[[2-(3-Chlorophenyl)-5-(trifluoromethyl)-2H-pyrazol-3-yl]-methyl-carbamoyl]amino]-2-fluoro-N,N-dimethyl-benzamide;

E14 1-[[5-tert-Butyl-2-(3-chlorophenyl)-2H-pyrazol-3-yl]-methyl]-3-[3-fluoro-4-(morpholine-4-carbonyl)-phenyl]-urea;

E15 1-[[2-(3-Chlorophenyl)-5-(trifluoromethyl)-2H-pyrazol-3-yl]-methyl]-3-[3-fluoro-4-(morpholine-4-carbonyl)-phenyl]-urea;

E16 N-[[2-(3-Chlorophenyl)-5-(trifluoromethyl)-2H-pyrazol-3-yl]-methyl]-2-[3-fluoro-4-(morpholine-4-carbonyl)-phenyl]-propionamide;

E17 N-[[5-tert-Butyl-2-(3-chlorophenyl)-2H-pyrazol-3-yl]-methyl]-2-[3-fluoro-4-(morpholine-4-carbonyl)-phenyl]-propionamide;

E18 4-[[[2-(3-Chlorophenyl)-5-(trifluoromethyl)-2H-pyrazol-3-yl]-methyl-carbamoyl]amino]-2-fluoro-N-(2-hydroxy-ethyl)-benzamide;

E19 4-[1-[[2-(3-Chlorophenyl)-5-(trifluoromethyl)-2H-pyrazol-3-yl]-methyl-carbamoyl]-ethyl]-2-fluoro-N-(oxetan-3-yl)-benzamide;

E20 4-[1-[[2-(3-Chlorophenyl)-5-(trifluoromethyl)-2H-pyrazol-3-yl]-methyl-carbamoyl]-ethyl]-2-fluoro-N-(1-methyl-piperidin-4-yl)-benzamide;

E21 4-[1-[[5-tert-Butyl-2-(3-chlorophenyl)-2H-pyrazol-3-yl]-methyl-carbamoyl]-ethyl]-2-fluoro-N-(1-methyl-piperidin-4-yl)-benzamide;

E22 4-[[[2-(3-Chlorophenyl)-5-(trifluoromethyl)-2H-pyrazol-3-yl]-methyl-carbamoyl]amino]-2-fluoro-N-tetrahydro-pyran-4-yl-benzamide;

E23 4-[1-[[2-(3-Chlorophenyl)-5-(trifluoromethyl)-2H-pyrazol-3-yl]-methyl-carbamoyl]-ethyl]-2-fluoro-N-tetrahydro-pyran-4-yl-benzamide;

E24 4-[1-[[5-tert-Butyl-2-(3-chlorophenyl)-2H-pyrazol-3-yl]-methyl-carbamoyl]-ethyl]-2-fluoro-N-tetrahydro-pyran-4-yl-benzamide;

E25 4-[[[5-tert-Butyl-2-(3-chlorophenyl)-2H-pyrazol-3-yl]-methyl-carbamoyl]-methyl]-N-phenyl-benzamide;

E26 4-[[[2-(3-Chlorophenyl)-5-(trifluoromethyl)-2H-pyrazol-3-yl]-methyl-carbamoyl]-methyl]-N-phenyl-benzamide;

E27 4-[1-[[5-tert-Butyl-2-(3-chlorophenyl)-2H-pyrazol-3-yl]-methyl-carbamoyl]-ethyl]-N-phenyl-benzamide;

E28 4-[1-[[2-(3-Chlorophenyl)-5-(trifluoromethyl)-2H-pyrazol-3-yl]-methyl-carbamoyl]-ethyl]-N-phenyl-benzamide;

E29 4-[1-[[5-tert-Butyl-2-(3-chlorophenyl)-2H-pyrazol-3-yl]-methyl-carbamoyl]-ethyl]-2-fluoro-N-phenyl-benzamide;

E30 4-[[[5-tert-Butyl-2-(3-chlorophenyl)-2H-pyrazol-3-yl]-methyl-carbamoyl]-methyl]-N-(4-chlorophenyl)-benzamide;

E31 4-[1-[[5-tert-Butyl-2-(3-chlorophenyl)-2H-pyrazol-3-yl]-methyl-carbamoyl]-ethyl]-N-(3-chlorophenyl)-benzamide;

E32 N-(3-Chlorophenyl)-4-[1-[[2-(3-chlorophenyl)-5-(trifluoromethyl)-2H-pyrazol-3-yl]-methyl-carbamoyl]-ethyl]-benzamide;

E33 N-(4-Chlorophenyl)-4-[1-[[2-(3-chlorophenyl)-5-(trifluoromethyl)-2H-pyrazol-3-yl]-methyl-carbamoyl]-ethyl]-benzamide;

E34 4-[1-[[5-tert-Butyl-2-(3-chlorophenyl)-2H-pyrazol-3-yl]-methyl-carbamoyl]-ethyl]-N-(4-chlorophenyl)-benzamide;

E35 4-[1-[[5-tert-Butyl-2-(3-chlorophenyl)-2H-pyrazol-3-yl]-methyl-carbamoyl]-ethyl]-N-(4-chlorophenyl)-2-fluoro-benzamide;

E36 4-[[[2-(3-Chlorophenyl)-5-(trifluoromethyl)-2H-pyrazol-3-yl]-methyl-carbamoyl]-methyl]-N-(4-fluorophenyl)-benzamide;

E37 4-[[[5-tert-Butyl-2-(3-chlorophenyl)-2H-pyrazol-3-yl]-methyl-carbamoyl]-methyl]-N-(4-fluorophenyl)-benzamide;

E38 4-[[[2-(3-Chlorophenyl)-5-(trifluoromethyl)-2H-pyrazol-3-yl]-methyl-carbamoyl]-methyl]-2-fluoro-N-(4-fluorophenyl)-benzamide;

E39 4-[[[5-tert-Butyl-2-(3-chlorophenyl)-2H-pyrazol-3-yl]-methyl-carbamoyl]-methyl]-2-fluoro-N-(4-fluorophenyl)-benzamide;

E40 4-[1-[[5-tert-Butyl-2-(3-chloro phenyl)-2H-pyrazol-3-yl]-methyl-carbamoyl]-ethyl]-N-(3-fluorophenyl)-benzamide;

E41 4-[1-[[2-(3-Chlorophenyl)-5-(trifluoromethyl)-2H-pyrazol-3-yl]-methyl-carbamoyl]-ethyl]-N-(3-fluorophenyl)-benzamide;

E42 4-[1-[[5-tert-Butyl-2-(3-chlorophenyl)-2H-pyrazol-3-yl]-methyl-carbamoyl]-ethyl]-N-(4-fluorophenyl)-benzamide;

E43 4-[1-[[2-(3-Chlorophenyl)-5-(trifluoromethyl)-2H-pyrazol-3-yl]-methyl-carbamoyl]-ethyl]j-N-(4-fluorophenyl)-benzamide;

E44 4-[1-[[5-tert-Butyl-2-(3-chlorophenyl)-2H-pyrazol-3-yl]-methyl-carbamoyl]-ethyl-]-2-fluoro-N-(4-fluorophenyl)-benzamide;

E45 4-[1-[[2-(3-Chlorophenyl)-5-(trifluoromethyl)-2H-pyrazol-3-yl]-methyl-carbamoyl]-ethyl]-2-fluoro-N-(4-fluorophenyl)-benzamide;

E46 N-(4-Chlorophenyl)-4-[1-[[2-(3-chlorophenyl)-5-(trifluoromethyl)-2H-pyrazol-3-yl]-methyl-carbamoyl]-ethyl]-2-fluoro-benzamide;

E47 4-[1-[[5-tert-Butyl-2-(3-chlorophenyl)-2H-pyrazol-3-yl]-methyl-carbamoyl]-ethyl]-N-[4-(trifluoromethyl)-phenyl]-benzamide;

E48 4-[1-[[2-(3-Chlorophenyl)-5-(trifluoromethyl)-2H-pyrazol-3-yl]-methyl-carbamoyl]-ethyl]-2-fluoro-N-[4-(trifluoromethyl)-phenyl]-benzamide;

E49 4-[1-[[5-tert-Butyl-2-(3-chlorophenyl)-2H-pyrazol-3-yl]-methyl-carbamoyl]-ethyl]-2-fluoro-N-[4-(trifluoromethyl)-phenyl]-benzamide;

E50 4-[[[5-tert-Butyl-2-(3-chlorophenyl)-2H-pyrazol-3-yl]-methyl-carbamoyl]-methyl]-N-[4-(trifluoromethyl)-phenyl]-benzamide;

E51 4-[[[2-(3-Chlorophenyl)-5-(trifluoromethyl)-2H-pyrazol-3-yl]-methyl-carbamoyl]-methyl]-N-[4-(trifluoromethyl)-phenyl]-benzamide;

E52 4-[1-[[2-(3-Chlorophenyl)-5-(trifluoromethyl)-2H-pyrazol-3-yl]-methyl-carbamoyl]-ethyl]-2-fluoro-N-thiazol-2-yl-benzamide;

E53 4-[1-[[5-tert-Butyl-2-(3-chlorophenyl)-2H-pyrazol-3-yl]-methyl-carbamoyl]-ethyl]-2-fluoro-N-thiazol-2-yl-benzamide;

E54 2-Chloro-4-[[[2-(3-chlorophenyl)-5-(trifluoromethyl)-2H-pyrazol-3-yl]-methyl-carbamoyl]amino]-benzoic acid;

E55 4-[[[5-tert-Butyl-2-(3-chlorophenyl)-2H-pyrazol-3-yl]-methyl-carbamoyl]amino]-2-chloro-benzoic acid;

E56 4-[[[5-tert-Butyl-2-(3-chlorophenyl)-2H-pyrazol-3-yl]-methyl-carbamoyl]amino]-2-methoxy-benzoic acid;

E57 4-[[[5-tert-Butyl-2-(3-chlorophenyl)-2H-pyrazol-3-yl]-methyl-carbamoyl]amino]-2-methoxy-benzoic acid methyl ester;

E58 4-[[[2-(3-Chlorophenyl)-5-(trifluoromethyl)-2H-pyrazol-3-yl]-methy-carbamoyl]amino]-2-methoxy-benzoic acid methyl ester;

E59 2-Chloro-4-[[[2-(3-chlorophenyl)-5-(trifluoromethyl)-2H-pyrazol-3-yl]-methyl-carbamoyl]amino]-benzoic acid methyl ester;

E60 4-[[[5-tert-Butyl-2-(3-chlorophenyl)-2H-pyrazol-3-yl]-methyl-carbamoyl]amino]-2-chloro-benzoic acid methyl ester;

E61 1-[[2-(3-Chlorophenyl)-5-(trifluoromethyl)-2H-pyrazol-3-yl]-methyl]-3-(3-fluoro-4-formyl-phenyl)-urea; and E62 4-[[[2-(3-Chlorophenyl)-5-(trifluoromethyl)-2H-pyrazol-3-yl]-methyl-carbamoyl]amino]-2-fluoro-benzoic acid;

in the form of an individual stereoisomer or a mixture of stereoisomers, and in the form of a free compound or a physiologically acceptable salt thereof.

Furthermore, preference may be given to compounds according to the invention of general formula (I) that cause a 50 percent displacement of capsaicin, which is present at a concentration of 100 nM, in a FLIPR assay with CHO K1 cells which were transfected with the human VR1 gene at a concentration of less than 2,000 nM, preferably less than 1,000 nM, particularly preferably less than 300 nM, most particularly preferably less than 100 nM, even more preferably less than 75 nM, additionally preferably less than 50 nM, most preferably less than 10 nM.

In the process, the $Ca^{2+}$ influx is quantified in the FLIPR assay with the aid of a $Ca^{2+}$-sensitive dye (type Fluo-4, Molecular Probes Europe BV, Leiden, the Netherlands) in a fluorescent imaging plate reader (FLIPR, Molecular Devices, Sunnyvale, USA), as described hereinafter.

The present invention further relates to a process for preparing compounds of the above-indicated general formula (I), according to which at least one compound of general formula (II), (II)

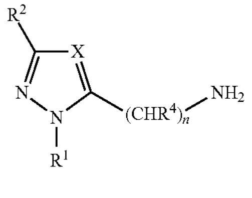

in which X, $R^1$, $R^2$, $R^4$ and n have one of the foregoing meanings, is reacted in a reaction medium, optionally in the presence of at least one suitable coupling reagent, optionally in the presence of at least one base, with a compound of general formula (III) or (IV), (III)

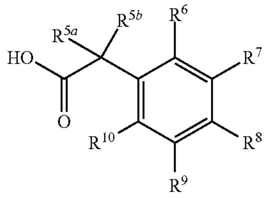

(IV)

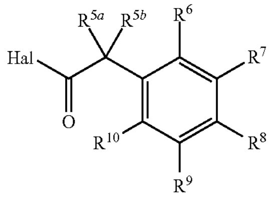

in which Hal represents a halogen, preferably CI or Br, and $R^{5a}$, $R^{5b}$, $R^6$, $R^7$, $R^8$, $R^9$ and $R^{10}$ each have one of the foregoing meanings, in a reaction medium, optionally in the presence of at least one suitable coupling reagent, optionally in the presence of at least one base, to form a compound of general formula (I), (I)

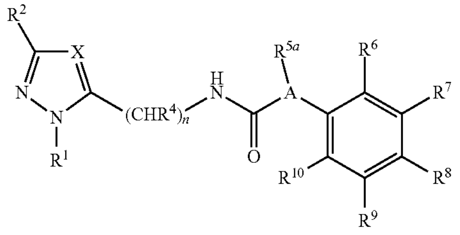

in which A represents $CR^{5b}$ and X, $R^1$, $R^2$, $R^4$, $R^{5a}$, $R^{5b}$, $R^6$, $R^7$, $R^8$, $R^9$, $R^{10}$ and n have one of the foregoing meanings;

or in that at least one compound of general formula (II), (II)

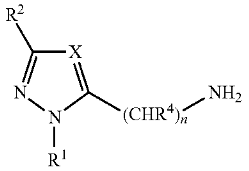

in which X, $R^1$, $R^2$, $R^4$ and n have one of the foregoing meanings, is reacted to form a compound of general formula (V)

(V)

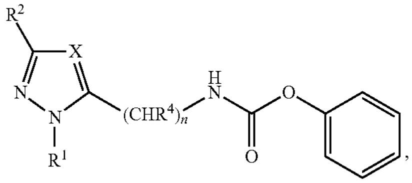

in which X, $R^1$, $R^2$, $R^4$ and n have one of the foregoing meanings, in a reaction medium, in the presence of phenyl chloroformate, optionally in the presence of at least one base and/or a coupling reagent, and said compound is if appropriate purified and/or isolated, and a compound of general formula (V) is reacted with a compound of general formula (VI), (VI)

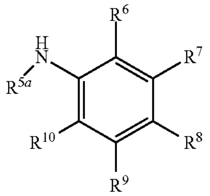

in which $R^6$, $R^7$, $R^8$, $R^9$ and $R^{10}$ have one of the foregoing meanings, in a reaction medium, optionally in the presence of at least one suitable coupling reagent, optionally in the presence of at least one base, to form a compound of general formula (I), (I)

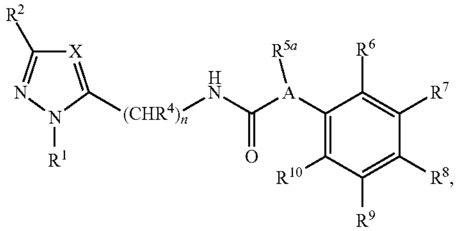

in which A represents N and X, $R^1$, $R^2$, $R^4$, $R^{5a}$, $R^6$, $R^7$, $R^8$ $R^9$ and $R^{10}$ and n have one of the foregoing meanings.

The reaction of compounds of the above-indicated general formulas (II) and (VI) with carboxylic acids of the above-indicated general formula (III) to form compounds of the above-indicated general formula (I) is carried out preferably in a reaction medium selected from the group consisting of diethyl ether, tetrahydrofuran, acetonitrile, methanol, ethanol, (1,2)-dichloroethane, dimethylformamide, dichloromethane and corresponding mixtures, optionally in the presence of at least one coupling reagent, preferably selected from the group consisting of 1-benzotriazolyloxy-tris-(dimethylamino)-phosphonium hexafluorophosphate (BOP), dicyclohexylcarbodiimide (DCC), N'-(3-dimethylaminopropyl)-N-ethylcarbodiimide (EDCl), diisopropylcarbodiimide, 1,1'-carbonyldiimidazole (CDI), N-[(dimethylamino)-1H-1,2,3-triazolo[4,5-b]pyridino-1-yl-methylene]-N-methylmethanaminium hexafluorophosphate N-oxide (HATU), O-(benzotriazol-1-yl)-N,N,N',N'-tetramethyluronium hexafluorophosphate (HBTU), O-(benzotriazol-1-yl)-N,N,N',N'-tetramethyluronium tetrafluoroborate (TBTU), N-hydroxybenzotriazole (HOBt) and 1-hydroxy-7-azabenzotriazole (HOAt), optionally in the presence of at least one organic base, preferably selected from the group consisting of triethylamine, pyridine, dimethylaminopyridine, N-methylmorpholine and diisopropylethylamine, preferably at temperatures of from −70° C. to 100° C.

Alternatively, the reaction of compounds of the above-indicated general formulae (II) and (VI) with carboxylic acid halides of the above-indicated general formula (IV), in which Hal represents a halogen as the leaving group, preferably a chlorine or bromine atom, to form compounds of the above-indicated general formula (I) is carried out in a reaction medium preferably selected from the group consisting of diethyl ether, tetrahydrofuran, acetonitrile, methanol, ethanol, dimethylformamide, dichloromethane and corresponding mixtures, optionally in the presence of an organic or inorganic base, preferably selected from the group consisting of triethylamine, dimethylaminopyridine, pyridine and diisopropylamine, at temperatures of from −70° C. to 100° C.

The compounds of the above-indicated formulae (II), (III), (IV), (V) and (VI) are each commercially available and/or can be prepared using conventional processes known to persons skilled in the art.

The reactions described above can each be carried out under the conventional conditions with which persons skilled in the art are familiar, for example with regard to pressure or the order in which the components are added. If appropriate, persons skilled in the art can determine the optimum procedure under the respective conditions by carrying out simple preliminary tests. The intermediate and end products obtained using the reactions described hereinbefore can each be purified and/or isolated, if desired and/or required, using conventional methods known to persons skilled in the art. Suitable purifying processes are for example extraction processes and chromatographic processes such as column chromatography or preparative chromatography. All of the process steps described hereinbefore, as well as the respective purification and/or isolation of intermediate or end products, can be carried out partly or completely under an inert gas atmosphere, preferably under a nitrogen atmosphere.

The substituted compounds according to the invention of the aforementioned general formula (I) and also corresponding stereoisomers can be isolated both in the form of their free bases, their free acids and also in the form of corresponding salts, in particular physiologically compatible salts.

The free bases of the respective substituted compounds according to the invention of the aforementioned general formula (I) and also of corresponding stereoisomers can be converted into the corresponding salts, preferably physiologically compatible salts, for example by reaction with an inorganic or organic acid, preferably with hydrochloric acid, hydrobromic acid, sulfuric acid, methanesulfonic acid, p-toluenesulfonic acid, carbonic acid, formic acid, acetic acid, oxalic acid, succinic acid, tartaric acid, mandelic acid, fumaric acid, maleic acid, lactic acid, citric acid, glutamic acid, saccharic acid, monomethylsebacic acid, 5-oxoproline, hexane-1-sulfonic acid, nicotinic acid, 2, 3 or 4-aminobenzoic acid, 2,4,6-trimethylbenzoic acid, α-lipoic acid, acetyl glycine, hippuric acid, phosphoric acid and/or aspartic acid. The free bases of the respective substituted compounds of the aforementioned general formula (I) and of corresponding stereoisomers can likewise be converted into the corresponding physiologically compatible salts using the free acid or a salt of a sugar additive, such as for example saccharin, cyclamate or acesulfame.

Accordingly, the free acids of the substituted compounds of the aforementioned general formula (I) and of corresponding stereoisomers can be converted into the corresponding physiologically compatible salts by reaction with a suitable base. Examples include the alkali metal salts, alkaline earth metals salts or ammonium salts $[NH_xR_{4-x}]^+$, in which x=0, 1, 2, 3 or 4 and R represents a branched or unbranched $C_{1-4}$ alkyl residue.

The substituted compounds according to the invention of the aforementioned general formula (I) and of corresponding stereoisomers can, if appropriate, like the corresponding acids, the corresponding bases or salts of these compounds, also be obtained in the form of their solvates, preferably in the form of their hydrates, using conventional methods known to persons skilled in the art.

If the substituted compounds according to the invention of the aforementioned general formula (I) are obtained, after preparation thereof, in the form of a mixture of their stereoisomers, preferably in the form of their racemates or other mixtures of their various enantiomers and/or diastereomers, they can be separated and if appropriate isolated using conventional processes known to persons skilled in the art. Examples include chromatographic separating processes, in particular liquid chromatography processes under normal pressure or under elevated pressure, preferably MPLC and HPLC processes, and also fractional crystallization processes. These processes allow individual enantiomers, for example diastereomeric salts formed by chiral stationary phase HPLC or by crystallization with chiral acids, for example (+)-tartaric acid, (−)-tartaric acid or (+)-10-camphorsulfonic acid, to be separated from one another.

The synthesis of the compounds of the invention can be effected in accordance with the following general reaction schemes.

General reaction scheme (scheme 1a):

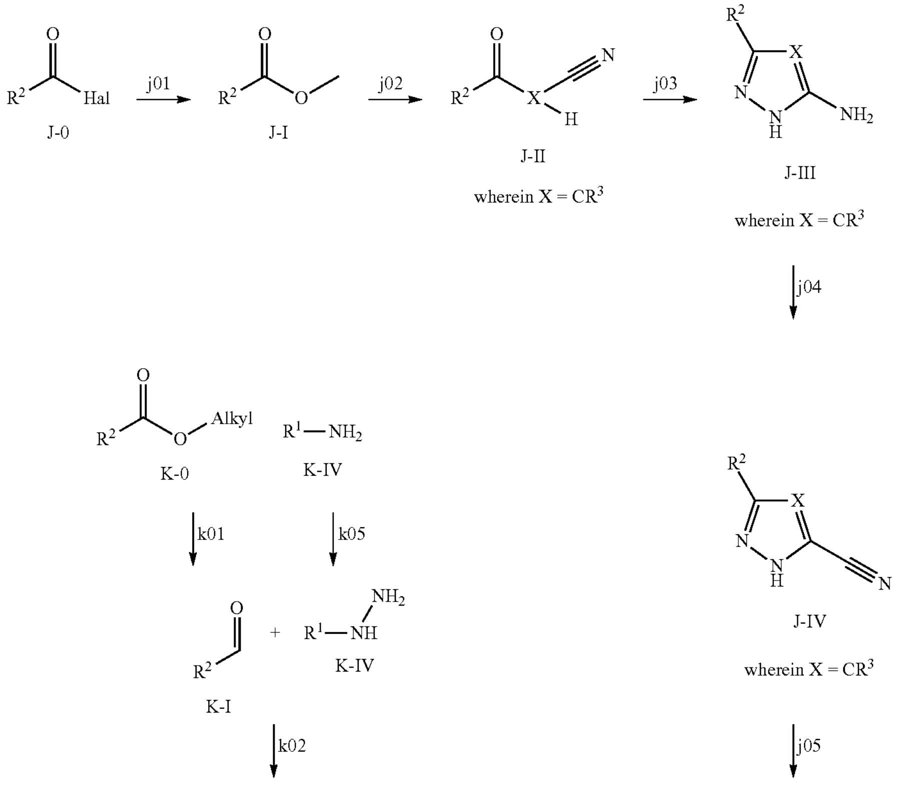

-continued

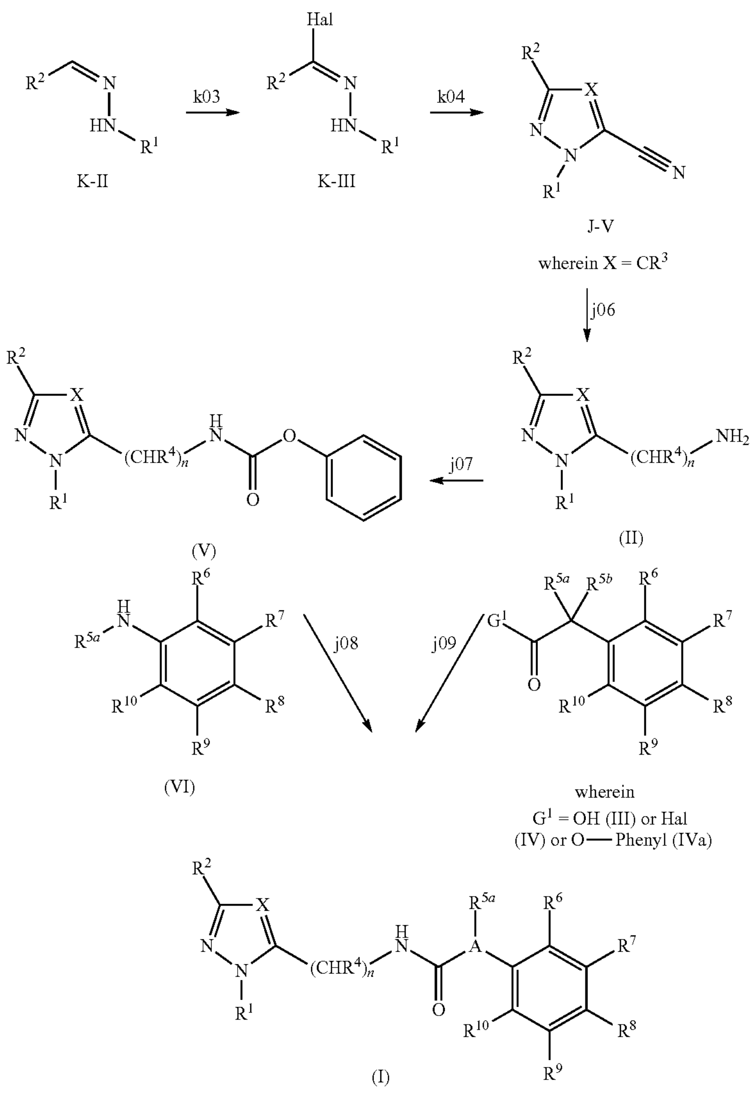

In step j01 an acid halide J-0, in which Hal preferably represents Cl or Br, can be esterified using methanol to form the compound J-I by methods with which persons skilled in the art is familiar.

In step j02 the methyl pivalate J-I can be converted into an oxoalkylnitrile J-II, wherein X═$CR^3$, by methods known to persons skilled in the art, such as for example using an alkyl nitrile $R^3CH_2$—CN, optionally in the presence of a base.

In step j03 the compound J-II can be converted into an amino-substituted pyrazolyl derivative J-III, wherein X═$CR^3$, by methods known to persons skilled in the art, such as for example using hydrazine hydrate, with cyclization.

In step j04 the amino compound J-III can first be converted into a diazonium salt by methods known to persons skilled in the art, such as for example using nitrite, and the diazonium salt can be converted into a cyano-substituted pyrazolyl derivative J-IV, wherein X ═$CR^3$, with elimination of nitrogen using a cyanide, optionally in the presence of a coupling reagent.

In step j05 the compound J-IV can be substituted in the N position by methods known to persons skilled in the art, for example using a halide $R^1$-Hal, optionally in the presence of a base and/or a coupling reagent, wherein Hal is preferably Cl, Br or I, or using a boronic acid $B(OH)_2R^1$ or a corresponding boronic acid ester, optionally in the presence of a coupling reagent and/or a base and the compound J-V, wherein X═$CR^3$, can in this way be obtained. If $R^1$ is linked to general formula (I) via a heteroatom (if $R^1$ represents substructure (T-1), for example, in which o represents 1 and Y can represent inter alia O, S, S(═O)$_2$, NH—C(═O) or $NR^{12}$), then the substitution can be carried out using methods known to persons skilled in the art, for example with the aid of hydroxylamine-O-sulfonic acid and subsequent conversion into secondary or tertiary amines, wherein Y═$NR^{13}$. In the case of Y═O, the substitution can be carried out using methods known to persons skilled in the art, for example with the aid of peroxy reagents and subsequent conversion into ether. In the case of Y═S(═O)$_2$, the substitution can be carried out by sulfonylation with sulfonyl chlorides, for example. In the case of Y═S, the preparation can for example be carried out by reaction with disulfides or else with sulfenyl chlorides or sulfene amides, or else by transformation into the mercaptan by methods known to persons skilled in the art and subsequent conversion into the thioether.

Alternatively, a second synthesis pathway, in which in step k01 an ester K-0 is first reduced to form the aldehyde K-I by methods known to persons skilled in the art, for example using suitable hydrogenation reagents such as metal hydrides, is suitable for preparing the compound J-V, wherein X═$CR^3$.

In step k02 the aldehyde K-I can then be reacted with a hydrazine K-V, which can be obtained in step k05, starting from the primary amine K-IV, by methods known to persons skilled in the art, to form the hydrazine K-II by methods known to persons skilled in the art with elimination of water.

In step k03 the hydrazine K-II can be halogenated, preferably chlorinated, by methods known to persons skilled in the art with the double bond intact, such as for example using a chlorination reagent such as NCS, and the compound K-III can in this way be obtained.

In step k04 the hydrazonoyl halide K-III can be converted into a cyano-substituted compound J-V, wherein X═$CR^3$, by methods known to persons skilled in the art, such as for example using a halogen-substituted nitrile, with cyclisation.

In step j06 the compound J-V can be hydrogenated by methods known to persons skilled in the art, for example using a suitable catalyst such as palladium/activated carbon or using suitable hydrogenation reagents, and the compound (II) can in this way be obtained.

In step j07 the compound (II) can be converted into the compound (V) by methods known to persons skilled in the art, such as, for example, using phenyl chloroformate, optionally in the presence of a coupling reagent and/or a base. In addition to the methods disclosed in the present document for preparing unsymmetrical ureas using phenyl chloroformate, there are further processes with which persons skilled in the art are familiar, based on the use of activated carbonic acid derivatives or isocyanates, if appropriate.

In step j08 the amine (VI) can be converted into the urea compound (I) (wherein A=N). This can be achieved by reaction with (V) by methods with which persons skilled in the art is familiar, optionally in the presence of a base.

In step j09 the amine (II) can be converted into the amide (I) (wherein A=C—$R^{5b}$). This can for example be achieved by reaction with an acid halide, preferably a chloride of formula (IV) by methods with which persons skilled in the art is familiar, optionally in the presence of a base or by reaction with an acid of formula (III), optionally in the presence of a suitable coupling reagent, for example HATU or CDI, if appropriate with the addition of a base. Further, the amine (II) may be converted into the amide (I) (wherein A=C—$R^{5b}$) by reaction of a compound (IVa) by methods with which persons skilled in the art is familiar, optionally in the presence of a base.

For preparing compounds (II), wherein X═N, it is necessary to take a third synthesis route according to the general reaction scheme 1b. The compounds (II) which are then obtained, wherein X═N, can subsequently be further reacted in accordance with the above-described steps j07-j09.

General reaction scheme (scheme 1b):

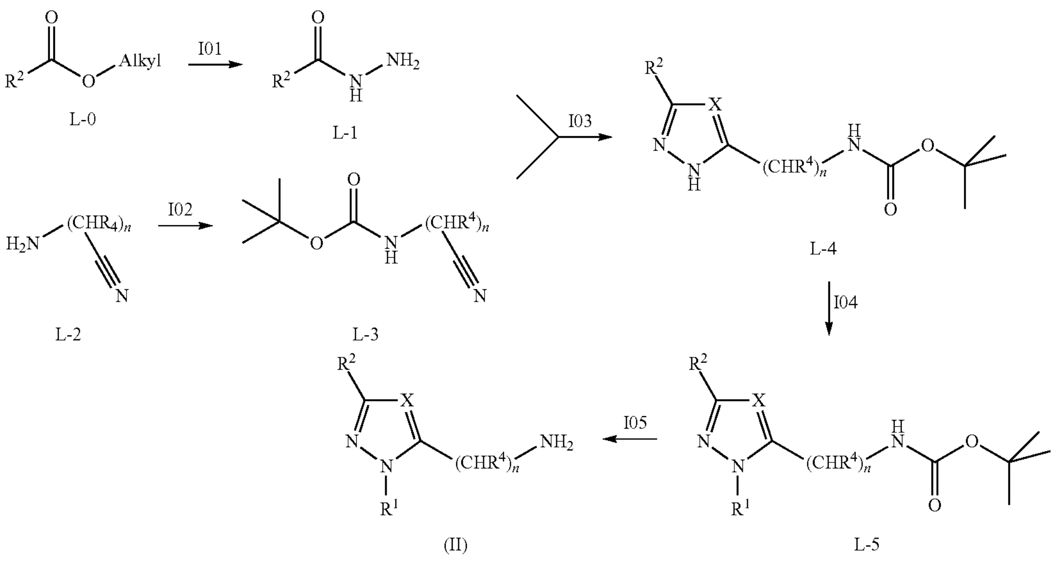

In step l01 a carboxylic acid alkyl ester L-0, preferably a methyl or ethyl ester, can be reacted with hydrazine hydrate to form the hydrazide L-1 by methods with which persons skilled in the art is familiar.

In step l02 the amino-substituted nitrile L-2 or the salts thereof can be reacted with boc anhydride to form the urethane L-3 by methods with which persons skilled in the art is familiar.

In step l03 L-1 and L-3 can be condensed in the presence of a base, preferably an alkali alcoholate, particularly preferably sodium methanolate, to form the triazole L-4, wherein X═N, by methods with which persons skilled in the art is familiar.

In step l04 the compound L-4, wherein X═N, can be substituted in the N position by methods known to persons skilled in the art, in a manner similar to the step j05 according to general reaction scheme 1a by the methods described hereinbefore, and compound L-5, wherein X═N, can in this way be obtained.

In step l05 the ester group in L-4 can be eliminated in the presence of an acid, preferably trifluoroacetic acid or hydrochloric acid, by methods known to persons skilled in the art, and the amine (II) can in this way be obtained.

The compounds according to general formula (I), wherein A=N, may be further prepared by a reaction sequence according to general reaction scheme 1c.

General reaction scheme (scheme 1c)

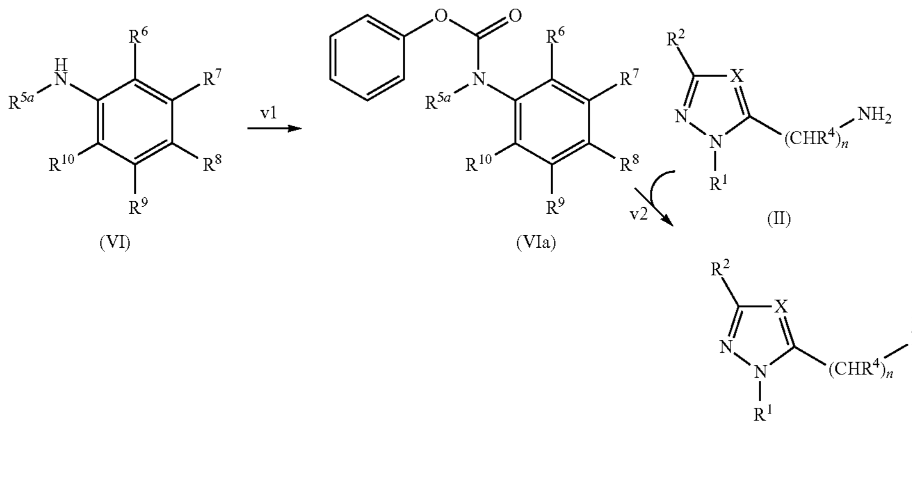

(VI) (VIa) (II) (I)

In step v1 the compound (VI) can be converted into the compound (VIa) by methods known to persons skilled in the art, such as for example using phenyl chloroformate, optionally in the presence of a coupling reagent and/or a base. In addition to the methods disclosed in the present document for preparing unsymmetrical ureas using phenyl chloroformate, there are further processes with which persons skilled in the art is familiar, based on the use of activated carbonic acid derivatives or isocyanates, if appropriate.

In step v2 the amine (II) can be converted into the urea compound (I) (wherein A=N).

This can be achieved by reaction with (VIa) by methods with which persons skilled in the art is familiar, optionally in the presence of a base.

The methods with which persons skilled in the art is familiar for carrying out the reaction steps j01 to j09 and also k01 to k05 and l01 to l05 as well as v1 and v2 may be inferred from the standard works on organic chemistry such as, for example, J. March, Advanced Organic Chemistry, Wiley & Sons, 6th edition, 2007; F. A. Carey, R. J. Sundberg, Advanced Organic Chemistry, Parts A and B, Springer, 5th edition, 2007; team of authors, Compendium of Organic Synthetic Methods, Wiley & Sons. In addition, further methods and also literature references can be issued by the common databases such as, for example, the Reaxys® database of Elsevier, Amsterdam, NL or the SciFinder® database of the American Chemical Society, Washington, US.

In particular, the compounds of formula (Q) can be prepared by a process according to which at least one compound of formula (Q-II), (Q-II)

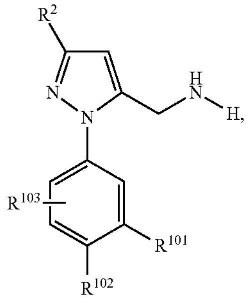

in which $R^{101}$, $R^{102}$, $R^{103}$ and $R^2$ have one of the foregoing meanings, is reacted in a reaction medium, optionally in the presence of at least one suitable coupling reagent, and optionally in the presence of at least one base, with a compound of general formula (Q-III) with D=OH or Hal, (Q-III)

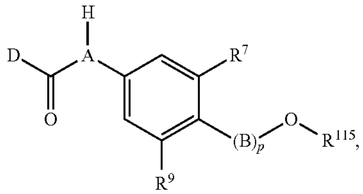

in which Hal represents a halogen, preferably Br or Cl, and $R^7$, $R^9$, B, $R^{115}$ and p each have one of the foregoing meanings and A denotes CH or $C(CH_3)$, in a reaction medium, optionally in the presence of at least one suitable coupling reagent, and optionally in the presence of at least one base, to form a compound of formula (Q), (Q)

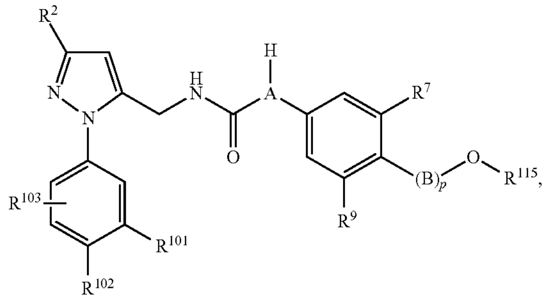

in which A represents CH or $C(CH_3)$ and $R^{101}$, $R^{102}$, $R^{103}$ and $R^2$ as well as $R^7$, $R^9$, B, $R^{115}$ and p have one of the foregoing meanings;

or in that at least one compound of formula (Q-II), (Q-II)

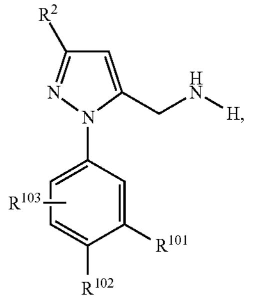

in which $R^{101}$, $R^{102}$, $R^{103}$ and $R^2$ have one of the foregoing meanings, is reacted to form a compound of formula (Q-IV), (Q-IV)

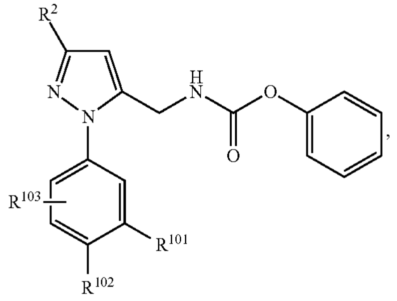

in which $R^{101}$, $R^{102}$, $R^{103}$ and $R^2$ have one of the foregoing meanings, in a reaction medium, in the presence of phenyl chloroformate, optionally in the presence of at least one base and/or at least one coupling reagent, and said compound is optionally purified and/or isolated, and a compound of formula (Q-IV) is reacted with a compound of formula (Q-V), (Q-V)

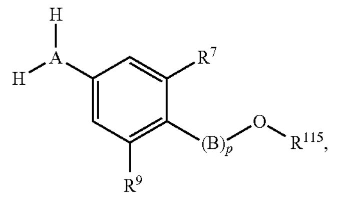

in which $R^7$, $R^9$, B, $R^{115}$ and p have one of the foregoing meanings, and A denotes N, in a reaction medium, optionally in the presence of at least one suitable coupling reagent, optionally in the presence of at least one base, to form a compound of general formula (Q), (Q)

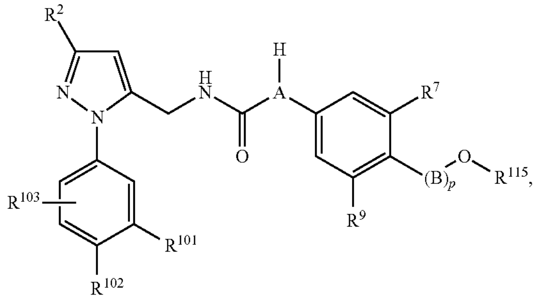

in which A represents N and $R^{101}$, $R^{102}$, $R^{103}$ and $R^2$ as well as $R^7$, $R^9$, B, $R^{115}$ and p have one of the foregoing meanings.

The reaction of compounds of the foregoing formula (Q-II) with carboxylic acids of the foregoing formula (Q-III), particularly with D=OH, to form compounds of the foregoing formula (Q) is preferably carried out in a reaction medium selected from the group consisting of diethyl ether, tetrahydrofuran, acetonitrile, methanol, ethanol, (1,2)-dichloroethane, dimethylformamide, dichloromethane and corresponding mixtures, optionally in the presence of at least one coupling reagent, preferably selected from the group consisting of 1-benzotriazolyloxy-tris-(dimethylamino)-phosphonium hexafluorophosphate (BOP), dicyclohexylcarbodiimide (DCC), N'-(3-dimethylaminopropyl)-N-ethylcarbodiimide (EDCl), diisopropylcarbodiimide, 1,1'-carbonyldiimidazole (CDI), N-[(dimethylamino)-1H-1,2,3-triazolo[4,5-b]pyridino-1-yl-methylene]-N-methylmethanaminium hexafluorophosphate N-oxide (HATU), O-(benzotriazol-1-yl)-N,N,N',N'-tetramethyluronium hexafluorophosphate (HBTU), O-(benzotriazol-1-yl)-N,N,N',N'-tetramethyluronium tetrafluoroborate (TBTU), N-hydroxybenzotriazole (HOBt) and 1-hydroxy-7-azabenzotriazole (HOAt), optionally in the presence of at least one organic base, preferably selected from the group consisting of triethylamine, pyridine, dimethylaminopyridine, N-methylmorpholine and diisopropylethylamine, preferably at temperatures of from −70° C. to 100° C.

Alternatively, the reaction of compounds of the above-indicated general formulae (Q-II) with carboxylic acid halides of the above-indicated general formula (Q-III) with D=Hal, in which Hal represents a halogen as the leaving group, preferably a chlorine or bromine atom, to form compounds of the above-indicated general formula (Q) is carried out in a reaction medium preferably selected from the group consisting of diethyl ether, tetrahydrofuran, acetonitrile, methanol, ethanol, dimethylformamide, dichloromethane and corresponding mixtures, optionally in the presence of an organic or inorganic base, preferably selected from the group consisting of triethylamine, dimethylaminopyridine, pyridine and diisopropylamine, at temperatures of from −70° C. to 100° C.

The compounds of the foregoing formulas (Q-II), (Q-III), (Q-IV), and (Q-V) are each commercially available and/or can be prepared using conventional processes known to the person skilled in the art. In particular, processes to prepare these compounds are e.g. disclosed in WO 2010/127855-A2, and WO 2010/127856-A2, the entire disclosures of each of which are incorporated herein by reference.

All reactions which can be utilized for synthesizing the compounds according to the present invention can each be carried out under the conventional conditions with which the person skilled in the art is familiar, for example with regard to pressure or the order in which the components are added. If appropriate, the person skilled in the art can determine the optimum procedure under the respective conditions by carrying out simple preliminary tests.

The intermediate and end products obtained using the reactions described hereinbefore can each be purified and/or isolated, if desired and/or required, using conventional methods known to the person skilled in the art. Suitable purifying processes are for example extraction processes and chromatographic processes such as column chromatography or preparative chromatography. All of the process steps of the reaction sequences which can be applied for synthesizing the compounds according to the present invention as well as the respective purification and/or isolation of intermediate or end products, can be carried out partly or completely under an inert gas atmosphere, preferably under a nitrogen atmosphere.

The substituted compounds according to the invention can be isolated both in the form of their free bases, and also in the form of corresponding salts, in particular physiologically acceptable salts, and further in the form of a solvate such as hydrate.

The free bases of the respective substituted compounds according to the invention can be converted into the corresponding salts, preferably physiologically acceptable salts, for example by reaction with an inorganic or organic acid, preferably with hydrochloric acid, hydrobromic acid, sulfuric acid, methanesulfonic acid, p-toluenesulfonic acid, carbonic acid, formic acid, acetic acid, oxalic acid, succinic acid, tartaric acid, mandelic acid, fumaric acid, maleic acid, lactic acid, citric acid, glutamic acid, saccharic acid, monomethylsebacic acid, 5-oxoproline, hexane-1-sulfonic acid, nicotinic acid, 2, 3 or 4-aminobenzoic acid, 2,4,6-trimethylbenzoic acid, α-lipoic acid, acetyl glycine, hippuric acid, phosphoric acid and/or aspartic acid. The free bases of the respective inventive substituted compounds and of corresponding stereoisomers can likewise be converted into the corresponding physiologically acceptable salts using the free acid or a salt of a sugar additive, such as for example saccharin, cyclamate or acesulfame.

Accordingly, the substituted compounds according to the invention such as the free acids of the substituted compounds according to the invention can be converted into the corresponding physiologically acceptable salts by reaction with a suitable base. Examples include the alkali metal salts, alkaline earth metals salts or ammonium salts $[NH_xR_{4-x}]^+$, in which x=0, 1, 2, 3 or 4 and R represents a branched or unbranched $C_{1-4}$ alkyl residue.

The substituted compounds according to the invention and of corresponding stereoisomers can if appropriate, like the corresponding acids, the corresponding bases or salts of these compounds, also be obtained in the form of their solvates, preferably in the form of their hydrates, using conventional methods known to the person skilled in the art.

If the substituted compounds according to the invention are obtained, after preparation thereof, in the form of a mixture of their stereoisomers, preferably in the form of their racemates or other mixtures of their various enantiomers and/or diastereomers, they can be separated and if appropriate isolated using conventional processes known to the person skilled in the art. Examples include chromatographic separating processes, in particular liquid chromatography processes under normal pressure or under elevated pressure, preferably MPLC and HPLC processes, and also fractional crystallization processes. These processes allow individual enantiomers, for example diastereomeric salts formed by chiral stationary phase HPLC or by crystallization with chiral acids, for example (+)-tartaric acid, (−)-tartaric acid or (+)-10-camphorsulfonic acid, to be separated from one another.

The chemicals and reaction components used in the reactions and schemes described below are available commercially or in each case can be prepared by conventional methods known to the person skilled in the art.

General reaction scheme 1Q (Scheme 1Q):

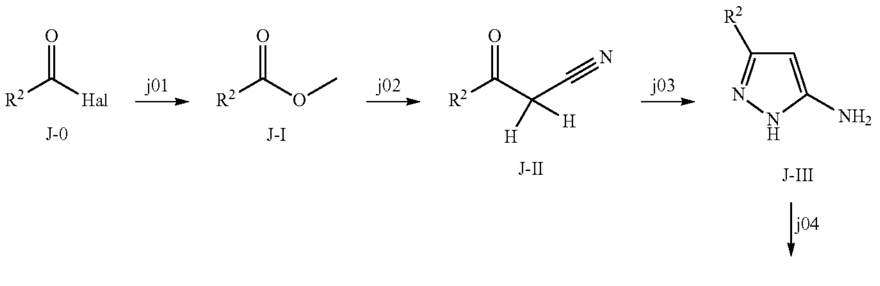

-continued
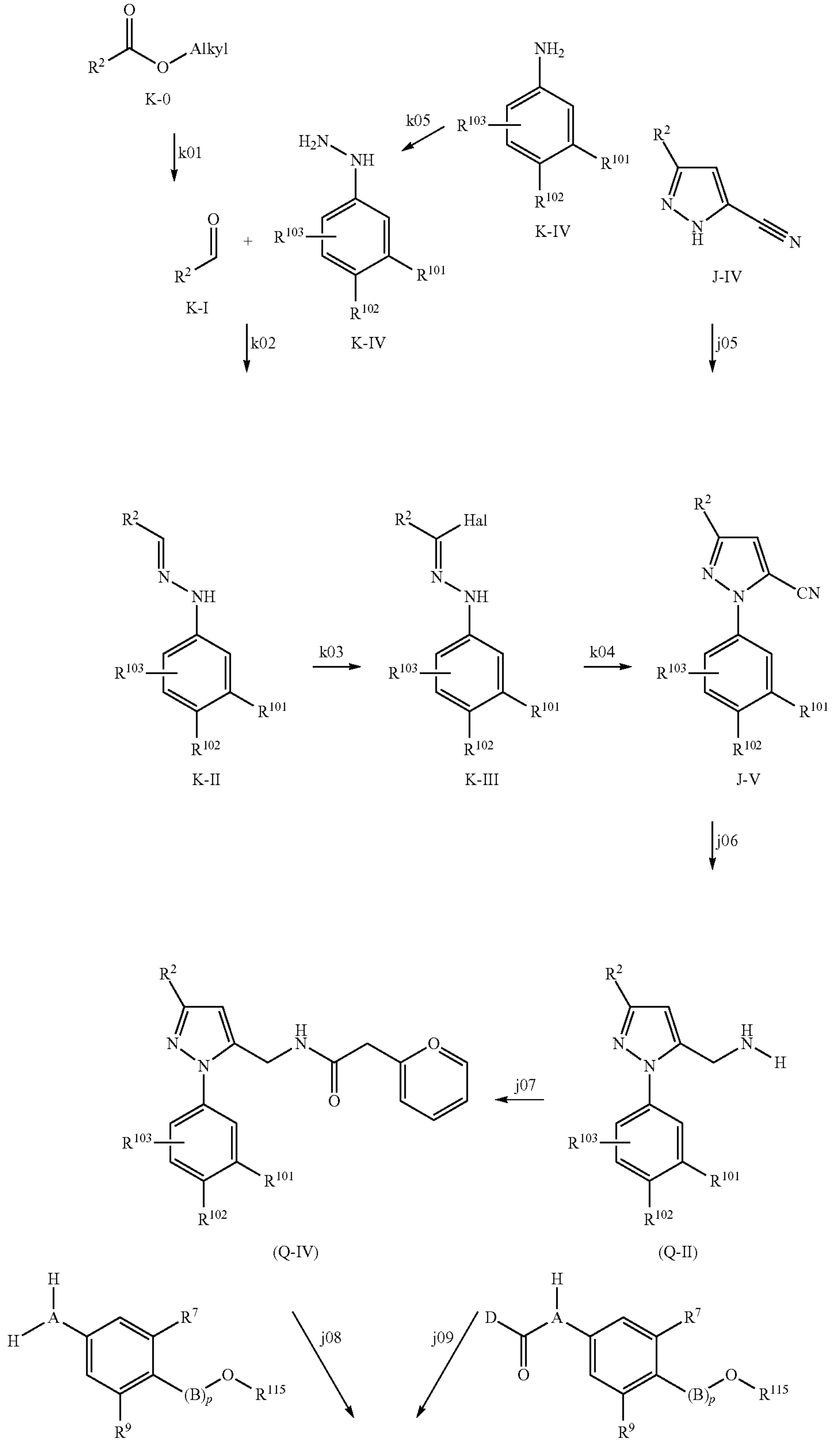
K-0
K-I
K-IV
K-IV
J-IV
K-II
K-III
J-V
(Q-IV)
(Q-II)
(Q-V)
wherein A = N
D = OH, Hal (Q-III)
or D = O—Ph (Q-IIIa)
wherein A = CH or
$C(CH_3)$ -continued

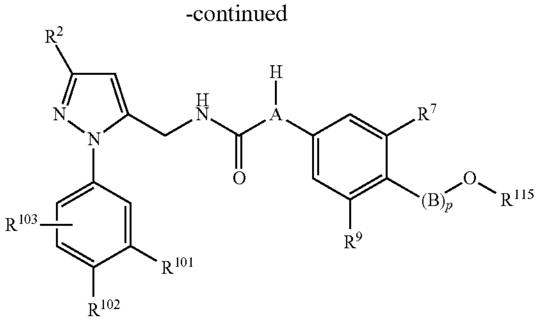

(Q)

In step j01 an acid halide j-0, in which Hal preferably represents Cl or Br, can be esterified using methanol to form the compound J-I by methods with which the person skilled in the art is familiar.

In step j02 the methyl pivalate J-I can be converted into an oxoalkylnitrile J-II by methods known to the person skilled in the art, such as for example using acetonitrile $CH_3$—CN, optionally in the presence of a base.

In step j03 the compound J-II can be converted into an amino-substituted pyrazolyl derivative J-III by methods known to the person skilled in the art, such as for example using hydrazine hydrate, with cyclization.

In step j04 the amino compound J-III can first be converted into a diazonium salt by methods known to the person skilled in the art, such as for example using nitrite, and the diazonium salt can be converted into a cyano-substituted pyrazolyl derivative J-IV with elimination of nitrogen using a cyanide, optionally in the presence of a coupling reagent.

In step j05 the compound J-IV can be substituted in the N position by methods known to the person skilled in the art, for example using a halide of partial structure (QS2), i.e. Hal-(QS2), optionally in the presence of a base and/or a coupling reagent, wherein Hal is preferably Cl, Br or I, or using a boronic acid $B(OH)_2$(QS2) or a corresponding boronic acid ester, optionally in the presence of a coupling reagent and/or a base and the compound J-V can in this way be obtained.

Alternatively, a second synthesis pathway, in which in step k01 an ester K-0 is first reduced to form the aldehyde K-I by methods known to the person skilled in the art, for example using suitable hydrogenation reagents such as metal hydrides, is suitable for preparing the compound J-V.

In step k02 the aldehyde K-I can then be reacted with a hydrazine K-V, which can be obtained in step k05, starting from the primary amine K-IV, by methods known to the person skilled in the art, to form the hydrazine K-II by methods known to the person skilled in the art with elimination of water.

In step k03 the hydrazine K-II can be halogenated, preferably chlorinated, by methods known to the person skilled in the art with the double bond intact, such as for example using a chlorination reagent such as NCS, and the compound K-III can in this way be obtained.

In step k04 the hydrazonoyl halide K-III can be converted into a cyano-substituted compound J-V by methods known to the person skilled in the art, such as for example using a halogen-substituted nitrile, with cyclization.

In step j06 the compound J-V can be hydrogenated by methods known to the person skilled in the art, for example using a suitable catalyst such as palladium/activated carbon or using suitable hydrogenation reagents, and the compound (Q-III) can in this way be obtained.

In step j07 the compound (Q-II) can be converted into the compound (Q-IV) by methods known to the person skilled in the art, such as for example using phenyl chloroformate, optionally in the presence of a coupling reagent and/or a base. In addition to the methods disclosed in the present document for preparing unsymmetrical ureas using phenyl chloroformate, there are further processes with which the person skilled in the art is familiar, based on the use of activated carbonic acid derivatives or isocyanates.

In step j08 the amine (Q-V) can be converted into the urea compound (Q) (wherein A=N). This can be achieved by reaction with (Q-IV) by methods with which the person skilled in the art is familiar, optionally in the presence of a base.

In step j09 the amine (Q-II) can be converted into the amide (Q) (wherein A=CH or $C(CH_3)$). This can for example be achieved by reaction with an acid halide, preferably a chloride of formula (Q-III) with D=Hal by methods with which the person skilled in the art is familiar, optionally in the presence of a base or by reaction with an acid of formula (Q-III) with D=OH, optionally in the presence of a suitable coupling reagent, for example HATU or CDI, if appropriate with the addition of a base. Further, the amine (Q-II) may be converted into the amide (Q) (wherein A is CH or $C(CH_3)$) by reaction of a compound (Q-IIIa) by methods with which the person skilled in the art is familiar, optionally in the presence of a base.

The compounds of formula (Q), wherein A is N, may be further prepared by a reaction sequence according to general reaction scheme 2.

General reaction scheme 2Q (scheme 2Q)

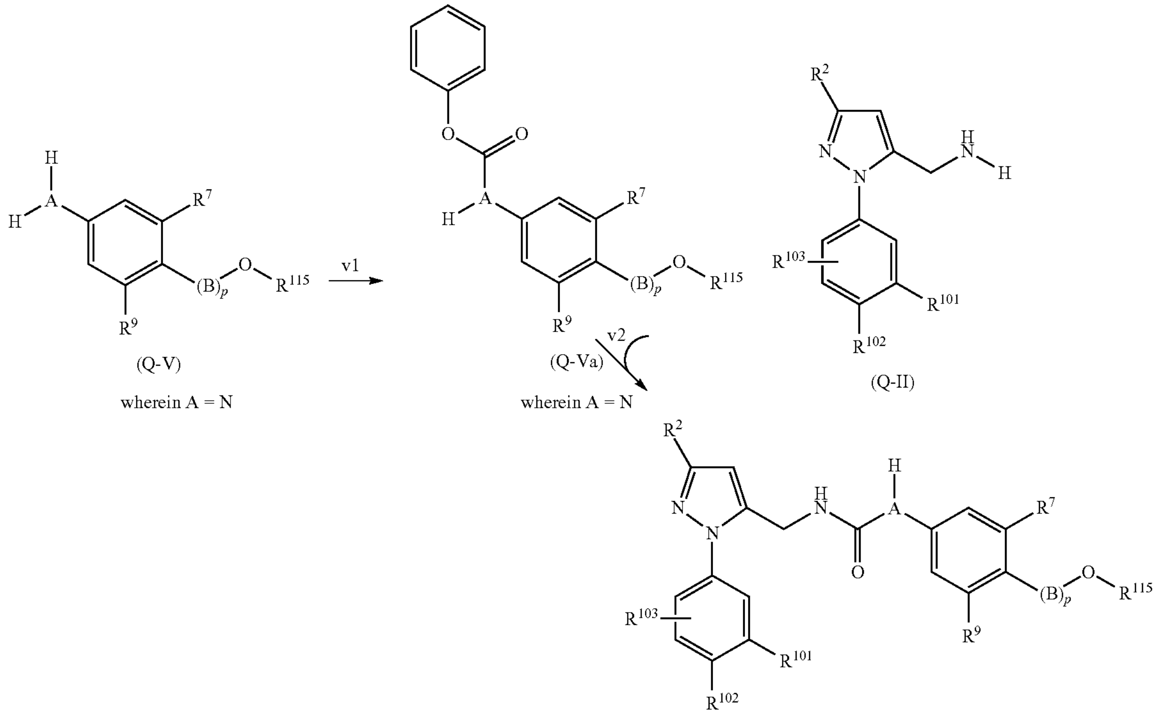

(Q-V) wherein A = N (Q-Va) wherein A = N (Q-II)

(Q) wherein A = N

In step v1 the compound (Q-V) can be converted into the compound (Q-Va) by methods known to the person skilled in the art, such as for example using phenyl chloroformate, optionally in the presence of a coupling reagent and/or a base. In addition to the methods disclosed in the present document for preparing unsymmetrical ureas using phenyl chloroformate, there are further processes with which the person skilled in the art is familiar, based on the use of activated carbonic acid derivatives or isocyanates, if appropriate.

In step v2 the amine (Q-II) can be converted into the urea compound (Q) (wherein A=N). This can be achieved by reaction with (Q-Va) by methods with which the person skilled in the art is familiar, optionally in the presence of a base.

The methods with which the person skilled in the art is familiar for carrying out the reaction steps j01 to j09 and also k01 to k05 as well as v1 and v2 may be inferred from the standard works on organic chemistry such as, for example, J. March, Advanced Organic Chemistry, Wiley & Sons, 6th edition, 2007; F. A. Carey, R. J. Sundberg, Advanced Organic Chemistry, Parts A and B, Springer, 5th edition, 2007; team of authors, Compendium of Organic Synthetic Methods, Wiley & Sons. In addition, further methods and also literature references can be issued by the common databases such as, for example, the Reaxys® database of Elsevier, Amsterdam, NL or the SciFinder® database of the American Chemical Society, Washington, US.

The compounds of formula (R) can, in particular, be prepared by a process according to which at least one compound of general formula (R-II), (R-II)

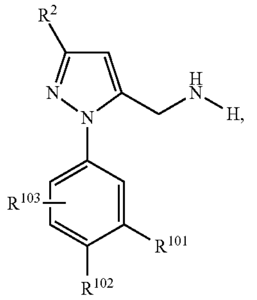

in which $R^{101}$, $R^{102}$, $R^{103}$ and $R^2$ have one of the foregoing meanings, is reacted in a reaction medium, optionally in the presence of at least one suitable coupling reagent, optionally in the presence of at least one base, with a compound of general formula (R-III) with D=OH or Hal, (R-III)

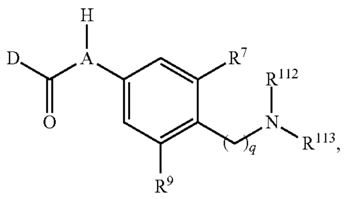

in which Hal represents a halogen, preferably Br or Cl, and $R^7$, $R^9$, $R^{112}$, $R^{113}$ and q each have one of the foregoing meanings and A denotes CH or $C(CH_3)$, in a reaction medium, optionally in the presence of at least one suitable coupling reagent, optionally in the presence of at least one base, to form a compound of general formula (R), (R)

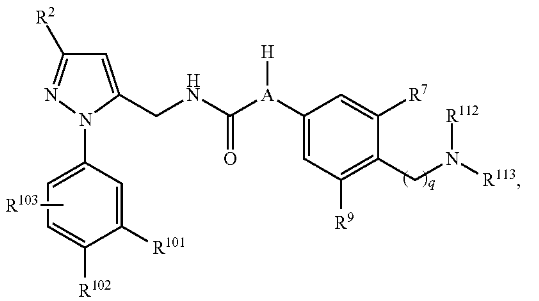

in which A represents CH or $C(CH_3)$ and $R^{101}$, $R^{102}$, $R^{103}$ and $R^2$ as well as $R^7$, $R^9$, $R^{112}$, $R^{113}$ and q have one of the foregoing meanings;

or in that at least one compound of general formula (R-II), (R-II)

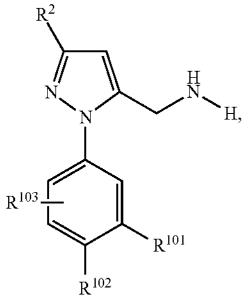

in which $R^{101}$, $R^{102}$, $R^{103}$ and $R^2$ have one of the foregoing meanings, is reacted to form a compound of general formula (R-IV), (R-IV)

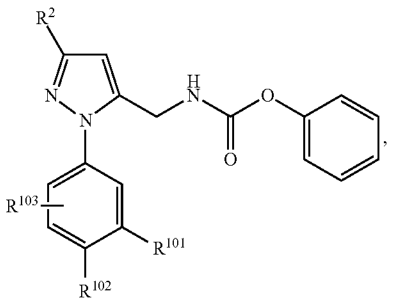

in which $R^{101}$, $R^{102}$, $R^{103}$ and $R^2$ have one of the foregoing meanings, in a reaction medium, in the presence of phenyl chloroformate, optionally in the presence of at least one base and/or at least one coupling reagent, and said compound is if appropriate purified and/or isolated, and a compound of general formula (R-IV) is reacted with a compound of general formula (R-V), (R-V)

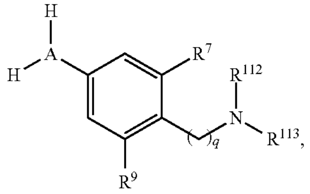

in which $R^7$, $R^9$, $R^{112}$, $R^{113}$ and q have one of the foregoing meanings, and A denotes N, in a reaction medium, optionally in the presence of at least one suitable coupling reagent, optionally in the presence of at least one base, to form a compound of general formula (R), (R)

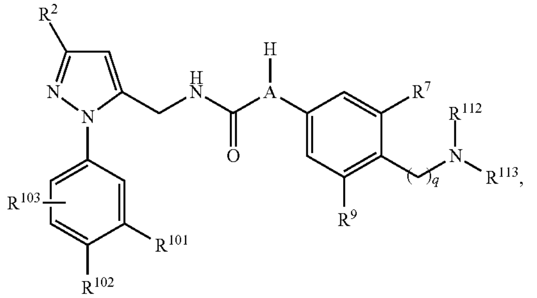

in which A represents N and $R^{101}$, $R^{102}$, $R^{103}$ and $R^2$ as well as $R^7$, $R^9$, $R^{112}$, $R^{113}$ and q have one of the foregoing meanings.

The reaction of compounds of the foregoing formula (R-II) with carboxylic acids of the foregoing formula (R-III), particularly with D=OH, to form compounds of the foregoing formula (R) is carried out preferably in a reaction medium selected from the group consisting of diethyl ether, tetrahydrofuran, acetonitrile, methanol, ethanol, (1,2)-dichloroethane, dimethylformamide, dichloromethane and corresponding mixtures, optionally in the presence of at least one coupling reagent, preferably selected from the group consisting of 1-benzotriazolyloxy-tris-(dimethylamino)-phosphonium hexafluorophosphate (BOP), dicyclohexylcarbodiimide (DCC), N'-(3-dimethylaminopropyl)-N-ethylcarbodiimide (EDCl), diisopropylcarbodiimide, 1,1'-carbonyldiimidazole (CDI), N-[(dimethylamino)-1H-1,2,3-triazolo[4,5-b]pyridino-1-yl-methylene]-N-methylmethanaminium hexafluorophosphate N-oxide (HATU), O-(benzotriazol-1-yl)-N,N,N',N'-tetramethyluronium hexafluorophosphate (HBTU), O-(benzotriazol-1-yl)-N,N,N',N'-tetramethyluronium tetrafluoroborate (TBTU), N-hydroxybenzotriazole (HOBt) and 1-hydroxy-7-azabenzotriazole (HOAt), optionally in the presence of at least one organic base, preferably selected from the group consisting of triethylamine, pyridine, dimethylaminopyridine, N-methylmorpholine and diisopropylethylamine, preferably at temperatures of from −70° C. to 100° C.

Alternatively, the reaction of compounds of the foregoing formula (R-II) with carboxylic acid halides of the foregoing formula (R-III) with D=Hal, in which Hal represents a halogen as the leaving group, preferably a chlorine or bromine atom, to form compounds of the foregoing formula (R) is carried out in a reaction medium preferably selected from the group consisting of diethyl ether, tetrahydrofuran, acetonitrile, methanol, ethanol, dimethylformamide, dichloromethane and corresponding mixtures, optionally in the presence of an organic or inorganic base, preferably selected from the group consisting of triethylamine, dimethylaminopyridine, pyridine and diisopropylamine, at temperatures of from −70° C. to 100° C.

The compounds of the foregoing formulas (R-II), (R-III), (R-IV), and (R-V) are each commercially available and/or can be prepared using conventional processes known to the person skilled in the art. In particular, processes to prepare these compounds are e.g. disclosed in WO 2010/127855-A2, and WO 2010/127856-A2, the entire disclosures of which are incorporated herein by reference.

All reactions which can be utilized for synthesizing the compounds of formula (R) can each be carried out under the conventional conditions with which the person skilled in the art is familiar, for example with regard to pressure or the order in which the components are added. If desired, a person skilled in the art can determine the optimum procedure under the respective conditions by carrying out simple preliminary tests. The intermediate and end products obtained using the reactions described above can each be purified and/or isolated, if desired and/or required, using conventional methods known to the person skilled in the art. Suitable purifying processes are for example extraction processes and chromatographic processes such as column chromatography or preparative chromatography. All of the process steps of the reaction sequences which can be applied for synthesizing the compounds according to the present invention as well as the respective purification and/or isolation of intermediate or end products, can be carried out partly or completely under an inert gas atmosphere, preferably under a nitrogen atmosphere.

The substituted compounds of formula (R) can be isolated both in the form of their free bases, and also in the form of corresponding salts, in particular physiologically acceptable salts, and further in the form of a solvate such as hydrate.

The free bases of the respective substituted compounds of formula (R) can be converted into the corresponding salts, preferably physiologically acceptable salts, for example by reaction with an inorganic or organic acid, preferably with hydrochloric acid, hydrobromic acid, sulfuric acid, methanesulfonic acid, p-toluenesulfonic acid, carbonic acid, formic acid, acetic acid, oxalic acid, succinic acid, tartaric acid, mandelic acid, fumaric acid, maleic acid, lactic acid, citric acid, glutamic acid, saccharic acid, monomethylsebacic acid, 5-oxoproline, hexane-1-sulfonic acid, nicotinic acid, 2, 3 or 4-aminobenzoic acid, 2,4,6-trimethylbenzoic acid, α-lipoic acid, acetyl glycine, hippuric acid, phosphoric acid and/or aspartic acid. The free bases of the respective inventive substituted compounds and of corresponding stereoisomers can likewise be converted into the corresponding physiologically acceptable salts using the free acid or a salt of a sugar additive, such as for example saccharin, cyclamate or acesulfame.

Accordingly, the substituted compounds of formula (R) such as the free acids of the substituted compounds of formula (R) can be converted into the corresponding physiologically acceptable salts by reaction with a suitable base. Examples include the alkali metal salts, alkaline earth metals salts or ammonium salts $[NH_xR_{4-x}]^+$, in which x=0, 1, 2, 3 or 4 and R represents a branched or unbranched $C_{1-4}$ alkyl residue.

The substituted compounds of formula (R) and of corresponding stereoisomers can if appropriate, like the corresponding acids, the corresponding bases or salts of these compounds, also be obtained in the form of their solvates, preferably in the form of their hydrates, using conventional methods known to the person skilled in the art.

If the substituted compounds of formula (R) are obtained, after preparation thereof, in the form of a mixture of their stereoisomers, preferably in the form of their racemates or other mixtures of their various enantiomers and/or diastereomers, they can be separated and if appropriate isolated using conventional processes known to the person skilled in the art. Examples include chromatographic separating processes, in particular liquid chromatography processes under normal pressure or under elevated pressure, preferably MPLC and HPLC processes, and also fractional crystallization processes. These processes allow individual enantiomers, for example diastereomeric salts formed by chiral stationary phase HPLC or by crystallization with chiral acids, for example (+)-tartaric acid, (−)-tartaric acid or (+)-10-camphorsulfonic acid, to be separated from one another.

The chemicals and reaction components used in the reactions and schemes described below are available commercially or in each case can be prepared by conventional methods known to persons skilled in the art.

General reaction scheme 1R (Scheme 1R):

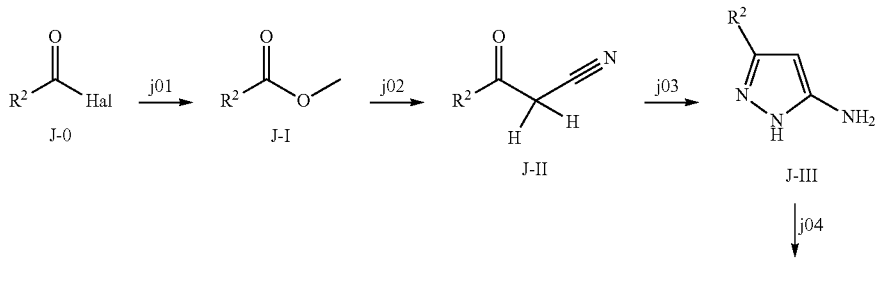

J-0 J-I J-II J-III

-continued
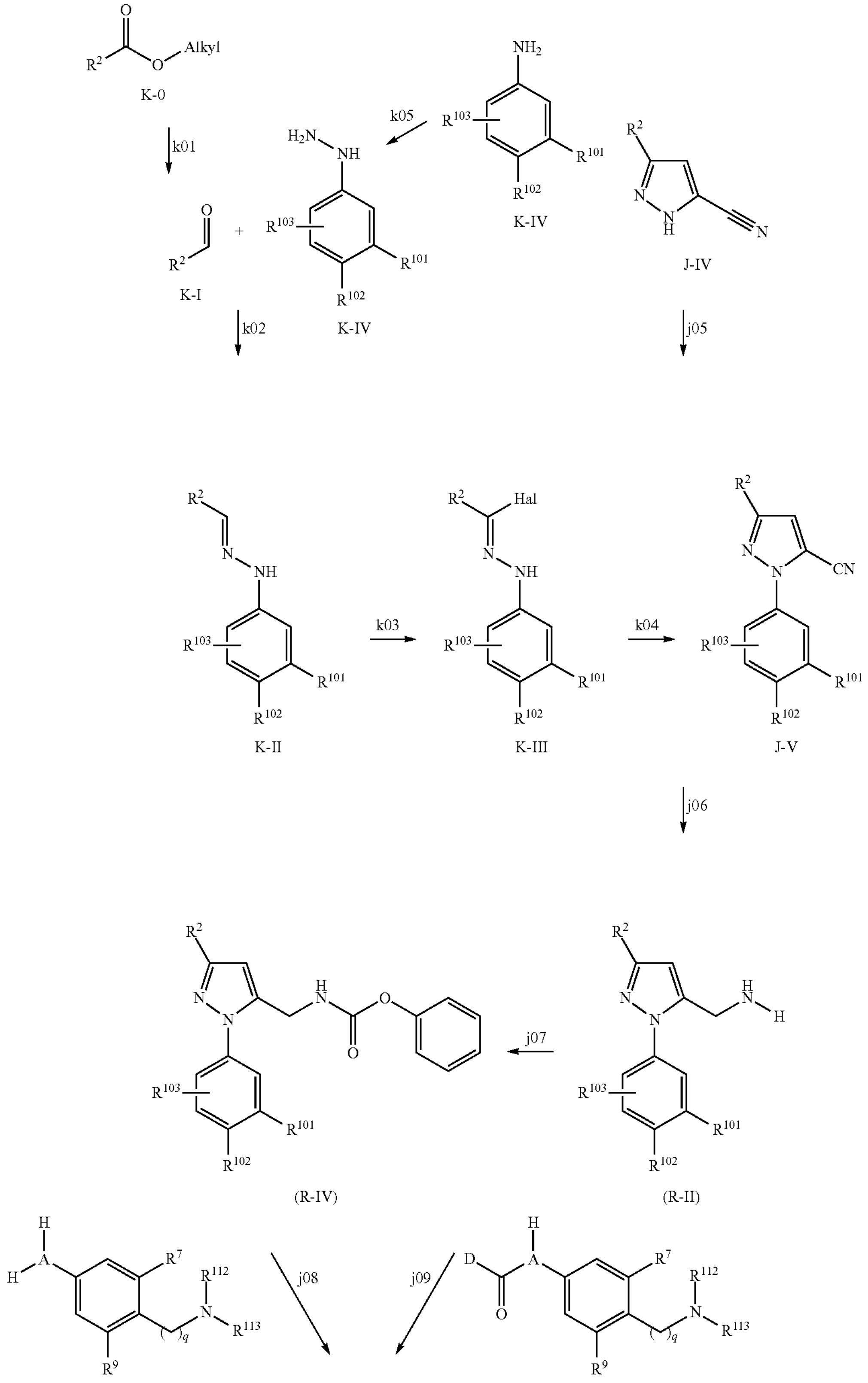
K-0, K-I, K-IV, J-IV, K-II, K-III, J-V, (R-IV), (R-II)
(R-V)
wherein A = N
D = OH, Hal (R-III)
or D = O—Ph (R-IIIa)
wherein A = CH or
$C(CH_3)$ -continued

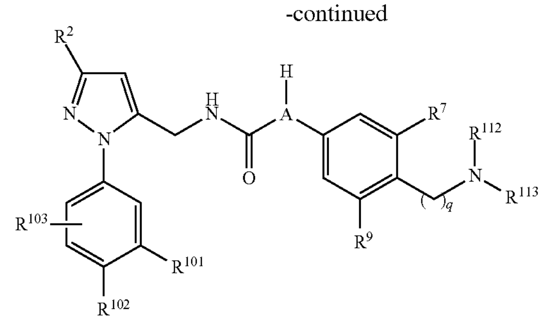

(R)

In step j01 an acid halide J-0, in which Hal preferably represents CI or Br, can be esterified using methanol to form the compound J-I by methods with which the person skilled in the art is familiar.

In step j02 the methyl pivalate J-I can be converted into an oxoalkylnitrile J-II by methods known to the person skilled in the art, such as for example using acetonitrile $CH_3$—CN, optionally in the presence of a base.

In step j03 the compound J-II can be converted into an amino-substituted pyrazolyl derivative J-III by methods known to the person skilled in the art, such as for example using hydrazine hydrate, with cyclization.

In step j04 the amino compound J-III can first be converted into a diazonium salt by methods known to the person skilled in the art, such as for example using nitrite, and the diazonium salt can be converted into a cyano-substituted pyrazolyl derivative J-IV with elimination of nitrogen using a cyanide, optionally in the presence of a coupling reagent.

In step j05 the compound J-IV can be substituted in the N position by methods known to the person skilled in the art, for example using a halide of partial structure (RS2), i.e. Hal-(RS2), optionally in the presence of a base and/or a coupling reagent, wherein Hal is preferably Cl, Br or I, or using a boronic acid $B(OH)_2$(RS2) or a corresponding boronic acid ester, optionally in the presence of a coupling reagent and/or a base and the compound J-V can be obtained in this way.

Alternatively, a second synthesis pathway, in which in step k01 an ester K-0 is first reduced to form the aldehyde K-I by methods known to the person skilled in the art, for example using suitable hydrogenation reagents such as metal hydrides, is suitable for preparing the compound J-V.

In step k02 the aldehyde K-I can then be reacted with a hydrazine K-V, which can be obtained in step k05, starting from the primary amine K-IV, by methods known to the person skilled in the art, to form the hydrazine K-II by methods known to the person skilled in the art with elimination of water.

In step k03 the hydrazine K-II can be halogenated, preferably chlorinated, by methods known to the person skilled in the art with the double bond intact, such as for example using a chlorination reagent such as NCS, and the compound K-III can be obtained in this way.

In step k04 the hydrazonoyl halide K-III can be converted into a cyano-substituted compound J-V by methods known to the person skilled in the art, such as for example using a halogen-substituted nitrile, with cyclization.

In step j06 the compound J-V can be hydrogenated by methods known to the person skilled in the art, for example using a suitable catalyst such as palladium/activated carbon or using suitable hydrogenation reagents, and the compound (R-II) can be obtained in this way.

In step j07 the compound (R-II) can be converted into the compound (R-IV) by methods known to the person skilled in the art, such as for example using phenyl chloroformate, optionally in the presence of a coupling reagent and/or a base. In addition to the methods disclosed in the present document for preparing unsymmetrical ureas using phenyl chloroformate, there are further processes with which the person skilled in the art is familiar, based on the use of activated carbonic acid derivatives or isocyanates, if appropriate.

In step j08 the amine (R-V) can be converted into the urea compound (R) (wherein A=N). This can be achieved by reaction with (R-IV) by methods with which the person skilled in the art is familiar, optionally in the presence of a base.

In step j09 the amine (R-II) can be converted into the amide (R) (wherein A=CH or $C(CH_3)$). This can for example be achieved by reaction with an acid halide, preferably a chloride of formula (R-III) with D=Hal by methods with which the person skilled in the art is familiar, optionally in the presence of a base or by reaction with an acid of formula (R-III) with D=OH, optionally in the presence of a suitable coupling reagent, for example HATU or CDI, if appropriate with the addition of a base. Further, the amine (R-II) may be converted into the amide (R) (wherein A=CH or $C(CH_3)$) by reaction of a compound (R-IIIa) by methods with which the person skilled in the art is familiar, optionally in the presence of a base.

The compounds of formula (R), in which A is N, may be further prepared by a reaction sequence according to general reaction scheme 2R.

General reaction scheme 2R (scheme 2R)

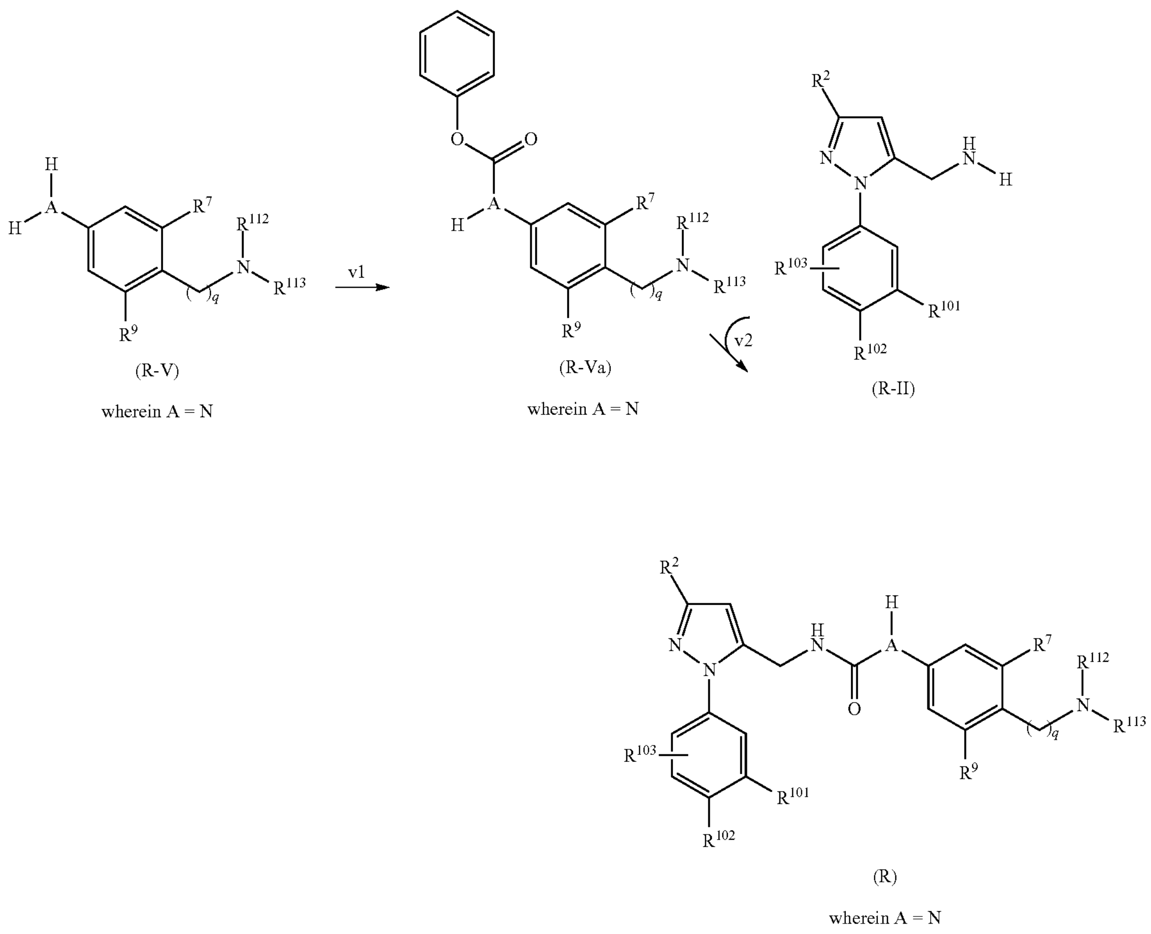

In step v1 the compound (R-V) can be converted into the compound (R-Va) by methods known to the person skilled in the art, such as for example using phenyl chloroformate, optionally in the presence of a coupling reagent and/or a base. In addition to the methods disclosed in the present document for preparing unsymmetrical ureas using phenyl chloroformate, there are further processes with which the person skilled in the art is familiar, based on the use of activated carbonic acid derivatives or isocyanates, if appropriate.

In step v2 the amine (R-II) can be converted into the urea compound (R) (wherein A=N). This can be achieved by reaction with (R-Va) by methods with which the person skilled in the art is familiar, optionally in the presence of a base.

The methods with which the person skilled in the art is familiar for carrying out the reaction steps j01 to j09 and also k01 to k05 as well as v1 and v2 may be inferred from the standard works on organic chemistry such as, for example, J. March, Advanced Organic Chemistry, Wiley & Sons, 6th edition, 2007; F. A. Carey, R. J. Sundberg, Advanced Organic Chemistry, Parts A and B, Springer, 5th edition, 2007; team of authors, Compendium of Organic Synthetic Methods, Wiley & Sons. In addition, further methods and also literature references can be issued by the common databases such as, for example, the Reaxys® database of Elsevier, Amsterdam, NL or the SciFinder® database of the American Chemical Society, Washington, US.

The compounds of formula (S) can, in particular, be prepared by a process according to which a compound of formula (S-II)

(S-II)

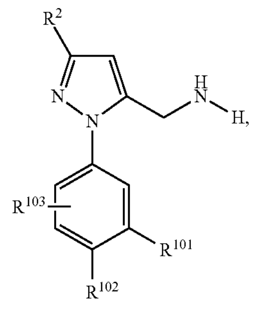

in which $R^{101}$, $R^{102}$, $R^{103}$ and $R^2$ have one of the foregoing meanings, is reacted in a reaction medium, optionally in the presence of at least one suitable coupling reagent, optionally in the presence of at least one base, with a compound of formula (S-III) in which D denotes OH or Hal,

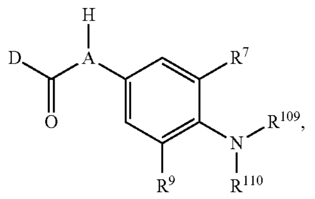

(S-III)

in which Hal represents a halogen, preferably Br or Cl, and $R^7$, $R^9$, $R^{109}$ and $R^{110}$ each have one of the foregoing meanings and A denotes CH or $C(CH_3)$, in a reaction medium, optionally in the presence of at least one suitable coupling reagent, optionally in the presence of at least one base, to form a compound of formula (S),

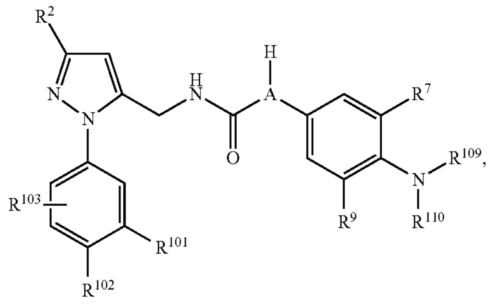

(S)

in which A represents CH or $C(CH_3)$, and $R^{101}$, $R^{102}$, $R^{103}$ and $R^2$ as well as $R^7$, $R^9$, $R^{109}$ and $R^{110}$ have one of the foregoing meanings;

or in which a compound of formula (S-II)

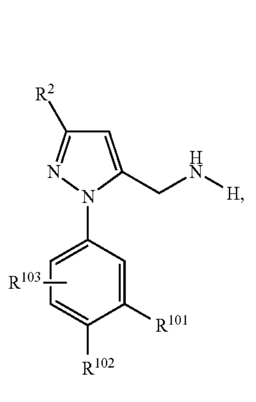

(S-II)

in which $R^{101}$, $R^{102}$, $R^{103}$ and $R^2$ have the respective foregoing meanings, is reacted to form a compound of formula (S-IV)

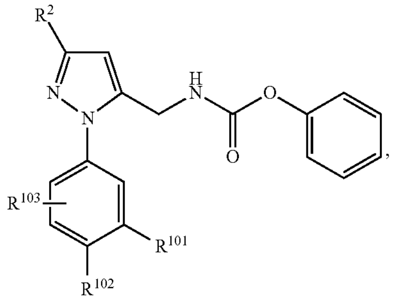

(S-IV)

in which $R^{101}$, $R^{102}$, $R^{103}$ and $R^2$ have the respective foregoing meanings, in a reaction medium, in the presence of phenyl chloroformate, optionally in the presence of at least one base and/or at least one coupling reagent, and said compound is optionally purified and/or isolated, and a compound of formula (S-IV) is reacted with a compound of formula (S-V)

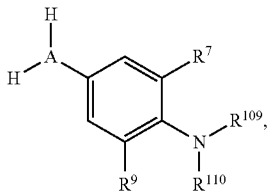

(S-V)

in which $R^7$, $R^9$, $R^{109}$ and $R^{110}$ have the respective foregoing meanings, and A denotes N, in a reaction medium, optionally in the presence of at least one suitable coupling reagent, and optionally in the presence of at least one base, to form a compound of formula (S)

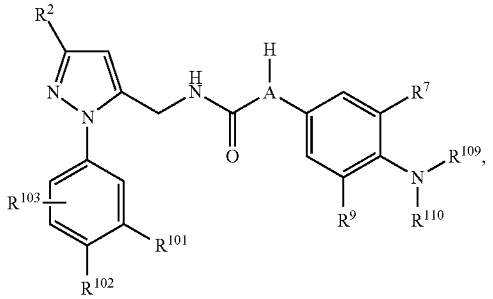

(S)

in which A represents N, and $R^{101}$, $R^{102}$, $R^{103}$ and $R^2$ as well as $R^7$, $R^9$, $R^{109}$ and $R^{110}$ have the respective foregoing meanings.

The reaction of compounds of the foregoing formula (S-II) with carboxylic acids of the foregoing formula (S-III), particularly with D=OH, to form compounds of the foregoing formula (S) preferably is carried out in a reaction medium selected from the group consisting of diethyl ether, tetrahydrofuran, acetonitrile, methanol, ethanol, (1,2)-dichloroethane, dimethylformamide, dichloromethane and corresponding mixtures, optionally in the presence of at least one coupling reagent, preferably selected from the group consisting of 1-benzotriazolyloxy-tris-(dimethylamino)-phosphonium hexafluorophosphate (BOP), dicyclohexylcarbodiimide (DCC), N'-(3-dimethylaminopropyl)-N-ethylcarbodiimide (EDCl), diisopropylcarbodiimide, 1,1'-carbonyldiimidazole (CDI), N-[(dimethylamino)-1H-1,2,3-triazolo[4,5-b]pyridino-1-yl-methylene]-N-methylmethanaminium hexafluorophosphate N-oxide (HATU), O-(benzotriazol-1-yl)-N,N,N',N'-tetramethyluronium hexafluorophosphate (HBTU), O-(benzotriazol-1-yl)-N,N,N',N'-tetramethyluronium tetrafluoroborate (TBTU), N-hydroxybenzotriazole (HOBt) and 1-hydroxy-7-azabenzotriazole (HOAt), optionally in the presence of at least one organic base, preferably selected from the group consisting of triethylamine, pyridine, dimethylaminopyridine, N-methylmorpholine and diisopropylethylamine, preferably at temperatures of from −70° C. to 100° C.

Alternatively, the reaction of compounds of the foregoing formula (S-II) with carboxylic acid halides of the foregoing formula (S-III) in which D denotes Hal, and Hal represents a halogen as the leaving group, preferably a chlorine or bromine atom, to form a compound of the foregoing formula (S) is carried out in a reaction medium preferably selected from the group consisting of diethyl ether, tetrahydrofuran, acetonitrile, methanol, ethanol, dimethylformamide, dichloromethane and corresponding mixtures, optionally in the presence of an organic or inorganic base, preferably selected from the group consisting of triethylamine, dimethylaminopyridine, pyridine and diisopropylamine, at temperatures of from −70° C. to 100° C.

The compounds of the foregoing formulas (S-II), (S-III), (S-IV), and (S-V) are each commercially available and/or can be prepared using conventional processes known to persons skilled in the art. In particular, processes to prepare these compounds are e.g. disclosed in WO 2010/127855-A2, and WO 2010/127856-A2, the entire disclosures of which are incorporated herein by reference.

All reactions which can be utilized for synthesizing the compounds of formula (S) can each be carried out under the conventional conditions with which the person skilled in the art is familiar, for example with regard to pressure or the order in which the components are added. If appropriate, the person skilled in the art can determine the optimum procedure under the respective conditions by carrying out simple preliminary tests. The intermediate and end products obtained using the reactions described hereinbefore can each be purified and/or isolated, if desired and/or required, using conventional methods known to the person skilled in the art. Suitable purifying processes include, for example, extraction processes and chromatographic processes such as column chromatography or preparative chromatography. All of the process steps of the reaction sequences which can be utilized for synthesizing the compounds of formula (S) as well as the respective purification and/or isolation of intermediate or end products, can be carried out partly or completely under an inert gas atmosphere, preferably under a nitrogen atmosphere.

The substituted compounds of formula (S) can be isolated either in the form of their free bases, or in the form of corresponding salts, in particular physiologically acceptable salts, and further in the form of a solvate such as hydrate.

The free bases of the respective substituted compounds of formula (S) can be converted into the corresponding salts, preferably physiologically acceptable salts, for example by reaction with an inorganic or organic acid, preferably with hydrochloric acid, hydrobromic acid, sulfuric acid, methanesulfonic acid, p-toluenesulfonic acid, carbonic acid, formic acid, acetic acid, oxalic acid, succinic acid, tartaric acid, mandelic acid, fumaric acid, maleic acid, lactic acid, citric acid, glutamic acid, saccharic acid, monomethylsebacic acid, 5-oxoproline, hexane-1-sulfonic acid, nicotinic acid, 2, 3 or 4-aminobenzoic acid, 2,4,6-trimethylbenzoic acid, α-lipoic acid, acetyl glycine, hippuric acid, phosphoric acid and/or aspartic acid. The free bases of the respective substituted compounds of formula (S) and of corresponding stereoisomers can likewise be converted into the corresponding physiologically acceptable salts using the free acid or a salt of a sugar additive, such as for example saccharin, cyclamate or acesulfame.

Accordingly, the substituted compounds of formula (S) such as the free acids of the substituted compounds of formula (S) can be converted into the corresponding physiologically acceptable salts by reaction with a suitable base. Examples include the alkali metal salts, alkaline earth metals salts or ammonium salts $[NH_xR_{4-x}]^+$, in which x=0, 1, 2, 3 or 4 and R represents a branched or unbranched $C_{1-4}$ alkyl residue.

The substituted compounds of formula (S) and the corresponding stereoisomers can if appropriate, like the corresponding acids, the corresponding bases or salts of these compounds, also be obtained in the form of their solvates, preferably in the form of their hydrates, using conventional methods known to the person skilled in the art.

If the substituted compounds of formula (S) are obtained, after preparation thereof, in the form of a mixture of their stereoisomers, preferably in the form of their racemates or other mixtures of their various enantiomers and/or diastereomers, they can be separated and optionally isolated using conventional processes known to persons skilled in the art. Examples include chromatographic separating processes, in particular liquid chromatography processes under normal pressure or under elevated pressure, preferably MPLC and HPLC processes, and also fractional crystallization processes. These processes allow individual enantiomers, for example diastereomeric salts formed by chiral stationary phase HPLC or by crystallization with chiral acids, for example (+)-tartaric acid, (−)-tartaric acid or (+)-10-camphorsulfonic acid, to be separated from one another.

The chemicals and reaction components used in the reactions and schemes described below are available commercially or in each case can be prepared by conventional methods known to persons skilled in the art.

General reaction scheme 1S (Scheme 1S):
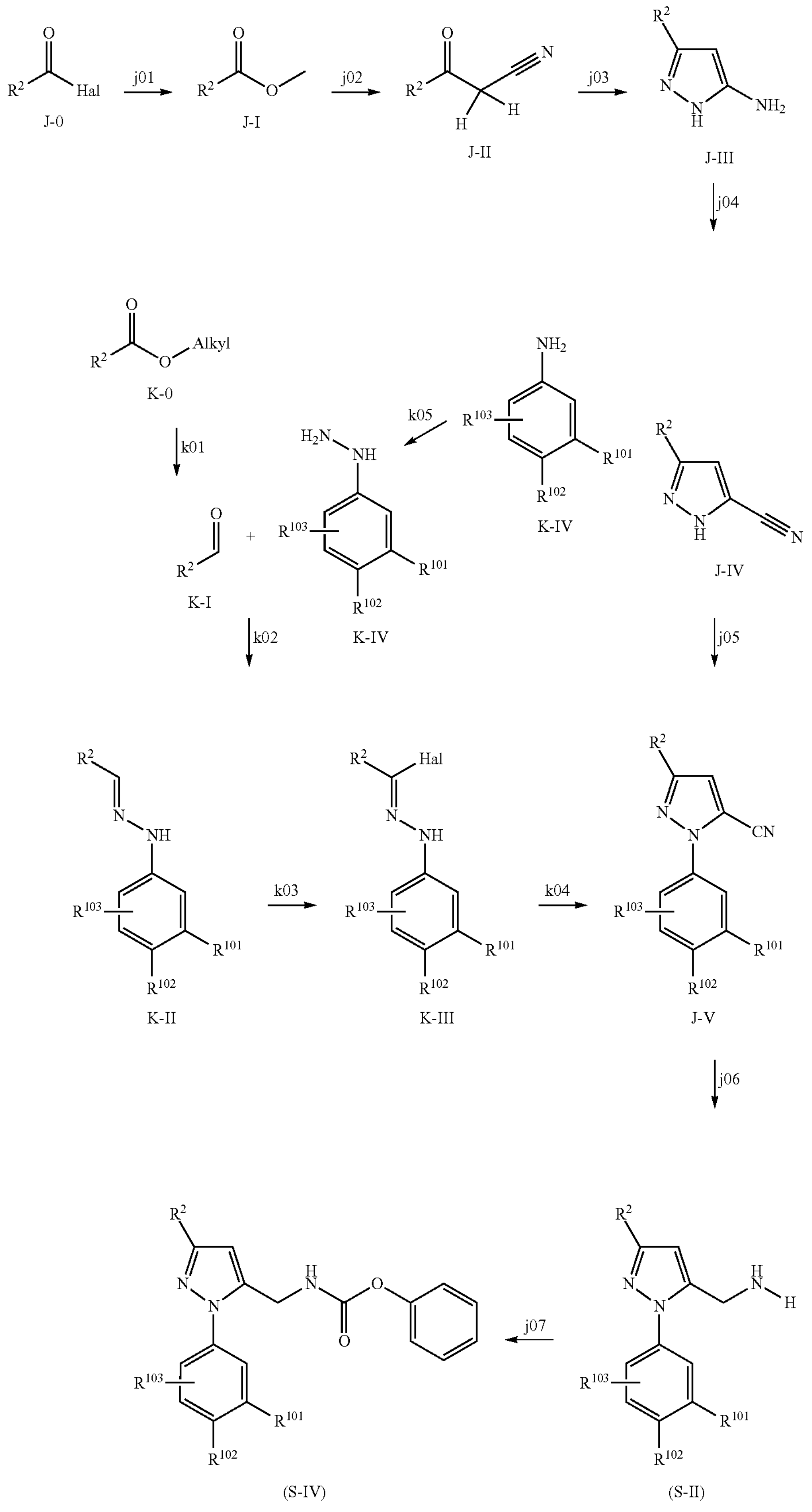

-continued

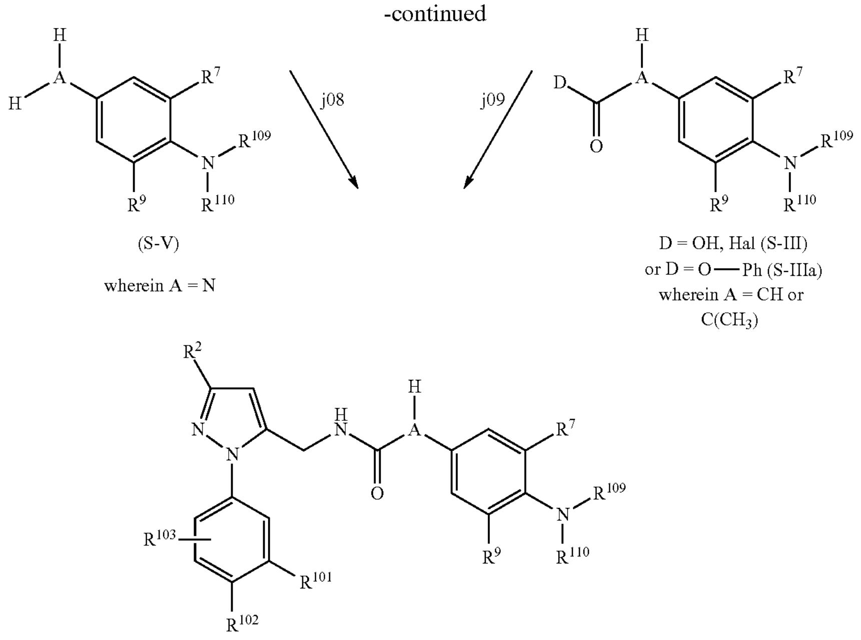

(S-V)

wherein A = N

D = OH, Hal (S-III)
or D = O—Ph (S-IIIa)
wherein A = CH or $C(CH_3)$ (S)

In step j01 an acid halide J-0, in which Hal preferably represents Cl or Br, can be esterified using methanol to form the compound J-I by methods with which the person skilled in the art is familiar.

In step j02 the methyl pivalate J-I can be converted into an oxoalkylnitrile J-II by methods known to the person skilled in the art, such as for example using acetonitrile $CH_3$—CN, optionally in the presence of a base.

In step j03 the compound J-II can be converted into an amino-substituted pyrazolyl derivative J-III by methods known to the person skilled in the art, such as for example using hydrazine hydrate, with cyclization.

In step j04 the amino compound J-III can first be converted into a diazonium salt by methods known to the person skilled in the art, such as for example using nitrite, and the diazonium salt can be converted into a cyano-substituted pyrazolyl derivative J-IV with elimination of nitrogen using a cyanide, optionally in the presence of a coupling reagent.

In step j05 the compound J-IV can be substituted in the N position by methods known to the person skilled in the art, for example using a halide of partial structure (SS2), i.e. Hal-(SS2), optionally in the presence of a base and/or a coupling reagent, wherein Hal is preferably Cl, Br or I, or using a boronic acid $B(OH)_2$(SS2) or a corresponding boronic acid ester, optionally in the presence of a coupling reagent and/or a base and the compound J-V can be obtained in this way.

Alternatively, a second synthesis pathway, in which in step k01 an ester K-0 is first reduced to form the aldehyde K-I by methods known to the person skilled in the art, for example using suitable hydrogenation reagents such as metal hydrides, is suitable for preparing the compound J-V.

In step k02 the aldehyde K-I can then be reacted with a hydrazine K-V, which can be obtained in step k05, starting from the primary amine K-IV, by methods known to the person skilled in the art, to form the hydrazine K-II by methods known to the person skilled in the art with elimination of water.

In step k03 the hydrazine K-II can be halogenated, preferably chlorinated, by methods known to the person skilled in the art with the double bond intact, such as for example using a chlorination reagent such as NCS, and the compound K-III can be obtained in this way.

In step k04 the hydrazonoyl halide K-III can be converted into a cyano-substituted compound J-V by methods known to persons skilled in the art, such as for example using a halogen-substituted nitrile, with cyclization.

In step j06 the compound J-V can be hydrogenated by methods known to persons skilled in the art, for example using a suitable catalyst such as palladium/activated carbon or using suitable hydrogenation reagents, and the compound (S-II) can be obtained in this way.

In step j07 the compound (S-II) can be converted into the compound (S-IV) by methods known to the person skilled in the art, such as for example using phenyl chloroformate, optionally in the presence of a coupling reagent and/or a base. In addition to the methods disclosed in the present document for preparing unsymmetrical ureas using phenyl chloroformate, there are further processes with which the person skilled in the art is familiar, based on the use of activated carbonic acid derivatives or isocyanates, if appropriate.

In step j08 the amine (S-V) can be converted into the urea compound (S) (wherein A=N). This can be achieved by reaction with (S-IV) by methods with which the person skilled in the art is familiar, optionally in the presence of a base.

In step j09 the amine (S-II) can be converted into the amide (S) (wherein A=CH or $C(CH_3)$). This can for example be achieved by reaction with an acid halide, preferably a chloride of formula (S-III) with D=Hal by methods with which the person skilled in the art is familiar, optionally in the presence of a base or by reaction with an acid of formula (S-III) with D=OH, optionally in the presence of a suitable coupling reagent, for example HATU or CDI, if appropriate with the addition of a base. Further, the amine (S-II) may be converted into the amide (S) (wherein A=CH or $C(CH_3)$) by reaction of a compound (S-IIIa) by methods with which the person skilled in the art is familiar, optionally in the presence of a base.

The compounds according to formula (S), wherein A=N, may be further prepared by a reaction sequence according to general reaction scheme 2.

2007; team of authors, Compendium of Organic Synthetic Methods, Wiley & Sons. In addition, further methods and also literature references can be issued by the common databases such as, for example, the Reaxys® database of Elsevier, Amsterdam, NL or the SciFinder® database of the American Chemical Society, Washington, US.

General reaction scheme 2S (scheme 2S)

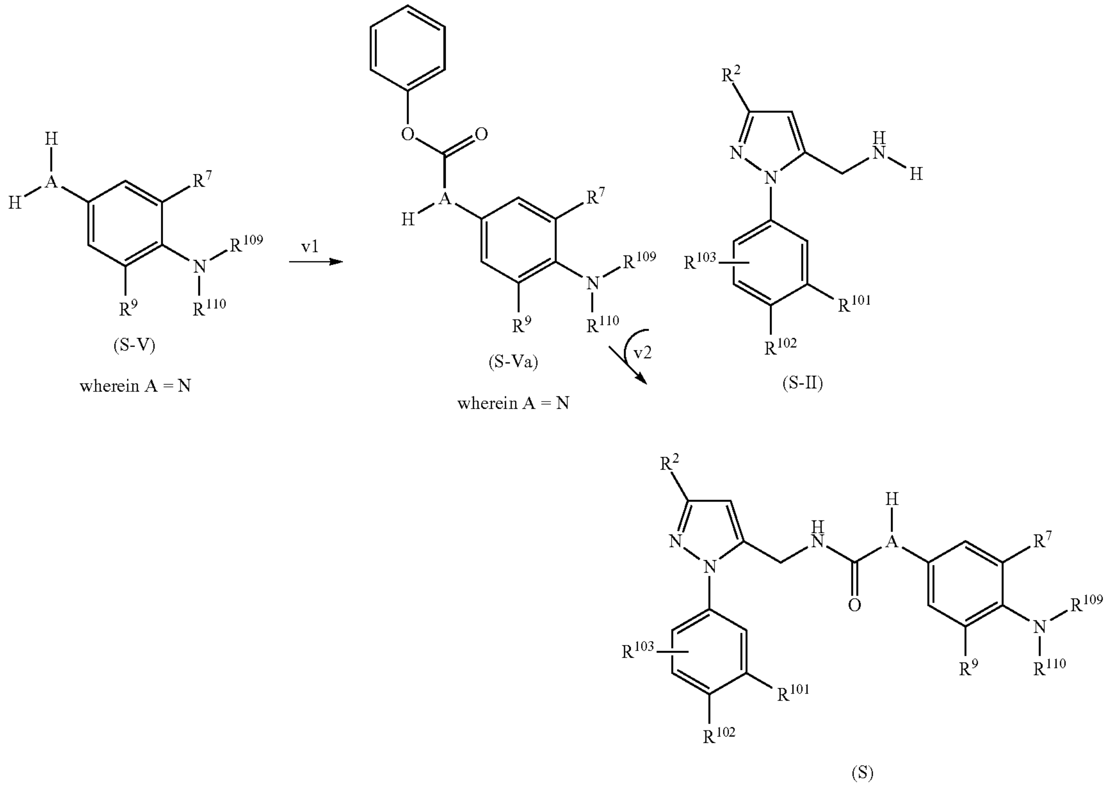

(S-V) wherein A = N (S-Va) wherein A = N (S-II)

(S) wherein A = N

In step v1 the compound (S-V) can be converted into the compound (S-Va) by methods known to the person skilled in the art, such as for example using phenyl chloroformate, optionally in the presence of a coupling reagent and/or a base. In addition to the methods disclosed in the present document for preparing unsymmetrical ureas using phenyl chloroformate, there are further processes with which the person skilled in the art is familiar, based on the use of activated carbonic acid derivatives or isocyanates, if appropriate.

In step v2 the amine (S-II) can be converted into the urea compound (S) (wherein A=N). This can be achieved by reaction with (S-Va) by methods with which the person skilled in the art is familiar, optionally in the presence of a base.

The methods with which persons skilled in the art are familiar for carrying out the reaction steps j01 to j09 and also k01 to k05 as well as v1 and v2 may be inferred from the standard works on organic chemistry such as, for example, J. March, Advanced Organic Chemistry, Wiley & Sons, 6th edition, 2007; F. A. Carey, R. J. Sundberg, Advanced Organic Chemistry, Parts A and B, Springer, 5th edition, In particular, the compounds of formula (T) can be prepared by a process according to which at least one compound of formula (T-II)

(T-II)

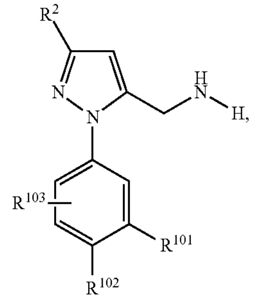

in which $R^{101}$, $R^{102}$, $R^{103}$ and $R^2$ have the foregoing respective meanings, is reacted in a reaction medium, optionally in the presence of at least one suitable coupling reagent, and optionally in the presence of at least one base, with a compound of general formula (T-III) in which D denotes OH or Hal (T-III)

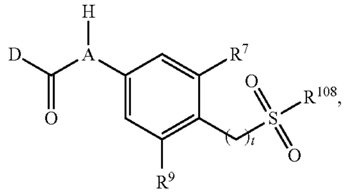

in which Hal represents a halogen, preferably Br or Cl, and $R^7$, $R^9$, $R^{108}$ and t each have the foregoing respective meanings and A denotes CH or $C(CH_3)$, in a reaction medium, optionally in the presence of at least one suitable coupling reagent, optionally in the presence of at least one base, to form a compound of general formula (T), (T)

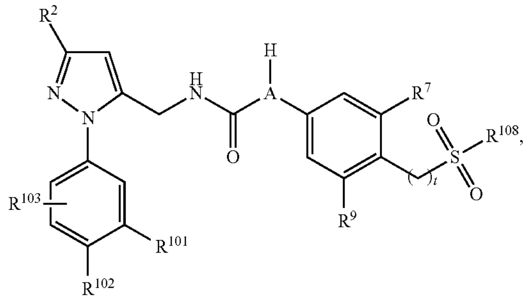

in which A represents CH or $C(CH_3)$ and $R^{101}$, $R^{102}$, $R^{103}$ and $R^2$ as well as $R^7$, $R^9$, $R^{108}$ and t have the foregoing respective meanings; or by a process in which a compound of formula (T-II)

(T-II)

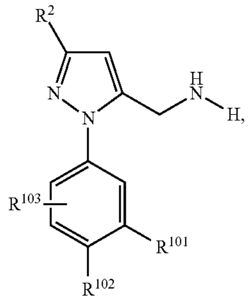

in which $R^{101}$, $R^{102}$, $R^{103}$ and $R^2$ have the foregoing respective meanings, is reacted to form a compound of formula (T-IV)

(T-IV)

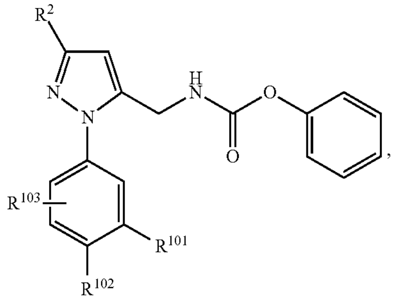

in which $R^{101}$, $R^{102}$, $R^{103}$ and $R^2$ have the foregoing respective meanings, in a reaction medium, in the presence of phenyl chloroformate, optionally in the presence of at least one base and/or at least one coupling reagent, and said compound is optionally purified and/or isolated, and a compound of formula (T-IV) is reacted with a compound of formula (T-V)

(T-V)

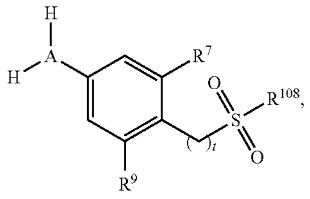

in which $R^7$, $R^9$, $R^{108}$ and t have the foregoing respective meanings, and A denotes N, in a reaction medium, optionally in the presence of at least one suitable coupling reagent, and optionally in the presence of at least one base, to form a compound of formula (T)

(T)

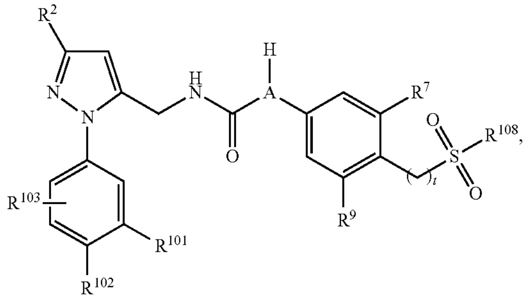

in which A represents N, and $R^{101}$, $R^{102}$, $R^{103}$ and $R^2$ as well as $R^7$, $R^9$, $R^{108}$ and t have the foregoing respective meanings.

The reaction of compounds of the foregoing formula (T-II) with carboxylic acids of the foregoing formula (T-III), particularly in which D denotes OH, to form compounds of the foregoing formula (T) preferably is carried out in a reaction medium selected from the group consisting of diethyl ether, tetrahydrofuran, acetonitrile, methanol, ethanol, (1,2)-dichloroethane, dimethylformamide, dichloromethane and corresponding mixtures, optionally in the presence of at least one coupling reagent, preferably selected from the group consisting of 1-benzotriazolyloxy-tris-(dimethylamino)-phosphonium hexafluorophosphate (BOP), dicyclohexylcarbodiimide (DCC), N'-(3-dimethylaminopropyl)-N-ethylcarbodiimide (EDCl), diisopropylcarbodiimide, 1,1'-carbonyldiimidazole (CDI), N-[(dimethylamino)-1H-1,2,3-triazolo[4,5-b]pyridino-1-yl-methylene]-N-methylmethanaminium hexafluorophosphate N-oxide (HATU), O-(benzotriazol-1-yl)-N, N,N',N'-tetramethyluronium hexafluorophosphate (HBTU), O-(benzotriazol-1-yl)-N,N,N',N'-tetramethyluronium tetrafluoroborate (TBTU), N-hydroxybenzotriazole (HOBt) and 1-hydroxy-7-azabenzotriazole (HOAt), and optionally in the presence of at least one organic base, preferably selected from the group consisting of triethylamine, pyridine, dimethylaminopyridine, N-methylmorpholine and diisopropylethylamine, preferably at temperatures of from −70° C. to 100° C.

Alternatively, the reaction of compounds of the foregoing formulae (T-II) with carboxylic acid halides of the foregoing formula (T-III) in which D denotes Hal, and Hal represents a halogen as the leaving group, preferably a chlorine or bromine atom, to form compounds of the foregoing formula (T) is carried out in a reaction medium preferably selected from the group consisting of diethyl ether, tetrahydrofuran, acetonitrile, methanol, ethanol, dimethylformamide, dichloromethane and corresponding mixtures, optionally in the presence of an organic or inorganic base, preferably selected from the group consisting of triethylamine, dimethylaminopyridine, pyridine and diisopropylamine, at temperatures of from −70° C. to 100° C.

The compounds of the above-indicated formulas (T-II), (T-III), (T-IV), and (T-V) are each commercially available and/or can be prepared using conventional processes known to persons skilled in the art. In particular, processes to prepare these compounds are e.g. disclosed in WO 2010/127855-A2, and WO 2010/127856-A2, the entire disclosures of each of which are incorporated herein by reference.

All reactions which can be utilized for synthesizing the compounds according to the present invention can each be carried out under the conventional conditions with which persons skilled in the art are familiar, for example with regard to pressure or the order in which the components are added. If desired, a person skilled in the art can determine the optimum procedure under the respective conditions by carrying out simple preliminary tests. The intermediate and end products obtained using the reactions described above can each be purified and/or isolated, if desired and/or required, using conventional methods known to persons skilled in the art. Suitable purifying processes include, for example, extraction processes and chromatographic processes such as column chromatography or preparative chromatography. All of the process steps of the reaction sequences which can be utilized for synthesizing the compounds according to the present invention as well as the respective purification and/or isolation of intermediate or end products, can be carried out partly or completely under an inert gas atmosphere, preferably under a nitrogen atmosphere.

The substituted compounds according to the invention can be isolated both in the form of their free bases, and also in the form of corresponding salts, in particular physiologically acceptable salts, and further in the form of a solvate such as hydrate.

The free bases of the respective substituted compounds according to the invention can be converted into the corresponding salts, preferably physiologically acceptable salts, for example by reaction with an inorganic or organic acid, preferably with hydrochloric acid, hydrobromic acid, sulfuric acid, methanesulfonic acid, p-toluenesulfonic acid, carbonic acid, formic acid, acetic acid, oxalic acid, succinic acid, tartaric acid, mandelic acid, fumaric acid, maleic acid, lactic acid, citric acid, glutamic acid, saccharic acid, monomethylsebacic acid, 5-oxoproline, hexane-1-sulfonic acid, nicotinic acid, 2, 3 or 4-aminobenzoic acid, 2,4,6-trimethylbenzoic acid, co-lipoic acid, acetyl glycine, hippuric acid, phosphoric acid and/or aspartic acid. The free bases of the respective inventive substituted compounds and of corresponding stereoisomers can likewise be converted into the corresponding physiologically acceptable salts using the free acid or a salt of a sugar additive, such as for example saccharin, cyclamate or acesulfame.

Accordingly, the substituted compounds according to the invention such as the free acids of the substituted compounds according to the invention can be converted into the corresponding physiologically acceptable salts by reaction with a suitable base. Examples include the alkali metal salts, alkaline earth metals salts or ammonium salts $[NH_xR_{4-x}]^+$, in which x=0, 1, 2, 3 or 4 and R represents a branched or unbranched $C_{1-4}$ alkyl residue.

The substituted compounds according to the invention and their corresponding stereoisomers can, if appropriate, like the corresponding acids, the corresponding bases or salts of these compounds, also be obtained in the form of their solvates, preferably in the form of their hydrates, using conventional methods known to persons skilled in the art.

If the substituted compounds according to the invention are obtained, after preparation thereof, in the form of a mixture of their stereoisomers, preferably in the form of their racemates or other mixtures of their various enantiomers and/or diastereomers, they can be separated and optionally isolated using conventional processes known to persons skilled in the art. Examples include chromatographic separating processes, in particular liquid chromatography processes under normal pressure or under elevated pressure, preferably MPLC and HPLC processes, and also fractional crystallization processes. These processes allow individual enantiomers, for example diastereomeric salts formed by chiral stationary phase HPLC or by crystallization with chiral acids, for example (+)-tartaric acid, (−)-tartaric acid or (+)-10-camphorsulfonic acid, to be separated from one another.

The chemicals and reaction components used in the reactions and schemes described below are available commercially or in each case can be prepared by conventional methods known to persons skilled in the art.

General reaction scheme 1T (Scheme 1T):
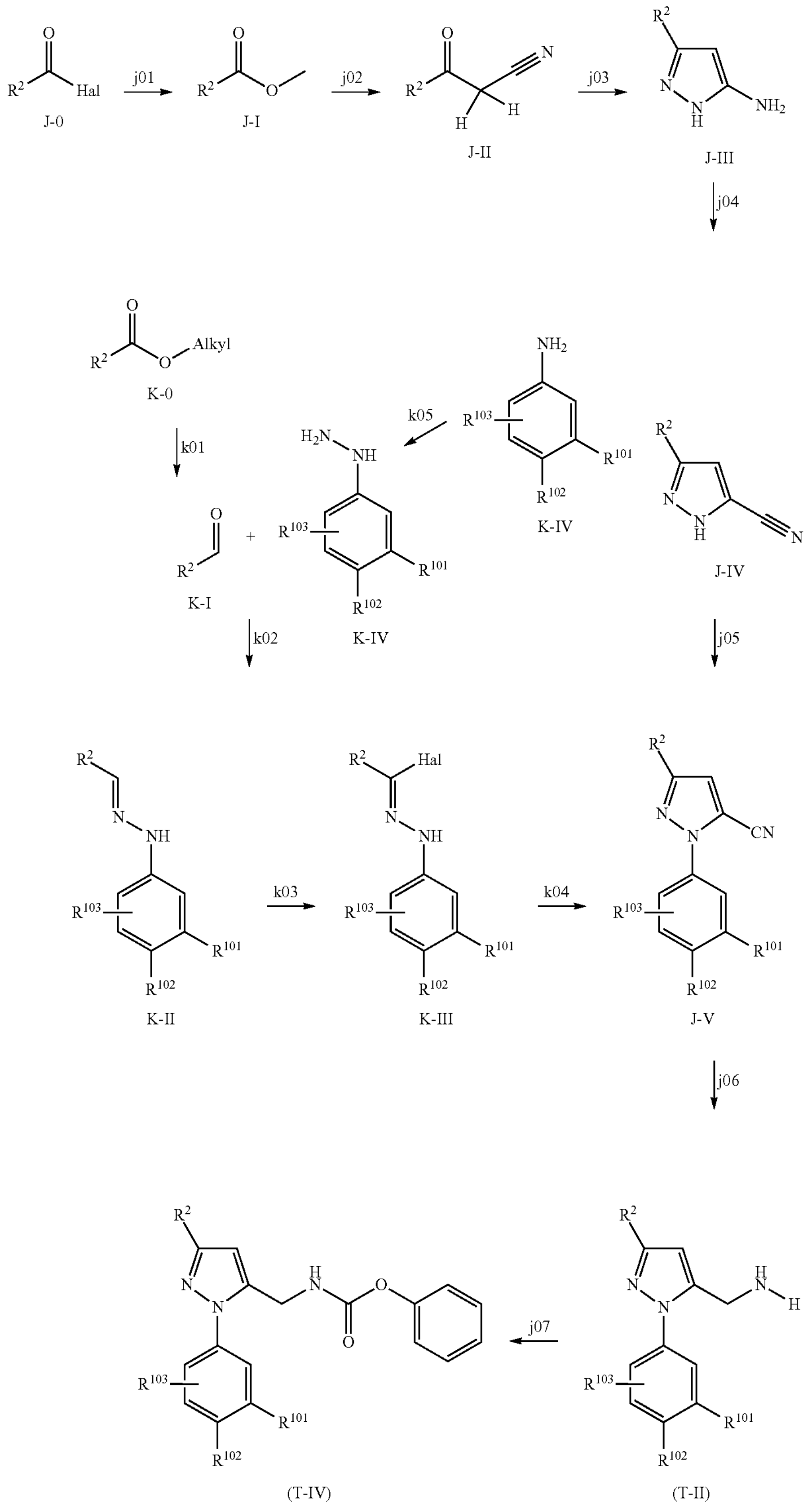

-continued

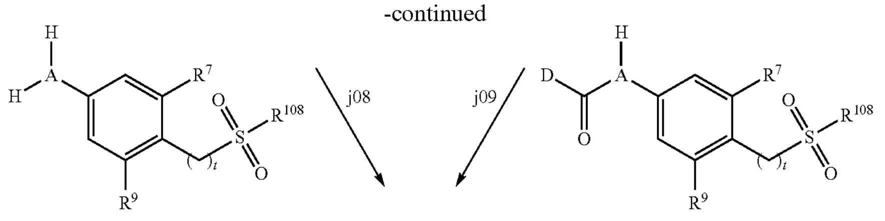

(T-V)

wherein A = N

D = OH, Hal (T-III)
or D = O—Ph (T-IIIa)
wherein A = CH or
$C(CH_3)$

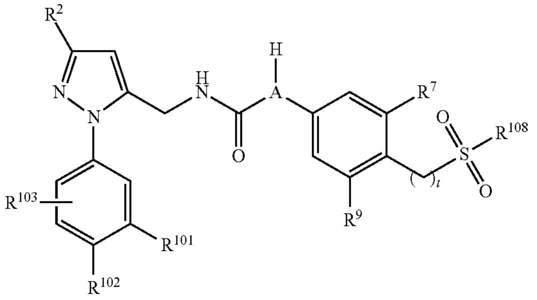

(T)

In step j01 an acid halide J-0, in which Hal preferably represents Cl or Br, can be esterified using methanol to form the compound J-I by methods with which persons skilled in the art are familiar.

In step j02 the methyl pivalate J-I can be converted into an oxoalkylnitrile J-II by methods known to persons skilled in the art, such as for example using acetonitrile $CH_3$—CN, optionally in the presence of a base.

In step j03 the compound J-II can be converted into an amino-substituted pyrazolyl derivative J-III by methods known to the person skilled in the art, such as for example using hydrazine hydrate, with cyclization.

In step j04 the amino compound J-III can first be converted into a diazonium salt by methods known to persons skilled in the art, such as for example using nitrite, and the diazonium salt can be converted into a cyano-substituted pyrazolyl derivative J-IV with elimination of nitrogen using a cyanide, optionally in the presence of a coupling reagent.

In step j05 the compound J-IV can be substituted in the N position by methods known to the person skilled in the art, for example using a halide of partial structure (TS2), i.e. Hal-(TS2), optionally in the presence of a base and/or a coupling reagent, wherein Hal is preferably Cl, Br or I, or using a boronic acid $B(OH)_2$(TS2) or a corresponding boronic acid ester, optionally in the presence of a coupling reagent and/or a base and the compound J-V can in this way be obtained.

Alternatively, a second synthesis pathway, in which in step k01 an ester K-0 is first reduced to form the aldehyde K-I by methods known to persons skilled in the art, for example using suitable hydrogenation reagents such as metal hydrides, is suitable for preparing the compound J-V.

In step k02 the aldehyde K-I can then be reacted with a hydrazine K-V, which can be obtained in step k05, starting from the primary amine K-IV, by methods known to the person skilled in the art, to form the hydrazine K-II by methods known to persons skilled in the art with elimination of water.

In step k03 the hydrazine K-II can be halogenated, preferably chlorinated, by methods known to the person skilled in the art with the double bond intact, such as for example using a chlorination reagent such as NCS, and the compound K-III can be obtained in this way.

In step k04 the hydrazonoyl halide K-III can be converted into a cyano-substituted compound J-V by methods known to the person skilled in the art, such as for example using a halogen-substituted nitrile, with cyclization.

In step j06 the compound J-V can be hydrogenated by methods known to persons skilled in the art, for example by using a suitable catalyst such as palladium/activated carbon or using suitable hydrogenation reagents, and the compound (T-II) can be obtained in this way.

In step j07 the compound (T-II) can be converted into the compound (T-IV) by methods known to persons skilled in the art, such as for example using phenyl chloroformate, optionally in the presence of a coupling reagent and/or a base. In addition to the methods disclosed in the present document for preparing unsymmetrical ureas using phenyl chloroformate, there are further processes with which persons skilled in the art are familiar, based on the use of activated carbonic acid derivatives or isocyanates, if appropriate.

In step j08 the amine (T-V) can be converted into the urea compound (T) (wherein A=N). This can be achieved by reaction with (T-IV) by methods with which the person skilled in the art is familiar, optionally in the presence of a base.

In step j09 the amine (T-II) can be converted into the amide (T) (wherein A=CH or $C(CH_3)$). This can for example be achieved by reaction with an acid halide, preferably a chloride of formula (T-III) in which D denotes Hal by methods with which persons skilled in the art are familiar, optionally in the presence of a base or by reaction with an acid of formula (T-II) in which D denotes OH, optionally in the presence of a suitable coupling reagent, for example HATU or CDI, and optionally with the addition of a base. Further, the amine (T-II) may be converted into the amide (T) (wherein A=CH or $C(CH_3)$) by reaction of a compound (T-IIIa) by methods with which persons skilled in the art are familiar, optionally in the presence of a base.

The compounds of formula (T), wherein A=N, may be further prepared by a reaction sequence according to general reaction scheme 2T.

General reaction scheme 2T (scheme 2T)

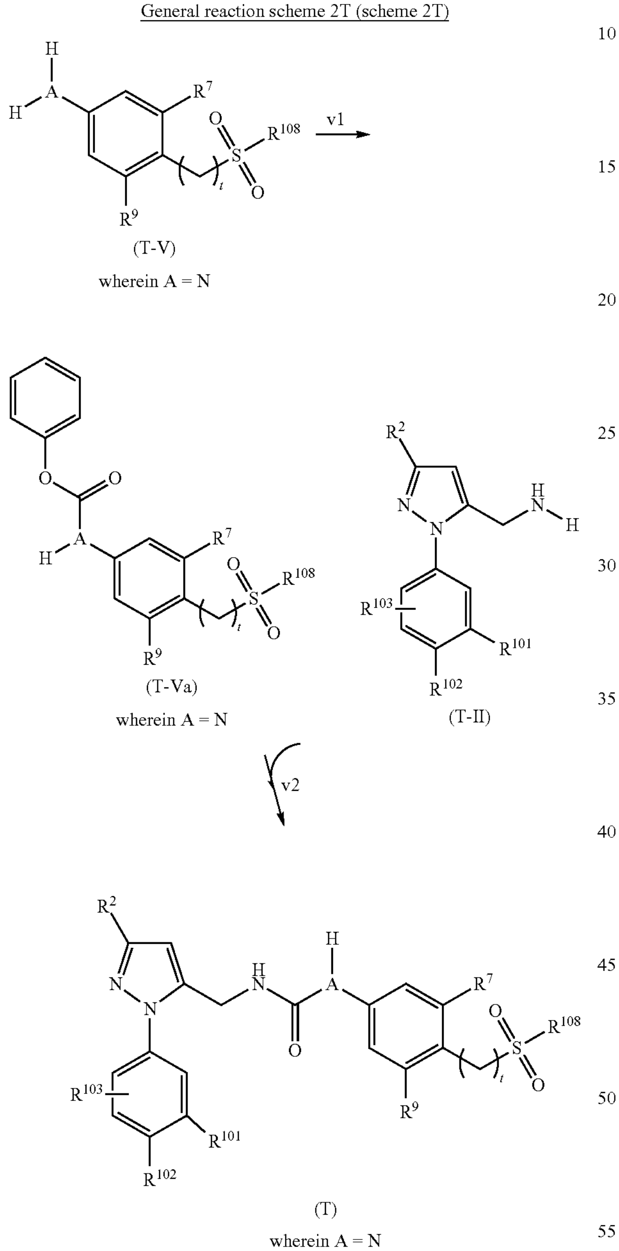

(T-V) wherein A = N (T-Va) wherein A = N (T-II)

(T) wherein A = N

In step v1 the compound (T-V) can be converted into the compound (T-Va) by methods known to the person skilled in the art, such as for example using phenyl chloroformate, optionally in the presence of a coupling reagent and/or a base. In addition to the methods disclosed in the present document for preparing unsymmetrical ureas using phenyl chloroformate, there are further processes with which the person skilled in the art is familiar, based on the use of activated carbonic acid derivatives or isocyanates, if appropriate.

In step v2 the amine (T-II) can be converted into the urea compound (T) (wherein A=N). This can be achieved by reaction with (T-Va) by methods with which the person skilled in the art is familiar, optionally in the presence of a base.

The methods with which persons skilled in the art are familiar for carrying out the reaction steps j01 to j09 and also k01 to k05 as well as v1 and v2 may be inferred from the standard works on organic chemistry such as, for example, J. March, Advanced Organic Chemistry, Wiley & Sons, 6th edition, 2007; F. A. Carey, R. J. Sundberg, Advanced Organic Chemistry, Parts A and B, Springer, 5th edition, 2007; team of authors, Compendium of Organic Synthetic Methods, Wiley & Sons. In addition, further methods and also literature references can be issued by the common databases such as, for example, the Reaxys® database of Elsevier, Amsterdam, NL or the SciFinder® database of the American Chemical Society, Washington, US.

In particular, the compounds of formula (U) of can be prepared by a process according to which at least one compound of formula (U-II), (U-II)

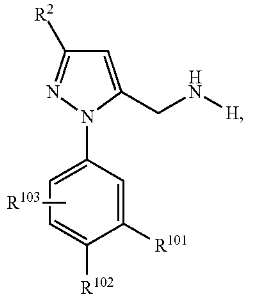

in which $R^{101}$, $R^{102}$, $R^{103}$ and $R^2$ have the foregoing respective meanings, is reacted in a reaction medium, optionally in the presence of at least one suitable coupling reagent, optionally in the presence of at least one base, with a compound of formula (U-III) in which D denotes OH or Hal, (U-III)

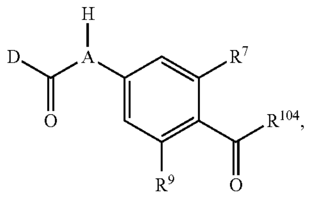

in which Hal represents a halogen, preferably Br or Cl, and $R^7$, $R^9$ and $R^{104}$ each have the foregoing respective meanings and A denotes CH or $C(CH_3)$, in a reaction medium, optionally in the presence of at least one suitable coupling reagent, and optionally in the presence of at least one base, to form a compound of formula (U), (U)

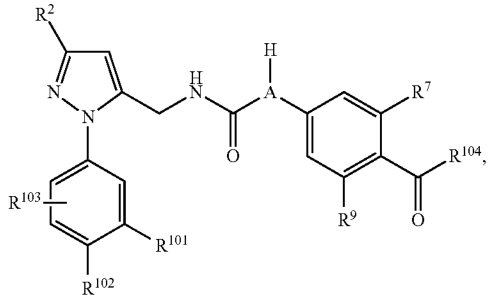

in which A represents CH or $C(CH_3)$, and $R^{101}$, $R^{102}$, $R^{103}$ and $R^2$ as well as $R^7$, $R^9$ and $R^{104}$, have the foregoing respective meanings;

or a process in which at least one compound of formula (U-II)

(U-II)

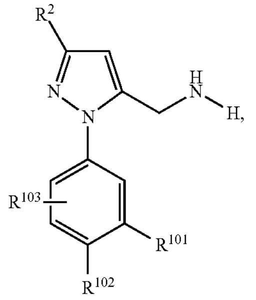

in which $R^{101}$, $R^{102}$, $R^{103}$ and $R^2$ have the foregoing respective meanings, is reacted to form a compound of formula (U-IV)

(U-IV)

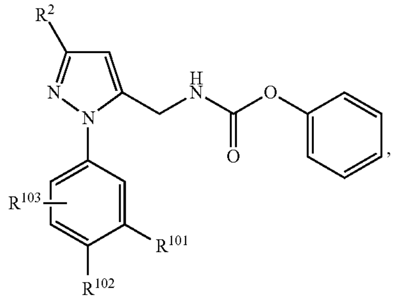

in which $R^{101}$, $R^{102}$, $R^{103}$ and $R^2$ have the foregoing respective meanings, in a reaction medium, in the presence of phenyl chloroformate, optionally in the presence of at least one base and/or at least one coupling reagent, and said compound is optionally purified and/or isolated, and a compound of formula (U-IV) is reacted with a compound of formula (U-V)

(U-V)

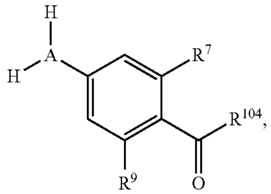

in which $R^7$, $R^9$ and $R^{104}$ have the foregoing respective meanings, and A denotes N, in a reaction medium, optionally in the presence of at least one suitable coupling reagent, and optionally in the presence of at least one base, to form a compound of formula (U)

(U)

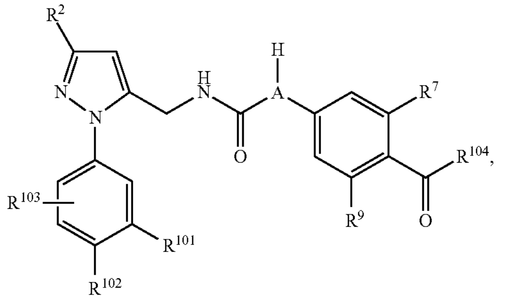

in which A represents N, and $R^{101}$, $R^{102}$, $R^{103}$ and $R^2$ as well as $R^7$, $R^9$ and $R^{104}$ have the foregoing respective meanings.

The reaction of compounds of the foregoing formula (U-II) with carboxylic acids of the foregoing formula (U-III), particularly in which D denotes OH, to form compounds of the foregoing formula (U) preferably is carried out in a reaction medium selected from the group consisting of diethyl ether, tetrahydrofuran, acetonitrile, methanol, ethanol, (1,2)-dichloroethane, dimethylformamide, dichloromethane and corresponding mixtures, optionally in the presence of at least one coupling reagent, preferably selected from the group consisting of 1-benzotriazolyloxy-tris-(dimethylamino)-phosphonium hexafluorophosphate (BOP), dicyclohexylcarbodiimide (DCC), N'-(3-dimethylaminopropyl)-N-ethylcarbodiimide (EDCl), diisopropylcarbodiimide, 1,1'-carbonyldiimidazole (CDI), N-[(dimethylamino)-1H-1,2,3-triazolo[4,5-b]pyridino-1-yl-methylene]-N-methylmethanaminium hexafluorophosphate N-oxide (HATU), O-(benzotriazol-1-yl)-N,N,N',N'-tetramethyluronium hexafluorophosphate (HBTU), O-(benzotriazol-1-yl)-N,N,N',N'-tetramethyluronium tetrafluoroborate (TBTU), N-hydroxybenzotriazole (HOBt) and 1-hydroxy-7-azabenzotriazole (HOAt), optionally in the presence of at least one organic base, preferably selected from the group consisting of triethylamine, pyridine, dimethylaminopyridine, N-methylmorpholine and diisopropylethylamine, preferably at temperatures of from −70° C. to 100° C.

Alternatively, the reaction of compounds of the foregoing formulas (U-II) with carboxylic acid halides of the foregoing formula (U-III) in which D denotes Hal, and in which Hal represents a halogen as the leaving group, preferably a chlorine or bromine atom, to form compounds of the foregoing formula (U) is carried out in a reaction medium preferably selected from the group consisting of diethyl ether, tetrahydrofuran, acetonitrile, methanol, ethanol, dimethylformamide, dichloromethane and corresponding mixtures, optionally in the presence of an organic or inorganic base, preferably selected from the group consisting of triethylamine, dimethylaminopyridine, pyridine and diisopropylamine, at temperatures of from −70° C. to 100° C.

The compounds of the foregoing formulas (U-II), (U-III), (U-IV), and (U-V) are each commercially available and/or can be prepared using conventional processes known to the person skilled in the art. In particular, processes to prepare these compounds are e.g. disclosed in WO 2010/127855-A2, and WO 2010/127856-A2, the entire disclosures of each of which are incorporated herein by reference.

All reactions which can be utilized for synthesizing the compounds of formula (U) can each be carried out under the conventional conditions with which persons skilled in the art are familiar, for example with regard to pressure or the order in which the components are added. If desired, persons skilled in the art can determine the optimum procedure under the respective conditions by carrying out simple preliminary tests. The intermediate and end products obtained using the reactions described hereinbefore can each be purified and/or isolated, if desired and/or required, using conventional methods known to persons skilled in the art. Suitable purifying processes include, for example, extraction processes and chromatographic processes such as column chromatography or preparative chromatography. All of the process steps of the reaction sequences which can be utilized for synthesizing the compounds of formula (U) as well as the respective purification and/or isolation of intermediate or end products, can be carried out partly or completely under an inert gas atmosphere, preferably under a nitrogen atmosphere.

The substituted compounds of formula (U) can be isolated both in the form of their free bases, and also in the form of corresponding salts, in particular physiologically acceptable salts, and further in the form of a solvate such as hydrate.

The free bases of the respective substituted compounds of formula (U) can be converted into the corresponding salts, preferably physiologically acceptable salts, for example by reaction with an inorganic or organic acid, preferably with hydrochloric acid, hydrobromic acid, sulfuric acid, methanesulfonic acid, p-toluenesulfonic acid, carbonic acid, formic acid, acetic acid, oxalic acid, succinic acid, tartaric acid, mandelic acid, fumaric acid, maleic acid, lactic acid, citric acid, glutamic acid, saccharic acid, monomethylsebacic acid, 5-oxoproline, hexane-1-sulfonic acid, nicotinic acid, 2, 3 or 4-aminobenzoic acid, 2,4,6-trimethylbenzoic acid, α-lipoic acid, acetyl glycine, hippuric acid, phosphoric acid and/or aspartic acid. The free bases of the respective inventive substituted compounds and of corresponding stereoisomers can likewise be converted into the corresponding physiologically acceptable salts using the free acid or a salt of a sugar additive, such as for example saccharin, cyclamate or acesulfame.

Accordingly, the substituted compounds of formula (U) such as the free acids of the substituted compounds of formula (U) can be converted into the corresponding physiologically acceptable salts by reaction with a suitable base. Examples include the alkali metal salts, alkaline earth metals salts or ammonium salts $[NH_xR_{4-x}]^+$, in which x=0, 1, 2, 3 or 4 and R represents a branched or unbranched $C_{1-4}$ alkyl residue.

The substituted compounds of formula (U) and of corresponding stereoisomers can, if appropriate, like the corresponding acids, the corresponding bases or salts of these compounds, also be obtained in the form of their solvates, preferably in the form of their hydrates, using conventional methods known to the person skilled in the art.

If the substituted compounds of formula (U) are obtained, after preparation thereof, in the form of a mixture of their stereoisomers, preferably in the form of their racemates or other mixtures of their various enantiomers and/or diastereomers, they can be separated and optionally isolated using conventional processes known to the person skilled in the art. Examples include chromatographic separating processes, in particular liquid chromatography processes under normal pressure or under elevated pressure, preferably MPLC and HPLC processes, and also fractional crystallization processes. These processes allow individual enantiomers, for example diastereomeric salts formed by chiral stationary phase HPLC or by crystallization with chiral acids, for example (+)-tartaric acid, (−)-tartaric acid or (+)-10-camphorsulfonic acid, to be separated from one another.

The chemicals and reaction components used in the reactions and schemes described below are available commercially or in each case can be prepared by conventional methods known to the person skilled in the art.

General reaction scheme 1U (Scheme 1U):

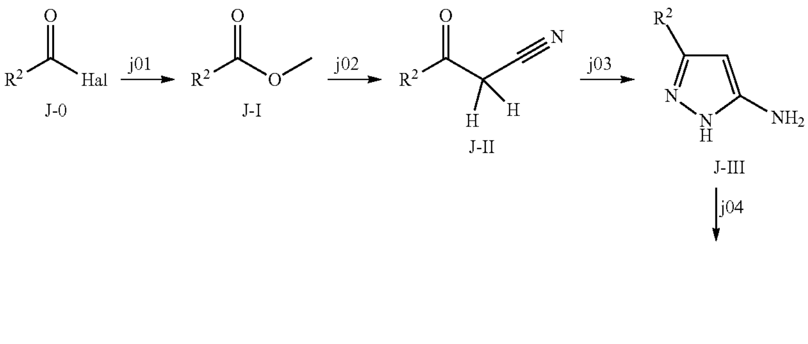

J-0
J-I
J-II
J-III

-continued
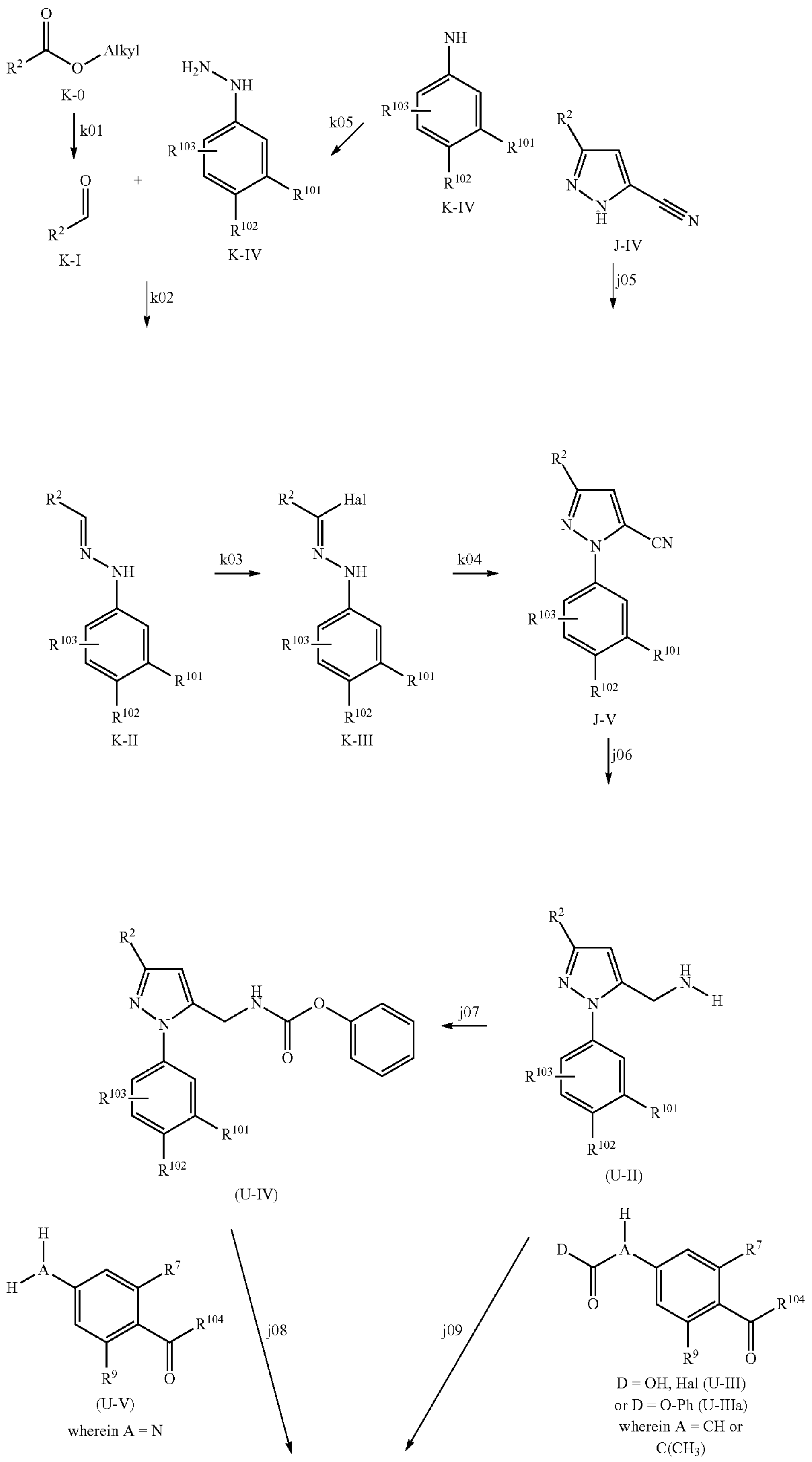

-continued

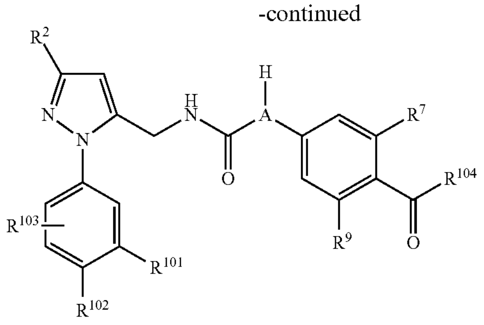

(U)

In step j01 an acid halide J-0, in which Hal preferably represents Cl or Br, can be esterified using methanol to form the compound J-I by methods with which the person skilled in the art is familiar.

In step j02 the methyl pivalate J-1 can be converted into an oxoalkylnitrile J-II by methods known to the person skilled in the art, such as for example using acetonitrile $CH_3$—CN, optionally in the presence of a base.

In step j03 the compound J-II can be converted into an amino-substituted pyrazolyl derivative J-III by methods known to the person skilled in the art, such as for example using hydrazine hydrate, with cyclization.

In step j04 the amino compound J-III can first be converted into a diazonium salt by methods known to the person skilled in the art, such as for example using nitrite, and the diazonium salt can be converted into a cyano-substituted pyrazolyl derivative J-IV with elimination of nitrogen using a cyanide, optionally in the presence of a coupling reagent.

In step j05 the compound J-IV can be substituted in the N position by methods known to the person skilled in the art, for example using a halide of partial structure (US2), i.e. Hal-(US2), optionally in the presence of a base and/or a coupling reagent, wherein Hal is preferably Cl, Br or I, or using a boronic acid $B(OH)_2$(US2) or a corresponding boronic acid ester, optionally in the presence of a coupling reagent and/or a base and the compound J-V can be obtained in this way.

Alternatively, a second synthesis pathway, in which in step k01 an ester K-0 is first reduced to form the aldehyde K-I by methods known to the person skilled in the art, for example using suitable hydrogenation reagents such as metal hydrides, is suitable for preparing the compound J-V.

In step k02 the aldehyde K-I can then be reacted with a hydrazine K-V, which can be obtained in step k05, starting from the primary amine K-IV, by methods known to the person skilled in the art, to form the hydrazine K-II by methods known to the person skilled in the art with elimination of water.

In step k03 the hydrazine K-II can be halogenated, preferably chlorinated, by methods known to the person skilled in the art with the double bond intact, such as for example using a chlorination reagent such as NCS, and the compound K-III can be obtained in this way.

In step k04 the hydrazonoyl halide K-III can be converted into a cyano-substituted compound J-V by methods known to the person skilled in the art, such as for example using a halogen-substituted nitrile, with cyclization.

In step j06 the compound J-V can be hydrogenated by methods known to persons skilled in the art, for example using a suitable catalyst such as palladium/activated carbon or using suitable hydrogenation reagents, and the compound (U-II) can in this way be obtained.

In step j07 the compound (U-II) can be converted into the compound (U-IV) by methods known to the person skilled in the art, such as for example using phenyl chloroformate, optionally in the presence of a coupling reagent and/or a base. In addition to the methods disclosed in the present document for preparing unsymmetrical ureas using phenyl chloroformate, there are further processes with which the person skilled in the art is familiar, based on the use of activated carbonic acid derivatives or isocyanates, if appropriate.

In step j08 the amine (U-V) can be converted into the urea compound (U) (wherein A=N). This can be achieved by reaction with (U-IV) by methods with which the person skilled in the art is familiar, optionally in the presence of a base.

In step j09 the amine (U-II) can be converted into the amide (U) (wherein A=CH or $C(CH_3)$). This can for example be achieved by reaction with an acid halide, preferably a chloride of formula (U-III) in which D denotes Hal by methods with which the person skilled in the art is familiar, optionally in the presence of a base or by reaction with an acid of formula (U-III) in which D denotes OH, optionally in the presence of a suitable coupling reagent, for example HATU or CDI, if appropriate with the addition of a base. Further, the amine (U-II) may be converted into the amide (U) (wherein A=CH or $C(CH_3)$) by reaction of a compound (U-IIIa) by methods with which the person skilled in the art is familiar, optionally in the presence of a base.

The compounds according to formula (U), wherein A=N, may be further prepared by a reaction sequence according to general reaction scheme 2U.

General reaction scheme 2U (scheme 2U)

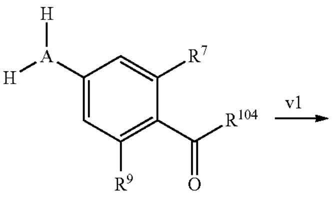

(U-V)

wherein A = N

-continued

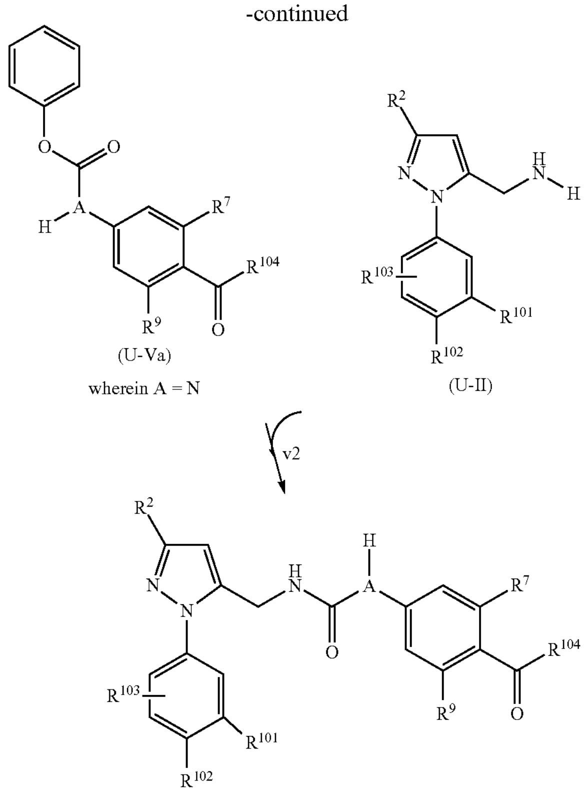

(U-Va)
wherein A = N (U-II)

(U)
wherein A = N

In step v1 the compound (U-V) can be converted into the compound (U-Va) by methods known to the person skilled in the art, such as for example using phenyl chloroformate, optionally in the presence of a coupling reagent and/or a base. In addition to the methods disclosed in the present document for preparing unsymmetrical ureas using phenyl chloroformate, there are further processes with which the person skilled in the art is familiar, based on the use of activated carbonic acid derivatives or isocyanates, if appropriate.

In step v2 the amine (U-II) can be converted into the urea compound (U) (wherein A=N). This can be achieved by reaction with (U-Va) by methods with which the person skilled in the art is familiar, optionally in the presence of a base.

The methods with which persons skilled in the art are familiar for carrying out the reaction steps j01 to j09 and also k01 to k05 as well as v1 and v2 may be inferred from the standard works on organic chemistry such as, for example, J. March, Advanced Organic Chemistry, Wiley & Sons, 6th edition, 2007; F. A. Carey, R. J. Sundberg, Advanced Organic Chemistry, Parts A and B, Springer, 5th edition, 2007; team of authors, Compendium of Organic Synthetic Methods, Wiley & Sons. In addition, further methods and also literature references can be issued by the common databases such as, for example, the Reaxys® database of Elsevier, Amsterdam, NL or the SciFinder® database of the American Chemical Society, Washington, US.

The substituted compounds according to the invention of the aforementioned general formula (I) and corresponding stereoisomers and also the respective corresponding acids, bases, salts and solvates are toxicologically safe and are therefore suitable as pharmaceutical active ingredients in pharmaceutical compositions.

The present invention therefore further relates to a pharmaceutical composition containing at least one compound according to the invention of the above-indicated formula (I), in each case if appropriate in the form of one of its isolated or pure stereoisomers, in particular enantiomers or diastereomers, its racemates or in the form of a mixture of stereoisomers, in particular the enantiomers and/or diastereomers, in any desired mixing ratio, or respectively in the form of a corresponding salt, or respectively in the form of a corresponding solvate, and also if appropriate one or more pharmaceutically compatible auxiliaries.

These pharmaceutical compositions according to the invention are suitable in particular for vanilloid receptor 1-(VR1/TRPV1) regulation, preferably for vanilloid receptor 1-(VR1/TRPV1) inhibition and/or for vanilloid receptor 1-(VR1/TRPV1) stimulation, i.e. they exert an agonistic or antagonistic effect.

Likewise, the pharmaceutical compositions according to the invention are preferably suitable for the inhibition and/or treatment of disorders or diseases which are mediated, at least in part, by vanilloid receptors 1.

The pharmaceutical composition according to the invention is suitable for administration to adults and children, including toddlers and babies.

The pharmaceutical composition according to the invention may be found as a liquid, semisolid or solid pharmaceutical form, for example in the form of injection solutions, drops, juices, syrups, sprays, suspensions, tablets, patches, capsules, plasters, suppositories, ointments, creams, lotions, gels, emulsions, aerosols or in multiparticulate form, for example in the form of pellets or granules, if appropriate pressed into tablets, decanted in capsules or suspended in a liquid, and also be administered as such.

In addition to at least one substituted compound of the above-indicated formula (I), if appropriate in the form of one of its individual stereoisomers, in particular enantiomers or diastereomers, its racemate or in the form of mixtures of the stereoisomers, in particular the enantiomers or diastereomers, in any desired mixing ratio, or if appropriate in the form of a corresponding salt or respectively in the form of a corresponding solvate, the pharmaceutical composition according to the invention conventionally contains further physiologically compatible pharmaceutical auxiliaries which can for example be selected from the group consisting of excipients, fillers, solvents, diluents, surface-active substances, dyes, preservatives, blasting agents, slip additives, lubricants, aromas and binders.

The selection of the physiologically compatible auxiliaries and also the amounts thereof to be used depend on whether the pharmaceutical composition is to be administered orally, subcutaneously, parenterally, intravenously, intraperitoneally, intradermally, intramuscularly, intranasally, buccally, rectally or locally, for example to infections of the skin, the mucous membranes and of the eyes. Preparations in the form of tablets, dragées, capsules, granules, pellets, drops, juices and syrups are preferably suitable for oral application; solutions, suspensions, easily reconstitutable dry preparations and also sprays are preferably suitable for parenteral, topical and inhalative application. The substituted compounds according to the invention used in the pharmaceutical composition according to the invention in a repository in dissolved form or in a plaster, agents promoting skin penetration being added if appropriate, are suitable percutaneous application preparations. Orally or percutaneously applicable preparation forms can release the respective substituted compound according to the invention also in a delayed manner.

The pharmaceutical compositions according to the invention are prepared with the aid of conventional means, devices, methods and process known in the art, such as are described for example in, "Remington's Pharmaceutical Sciences", A. R. Gennaro (Editor), $17^{th}$ edition, Mack Publishing Company, Easton, Pa., 1985, in particular in Part 8, Chapters 76 to 93. The corresponding description is introduced herewith by way of reference and forms part of the disclosure. The amount to be administered to the patient of the respective substituted compounds according to the invention of the above-indicated general formula I may vary and is for example dependent on the patient's weight or age and also on the type of application, the indication and the severity of the disorder. Conventionally 0.001 to 100 mg/kg, preferably 0.05 to 75 mg/kg, particularly preferably 0.05 to 50 mg of at least one such compound according to the invention are applied per kg of the patient's body weight.

The pharmaceutical composition according to the invention is preferably suitable for the treatment and/or inhibition of one or more disorders selected from the group consisting of pain selected from the group consisting of acute pain, chronic pain, neuropathic pain and visceral pain; joint pain; hyperalgesia; allodynia; causalgia; migraine; depression; nervous affection; axonal injuries; neurodegenerative diseases, preferably selected from the group consisting of multiple sclerosis, Alzheimer's disease, Parkinson's disease and Huntington's disease; cognitive dysfunctions, preferably cognitive deficiency states, particularly preferably memory disorders; epilepsy; respiratory diseases, preferably selected from the group consisting of asthma, bronchitis and pulmonary inflammation; coughs; urinary incontinence; overactive bladder (OAB); disorders and/or injuries of the gastrointestinal tract; duodenal ulcers; gastric ulcers; irritable bowel syndrome; strokes; eye irritations; skin irritations; neurotic skin diseases; allergic skin diseases; psoriasis; vitiligo; herpes simplex; inflammations, preferably inflammations of the intestine, the eyes, the bladder, the skin or the nasal mucous membrane; diarrhoea; pruritus; osteoporosis; arthritis; osteoarthritis; rheumatic diseases; eating disorders, preferably selected from the group consisting of bulimia, cachexia, anorexia and obesity; medication dependency; misuse of medication; withdrawal symptoms in medication dependency; development of tolerance to medication, preferably to natural or synthetic opioids; drug dependency; misuse of drugs; withdrawal symptoms in drug dependency; alcohol dependency; misuse of alcohol and withdrawal symptoms in alcohol dependency; for diuresis; for antinatriuresis; for influencing the cardiovascular system; for increasing vigilance; for the treatment of wounds and/or burns; for the treatment of severed nerves; for increasing libido; for modulating movement activity; for anxiolysis; for local anaesthesia and/or for inhibiting undesirable side effects, preferably selected from the group consisting of hyperthermia, hypertension and bronchoconstriction, triggered by the administration of vanilloid receptor 1 (VR1/TRPV1 receptor) agonists, preferably selected from the group consisting of capsaicin, resiniferatoxin, olvanil, arvanil, SDZ-249665, SDZ-249482, nuvanil and capsavanil.

Particularly preferably, the pharmaceutical composition according to the invention is suitable for the treatment and/or inhibition of one or more disorders selected from the group consisting of pain, preferably of pain selected from the group consisting of acute pain, chronic pain, neuropathic pain and visceral pain; joint pain; migraine; depression; neurodegenerative diseases, preferably selected from the group consisting of multiple sclerosis, Alzheimer's disease, Parkinson's disease and Huntington's disease; cognitive dysfunctions, preferably cognitive deficiency states, particularly preferably memory disorders; inflammations, preferably inflammations of the intestine, the eyes, the bladder, the skin or the nasal mucous membrane; urinary incontinence; overactive bladder (OAB); medication dependency; misuse of medication; withdrawal symptoms in medication dependency; development of tolerance to medication, preferably development of tolerance to natural or synthetic opioids; drug dependency; misuse of drugs; withdrawal symptoms in drug dependency; alcohol dependency; misuse of alcohol and withdrawal symptoms in alcohol dependency.

Most particularly preferably, the pharmaceutical composition according to the invention is suitable for the treatment and/or inhibition of pain, preferably of pain selected from the group consisting of acute pain, chronic pain, neuropathic pain and visceral pain, and/or urinary incontinence.

The present invention further relates to the use of at least one compound according to the invention and also if appropriate of one or more pharmaceutically compatible auxiliaries for the preparation of a pharmaceutical composition for vanilloid receptor 1-(VR1/TRPV1) regulation, preferably for vanilloid receptor 1-(VR1/TRPV1) inhibition and/or for vanilloid receptor 1-(VR1/TRPV1) stimulation.

Preference is given to the use of at least one substituted compound according to the invention and also if appropriate of one or more pharmaceutically compatible auxiliaries for the preparation of a pharmaceutical composition for the inhibition and/or treatment of disorders or diseases which are mediated, at least in part, by vanilloid receptors 1.

Particular preference is given to the use of at least one compound according to the invention and also if appropriate of one or more pharmaceutically compatible auxiliaries for the preparation of a pharmaceutical composition for the treatment and/or inhibition of one or more disorders selected from the group consisting of pain, preferably of pain selected from the group consisting of acute pain, chronic pain, neuropathic pain and visceral pain and joint pain.

Particular preference is given to the use of at least one compound according to the invention and also if appropriate of one or more pharmaceutically compatible auxiliaries for the preparation of a pharmaceutical composition for the treatment and/or inhibition of one or more disorders selected from the group consisting of hyperalgesia; allodynia; causalgia; migraine; depression; nervous affection; axonal injuries; neurodegenerative diseases, preferably selected from the group consisting of multiple sclerosis, Alzheimer's disease, Parkinson's disease and Huntington's disease; cognitive dysfunctions, preferably cognitive deficiency states, particularly preferably memory disorders; epilepsy; respiratory diseases, preferably selected from the group consisting of asthma, bronchitis and pulmonary inflammation; coughs; urinary incontinence; overactive bladder (OAB); disorders and/or injuries of the gastrointestinal tract; duodenal ulcers; gastric ulcers; irritable bowel syndrome; strokes; eye irritations; skin irritations; neurotic skin diseases; allergic skin diseases; psoriasis; vitiligo; herpes simplex; inflammations, preferably inflammations of the intestine, the eyes, the bladder, the skin or the nasal mucous membrane; diarrhoea; pruritus; osteoporosis; arthritis; osteoarthritis; rheumatic diseases; eating disorders, preferably selected from the group consisting of bulimia, cachexia, anorexia and obesity; medication dependency; misuse of medication; withdrawal symptoms in medication dependency; development of tolerance to medication, preferably to natural or synthetic opioids; drug dependency; misuse of drugs; withdrawal symptoms in drug dependency; alcohol dependency; misuse of alcohol and withdrawal symptoms in alcohol dependency; for diuresis; for antinatriuresis; for influencing the cardiovascular system; for increasing vigilance; for the treatment of wounds and/or burns; for the treatment of severed nerves; for increasing libido; for modulating movement activity; for anxiolysis; for local anaesthesia and/or for inhibiting undesirable side effects, preferably selected from the group consisting of hyperthermia, hypertension and bronchoconstriction, triggered by the administration of vanilloid receptor 1 (VR1/TRPV1 receptor) agonists, preferably selected from the group consisting of capsaicin, resiniferatoxin, olvanil, arvanil, SDZ-249665, SDZ-249482, nuvanil and capsavanil.

Most particular preference is given to the use of at least one substituted compound according to the invention and also if appropriate of one or more pharmaceutically compatible auxiliaries for the preparation of a pharmaceutical composition for the treatment and/or inhibition of one or more disorders selected from the group consisting of pain, preferably of pain selected from the group consisting of acute pain, chronic pain, neuropathic pain and visceral pain; joint pain; migraine; depression; neurodegenerative diseases, preferably selected from the group consisting of multiple sclerosis, Alzheimer's disease, Parkinson's disease and Huntington's disease; cognitive dysfunctions, preferably cognitive deficiency states, particularly preferably memory disorders; inflammations, preferably inflammations of the intestine, the eyes, the bladder, the skin or the nasal mucous membrane; urinary incontinence; overactive bladder (OAB); medication dependency; misuse of medication; withdrawal symptoms in medication dependency; development of tolerance to medication, preferably development of tolerance to natural or synthetic opioids; drug dependency; misuse of drugs; withdrawal symptoms in drug dependency; alcohol dependency; misuse of alcohol and withdrawal symptoms in alcohol dependency.

Particular preference is given to the use of at least one substituted compound according to the invention and also if appropriate of one or more pharmaceutically compatible auxiliaries for the preparation of a pharmaceutical composition for the treatment and/or inhibition of pain, preferably selected from the group consisting of acute pain, chronic pain, neuropathic pain and visceral pain, and/or urinary incontinence.

The present invention further relates to at least one substituted compound according to the invention and also if appropriate to one or more pharmaceutically compatible auxiliaries for vanilloid receptor 1-(VR1/TRPV1) regulation, preferably for vanilloid receptor 1-(VR1/TRPV1) inhibition and/or for vanilloid receptor 1-(VR1/TRPV1) stimulation.

Preference is given to at least one substituted compound according to the invention and also if appropriate to one or more pharmaceutically compatible auxiliaries for the inhibition and/or treatment of disorders or diseases which are mediated, at least in some cases, by vanilloid receptors 1.

Particular preference is given to at least one compound according to the invention and also if appropriate to one or more pharmaceutically compatible auxiliaries for the treatment and/or inhibition of one or more disorders selected from the group consisting of pain, preferably of pain selected from the group consisting of acute pain, chronic pain, neuropathic pain and visceral pain and joint pain.

Particular preference is given to at least one compound according to the invention and also if appropriate to one or more pharmaceutically compatible auxiliaries for the treatment and/or inhibition of one or more disorders selected from the group consisting of hyperalgesia; allodynia; causalgia; migraine; depression; nervous affection; axonal injuries; neurodegenerative diseases, preferably selected from the group consisting of multiple sclerosis, Alzheimer's disease, Parkinson's disease and Huntington's disease; cognitive dysfunctions, preferably cognitive deficiency states, particularly preferably memory disorders; epilepsy; respiratory diseases, preferably selected from the group consisting of asthma, bronchitis and pulmonary inflammation; coughs; urinary incontinence; overactive bladder (OAB); disorders and/or injuries of the gastrointestinal tract; duodenal ulcers; gastric ulcers; irritable bowel syndrome; strokes; eye irritations; skin irritations; neurotic skin diseases; allergic skin diseases; psoriasis; vitiligo; herpes simplex; inflammations, preferably inflammations of the intestine, the eyes, the bladder, the skin or the nasal mucous membrane; diarrhoea; pruritus; osteoporosis; arthritis; osteoarthritis; rheumatic diseases; eating disorders, preferably selected from the group consisting of bulimia, cachexia, anorexia and obesity; medication dependency; misuse of medication; withdrawal symptoms in medication dependency; development of tolerance to medication, preferably to natural or synthetic opioids; drug dependency; misuse of drugs; withdrawal symptoms in drug dependency; alcohol dependency; misuse of alcohol and withdrawal symptoms in alcohol dependency; for diuresis; for antinatriuresis; for influencing the cardiovascular system; for increasing vigilance; for the treatment of wounds and/or burns; for the treatment of severed nerves; for increasing libido; for modulating movement activity; for anxiolysis; for local anaesthesia and/or for inhibiting undesirable side effects, preferably selected from the group consisting of hyperthermia, hypertension and bronchoconstriction, triggered by the administration of vanilloid receptor 1 (VR1/TRPV1 receptor) agonists, preferably selected from the group consisting of capsaicin, resiniferatoxin, olvanil, arvanil, SDZ-249665, SDZ-249482, nuvanil and capsavanil.

Most particular preference is given to at least one compound according to the invention and also if appropriate to one or more pharmaceutically compatible auxiliaries for the treatment and/or inhibition of one or more disorders selected from the group consisting of pain, preferably of pain selected from the group consisting of acute pain, chronic pain, neuropathic pain and visceral pain; joint pain; migraine; depression; neurodegenerative diseases, preferably selected from the group consisting of multiple sclerosis, Alzheimer's disease, Parkinson's disease and Huntington's disease; cognitive dysfunctions, preferably cognitive deficiency states, particularly preferably memory disorders; inflammations, preferably inflammations of the intestine, the eyes, the bladder, the skin or the nasal mucous membrane; urinary incontinence; overactive bladder (OAB); medication dependency; misuse of medication; withdrawal symptoms in medication dependency; development of tolerance to medication, preferably development of tolerance to natural or synthetic opioids; drug dependency; misuse of drugs; withdrawal symptoms in drug dependency; alcohol dependency; misuse of alcohol and withdrawal symptoms in alcohol dependency.

Particular preference is given to at least one compound according to the invention and also if appropriate to one or more pharmaceutically compatible auxiliaries for the treatment and/or inhibition of pain, preferably selected from the group consisting of acute pain, chronic pain, neuropathic pain and visceral pain, and/or urinary incontinence.

The present invention further relates to at least one substituted compound according to the invention and also if appropriate to one or more pharmaceutically compatible auxiliaries for use in vanilloid receptor 1-(VR1/TRPV1) regulation, preferably for use in vanilloid receptor 1-(VR1/TRPV1) inhibition and/or for vanilloid receptor 1-(VR1/TRPV1) stimulation.

Preference is given to at least one substituted compound according to the invention and also if appropriate to one or more pharmaceutically compatible auxiliaries for use in the inhibition and/or treatment of disorders or diseases which are mediated, at least in some cases, by vanilloid receptors 1.

Particular preference is given to at least one compound according to the invention and also if appropriate to one or more pharmaceutically compatible auxiliaries for use in the treatment and/or inhibition of one or more disorders selected from the group consisting of pain, preferably of pain selected from the group consisting of acute pain, chronic pain, neuropathic pain and visceral pain and joint pain.

Particular preference is given to at least one compound according to the invention and also if appropriate to one or more pharmaceutically compatible auxiliaries for use in the treatment and/or inhibition of one or more disorders selected from the group consisting of hyperalgesia; allodynia; causalgia; migraine; depression; nervous affection; axonal injuries; neurodegenerative diseases, preferably selected from the group consisting of multiple sclerosis, Alzheimer's disease, Parkinson's disease and Huntington's disease; cognitive dysfunctions, preferably cognitive deficiency states, particularly preferably memory disorders; epilepsy; respiratory diseases, preferably selected from the group consisting of asthma, bronchitis and pulmonary inflammation; coughs; urinary incontinence; overactive bladder (OAB); disorders and/or injuries of the gastrointestinal tract; duodenal ulcers; gastric ulcers; irritable bowel syndrome; strokes; eye irritations; skin irritations; neurotic skin diseases; allergic skin diseases; psoriasis; vitiligo; herpes simplex; inflammations, preferably inflammations of the intestine, the eyes, the bladder, the skin or the nasal mucous membrane; diarrhoea; pruritus; osteoporosis; arthritis; osteoarthritis; rheumatic diseases; eating disorders, preferably selected from the group consisting of bulimia, cachexia, anorexia and obesity; medication dependency; misuse of medication; withdrawal symptoms in medication dependency; development of tolerance to medication, preferably to natural or synthetic opioids; drug dependency; misuse of drugs; withdrawal symptoms in drug dependency; alcohol dependency; misuse of alcohol and withdrawal symptoms in alcohol dependency; for diuresis; for antinatriuresis; for influencing the cardiovascular system; for increasing vigilance; for the treatment of wounds and/or burns; for the treatment of severed nerves; for increasing libido; for modulating movement activity; for anxiolysis; for local anaesthesia and/or for inhibiting undesirable side effects, preferably selected from the group consisting of hyperthermia, hypertension and bronchoconstriction, triggered by the administration of vanilloid receptor 1 (VR1/TRPV1 receptor) agonists, preferably selected from the group consisting of capsaicin, resiniferatoxin, olvanil, arvanil, SDZ-249665, SDZ-249482, nuvanil and capsavanil.

Most particular preference is given to at least one compound according to the invention and also if appropriate to one or more pharmaceutically compatible auxiliaries for use in the treatment and/or inhibition of one or more disorders selected from the group consisting of pain, preferably of pain selected from the group consisting of acute pain, chronic pain, neuropathic pain and visceral pain; joint pain; migraine; depression; neurodegenerative diseases, preferably selected from the group consisting of multiple sclerosis, Alzheimer's disease, Parkinson's disease and Huntington's disease; cognitive dysfunctions, preferably cognitive deficiency states, particularly preferably memory disorders; inflammations, preferably inflammations of the intestine, the eyes, the bladder, the skin or the nasal mucous membrane; urinary incontinence; overactive bladder (OAB); medication dependency; misuse of medication; withdrawal symptoms in medication dependency; development of tolerance to medication, preferably development of tolerance to natural or synthetic opioids; drug dependency; misuse of drugs; withdrawal symptoms in drug dependency; alcohol dependency; misuse of alcohol and withdrawal symptoms in alcohol dependency.

Particular preference is given to at least one compound according to the invention and also if appropriate to one or more pharmaceutically compatible auxiliaries for use in the treatment and/or inhibition of pain, preferably selected from the group consisting of acute pain, chronic pain, neuropathic pain and visceral pain, and/or urinary incontinence.

Another aspect of the present invention is a method for vanilloid receptor 1-(VR1/TRPV1) regulation, preferably for vanilloid receptor 1-(VR1/TRPV1) inhibition and/or for vanilloid receptor 1-(VR1/TRPV1) stimulation, and, further, a method of treatment and/or inhibition of disorders and/or diseases, which are mediated, at least in part, by vanilloid receptors 1, in a mammal, preferably of disorders and/or diseases selected from the group consisting of pain, preferably pain selected from the group consisting of acute pain, chronic pain, neuropathic pain, visceral pain and joint pain; hyperalgesia; allodynia; causalgia; migraine; depression; nervous affection; axonal injuries; neurodegenerative diseases, preferably selected from the group consisting of multiple sclerosis, Alzheimer's disease, Parkinson's disease and Huntington's disease; cognitive dysfunctions, preferably cognitive deficiency states, particularly preferably memory disorders; epilepsy; respiratory diseases, preferably selected from the group consisting of asthma, bronchitis and pulmonary inflammation; coughs; urinary incontinence; overactive bladder (OAB); disorders and/or injuries of the gastrointestinal tract; duodenal ulcers; gastric ulcers; irritable bowel syndrome; strokes; eye irritations; skin irritations; neurotic skin diseases; allergic skin diseases; psoriasis; vitiligo; herpes simplex; inflammations, preferably inflammations of the intestine, the eyes, the bladder, the skin or the nasal mucous membrane; diarrhoea; pruritus; osteoporosis; arthritis; osteoarthritis; rheumatic diseases; eating disorders, preferably selected from the group consisting of bulimia, cachexia, anorexia and obesity; medication dependency; misuse of medication; withdrawal symptoms in medication dependency; development of tolerance to medication, preferably to natural or synthetic opioids; drug dependency; misuse of drugs; withdrawal symptoms in drug dependency; alcohol dependency; misuse of alcohol and withdrawal symptoms in alcohol dependency; for diuresis; for antinatriuresis; for influencing the cardiovascular system; for increasing vigilance; for the treatment of wounds and/or burns; for the treatment of severed nerves; for increasing libido; for modulating movement activity; for anxiolysis; for local anaesthesia and/or for inhibiting undesirable side effects, preferably selected from the group consisting of hyperthermia, hypertension and bronchoconstriction, triggered by the administration of vanilloid receptor 1 (VR1/TRPV1 receptor) agonists, preferably selected from the group consisting of capsaicin, resiniferatoxin, olvanil, arvanil, SDZ-249665, SDZ-249482, nuvanil and capsavanil, which comprises administering an effective amount of at least one substituted compound according to the invention to the mammal.

The effectiveness against pain can be shown, for example, in the Bennett or Chung model (Bennett, G. J. and Xie, Y. K., A peripheral mononeuropathy in rat that produces disorders of pain sensation like those seen in man, Pain 1988, 33(1), 87-107; Kim, S. H. and Chung, J. M., An experimental model for peripheral neuropathy produced by segmental spinal nerve ligation in the rat, Pain 1992, 50(3), 355-363), by tail flick experiments (e.g. according to D'Amour und Smith (J. Pharm. Exp. Ther. 72, 74 79 (1941)) or by the formalin test (e.g. according to D. Dubuisson et al., Pain 1977, 4, 161-174).

Pharmacological Methods

I. Functional Testing Carried Out on the Vanilloid Receptor 1 (VR1/TRPV1 Receptor)

The agonistic or antagonistic effect of the substances to be tested on the rat-species vanilloid receptor 1 (VR1/TRPV1) can be determined using the following assay. In this assay, the influx of $Ca^{2+}$ through the receptor channel is quantified with the aid of a $Ca^{2+}$-sensitive dye (type Fluo-4, Molecular Probes Europe BV, Leiden, the Netherlands) in a fluorescent imaging plate reader (FLIPR, Molecular Devices, Sunnyvale, USA).

Method:

Complete Medium:

50 ml HAMS F12 nutrient mixture (Gibco Invitrogen GmbH, Karlsruhe, Germany) with 10% by volume of FCS (foetal calf serum, Gibco Invitrogen GmbH, Karlsruhe, Germany, heat-inactivated);

2 mM L-glutamine (Sigma, Munich, Germany);

1% by weight of AA solution (antibiotic/antimyotic solution, PAA, Pasching, Austria), and 25 ng/ml NGF medium (2.5 S, Gibco Invitrogen GmbH, Karlsruhe, Germany)

Cell Culture Plate:

Poly-D-lysine-coated, black 96-well plates having a clear base (96-well black/clear plate, BD Biosciences, Heidelberg, Germany) are additionally coated with laminin (Gibco Invitrogen GmbH, Karlsruhe, Germany), the laminin being diluted with PBS (Ca—Mg-free PBS, Gibco Invitrogen GmbH, Karlsruhe, Germany) to a concentration of 100 μg/ml. Aliquots having a laminin concentration of 100 μg/ml are removed and stored at −20° C. The aliquots are diluted with PBS in a ratio of 1:10 to 10 μg/ml of laminin and respectively 50 μL of the solution are pipetted into a recess in the cell culture plate. The cell culture plates are incubated for at least two hours at 37° C., the excess solution is removed by suction and the recesses are each washed twice with PBS. The coated cell culture plates are stored with excess PBS which is not removed until just before the feeding of the cells.

Preparation of the Cells:

The vertebral column is removed from decapitated rats and placed immediately into cold HBSS buffer (Hank's buffered saline solution, Gibco Invitrogen GmbH, Karlsruhe, Germany), i.e. buffer located in an ice bath, mixed with 1% by volume (percent by volume) of an AA solution (antibiotic/antimyotic solution, PAA, Pasching, Austria). The vertebral column is cut longitudinally and removed together with fasciae from the vertebral canal. Subsequently, the dorsal root ganglia (DRG) are removed and again stored in cold HBSS buffer mixed with 1% by volume of an AA solution. The DRG, from which all blood remnants and spinal nerves have been removed, are transferred in each case to 500 μL of cold type 2 collagenase (PAA, Pasching, Austria) and incubated for 35 minutes at 37° C. After the addition of 2.5% by volume of trypsin (PAA, Pasching, Austria), incubation is continued for 10 minutes at 37° C. After complete incubation, the enzyme solution is carefully pipetted off and 500 μL of complete medium are added to each of the remaining DRG. The DRG are respectively suspended several times, drawn through cannulae No. 1, No. 12 and No. 16 using a syringe and transferred to a 50 ml Falcon tube which is filled up to 15 ml with complete medium. The contents of each Falcon tube are respectively filtered through a 70 μm Falcon filter element and centrifuged for 10 minutes at 1,200 rpm and RT. The resulting pellet is respectively taken up in 250 μL of complete medium and the cell count is determined.

The number of cells in the suspension is set to $3\times10^5$ per ml and 150 μL of this suspension are in each case introduced into a recess in the cell culture plates coated as described hereinbefore. In the incubator the plates are left for two to three days at 37° C., 5% by volume of $CO_2$ and 95% relative humidity. Subsequently, the cells are loaded with 2 μM of Fluo-4 and 0.01% by volume of Pluronic F127 (Molecular Probes Europe BV, Leiden, the Netherlands) in HBSS buffer (Hank's buffered saline solution, Gibco Invitrogen GmbH, Karlsruhe, Germany) for 30 min at 37° C., washed 3 times with HBSS buffer and after further incubation for 15 minutes at RT used for $Ca^{2+}$ measurement in a FLIPR assay. The $Ca^{2+}$-dependent fluorescence is in this case measured before and after the addition of substances (λex=488 nm, λem=540 nm). Quantification is carried out by measuring the highest fluorescence intensity (FC, fluorescence counts) over time.

FLIPR Assay:

The FLIPR protocol consists of 2 substance additions. First the compounds to be tested (10 μM) are pipetted onto the cells and the $Ca^{2+}$ influx is compared with the control (capsaicin 10 μM). This provides the result in % activation based on the $Ca^{2+}$ signal after the addition of 10 μM of capsaicin (CP). After 5 minutes' incubation, 100 nM of capsaicin are applied and the $Ca^{2+}$ influx is also determined.

Desensitising agonists and antagonists lead to suppression of the $Ca^{2+}$ influx. The % inhibition is calculated compared to the maximum achievable inhibition with 10 μM of capsaicin.

Triple analyses (n=3) are carried out and repeated in at least 3 independent experiments (N=4).

Starting from the percentage displacement caused by different concentrations of the compounds to be tested of general formula I, $IC_{50}$ inhibitory concentrations which cause a 50-percent displacement of capsaicin were calculated. $K_i$ values for the test substances were obtained by conversion by the Cheng-Prusoff equation (Cheng, Prusoff; Biochem. Pharmacol. 22, 3099-3108, 1973).

II. Functional Tests Carried Out on the Vanilloid Receptor (VR1)

The agonistic or antagonistic effect of the substances to be tested on the vanilloid receptor 1 (VR1) can also be determined using the following assay. In this assay, the influx of $Ca^{2+}$ through the channel is quantified with the aid of a $Ca^{2+}$-sensitive dye (type Fluo-4, Molecular Probes Europe By, Leiden, the Netherlands) in a fluorescent imaging plate reader (FLIPR, Molecular Devices, Sunnyvale, USA).

Method:

Chinese hamster ovary cells (CHO K1 cells, European Collection of Cell Cultures (ECACC) United Kingdom) are stably transfected with the VR1 gene. For functional testing, these cells are plated out on poly-D-lysine-coated black 96-well plates having a clear base (BD Biosciences, Heidelberg, Germany) at a density of 25,000 cells/well. The cells are incubated overnight at 37° C. and 5% $CO_2$ in a culture medium (Ham's F12 nutrient mixture, 10% by volume of FCS (foetal calf serum), 18 μg/ml of L-proline). The next day the cells are incubated with Fluo-4 (Fluo-4 2 μM, 0.01% by volume of Pluronic F127, Molecular Probes in HBSS (Hank's buffered saline solution), Gibco Invitrogen GmbH, Karlsruhe, Germany) for 30 minutes at 37° C. Subsequently, the plates are washed three times with HBSS buffer and after further incubation for 15 minutes at RT used for $Ca^{2+}$ measurement in a FLIPR assay. The $Ca^{2+}$-dependent fluorescence is measured before and after the addition of the substances to be tested (λex wavelength=488 nm, λem=540 nm). Quantification is carried out by measuring the highest fluorescence intensity (FC, fluorescence counts) over time.

FLIPR Assay:

The FLIPR protocol consists of 2 substance additions. First the compounds to be tested (10 μM) are pipetted onto the cells and the $Ca^{2+}$ influx is compared with the control (capsaicin 10 μM) (% activation based on the $Ca^{2+}$ signal after the addition of 10 μM of capsaicin). After 5 minutes' incubation, 100 nM of capsaicin are applied and the $Ca^{2+}$ influx is also determined.

Desensitising agonists and antagonists led to suppression of the $Ca^{2+}$ influx. The % inhibition is calculated compared to the maximum achievable inhibition with 10 μM of capsaicin.

Starting from the percentage displacement caused by different concentrations of the compounds to be tested of general formula I, $IC_{50}$ inhibitory concentrations which cause a 50-percent displacement of capsaicin were calculated. $K_i$ values for the test substances were obtained by conversion by the Cheng-Prusoff equation (Cheng, Prusoff; Biochem. Pharmacol. 22, 3099-3108, 1973).

III. Formalin Test Carried Out on Mice

In the formalin test, the testing to determine the antinociceptive effect of the compounds according to the invention is carried out on male mice (NMRI, 20 to 30 g body weight, Iffa, Credo, Belgium).

In the formalin test as described by D. Dubuisson et al., Pain 1977, 4, 161-174, a distinction is drawn between the first (early) phase (0 to 15 minutes after the injection of formalin) and the second (late) phase (15 to 60 minutes after the injection of formalin). The early phase, as an immediate reaction to the injection of formalin, is a model of acute pain, whereas the late phase is regarded as a model of persistent (chronic) pain (T. J. Coderre et al., Pain 1993, 52, 259-285). The corresponding descriptions in the literature are introduced herewith by way of reference and form part of the disclosure.

The compounds according to the invention are tested in the second phase of the formalin test to obtain information about the effects of substances on chronic/inflammatory pain.

The moment at which the compounds according to the invention are applied before the injection of formalin is selected as a function of the type of application of the compounds according to the invention. 10 mg of the test substances/kg of body weight are applied intravenously 5 minutes before the injection of formalin which is carried out by a single subcutaneous injection of formalin (20 μL, 1% aqueous solution) into the dorsal side of the right hind paw, thus inducing in free moving test animals a nociceptive reaction which manifests itself in marked licking and biting of the paw in question.

Subsequently, the nociceptive behaviour is continuously detected by observing the animals over a test period of three minutes in the second (late) phase of the formalin test (21 to 24 minutes after the injection of formalin). The pain behaviour is quantified by adding up the seconds over which the animals display licking and biting of the paw in question during the test period.

The comparison is carried out respectively with control animals which are given vehicles (0.9% aqueous sodium chloride solution) instead of the compounds according to the invention before the administration of formalin. Based on the quantification of the pain behavior, the effect of the substance is determined in the formalin test as a percentage change relative to the corresponding control.

After the injection of substances having an antinociceptive effect in the formalin test, the described behaviour of the animals, i.e. licking and biting, is reduced or eliminated.

IV. Testing of Analgesic Efficacy in the Writhing Test

The testing of analgesic efficacy in the compounds according to the invention of general formula I was carried out by phenylquinone-induced writhing in mice (modified in accordance with I. C. Hendershot and J. Forsaith (1959), J. Pharmacol. Exp. Ther. 125, 237-240). The corresponding description in the literature is introduced herewith by way of reference and forms part of the disclosure.

Male NMRI mice weighing from 25 to 30 g were used for this purpose. 10 minutes after intravenous administration of the compounds to be tested, groups of 10 animals per compound dose received 0.3 ml/mouse of a 0.02% aqueous solution of phenylquinone (phenylbenzoquinone, Sigma, Deisenhofen, Germany; solution prepared by adding 5% by weight of ethanol and storage in a water bath at 45° C.) applied intraperitoneally. The animals were placed individually into observation cages. A pushbutton counter was used to record the number of pain-induced stretching movements (what are known as writhing reactions=straightening of the torso with stretching of the rear extremities) for 5 to 20 minutes after the administration of phenylquinone. The control was provided by animals which had received only physiological saline solution. All the compounds were tested at the standard dosage of 10 mg/kg.

V. Hypothermia Assay Carried Out on Mice

Description of the Method:

The hypothermia assay is carried out on male NMRI mice (weight 25-35 grams, breeder IFFA CREDO, Brussels, Belgium). The animals were kept under standardised conditions: light/dark rhythm (from 6:00 to 18:00 light phase; from 18:00 to 6:00 dark phase), RT 19-22° C., relative humidity 35-70%, 15 room air changes per hour, air movement <0.2 m/sec. The animals received standard feed (ssniff R/M-Haltung, ssniff Spezialdiäten GmbH, Soest, Germany) and tap water. Water and feed were withdrawn during the experiment. All the animals were used only once during the experiment. The animals had an acclimatisation period of at least 5 days.

Acute application of capsaicin (VR-1 agonist) leads to a drop in the core temperature of the body in rats and mice due to stimulation of heat sensors. Only specifically effective VR-1 receptor antagonists can antagonise the capsaicin-induced hypothermia. By contrast, hypothermia induced by morphine is not antagonised by VR-1 antagonists. This model is therefore suitable for identifying substances with VR-1 antagonistic properties via their effect on body temperature.

Measurement of the core temperature was carried out using a digital thermometer (Thermalert TH-5, physitemp, Clifton N.J., USA). The sensing element is in this case inserted into the rectum of the animals.

To give an individual basic value for each animal, the body temperature is measured twice at an interval of approx. half an hour. One group of animals (n=6 to 10) then receives an intraperitoneal (i.p.) application of capsaicin 3 mg/kg and vehicle (control group). Another group of animals receives the substance to be tested (i.v. or p.o.) and additionally capsaicin (3 mg/kg) i.p. The test substance is applied i.v. 10 min, or p.o 15 minutes, prior to capsaicin. The body temperature is then measured 7.5/15 and 30 min following capsaicin (i.v.+i.p.) or 15/30/60/90/120 min (p.o.+i.p.) following capsaicin. In addition, one group of animals is treated with the test substance only and one group with vehicle only. The evaluation or representation of the measured values as the mean+/−SEM of the absolute values is carried out as a graphical representation. The antagonistic effect is calculated as the percentage reduction of the capsaicin-induced hypothermia.

VI. Neuropathic Pain in Mice

Efficacy in neurotic pain was tested using the Bennett model (chronic constriction injury; Bennett und Xie, 1988, Pain 33: 87-107).

Three loose ligatures are tied around the right ischiadic nerve of Ketavet/Rompun-anaesthetised NMRI mice weighing 16-18 g. The animals develop hypersensitivity of the innervated paw caused by the damaged nerve, which hypersensitivity is quantified, following a recovery phase of one week, over a period of approximately three weeks by a cold metal plate (temperature 4° C.) (cold allodynia). The animals are observed on this plate over a period of 2 min and the withdrawal reactions of the damaged paw are counted. Based on the pre-value prior to the application of the substance, the substance's effect over a certain period of time is determined at various points in time (for example 15, 30, 45, or 60 min following application) and the resultant area under the curve (AUC) and/or the inhibition of cold allodynia at the individual measuring points is/are expressed as a percentage effect relative to the vehicle control (AUC) or to the starting value (individual measuring points). The group size is n=10, the significance of an antiallodynic effect (*=p<0.05) is determined with the aid of an analysis of variance with repeated measures and Bonferroni post hoc analysis.

The invention will be described in further detail hereinafter with reference to illustrative examples. This description is intended merely by way of example and does not limit the scope and concept of the invention.

EXAMPLES

The indication "equivalents" ("eq.") means molar equivalents, "RT" means room temperature, "M" and "N" are indications of concentration in mol/l, "aq." means aqueous, "sat." means saturated, "sol." means solution, "conc." means concentrated.

Further Abbreviations:

AcOH acetic acid
d days
BOP 1-benzotriazolyloxy-tris-(dimethylamino)phosphonium hexafluorophosphate
$BH_3.S(CH_3)_2$ borane-methyl sulfide complex ($BH_3$-DMS)
BINAP 2,2'-bis(diphenylphosphino)-1,1'-binaphthyl
brine saturated sodium chloride solution (NaCl sol.)
bipy 2,2'-bipyridine/2,2'-bipyridyl
Boc tert-butyloxycarbonyl
n-BuLi n-butyllithium
CC column chromatography on silica gel
$CH_3COOK$ potassium acetate
DBU 1,8-diazabicyclo[5.4.0]undec-7-en
DMA dimethylamine
DCC N,N'-dicyclohexylcarbodiimide
DCM dichloromethane
DIPEA N,N-diisopropylethylamine
DMF N,N-dimethylformamide
DMAP 4-dimethylaminopyridine
DMSO dimethyl sulfoxide
DPPF 1,1'-bis(diphenylphosphino)ferrocene
EDC N-(3-dimethylaminopropyl)-N'-ethylcarbodiimide
EDCl N-ethyl-N'-(3-dimethylaminopropyl)carbodiimide hydrochloride
EtOAc ethyl acetate
ether diethyl ether
EtOH ethanol
sat. saturated
h hour(s)
$H_2O$ water
GC gas chromatography
HBTU O-(benzotriazol-1-yl)-N,N,N',N'-tetramethyluronium hexafluorophosphate
HOBt N-hydroxybenzotriazole
LAH lithium aluminium hydride
LG leaving group
m/z mass-to-charge ratio
MeCN acetonitrile
MeOH methanol
min minutes
MS mass spectrometry
NA not available
$NEt_3$ triethylamine
NBS N-bromosuccinimide
TEA triethylamine
$NiBr_2$ bipy complex of nickel(II) bromide and 2,2'-bipyridine
NMO N-methylmorpholine-N-oxide
NMP N-methyl-2-pyrrolidon
Pd/C palladium on charcoal
$Pd_2(dba)_3$ tris(dibenzylideneacetone)dipalladium(0)
$Pd(dppf)Cl_2$ [1,1'-bis(diphenylphosphino)ferrocene]dichloropalladium(II)
$Pd(PPh_3)_4$ tetrakis(triphenylphosphine)palladium(0)
PE petroleum ether
TBAF tetra-n-butylammonium fluoride
TBTU O-(benzotriazol-1-yl)-N,N,N',N'-tetramethyluronium tetrafluoroborate
TBDMSCl tert-butyldimethylsilyl chloride
TLC thin layer chromatography
$R_f$ retention factor
SC silica gel column chromatography
THF tetrahydrofuran
TFA trifluoroacetic acid
TLC thin layer chromatography
v/v volume ratio
w/w weight in weight The yields of the compounds prepared were not optimized. All temperatures are uncorrected.

All starting materials which are not explicitly described were either commercially available (the details of suppliers such as for example Acros, Avocado, Aldrich, Bachem, Fluka, Lancaster, Maybridge, Merck, Sigma, TCI, Oakwood, etc. can be found in the Symyx® Available Chemicals Database of MDL, San Ramon, US, for example) or the synthesis thereof has already been described precisely in the specialist literature (experimental guidelines can be looked up in the Reaxys® Database of Elsevier, Amsterdam, NL, for example) or can be prepared using the conventional methods known to persons skilled in the art.

The stationary phase used for the column chromatography was silica gel 60 (0.04-0.063 mm) from E. Merck, Darmstadt. The thin-layer chromatographic tests were carried out using HPTLC precoated plates, silica gel 60 F 254, from E. Merck, Darmstadt.

The mixing ratios of solvents, mobile solvents or for chromatographic tests are respectively specified in volume/volume.

All the intermediate products and example compounds were analytically characterised by $^1$H-NMR spectroscopy. In addition, mass spectrometry tests (MS, m/z indication for $[M+H]^+$) were carried out for all the example compounds and selected intermediate products.

Synthesis of Intermediate Products

1. Synthesis of 3-tert-butyl-1-methyl-1H-pyrazol-5-yl-methanamine (Steps j01-j06)

Step j01: Pivaloyl chloride (J-0) (1 eq., 60 g) was added dropwise to a solution of MeOH (120 ml) within 30 min at 0° C. and the mixture was stirred for 1 h at room temperature. After the addition of water (120 ml), the separated organic phase was washed with water (120 ml), dried over sodium sulfate and codistilled with dichloromethane (150 ml). The liquid product J-I was able to be obtained at 98.6% purity (57 g).

Step j02: NaH (50% in paraffin oil) (1.2 eq., 4.6 g) was dissolved in 1,4-dioxane (120 ml) and the mixture was stirred for a few minutes. Acetonitrile (1.2 eq., 4.2 g) was added dropwise within 15 min and the mixture was stirred for a further 30 min. The methyl pivalate (J-I) (1 eq., 10 g) was added dropwise within 15 min and the reaction mixture was refluxed for 3 h. After complete reaction, the reaction mixture was placed in iced water (200 g), acidified to pH 4.5 and extracted with dichloromethane (12×250 ml). The combined organic phases were dried over sodium sulfate, distilled and after recrystallization from hexane (100 ml) 5 g of the product (J-II) (51% yield) was able to be obtained as a solid brown substance.

Step j03: At room temperature 4,4-dimethyl-3-oxopentanenitrile (J-II) (1 eq., 5 g) was taken up in EtOH (100 ml), mixed with hydrazine hydrate (2 eq., 4.42 g) and refluxed for 3 h. The residue obtained after removal of the EtOH by distillation was taken up in water (100 ml) and extracted with EtOAc (300 ml). The combined organic phases were dried over sodium sulfate, the solvent was removed under vacuum and the product (J-III) (5 g, 89% yield) was obtained as a light red solid after recrystallization from hexane (200 ml).

Step j04: 3-Tert-butyl-1H-pyrazol-5-amine (J-III) (1 eq., 40 g) was dissolved in dilute HCl (120 ml of HCl in 120 ml of water) and mixed dropwise with $NaNO_2$ (1.03 eq., 25 g in 100 ml) at 0-5° C. over a period of 30 min. After stirring for 30 minutes, the reaction mixture was neutralized with $Na_2CO_3$. A diazonium salt obtained by reaction of KCN (2.4 eq., 48 g), water (120 ml) and CuCN (1.12 eq., 31 g) was added dropwise to the reaction mixture within 30 min and the mixture was stirred for a further 30 min at 75° C. After complete reaction, the reaction mixture was extracted with EtOAc (3×500 ml), the combined organic phases were dried over sodium sulfate and the solvent was removed under vacuum. The purification ($SiO_2$, 20% EE/hexane) of the residue by column chromatography produced a white solid (J-IV) (6.5 g, 15.1% yield).

Step j05 (Method 1):

3-tert.-butyl-1H-pyrazol-5-carbonitrile (J-IV) (10 mmol) was added to a suspension of NaH (60%) (12.5 mmol) in DMF (20 ml) at room temperature while stirring. After stirring for 15 minutes, methyl iodide (37.5 mmol) was added dropwise to this reaction mixture at room temperature. After stirring for 30 min at 100° C., the reaction mixture was mixed with water (150 ml) and extracted with dichloromethane (3×75 ml). The combined organic extracts were washed with water (100 ml) and sat. NaCl solution (100 ml) and dried over magnesium sulfate. After removal of the solvent under vacuum, the residue was purified by column chromatography ($SiO_2$, various mixtures of EtOAc and cyclohexane as the mobile solvent) and the product J-V was obtained.

Step j06:

Method 1:

J-V was dissolved together with palladium on carbon (10%, 500 mg) and concentrated HCl (3 ml) in MeOH (30 ml) and exposed to a hydrogen atmosphere for 6 hours at room temperature. The reaction mixture was filtered over celite and the filtrate was concentrated under vacuum. The residue was purified by flash chromatography ($SiO_2$, EtOAc) and the product (II) was obtained in this way.

Method 2:

J-V was dissolved in THF (10 ml) and $BH_3.S(CH_3)_2$ (2.0 M in THF, 3 ml, 3 equivalent) was added thereto. The reaction mixture was heated to reflux for 8 hours, aq. 2 N HCl (2 N) was added thereto and the reaction mixture was refluxed for a further 30 minutes. The reaction mixture was mixed with aq. NaOH solution (2N) and washed with EtOAc. The combined organic phases were washed with sat. aq. NaCl solution and dried over magnesium sulfate. The solvent is removed under vacuum and the residue is purified by column chromatography ($SiO_2$, various mixtures of dichloromethane and methanol as the mobile solvent) and the product (II) (3-tert-butyl-1-methyl-1H-pyrazol-5-yl) methanamine) is obtained in this way.

2. The Following Further Intermediate Products were Synthesized in a Similar Manner Using the Process Described Above Under 1

3-tert-butyl-1-hexyl-1H-pyrazol-5-yl-methanamine

3. Alternatively, Step j05 can Also be Carried Out as Follows (Method 2)

Step j05 (Method 2):

A mixture of 3-tert-butyl-1H-pyrazol-5-carbonitrile (J-IV) (10 mmol), a boronic acid $B(OH)_2R^1$ or a corresponding boronic acid ester (20 mmol) and copper (II) acetate (15 mmol) is placed in dichloromethane (200 ml), mixed with pyridine (20 mmol) while stirring at room temperature and the mixture is stirred for 16 h. After removal of the solvent under vacuum, the resulting residue is purified by column chromatography ($SiO_2$, various mixtures of EtOAc and cyclohexane as the mobile solvent) and the product J-V is obtained in this way.

The following further intermediate products were prepared in this way (steps j01-j06):

(3-tert-butyl-1-cyclohexenyl-1H-pyrazol-5-yl)-methanamine (3-tert-butyl-1-phenyl-1H-pyrazol-5-yl)-methanamine (3-tert-butyl-1-p-tolyl-1H-pyrazol-5-yl)-methanamine (3-tert-butyl-1-(4-tert-butylphenyl)-1H-pyrazol-5-yl)methanamine (3-tert-butyl-1-(4-chlorophenyl)-1H-pyrazol-5-yl)methanamine (3-tert-butyl-1-(3-chlorophenyl)-1H-pyrazol-5-yl)methanamine (3-tert-butyl-1-(3-chloro-fluorophenyl)-1H-pyrazol-5-yl)methanamine (3-tert-butyl-1-(4-methoxyphenyl)-1H-pyrazol-5-yl)methanamine (E)-(3-tert-butyl-1-(4-methylstyryl)-1H-pyrazol-5-yl)methanamine

4. Synthesis of 1-(3-chlorophenyl)-3-(trifluoromethyl)-1H-pyrazol-5-yl-methanamine (steps k01-k05 and j06)

Step k01: LAlH (lithium aluminium hydride) (0.25 eq., 0.7 g) was dissolved in dry diethyl ether (30 ml) under a protective gas atmosphere and stirred for 2 h at room temperature. The suspension obtained was taken up in diethyl ether (20 ml). Ethyl-2,2,2-trifluoroacetate (K-0) (1 eq., 10 g) was taken up in dry diethyl ether (20 ml) and added dropwise to the suspension at −78° C. over a period of 1 h. The mixture was then the stirred for a further 2 h at −78° C. EtOH (95%) (2.5 ml) was then added dropwise, the reaction mixture was heated to room temperature and placed on iced water (30 ml) with concentrated $H_2SO_4$ (7.5 ml). The organic phase was separated and concentrated under vacuum and the reaction product K-I was immediately introduced into the next reaction step k02.

Step k05: 3-chloroaniline (K-IV) (1 eq., 50 g) was dissolved at −5 to 0° C. in concentrated HCl (300 ml) and stirred for 10 min. A mixture of $NaNO_2$ (1.2 eq., 32.4 g), water (30 ml), $SnCl_2.2H_2O$ (2.2 eq., 70.6 g) and concentrated HCl (100 ml) was added dropwise over a period of 3 h while maintaining the temperature. After stirring for a further 2 h at −5 to 0° C., the reaction mixture was set to pH 9 using NaOH solution and extracted with EtOAc (250 ml). The combined organic phases were dried over magnesium sulfate and the solvent was removed under vacuum. The purification by column chromatography ($SiO_2$, 8% EtOAc/hexane) produced 40 g (72% yield) of (3-chlorophenyl) hydrazine (K-IV) as a brown oil.

Step k02: The aldehyde (K-I) (2 eq., 300 ml) obtained from k01 and (3-chlorophenyl)hydrazine (K-IV) (1 eq., 20 g) were placed in EtOH (200 ml) and refluxed for 5 h. The solvent was removed under vacuum, the residue was purified by column chromatography ($SiO_2$, hexane) and the product (25 g, 72% yield) K-II was obtained as a brown oil.

Step k03: The hydrazine K-II (1 eq., 25 g) was dissolved in DMF (125 ml). N-chlorosuccinimide (1.3 eq., 19.5 g) was added portionwise at room temperature within 15 min and the mixture was stirred for 3 h. The DMF was removed by distillation and the residue was taken up in EtOAc. The EtOAc was removed under vacuum, the resulting residue was purified by column chromatography ($SiO_2$, hexane) and the product K-III (26.5 g, 92% yield) was obtained as a pink-coloured oil.

Step k04: At room temperature the hydrazonoyl chloride K-III (1 eq., 10 g) was taken up in toluene (150 ml) and mixed with 2-chloroacrylonitrile (2 eq., 6.1 ml) and TEA (2 eq., 10.7 ml). This reaction mixture was stirred for 20 h at 80° C. The mixture was then diluted with water (200 ml) and the phases were separated. The organic phase was dried over magnesium sulfate and the solvent was removed under vacuum. The residue was purified by column chromatography ($SiO_2$, 5% EtOAc/hexane) and the product (5.5 g, 52% yield) was obtained as a white solid J-V.

Step j06 (Method 3):

The carbonitrile J-V (1 eq., 1 g) was dissolved in methanolic ammonia solution (150 ml, 1:1) and hydrogenated in an H-cube (10 bar, 80° C., 1 ml/min, 0.25 mol/L). After removal of the solvent under vacuum, (1-(3-chlorophenyl)-3-(trifluoromethyl)-1H-pyrazol-5-yl)methanamine (II) was able to be obtained as a white solid (0.92 g, 91% yield).

5. The Following Further Intermediate Products were Synthesised in a Similar Manner Using the Process Described Hereinbefore Under 4

(1-(4-(chlorophenyl)-3-(trifluoromethyl)-1H-pyrazol-5-yl)methanamine (1-(3-chloro-4-fluorophenyl)-3-(trifluoromethyl)-1H-pyrazol-5-yl)methanamine

6. Preparation of Selected Acids of General Formula (III)

6.1 Synthesis of 2-(4-(N,N-dimethylsulfamoyl)-3-fluorophenyl)propanoic acid

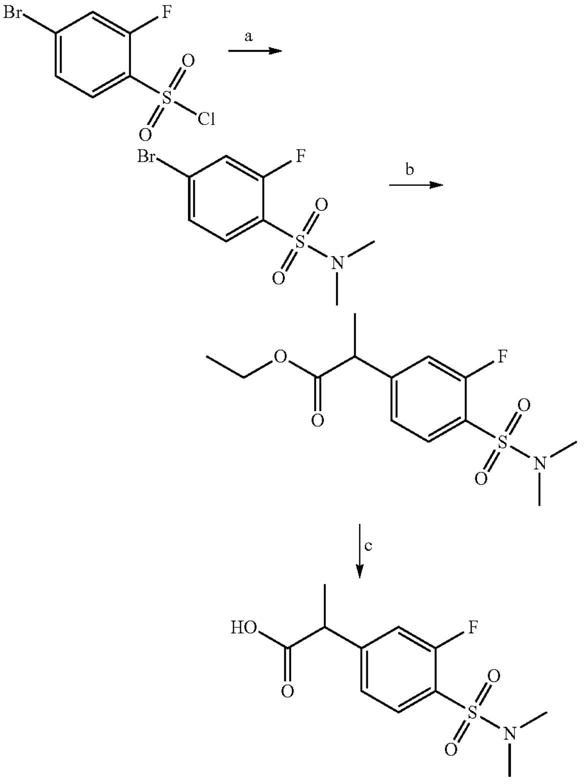

Step a: 4-bromo-2-fluorobenzene sulfonyl chloride (9.15 mmol, 2.5 g) was dissolved in dichloromethane (75 ml) at room temperature, mixed with dimethylamine (2 mol/l in MeOH) (18.3 mmol, 9.15 ml) and stirred for 2 h at room temperature after addition of the pyridine (32 mmol, 2.58 ml). The reaction mixture was mixed with water (75 ml) and the organic phase was separated off. The aqueous phase was extracted with EtOAc (2×75 ml), the organic phases were combined and dried over magnesium sulfate. After removal of the solvent under vacuum, 2.51 g (97% yield) of the product could be obtained.

Step b: step-a-product (8.9 mmol, 2.5 g) and ethyl-2-chloropropionate (11.5 mmol, 1.57 g) were dissolved in DMF (15 ml) at room temperature under a protective gas atmosphere. Subsequently, manganese (17.7 mmol, 0.974 g), (2,2'-bipyridine) nickel (II) dibromide (0.62 mmol, 0.231 g) and TFA (0.23 mmol, 18 μL) were added and stirred for 48 h at 50° C. After cooling of the reaction mixture to room temperature, the mixture was hydrolysed with 1 N HCl (25 ml) and the mix was extracted with diethyl ether (3×25 ml). The combined organic phases were washed with water (25 ml) and aq. sat. NaCl solution (25 ml) and dried over magnesium sulfate. The solvent was removed under vacuum and the residue was purified by column chromatography ($SiO_2$, dichloromethane/MeOH=15:1) and the product was obtained in this way.

Step c: Step-b-product (5.9 mmol, 1.8 g) was dissolved in a THF-water mix (15 ml, 2:1), LiOH (17.8 mmol, 0.414 g) was added and refluxed for 10 h. The reaction mixture was extracted with diethyl ether (25 ml), the aqueous phase was acidified to pH 2 using 1 N HCl and extracted with EtOAc (3×25 ml). The combined organic phases were dried over magnesium sulfate and the solvent was concentrated to dryness under vacuum. 2-(4-(N,N-dimethylsulfamoyl)-3-fluorophenyl)propanoic acid (C) could be obtained at a 48% yield (0.78 g).

6.2 Synthesis of 2-(4-methoxy-3,5-dimethylphenyl)acetic acid

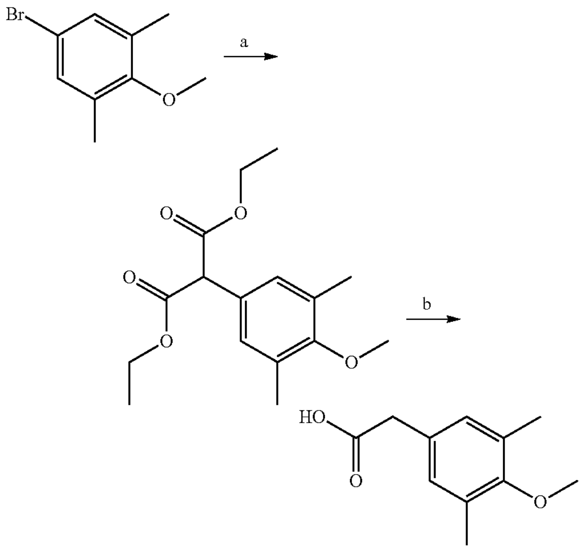

Step a: Bromo-2,6-dimethylanisol (23.2 mmol, 5 g), CuBr (46.5 mmol, 6.67 g) and diethyl malonate (46.5 mmol, 7.09 ml) were dissolved in 1,4-dioxane (30 ml). NaH (60% in mineral oil) (51.1 mmol, 1.225 g) was added slowly at room temperature while stirring and the mixture was stirred for 10 h at 100° C. After cooling of the reaction mixture, a brown solid was removed by filtration and the filtrate was concentrated under vacuum. The purification by column chromatography ($SiO_2$, EtOAc/cyclohexane, 1:2) produces 0.87 g (13% yield) of the malonic acid diethyl ester.

Step b: The malonic acid diethyl ester (0.34 mmol, 0.1 g) obtained was then dissolved in 2 N NaOH/THF:$H_2O$ (1:1) (350 μL) and refluxed for 3 h. After acidifying the reaction mixture to pH 1 using conc. HCl, the mixture was stirred for a further hour at room temperature. The solution was then set to pH 13 using 1 N NaOH and extracted with diethyl ether (20 ml). The aqueous phase was set to pH 5 using 1 N HCl and extracted with EtOAc (3×20 ml). The combined organic phases were washed with sat. NaCl solution, dried over magnesium sulfate and filtered. After removal of the solvent under vacuum, 0.021 g (32% yield) of the desired 2-(4-methoxy-3,5-dimethylphenyl)acetic acid could be obtained.

6.3 Synthesis of 2-(3,5-difluoro-4-hydroxyphenyl)acetic acid (employed for the synthesis of example compound no. 147)

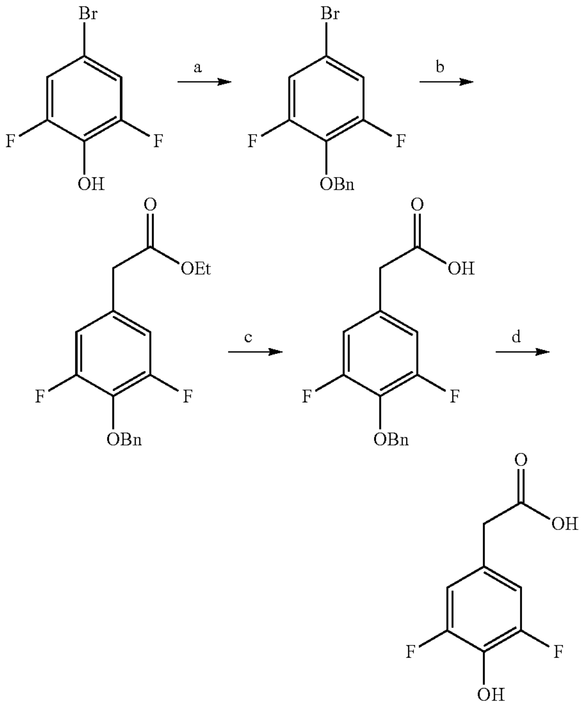

Step a: 4-bromo-2,6-difluorophenol (5 g, 23.92 mmol) was dissolved in dimethylformamide (50 mL) in 250 ml round bottom flask equipped with argon atmosphere. Potassium carbonate (5 g, 35.55 mmol) was added and stirred for 10 minutes, followed by addition of benzyl bromide (4.5 g, 26.31 mmol) and stirred at ambient temperature for 4 h. TLC showed (hexane, $R_f$: 0.8) complete conversion of starting material. The reaction mixture was diluted with water (500 mL) and extracted with ethyl acetate (3×100 mL). The combined organic part was dried over anhydrous magnesium sulfate and concentrated under reduced pressure to afford crude material, which was purified by column chromatography (silica gel: 100-200 mesh, eluent: 5% ethyl acetate in hexane) to afford the pure compound (7 g, 95.8%).

Step b: In a 50 mL two necked round bottom flask step-a product (2 g, 6.68 mmol), ethyl chloroacetate (1.06 g, 8.69 mmol), and dimethylformamide (14 mL) were charged. The system was degassed and refilled with argon followed by addition of Mn (735 mg, 13.36 mmol) and $NiBr_2$.bipy (202 mg, 0.53 mmol). Finally trifluoroacetic acid (14 μL) was added and the reaction mixture was degassed and refilled with argon. Then it was heated to 65° C. for one and half hour. TLC showed (10% ethyl acetate in hexane, $R_f$: 0.4) complete conversion of starting material. The reaction mixture was diluted with water (50 mL) and HCl (4N, 0.5 mL) and extracted with ethyl acetate (3×50 mL). The combined organic part was dried over anhydrous magnesium sulfate and concentrated under reduced pressure to afford crude material which was purified by column chromatography (silica gel: 100-200 mesh, eluent: 10% ethyl acetate in hexane) to afford 700 mg product. $^1$H NMR (DMSO-$d_6$, 400 MHz): δ 7.54 (t, 1H), 7.15 (d, 2H), 4.16 (q, 2H), 3.64 (s, 2H), 1.26 (t, 3H).

Step c: Step-b product (700 mg, 2.6 mmol) was dissolved in THF (4 mL). LiOH (4 mL, 1M, 4 mmol) was added to it. The reaction mixture was stirred at ambient temperature for 2 h. TLC showed (60% ethyl acetate in hexane, $R_f$: 0.2) complete conversion of starting material. The reaction mixture was diluted with water (30 mL) and washed with ethyl acetate (2×30 mL). The aqueous part was acidified with 4N HCl (pH ~2) and extracted with in ethyl acetate (3×40 mL). The combined organic layer was washed with water (50 mL) and brine (50 mL). It was dried over anhydrous magnesium sulfate and concentrated under reduced pressure to afford 500 mg pure compound. $^1$H NMR (DMSO-$d_6$, 400 MHz): δ 12.45 (s, 1H), 7.32-7.42 (m, 5H), 7.03 (d, 2H), 5.13 (s, 2H), 3.56 (s, 2H)

Step d: Step-c product (1.4 g, 5 mmol) was dissolved in EtOH (14 mL). Palladium on carbon (140 mg, 10% Pd) was added to it under argon atmosphere. The reaction mixture was hydrogenated at 50 psi hydrogen pressure for 16 h. TLC showed (in ethyl acetate, $R_f$: 0.1) complete conversion of starting material. The reaction mixture was filtered over celite bed and washed with ethyl acetate and concentrated under reduced pressure to afford desired product (800 mg, 84.5%). $^1$H NMR (DMSO-$d_6$, 400 MHz): δ 12.38 (bs, 1H), 10.03 (bs, 1H), 6.92 (d, 2H), 3.49 (s, 2H); LCMS [M−H]: 187.

6.4 Synthesis of 2-(3,5-difluoro-4-hydroxyphenyl)propanoic acid (employed for the synthesis of example compound no. 46)

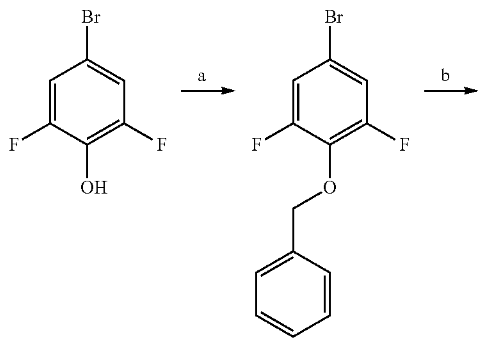

-continued

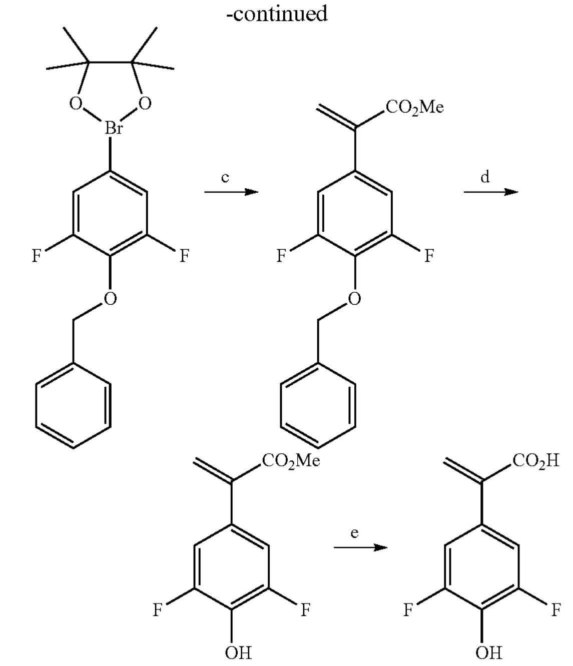

Step a: To a stirred solution of 4-bromo-2,6-difluorophenol (8 g, 38.27 mmol) in dimethyl formamide (80 mL), potassium carbonate (7.9 g, 57.41 mmol) was added and stirred for 15 minutes at ambient temperature. Then benzyl bromide (7.85 g, 45.93 mmol) was added dropwise for 10 minutes. It was allowed to stir at ambient temperature for 10 h. Water (800 mL) was added to it and extracted with ethyl acetate (3×100 mL). The combined organic layer was dried over magnesium sulfate and concentrated to yield crude product, which was purified through column chromatography (silica gel: 100-200 mesh; eluent: 5% ethyl acetate in hexane) to afford compound (10.2 g, 87.8%).

Step b: To a stirred solution of step-a product (5 g, 16.72 mmol) in toluene (120 mL), bis(pinacolato)diboron (5 g, 19.68 mmol) was added and deoxygenated twice. Potassium phenoxide (3.3 g, 24.61 mmol), $PdCl_2(PPh_3)_2$ (0.35 g, 0.49 mmol) and $PPh_3$ (0.26 g, 0.98 mmol) were added simultaneously to it and again deoxygenated with argon. The reaction was heated at 60° C. and maintained the same temperature for 12 h. The reaction mixture was filtered through celite bed and the filtrate was taken in ethyl acetate (200 mL) and was washed with water (2×100 mL). The final organic layer was dried over anhydrous magnesium sulfate and concentrated to yield the crude compound, which was purified through column chromatography (silica: 100-200 mesh, eluent: 3% ethyl acetate in hexane) to afford compound (3.0 g, 51.9%). $^1$H NMR (DMSO-$d_6$, 400 MHz): δ7.35-7.42 (m, 6H), 7.24 (d, 2H), 5.2 (s, 2H), 1.27 (s, 12H).

Step c: To a stirred solution of step-b product (2.5 g, 7.22 mmol) in a mixture of toluene and EtOH (1:1, 20 mL) compound 4 (2.53 g, 10.83 mmol) was added and deoxygenated twice. $PdCl_2$ (dppf) (264 mg, 0.36 mmol) and 2M sodium carbonate solution (7.2 mL) was added simultaneously and finally heated at 90° C. for 3 h. The reaction mixture was diluted with water (100 mL) and was extracted with ethyl acetate (2×50 mL). The combined organic layer was dried over anhydrous magnesium sulfate and concentrated to afford crude compound, which was purified through column chromatography (silica: 100-200 mesh, eluent: 2% ethyl acetate in hexane) to obtain pure compound (1.2 g, 54.5%). $^1H$ NMR (DMSO-$d_6$, 400 MHz): δ 7.35-7.44 (m, 5H), 7.27 (d, 2H), 6.2 (s, 1H), 6.14 (s, 1H), 5.19 (s, 2H), 3.7 (s, 3H).

Step d: Step-c product (2.5 g, 8.21 mmol) was dissolved in ethyl acetate (25 mL) and was taken in Parr hydrogenation bottle followed by palladium on charcoal (300 mg, 10% Pd) and was hydrogenated at 50 psi for 10 h. The reaction mixture was filtered through celite bed and was concentrated to obtain the crude compound (1.6 g, 90%). $^1H$ NMR (DMSO-$d_6$, 400 MHz): δ 10.08 (s, 1H), 6.93 (d, 2H), 3.70-3.76 (q, 1H), 3.58 (s, 3H), 1.34 (d, 3H).

Step e: To a stirred solution of step-d product (2.0 g, 9.25 mmol) in THF (19 mL), aqueous LiOH solution (1M, 19 mL) was added. The reaction mixture was stirred at ambient temperature for 10 h. TLC showed complete conversion of starting material. The organic solvent was concentrated and water (50 mL) was added to the residue. This aqueous part was washed with ethyl acetate (30 mL). The aqueous layer was acidified with 1N HCl up to pH 2 and extracted with ethyl acetate (3×25 mL). The combined organic layer was dried over anhydrous magnesium sulfate and concentrated to afford desired product (1.7 g, 91%).

$^1H$ NMR (DMSO-$d_6$, 400 MHz): δ 12.3 (bs0, 1H), 10.03 (bs, 1H), 6.94 (d, 2H), 3.58-3.61 (q, 1H), 1.30 (d, 3H); GCMS (m/z)[M−H]: 201.

6.5 Synthesis of 2-(3-fluoro-4-(trifluoromethyl)phenylacetic acid (employed for the synthesis of example compound no. 140)

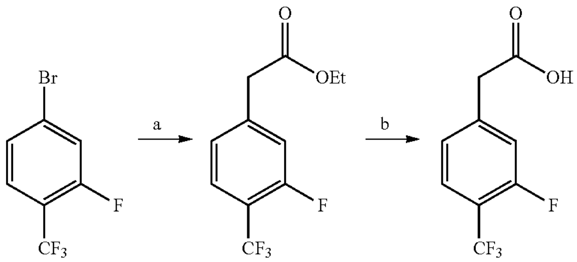 [SMILES: Fc1cc(Br)ccc1C(F)(F)F ; CCOC(=O)Cc1ccc(C(F)(F)F)c(F)c1 ; O=C(O)Cc1ccc(C(F)(F)F)c(F)c1]

Step a: In a 50 mL two necked round bottom flask 4-bromo-2-fluoro-1-(trifluoromethyl)benzene (0.5 g, 2.05 mmol), ethyl chloroacetate (328 mg, 2.67 mmol), and dimethylformamide (4 mL) were charged. The system was degassed and re filled with argon followed by addition of Mn (225 mg, 4.1 mmol) and $NiBr_2$.bipy (62 mg, 0.16 mmol). Finally TFA (4.1 μL) was added and the reaction mixture was degasified and refilled with argon. Then it was heated to 65° C. for one hour. TLC showed (10% ethyl acetate in hexane, $R_f$: 0.2) complete conversion of starting material. The reaction mixture was diluted with water (50 mL) and HCl (4N, 0.5 mL) and extracted with ethyl acetate (3×40 mL). The combined organic part was dried over anhydrous magnesium sulfate and concentrated under reduced pressure to afford crude material which was purified by column chromatography (silica gel: 100-200 mesh, eluent: 10% ethyl acetate in hexane) to afford the pure compound (490 mg, 27%). $^1H$ NMR (DMSO-$d_6$, 400 MHz): δ 7.54 (t, 1H), 7.15 (d, 2H), 4.16 (q, 2H), 3.64 (s, 2H), 1.26 (t, 3H).

Step b: Step-a product (1.48 g, 6 mmol) was dissolved in THF (9 mL). LiOH (9 mL, 1M, 9 mmol) was added to it. The reaction mixture was stirred at ambient temperature for 2 h. TLC showed (60% ethyl acetate in hexane, $R_f$: 0.2) complete conversion of starting material. The reaction mixture was diluted with water (50 mL) and washed with ethyl acetate (2×40 mL). The aqueous part was acidified with 4N HCl (pH ~2) and extracted with in ethyl acetate (3×50 mL). The combined organic layer was washed with water (50 mL) and brine (50 mL). The combined organic part was dried over anhydrous magnesium sulfate and concentrated under reduced pressure to afford desired product (1.2 g, 94%). $^1H$ NMR (DMSO-$d_6$, 400 MHz): δ 12.58 (s, 1H), 7.72 (t, 1H), 7.43 (d, 1H), 7.32 (d, 1H), 3.74 (s, 2H); LCMS [M−H—$CO_2$]: 177.

6.6 Synthesis of 2-(3-fluoro-4-(trifluoromethyl)phenyl)propanoic acid (employed for the synthesis of example compound no. 141)

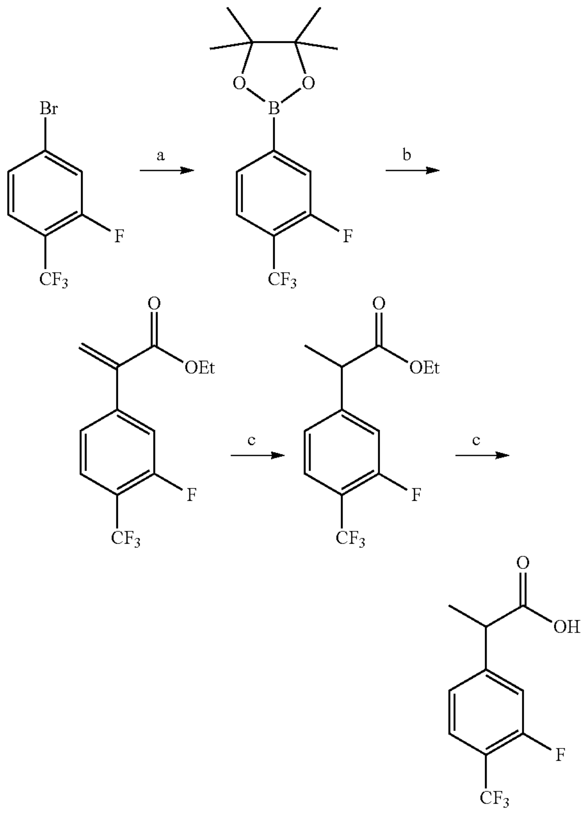

Step a: To a stirred solution of 4-bromo-2-fluoro-1-(trifluoromethyl)benzene (5 g, 20.57 mmol) in 1,4-dioxane (400 mL), bis(pinacolato)diboron (5.2 g, 20.57 mmol) was added and deoxygenated twice. Potassium acetate (6.05 g, 61.72 mmol), $PdCl_2(PPh_3)_2$ (0.43 g, 0.61 mmol) were added to it and again deoxygenated. The reaction was heated to 100° C. for 12 h. The reaction mixture was filtered through celite bed and evaporated to dryness. It was taken in ethyl acetate (200 mL) and was washed with water (2×100 mL). The final organic layer was dried over anhydrous magnesium sulfate and evaporated to dryness to afford crude compound, which was purified through column chromatography (silica: 100-20 mesh, eluent: 5% ethyl acetate in hexane) to afford compound (4 g, 67%).

Step b: To a stirred solution of step-a product (4 g, 13.78 mmol) in toluene (50 mL) ethyl 2-(trifluoromethylsulfonyloxy)acrylate (4.1 g, 17.92 mmol) was added and deoxygenated twice. $Pd(PPh_3)_4$ (0.8 g, 0.68 mmol) was added and again deoxygenated. 2M sodium carbonate solution (16 mL) was added and heated at 60° C. for 10 h. The reaction mixture was diluted with water (100 mL) and was extracted with ethyl acetate (2×100 mL). The combined organic layer was dried over anhydrous magnesium sulfate and evaporated to dryness to afford crude compound, which was purified through column chromatography (silica: 100-200 mesh, eluent: 2% ethyl acetate in hexane) to obtained 1.8 g pure compound (52.6%). $^1$H NMR (DMSO-$d_6$, 400 MHz): δ 7.78 (t, 1H), 7.63 (d, 1H), 7.48 (d, 1H), 6.45 (s, 1H), 6.25 (s, 1H), 3.77 (s, 3H).

Step c: Step-b product (1.8 g, 7.62 mmol) in (20 mL) was dissolved in ethyl acetate and was taken in Parr hydrogenation bottle followed by palladium on charcoal (180 mg, 10% Pd) and was hydrogenated at 50 psi for 10 h. The reaction mixture was filtered through celite bed and was concentrated to obtain 1.7 g of the crude compound (94%). $^1$H NMR (DMSO-$d_6$, 400 MHz): δ 7.73 (t, 1H), 7.47 (d, 1H), 7.34 (d, 1H), 3.99 (q, 1H), 3.61 (s, 3H), 1.42 (d, 3H).

Step d: To a stirred solution of step-c product (1.7 g, 6.79 mmol) in THF (12 mL), 1M LiOH (12 mL) was added. The reaction mixture was stirred at ambient temperature for 30 minutes. TLC showed complete conversion of starting material. The organic solvent was concentrated and water (50 mL) was added to the residue. This aqueous part was washed with ethyl acetate (30 mL). The aqueous layer was acidified with 1N HCl up to pH 2 and extracted with ethyl acetate (3×25 mL). The combined organic layer was dried over anhydrous magnesium sulfate and evaporated to dryness to obtained compound (1.3 g, 81%). $^1$H NMR (DMSO-$d_6$, 400 MHz): δ 12.59 (bs, 1H), 7.73 (t, 1H), 7.45 (d, 1H), 7.34 (d, 1H), 3.86 (q, 1H), 1.40 (d, 3H); GCMS (m/z): 236.

6.7 Synthesis of 2-(4-cyclopropyl-3-fluorophenyl)propanoic acid (employed for the synthesis of example compound no. 125)

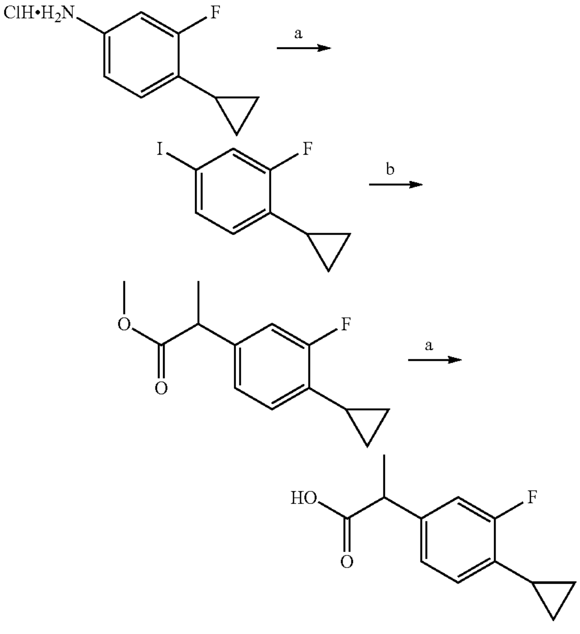

Step a: To a suspension of potassium iodide (9 g, 94.42 mmol) and isoamyl nitrite (4.89 mL, 36.34 mmol) in acetonitrile (30 mL), a solution of 4-cyclopropyl-3-fluoroaniline hydrochloride (3.4 g, 18.18 mmol) in acetonitrile (20 mL) was added at 0° C. After addition reaction mixture was stirred at room temperature for 30 h. Acetonitrile was evaporated; the obtained residue was diluted with ethyl acetate (250 mL), washed with water (2×100 mL), brine solution (50 mL), dried ($Na_2SO_4$) and concentrated. The obtained crude compound was purified by column chromatography (100-200 mesh Silica gel) using petroleum ether as eluent to afford a yellow liquid (4.1 g, 57.6%).

Step b: A solution of step-a product (1.9 g, 7.25 mmol) and methyl-2-bromopropanoate (2.22 mL, 18.12 mmol) in dimethylformamide (20 mL) was degassed with Argon, added 2,2'-bipyridyl (0.113 g, 0.723 mmol), $NiBr_2$ (158 mg, 0.723 mmol), Mn powder (796 mg, 14.49 mmol), TFA (cat) at room temperature and the reaction mixture was stirred at 75° C. for 24 h. The reaction mixture was cooled to room temperature, diluted with ether (200 mL), washed with water (100 mL), brine solution (30 mL), dried ($Na_2SO_4$), filtered and concentrated. The obtained crude compound was purified by column chromatography (100-200 mesh Silica gel) using 5% ethyl acetate in petroleum ether as eluent to afford product as pale yellow liquid (520 mg, 32%).

Step c: To a solution of step-b product (1.2 g, 5.4 mmol) in MeOH (3 mL), THF (6 mL), $H_2O$ (6 mL), $LiOH.H_2O$ (900 mg, 21.61 mmol) was added at room temperature and the reaction mixture stirred at room temperature for 3 h. The reaction mixture was concentrated under reduced pressure and residual aqueous layer was diluted with water (75 mL), washed with ethyl acetate (50 mL) to remove the impurities. The aqueous layer was acidified (pH~4) using 1N aq. HCl (5 mL) and extracted with ethyl acetate (2×50 mL). The combined organic layer washed with brine solution (15 ml), dried ($Na_2SO_4$), filtered and concentrated. The obtained crude compound was purified by column chromatography (100-200 mesh Silica gel) using 5% ethyl acetate in petroleum ether as eluent to afford compound title compound as pale yellow liquid (650 mg, 58%).

6.8 Synthesis of 2-(3-fluoro-4-((2-methoxyethoxy)methyl)phenyl)propanoic acid (employed for the synthesis of example compound no. 142)

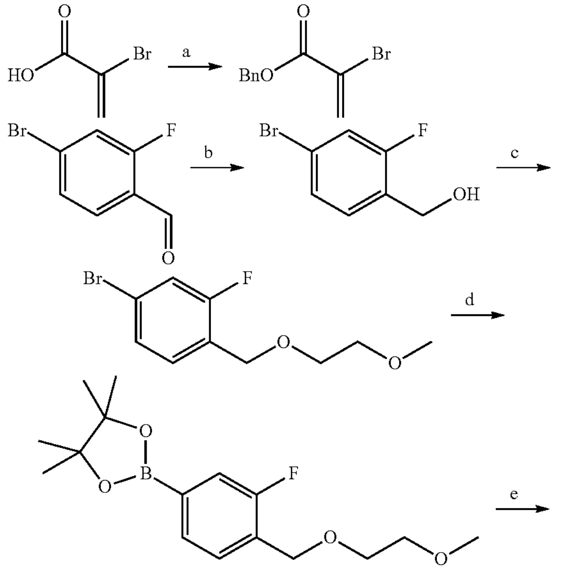

-continued

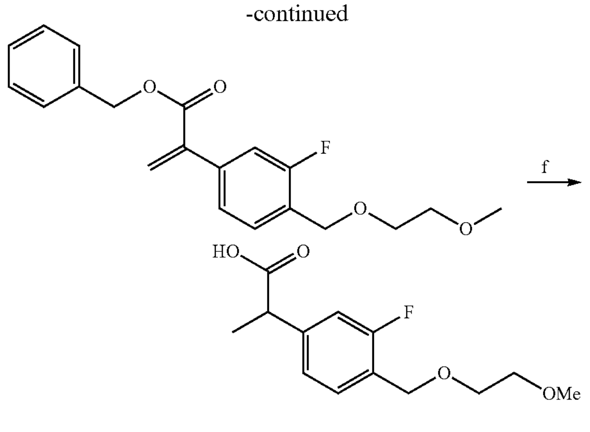

Step a: A suspension of 2-bromoacrylic acid (10 g, 66.66 mmol), BnBr (9 mL, 73.72 mmol) and potassium carbonate (18 g, 133.3 mmol). in acetonitrile (100 ml) was stirred at 80° C. for 3 h until complete consumption. The reaction mixture was filtered and concentrated. The obtained crude compound was purified by column chromatography (100-200 mesh silica gel) using 5% ethyl acetate in petroleum ether as eluent to afford a yellow liquid (10 g, 62.8%).

Step b: To a stirred solution of 4-bromo-2-fluoro benzaldehyde (15 g, 79.36 mmol) in MeOH (100 mL) at 0° C. to −5° C., added $NaBH_4$ (6.0 g, 158.73 mmol) in equal portions and stirred at room temperature. The reaction mixture was diluted with ice cold water (100 mL) and concentrated under reduced pressure. The obtained aqueous residue was extracted with ethyl acetate (2×200 mL); the ethyl acetate layer was washed with brine solution (50 mL), dried over anhydrous $NaSO_4$, filtered and concentrated to afford a colorless oil (15 g, 99%).

Step c: To a stirred solution of step-b product (10 g, 49.02 mmol) in THF (250 ml) at 0° C., added 60% NaH (2.93 g, 73.53 mmol) slowly in portions. After addition, the suspension was heated to 50° C. for 30 minutes, cooled to room temperature, added 1-bromo-2-methoxy ethane (5 ml, 53.92 mmol) and stirred at room temperature for 20 h. The reaction mixture was diluted with ice cold water (100 mL) and concentrated under reduced pressure. The obtained aqueous residue was extracted with ethyl acetate (2×150 mL); the combined ethyl acetate layer was washed with brine solution (50 mL), dried over anhydrous $NaSO_4$, filtered and concentrated. The obtained crude compound was purified by column chromatography (100-200 mesh silica gel) using 5% ethyl acetate in petroleum ether as eluent to afford product as yellow liquid (6 g, 47%).

Step d: A stirred suspension of step-c product (6 g, 22.8 mmol), bis(pinacolato)diboron (5.8 g, 22.8 mmol), potassium acetate (6.7 g, 68.4 mmol) in THF (50 ml) was deoxygenated by purging with a stream of Argon for 30 minutes, and added Pd $(PPh_3)_2Cl_2$ (36.5 mg, 0.228 mmol), purging was continued for further 10 minutes. The reaction mixture was stirred at 100° C. for 1 h. The reaction mixture was concentrated and the obtained crude compound was purified by column chromatography (100-200 mesh silica gel) using 10% ethyl acetate in petroleum ether as eluent to afford product as a pale yellow oil (5 g, 61.7%).

Step e: A suspension of step-d product (5 g, 16.129 mmol), caesium carbonate (15.7 g, 48.38 mmol) in dimethylformamide (50 ml) was deoxygenated by purging Argon for 30 minutes at room temperature. Pd(dppf)$C_2$ (657 mg, 0.806 mmol) was added and purging was continued. After 10 minutes, step-a product (4.6 g, 19.35 mmol) was added and stirred at 100° C. for 1 h. The reaction mixture was diluted with ethyl acetate (200 mL), filtered through a celite pad, washed with ethyl acetate (2×25 mL). The filtrate was washed with water (2×100 mL), brine (50 mL), dried over anhydrous $NaSO_4$, filtered and concentrated. The obtained crude compound was purified by column chromatography (100-200 mesh silica gel) using 10% ethyl acetate in petroleum ether as eluent to afford product as pale brown oil (1.4 g, 25%).

Step f: A suspension of step-e product (2.8 g, 8.139 mmol), 10% Pd/C (300 mg) in MeOH (20 ml) was hydrogenated (balloon pressure) at room temperature for 1 h. The reaction mixture was filtered through celite pad, washed with MeOH (2×15 mL). The combined filtrate was concentrated and the obtained crude compound was purified by column chromatography (100-200 mesh silica gel) using 30% ethyl acetate in petroleum ether as eluent to afford title compound as colorless oil (1.2 g, 57.7%).

6.9 Synthesis of 2-(4-(phenylcarbamoyl)phenyl)propanoic acid (employed for the synthesis of example compound no. 143)

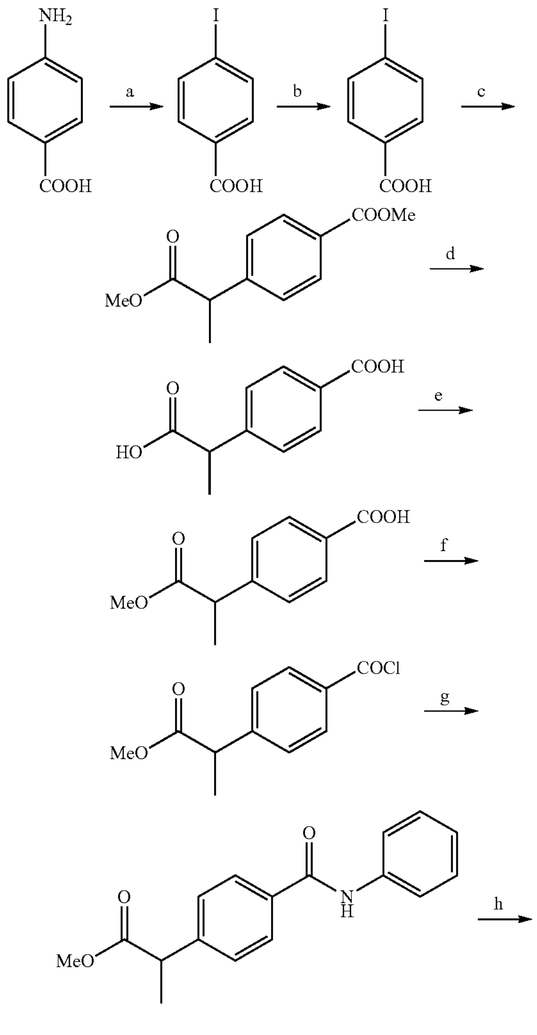

-continued

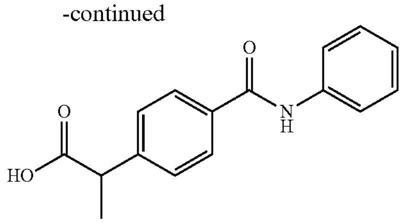

Step a: A solution of sulfuric acid (118 ml) in water (500 ml) was added to 4-aminobenzoic acid (150 g, 1094 mmol) and stirred the contents for 10 minutes at 0° C. Then a solution of sodium nitrite (98.1 g, 1420 mmol, 1.3 eq) in water (500 ml) was added dropwise for 2 h at 0° C. and stirred the contents for 1 hr at the same temperature. In another round-bottom flask, a solution of sulfuric acid (118 ml) in water (500 ml) was added to potassium iodide (253.3 g, 1520 mmol, 1.4 eq) and the stirred the contents for 15 minutes at 0° C. Above prepared diazonium solution was added dropwise at 0° C. for 2 h. Overall reaction mixture was allowed to stir for 1 hr at 0° C. and later for another 1 hr at 40° C. Progress of the reaction was monitored by TLC (50% ethyl acetate-hexane, $R_f$~0.1). On completion of the reaction, ice cold water (500 ml) was added and filtered the contents. Residue was washed with sodiumthio sulfate solution (2×100 ml) and dried to obtain the crude product as dark brown colored solid (125 g, crude).

Step b: To a solution of the crude step-a product (125 g) in acetone (800 ml), potassium carbonate (103 g, 750 mmol, 1.5 eq) and stirred for some time at room temperature. DMS (76.2 g, 600 mmol, 1.2 eq) taken in acetone (500 ml) was added dropwise for 30 minutes and the reaction mixture was allowed to stir for 8 h at room temperature. Progress of the reaction was monitored by TLC (50% ethyl acetate-hexane, $R_f$~0.6). On completion of the reaction, reaction contents were filtered over a celite bed and washed with acetone (100 ml). Filtrate was concentrated under reduced pressure, residue was taken in dichloromethane (250 ml) and washed with cold water (2×100 ml). Combined organic layer was dried over sodium sulfate, concentrated under reduced pressure and the crude product obtained was purified by column chromatography (silica gel, 5% ethyl acetate-hexane) to yield the required product as a white solid (60 g, 45%).

Step c: To a solution of step-b product (10 g, 39 mmol) in dimethylformamide (DMF) (150 ml, 15 times), 2-chloropropionate (14 g, 110 mmol, 3 eq) was added and stirred the contents for 30 minutes while nitrogen gas is being bubbled. Manganese (4.2 g, 70 mmol, 2 eq) was added and stirred the contents for 30 minutes under $N_2$ atmosphere. $NiBr_2$.bypridine (1.42 g, 2.6 mmol, 0.07 eq) was added and stirred for 30 minutes under $N_2$ atmosphere. Then a 15-20 drops of TFA was added stirred the contents for 1 hr. Progress of the reaction was monitored by TLC (10% ethyl acetate-hexane, $R_f$~0.4). On completion of the reaction, water (30 ml) was added and stirred the contents for 30 minutes. Then the contents were filtered and the bed was washed with hexane (2×50 ml). Filtrate was extracted with hexane (4×100 ml) and the obtained aqueous layer was extracted with hexane (2×50 ml). Combined extract was dried over sodium sulfate, concentrated under reduced pressure and the crude product obtained was purified by column chromatography (silica gel, 3% ethyl acetate-hexane) to yield the required product as a red colored liquid (6 g, 70%).

Step d: To a stirred solution of step-c product (6 g, 27 mmol) in MeOH (60 ml, 10 times), a solution of sodium hydroxide (2.7 g, 67 mmol, 2.5 eq) in water (60 ml, 10 times) was added dropwise at room temperature. Overall reaction mixture was allowed to stir for 3 h at room temperature. Progress of the reaction was monitored by TLC (50% ethyl acetate-hexane, $R_f$~0.1). As the reaction not moved completely, reaction contents were allowed to stir for another 5 h. Again TLC was checked and confirmed that the starting material was disappeared. Methanol was distilled off completely and the residue was cooled to 0° C. Then the contents were acidified at a pH~2 with 6N HCl solution and solid thrown out was filtered. Solid obtained was dissolved in ethyl acetate (100 ml), dried over sodium sulfate and concentrated under reduced pressure to yield the required product as an off white solid (4.5 g, 86%).

Step d: To a stirred solution of step-d product (2.5 g, 12 mmol) in dry MeOH (25 ml, 10 times), TMS Chloride (1.39 g (1.64 ml), 12 mmol, 1 eq) was added dropwise and the reaction mixture was allowed to stir for 2 h at room temperature. Progress of the reaction was monitored by TLC (50% ethyl acetate-hexane, $R_f$~0.4). On completion of the reaction, MeOH was distilled off completely under reduced pressure. Residue was taken in dichloromethane (50 ml) and washed with sodium bicarbonate solution (2×50 ml). Aqueous layer was washed with ethyl acetate (50 ml) followed by hexane (50 ml). Then the aqueous layer was cooled to 0° C., acidified with to a pH~2 6N HCl solution and the solid thrown out was filtered. Solid obtained was dissolved in ethyl acetate (100 ml), dried over sodium sulfate and concentrated under reduced pressure to yield the required product as an off white solid (1.54 g, 61%).

Step f-g: To a stirred solution of step-e product (2.3 g, 10 mmol) in dichloromethane (23 ml), oxalyl chloride (2.08 g (1.44 ml), 16 mmol, 1.5 eq) followed by catalytic amount of dimethylformamide were added at room temperature. Reaction contents were stirred for 20 minutes at room temperature. Progress of the reaction was monitored by TLC (5% ethyl acetate-hexane, $R_f$~0.7). As the reaction not moved completely, reaction contents were heated to 40° C. and stirred for 1 hr at the same temperature. Again TLC was checked and confirmed that the starting material was disappeared. Dichloromethane was distilled off completely under reduced pressure. In another round-bottom flask, TEA (triethylamine) (3.2 g (2.5 ml), 25 mmol, 2.5 eq) was added to a solution of aniline (0.83 g, 9 mmol) in dichloromethane (10 ml) and stirred the contents for 15 minutes at 0° C. Then the above prepared acid chloride was taken in dichloromethane (13 ml) and added dropwise at 0° C. and the overall reaction mixture was allowed to stir for 1 hr at 00° C. Progress of the reaction was monitored by TLC (5% ethyl acetate-hexane, $R_f$~0.3). On completion of the reaction, water (10 ml) was added and the layers formed were separated out. Organic layer was dried over sodium sulfate and concentrated under reduced pressure to yield the required product as an off white solid (3 g, 96%).

Step h: To a solution of step-g product (3 g, 10 mmol) in THF (30 ml, 10 times), water (30 ml, 10 times) was added and the reaction contents were stirred for 15 minutes at room temperature. Then LiOH (0.5 g, 21 mmol, 2 eq) was added and the overall reaction mixture was allowed to stir for 5 h at room temperature. Progress of the reaction was monitored by TLC (5% ethyl acetate-hexane, $R_f$~0.1). On completion of the reaction, THF was distilled off completely under reduced pressure. Aqueous layer was washed with ethyl acetate (50 ml) followed by hexane (50 ml). Then the aqueous layer was cooled to 0° C., acidified to a pH~2 with 6N HCl solution and the solid thrown out was filtered. Solid obtained was dissolved in ethyl acetate (100 ml), dried over sodium sulfate and concentrated under reduced pressure to yield the required product as an off white solid (2.15 g, 75%).

6.10 General scheme for the synthesis of 2-(4-sulfonamidophenyl)propanoic acids Scheme 2:
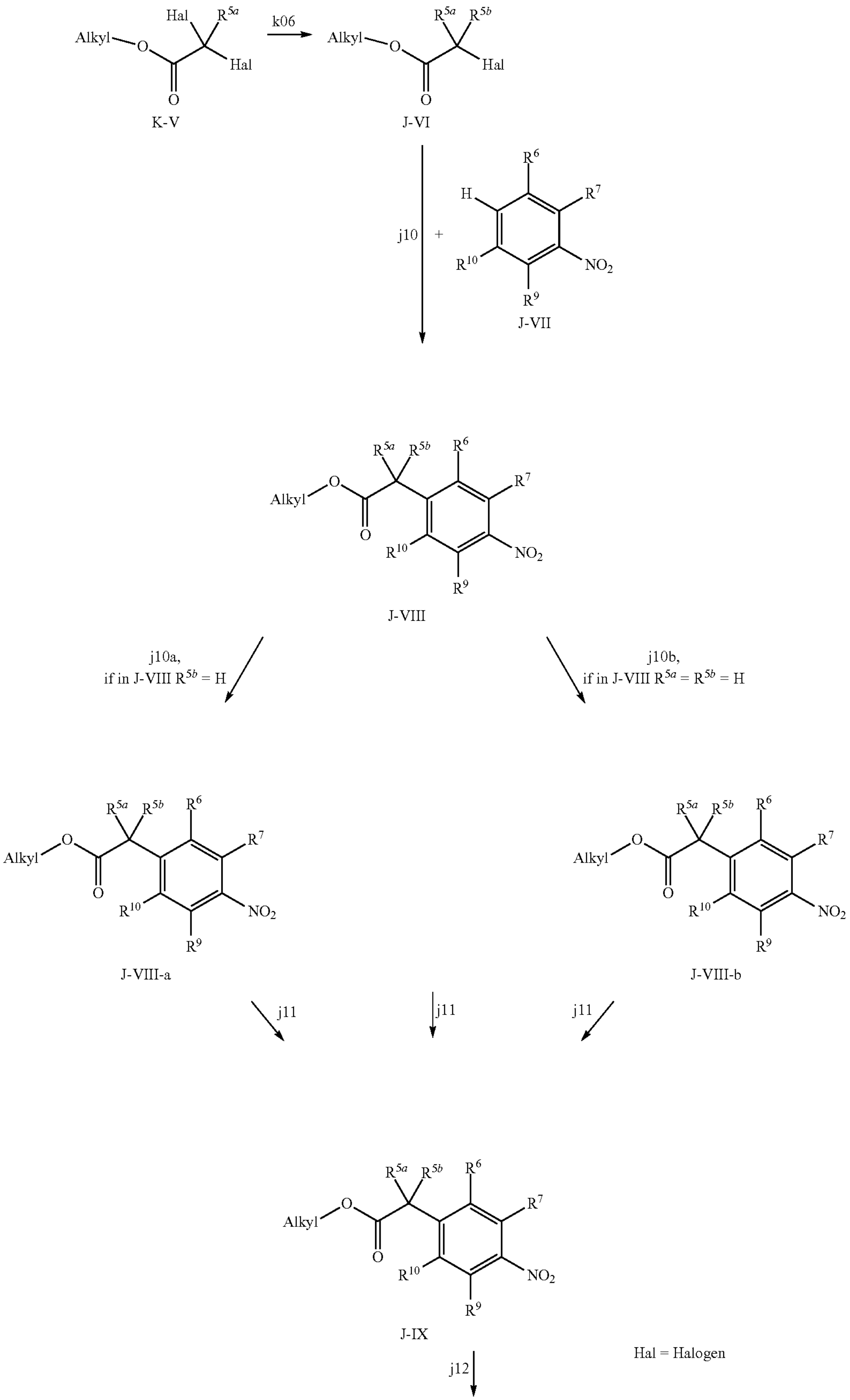
Hal = Halogen -continued

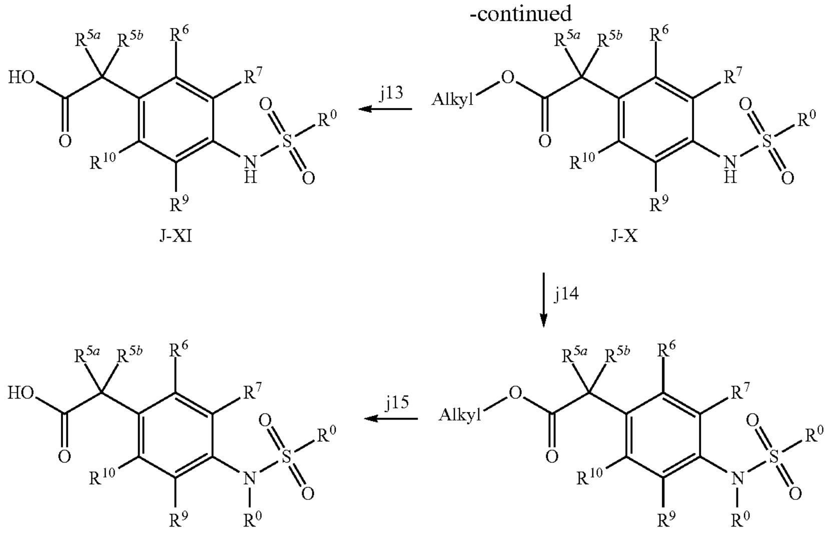

J-XI J-X

J-XIII J-XII

In step j10 the nitro-substituted phenyl J-VII can be reacted to form the compound J-VIII by methods known to persons skilled in the art, for example in a substitution reaction using a singly halogenated, preferably singly chlorinated or brominated ester J-VI, optionally in the presence of a base.

If appropriate, the singly halogenated, preferably singly chlorinated ester J-VI, for which $R^{5b}$≠H, can be prepared in a preceding step k06 from a dihalogen carboxylic acid ester K-V, wherein halogen is preferably Br or Cl, by methods known to persons skilled in the art, in order in this way to introduce the residue $R^{5b}$ ($R^{5b}$≠H) into J-VI.

If, in step j10, use is made of compounds J-VI for which $R^{5a}$ and $R^{5b}$ are each H or for which the substituent is $R^{5b}$═H, then functional groups in the positions $R^{5a}$ and $R^{5b}$ or the position $R^{5b}$ can each be introduced in the synthesis sequence at a later point in time, for example after step j10 and before step j11. In this case, compounds J-VIII, in which $R^{5b}$═H, or compounds J-VIII, in which $R^{5a}$ and $R^{5b}$ each ═H, are reacted in a further step j10a and j10b respectively, which are each carried out between the steps j10 and j11, to form compounds J-VII-a, in which $R^{5b}$ H, or compounds J-VIII-b, in which $R^{5a}$ and $R^{5b}$ each —H. The compounds J-VIII-a and J-VIII-b can subsequently be reacted further in step j11.

In step j11 the nitro function of the compound J-VIII (or J-VIII-a or J-VIII-b) can be converted into an aniline derivative J-IX by methods known to persons skilled in the art, such as for example by hydrogenation with hydrogen or by reduction by acidic metal salt solutions.

In step j12 the aniline compound J-IX can be reacted to form the compound J-X by methods known to persons skilled in the art, for example using a halogenated, preferably chlorinated sulfonyl compound of formula $R^0$—S(═O)$_2$—Hal, preferably $R^0$—S(═O)$_2$—Cl, optionally in the presence of a base.

J-X can be reacted to form the compound J-XI immediately in step j13 using an ester cleavage known to persons skilled in the art, for example using a base or an acid. However, alternatively, the sulfonyl amino function of J-X can in step j14 first be N-substituted to form the compound J-XII by methods known to persons skilled in the art, for example using a halide $R^0$-Hal, preferably an iodide $R^0$—I, and the aforementioned ester cleavage to form J-XIII can then subsequently be carried out in step j15.

The methods with which persons skilled in the art is familiar for carrying out the reaction steps j10 to j15 and also k06 may be inferred from the standard works on Organic Chemistry such as, for example, J. March, Advanced Organic Chemistry, Wiley & Sons, 6th edition, 2007; F. A. Carey, R. J. Sundberg, Advanced Organic Chemistry, Parts A and B, Springer, 5th edition, 2007); team of authors, Compendium of Organic Synthetic Methods, Wiley & Sons. In addition, further methods and also literature references can be issued by the common databases such as, for example, the Reaxys® database of Elsevier, Amsterdam, NL or the SciFinder® database of the American Chemical Society, Washington, US.

6.10.1 Synthesis of 2-(3-fluoro-4-(sulfonamido)phenyl)propanoic acids

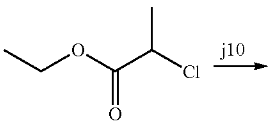

J-VI

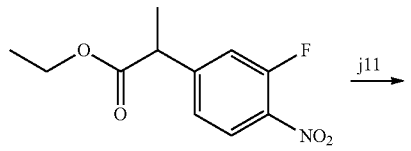

J-VIII

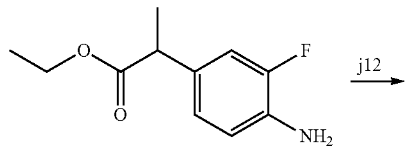

J-IX

-continued

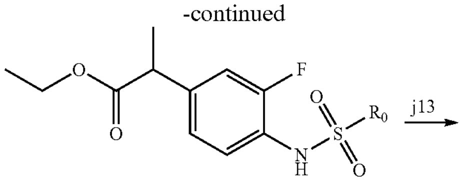

J-X

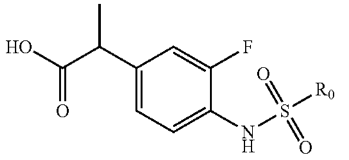

J-XI

Step j10: Under a nitrogen atmosphere, 3 equivalents of potassium tert. butyloxide are slurried in DMF and cooled to −40° C. A mixture of o-fluoronitrobenzene (J-VII) (1 equivalent) and ethyl-2-chloropropionate (J-VI) (1.2 equivalent) is then added while maintaining this temperature and the mixture is stirred for 10 minutes. The reaction mixture is diluted with acetic acid and with water at −40° C. The aqueous phase is then repeatedly extracted with 20% EtOAc in hexane, the combined organic phases are washed with water and sat. aq. NaCl sol. and dried over magnesium sulfate. The concentrated organic phase is purified by column chromatography ($SiO_2$, 10% EtOAc/hexane), as a result of which the product J-VIII is obtained.

Step j11: A suspension of J-VIII (1 equivalent) and palladium on activated carbon (10% Pd) in EtOH is hydrogenated for 1 h under a hydrogen atmosphere. The suspension is removed by filtration, concentrated under vacuum and purified by column chromatography ($SiO_2$, EtOAc/hexane) and J-IX is obtained in this way.

Step j12: J-IX (1 equivalent) is placed in dichloromethane and pyridine and cooled to 0° C. Compounds of general formula Cl—S(=O)$_2$—R (1.5 equivalents) are added dropwise at 0° C. and the reaction mixture is stirred for 2 h at room temperature. After recooling of the mixture to 0° C., the mixture is acidified to pH 3 using 4 N aq. HCl. The organic phase is repeatedly extracted with dichloromethane. The combined organic phases are washed with water and sat. aq. NaCl sol., dried over magnesium sulfate and concentrated to dryness. The purification ($SiO_2$, EtOAc/hexane) by column chromatography produces the desired product J-X.

Step j13: 1 equivalent of J-X is dissolved in a 2:1 mix of THF/water and stirred for 15 minutes. 3 equivalents of LiOH, which is also dissolved in a 2:1 THF/water mix, are added to this solution and the suspension is stirred for 2 h at 45° C. While cooling, the aqueous phase is set to pH 1 using 4 N aq. HCl and repeatedly extracted with dichloromethane. The combined organic phases are dried over magnesium sulfate and concentrated under reduced pressure and the product J-XI is obtained in this way.

6.10.2 Synthesis of 2-(3,5-difluoro-4-(methylsulfonamido)phenyl)propanoic acid

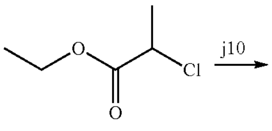

J-VI

-continued

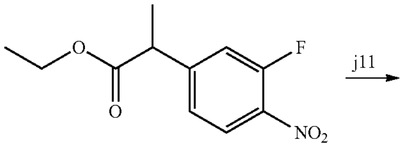

J-VIII

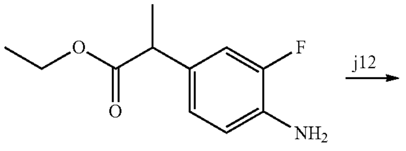

J-IX

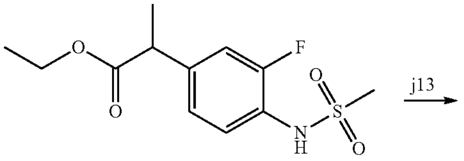

J-X

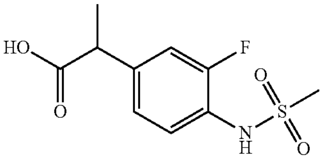

J-XI

Step j10: KOtBu (31.85 mmol, 3.57 g) was dissolved in DMF (30 ml) and cooled to −45° C. A mix of ethyl-2-chloropropionate (15.9 mmol, 2 ml) and 1,3-difluoro-2-nitrobenzene (15.7 mmol, 2.5 g) was slowly added dropwise to the solution, which was kept at −40° C., and after addition the mixture was stirred for a further 1 h. For working up, the reaction mix was set to pH 4 using 16% HCl and diluted with water (150 ml). The mix was extracted with EtOAc (3×50 ml), the combined organic phases were washed with water (50 ml) and sat. NaCl solution (2×50 ml) and dried over magnesium sulfate. After removal of the solvent under vacuum, the product was obtained as an oil (4.12 g, 99% yield).

Step j11: The difluoronitrophenylpropanoate (10 mmol, 2.59 g) was dissolved in EtOH/EtOAc (200 ml, 1:1) and hydrogenated in an H-cube (1 bar, 25° C., 1 ml/min, 0.25 mol/L). After removal of the solvent under vacuum, the difluoroaminopropionate could be obtained as an oil (2.27 g, 99% yield).

Step j12: The difluoroaminophenylpropanoate (5 mmol, 1.15 g) was dissolved in pyridine (4 ml), cooled to 0° C. under a protective gas atmosphere and mixed dropwise with methanesulfonyl chloride (7.5 mmol, 582 μL). After stirring for one hour at 0° C., the reaction mixture was mixed with water (25 ml) while being cooled with ice, set to pH 1 using 16% HCl and extracted with dichloromethane (2×50 ml). The organic phases were combined, dried over magnesium sulfate and the solvent was removed under vacuum. The purification ($SiO_2$, cyclohexane/EtOAc 2:1) of the residue by column chromatography produced 0.458 g of product (28% yield).

Step j13: The product of the mesylation (1.46 mmol, 0.45 g) was dissolved in THF/water (5 ml, 2:1), LiOH (4.39 mmol, 0.105 g) was added and the mixture was refluxed for 12 h. Water (25 ml) and diethyl ether (25 ml) were added to the reaction mix. After phase separation, the aqueous phase was acidified to pH 2 using HCl and extracted with dichloromethane (3×25 ml). The combined organic phases were dried over magnesium sulfate and the solvent was removed under vacuum. The product was obtained as a white solid (0.402 g, 98% yield).

6.10.3 Synthesis of 2-(3-fluoro-4(methylsulfonylamino)phenyl)propanoic acid

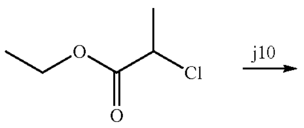

J-VI

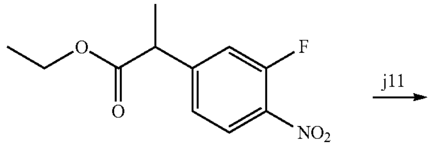

J-VIII

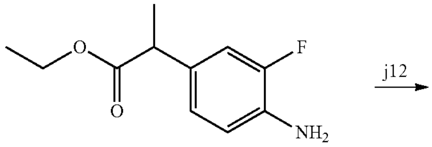

J-IX

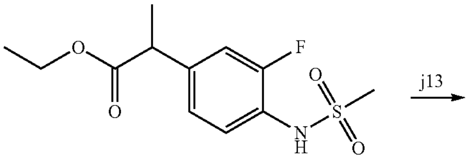

J-X

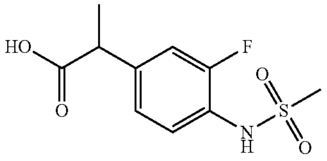

J-XI

Step j10: Potassium tert. butyloxide (1,000 g, 8.93 mol) was placed under a nitrogen atmosphere and the slurry obtained after addition von 4 l of DMF was cooled to −40° C. A mixture of o-fluoronitrobenzene (420 g, 2.97 mol) and ethyl-2-chloropropionate (488 g, 3.57 mol) was added while maintaining this temperature and stirred for 10 minutes. The reaction mixture was quenched with HOAc at −40° C. and diluted with 30 l of water. The liquid phase was repeatedly extracted with 20% EtOAc in hexane (3×15 l), the combined organic phases were washed with water (4×10 l) and sat. aq. NaCl (10 l) and dried over MgSO4. The concentrated organic phase was purified by column chromatography (silica gel. 100-200 mesh, eluent: 10% EtOAc in hexane) and produced 483 g of the nitroester (67.3%). $^1$H NMR ($CDCl_3$, 400 MHz): δ [ppm]8.01 (t, 1H), 7.21-7.26 (m, 2H), 4.06-4.19 (m, 2H), 3.76 (q, 1H), 1.50 (d, 3H), 1.22 (t, 3H). HPLC: 97%.

Step j11: The nitroester (250 g, 0.248 mol) and MeOH (1.1 l), followed by palladium on activated carbon (10 g, 10% Pd), were introduced in a 2 l Parr hydrogenator under a nitrogen atmosphere, flushed with nitrogen and hydrogenated at 45 psi for 3 h at room temperature. The reaction mix was removed by filtration and washed with 1 l of MeOH. The brown liquid obtained after concentration of the organic phase was purified by column chromatography (silica gel: 100-200 mesh, eluent: 10% EtOAc in hexane). 118.8 g of the amino ester (54.24%) were obtained. $^1$H NMR (DMSO-$d_6$, 400 MHz): δ [ppm]6.88 (dd, 1H), 6.78 (dd, 1H), 6.69 (t, 1H), 3.96-4.06 (m, 2H), 3.55-3.60 (q, 1H), 1.29 (d, 3H), 1.15 (t, 3H). Qualitative HPLC: 99%.

Step j12: The amino ester (110 g, 0.52 mol) was placed in 900 ml of dichloromethane and pyridine (63 ml, 0.78 mol) and cooled to 0° C. Methanesulfonyl chloride (44.4 ml, 0.57 mol) was added dropwise at 0° C. and the reaction mixture was stirred for 2 h at room temperature. After recooling of the mixture to 0° C., the mixture was acidified to pH 3 using 4 N HCl. The organic phase was repeatedly extracted with dichloromethane (3×600 ml). The combined organic phases were washed with water (2×1 l) and sat. aq. NaCl sol. (1×1 l), dried over $MgSO_4$ and concentrated to dryness. The purification by column chromatography (silica gel: 100-200 mesh, eluent; 15% EtOAc in hexane) produced 85.8 g of product (56.9%). $^1$H NMR (DMSO-$d_6$, 400 MHz): δ [ppm] 7.33 (t, 1H), 7.21 (d, 1H), 7.10 (dd, 1H), 4.01-4.10 (m, 2H), 3.80 (q, 1H), 3.01 (s, 3H), 1.37 (d, 3H), 1.13 (t, 3H). Qualitative HPLC: 99%.

Step j13 is carried out as described under 6.10.2.

6.10.4 Synthesis of N-methyl-2-(3-fluoro-(4-methylsulfonylamino)phenyl)propanoic acid

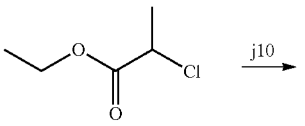

J-VI

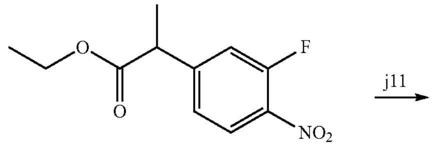

J-VIII

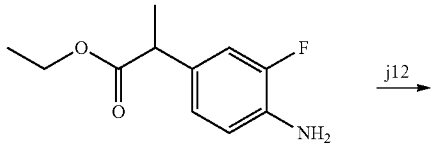

J-IX

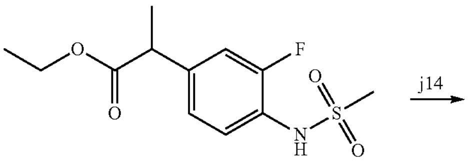

J-X

-continued

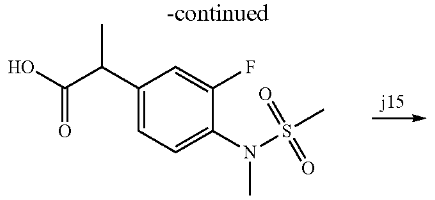

J-XI

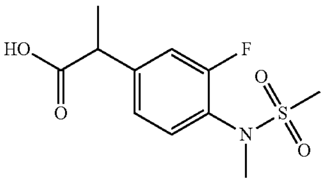

Steps j10 to j12 are carried out as described under 6.10.3.

Step j14: 1 equivalent of ethyl 2-[3-fluoro-4(methylsulfonylamino)phenyl]propanoate was added to a suspension of 1.25 equivalents of NaH (60%) in DMF and the mixture was stirred for 30 minutes at room temperature. 3.75 equivalents of methyl iodide were added portionwise to this reaction mixture and the mixture was stirred for 1.5 h at 100° C. and slowly cooled to room temperature. After the addition of water, the reaction mix was extracted twice with EtOAc, the combined organic phases were repeatedly washed with sat. aq. NaCl sol., dried over $MgSO_4$ and concentrated. The crude product J-XI was further processed immediately in step j15.

Step j15: 1 equivalent of J-XI was dissolved in a 2:1 THF/water mix and stirred for 15 minutes. 3 equivalents of LiOH, which is also dissolved in a 2:1 THF/water mix, are added to this solution and the mixture is stirred for 2 h at 45° C. While cooling, the aqueous phase is set to pH 1 using 4 N HCl and repeatedly extracted with dichloromethane. The combined organic phases are dried over $MgSO_4$ and concentrated under reduced pressure.

6.11 Synthesis of further 2-(3-fluoro-(4-methylsulfonylamido)phenyl-propanoic and acetic acids

6.11.1 Acids Wherein $R^{5b}$=$C_{1-10}$ Alkyl (Preferably $CH_3$, $CH_2$—$CH_3$, $CH_2$—$CH_2$—$CH_3$)

The substituent $R^{5b}$ is introduced in a reaction step j10a intervening between j10 and j11 as in scheme 2.

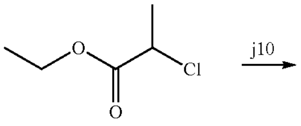

J-VI

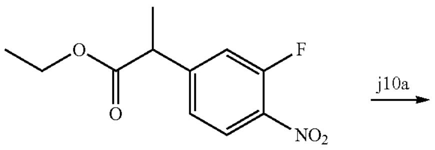

J-VIII

-continued

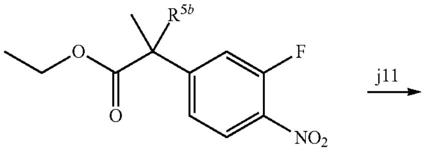

J-VIII-a

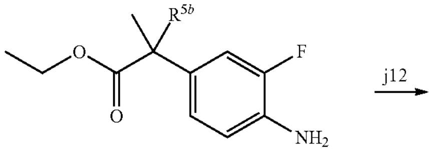

J-IX

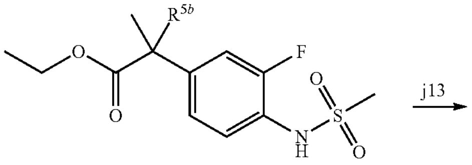

J-X

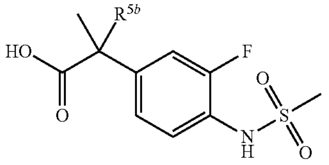

J-XI

Steps j10 and also j11 to j13 are carried out as described above.

Step j10a: 0.75 equivalents of alkyl iodide ($R^{5b}$—I) are slowly added dropwise to a solution of J-VIII (1 equivalent) and NaH (0.6 equivalents) in DMF at 0° C. and the reaction batch is stirred for approx. 10 minutes. Afterwards the reaction mixture is quenched with 1 N HCl sol., diluted with water and repeatedly extracted with diethyl ether. The combined organic phases are washed with water and sat. aq. NaCl sol., dried over $MgSO_4$ and concentrated under vacuum. A further purification of the crude product can be carried out by column chromatography (silica gel: 100-200 mesh, eluent: 10-20% EtOAc in hexane), as a result of which the product J-VIII-a is obtained.

6.11.2 Acids in which $R^{5a}$ and $R^{5b}$ Form Together with the Carbon Atom Connecting them a $C_{3-10}$ Cycloalkyl The substituents $R^{5a}$ and $R^{5b}$ are introduced in a reaction step j10b intervening between j10 and j11 as in scheme 2.

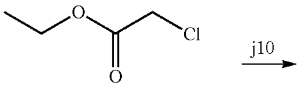

J-VI

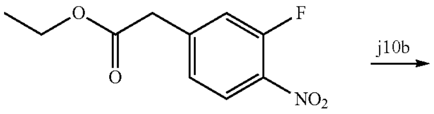

J-VIII

-continued

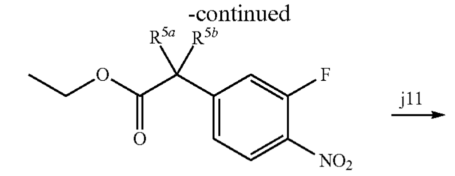

J-VIII-b

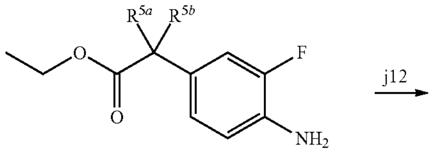

J-IX

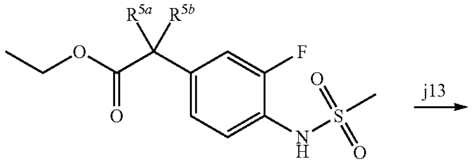

J-X

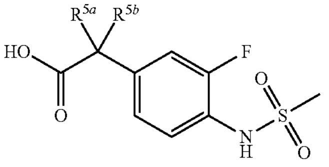

J-XI

Step j10: At 0° C. a mixture of 3-fluorophenyl acetate (1 equivalent) and sulfuric acid (0.261 equivalents) is added dropwise to a solution of nitric acid (1 equivalent) and the mixture is stirred for 2 h. The reaction mix is diluted with iced water and repeatedly extracted with EtOAc. The combined organic phases are washed with water, concentrated under vacuum and purified by column chromatography (eluent: EtOAc/hexane) and J-VIII is obtained in this way.

Step j10b: NaH (10 equivalents) is slowly added to the J-VIII (1 equivalent) dissolved in dry THF, the mixture is stirred for 10 minutes and the corresponding 1,1-dihalogenalkyl compound, preferably a dibromoalkyl compound (5 equivalents), is then added. Within 30 minutes the mixture is heated to room temperature heated and quenched with sat. aq. $NH_4Cl$ sol. After aqueous working up, the crude product obtained is purified by flash chromatography (eluent: EtOAc/hexane) and J-VIII-b is obtained in this way.

Steps j11 to j13 are carried out as described hereinbefore.

6.11.3 Synthesis of 2-cyclohexyl-2-(3-fluoro-4-(methylsulfonamido)phenyl)acetic acid

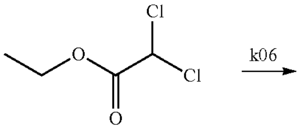

-continued

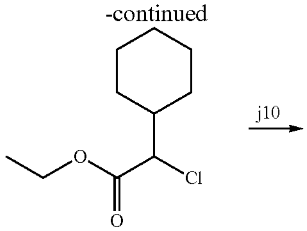

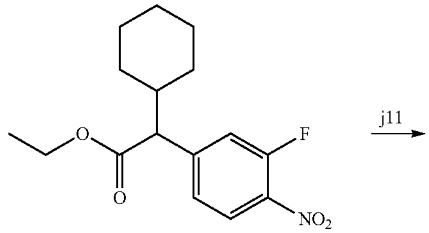

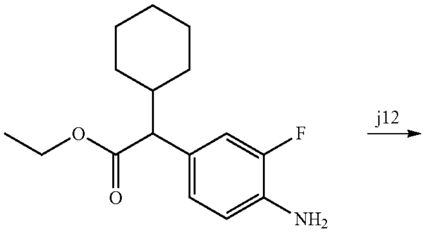

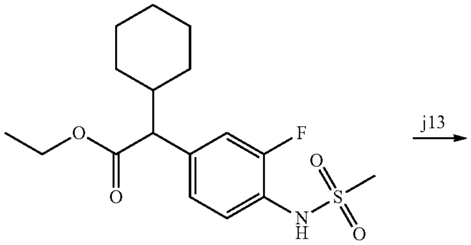

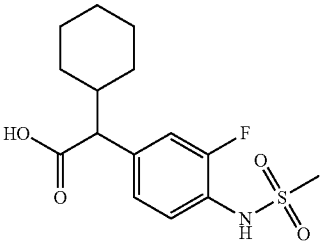

Step k06: Ethyl 2-chloro-2-cyclohexyl acetate 170 ml of dry THF were mixed with 100 ml of 1 M $BH_3$-THF complex (100 mmol) at room temperature under a nitrogen atmosphere. Within 5 minutes 12.3 ml of cis-1,5-cyclooctadiene (100 mmol) were added dropwise to this mix, wherein the temperature rose to 45° C. The reaction mix was boiled to reflux for 1.5 h, recooled to 45° C., mixed with 10.1 ml of cyclohexene (100 mmol) and stirred for a further 2 h at 45° C. After cooling of the reaction batch in an ice bath, 12.2 ml of ethyl dichloroacetate (100 mmol) were added in 50 ml of tert. butanol, the mixture was stirred for 15 minutes and within a further 15 minutes 1 M potassium tert. butylate (100 mmol, 100 ml) was added dropwise. The reaction mix was stirred for a further 15 minutes, mixed with 33 ml of 3 M sodium acetate sol. (100 mmol) and 22.5 ml of 30% $H_2O$ (750 mmol) were carefully added dropwise. The mix was stirred for 30 minutes at room temperature and subsequently salted out with NaCl; the organic phase was dried over $MgSO_4$ and the solvent was removed under reduced pressure. After washing of the solid residue with tert. BME, cyclohexane tert. BME (9:1), tert. BME and EtOAc, 7.6 g (37.4%) of product could be obtained.

Step j10: Ethyl 2-cyclohexyl-2-(3-fluoro-4-nitrophenyl)acetate 8.2 g of potassium tert. butylate were dissolved in 70 ml of DMF and cooled to −45° C. For this purpose, a mix of ethyl 2-chloro-2-cyclohexylacetate (36.6 mmol, 7.5 g) and 1-fluoro-2-nitrobenzene (36.6 mmol, 3.9 ml) was carefully added dropwise and stirred for a further 20 minutes. The reaction mix was set to pH 4 using 16% HCl, diluted with 25 ml of water and extracted with EtOAc (3×50 ml). Once combined, the organic phases were washed with water and sat. aq. NaCl sol., dried over $MgSO_4$ and concentrated under vacuum. The resulting residue was purified by column chromatography (silica gel: mesh 100-200, eluent: 10% EtOAc in cyclohexane) and produced 5.5 g (49%) of product.

Step j11: Ethyl 2-(4-amino-3-fluorophenyl)-2-cyclohexylacetate

The ethyl 2-cyclohexyl-2-(3-fluoro-4-nitrophenyl)acetate was dissolved in a 1:1 mix of EtOH and EtOAc (420 ml) and hydrogenated in an H-cube (1 bar, 25° C., 1 ml/min and 0.25 mol/L). After removal of the solvent and drying, 5 g (quantitative turnover) of product could be obtained.

Step j12: Ethyl 2-cyclohexyl-2-(3-fluoro-4-(methylsulfonamido)phenyl)acetate The amine compound (5 g, 17.9 mmol) was dissolved in 15 ml of pyridine, cooled to 0° C. under a nitrogen atmosphere and mixed with 2 ml of methanesulfonyl chloride (26.8 mmol) and stirred for a further 1 h at 0° C. The reaction mix was mixed with 15 ml of water while being cooled with ice and set to pH 1 using 16% HCl. After extraction of the mix with dichloromethane (3×50 ml), the organic phases were combined, dried over $MgSO_4$ and concentrated under vacuum. The crude product was purified by column chromatography (silica gel: 100-200 mesh, eluent: 50% EtOAc in cyclohexane), producing 5.4 g (85.4%) of product.

Step j13: 2-cyclohexyl-2-(3-fluoro-4-(methylsulfonamido)phenyl)acetic acid

The phenylacetate (15.2 mmol, 5.4 g) was dissolved in a mix of 30 ml of THF and 15 ml of water, mixed with 1.09 g of LiOH (45.7 mmol) and boiled to reflux for 6 h and stirred for a further 12 h at room temperature. 15 ml of water were added to the reaction mix and the phases were separated. The aqueous phase was acidified using HCl and repeatedly extracted with dichloromethane (3×50 ml). The combined organic phases were dried over $MgSO_4$, concentrated and the resulting residue was purified by column chromatography (silica gel: 100-200 mesh, eluent: 50% EtOAc in cyclohexane). Yield 1.05 g (21%).

6.11.4 Synthesis of 2-(3-fluoro-4-(methylsulfonamido)phenyl)-2-phenylacetic acid

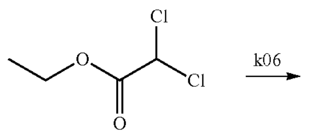

-continued

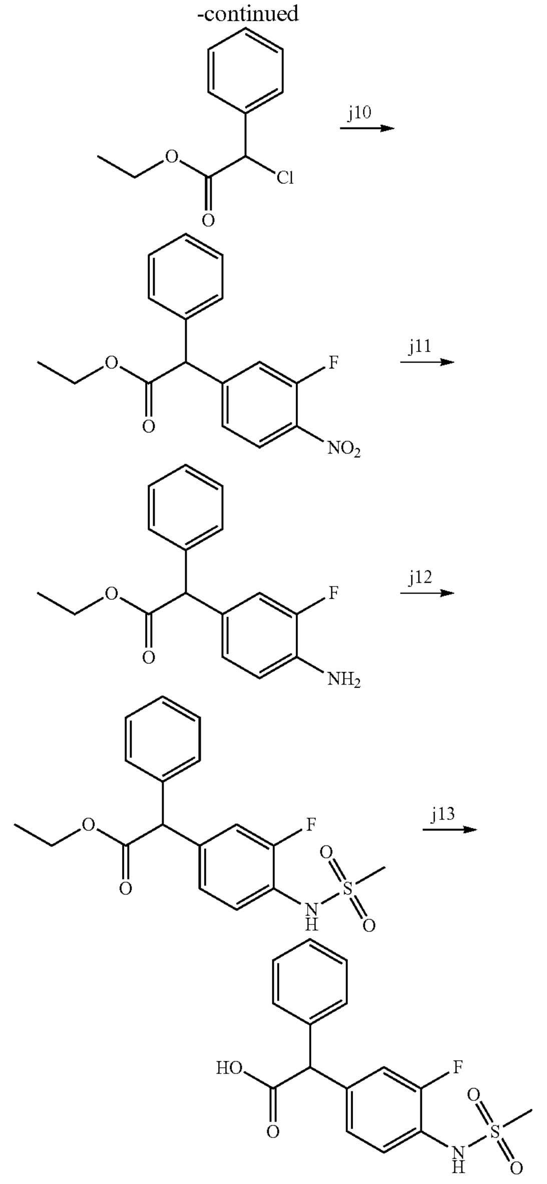

Step k06: Ethyl 2-chloro-2-phenylacetate

Chlorophenyl acetyl chloride (53 mmol, 7.6 ml) was added dropwise to a solution of triethylamine (63.5 mmol, 8.7 ml) in methanol at 0° C. and the mixture was subsequently stirred for 3.5 h at room temperature. The reaction mix was then placed in 100 ml of water and repeatedly extracted with EtOAc (3×100 ml). Once combined, the organic phases were dried over MgSO4, concentrated under vacuum and 8.76 g (83.4%) of product was obtained.

Step j10: Ethyl 2-(3-fluoro-4-nitrophenyl)-2-phenylacetate 9.8 g of potassium tert. butylate were dissolved in 90 ml of DMF and cooled to −45° C. For this purpose, a mix of ethyl 2-chloro-2-phenylacetate (43.8 mmol, 8.7 g) and 1-fluoro-2-nitrobenzene (43.8 mmol, 4.6 ml) was carefully added dropwise and the mixture was stirred for a further 20 minutes. The reaction mix was set to pH 4 using 16% HCl, diluted with 25 ml of water and extracted with EtOAc (3×50 ml). Once combined, the organic phases were washed with water and sat. aq. NaCl sol., dried over $MgSO_4$ and concentrated under vacuum. The resulting residue was purified by column chromatography (silica gel: mesh 100-200, eluent: 10% EtOAc in cyclohexane) and produced 5.9 g (44.9%) of product.

Step j11: Ethyl 2-(4-amino-3-fluorophenyl)-2-phenylacetate

The ethyl 2-phenyl-2-(3-fluoro-4-nitrophenyl)acetate was dissolved in a 1:1 mix of EtOH and EtOAc (465 ml) and hydrogenated in an H-cube (1 bar, 25° C., 1 ml/min and 0.25 mol/L). After removal of the solvent and drying, 5.2 g (97.5%) of product could be obtained.

Step j12: Ethyl 2-phenyl-2-(3-fluoro-4-(methylsulfonamido)phenyl)acetate

The amine compound (5.2 g, 19 mmol) was dissolved in 15 ml of pyridine, cooled to 0° C. under a nitrogen atmosphere and mixed with 2.2 ml of methanesulfonyl chloride (28.5 mmol) and stirred for a further 1 h at 0° C. The reaction mix was mixed with 15 ml of water while being cooled with ice and set to pH 1 using 16% HCl. After extraction of the mix with dichloromethane (3×50 ml), the organic phases were combined, dried over $MgSO_4$ and concentrated under vacuum. The crude product was purified by column chromatography (silica gel: 100-200 mesh, eluent: 50% EtOAc in cyclohexane), producing 5.8 g (87%) of product.

Step j13: 2-phenyl-2-(3-fluoro-4-(methylsulfonamido)phenyl)acetic acid

The phenylacetate (16.5 mmol, 5.8 g) was dissolved in a mix of 32 ml of THF and 16 ml of water, mixed with 1.18 g of LiOH (49.5 mmol) and boiled to reflux for 15 h. 15 ml of water were added to the reaction mix and the phases were separated. The aqueous phase was acidified using HCl and repeatedly extracted with dichloromethane (3×50 ml). The combined organic phases were dried over MgSO4, concentrated and the resulting residue was purified by column chromatography (silica gel: 100-200 mesh, eluent: 50% EtOAc in cyclohexane). Yield 3.3 g (61.3%).

6.11.5 Synthesis of 2-(3-fluoro-4-(methylsulfonamido)phenyl)-2-(3-fluorophenyl)acetic acid (employed for the synthesis of example compound no. 66)

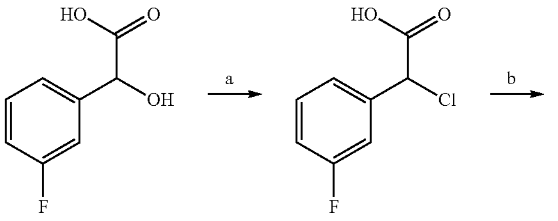

-continued

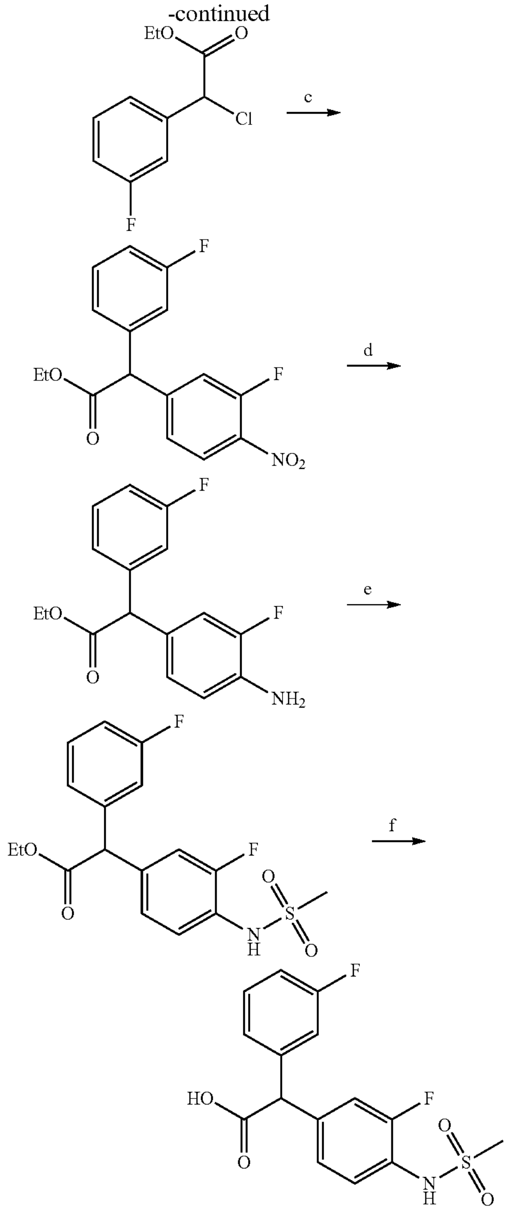

Step a: 2-(3-fluorophenyl)-2-hydroxyacetic acid (12 g, 70.5 mmol), was dissolved in THF (120 mL). Thionyl chloride (10 g, 84.6 mmol) was added to it. Catalytic amount of dimethylformamide (1 mL) was added to the reaction mixture. The reaction mixture was stirred at ambient temperature for overnight. The organic solvent was removed under reduced pressure; the residue was diluted with water (200 mL) and extracted with dichloromethane (2×200 mL). The combined organic layer was dried over anhydrous magnesium sulfate and concentrated under reduced pressure to afford 12 g crude compound.

Step b: The crude step-a product (12 g) was dissolved in benzene (240 mL). EtOH (120 mL) and sulfuric acid (2 mL) was added to it. The reaction mixture was refluxed for 4 h using Dean stark apparatus. TLC (5% ethyl acetate-Hexane, $R_f$=0.7) showed complete consumption of starting material. The organic solvent was removed under reduced pressure and the residue was diluted with water (200 mL). The aqueous part was extracted with 20% ethyl acetate in hexane (3×200 mL). The combined organic layer was dried over anhydrous magnesium sulfate and concentrated under reduced pressure to afford a yellow residue, which was purified by column chromatography (silica gel: 100-200 mesh, eluent: 2% ethyl acetate in hexane) to afford a light yellow liquid compound (8.2 g, 59.5%).

Step c: To a stirred suspension of potassium tertiary butoxide (8.5 g, 75.75 mmol) in dimethylformamide (50 mL), a mixture of step-b product (8.2 g, 38 mmol) and 1-fluoro-2-nitrobenzene (5.34 g, 38 mmol) in dimethylformamide (30 mL) was added at −30° C. The reaction mixture was stirred for 30 minutes at the same temperature. TLC (10% ethyl acetate-Hexane, $R_f$=0.6) showed complete consumption of starting material. Reaction mixture was diluted with water (800 mL) and extracted with 20% ethyl acetate in hexane (3×200 mL). Then the organic layer was dried over anhydrous magnesium sulfate. The removal of organic solvent under reduced pressure afforded a brown liquid compound, which was purified by column chromatography (silica gel: 100-200 mesh, eluent: 2% ethyl acetate in hexane) to afford a light brown liquid compound (3.2 g, 26%).

Step d: In a 250 mL round-bottom flask step-c product (3.2 g, 10 mmol) was dissolved in ethyl acetate (50 mL). Palladium on charcoal (150 mg, 10% Pd) was added under nitrogen atmosphere. It was stirred under atmospheric hydrogen pressure for 12 h. TLC (20% ethyl acetate in hexane, $R_f$=0.3) showed complete conversion of starting material. The reaction mixture was filtered over celite bed and the bed was washed with ethyl acetate (3×50 mL). The organic layer was concentrated to afford a yellow residue, which was purified through column chromatography (silica gel: 100-200 mesh, eluent: 10% ethyl acetate in hexane) to afford the pure amine compound (2.3 g, 79%).

Step e: Step-d product (2.3 g, 7.8 mmol) was dissolved in dichloromethane (35 mL). Pyridine (1.9 mL, 23.4 mmol) was added to it. Methanesulfonyl chloride (1.1 g, 9.4 mmol) was added dropwise to the reaction mixture at 0° C. and stirred for 16 h at ambient temperature. TLC (20% ethyl acetate in hexane, $R_f$=0.2) showed complete consumption of starting material. The reaction mixture was diluted with dichloromethane (100 mL) and washed with water (3×50 mL). The organic layer was then dried over anhydrous magnesium sulfate and concentrated to afford a solid compound, which was purified through column chromatography (silica gel: 100-200 mesh, eluent: 15% ethyl acetate in hexane) to afford the pure compound (2.8 g, 96%). $^1$H NMR ($CDCl_3$, 400 MHz): δ 7.55 (t, 1H), 7.30-7.35 (q, 1H), 6.98-7.18 (m, 5H), 6.50 (s, 1H), 4.21-4.27 (q, 2H), 3.04 (s, 3H), 1.28 (t, 3H).

Step f: Step-e product (2.8 g, 7.5 mmol), was dissolved in THF (30 mL). Aqueous LiOH solution (1M, 23 mL, 23 mmol) was added dropwise at 0° C. to it. The reaction mixture was then stirred at ambient temperature for 16 h. TLC (30% ethyl acetate-Hexane, $R_f$=0.05) showed complete consumption of starting material. The solvent was removed under reduced pressure and residue was diluted with water (70 mL). The aqueous layer was washed with ethyl acetate (70 mL) and aqueous part was acidified with 2N HCl up to pH=3-4. The acidified aqueous part was then extracted with ethyl acetate (3×150 mL). The combine organic part was dried over anhydrous magnesium sulfate and concentrated under reduced pressure to afford a white solid compound. (1.8 g, 70%). $^1$H NMR (DMSO-$d_6$, 400 MHz): δ 12.99 (bs, 1H), 9.58 (s, 1H), 7.08-7.41 (m, 7H), 5.16 (s, 1H), 3.01 (s, 3H); Mass (M+1): 342.

6.11.6 Synthesis of 2-(3-fluoro-4-(methylsulfonamido)phenyl)-2-p-tolylacetic acid (employed for the synthesis of example compound no. 68)

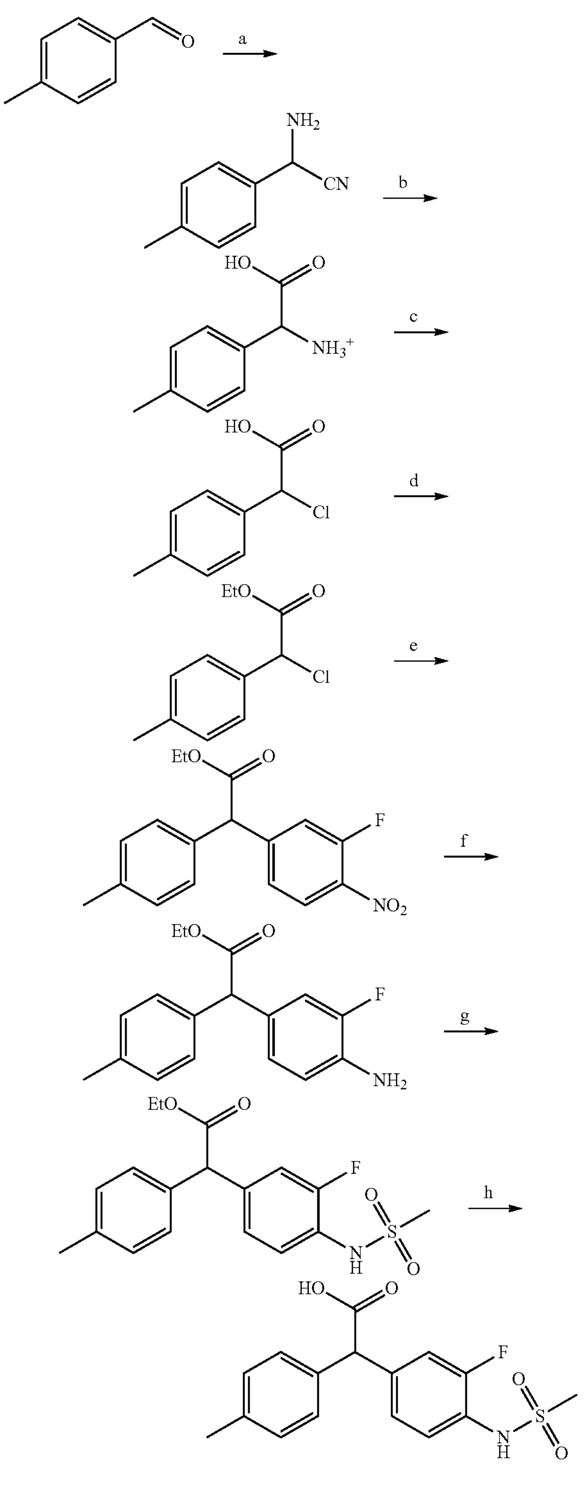

Step a: Sodium cyanide (7.3 g, 149.8 mmol) was dissolved in water (30 mL) and ammonium chloride (13.3 g, 249.6 mmol) was added to it. 4-Methylbenzaldehyde (15 g, 124.8 mmol) in MeOH (25 mL) was added to the reaction mixture and stirred it at ambient temperature for two days.

TLC (5% ethyl acetate-Hexane, $R_f$=0.4) showed complete consumption of starting material. Water (100 mL) and benzene (100 mL) was added to the reaction mixture and stirred for 10 minutes. The separated organic layer was dried over anhydrous magnesium sulfate and concentrated under reduced pressure to afford a yellow liquid compound (17 g, crude).

Step b: The crude step-a product (17 g) was dissolved 6N HCl (136 mL) and refluxed for 20 h. HCl was removed under reduced pressure. The residue was diluted with EtOH (2×200 mL) and concentrated under reduced pressure. Finally ethyl acetate (250 mL) was added and stirred at 70° C. for 1 hour. A solid came out upon cooling and it was filtered through glass-sintered funnel to afford yellow crystalline solid compound (15 g, crude).

Step c: Step-b product (15 g, 74.4 mmol) was dissolved in HCl (300 mL) and it was cooled to −5° C. Sodium nitrite solution (9.75 g, 141.3 mmol) in water (45 mL) was added dropwise over the period of 30 minutes. After complete addition, reaction mixture was stirred at ambient temperature for 3 h. TLC (in ethyl acetate $R_f$=0.3) showed complete consumption of starting material. The aqueous part was extracted in ethyl acetate (3×250 mL). The organic layer was washed with water (2×200 mL) and finally with brine (200 mL). The washed organic layer was dried over anhydrous magnesium sulfate and concentrated under reduced pressure to afford a yellow solid (12.5 g, crude).

Step d: Step-c product (10 g, 54 mmol) was dissolved in benzene (200 mL). EtOH (100 mL) and sulfuric acid (2 mL) was added to it. The reaction mixture was refluxed for 4 h. TLC (in 5% ethyl acetate-Hexane, $R_f$=0.7) showed complete consumption of starting material. The organic solvent was removed under reduced pressure and the residue was diluted with water (200 mL). The aqueous part was extracted with 20% ethyl acetate in hexane (3×200 mL). The combined organic layer was dried over anhydrous magnesium sulfate and concentrated under reduced pressure to afford a yellow residue, which was purified by column chromatography (silica gel: 100-200 mesh, eluent: 2% ethyl acetate in hexane) to afford a light yellow liquid compound (10 g, 87%).

Step e: To a stirred suspension of potassium tertiary butoxide (10.6 g, 94 mmol) in dimethylformamide (60 mL), a mixture of step-d product (10 g, 47 mmol) and 1-fluoro-2-nitrobenzene (6.6 g, 47 mmol) in dimethylformamide (40 mL) was added at −30° C. The reaction mixture was stirred for 30 minutes at the same temperature. TLC (10% ethyl acetate-Hexane, $R_f$=0.6) showed complete consumption of starting material. Reaction mixture was diluted with water (1 L) and extracted with 20% ethyl acetate in hexane (3×250 mL). Then the organic layer was dried over anhydrous magnesium sulfate. The removal of organic solvent under reduced pressure afforded a yellowish compound, which was purified by column chromatography (silica gel: 100-200 mesh, eluent: 2% ethyl acetate in hexane) to afford a yellow liquid compound (10.4 g, 68%). $^1$H NMR ($CDCl_3$, 400 MHz): δ 8.12 (t, 1H), 7.55 (dd, 1H), 7.37 (dd, 1H), 7.16-7.23 (m, 4H), 5.38 (s, 1H), 4.13-4.18 (m, 2H), 2.27 (s, 3H), 1.16 (t, 3H).

Step f: In a 500 mL round-bottom flask step-e product (10.4 g, 33 mmol) was dissolved in ethyl acetate (150 mL). Palladium on charcoal (520 mg, 10% Pd) was added under nitrogen atmosphere. It was stirred under atmospheric hydrogen pressure for 12 h. TLC (20% ethyl acetate in hexane, $R_f$=0.3) showed complete conversion of starting material. The reaction mixture was filtered over celite bed and the bed was washed with ethyl acetate (3×100 mL). The organic layer was concentrated to afford a yellow residue, which was purified through column chromatography (silica gel: 100-200 mesh, eluent: 10% ethyl acetate in hexane) to afford the pure amine compound (8 g, 85%). $^1$H NMR ($CDCl_3$, 400 MHz): δ 7.10-7.15 (m, 4H), 6.89 (dd, 1H), 6.80 (dd, 1H), 6.68 (t, 1H), 5.09 (s, 1H), 4.92 (s, 1H), 4.07-4.12 (m, 2H), 2.25 (s, 3H), 1.15 (t, 3H).

Step g: Step-f product (8 g, 27.8 mmol) was dissolved in dichloromethane (120 mL). Pyridine (6.7 mL, 83.5 mmol) was added to it. Methanesulfonylchloride (3.8 g, 33.4 mmol) was added dropwise to the reaction mixture at 0° C. and stirred for 16 h at ambient temperature. TLC (20% ethyl acetate in hexane, $R_f$=0.2) showed complete conversion of starting material. The reaction mixture was diluted with dichloromethane (200 mL) and washed with water (3×200 mL). The organic layer was then dried over anhydrous magnesium sulfate and concentrated to afford a solid compound, which was purified through column chromatography (silica gel: 100-200 mesh, eluent: 15% ethyl acetate in hexane) to afford the pure compound (8.8 g, 78.6%). $^1$H NMR ($CDCl_3$, 400 MHz): δ 9.57 (s, 1H), 7.32 (t, 1H), 7.12-7.21 (m, 6H), 5.16 (s, 1H), 4.10-4.16 (m, 2H), 3.00 (s, 3H), 2.26 (s, 3H), 1.16 (t, 3H).

Step h: Step-g product (4 g, 10.9 mmol), was dissolved in THF (60 mL). Aqueous LiOH solution (1M, 33 mL, 33 mmol) was added dropwise at 0° C. to it. The reaction mixture was then stirred at ambient temperature for 16 h. TLC (30% ethyl acetate-Hexane, $R_f$=0.05) showed complete consumption of starting material. The solvent was removed under reduced pressure and residue was diluted with water (70 mL). The aqueous layer was washed with ethyl acetate (50 mL) and aqueous part was acidified with 2N HCl up to pH=3-4. The acidified aqueous part was then extracted with ethyl acetate (3×50 mL). The combine organic part was dried over anhydrous magnesium sulfate and concentrated under reduced pressure to afford a white solid compound (3.1 g, 84%). $^1$H NMR ($CDCl_3$, 400 MHz): δ 9.57 (s, 1H), 7.32 (t, 1H), 7.12-7.21 (m, 6H), 5.16 (s, 1H), 3.00 (s, 3H), 2.26 (s, 3H).

6.11.7 Synthesis of 2-(3-fluoro-4-(methylsulfonamido)phenyl)-3-phenylpropanoic acid (employed for the synthesis of example compound no. 145)

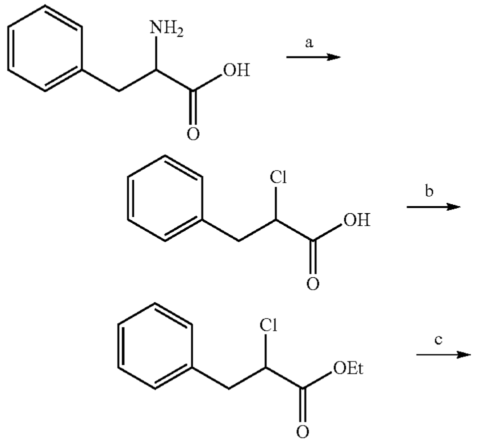

-continued

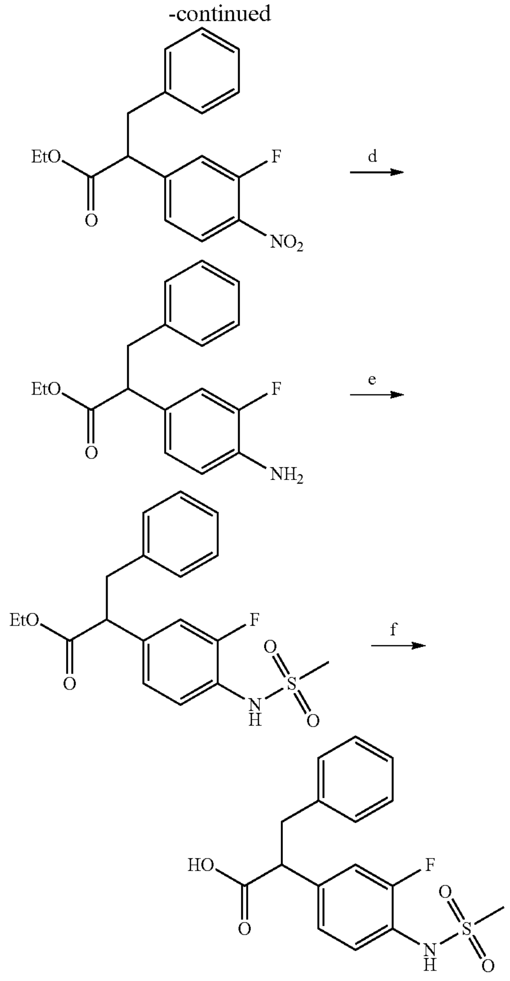

Step a: 2-amino-3-phenylpropanoic acid (10 g, 60.5 mmol) was dissolved in concentrated HCl (200 mL) and was cooled to −5° C. Sodium nitrite solution (7.9 g, 115 mmol) in water (30 mL) was added dropwise over the period of 30 minutes. After complete addition reaction mixture was stirred at ambient temperature for 2 h. TLC (in 50% ethyl acetate-Hexane, $R_f$=0.4) showed complete consumption of starting material. The aqueous part was extracted in ethyl acetate (3×200 mL). The overall organic layer was washed with water (2×200 mL) and finally with brine (200 mL). The washed organic layer was dried over anhydrous magnesium sulfate and concentrated under reduced pressure to afford a yellow liquid (12 g, crude).

Step b: Step-a product (12 g, 65 mmol) dissolved in benzene (240 mL). EtOH (120 mL) and sulfuric acid (2 mL) was added to it. The reaction mixture was refluxed for 4 h using Deanstark apparatus. TLC (20% ethyl acetate in hexane, $R_f$=0.6) showed complete consumption of starting material. The organic solvent was concentrated under reduced pressure and the residue was diluted with water (200 mL). The aqueous layer was extracted with 30% ethyl acetate in hexane (3×200 mL). The overall organic layer was dried over anhydrous magnesium sulfate and concentrated under reduced pressure to get a yellowish residue, which was purified by column chromatography (silica gel: 100-200 mesh; eluent: 2% ethyl acetate in hexane) to afford a light yellow liquid compound. (10 g, 87%). $^1$H NMR ($CDCl_3$, 400 MHz): δ 7.23-7.35 (m, 5H), 4.81 (q, 1H), 4.11 (q, 2H), 3.10-3.34 (m, 2H), 1.14 (t, 3H).

Step c: To a stirred suspension of potassium tert-butoxide (14.3 g, 127 mmol) in dimethylformamide (90 mL), a mixture of step-b product (13.5 g, 63.5 mmol) and 1-fluoro 2-nitrobenzene (7.12 g, 63.5 mmol) in dimethylformamide (50 mL) was added at −30° C. The reaction mixture was stirred for 30 minutes at the same temperature. TLC (10% ethyl acetate-Hexane, $R_f$=0.4) showed complete consumption of starting material. Reaction mixture was diluted with water (1.5 L) and extracted with 20% ethyl acetate in hexane (3×250 mL). Then the organic layer was dried over anhydrous magnesium sulfate. The removal of organic solvent under reduced pressure afforded a yellowish compound, which was purified by column chromatography (silica gel: 100-200 mesh, eluent: 2% ethyl acetate in hexane) to afford a light brown solid (14.5 g, 72%). $^1$H NMR ($CDCl_3$, 400 MHz): δ 6.64-7.24 (m, 8H), 3.96 (q, 2H), 3.77 (t, 1H), 3.18 (q, 1H), 2.90 (q, 1H), 1.02 (t, 3H).

Step d: In a 500 mL round-bottom flask step-c product (14.5 g, 45.7 mmol) was dissolved in ethyl acetate (300 mL). Palladium on charcoal (0.700 mg, 10% Pd) was added under nitrogen atmosphere. It was stirred under atmospheric hydrogen pressure for 12 h. TLC (20% ethyl acetate in hexane, $R_f$=0.4) showed complete conversion of starting material. Reaction mixture was filtered over celite bed and washed with ethyl acetate (3×150 mL). The organic layer was concentrated to afford a yellowish residue, which was purified through column chromatography (silica gel: 100-200 mesh, eluent: 10% ethyl acetate in hexane) to afford the pure amine compound (12.5 g, 95%). $^1$H NMR ($CDCl_3$, 400 MHz): δ 6.64-7.24 (m, 8H), 5.06 (s, 2H), 3.96 (q, 2H), 3.77 (t, 1H), 3.18 (q, 1H), 2.90 (q, 1H), 1.02 (t, 3H).

Step e: Step-d product (12.5 g, 43.5 mmol) was dissolved in dichloromethane (190 mL). Pyridine (10.5 mL, 130.5 mmol) was added to it. Methanesulfonylchloride (6 g, 47.85 mmol) was added dropwise to the reaction mixture at 0-5° C. and stirred for 16 h at ambient temperature. TLC (20% ethyl acetate in hexane, $R_f$=0.2) showed complete conversion of starting material. Reaction mixture was diluted with dichloromethane (200 mL) and washed with water (3×200 mL). The organic layer was then dried over anhydrous magnesium sulfate and concentrated to afford a solid compound, which was purified through column chromatography (silica gel: 100-200 mesh, eluent: 20% ethyl acetate in hexane) to afford the pure compound (13.5 g, 85%). $^1$H NMR ($CDCl_3$, 400 MHz): δ 9.57 (s, 1H), 7.14-7.34 (m, 8H), 3.94-4.04 (m, 3H), 3.25 (q, 1H), 2.97-3.02 (m, 4H), 1.03 (t, 3H).

Step f: Step-e product (4 g, 11 mmol), was dissolved in THF (60 mL). LiOH solution (1M, 33 mL, 33 mmol) was added dropwise at 10-15° C. to it. The reaction mixture was then stirred at ambient temperature for 16 h. TLC (in 30% ethyl acetate-Hexane, $R_f$=0.05) showed complete consumption of starting material. The solvent was removed under reduced pressure and residue was diluted with water (150 mL). The aqueous layer was washed with ethyl acetate (150 mL) and aqueous part was acidified with 2N aqueous HCl solution up to pH=3-4. The acidified aqueous part was then extracted with ethyl acetate (3×150 mL). The organic layer was dried over anhydrous magnesium sulfate and concentrated under reduced pressure afforded a white solid compound (3 g, 81%). $^1$H NMR ($CDCl_3$, 400 MHz): δ 12.53 (s, 1H), 9.56 (s, 1H), 7.15-7.33 (m, 8H), 3.91 (t, 1H), 3.26 (q, 1H), 3.00 (s, 3H), 2.96 (t, 1H). MS m/z (M+1): 338.

7. Preparation of Selected Amines of General Formula (VI)

7.1 Synthesis of 4-cyclopropyl-3-fluoroaniline hydrochloride (employed for the synthesis of example compound no. 126)

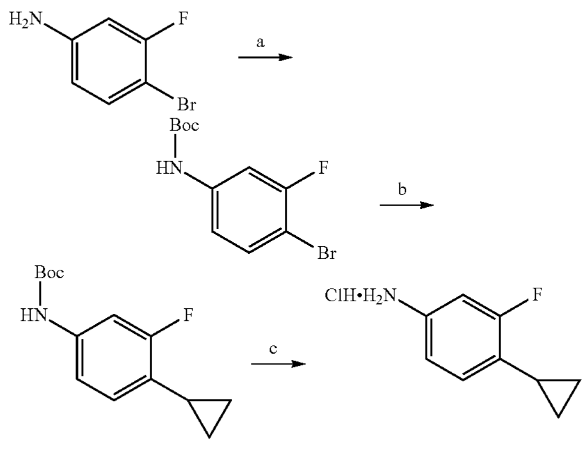

Step a: To a mixture of 4-bromo 3-fluoro aniline (5 g, 26.4 mmol) in water (40 mL), was added Boc-anhydride (6.4 g, 29.09 mmol) and stirred at room temperature for 16 h until complete consumption. To the clear solution water (50 mL) was added to obtain white precipitate, the solid filtered, washed with water (2×20 mL) and dried under reduced pressure to afford a white solid (5.82 g, 76%).

Step b: A suspension containing step-a product (1 g, 3.46 mmol), cyclopropyl boronic acid (0.74 mmol), tricyclohexyl phosphine (0.387 mg, 1.38 mmol), tripotassium phosphate (3.67 g, 17.38 mmol) in toluene (10 mL) and water (10 mL) was degassed by purging Ar for 30 minutes and $Pd(OAc)_2$ (155 mg, 0.69 mmol) was added. The mixture was stirred in a sealed tube at 110° C. for 20 h. The reaction mixture was cooled to room temperature, diluted with ethyl acetate (200 mL), washed with water (2×30 mL), brine solution (25 ml), dried ($Na_2SO_4$) and concentrated under reduced pressure to give a residue. Purification by column chromatography (silica gel; 100-200 mesh; eluent: 2% ethyl acetate-petroleum ether) afforded a white solid (600 mg, 69%).

Step c: To step-b product (2.65 g, 10.55 mmol), a solution of HCl in diethyl ether (60 ml) was added at 0° C. and the mixture was stirred at room temperature for 36 h. The solid was filtered, washed with ether (3×10 mL), pentane (3×10 mL) and dried to afford desired compound as white solid (810 mg, 43%).

7.2 Synthesis of 4-(cyclopropylethynyl)-3-fluoroaniline (employed for the synthesis of example compound no. 139)

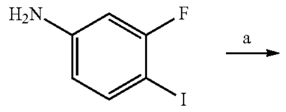

-continued

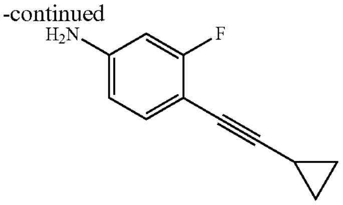

Step a: To a stirred solution of 4-iodo 3-fluoro aniline (2.25 g, 9.49 mmol) in THF (25 ml) at 0° C. to −5° C., CuI (90 mg, 0.47 mmol) and $Et_3N$ (3.5 ml, 25.62 mmol) were added. The reaction mixture was deoxygenated by purging with a stream of Argon for 30 minutes at −5° C. Addition of $Pd(dppf)Cl_2.CH_2Cl_2$ (346 mg, 0.47 mmol) and purging was continued. After 10 minutes, cyclopropyl acetylene (0.72 ml, 8.54 mmol) was added at −5° C. and stirred at room temperature for 16 h. The reaction mixture was diluted with ether (200 mL), filtered through celite pad, washed with ether (2×25 mL). The filtrate was concentrated and the residue purified by column chromatography (100-200 mesh silica gel) using hexane as eluent to afford title compound as pale brown liquid (750 mg, 45%).

8. Preparation of Selected Carbamate Phenyl Esters of General Formula (VIa) or (V) and Phenyl Esters of General Formula (IVa)

8.1 Synthesis of methyl phenyl (3-tert-butyl-1-(3-chlorophenyl)-1H-pyrazol-5-yl)methylcarbamate (employed for the synthesis of example compounds no. 57-65, 122 and 144)

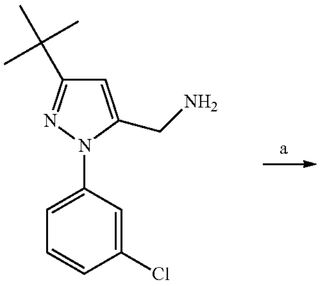

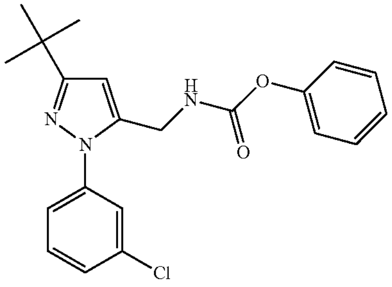

Step a: To a solution of (3-tert-butyl-1-(3-chlorophenyl)-1H-pyrazol-5-yl)methanamine (5 g, 18 mmol) in dimethylformamide (25 ml, 5 times), potassium carbonate (9.16 g, 66 mmol, 3.5 eq) was added and cooled the contents to 0° C. Then phenyl chloroformate (3.28 g (2.65 ml), 20 mmol, 1.1 eq) was added dropwise for 15 minutes and the overall reaction mixture was stirred for another 15 minutes at 0° C. Progress of the reaction was monitored by TLC (20% ethyl acetate-hexane, $R_f$~0.3). On completion of the reaction, reaction contents were filtered, filtrate was diluted with cold water (100 ml) and the product extracted with ethyl acetate (3×25 ml). Combined organic layer was washed with brine solution (100 ml), dried over sodium sulfate and concentrated under reduced pressure. Crude product obtained was purified by column chromatography (silica gel, 10% ethyl acetate-hexane) to yield the required product as a white solid (3.2 g, 45%).

9. Preparation of Additional Selected Pyrazol Derivatives According to General Formula (II)

9.1 Synthesis of (1-(3-chlorophenyl)-4-methyl-3-(trifluoromethyl)-1H-pyrazol-5-yl)methanamine (employed for the synthesis of example compounds no. 84 and 134)

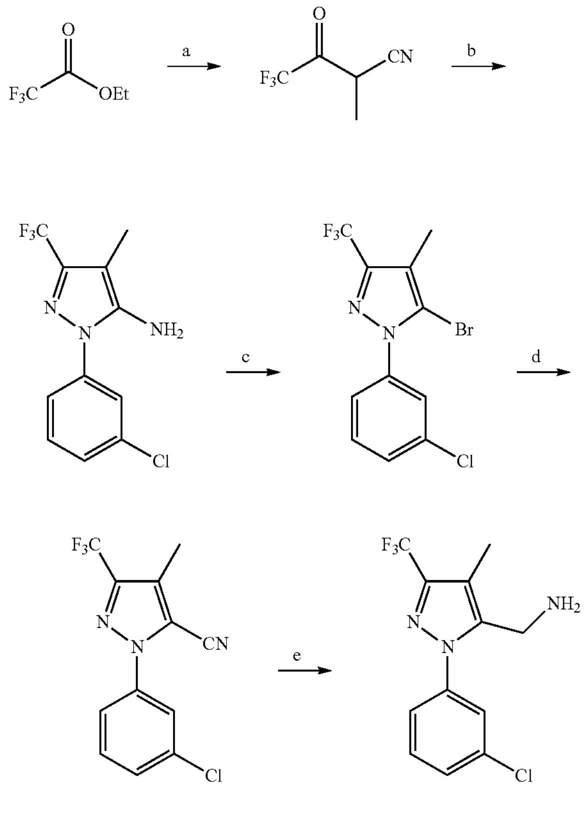

Step a: To a solution of diispropylamine (40.8 g (57 ml), 0.404 mol, 2.3 eq) in THF (400 ml), n-BuLi (1.6 molar) (24.7 g (258.3 ml, 0.38 mol, 2.2 eq) was added drop wise for 2 hrs at −20° C. and stirred the contents for 30-45 min at 0° C. Cooled the contents to −75° C., a solution of ethyl 2,2,2-trifluoroacetate (25 g, 0.17 mol) in THF (200 ml) was added drop wise for 2 hrs. The reaction mixture was stirred initially for 1 hr at −75° C. and later for another 1 hr at rt. Progress of the reaction was monitored by TLC (50% ethyl acetate/hexane, $R_f$~0.5). On completion of the reaction, quenched the reaction with ice water (700 ml) and the solvents were distilled off completely. Residue washed with DCM (3×300 ml), acidified the contents with 30% HCl solution and the product extracted with ether (3×400 ml). Combined organic layer was dried over sodium sulfate, concentrated under reduced pressure and the crude product obtained was distilled under vacuum to yield the product at 35° C./0.1 mm as a colorless liquid (17 g, 64% yield).

Step b: A step-a product (10 g, 0.066 mol) was taken in ethanolic HCl (300 ml, 30 times) and 3-chlorophenyl hydrazine (9.43 g, 0.066 mol, 1 eq) was added. The reaction mixture was heated to reflux for 2 hrs. Progress of the reaction was monitored by TLC (20% ethyl acetate/hexane, $R_f$~0.3). On completion of the reaction, reaction contents were concentrated and the residue taken in water (200 ml). Basified the contents to a pH~12 with 1N NaOH solution and filtered the contents. Solid obtained was taken in ethyl acetate (200 ml), dried the contents over sodium sulfate and concentrated under reduced pressure to yield the required product as a red colored solid (12 g, 65% yield).

Step c: Cupric bromide (11.33 g, 0.0511 mol, 1.2 eq) was taken in acetonitrile (176 ml) and heated to 150° C. Then n-butyl nitrite (6.59 g (7.47 ml), 0.063 mol, 1.5 eq) was added followed by a solution of step-b product (11.75 g, 0.042 mol) in acetonitrile (176 ml) was added drop wise for 30 min at 150° C. and stirred for 15 min. Progress of the reaction was monitored by TLC (5% ethyl acetate/hexane, $R_f$~0.7). On completion of the reaction, acetonitrile was distilled off, residue was taken in ice cold water (300 ml) and the product extracted with ethyl acetate (5×100 ml). Combined extract was dried over sodium sulfate, concentrated under reduced pressure and the crude product obtained was subjected to column chromatography (silica gel, pure hexane). Pure product was not isolated and a mixture was obtained as a red colored liquid (16 g, crude) and the same product used for the next step.

Step d: To a solution of step-c product (13 g, 0.038 mol) in NMP (130 ml, 10 times), copper cyanide (6.8 g, 0.076 mol, 2 eq), sodium iodide (100 mg, catalytic) were added. The reaction mixture was placed in a pre-heated oil bath at 180° C. and allowed to stir for 8 hr. Progress of the reaction was monitored by TLC (5% ethyl acetate/hexane, $R_f$~0.4). On completion of the reaction, diluted the reaction contents with water (200 ml) and the product extracted with ethyl acetate (5×100 ml). Combined extract was washed with cold water (5×50 ml), dried over sodium sulfate and concentrated under reduced pressure. The crude product obtained was purified by column chromatography (silica gel, 2% ethyl acetate/hexane) to yield the required product as a pale yellow colored solid (8 g).

Step e: To a solution of step-d product (5 g, 0.017 mol) in dry THF (30 ml, 6 times), Boran-THF in THF (70 ml) was added drop wise for 30 min at 0-5° C. Reaction mixture was slowly heated to 50° C. and allowed to stir for 12 hrs. Progress of the reaction was monitored by TLC (75% ethyl acetate/hexane, $R_f$~0.2). On completion of the reaction, acidified the contents to 0-5° C. with conc.HCl at 0° C. and stirred the contents for 2 hrs at rt. Then basified the contents to a pH~12 with 10% NaOH solution and the product extracted with ethyl acetate (5×50 ml). Combined extract was dried over sodium sulfate and concentrated under reduced pressure. Solid obtained was washed with 10% ether/hexane and dried to yield the required product as a white colored solid (3 g, 59% yield, mp 82-86° C.).

9.2 Synthesis of (1-(3-chlorophenyl)-3-cyclopropyl-1H-pyrazol-5-yl)methanamine hydrochloride (employed for the synthesis of example compound no. 128)

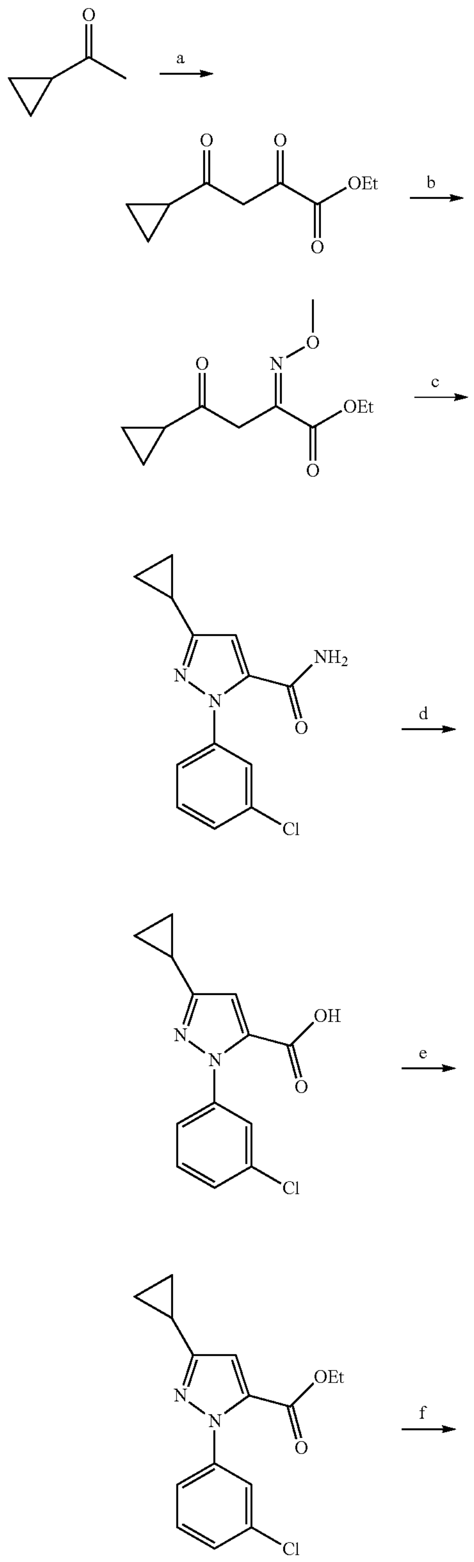

-continued

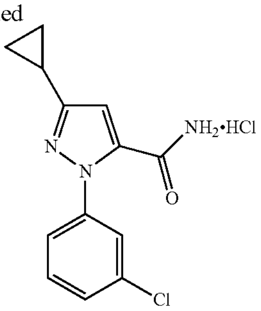

Step a: To a solution of sodium ethoxide (freshly prepared by dissolving sodium (1 g, 8.2 mmol, 1.2 eq) in EtOH (30 mL)), diethyl oxalate (0.92 mL, 6.85 mmol, 1 eq) was added at room temperature followed by addition of cyclopropyl methyl ketone (0.74 mL, 7.5 mmol, 1.1 eq) dropwise at 0° C. The reaction mixture was slowly warmed to room temperature and stirred for 3 h. Ice cold water (10 mL) was added and EtOH was evaporated under reduced pressure. The residual aqueous layer was diluted with 2 N aq. HCl (15 mL) and extracted with diethyl ether (2×25 mL). The organic layer was washed with brine solution and dried ($Na_2SO_4$), filtered and concentrated to give a pale brown liquid (400 mg, 31%).

Step b: To a solution of step-a product (200 mg, 0.543 mmol, 1 eq) in EtOH (8 mL), methoxylamine hydrochloride (30% solution in water, 0.4 mL, 0.651 mmol, 1.2 eq) was added at room temperature and the reaction mixture stirred for 1 h. EtOH was evaporated under reduced pressure and the residual aqueous layer was extracted with ethyl acetate (15 mL). The organic layer was washed with water (10 mL), brine solution (10 ml), dried ($Na_2SO_4$), filtered and concentrated under reduced pressure to give a pale yellow liquid (180 mg, 78%).

Step c: A mixture of step-b product (1.1 g, 5.164 mmol, 1 eq) and 3-chlorophenyl hydrazine hydrochloride (1.84 g, 10.27 mmol, 2 eq) was taken in acetic acid (20 mL), 2-methoxy EtOH (10 mL) and the reaction mixture was heated at 105° C. for 3 h. Solvent was evaporated and the residue was extracted with ethyl acetate (60 mL). The organic layer washed with water (10 mL), brine solution (10 ml), dried ($Na_2SO_4$), filtered and concentrated under reduced pressure to give a residue. Purification by column chromatography (silica gel: 100-200 mesh; eluent: ethyl acetate-petroleum ether (4:96)) afforded a pale brown semi solid (1.15 g, 77%).

Step d: To a solution of step-c product (2.5 g, 8.62 mmol, 1 eq) in THF (15 mL)—MeOH (9 mL)—water (3 mL), LiOH (1.08 g, 25.71 mmol, 3 eq) was added at 0° C. and the reaction mixture was stirred for 2 h at room temperature. Solvent was evaporated and pH of the residue was adjusted to ~3 sing 2 N aqueous HCl (1.2 mL). The acidic aqueous layer was extracted with ethyl acetate (2×60 mL); the combined organic layer washed with water (10 mL), brine solution (10 ml), dried ($Na_2SO_4$), filtered and concentrated under reduced pressure to give an off white solid (1.4 g, 62%).

Step e: To a solution of step-d product (1.4 g, 5.34 mmol, 1 eq) in 1,4-dioxane (30 mL), pyridine (0.25 mL, 3.2 mmol, 0.6 eq) and $(Boc)_2O$ (1.4 mL, 6.37 mmol, 1.2 eq) were added at 0° C. and the resulting mixture was stirred for 30 minutes at the same temperature. Ammonium bicarbonate (0.84 g, 10.63 mmol, 2 eq) was added at 0° C. and the reaction mixture was stirred at room temperature overnight. The reaction mixture was diluted with water (10 mL) and the aqueous layer was extracted with ethyl acetate (2×30 mL). The organic layer was washed with 2N HCl (20 mL), water (10 mL), brine solution (10 ml), dried ($Na_2SO_4$), filtered and concentrated under reduced pressure to give a residue. Purification by column chromatography (silica gel: 100-200 mesh; eluent: ethyl acetate-petroleum ether (16:84)) gave a white solid (1 g, 72%).

Step f: To a solution of step-e product (2 g, 7.66 mmol, 1 eq) in THF (25 mL), $BH_3$.DMS (1.44 mL, 15.32 mmol, 2 eq) was added at 0° C. and the reaction mixture was heated at 70° C. for 3 h. The reaction mixture was cooled to 0° C. and MeOH (15 mL) was added and reaction mixture heated at reflux for 1 h. The reaction mixture was brought to room temperature and solvent was evaporated under reduced pressure. The residue was dissolved in ether (15 mL), cooled to 0° C. and a solution of HCl in 1,4-dioxane (3 mL) was added (pH of the reaction mixture ~4). The precipitated solid was filtered and washed with diethyl ether (5 mL, thrice) to give the hydrochloride salt compound as a white solid (600 mg, 28%).

9.3 Synthesis of (3-tert-butyl-1-(pyridin-2-yl)-1H-pyrazol-5-yl)methanamine (employed for the synthesis of example compound no. 127)

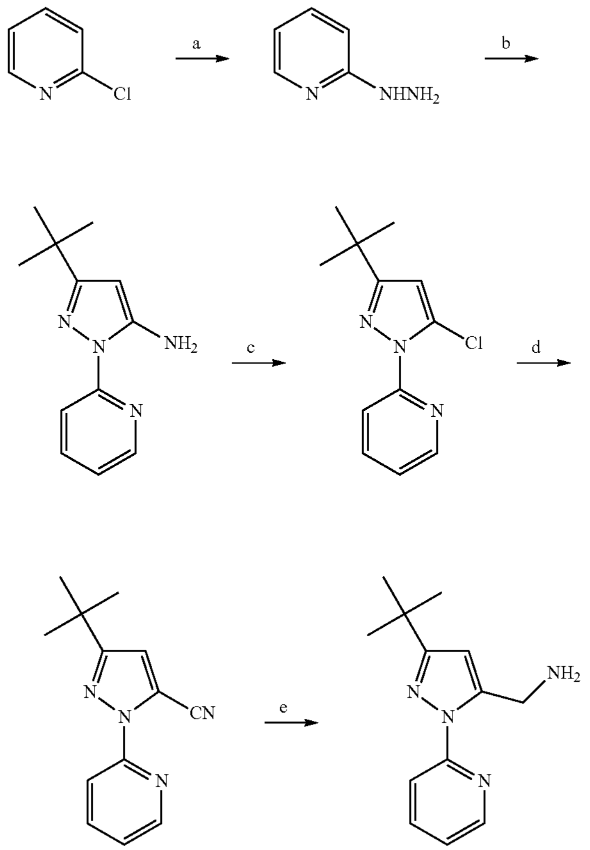

Step a: To a solution of 2-chloropyridine (20 g, 0.17 mol) in ethanol (100 ml, 5 times), hydrazine hydrate (132 ml, 6.6 times) was added and the reaction mixture was heated to reflux for 15 hrs. Progress of the reaction was monitored by TLC (40% ethyl acetate/hexane, $R_f$~0.1). As the reaction not completed, continued to reflux for another 15 hrs and monitored by TLC. On completion of the reaction, ethanolic hydrazine hydrochloride was distilled off completely at 100° C., residue was taken in DCM (500 ml) and washed the contents with saturated sodium carbonate solution (100 ml). Combined organic layer was dried over sodium sulfate and concentrated under reduced pressure to obtain the crude product as a low melting solid (11 g, crude). The crude product obtained was directly used for the next step.

Step b: To a stirred solution of step-a product (11 g, crude) in ethanol (110 ml, 10 times), 4,4-dimethyl-3-oxopentanenitrile (11.3 g, 0.09 mol, 0.9 eq) was added portion wise followed by catalytic amount of HCl. The reaction mixture was heated to 100° C. and refluxed for 6 hrs. Progress of the reaction was monitored by TLC (20% ethyl acetate/hexane, $R_f$~0.7).

On completion of the reaction, ethanol was distilled off, residue was taken in water (200 ml) and the product extracted with ethyl acetate (2×100 ml). Combined extract was dried over sodium sulfate, concentrated under reduced pressure and the crude product obtained was purified by column chromatography (silica gel, 10% ethyl acetate/hexane) to yield the required product as an off white solid (18 g).

Step c: To a solution of step-b product (4 g, 0.01 mol) in acetonitrile (80 ml), cupric chloride (12.3 g, 0.09 mol, 5 eq) was added. A solution of tert-butyl nitrite (2.8 (3.3 ml), 0.023 mol, 1.5 eq) in acetonitrile (40 ml (total 120 ml, 30 times)) was added drop wise for 10 min and the overall reaction mass was stirred for 5 hrs at rt. Progress of the reaction was monitored by TLC (10% ethyl acetate/hexane, $R_f$~0.3). On completion of the reaction, acetonitrile was distilled off, residue was taken in water (100 ml) and the product extracted with ethyl acetate (2×200 ml). Combined extract was dried over sodium sulfate, concentrated under reduced pressure and the crude product was purified by column chromatography (silica gel, 4% ethyl acetate/hexane) to yield the required product as a pale yellow colored liquid (2.1 g, 48% yield).

Step d: To a stirred solution of step-c product (2.1 g, 0.008 mol) in NMP (21 ml, 1 time), copper cyanide (1.56 g, 0.017 mol, 2 eq) was added portion wise followed by a catalytic amount of sodium iodide was added. The reaction mixture was heated to 180° C. and maintained at that temperature for 4 hrs. Progress of the reaction was monitored by TLC (10% ethyl acetate/hexane, $R_f$~0.5). On completion of the reaction, diluted the reaction contents with ethyl acetate, filtered the contents through celite bed and the filtrate washed with cold water (50 ml). Organic layer was dried over sodium sulfate, concentrated under reduced pressure and the crude product was purified by column chromatography (silica gel, 6-8% ethyl acetate/hexane) to yield the required product as an off white solid (0.8 g, 40% yield).

Step e: To a solution of step-d product (1.5 g, 0.006 mol) in methanol (20 ml), catalytic amount of raney nickel. The reaction mixture was hydrogenated for 1 hr at 60 psi. Progress of the reaction was monitored by TLC (15% ethyl acetate/hexane, $R_f$~0.1). On disappearance of the starting material, filtered the contents on celite bed and washed with methanol. To the filtrate was purified by column chromatography (silica gel, 6% ethyl acetate/hexane) to yield the titled product as a cream colored oil (1.4 g, 97% yield).

9.4 Synthesis of (1-(pyridin-3-yl)-3-(trifluoromethyl)-1H-pyrazol-5-yl)methanamine hydrochloride (employed for the synthesis of example compound no. 136)

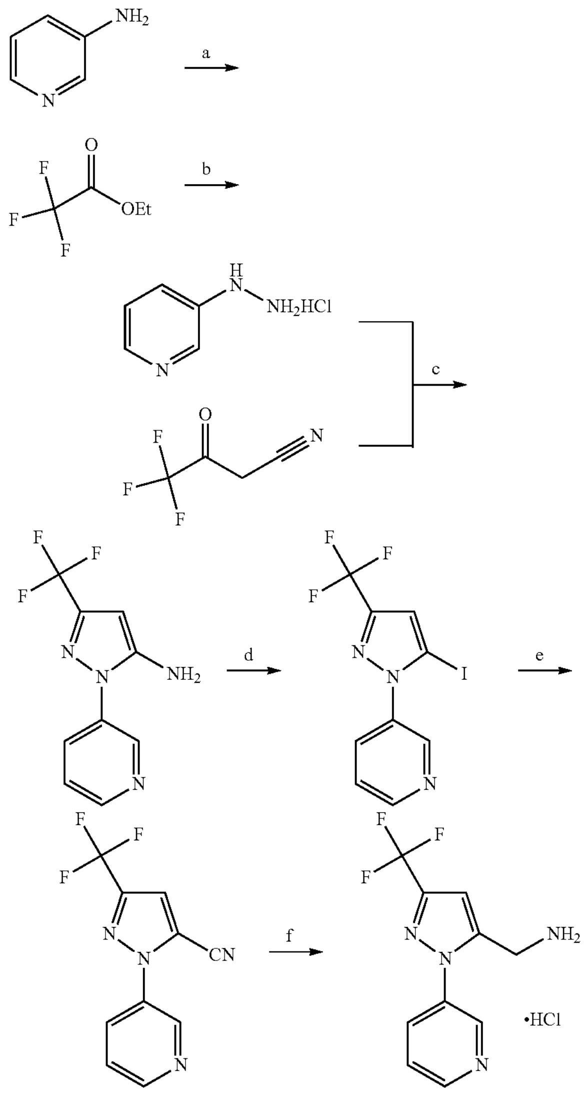

Step a: To a cold solution of pyridin-3-amine (40 g, 425.5 mmol) in conc. HCl (500 mL) at 0° C., a solution of $NaNO_2$ (35.23 g, 510.6 mmol) in water (40 mL) was added dropwise maintaining the temperature at 0° C. for 15 minutes. After addition the solution was stirred for 20 minutes. This solution was added to a solution of $SnCl_2$ (177.5 g, 936.3 mmol) in conc. HCl (100 mL) dropwise maintaining the temperature at 0° C. for 20 minutes and the resulting yellow solution was stirred at 0° C. for 30 minutes. The obtained yellow solid was filtered, washed with water (3×50 mL) and dried afford product (106.5 g, crude) as yellow solid.

Step b: To a cold suspension of NaH (60% dispersion in oil, 29.26 g, 731.7 mmol) in 1,4-dioxane (450 mL), acetonitrile (38.46 mL, 731.7 mmol) was added dropwise at 0° C. and stirred for 30 minutes. The reaction mixture was cooled to −5° C., ethyl 2,2,2-trifluoroacetate (83.12 g, 585.36 mmol) was slowly added and the reaction mixture allowed to stir at room temperature for 16 h. The reaction mixture was cooled to 0° C., quenched with MeOH (150 mL), diluted with ethyl acetate (300 mL) and pH adjusted to ~4 using dilute aqueous HCl. The organic layer was separated and the aqueous layer was extracted with ethyl acetate (2×250 mL). The combined ethyl acetate layer was washed with water (250 mL), brine solution (200 mL), dried ($Na_2SO_4$), filtered and concentrated under reduced pressure to afford a brown liquid (57 g). The crude compound was used as such without further purification.

Step c: A solution of step-b product (57 g, crude; 416.05 mmol) and step-a product (60.5 g, 416.05 mmol) in EtOH (650 mL) was stirred at reflux for 3 h. The reaction mixture was concentrated; the obtained residue was diluted with ethyl acetate (2 L), washed with water (2×500 mL), brine solution (500 mL), dried ($Na_2SO_4$), filtered and concentrated under reduced pressure to give a residue. Purification by column chromatography (silica gel; 100-200 mesh; eluent: 30% ethyl acetate in petroleum ether) afforded a yellow solid (31.48 g).

Step d: To a cold suspension of potassium iodide (51.3 g, 309.21 mmol) and isoamyl nitrite (41.16 mL, 309.21 mmol) in dry acetonitrile (350 mL), a solution of step-c product (23.5 g, 103.07 mmol) in acetonitrile (100 mL) was added dropwise at 0° C. and the reaction mixture was stirred at 100° C. for 20 h. The reaction mixture was concentrated; the obtained residue was diluted with ethyl acetate (1 L), washed with water (2×400 mL), brine solution (200 mL), dried ($Na_2SO_4$), filtered and concentrated to give a residue. Purification by column chromatography (silica gel; 100-200 mesh; eluent: 30% ethyl acetate in petroleum ether) afforded a pale yellow solid (16.52 g, 37%).

Step e: To a solution of step-d product (16.5 g, 48.67 mmol) in dry NMP (150 mL), CuCN (6.53 g, 73.0 mmol) was added and the reaction mixture was stirred at 200° C. for 2 h. The reaction mixture was cooled to room temperature, quenched with ethylene diamine (50 mL) and diluted with ethyl acetate (800 mL). The obtained suspension was filtered through celite bed, washed with ethyl acetate (2×100 mL). The combine filtrate was washed with water (2×300 mL), brine solution (250 mL), dried ($Na_2SO_4$), filtered and concentrated under reduced pressure to give a residue. Purification by column chromatography (silica gel; 100-200 mesh; eluent: 20-30% ethyl acetate in petroleum ether) to afford a yellow solid (5.12 g, 44%).

Step f: To a solution of step-e product (4.5 g, 18.9 mmol) in saturated methanolic $NH_3$ (50 mL), Raney-Nickel (3 g, wet, washed with MeOH (4×5 mL)) was added and the mixture was hydrogenated in a Parr hydrogenator at 40 Psi pressure at room temperature for 4 h. The reaction mixture was filtered through celite and the filtrate was concentrated under reduced pressure. The obtained residue was stirred in sat. HCl in ether (50 mL) for 2 h. Ether was decanted, the obtained solid was washed with ether (3×10 mL), vacuum dried to afford product compound as light brown solid (1.2 g, 23%).

9.5 Synthesis of 5-(aminomethyl)-3-tert-butyl-N-(2,2,2-trifluoroethyl)-1H-pyrazol-1-amine (employed for the synthesis of example compound no. 98)

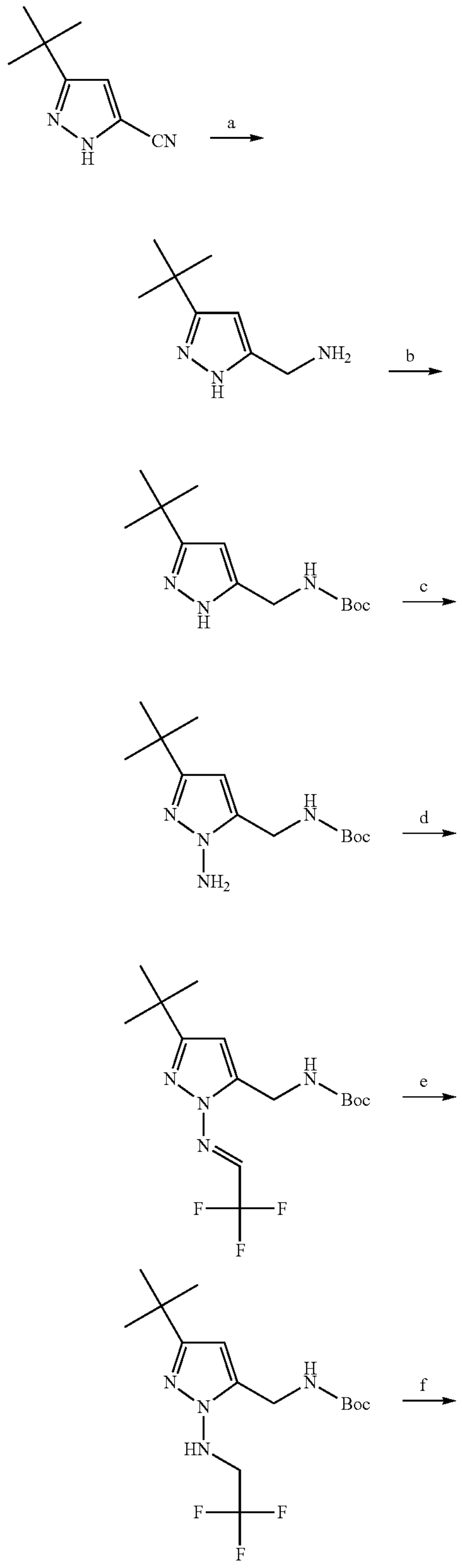

-continued

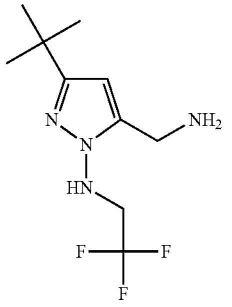

Step a: To a solution of tert-butyl-1H-pyrazole-5-carbonitrile (5 g, 0.033 mol) in methanol (100 ml, 20 times), Raney nickel (5 g, 1 times) was added and the reaction mixture was hydrogenated for 1-2 hrs 70 psi. Progress of the reaction was monitored by TLC (40% ethyl acetate/hexane, $R_f$~0.1). On completion of the reaction, filtered the reaction contents and the bed was washed with methanol (100 ml). Methanol was distilled off completely and the crude product obtained as a pale yellow colored liquid (5 g., crude) was directly used for the next step.

Step b: To a stirred solution of step-a product (5 g, crude) in methanol (50 ml, 10 times), sodium carbonate (5.1 g, 0.04 mol, 1.5 eq) was added and stirred for 15 min. Cooled the contents to 0° C., Boc anhydride (6.97 g, 1.1 eq) was added drop wise for 10 min and the overall reaction mixture was stirred for 30 min at 0° C. Progress of the reaction was monitored by TLC (50% ethyl acetate/hexane, $R_f$~0.3). On completion of the reaction, methanol was distilled off completely, residue was taken in water (100 ml) and the product extracted with ethyl acetate (2×100 ml). Combined extract was dried over sodium sulfate, concentrated under reduced pressure and the crude compound was recrystallized from hexane to yield the required product as a white solid (4.5 g).

Step c: To a stirred solution of step-b product (5 g, 0.019 mol) in DMF (50 ml, 10 times), sodium hydroxide (7.9 g, 0.19 mol, 10 eq) was added. Cooled the contents to 0° C., Hydroxylamine-o-sulfonic acid (6.4 g, 0.057 mol, 3 eq) was added portion wise for 30 min and the reaction mixture was stirred for 2 hrs at 0° C. Progress of the reaction was monitored by TLC (30% ethyl acetate/hexane, $R_f$~0.4). On completion of the reaction, poured the reaction contents into crushed ice (200 g) and filtered the contents. Solid obtained was taken in hexane (100 ml), filtered and dried to yield the required product as a white solid (4 g, 75% yield).

Step d: To a stirred solution of step-c product (2 g, 0.001 mol) in ethanol (20 ml, 10 times), ether containing trifluoroacetaldehyde (1.41 g in 50 ml (0.014 mol, 2 eq)) was added. The reaction mixture was stirred for 12 hrs at rt. Progress of the reaction was monitored by TLC (10% ethyl acetate/hexane, $R_f$~0.7). On completion of the reaction, ethanol was distilled off completely and the crude product obtained was purified by column chromatography (silica gel, hexane) to yield the required product as a white solid (2 g, 77% yield).

Step e: To a stirred solution of step-d product (1.7 g, 0.0048 mol) in methanol (170 ml), 10% Pd/C (0.5 g, catalytic) was added. The reaction mixture was stirred for 12 hrs under Hydrogen balloon pressure. Progress of the reaction was monitored by TLC (10% ethyl acetate/hexane, $R_f$~0.3). On completion of the reaction, filtered the contents over celite bed and the bed washed with methanol. Methanol distilled off from the filtrate and the crude product obtained was purified by column chromatography (basic alumina, hexane) to yield the titled product as a white solid (1.02 g, 50% yield, mp 80-83° C.).

Step f: To a stirred solution of Boc-compound step e product (1.0 g), DCM (20 ml) was added at RT and stirred for about 20 min. This reaction mixture was cooled to 0-5° C. and pass the HCl gas for about 30 min. Progress of the reaction was monitored by TLC (10% ethyl acetate/hexane/50% ethyl acetate/hexane). On completion of the reaction, distill off DCM. Add water (20 ml) then extract the compound with 20% IPA/$CHCl_3$ and the layer were separated. The organic layer was distilled off under reduced pressure and dried under high vacuum. The crude product was obtained by washing with heptane and drying under high vacuum. The compound was obtained light yellow colored viscous liquid (0.65 g, 91% yield).

9.6 Synthesis of (1-(4-methoxybenzyl)-3-(trifluoromethyl)-1H-pyrazol-5-yl)methanamine (employed for the synthesis of example compound no. 132)

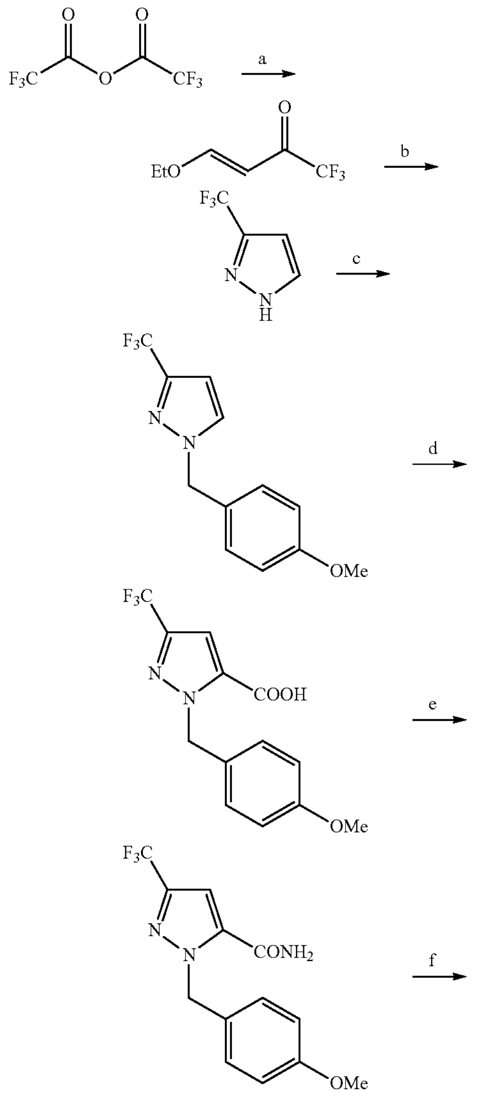

-continued

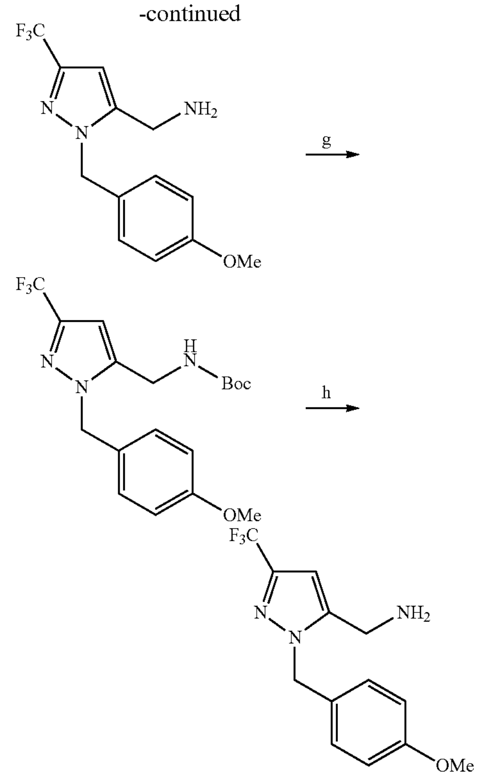

Step a: DMAP (4.25 g, 0.034 mol, 0.01 eq) was added to DCM (3 ltrs) and cooled the contents to −10° C. Trifluoroacetic anhydride (765 g (510 ml), 3.2 mol, 1.05 eq) was added followed by ethyl vinyl ether (250 g, 3.04 mol) was added drop wise for 45 min at −10° C. Then the overall reaction mixture was initially stirred for 8 hrs at 0° C. and later for overnight at RT. Progress of the reaction was monitored by TLC (10% ethyl acetate/hexane, $R_f$~0.7). On completion of the reaction, reaction contents were quenched with saturated $NaHCO_3$ solution (600 ml) and organic layer was separated. Aqueous layer was extracted with DCM (2×500 ml). Combined organic layer was washed with water (2×1 ltr), dried over sodium sulfate and concentrated under reduced pressure to obtain the crude product as a brown colored liquid (450 g, crude).

Step b: Hydrazine dihydrochloride (225 g, 2.14 mol, 1.6 eq) was taken in ethanol (1400 ml) and stirred well. TEA (135.4 g (185.4 ml), 1.34 mol, 1 eq) was added drop wise for 45 min at RT. Then step-a product (225 g, crude) was added drop wise at RT and the overall reaction mixture was refluxed for overnight. Progress of the reaction was monitored by TLC (20% ethyl acetate/hexane, $R_f$~0.4). On completion of the reaction, ethanol was distilled off completely, residue was taken in ice water (500 ml) and the product extracted with ethyl acetate (2×400 ml). Combined extract was washed with ice water (300 ml), dried over sodium sulfate and concentrated under reduced pressure to yield the required product as and off white solid (195 g).

Step c: NaH (33.08 g (19.85, 60%), 1.5 eq) was added to small quantity of hexane and stirred well for 10 min. Hexane was decanted, dry DMF (500 ml) was added drop wise under $N_2$ atmosphere and stirred well. A solution of step-b product (75 g, 0.55 mol) in DMF (125 ml) was added drop wise under $N_2$ atmosphere. Then a solution of 4-methoxylbenzoyl chloride (86.3 g, 0.55 mol, 1 eq) in DMF (125 ml) was added drop wise and the overall reaction mixture was allowed to stir for 12 hrs at RT. Progress of the reaction was monitored by TLC (10% ethyl acetate/hexane, $R_f$~0.4). On completion of the reaction, reaction contents were poured into ice water (500 ml) and the product extracted with ethyl acetate (2×400 ml). Then the contents were dried over sodium sulfate and concentrated under reduced pressure to yield the required product as a brown colored liquid (125 g, 88% yield).

Step d: Diisopropyl amine (28.4 (39.4 ml), 1.2 eq) was taken in THF (500 ml), stirred well and cooled the contents to 0° C. n-BuLi (234.4 ml, 1.5 eq) was added drop wise at 0° C. and cooled the contents to −78° C. A solution of step-c product (62 g, 0.24 mol) in THF (200 ml) was added drop wise for 30 min and stirred the contents for another 30 min at −78° C. Then dry $CO_2$ gas was bubbled through the reaction mixture for 1.5 hrs and the progress of the reaction was monitored by TLC (10% ethyl acetate/hexane, $R_f$~0.1). On completion of the reaction, reaction contents were poured into ice water (300 ml) and the aqueous layer was extracted with ethyl acetate (2×200 ml) in basic condition. Aqueous layer was acidified with 20% HCl solution and extracted with ethyl acetate (2×200 ml). Combined organic layer was dried over sodium sulfate and concentrated under reduced pressure to yield the required product as an off white solid (42 g, 58% yield).

Step e: To a solution of step-d product (50 g, 0.16 mol) in DCM (750 ml, 15 times), catalytic amount of DMF was added and cooled to 0° C. Thionyl chloride (99.3 g (61 ml), 0.83 mol, 5 eq) was added drop wise for 30 min at 0° C. Overall reaction mixture was slowly heated to a reflux temperature and allowed to reflux for 2 hrs. Progress of the reaction was monitored by TLC (10% ethyl acetate/hexane, $R_f$~0.4). On disappearance of the starting material, DCM was distilled off completely. Above prepared acid chloride was dissolved in DCM (500 ml) and added drop wise to aqueous ammonia solution (600-700 ml) at 0° C. Overall reaction mixture was allowed to stir for 1 hr and the progress of the reaction was monitored by TLC (10% ethyl acetate/hexane, $R_f$~0.7). On completion of the reaction, ice cold water (200 ml) was added and the product extracted with ethyl acetate (2×200 ml). Combined organic layer was dried over sodium sulfate and concentrated under reduced pressure to yield the required product as an off white solid (37 g, crude). Crude product obtained was directly used for the next step.

Step f: LAH (4.7 g, 0.12 mol, 1 eq) was added to small quantity of hexane and stirred well for 10 min. Hexane was decanted and THF (250 ml) was added to LAH under cold condition. Then a solution of step-e product (37 g, 0.12 mol) in THF (120 ml) was added drop wise for 30 min at 0° C. and reaction mixture was heated to reflux for 5 hrs. Progress of the reaction was monitored by TLC (50% ethyl acetate/hexane, $R_f$~0.2). As the reaction moved completely, LAH (2.3 g) was added and refluxed for another 4 hrs. This time reaction was moved completely. Then the reaction contents were slowly added to saturated solution of sodium sulfate (1 ltr) and the product extracted with ethyl acetate (2×500 ml). Combined extract was dried over sodium sulfate and concentrated under reduced pressure to obtain the crude product as an off white solid (32.5 g). Crude product obtained was directly used for the next step.

Step g: To a solution of step-f product ((80 g, 0.28 mol) in DCM (600 ml) cooled at 0° C., TEA (22.7 g (30.2 ml), 0.026 mol, 0.8 eq) was added drop wise for 10 min. Then Boc anhydride (61.2 g (62.5 ml), 0.28 mol, 1 eq) taken in DCM (200 ml) was added drop wise for 20-30 min at 0° C. Overall reaction mixture initially stirred for 30 min at 0° C. and alter for another 30 min at RT. Progress of the reaction was monitored by the TLC (20% ethyl acetate/hexane, $R_f$~0.6). On completion of the reaction, DCM was distilled off completely, residue was taken in ice water (500 ml) and the product extracted with ethyl acetate (2×300 ml). Combined extract was dried over sodium sulfate and concentrated under reduced pressure. Crude product obtained was recrystallized from hexane (200 ml) to yield the required product as an off white solid (80 g, 74% yield).

Step h: Step-g (5 g, 0.012 mol) product was taken in DCM (30 ml, 6 times) and cooled to 0° C. HCl gas was bubbled through the reaction mixture for 45 min at 0° C. Progress of the reaction was monitored by TLC (30% ethyl acetate/hexane, $R_f$~0.2). On completion of the reaction, DCM was distilled off completely. Residue was taken in ice water (200 ml) and the product extracted with 20% ethyl acetate/hexane (2×100 ml). Aqueous layer was basified to a pH~10 with 2N NaOH solution and extracted with ethyl acetate (5×100 ml). Combined organic layer was washed with water (2×200 ml), dried over sodium sulfate and concentrated under reduced pressure to yield the required product as an yellow colored liquid (2.4 g, 64% yield).

9.7 Synthesis of N-(5-(aminomethyl)-3-(trifluoromethyl-1H-pyrazol-1-yl)benzamide (employed for the synthesis of example compound no. 146)

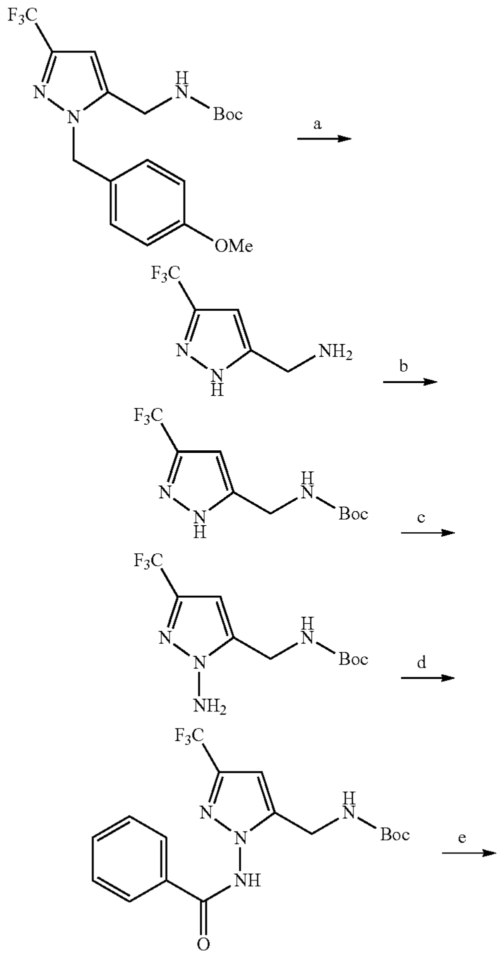

-continued

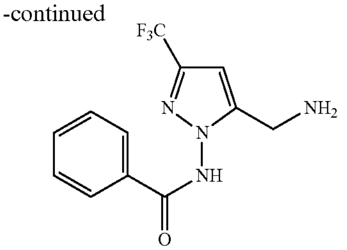

Step a: To a stirred solution of tert-butyl (1-(4-methoxybenzyl)-3-(trifluoromethyl)-1H-pyrazol-5-yl)methylcarbamate (20 g, 0.052 mol) in toluene (300 ml, 15 times) cooled at 0° C., aluminum chloride (17.34 g, 0.129 mol, 2.5 eq) was added portion wise for 30 min. Reaction mixture was slowly heated to 50-60° C. and allowed stir for 2 hrs at the same temperature. Progress of the reaction was monitored by TLC (20% ethyl acetate/hexane, $R_f$~0.1). On completion of the reaction, reaction contents were quenched with dilute HCl, ice cold water (300 ml) was added and extracted with ethyl acetate (2×100 ml). Aqueous layer was basified with sodium hydroxide solution and extracted with ethyl acetate. Combined extract was dried over sodium sulfate and concentrated under reduced pressure to obtain the crude product as a brown colored solid (4.6 g). The crude product obtained was directly used for the next step.

Step b: To a stirred solution of step-a product (5.7 g, 0.034 mol) in DCM (37 ml) cooled at 0° C., TEA (1.74 g (2.4 ml), 0.017 mol, 0.5 eq) was added drop wise for 10 min. Then Boc anhydride (3.76 g (3.9 ml), 0.017 mol, 0.5 eq) taken in DCM (20 ml) was added drop wise for 10-15 min at 0° C. Overall reaction mixture initially stirred for 30 min at 0° C. and alter for another 30 min at RT. Progress of the reaction was monitored by the TLC (20% ethyl acetate/hexane, $R_f$~0.6). As the reaction not moved completely, Boc anhydride (0.3 eq) was added and stirred for another 15 min at RT. Progress of the reaction was monitored by TLC and found that the reaction moved completely. DCM was distilled off completely, residue was taken in ice water (300 ml) and the product extracted with ethyl acetate (2×200 ml). Combined extract was dried over sodium sulfate and concentrated under reduced pressure to yield the required product as and off white solid (7 g, 76% yield).

Step c: A solution of step-b product (10 g, 0.037 mol) in DMF (50 ml) was added drop wise to a mixture of NaH (1.85 g, 0.077 mol, 1.2 eq) in DMF (50 ml) for 45 min at RT. Then 0.5M monochloro amine solution (322 ml) was added drop wise for 30 min and the overall reaction mixture was allowed to stir for 20 min at RT. Progress of the reaction was monitored by TLC (30% ethyl acetate/hexane, $R_f$~0.5). On completion of the reaction, reaction contents were quenched with saturate $Na_2S_2O_3$ solution in cold condition and the product was extracted with ethyl acetate (5×100 ml). Combined extract was dried over sodium sulfate, concentrated under reduced pressure and the crude product obtained was purified by column chromatography (silica gel, 4% ethyl acetate/hexane) to yield the required product as an off white solid (4 g, 62% yield).

Step d: To a solution of step-c product (1.2 g, 0.0042 mol) in toluene (12 ml, 10 times), potassium carbonate (1.18 g, 2 eq), water (12 ml, 10 times) and TBAB (0.137 g, 0.0004 mol, 0.1 eq) were added. Then the contents were stirred for 15 min and cooled to 0° C. Benzoyl chloride (0.72 g, 0.005 mol, 1.2 eq) taken in toluene (6 ml) was added drop wise at 0° C. and the overall reaction mixture was stirred for 2 hrs at RT. Progress of the reaction was monitored by TLC (30% ethyl acetate/hexane, $R_f$~0.6). On completion of the reaction, ice water (100 ml) was added, organic layer separated and the aqueous layer extracted with ethyl acetate (5×75 ml). Combined organic layer was washed with water (2×100 ml) and dried over sodium sulfate. Then the contents were concentrated under reduced pressure and the crude product obtained was purified by column chromatography (silica gel, 3% ethyl acetate/hexane) to yield the required product as a pale yellow colored liquid (1.1 g, 67% yield).

Step e: To a solution of step-d product (1.1 g, 0.0028 mol) in DCM (11 ml, 10 times) cooled to at 0° C., trifluoroacetic acid (2.2 ml, 2 times) was added drop wise. Overall reaction mixture was allowed to stir for 1-1.5 hrs at RT. Progress of the reaction was monitored by TLC (10% ethyl acetate/hexane, $R_f$~0.2). On completion of the reaction, DCM was distilled off completely. Residue was taken in cold water (200 ml), basified with saturated $NaHCO_3$ solution and the product extracted with ethyl acetate (4×50 ml). Combined extract was washed with water (2×50 ml), dried over sodium sulfate and concentrated under reduced pressure. Crude product obtained was purified by column chromatography (silica gel, 10% ethyl acetate/hexane) to yield the required product as a white solid (0.24 g, 30% yield).

9.8 Synthesis of 5-(aminomethyl)-N-(pyridin-2-ylmethyl)-3-(trifluoromethyl)-1H-pyrazol-1-amine (employed for the synthesis of example compound no. 129)

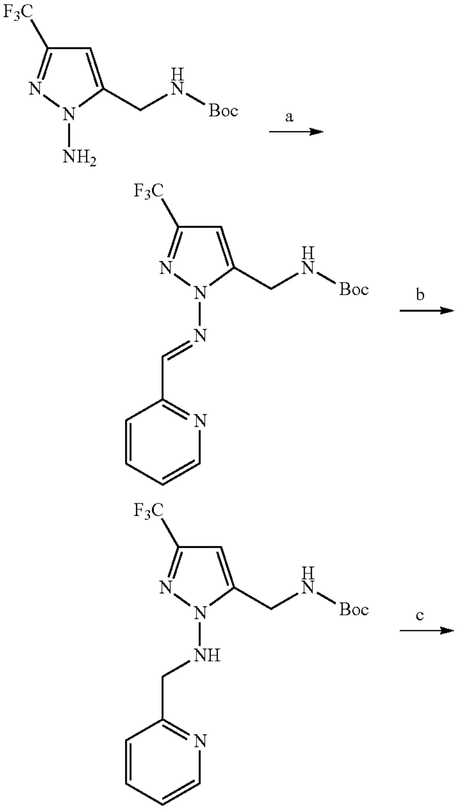

-continued

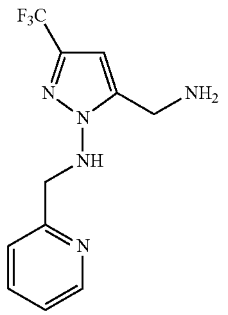

Step a: To a solution of tert-butyl (1-amino-3-(trifluoromethyl)-1H-pyrazol-5-yl)methylcarbamate (2 g, 0.0071 mol) in methanol (15 ml), picolinaldehyde (1.14 g (1 ml), 0.016 mol, 1.5 eq) taken in methanol (5 ml) was added. Then the reaction mixture was acidified with acetic acid (0.2 ml, catalytic) and heated to reflux for 24 hrs. Progress of the reaction was monitored by TLC (10% ethyl acetate/hexane, $R_f$~0.4). On completion of the reaction, methanol was distilled off completely. Residue was taken in ice water (200 ml) and the product extracted with ethyl acetate (4×50 ml). Combined extract was washed with water (2×50 ml), dried over sodium sulfate and the ethyl acetate was distilled off completely. Crude product obtained was recrystallized from hexane (10 ml) to yield the required product as liquid (2 g, 76% yield).

Step b: To a solution of step-a product (2 g, 0.0054 mol) in methanol (20 ml, 10 times) cooled to at 0° C., $NaBH_4$ (0.2 g, 0.0054 mol, 1 eq) was added slowly. Overall reaction mixture was allowed to stir for 1 hr at RT. Progress of the reaction was monitored by TLC (20% ethyl acetate/hexane, Rf~0.2). On completion of the reaction, methanol was distilled off completely. Residue was taken in cold water (100 ml) and the product extracted with ethyl acetate (5×50 ml). Combined extract was washed with water (2×50 ml), dried over sodium sulfate and concentrated under reduced pressure. Crude product obtained was purified by column chromatography (silica gel, 10% ethyl acetate/hexane) to yield the required product pale yellow colored solid (1.1 g, 57% yield).

Step c: To a solution of the Boc compound step b product (1.1 g) in DCM (11 ml, 10 times) cooled to at 0° C., trifluoroacetic acid (2.2 ml, 2 times) was added drop wise. Overall reaction mixture was allowed to stir for 1-1.5 hrs at RT. Progress of the reaction was monitored by TLC (10% ethyl acetate/hexane, $R_f$~0.2). On completion of the reaction, DCM was distilled off completely. Residue was taken in cold water (200 ml), basified with saturated $NaHCO_3$ solution and the product extracted with ethyl acetate (4×50 ml). Combined extract was washed with water (2×50 ml), dried over sodium sulfate and concentrated under reduced pressure. Crude product obtained was purified by column chromatography (silica gel, 10% ethyl acetate/hexane) to yield the required product as a white solid (0.425 g, 53% yield).

9.9 Synthesis (3-tert-butyl-1-(phenylsulfonyl)-1H-pyrazol-5-yl)methanamine (employed for the synthesis of example compound no. 108)

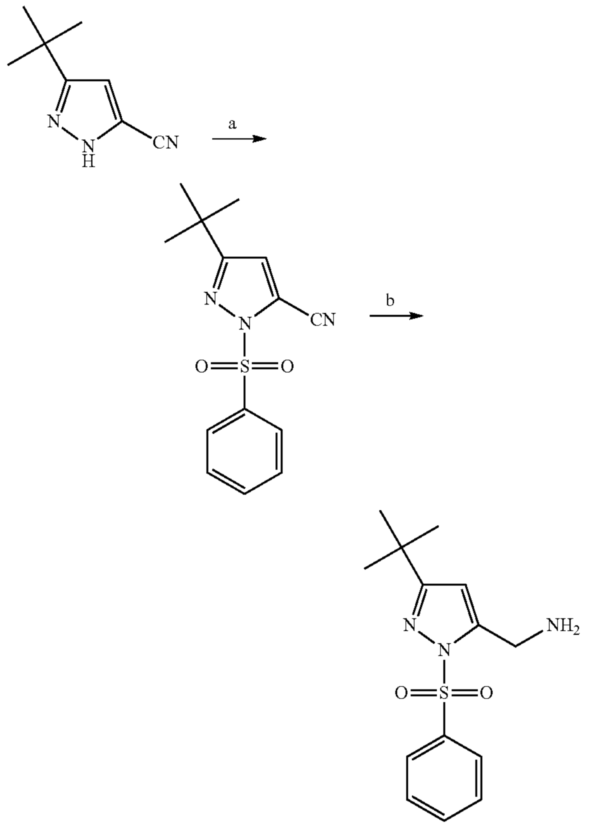

Step a: To a stirred solution of 3-tert-butyl-1H-pyrazole-5-carbonitrile (3 g, 20 mmol) in dichloromethane (30 ml, 10 times) TEA (2.44 g (3.36 ml), 24 mmol, 1.2 eq) was added at 0° C. Then phenylsulfonyl chloride (2.84 g (2 ml), 10 mmol, 0.8 eq) was added at 0° C. and the reaction mass was stirred for 12 h at room temperature. Progress of the reaction was monitored by TLC (20% ethyl acetate-hexane, Rf~0.6). On completion of the reaction, ice water (20 ml) was added to reaction mixture, organic layer was separated and washed with 1N HCl (2×20 ml followed by with water (2×15 ml), Dried the contents over sodium sulfate, concentrated under reduced pressure and the crude product obtained was recrystallized from hexane to yield the required product as an off white solid (4 g, 68%).

Step b: To a solution of step-a product (2.3 g, 7 mmol) in THF (23 ml, 10 times) Boran-DMS (1.81 g (23.8 ml, 20 mmol, 3 eq) was added dropwise at 0-5° C. Then the reaction mixture was heated to 80° C. and stirred for 5 h. Progress of the reaction mixture was monitored by TLC (75% ethyl acetate-hexane, $R_f$~0.6). On completion of the reaction, quenched the reaction mixture with dilute HCl below 5° C. and stirred the contents for 12 h. Again TLC was monitored (75% ethyl acetate-hexane, $R_f$~0.4). Then the reaction contents were poured in ice water (100 ml) and the compound extracted with ethyl acetate (4×40 ml). Aqueous layer was basified with 2N NaOH solution at 0-5° C. and the compound extracted with ethyl acetate (5×20 ml). The combined extract was washed with water (2×50 ml), dried over sodium sulfate and concentrated under reduced pressure to obtain the crude product as pale yellow colored liquid (750 mg).

Synthesis of the Example Compounds

1. Preparation of Amides (A=$CR^{5b}$)

General directions for reacting amines of general formula (II) with carboxylic acids of general formula (III) or carboxylic acid derivatives of general formula (IV) to form compounds of general formula (I), wherein A=$CR^{5b}$ (amides), as in scheme 1a (step j09).

1.1 Method A:

The acid of general formula (III) (1 equivalent), the amine of general formula (II) (1.2 equivalents) and EDCl (1.2 equivalents) are stirred in DMF (10 mmol of acid/20 ml) for 12 hours at RT and water is subsequently added thereto. The reaction mixture is repeatedly extracted with EtOAc, the aqueous phase is saturated with NaCl and subsequently reextracted with EtOAc. The combined organic phases are washed with 1 N HCl and brine, dried over magnesium sulfate and the solvent is removed under vacuum. The residue is purified by flash chromatography ($SiO_2$, EtOAc/hexane in different ratios such as 1:2) and the product (I) is obtained in this way.

1.2 Method B:

The acid of general formula (III) (1 equivalent) and the amine of general formulae (II) (1.1 equivalents) are dissolved in dichloromethane (1 mmol of acid in 6 ml) and mixed with EDCl (1.5 equivalents), HOBt (1.4 equivalents) and triethylamine (3 equivalents) at 0° C. The reaction mixture is stirred for 20 h at room temperature and the crude product is purified by column chromatography ($SiO_2$, n-hexane/EtOAc in different ratios such as 2:1) and (1) is obtained in this way.

1.3 Method C:

The acid of general formula (III) (1 equivalent) is first mixed with a chlorinating agent, preferably with thionyl chloride and the mixture obtained in this way is boiled under reflux and the acid (III) is in this way converted into the corresponding acid chloride (IV). The amine of general formulae (II) (1.1 equivalents) is dissolved in dichloromethane (1 mmol of acid in 6 ml) and mixed with triethylamine (3 equivalents) at 0° C. The reaction mixture is stirred for 20 h at room temperature and the crude product is purified by column chromatography ($SiO_2$, n-hexane/EtOAc in different ratios such as 2:1) and (I) is obtained in this way.

1.4 Method D:

The phenyl ester (IVa) obtained (1 equivalent) and the corresponding amine (II) (1.1 equivalents) are dissolved in THF (10 mmol of the reaction mixture in 120 ml) and stirred for 16 h at room temperature after addition of DBU (1.5 equivalents). After removal of the solvent under vacuum, the resulting residue is purified by flash chromatography ($SiO_2$, EtOAc/hexane in different ratios such as 1:1) and (I) is obtained in this way.

The following example compounds 1-56, 66-80, 117-121, 124-125, 127-138, 140-143 and 145-147 were obtained using one of the methods described above.

| | |
|---|---|
| 1 | N-((3-tert-butyl-1H-pyrazol-5-yl)methyl)-2-(3-fluoro-4-(methylsulfonamido)phenyl)propanamide |
| 2 | (S)-N-((3-tert-butyl-1H-pyrazol-5-yl)methyl)-2-(3-fluoro-4-(methylsulfonamido)phenyl)propanamide |
| 3 | N-((3-tert-butyl-1-methyl-1H-pyrazol-5-yl)methyl)-2-(3-fluoro-4-(methylsulfonamido)phenyl)propanamide |
| 4 | (S)-N-((3-tert-butyl-1-methyl-1H-pyrazol-5-yl)methyl)-2-(3-fluoro-4-(methylsulfonamido)phenyl)propanamide |
| 5 | N-((3-tert-butyl-1-hexyl-1H-pyrazol-5-yl)methyl)-2-(3-fluoro-4-(methylsulfonamido)phenyl)propanamide |

-continued

| | |
|---|---|
| 6 | (S)-N-((3-tert-butyl-1-hexyl-1H-pyrazol-5-yl)methyl)-2-(3-fluoro-4-(methylsulfonamido)phenyl)propanamide |
| 7 | N-((3-tert-butyl-1-cyclohexyl-1H-pyrazol-5-yl)methyl)-2-(3-fluoro-4-(methylsulfonamido)phenyl)propanamide |
| 8 | (S)-N-((3-tert-butyl-1-cyclohexenyl-1H-pyrazol-5-yl)methyl)-2-(3-fluoro-4-(methylsulfonamido)phenyl)propanamide |
| 9 | 2-(3-fluoro-4-(methylsulfonamido)phenyl)-N-((3-methyl-1-phenyl-1H-pyrazol-5-yl)methyl)propanamide |
| 10 | N-((3-chloro-1-phenyl-1H-pyrazol-5-yl)methyl)-2-(3-fluoro-4-(methylsulfonamido)phenyl)propanamide |
| 11 | 2-(3-fluoro-4-(methylsulfonamido)phenyl)-N-((3-(4-fluorophenyl)-1-phenyl-1H-pyrazol-5-yl)methyl)propanamide |
| 12 | N-((3-tert-butyl-1-p-tolyl-1H-pyrazol-5-yl)methyl)-2-(3-fluoro-4-(methylsulfonamido)phenyl)propanamide |
| 13 | N-((3-tert-butyl-1-(4-tert-butylphenyl)-1H-pyrazol-5-yl)methyl)-2-(3-fluoro-4-(methylsulfonamido)phenyl)propanamide |
| 14 | N-((3-tert-butyl-1-(4-chlorophenyl)-1H-pyrazol-5-yl)methyl)-2-(3-fluoro-4-(methylsulfonamido)phenyl)propanamide |
| 15 | (S)-N-((3-tert-butyl-1-(4-chlorophenyl)-1H-pyrazol-5-yl)methyl)-2-(3-fluoro-4-(methylsulfonamido)phenyl)propanamide |
| 16 | N-((3-tert-butyl-1-(3-chlorophenyl)-1H-pyrazol-5-yl)methyl)-2-(3-fluoro-4-(methylsulfonamido)phenyl)propanamide |
| 17 | (S)-N-((3-tert-butyl-1-(3-chlorophenyl)-1H-pyrazol-5-yl)methyl)-2-(3-fluoro-4-(methylsulfonamido)phenyl)propanamide |
| 18 | N-((3-tert-butyl-1-(3-chloro-4-fluorophenyl)-1H-pyrazol-5-yl)methyl)-2-(3-fluoro-4-(methylsulfonamido)phenyl)propanamide |
| 19 | (E)-N-((3-tert-butyl-1-(4-methylstyryl)-1H-pyrazol-5-yl)methyl)-2-(3-fluoro-4-(methylsulfonamido)phenyl)propanamide |
| 20 | N-((3-tert-butyl-1-(4-methoxyphenyl)-1H-pyrazol-5-yl)methyl)-2-(3-fluoro-4-(methylsulfonamido)phenyl)propanamide |
| 21 | N-((1-(4-chlorophenyl)-3-(trifluoromethyl)-1H-pyrazol-5-yl)methyl)-2-(3-fluoro-4-(methylsulfonamido)phenyl)propanamide |
| 22 | (R)-N-((1-(4-chlorophenyl)-3-(trifluoromethyl)-1H-pyrazol-5-yl)methyl)-2-(3-fluoro-4-(methylsulfonamido)phenyl)propanamide |
| 23 | (S)-N-((1-(4-chlorophenyl)-3-(trifluoromethyl)-1H-pyrazol-5-yl)methyl)-2-(3-fluoro-4-(methylsulfonamido)phenyl)propanamide |
| 24 | N-((1-(3-chlorophenyl)-3-(trifluoromethyl)-1H-pyrazol-5-yl)methyl)-2-(3-fluoro-4-(methylsulfonamido)phenyl)propanamide |
| 25 | (R)-N-((1-(3-chlorophenyl)-3-(trifluoromethyl)-1H-pyrazol-5-yl)methyl)-2-(3-fluoro-4-(methylsulfonamido)phenyl)propanamide |
| 26 | (S)-N-((1-(3-chlorophenyl)-3-(trifluoromethyl)-1H-pyrazol-5-yl)methyl)-2-(3-fluoro-4-(methylsulfonamido)phenyl)propanamide |
| 27 | N-((3-tert-butyl-1-(3-chlorophenyl)-1H-pyrazol-5-yl)methyl)-2-(3-methoxy-4-(methylsulfonamido)phenyl)propanamide |
| 28 | N-((1-(3-chlorophenyl)-3-(trifluoromethyl)-1H-pyrazol-5-yl)methyl)-2-(3-methoxy-4-(methylsulfonamido)phenyl)propanamide |
| 29 | N-((3-tert-butyl-1-(3-chlorophenyl)-1H-pyrazol-5-yl)methyl)-2-(3,5-difluoro-4-(methylsulfonamido)phenyl)propanamide |
| 30 | N-((1-(3-chlorophenyl)-3-(trifluoromethyl)-1H-pyrazol-5-yl)methyl)-2-(3,5-difluorophenyl)propanamide |
| 31 | 2-(4-bromo-3-fluorophenyl)-N-((1-(3-chlorophenyl)-3-(trifluoromethyl)-1H-pyrazol-5-yl)methyl)propanamide |
| 32 | N-((3-tert-butyl-1-(3-chlorophenyl)-1H-pyrazol-5-yl)methyl)-2-(4-isobutylphenyl)propanamide |
| 33 | N-((3-tert-butyl-1-(3-chlorophenyl)-1H-pyrazol-5-yl)methyl)-2-(3-fluoro-4-(methylsulfonamidomethyl)phenyl)propanamide |
| 34 | N-((1-(3-chlorophenyl)-3-(trifluoromethyl)-1H-pyrazol-5-yl)methyl)-2-(3-fluoro-4-(furan-3-yl)phenyl)propanamide |
| 35 | N-((3-tert-butyl-1-(3-chlorophenyl)-1H-pyrazol-5-yl)methyl)-2-(2-fluorobiphenyl-4-yl)propanamide |
| 36 | N-((1-(3-chlorophenyl)-3-(trifluoromethyl)-1H-pyrazol-5-yl)methyl)-2-(4-(1,2-dihydroxyethyl)-3-fluorophenyl)propanamide |
| 37 | 4-(1-((1-(3-chlorophenyl)-3-(trifluoromethyl)-1H-pyrazol-5-yl)methylamino)-1-oxopropan-2-yl)-2-fluorobenzamide |
| 38 | 4-(1-((1-(3-chlorophenyl)-3-(trifluoromethyl)-1H-pyrazol-5-yl)methylamino)-1-oxopropan-2-yl)-N-ethylbenzamide |
| 39 | 4-(1-((1-(3-chlorophenyl)-3-(trifluoromethyl)-1H-pyrazol-5-yl)methylamino)-1-oxopropan-2-yl)-2-fluoro-N-phenylbenzamide |
| 40 | 4-(1-((1-(3-chlorophenyl)-3-(trifluoromethyl)-1H-pyrazol-5-yl)methylamino)-1-oxopropan-2-yl)-N-(4-fluorophenyl)benzamide |
| 41 | 4-(1-((1-(3-chlorophenyl)-3-(trifluoromethyl)-1H-pyrazol-5-yl)methylamino)-1-oxopropan-2-yl)-N-(4-(trifluoromethyl)phenyl)benzamide |
| 42 | 4-(1-((1-(3-chlorophenyl)-3-(trifluoromethyl)-1H-pyrazol-5-yl)methylamino)-1-oxopropan-2-yl)-N-(pyridin-4-yl)benzamide |
| 43 | N-((1-(3-chlorophenyl)-3-(trifluoromethyl)-1H-pyrazol-5-yl)methyl)-2-(4-(trifluormethoxy)phenyl)propanamide |

-continued

| | |
|---|---|
| 44 | N-((1-(3-chlorophenyl)-3-(trifluoromethyl)-1H-pyrazol-5-yl)methyl)-2-(3,5-dibromo-4-hydroxyphenyl)acetamide |
| 45 | N-((1-(3-chlorophenyl)-3-(trifluoromethyl)-1H-pyrazol-5-yl)methyl)-2-(3,5-dibromo-4-hydroxyphenyl)propanamide |
| 46 | N-((3-tert-butyl-1-(3-chlorophenyl)-1H-pyrazol-5-yl)methyl)-2-(3,5-difluoro-4-hydroxyphenyl)propanamide |
| 47 | N-((1-(3-chlorophenyl)-3-(trifluoromethyl)-1H-pyrazol-5-yl)methyl)-2-(3,5-difluoro-4-methoxyphenyl)propanamide |
| 48 | N-((3-tert-butyl-1-(3-chlorophenyl)-1H-pyrazol-5-yl)methyl)-2-(4-methoxy-3,5-dimethylphenyl)acetamide |
| 49 | N-((3-tert-butyl-1-(3-chlorophenyl)-1H-pyrazol-5-yl)methyl)-2-(4-(N,N-dimethylsulfamoyl)-3-fluorophenyl)propanamide |
| 50 | N-((1-(3-chlorophenyl)-3-(trifluoromethyl)-1H-pyrazol-5-yl)methyl)-2-(4-(4-chlorophenylamino)phenyl)propanamide |
| 51 | N-((1-(3-chlorophenyl)-3-(trifluoromethyl)-1H-pyrazol-5-yl)methyl)-2-(4-(4-methoxyphenylamino)phenyl)propanamide |
| 52 | 2-(4-amino-3,5-difluorophenyl)-N-((1-(3-chlorophenyl)-3-(trifluoromethyl)-1H-pyrazol-5-yl)methyl)propanamide |
| 53 | 2-(4-acetamido-3-fluorophenyl)-N-((1-(3-chlorophenyl)-3-(trifluoromethyl)-1H-pyrazol-5-yl)methyl)propanamide |
| 54 | N-(4-(1-((1-(3-chlorophenyl)-3-(trifluoromethyl)-1H-pyrazol-5-yl)methylamino)-1-oxopropan-2-yl)-2-fluorophenyl)benzamide |
| 55 | N-((3-tert-butyl-1-(3-chlorophenyl)-1H-pyrazol-5-yl)methyl)-2-[4-(1,1-dioxidoisothiazolidin-2-yl)-3-fluorophenyl]propanamide |
| 56 | N-((3-tert-butyl-1-(3-chlorophenyl)-1H-pyrazol-5-yl)methyl)-2-(4-(N,N-dimethylsulfamoyl)-3-fluorophenyl)propanamide |
| 66 | N-((3-tert-butyl-1-(3-chlorophenyl)-1H-pyrazol-5-yl)methyl)-2-(3-fluoro-4-(methylsulfonamido)phenyl)-2-(3-fluorophenyl)acetamide |
| 67 | N-((3-tert-butyl-1-(3-chlorophenyl)-1H-pyrazol-5-yl)methyl)-2-cyclohexyl-2-(3-fluoro-4-(methylsulfonamido)phenyl)acetamide |
| 68 | N-((3-tert-butyl-1-(3-chlorophenyl)-1H-pyrazol-5-yl)methyl)-2-(3-fluoro-4-(methylsulfonamido)phenyl)-2-p-tolylacetamide |
| 69 | N-((3-tert-butyl-1-(3-chlorophenyl)-1H-pyrazol-5-yl)methyl)-2-(3-chloro-4-(methylthio)phenyl)propanamide |
| 70 | N-((3-tert-butyl-1-(3-chlorophenyl)-1H-pyrazol-5-yl)methyl)-2-(3-chloro-4-(methylsulfonyl)phenyl)propanamide |
| 71 | N-((3-tert-butyl-1-(3-chlorophenyl)-1H-pyrazol-5-yl)methyl)-2-(3-fluoro-4-(methylthio)phenyl)propanamide |
| 72 | N-((3-tert-butyl-1-(3-chlorophenyl)-1H-pyrazol-5-yl)methyl)-2-(3-fluoro-4-(methylsulfonyl)phenyl)propanamide |
| 73 | N-((3-tert-butyl-1-(3-chlorophenyl)-1H-pyrazol-5-yl)methyl)-2-(3-fluorophenyl)acetamide |
| 74 | N-((1-(3-chlorophenyl)-3-(trifluoromethyl)-1H-pyrazol-5-yl)methyl)-2-(3-fluorophenyl)acetamide |
| 75 | N-[[5-tert-butyl-2-(3-chlorophenyl)-2H-[1,2,4]triazol-3-yl]-methyl]-2-[3-fluoro-4-(methanesulfonamido)phenyl]propionamide |
| 76 | N-[[2-(3-chlorophenyl)-5-(trifluoromethyl)-2H-[1,2,4]triazol-3-yl]-methyl]-2-[3-fluoro-4-(methanesulfonamido)phenyl]propionamide |
| 77 | N-[(5-tert-butyl-2-cyclohexyl-2H-[1,2,4]triazol-3-yl)-methyl]-2-[3-fluoro-4-(methanesulfonamido)phenyl]propionamide |
| 78 | N-[[2-cyclohexyl-5-(trifluoromethyl)-2H-[1,2,4]triazol-3-yl]-methyl]-2-[3-fluoro-4-(methanesulfonamido)phenyl]propionamide |
| 79 | N-[(5-tert-butyl-2-pyridin-3-yl-2H-[1,2,4]triazol-3-yl)-methyl]-2-[3-fluoro-4-(methanesulfonamido)phenyl]propionamide |
| 80 | 2-[3-fluoro-4-(methanesulfonamido)phenyl]-N-[[2-pyridin-3-yl-5-(trifluoromethyl)-2H-[1,2,4]triazol-3-yl]-methyl]propionamide |
| 117 | N-((1-(3-chlorophenyl)-3-(trifluoromethyl)-1H-pyrazol-5-yl)methyl)-2-(3-fluorophenyl)-2-methylpropanamide |
| 118 | N-((3-tert-butyl-1-(3-chlorophenyl)-1H-pyrazol-5-yl)methyl)-1-(3-fluorophenyl)cyclopropancarboxamide |
| 119 | N-((1-(3-chlorophenyl)-3-(trifluoromethyl)-1H-pyrazol-5-yl)methyl)-1-(3-fluorophenyl)cyclobutancarboxamide |
| 120 | N-((1-(3-chlorophenyl)-3-(trifluoromethyl)-1H-pyrazol-5-yl)methyl)-1-(3-fluorophenyl)cyclopentancarboxamide |
| 121 | N-((1-(3-chlorophenyl)-3-(trifluoromethyl)-1H-pyrazol-5-yl)methyl)-1-(3-fluorophenyl)cyclohexancarboxamide |
| 124 | N-((1-(3-chloro-4-fluorophenyl)-3-(trifluoromethyl)-1H-pyrazol-5-yl)methyl)-2-(3-fluoro-4-(methylsulfonylmethyl)phenyl)propanamide |
| 125 | N-((3-tert-butyl-1-(3-chlorophenyl)-1H-pyrazol-5-yl)methyl)-2-(4-cyclopropyl-3-fluorophenyl)propanamide |

-continued

| | |
|---|---|
| 127 | N-((3-tert-butyl-1-(pyridin-2-yl)-1H-pyrazol-5-yl)methyl)-2-(3-fluoro-4-(methylsulfonamidmethyl)phenyl)propanamide |
| 128 | N-((1-(3-chlorophenyl)-3-cyclopropyl-1H-pyrazol-5-yl)methyl)-2-(3-fluoro-4-(methylsulfonylmethyl)phenyl)propanamide |
| 129 | 2-(3-fluoro-4-(methylsulfonamidmethyl)phenyl)-N-((1-(pyridin-2-ylmethylamino)-3-(trifluoromethyl)-1H-pyrazol-5-yl)methyl)propanamide |
| 130 | N-((1-(3-chlorophenyl)-4-methyl-3-(trifluoromethyl)-1H-pyrazol-5-yl)methyl)-2-(3-fluorophenyl)acetamide |
| 131 | 2-(3-fluorophenyl)-N-((1-pentyl-3-(trifluoromethyl)-1H-pyrazol-5- yl)methyl)acetamide |
| 132 | 2-(3-fluorophenyl)-N-((1-(4-methoxybenzyl)-3-(trifluoromethyl)-1H-pyrazol-5-yl)methyl)acetamide |
| 133 | N-((3-tert-butyl-1-(2,2,2-trifluoroethylamino)-1H-pyrazol-5-yl)methyl)-2-(3-fluorophenyl)acetamide |
| 134 | N-((1-(3-chlorophenyl)-4-methyl-3-(trifluoromethyl)-1H-pyrazol-5-yl)methyl)-2-(3-fluoro-4-(methylsulfonamid-methyl)phenyl)propanamide |
| 135 | N-((3-tert-butyl-1-(3-chlorophenyl)-1H-1,2,4-triazol-5-yl)methyl)-2-(3-fluorophenyl)acetamide |
| 136 | 2-(3-fluorophenyl)-N-((1-(pyridin-3-yl)-3-(trifluoromethyl)-1H-pyrazol-5-yl)methyl)acetamide |
| 137 | N-((1-cyclohexyl-3-(trifluoromethyl)-1H-pyrazol-5-yl)methyl)-2-(3-fluoro-4-(methylsulfonamidmethyl)phenyl)propanamide |
| 138 | 2-(3-fluoro-4-(methylsulfonamidmethyl)phenyl)-N-((1-(tetrahydro-2H-pyran-4-yl)-3-(trifluoromethyl)-1H-pyrazol-5-yl)methyl)propanamide |
| 140 | N-((1-(3-chlorophenyl)-3-(trifluoromethyl)-1H-pyrazol-5-yl)methyl)-2-(3-fluoro-4-(trifluoromethyl)phenyl)acetamide |
| 141 | N-((1-(3-chlorophenyl)-3-(trifluoromethyl)-1H-pyrazol-5-yl)methyl)-2-(3-fluoro-4-(trifluoromethyl)phenyl)propanamide |
| 142 | N-((3-tert-butyl-1-(3-chlorophenyl)-1H-pyrazol-5-yl)methyl)-2-(3-fluoro-4-((2-methoxyethoxy)methyl)phenyl)propanamide |
| 143 | 4-(1-((1-(3-chlorophenyl)-3-(trifluoromethyl)-1H-pyrazol-5-yl)methylamino)-1-oxopropan-2-yl)-N-phenylbenzamide |
| 145 | N-((1-(3-chlorophenyl)-3-(trifluoromethyl)-1H-pyrazol-5-yl)methyl)-2-(3-fluoro-4-(methylsulfonamid)phenyl)-3-phenylpropanamide |
| 146 | N-(5-((2-(3-fluorophenyl)acetamide)methyl)-3-(trifluoromethyl)-1H-pyrazol-1-yl)benzamide |
| 147 | N-((1-(3-chlorophenyl)-3-(trifluoromethyl)-1H-pyrazol-5-yl)methyl)-2-(3,5-difluoro-4-hydroxyphenyl)acetamide |

2. Preparation of Ureas (A=N)

General directions for reacting amines of general formula (II) or (VI) with phenyl chloroformate to form compounds of formula (V) or (Via) (step j07 and step v1, respectively) and subsequent reaction of compounds of formula (V) with amines of general formula (VI) or of compounds of formula (Via) with amines of general formula (II) to form compounds of general formula (I), wherein A=N, as in scheme 1a and 1c (step j08 and step v2, respectively):

Step j07/step v1: The amine of general formula (II) or (VI) (1 equivalent) is placed in dichloromethane (10 mmol of amine in 70 ml) and phenyl chloroformate (1.1 equivalents) is added thereto at room temperature and the mixture is stirred for 30 min. After removal of the solvent under vacuum, the residue is purified by flash chromatography ($SiO_2$, diethyl ether/hexane in different ratios such as 1:2) and (V) or (VIa) is obtained in this way.

Step j08/step v2: The carbamic acid phenyl ester (V) or (VIa) obtained (1 equivalent) and the corresponding amine (VI) or (II) (1.1 equivalents) are dissolved in THF (10 mmol of the reaction mixture in 120 ml) and stirred for 16 h at room temperature after addition of DBU (1.5 equivalents). After removal of the solvent under vacuum, the resulting residue is purified by flash chromatography ($SiO_2$, EtOAc/hexane in different ratios such as 1:1) and (I) is obtained in this way.

The following example compounds 57-65, 122-123, 126, 139 and 144 were obtained using one of the methods described above.

| | |
|---|---|
| 57 | 1-((3-tert-butyl-1-(3-chlorophenyl)-1H-pyrazol-5-yl)methyl)-3-(3,5-difluorophenyl)urea |
| 58 | 1-(4-bromo-3-fluorophenyl)-3-((3-tert-butyl-1-(3-chlorophenyl)-1H-pyrazol-5-yl)methyl)urea |
| 59 | 1-((3-tert-butyl-1-(3-chlorophenyl)-1H-pyrazol-5-yl)methyl)-3-(4-(trifluoromethyl)phenyl)urea |
| 60 | 1-((3-tert-butyl-1-(3-chlorophenyl)-1H-pyrazol-5-yl)methyl)-3-(4-(difluormethoxy)phenyl)urea |
| 61 | 1-((3-tert-butyl-1-(3-chlorophenyl)-1H-pyrazol-5-yl)methyl)-3-(3,5-difluoro-4-methoxyphenyl)urea |
| 62 | 1-((3-tert-butyl-1-(3-chlorophenyl)-1H-pyrazol-5-yl)methyl)-3-(4-methoxy-3,5-dimethylphenyl)urea |
| 63 | 1-((3-tert-butyl-1-(3-chlorophenyl)-1H-pyrazol-5-yl)methyl)-3-(3-fluoro-4-(methylsulfonyl)phenyl)urea |
| 64 | 1-((3-tert-butyl-1-(3-chlorophenyl)-1H-pyrazol-5-yl)methyl)-3-(4-(phenylamino)phenyl)urea |
| 65 | 4-(3-((3-tert-butyl-1-(3-chlorophenyl)-1H-pyrazol-5-yl)methyl)ureido)-N-(4-fluorophenyl)benzamide |

-continued

| | |
|---|---|
| 122 | 1-((3-tert-butyl-1-(4-fluorophenyl)-1H-pyrazol-5-yl)methyl)-3-(3-fluorophenyl)urea |
| 123 | 3-((1-(3-chlorophenyl)-3-(trifluoromethyl)-1H-pyrazol-5-yl)methyl)-1-(3-fluorophenyl)-1-methylurea |
| 126 | 1-((1-(3-chlorophenyl)-3-(trifluoromethyl)-1H-pyrazol-5-yl)methyl)-3-(4-cyclopropyl-3-fluorophenyl)urea |
| 139 | 1-((1-(3-chlorophenyl)-3-(trifluoromethyl)-1H-pyrazol-5-yl)methyl)-3-(4-(cyclopropylethynyl)-3-fluorophenyl)urea |
| 144 | 1-((3-tert-butyl-1-(3-chlorophenyl)-1H-pyrazol-5-yl)methyl)-3-(3-fluoro-4-morpholinphenyl)urea |

The methods illustrated hereinbefore for synthesising the compounds according to the invention enable a person skilled in the art also to synthesise the following example compounds 81-116:

| | |
|---|---|
| 81 | N-[[5-tert-butyl-2-(6-chloropyridin-2-yl)-2H-pyrazol-3-yl]-methyl]-2-[3-fluoro-4-(methanesulfonamido)phenyl]propionamide |
| 82 | N-[[5-tert-butyl-2-(3,3-difluorocyclobutanecarbonyl)-2H-pyrazol-3-yl]-methyl]-2-[3-fluoro-4-(methanesulfonamido)phenyl]propionamide |
| 83 | N-[[2-(3-chlorophenyl)-4-methyl-5-(trifluoromethyl)-2H-pyrazol-3-yl]-methyl]-2-[3-fluoro-4-(methanesulfonamido)phenyl]propionamide |
| 84 | N-[[2-(dipropylamino)-5-(trifluoromethyl)-2H-pyrazol-3-yl]-methyl]-2-[4-(methanesulfonamido)-3-methoxyphenyl]propionamide |
| 85 | N-[[2-(dipropylamino)-5-(trifluoromethyl)-2H-pyrazol-3-yl]-methyl]-2-[3-fluoro-4-(hydroxymethyl)phenyl]propionamide |
| 86 | N-[[2-(dipropylamino)-5-(trifluoromethyl)-2H-pyrazol-3-yl]-methyl]-2-[3-fluoro-4-(methanesulfonamido)phenyl]propionamide |
| 87 | N-[[2-(dipropylamino)-5-(trifluoromethyl)-2H-pyrazol-3-yl]-methyl]-2-(3-fluorophenyl)acetamide |
| 88 | 4-[1-[[2-(dipropylamino)-5-(trifluoromethyl)-2H-pyrazol-3-yl]-methyl-carbamoyl]ethyl]-2-fluorobenzamide |
| 89 | 4-[1-[[2-(dipropylamino)-5-(trifluoromethyl)-2H-pyrazol-3-yl]-methyl-carbamoyl]ethyl]-N-pyridin-2-yl-benzamide |
| 90 | 2-[3-fluoro-4-(hydroxymethyl)phenyl]-N-[[2-piperidin-1-yl-5-(trifluoro-methyl)-2H-pyrazol-3-yl]-methyl]propionamide |
| 91 | 2-[3-fluoro-4-(2-hydroxyethyl)phenyl]-N-[[2-piperidin-1-yl-5-(trifluoro-methyl)-2H-pyrazol-3-yl]-methyl]propionamide |
| 92 | 2-[3-fluoro-4-(methanesulfonamido)phenyl]-N-[[2-piperidin-1-yl-5-(tri-fluoromethyl)-2H-pyrazol-3-yl]-methyl]propionamide |
| 93 | 2-[4-(methanesulfonamido)-3-methoxyphenyl]-N-[[2-piperidin-1-yl-5-(tri-fluoromethyl)-2H-pyrazol-3-yl]-methyl]propionamide |
| 94 | 2-[4-(1,2-dihydroxyethyl)-3-fluorophenyl]-N-[[2-piperidin-1-yl-5-(tri-fluoromethyl)-2H-pyrazol-3-yl]-methyl]propionamide |
| 95 | 2-(3-fluorophenyl)-N-[[2-piperidin-1-yl-5-(trifluoromethyl)-2H-pyrazol-3-yl]-methyl]acetamide |
| 96 | 2-fluoro-4-[1-[[2-piperidin-1-yl-5-(trifluoromethyl)-2H-pyrazol-3-yl]-methylcarbamoyl]ethyl]benzamide |
| 97 | 2-[3-fluoro-4-(methanesulfonamido)phenyl]-N-[[2-[(4-fluorophenyl)methyl-methylamino]-5-(trifluoromethyl)-2H-pyrazol-3-yl]-methyl]propionamide |
| 98 | N-[[5-tert-butyl-2-(2,2,2-trifluoroethylamino)-2H-pyrazol-3-yl]-methyl]-2-[3-fluoro-4-(methanesulfonamido)phenyl]propionamide |
| 99 | N-[[2-butoxy-5-(trifluoromethyl)-2H-pyrazol-3-yl]-methyl]-2-[3-fluoro-4-(hydroxymethyl)phenyl]propionamide |
| 100 | N-[[2-butoxy-5-(trifluoromethyl)-2H-pyrazol-3-yl]-methyl]-2-[3-fluoro-4-(methanesulfonamido)phenyl]propionamide |
| 101 | N-[[2-butoxy-5-(trifluoromethyl)-2H-pyrazol-3-yl]-methyl]-2-[4-(methane-sulfonamido)-3-methoxyphenyl]propionamide |
| 102 | N-[(2-butoxy-5-tert-butyl-2H-pyrazol-3-yl)-methyl]-2-(3-fluorophenyl)acetamide; |
| 103 | N-[[2-cyclopentyloxy-5-(trifluoromethyl)-2H-pyrazol-3-yl]-methyl]-2-[3-fluoro-4-(methanesulfonamido)phenyl]propionamide |
| 104 | N-[[2-cyclopentyloxy-5-(trifluoromethyl)-2H-pyrazol-3-yl]-methyl]-2-[4-(methanesulfonamido)-3-methoxyphenyl]propionamide |
| 105 | 2-(3-fluorophenyl)-N-[[2-[(4-methoxyphenyl)methoxy]-5-(trifluoromethyl)-2H-pyrazol-3-yl]-methyl]acetamide |
| 106 | N-[[5-tert-butyl-2-(3-cyano-5-fluorophenoxy)-2H-pyrazol-3-yl]-methyl]-2-(3-fluorophenyl)acetamide |
| 107 | N-[[2-(cyclohexylsulfanyl)-5-(trifluoromethyl)-2H-pyrazol-3-yl]-methyl]-2-[3-fluoro-4-(methanesulfonamido)phenyl]propionamide; |
| 108 | N-[[2-(benzenesulfonyl)-5-tert-butyl-2H-pyrazol-3-yl]-methyl]-2-(3-fluoro-phenyl)acetamide |
| 109 | N-[[2-cyclohexyl-5-(trifluoromethyl)-2H-[1,2,4]triazol-3-yl]-methyl]-2-[4-(methanesulfonamido)-3-methoxyphenyl]propionamide |
| 110 | N-[[2-cyclohexyl-5-(trifluoromethyl)-2H-[1,2,4]triazol-3-yl]-methyl]-2-(3-fluorophenyl)acetamide |

-continued

| | |
|---|---|
| 111 | 4-[1-[[2-cyclohexyl-5-(trifluoromethyl)-2H-[1,2,4]triazol-3-yl]-methyl-carbamoyl]ethyl]-2-fluorobenzamide |
| 112 | 2-[3-fluoro-4-(hydroxymethyl)phenyl]-N-[[2-hexyl-5-(trifluoromethyl)-2H-[1,2,4]triazol-3-yl]-methyl]propionamide |
| 113 | 4-[1-[[2-cyclobutyl-5-(trifluoromethyl)-2H-[1,2,4]triazol-3-yl]-methyl-carbamoyl]ethyl]-2-fluorobenzamide |
| 114 | N-[[5-tert-butyl-2-(3,3-difluorocyclobutanecarbonyl)-2H-[1,2,4]triazol-3-yl]-methyl]-2-[3-fluoro-4-(methanesulfonamido)phenyl]propionamide |
| 115 | N-[[5-tert-butyl-2-(3-cyano-5-fluorophenoxy)-2H-[1,2,4]triazol-3-yl]-methyl]-2-(3-fluorophenyl)acetamide |
| 116 | N-[[2-(benzenesulfonyl)-5-tert-butyl-2H-[1,2,4]triazol-3-yl]-methyl]-2-(3-fluorophenyl)acetamide |

TABLE 1

Mass Spectrometric Data for Example Compounds

| Example compound | [M + H] | Example compound | [M + H] |
|---|---|---|---|
| 1 | 397.2 | 20 | 503.2 |
| 2 | 397.2 | 21 | 518.9 |
| 3 | 411.2 | 22 | 518.9 |
| 4 | 411.2 | 23 | 518.9 |
| 5 | 481.1 | 24 | 518.9 |
| 6 | 481.1 | 25 | 518.9 |
| 7 | 479.3 | 26 | 518.9 |
| 8 | 477.1 | 27 | 519.3 |
| 12 | 478.2 | 28 | 531.2 |
| 13 | 529.3 | 29 | 525.3 |
| 14 | 507.0 | 30 | 444.0 |
| 15 | 507.0 | 33 | 521.3 |
| 16 | 507.2 | 39 | 545.4 |
| 17 | 507.0 | 40 | 545.0 |
| 18 | 525.2 | 41 | 595.3 |
| 19 | 513.2 | 47 | 474.3 |
| 49 | 521.3 | 130 | 426.3 |
| 55 | 533.3 | 131 | 372.1 |
| 56 | 521.3 | 132 | 422.1 |
| 61 | 449.3 | 133 | 387.3 |
| 74 | 412.1 | 134 | 546.9 |
| 117 | 440.2 | 135 | 401.3 |
| 118 | 426.3 | 137 | 505.0 |
| 119 | 452.2 | 139 | 477.2 |
| 120 | 466.3 | 141 | 493.9 |
| 122 | 385.1 | 142 | 502.0 |
| 123 | 427.0 | 143 | 527.0 |
| 125 | 454.0 | 144 | 486.1 |
| 126 | 452.9 | 147 | 446.0 |
| 127 | 488.2 | | |
| 128 | 504.9 | | |
| 129 | 529.3 | | |

Synthesis of Selected Intermediate Products

1. Synthesis of (3-tert-butyl-1-(3-chlorophenol)-1H-pyrazol-5-yl)methanamine (steps 101-106)

Step j01: Pivaloyl chloride (J-0) (1 eq., 60 g) was added dropwise to a solution of methanol (120 mL) within 30 min at 0° C. and the mixture was stirred for 1 h at room temperature. After the addition of water (120 mL), the separated organic phase was washed with water (120 mL), dried over sodium sulfate and codistilled with dichloromethane (150 mL). The liquid product J-I was able to be obtained at 99% purity (57 g).

Step j02: NaH (50% in paraffin oil) (1.2 equivalents, 4.6 g) was dissolved in 1,4-dioxane (120 mL) and the mixture was stirred for a few minutes. Acetonitrile (1.2 equivalents, 4.2 g) was added dropwise within 15 min and the mixture was stirred for a further 30 min. The methyl pivalate (J-I) (1 equivalents, 10 g) was added dropwise within 15 min and the reaction mixture was refluxed for 3 h. After complete reaction, the reaction mixture was placed in iced water (200 g), acidified to pH 4.5 and extracted with dichloromethane (12×250 mL). The combined organic phases were dried over sodium sulfate, distilled and after recrystallization from n-hexane (100 mL) 5 g of the product (J-II) (51% yield) was able to be obtained as a solid brown substance.

Step j03: At room temperature 4,4-dimethyl-3-oxopentanenitrile (J-III) (1 equivalents, 5 g) was taken up in ethanol (100 mL), mixed with hydrazine hydrate (2 equivalents, 4.42 g) and refluxed for 3 h. The residue obtained after removal of the ethanol by distillation was taken up in water (100 mL) and extracted with ethyl acetate (300 mL). The combined organic phases were dried over sodium sulfate, the solvent was removed under vacuum and the product (J-III) (5 g, 89% yield) was obtained as a light red solid after recrystallization from n-hexane (200 mL).

Step j04: 3-Tert-butyl-1H-pyrazol-5-amine (J-III) (1 equivalents, 40 g) was dissolved in diluted HCl (120 mL of HCl in 120 mL of water) and mixed dropwise with $NaNO_2$ (1.03 equivalents, 25 g in 100 mL) at 0-5° C. over a period of 30 min. After stirring for 30 minutes, the reaction mixture was neutralised with $Na_2CO_3$. A diazonium salt obtained by reaction of KCN (2.4 equivalents, 48 g), water (120 mL) and CuCN (1.12 equivalents, 31 g) was added dropwise to the reaction mixture within 30 min and the mixture was stirred for a further 30 min at 75° C. After complete reaction, the reaction mixture was extracted with ethyl acetate (3×500 mL), the combined organic phases were dried over sodium sulfate and the solvent was removed under vacuum. The purification (silica gel: 100-200 mesh, eluent: 20% ethyl acetate/n-hexane) of the residue by column chromatography produced a white solid (J-IV) (6.5 g, 15%).

Step j05 (Method 1):

3-tert.-butyl-1H-pyrazol-5-carbonitrile (J-IV) (10 mmol) was added to a suspension of NaH (60%) (12.5 mmol) in dimethylformamide (20 mL) at room temperature while stirring. After stirring for 15 minutes, 1-iodo-3-chlorobenzene (37.5 mmol) was added dropwise to this reaction mixture at room temperature. After stirring for 30 min at 100° C., the reaction mixture was mixed with water (150 mL) and extracted with dichloromethane (3×75 mL). The combined organic extracts were washed with water (100 mL) and sat. NaCl solution (100 mL) and dried over magnesium sulfate. After removal of the solvent under vacuum, the residue was purified by column chromatography (silica gel: 100-200 mesh, eluent: various mixtures of ethyl acetate and cyclohexane as the mobile solvent) and the product J-V was obtained.

Step j05 (Method 2):

A mixture of 3-tert-butyl-1H-pyrazol-5-carbonitrile (J-IV) (10 mmol), a boronic acid $B(OH)_2$(3-chlorophenyl) or a corresponding boronic acid ester (20 mmol) and copper (II) acetate (15 mmol) is placed in dichloromethane (200 mL), mixed with pyridine (20 mmol) while stirring at room temperature and the mixture is stirred for 16 h. After removal of the solvent under vacuum, the resulting residue is purified by column chromatography (silica gel: 100-200 mesh, eluent: various mixtures of ethyl acetate and cyclohexane as the mobile solvent) and the product J-V is in this way obtained.

Step j06: (Method 1):

J-V was dissolved together with palladium on carbon (10%, 500 mg) and concentrated HCl (3 mL) in methanol (30 mL) and exposed to a hydrogen atmosphere for 6 h at room temperature. The reaction mixture was filtered over celite and the filtrate was concentrated under vacuum. The residue was purified by flash chromatography (silica gel: 100-200 mesh, eluent: ethyl acetate) and the product (U-II) was in this way obtained.

Step j06: (Method 2):

J-V was dissolved in tetrahydrofuran (10 mL) and $BH_3$—$S(CH_3)_2$ (2.0 M in tetrahydrofuran, 3 mL, 3 equivalents) was added thereto. The reaction mixture was heated to reflux for 8 h, aq. 2 N HCl (2 N) was added thereto and the reaction mixture was refluxed for a further 30 minutes. The reaction mixture was mixed with aq. NaOH solution (2N) and washed with ethyl acetate. The combined organic phases were washed with sat. aq. NaCl solution and dried over magnesium sulfate. The solvent is removed under vacuum and the residue is purified by column chromatography (silica gel: 100-200 mesh, eluent: various mixtures of dichloromethane and methanol as the mobile solvent) and the product (U-II) is in this way obtained.

The following further intermediate products were/can be synthesized in a similar manner using the process described above under 1:

(3-tert-butyl-1-(3-chloro-4-fluorophenyl)-1H-pyrazol-5-yl)methanamine (3-tert-butyl-1-(3,4-difluorophenyl)-1H-pyrazol-5-yl)methanamine (3-tert-butyl-1-(3-fluorophenyl)-1H-pyrazol-5-yl)methanamine (3-tert-butyl-1-(4-fluorophenyl)-1H-pyrazol-5-yl)methanamine (3-tert-butyl-1-(3-trifluoromethylphenyl)-1H-pyrazol-5-yl)methanamine (3-tert-butyl-1-(3-trifluoromethoxyphenyl)-1H-pyrazol-5-yl)methanamine (3-tert-butyl-1-(3-methylphenyl)-1H-pyrazol-5-yl)methanamine (3-tert-butyl-1-(4-chlorophenyl)-1H-pyrazol-5-yl)methanamine (3-tert-butyl-1-(3,5-difluorophenyl)-1H-pyrazol-5-yl)methanamine (3-tert-butyl-1-((3-difluoromethyl)phenyl)-1H-pyrazol-5-yl)methanamine (3-tert-butyl-1-(3-fluoro-5-methylphenyl)-1H-pyrazol-5-yl)methanamine (3-tert-butyl-1-(3-cyanophenyl)-1H-pyrazol-5-yl)methanamine (3-tert-butyl-1-(3-methoxymethylphenyl)-1H-pyrazol-5-yl)methanamine (3-tert-butyl-1-(3-methoxyphenyl)-1H-pyrazol-5-yl)methanamine (3-tert-butyl-1-(3-dimethylaminophenyl)-1H-pyrazol-5-yl)methanamine

2. Synthesis of 1-(3-chlorophenyl)-3-(trifluoromethyl)-1H-pyrazol-5-yl-methanamine (Steps k01-k05 and j06)

Step k01: LAlH (lithium aluminium hydride) (0.25 equivalents, 0.7 g) was dissolved in dry diethyl ether (30 mL) under a protective gas atmosphere and stirred for 2 h at room temperature. The suspension obtained was taken up in diethyl ether (20 mL). Ethyl-2,2,2-trifluoroacetate (K-0) (1 equivalent, 10 g) was taken up in dry diethyl ether (20 mL) and added dropwise to the suspension at −78° C. over a period of 1 h. The mixture was then the stirred for a further 2 h at −78° C. ethanol (95%) (2.5 mL) was then added dropwise, the reaction mixture was heated to room temperature and placed on iced water (30 mL) with concentrated $H_2SO_4$ (7.5 mL). The organic phase was separated and concentrated under vacuum and the reaction product K-I was immediately introduced into the next reaction step k02.

Step k05: 3-chloroaniline (K-IV) (1 equivalent, 50 g) was dissolved at −5 to 0° C. in concentrated HCl (300 mL) and stirred for 10 min. A mixture of $NaNO_2$ (1.2 equivalents, 32.4 g), water (30 mL), $SnCl_2.2H_2O$ (2.2 equivalents, 70.6 g) and concentrated HCl (100 mL) was added dropwise over a period of 3 h while maintaining the temperature. After stirring for a further 2 h at −5 to 0° C., the reaction mixture was set to pH 9 using NaOH solution and extracted with ethyl acetate (250 mL). The combined organic phases were dried over magnesium sulfate and the solvent was removed under vacuum. The purification by column chromatography (silica gel: 100-200 mesh, eluent: 8% ethyl acetate/n-hexane) produced 40 g (72%) of (3-chlorophenyl)hydrazine (K-IV) as a brown oil.

Step k02: The aldehyde (K-I) (2 equivalents, 300 mL) obtained from k01 and (3-chlorophenyl)hydrazine (K-IV) (1 equivalent, 20 g) were placed in ethanol (200 mL) and refluxed for 5 h. The solvent was removed under vacuum, the residue was purified by column chromatography (silica gel: 100-200 mesh, eluent: n-hexane) and the product (25 g, 72%) K-II was obtained as a brown oil.

Step k03: The hydrazine K-II (1 equivalent, 25 g) was dissolved in dimethylformamide (125 mL). N-chlorosuccinimide (1.3 equivalents, 19.5 g) was added portionwise at room temperature within 15 min and the mixture was stirred for 3 h. The dimethylformamide was removed by distillation and the residue was taken up in ethyl acetate. The ethyl acetate was removed under vacuum, the resulting residue was purified by column chromatography (silica gel: 100-200 mesh, eluent: n-hexane) and the product K-III (26.5 g, 92%) was obtained as a pink-coloured oil.

Step k04: At room temperature the hydrazonoyl chloride K-III (1 equivalent, 10 g) was taken up in toluene (150 mL) and mixed with 2-chloroacrylonitrile (2 equivalents, 6.1 mL) and triethylamine (2 equivalents, 10.7 mL). This reaction mixture was stirred for 20 h at 80° C. The mixture was then diluted with water (200 mL) and the phases were separated. The organic phase was dried over magnesium sulfate and the solvent was removed under vacuum. The residue was purified by column chromatography (silica gel: 100-200 mesh, eluent: 5% ethyl acetate/n-hexane) and the product (5.5 g, 52%) was obtained as a white solid J-V.

Step j06 (Method 3):

The carbonitrile J-V (1 equivalent, 1 g) was dissolved in methanolic ammonia solution (150 mL, 1:1) and hydrogenated in an H-cube (10 bar, 80° C., 1 mL/min, 0.25 mol/L). After removal of the solvent under vacuum, (1-(3-chlorophenyl)-3-(trifluoromethyl)-1H-pyrazol-5-yl)methanamine (II) was able to be obtained as a white solid (0.92 g, 91%).

The following further intermediate products were/can be synthesized in a similar manner using the process described hereinbefore under 2:

(1-(3-fluorophenyl)-3-(trifluoromethyl)-1H-pyrazol-5-yl)methanamine (1-(4-fluorophenyl)-3-(trifluoromethyl)-1H-pyrazol-5-yl)methanamine (1-(3-chloro-4-fluorophenyl)-3-(trifluoromethyl)-1H-pyrazol-5-yl)methanamine (1-(3,4-difluorophenyl)-3-(trifluoromethyl)-1H-pyrazol-5-yl)methanamine (1-(3-methoxyphenyl)-3-(trifluoromethyl)-1H-pyrazol-5-yl)methanamine (1-(3-isopropylphenyl)-3-(trifluoromethyl)-1H-pyrazol-5-yl)methanamine (1-(3-trifluoromethylphenyl)-3-(trifluoromethyl)-1H-pyrazol-5-yl)methanamine (1-(4-chlorophenyl)-3-(trifluoromethyl)-1H-pyrazol-5-yl)methanamine (1-(3-methylphenyl)-3-(trifluoromethyl)-1H-pyrazol-5-yl)methanamine 3. Preparation of methyl phenyl (3-tert-butyl-1-(3-chlorophenyl)-1H-pyrazol-5-yl)methylcarbamate

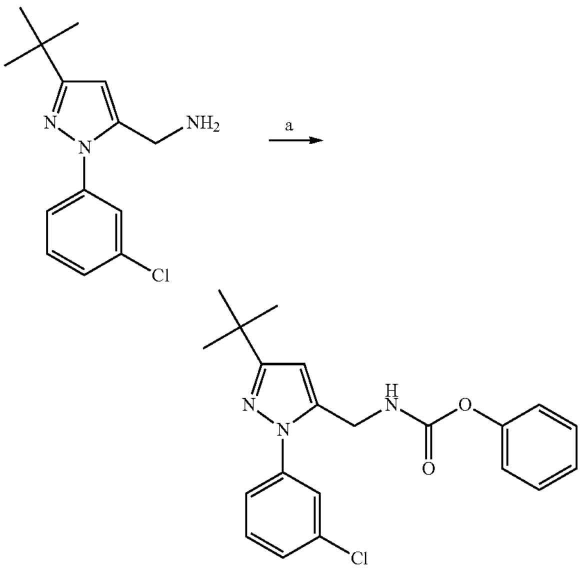

Step a: To a solution of (3-tert-butyl-1-(3-chlorophenyl)-1H-pyrazol-5-yl)methanamine (5 g, 18 mmol) in dimethylformamide (25 mL), potassium carbonate (9.16 g, 66 mmol, 3.5 eq) was added and cooled the contents to 0° C. Then phenyl chloroformate (3.28 g (2.65 mL), 20 mmol, 1.1 equivalents) was added dropwise for 15 minutes and the overall reaction mixture was stirred for another 15 minutes at 0° C. Progress of the reaction was monitored by TLC (20% ethyl acetate-n-hexane). On completion of the reaction, reaction contents were filtered, filtrate was diluted with cold water (100 mL) and the product extracted with ethyl acetate (3x25 mL). Combined organic layer was washed with brine solution (100 mL), dried over sodium sulfate and concentrated under reduced pressure. Crude product obtained was purified by column chromatography (silica gel: 100-200 mesh, eluent: 10% ethyl acetate in n-hexane) to yield the required product as a white solid (3.2 g, 45%).

4. Preparation of (1-(3-chlorophenyl)-3-cyclopropyl-1H-pyrazol-5-yl)methanamine hydrochloride

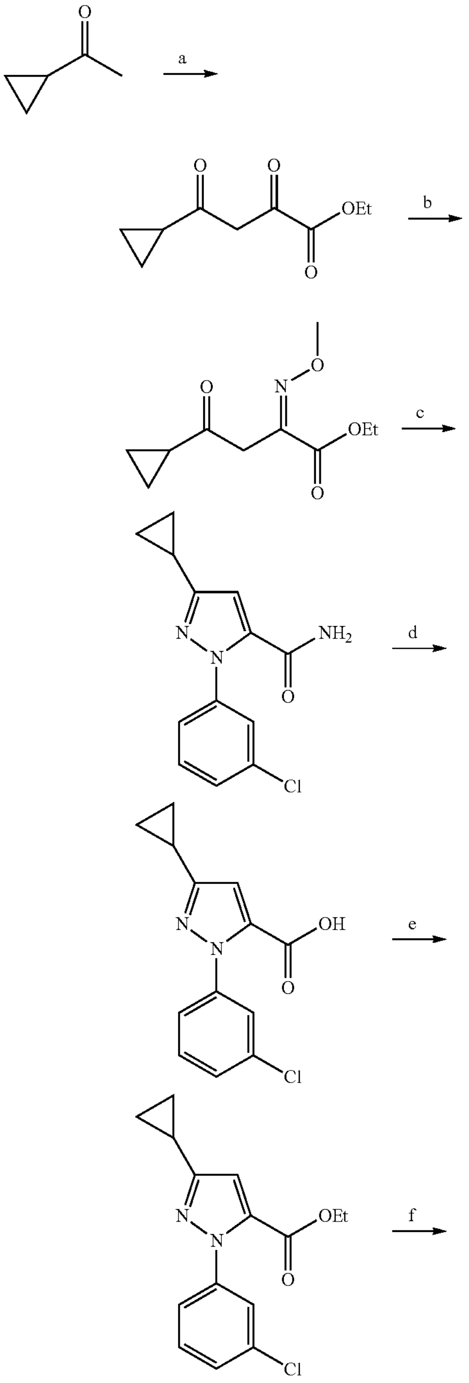

-continued

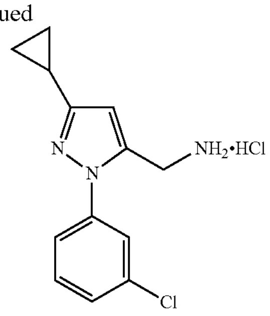

Step a: To a solution of sodium ethoxide (freshly prepared by dissolving sodium (1 g, 8.2 mmol, 1.2 equivalents) in ethanol (30 mL)), diethyl oxalate (0.92 mL, 6.85 mmol, 1 equivalent) was added at room temperature followed by addition of cyclopropyl methyl ketone (0.74 mL, 7.5 mmol, 1.1 equivalents) dropwise at 0° C. The reaction mixture was slowly warmed to room temperature and stirred for 3 h. Ice cold water (10 mL) was added and ethanol was evaporated under reduced pressure. The residual aqueous layer was diluted with 2 N aq. HCl (15 mL) and extracted with diethyl ether (2×25 mL). The organic layer was washed with brine solution and dried over sodium sulfate, filtered and concentrated to give a pale brown liquid (400 mg, 31%).

Step b: To a solution of step-a product (200 mg, 0.543 mmol, 1 equivalent) in ethanol (8 mL), methoxylamine hydrochloride (30% solution in water, 0.4 mL, 0.651 mmol, 1.2 equivalents) was added at room temperature and the reaction mixture stirred for 1 h. ethanol was evaporated under reduced pressure and the residual aqueous layer was extracted with ethyl acetate (15 mL). The organic layer was washed with water (10 mL), brine solution (10 mL), dried over sodium sulfate, filtered and concentrated under reduced pressure to give a pale yellow liquid (180 mg, 78%).

Step c: A mixture of step-b product (1.1 g, 5.164 mmol, 1 equivalent) and 3-chlorophenyl hydrazine hydrochloride (1.84 g, 10.27 mmol, 2 equivalents) was taken in acetic acid (20 mL), 2-methoxy ethanol (10 mL) and the reaction mixture was heated at 105° C. for 3 h. Solvent was evaporated and the residue was extracted with ethyl acetate (60 mL). The organic layer washed with water (10 mL), brine solution (10 mL), dried over sodium sulfate, filtered and concentrated under reduced pressure to give a residue. Purification by column chromatography (silica gel: 100-200 mesh; eluent: ethyl acetate-petroleum ether (4:96)) afforded a pale brown semi solid (1.15 g, 77%).

Step d: To a solution of step-c product (2.5 g, 8.62 mmol, 1 eq) in tetrahydrofuran (15 mL)—methanol (9 mL)—water (3 mL), lithium hydroxide (1.08 g, 25.71 mmol, 3 equivalents) was added at 0° C. and the reaction mixture was stirred for 2 h at room temperature. Solvent was evaporated and pH of the residue was adjusted to ~3 sing 2 N aqueous HCl (1.2 mL). The acidic aqueous layer was extracted with ethyl acetate (2×60 mL); the combined organic layer washed with water (10 mL), brine solution (10 mL), dried over sodium sulfate, filtered and concentrated under reduced pressure to give an off white solid (1.4 g, 62%).

Step e: To a solution of step-d product (1.4 g, 5.34 mmol, 1 equivalent) in 1,4-dioxane (30 mL), pyridine (0.25 mL, 3.2 mmol, 0.6 equivalents) and di-tert-butyl dicarbonate (1.4 mL, 6.37 mmol, 1.2 equivalents) were added at 0° C. and the resulting mixture was stirred for 30 minutes at the same temperature. Ammonium bicarbonate (0.84 g, 10.63 mmol, 2 equivalents) was added at 0° C. and the reaction mixture was stirred at room temperature overnight. The reaction mixture was diluted with water (10 mL) and the aqueous layer was extracted with ethyl acetate (2×30 mL). The organic layer was washed with 2N HCl (20 mL), water (10 mL), brine solution (10 mL), dried over sodium sulfate, filtered and concentrated under reduced pressure to give a residue. Purification by column chromatography (silica gel: 100-200 mesh; eluent: ethyl acetate-petroleum ether (16:84)) gave a white solid (1 g, 72%).

Step f: To a solution of step-e product (2 g, 7.66 mmol, 1 equivalent) in tetrahydrofuran (25 mL), $BH_3$.DMS (1.44 mL, 15.32 mmol, 2 equivalents) was added at 0° C. and the reaction mixture was heated at 70° C. for 3 h. The reaction mixture was cooled to 0° C. and methanol (15 mL) was added and reaction mixture heated at reflux for 1 h. The reaction mixture was brought to room temperature and solvent was evaporated under reduced pressure. The residue was dissolved in ether (15 mL), cooled to 0° C. and a solution of HCl in 1,4-dioxane (3 mL) was added (pH of the reaction mixture ~4). The precipitated solid was filtered and washed with diethyl ether (5 mL, thrice) to give the hydrochloride salt compound as a white solid (600 mg, 28%).

Synthesis of Example Compounds

1. Preparation of Amides (A=CH or $C(CH_3)$)

General directions for reacting amines of general formula (Q-II) with carboxylic acids of general formula or carboxylic acid derivatives of general formula (Q-III) to form compounds of general formula (Q), wherein A=CH or $C(CH_3)$ (amides), as in scheme 1 (step j09).

1.1 Method A:

The acid of general formula (Q-III) (1 equivalent), the amine of general formula (Q-II) (1.2 equivalents) and EDCl (1.2 equivalents) are stirred in DMF (10 mmol of acid/20 mL) for 12 hours at RT and water is subsequently added thereto. The reaction mixture is repeatedly extracted with EtOAc, the aqueous phase is saturated with NaCl and subsequently reextracted with EtOAc. The combined organic phases are washed with 1 N HCl and brine, dried over magnesium sulfate and the solvent is removed under vacuum. The residue is purified by flash chromatography ($SiO_2$, EtOAc/hexane in different ratios such as 1:2) and the product (Q) is in this way obtained.

1.2 Method B:

The acid of general formula (Q-III) (1 equivalent) and the amine of general formulae (Q-II) (1.1 equivalents) are dissolved in dichloromethane (1 mmol of acid in 6 mL) and mixed with EDCl (1.5 equivalents), HOBt (1.4 equivalents) and triethylamine (3 equivalents) at 0° C. The reaction mixture is stirred for 20 h at room temperature and the crude product is purified by column chromatography ($SiO_2$, n-hexane/EtOAc in different ratios such as 2:1) and (Q) is in this way obtained.

1.3 Method C:

The acid of general formula (Q-III) (1 equivalent) is first mixed with a chlorinating agent, preferably with thionyl chloride and the mixture obtained in this way is boiled under reflux and the acid (Q-III) is in this way converted into the corresponding acid chloride. The amine of general formulae (Q-II) (1.1 equivalents) is dissolved in dichloromethane (1 mmol of acid in 6 mL) and mixed with triethylamine (3 equivalents) at 0° C. The reaction mixture is stirred for 20 h at room temperature and the crude product is purified by column chromatography ($SiO_2$, n-hexane/EtOAc in different ratios such as 2:1) and (Q) is in this way obtained.

1.4 Method D:

The phenyl ester (Q-IIIa) (1 equivalent) and the corresponding amine (Q-II) (1.1 equivalents) are dissolved in THF (10 mmol of the reaction mixture in 120 mL) and stirred for 16 h at room temperature after addition of DBU (1.5 equivalents). After removal of the solvent under vacuum, the resulting residue is purified by flash chromatography ($SiO_2$, EtOAc/hexane in different ratios such as 1:1) and (Q) is in this way obtained.

The example compounds A1-A7, A9, A10, A29-A45, A47-A52, A98-A104, A111-A123, A136-A139 and A145-A148 were obtained using one of the methods described above. The example compounds A46, A124-126 and A149 can be prepared by using one of the methods described above.

Likewise, the example compounds B1-B10, B13, B15-B23, B26, B29-B30, B37, B42-B43, B47, B63-B68, B76, B82, B88, B93-B98 and B102-8103 were obtained using one of the methods described above. The example compounds B104 and B106-B107 can be prepared by using one of the methods described above.

In a similar manner the example compounds C1-C3 were obtained using one of the methods described above.

The example compounds D1-D10 were obtained using one of the methods described above, and the example compounds D11-D25 can be obtained using one of the methods described above.

The example compounds E1-E4, E10, E11, E16, E17, E19-E21 and E23-E53 also were obtained using one of the methods described above.

2. Preparation of Ureas (A=N)

General directions for reacting amines of general formula (Q-II) or (Q-V) with phenyl chloroformate to form compounds of formula (Q-IV) or (Q-Va) (scheme 1, step j07 and scheme 2, step v1) and subsequent reaction of compounds of formula (Q-IV) with amines of general formula (Q-V) (scheme 1, step j08) or of compounds of formula (Q-Va) with amines of general formula (Q-II) (scheme 2, step v2) to form compounds of general formula (Q), wherein A=N:

Step j07/step v1: The amine of general formula (Q-II) or (Q-V) (1 equivalent) is placed in dichloromethane (10 mmol of amine in 70 mL) and phenyl chloroformate (1.1 equivalents) is added thereto at room temperature and the mixture is stirred for 30 min. After removal of the solvent under vacuum, the residue is purified by flash chromatography ($SiO_2$, diethyl ether/hexane in different ratios such as 1:2) and (Q-IV) or (Q-Va) is in this way obtained.

Step j08/step v2: The carbamic acid phenyl ester (Q-IV) or (Q-Va) obtained (1 equivalent) and the corresponding amine (Q-V) or (Q-II) (1.1 equivalents) are dissolved in THF (10 mmol of the reaction mixture in 120 mL) and stirred for 16 h at room temperature after addition of DBU (1.5 equivalents). After removal of the solvent under vacuum, the resulting residue is purified by flash chromatography ($SiO_2$, EtOAc/hexane in different ratios such as 1:1) and (Q) is obtained in this way.

The example compounds A8, A11-A25, A27-A28, A53-A97, A105-A110, A127-A134, A140-A141 and A150-A159 were obtained using one of the methods described above. The example compounds A26, A135 and A142-A144 can be prepared by using one of the methods described above.

Likewise, the example compounds B11-B12, B15, B24-B25, B27-B28, B31-B36, B38-B41, B44-B46, B48-B62, B69-B75, B77-B81, B83-B87, B89-B92 and B99-B101 were obtained using one of the methods described herein-before. The example compound B105 can be prepared by using one of the methods described above.

In a similar manner the example compounds C4-C13 were obtained using one of the methods described above.

The example compounds D26-D29, D31 and D33 were obtained using one of the methods described above, and the example compounds D30 and D32 can be prepared by using one of the methods described above.

The example compounds E5-E9, E12-E15, E18, E22 and E54-E62 also were obtained using one of the methods described above.

DETAILED SYNTHESIS OF SELECTED EXAMPLE COMPOUNDS

Synthesis of Example A17

1-[[5-tert-Butyl-2-(3-chlorophenyl)-2H-pyrazol-3-yl]-methyl]-3-[3-fluoro-4-(2-methoxy-ethoxy)-phenyl]-urea

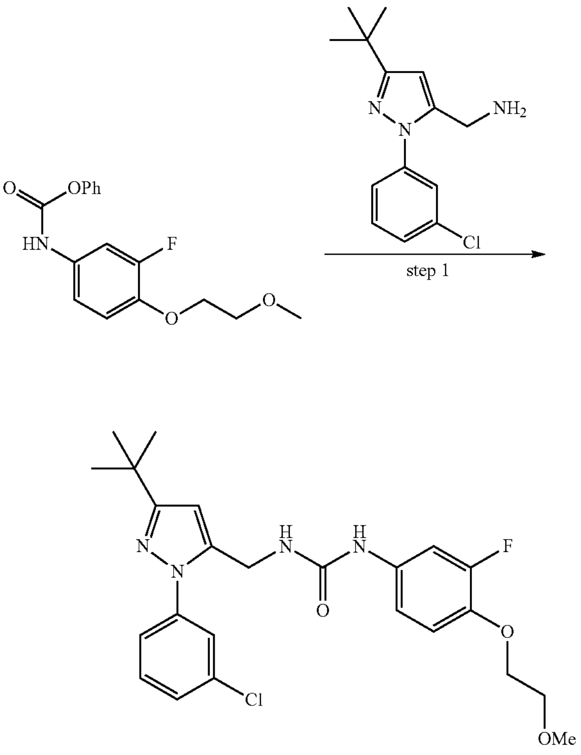

Step 1: To a stirred solution of (3-tert-butyl-1-(3-chlorophenyl)-1H-pyrazol-5-yl)methanamine (synthesis described for example A18) (81 mg, 0.31 mmol, 1.0 eq.) in MeCN (7 mL) was added TEA (0.17 mL, 1.2 mmol, 4.0 eq.) followed by phenyl 3-fluoro-4-(2-methoxyethoxyl)phenylcarbamate (95 mg, 0.31 mmol, 1.0 eq.) at RT and stirred at reflux for 16 h. The solvent was evaporated under vacuum. The crude product obtained was purified by column chromatography (eluent EtOAc/n-hexane 1:1) to yield example A17 (121 mg; 83%).

Synthesis of Example A18

1-[[2-(3-Chlorophenyl)-5-(trifluoromethyl)-2H-pyrazol-3-yl]-methyl]-3-[3-fluoro-4-(2-methoxy-ethoxy)-phenyl]-urea

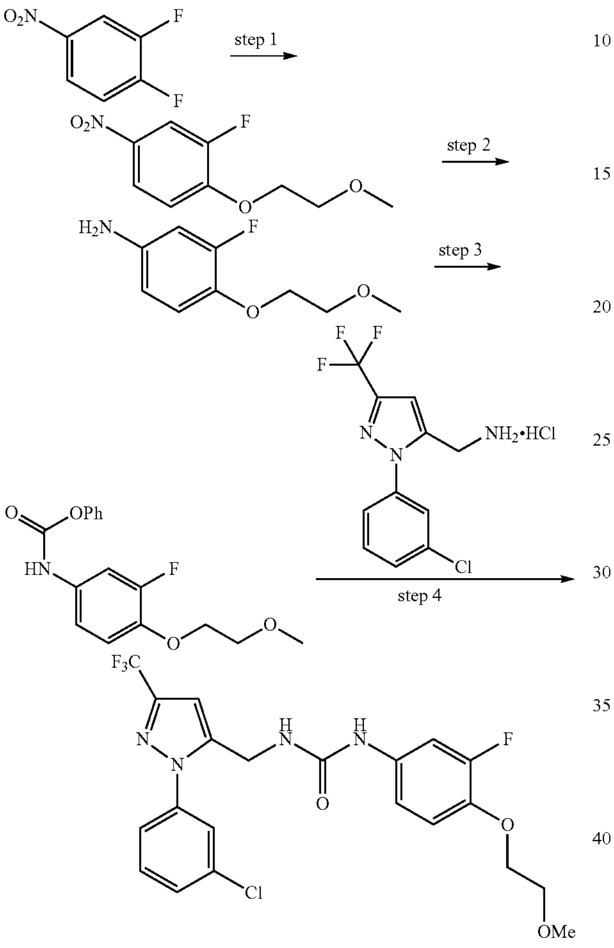

Step 1: To a stirred suspension of methyl glycol (2.2 mL, 28.28 mmol, 1.5 eq.) and $K_2CO_3$ (7.8 g, 56.60 mmol, 3.0 eq.) in DMF (20 mL) was added 1,2-difluoro-4-nitrobenzene (3.0 g, 18.85 mmol, 1.0 eq.) and the mixture was stirred for 16 h at 70° C. The reaction mixture was cooled and diluted with water (30 mL) and extracted with ethyl acetate (40 mL). The organic layer was separated and washed with water (50 mL), brine (50 mL), and dried over sodium sulfate and the solvent evaporated under vacuum. The crude product was washed with n-pentane (30 mL) to obtain 2-fluoro-1-(2-methoxyethoxy)-4-nitrobenzene (3 g, 74%, as solid; TLC system: EtOAc/PE (1:9), $R_f$: 0.2).

Step 2: To a stirred solution of 2-fluoro-1-(2-methoxyethoxy)-4-nitrobenzene (2.5 g, 11.62 mmol, 1.0 eq.) in ethanol (20 mL) was added 10% Pd/C (500 mg) and stirred in hydrogen gas atmosphere for 16 h at RT. The catalyst was filtered over a celite pad and the filtrate was concentrated to get 3-fluoro-4-(2-methoxyethoxy)aniline (2.0 g, 93.9%; TLC system: EtOAc/PE (3:7), $R_f$: 0.3).

Step 3: To a stirred solution of 3-fluoro-4-(2-methoxyethoxy)aniline (2.0 g, 10.8 mmol, 1.0 eq) in acetone (50 mL) was added pyridine (2.5 mL, 32.4 mol, 3.0 eq.) and phenyl chloroformate (1.36 mL, 10.8 mmol, 1.0 eq.) at 0° C. and stirred at RT for 1 h. The solvent was evaporated, the residue diluted with EtOAc (50 mL), washed with water (100 mL), brine (20 mL) and evaporated again. The resulting residue was purified by column chromatography using EtOAc/PE (1:4) as eluent to yield phenyl 3-fluoro-4-(2-methoxyethoxyl)phenylcarbamate (2.7 g, 76.8%) as a white solid (TLC system: EtOAc/PE (3:7), $R_f$: 0.5).

Step 4: To a stirred solution of (1-(3-chlorophenyl)-3-(trifluoromethyl)-1H-pyrazol-5-yl)methanamine hydrochloride (102 mg, 0.327 mmol, 1.0 eq.) in DCM (5.0 mL) was added TEA (1.36 mL, 0.981 mmol, 3.0 eq) followed by phenyl 3-fluoro-4-(2-methoxyethoxyl)phenylcarbamate (100 mg, 0.327 mmol, 1.0 eq.) at RT and stirred for 16 h. The reaction mixture was diluted with water (10 mL) and extracted with ethyl acetate (15 mL). The organic layer was washed with water (10 mL) and brine (5 mL), dried over anhydrous $Na_2SO_4$, and the solvent evaporated under vacuum. The crude product obtained was purified by neutral alumina column chromatography using MeOH/$CHCl_3$ (1:9) as eluent to yield 1-((1-(3-chlorophenyl)-3-(trifluoromethyl)-1H-pyrazol-5-yl)methyl)-3-(3-fluoro-4-(2-methoxyethoxy)-phenyl)urea (example A18) (85 mg, 53%) as a white solid (TLC system: MeOH/$CHC_3$ (1:9), $R_f$: 0.5).

Synthesis of Example A25

1-[[2-(3-Chlorophenyl)-5-(trifluoromethyl)-2H-pyrazol-3-yl]-methyl]-3-[4-(2,3-dihydroxy-propoxy)-3-fluoro-phenyl]-urea

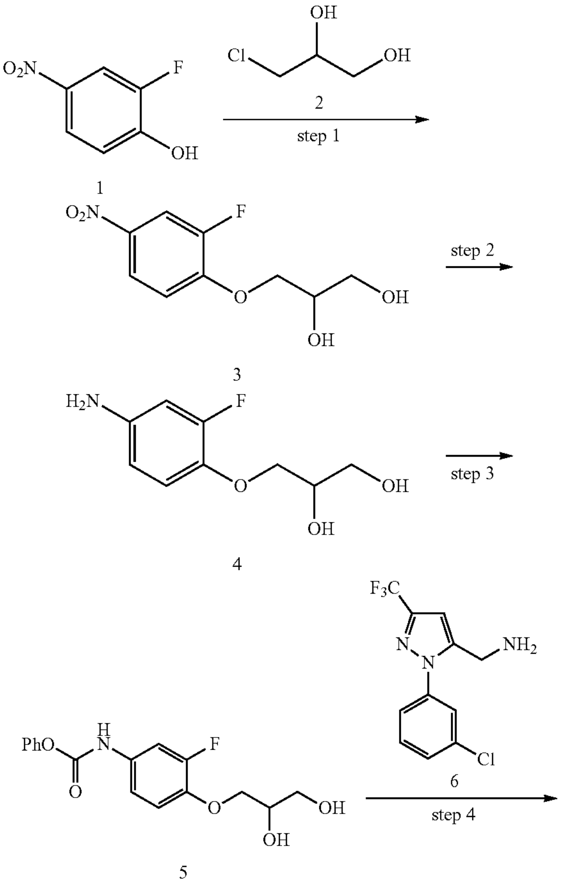

-continued

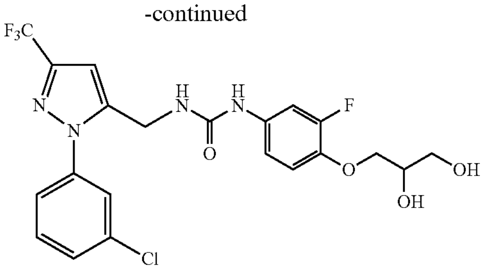

7

Step 1: To a stirred solution of 1 (300 mg, 1.91 mmol) in anhydrous DMF was added sodium hydride (99 mg, 2.48 mmol) and 3-chloro-1,2-propanediol 2 (0.21 mL, 2.48 mmol). The reaction mixture was stirred overnight under reflux. The reaction mixture was cooled to room temperature when the reaction was finished. The reaction mixture was extracted with EtOAc and washed with water and brine. The organic layer was dried over $MgSO_4$ and filtered. The solvent of the filtrate was removed under low pressure. The crude product was purified by column chromatography to produce 3 (234 mg, 53%).

Step 2: Starting material 3 (234 mg, 1.01 mmol) was dissolved in MeOH. Pd/C (23 mg) was added to it. The resulting mixture was stirred at room temperature for 2 h under $H_2$. TLC showed complete consumption of starting material. The mixture was filtered through celite bed and the filtrate was concentrated under reduced pressure to afford desired compound 4. (202 mg, 99%)

Step 3: Compound 4 (202 mg, 1.00 mmol) was dissolved in MeCN. To the reaction mixture were added to pyridine (0.09 mL, 1.10 mmol) and phenyl chloroformate (0.14 mL, 1.10 mmol) and stirred at room temperature for 3 h. TLC showed complete consumption of starting material. The reaction mixture was diluted with water and extracted with EtOAc. The organic part was washed with water and brine. The organic layer was dried over $MgSO_4$ and concentrated under reduced pressure. The crude product was purified by column chromatography to give pure compound 5. (81 mg, 25%)

Step 4: To a solution of compound 5 (40 mg, 0.12 mmol) in DMF was added DMAP (15 mg, 0.12 mmol) and amine 6 (38 mg, 0.14 mmol) at room temperature. The reaction mixture was heated to 50° C. overnight (about 12-15 h). TLC showed complete consumption of starting material. The reaction mixture was diluted with water and extracted with EtOAc. The organic part was washed with water and brine. The organic layer was dried over $MgSO_4$ and concentrated under reduced pressure. The crude product was purified by column chromatography to produce pure compound 7 (57 mg, 90%).

$^1H$ NMR (300 MHz, DMSO-$d_6$) δ 8.70 (s, 1H, Ar—NH), 7.74 (s, 1H, Ar—H), 7.61 (m, 3H, Ar—H), 7.40 (dd, 1H, $J_1$=13.92 Hz, $J_2$=2.19 Hz, Ar—H), 7.05 (t, 1H, J=9.15 Hz, Ar—H), 6.98 (m, 1H, Ar—H), 6.81 (s, 1H, Ar—H), 6.72 (t, 1H, J=5.49 Hz, Ar—H), 5.10 (m, 1H, R—CH(OH)—R'), 4.60 (t, 1H, J=8.61 Hz, R—CH—O), 4.38 (m, 3H, ArO—$CH_2$ and R—CH(OH)—R'), 4.28~4.16 (m, 2H, Ar—$CH_2$)

Synthesis of Example A30

N-[[2-(3-Chlorophenyl)-5-(trifluoromethyl)-2H-pyrazol-3-yl]-methyl]-2-[3-fluoro-4-(hydroxymethyl)-phenyl]-acetamide

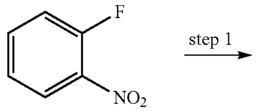

1

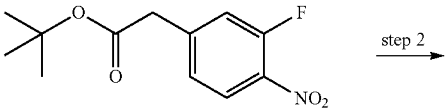

2

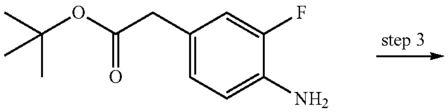

3

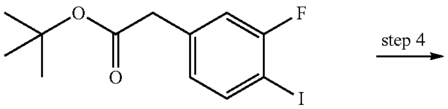

4

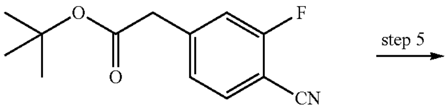

5

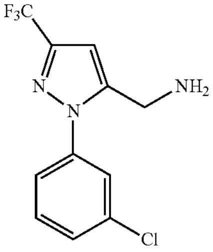

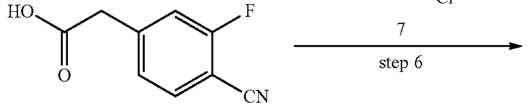

6

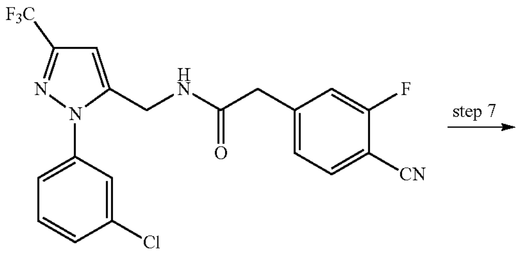

8

-continued

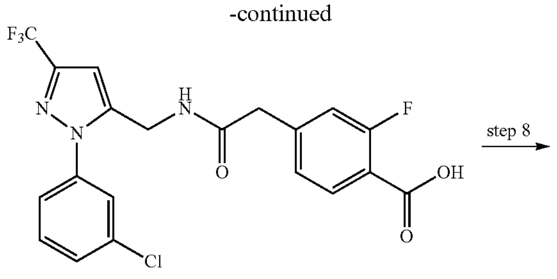

9

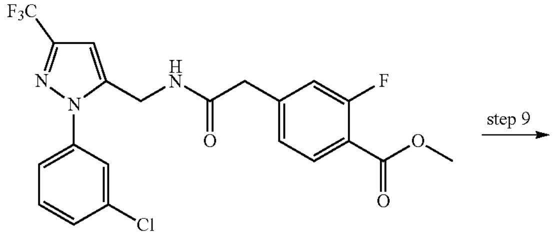

10

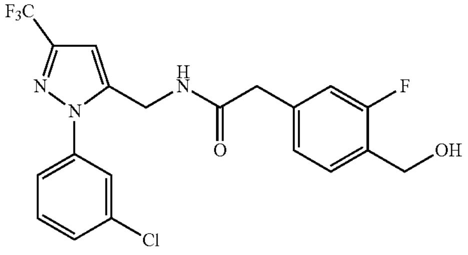

11

Step 1: A mixture of potassium tert-butoxide (5.58 g) in NMP (40 mL) was cooled under nitrogen to −20° C. A mixture of 2-fluoronitrobenzene (2 g) and tert-butylchloroacetate (3 mL) in NMP (40 mL) was added slowly at −10° C. to −20° C. After 30 minutes, a further portion of potassium tert-butoxide (1.59 g) was added. The reaction mass was quenched into 30 mL of 2M HCl and 20 g crushed ice, then 40 mL n-hexane was added and the mixture stirred for 10 minutes. The layers were separated and the aqueous layer was extracted with n-hexane (2×30 mL). The combined n-hexane layer were washed with brine (2×20 mL), then dried over anhydrous sodium sulfate, then filtered and washed with 20 mL hexane. The solvent was then evaporated and purified by CC to give the desired compound 2 (2.17 g) as a yellow liquid by 60% yield.

Step 2: 10% Pd/C was added to a solution of 2 (2.17 g) in methanol and the mixture was charged with $H_2$ (gas). After stirring the reaction mixture for 2 h, the mixture was filtered using Celite and purified by column chromatography. 3 (959 mg) was obtained as yellow oil by 44% yield.

Step 3: To a solution of p-TsOH.$H_2O$ (2.15 g, 11.28 mmol) in MeCN (20 mL) was added 3 (959 mg, 3.76 mmol). The resulting suspension was cooled to 10-15° C. and to this was added, gradually, a solution of $NaNO_2$ (519 mg, 7.52 mmol) and KI (1.56 g, 9.4 mmol) in $H_2O$. The reaction mixture was stirred for 10 min then allowed to come to 20° C. and stirred until the starting material was consumed. To the reaction mixture was then added $H_2O$ (50 mL), $NaHCO_3$ (1 M; until pH=9-10) and $Na_2S_2O_3$ (2M, 10 mL). The precipitated aromatic iodide was filtered out and the mixture was extracted with EtOAc and purified by column chromatography. 4 (474 mg) was obtained as yellow oil by 38% yield.

Step 4: Compound 4 (474 mg), $Pd_2(dba)_3$ (2 mol %), dppf (4 mol %), Zn powder (12 mol %) and $Zn(CN)_2$ (1.5 equiv.) were placed in a flask which was flushed with $N_2$. DMA (0.02 equiv.) was added via syringe. The resulting mixture was heated at 120° C. under $N_2$ with vigorous agitation until TLC showed the disappearance of 4 (15 h). The mixture was cooled to room temperature, diluted with ethyl acetate (50 mL), and then washed with 2 N $NH_4OH$ solution and brine. After drying over $Na_2SO_4$, the ethyl acetate solution was concentrated by rotary evaporation. The residue was purified by CC using a mixed solvent of ethyl acetate and n-hexane to afford 5 (260 mg) as off white solid (78% yield).

Step 5: Compound 5 (260 mg) and 4M HCl in 1,4-dioxane (7 mL) was stirred for 18 h at about 25° C. Nitrogen was bubbled through the mixture to remove excess HCl over 7 h, then the mixture was concentrated. Toluene (2 mL) was distilled off then the residue was stirred with hexane (2 mL) for 10 minutes. The hexane was decanted off, and the residue was stirred with hexane (1 mL) for 10 minutes. Then the hexane was decanted off. The residue was stirred with toluene (1.5 mL) for 2 h at about 25° C. The solid was filtered and washed with 1:1 toluene/hexane (10 mL), then dried under vacuum to give the desired compound 6 (160 mg) as light brown solid by 80% yield.

Step 6: A solution of the carboxylic acid 6 (1.0 eq.) in DCM was cooled in an ice-bath and EDC (1.05 eq.), HOBt (1.05 eq.), TEA (3 equiv), and 7 (1.0 eq.) were added consecutively. The reaction mixture was stirred overnight at room temperature. Water was added to the reaction mixture and it was extracted with DCM. The combined organic extracts were washed successively with a saturated $NaHCO_3$ solution, 0.5 N HCl, and then water, and dried over $MgSO_4$. Evaporation of the solvent followed by CC using (EtOAc/n-hexane) afforded the 8 (230 mg) as off white solid (62% yield).

Step 7: Compound 8 (1.206 g) was suspended in 1:1 EtOH/4N NaOH (20 mL) and heated to 80° C. for 4 h. Upon completion, the reaction was concentrated to remove EtOH and then was placed in an ice bath and neutralized to pH=7 by the addition of conc. HCl. The reaction volume was doubled by the addition of water, and allowed to cool in the ice bath before acidification by 1N HCl to pH=4-5, extracted with EtOAc. The extracted organic layer was dried over $Na_2SO_4$ and removed EtOAc by evaporation. The desired amide 9 was obtained as brown oil and was carried on the next step without further purification.

Step 8: To a stirred solution of 9 (1 equiv) in methanol, under ice-cooling, was added thionyl chloride (2.5 equiv) dropwise over 15 minutes. After stirring the reaction mixture for 15 minutes at 0° C., removed ice-bath and continue reaction at 40° C. for 4 h, methanol is distilled out and water is added. The mixture is extracted with ethyl acetate and washed with saturated sodium bicarbonate solution, and brine. Drying ($MgSO_4$) and evaporation of the ethyl acetate and purification by column chromatography (EtOAc/n-hexane) gave the ester 10 (76 mg) in pure form as a brown solid (30% yield.

Step 9: A solution of compound 10 (76 mg, 0.16 mmol, 1 equiv) in anhydrous THF was drop-wise added to lithium aluminum hydride (1.5 equiv) in anhydrous THF at 0° C. The reaction mixture was stirred at 0° C. for 2 h. After that, brine was added slowly at 0° C., then THF was removed by evaporation and the mixture extracted with ethyl acetate and water. The extracted organic layer was dried over $Na_2SO_4$ and ethyl acetate was removed by evaporation. The residue was purified by CC (EtOAc/n-hexane) and product 11 (43 mg) was obtained as a white solid by 60% yield.

$^1$H NMR (300 MHz, $CD_3OD$): δ7.58 (s, 1H), 7.49-7.52 (m, 2H), 7.42-7.46 (m, 1H), 7.36-7.38 (m, 1H), 6.94-7.01 (m, 2H), 6.66 (s, 1H), 4.63 (s, 2H), 4.45 (d, J=2.19 Hz, 2H), 3.46 (d, J=2.19 Hz, 2H).

Synthesis of Example A33

N-[[2-(3-Chlorophenyl)-5-(trifluoromethyl)-2H-pyrazol-3-yl]-methyl]-2-[3-fluoro-4-(hydroxymethyl)-phenyl]-propionamide

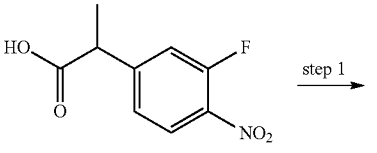

1

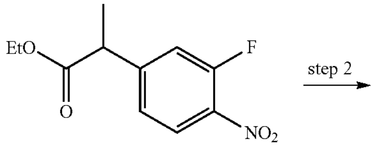

2

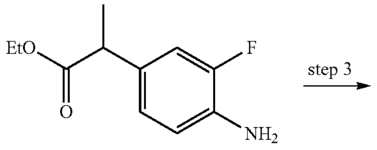

3

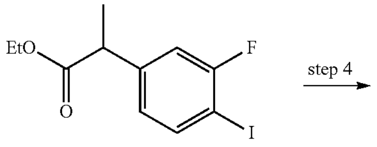

4

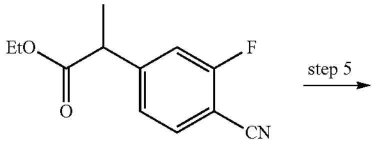

5

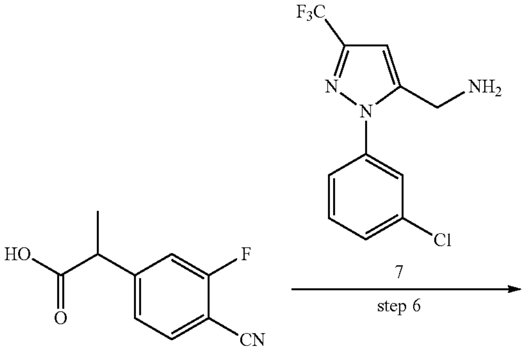

7

6

-continued

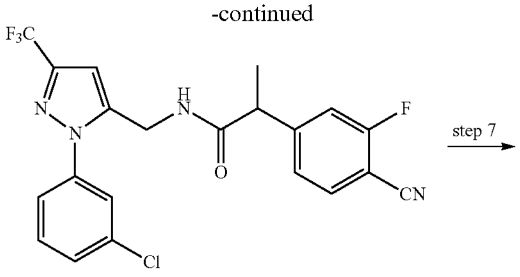

8

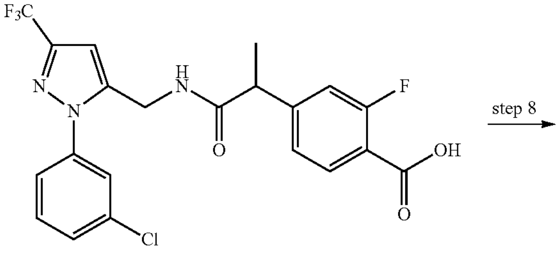

9

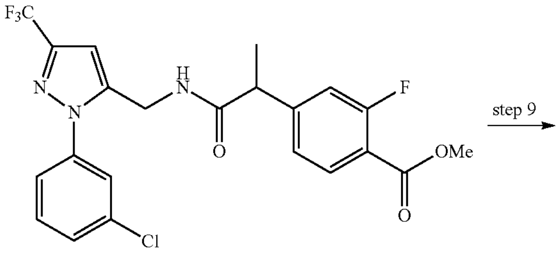

10

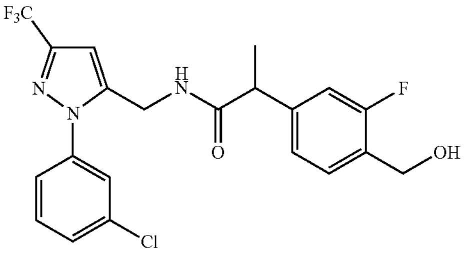

11

Step 1: To a stirred solution of 1 (6 g, 28.15 mmol) in 60 mL of methanol, under ice-cooling, was added thionyl chloride (5.12 mL, 70.37 mmol) dropwise over 15 minutes. After stirring the reaction mixture for 2 h, methanol was distilled and 60 mL of water was added. The residue was extracted with ethyl acetate and washed with 50 mL of saturated sodium bicarbonate solution, brine. After drying (over $MgSO_4$) and evaporation of the ethyl acetate and purification of the residue by CC, 2 was obtained as a yellow oil in 98% yield.

Step 2: 10% Pd/C was added to a solution of 2 in methanol and the mixture was charged with $H_2$ (gas). After stirring the reaction mixture for 6 h, the mixture was filtered using Celite and the residue was purified by CC to obtain 3 obtained as a yellow oil by 90% yield.

Step 3: To a solution of p-TsOH.$H_2O$ (6.45 g, 34 mmol) in Me CN (20 mL) was added 3 (11.3 mmol). The resulting suspension was cooled to 10-15° C. and to this was added, gradually, a solution of $NaNO_2$ (1.56 g, 22.6 mmol) and KI (4.69 g, 28.3 mmol) in $H_2O$. The reaction mixture was stirred for 10 min then allowed to come to 20° C. and stirred until the starting material was consumed. To the reaction mixture was then added $H_2O$ (50 mL), $NaHCO_3$ (1 M; until pH=9-10) and $Na_2S_2O_3$ (2M, 10 mL). The precipitated solid was extracted with EtOAc. The organic layer was washed with water, dried ($MgSO_4$) and concentrated in vacuo. The residue was purified by CC using EtOAc/n-hexane as solvent system to give the desired product 4 as a yellow oil (2.19 g, 63% yield).

Step 4: Compound 4, $Pd_2(dba)_3$ (2 mol %), dppf (4 mol %), Zn powder (12 mol %) and $Zn(CN)_2$ (1.5 equiv.) were placed in a flask which was flushed with $N_2$. DMA (0.02 equiv.) was added via syringe. The resulting mixture was heated at 120° C. under $N_2$ with vigorous agitation until TLC showed the disappearance of 4 (15 h). The mixture was cooled to room temperature, diluted with ethyl acetate (50 mL), and then washed with 2 N $NH_4OH$ solution and brine. After drying over $Na_2SO_4$, the ethyl acetate solution was concentrated by rotary evaporation. The residue was purified by CC using a mixed solvent of ethyl acetate and n-hexane to afford methyl 2-(4-cyano-3-fluorophenyl)propanoate 5 as yellow oil (80% yield).

Step 5: To a solution of 5 (2.15 g, 10.4 mmol) in THF (10 mL) was added a 20 mL mixture solvents of THF and $H_2O$ (1:1), and $LiOH.H_2O$ (1.09 g, 26 mmol). The reaction mixture was stirred at room temperature for 2 h. To the reaction mixture was then added $H_2O$ (50 mL), it was cooled, and acidified by diluted HCl until a pH of 1-2. The mixture is extracted with ethyl acetate. The organic layer was washed with water, dried ($Mg_2SO_4$) and concentrated in vacuo to gain product 6 as off white solid (1.98 g, 99% yield). The product was carried on to the next step without further purification Step 6: A solution of the carboxylic acid 6 (1.0 eq.) in DCM was cooled in an ice-bath and EDC (1.05 eq.), HOBt (1.05 eq.), TEA (3 eq.), and 7 (1.0 eq.) were added consecutively. The reaction mixture was stirred overnight at room temperature. Water was added to the reaction mixture and it was extracted with DCM. The combined organic extracts were washed successively with a saturated $NaHCO_3$ solution, 0.5 N HCl, and then water, and dried over $MgSO_4$. Evaporation of the solvent followed by CC (EtOAc/n-hexane) afforded the desired amide 8 as off white solid (60% yield).

Step 7: Compound 8 (1.206 g) was suspended in 1:1 EtOH/4N NaOH (20 mL) and the mixture was heated to 80° C. for 4 h. Upon completion, the mixture was concentrated to remove EtOH and then was placed in an ice bath and neutralized to pH=7 by the addition of conc. HCl. The reaction volume was doubled by the addition of water, and allowed to cool in the ice bath before acidification by 1N HCl to pH=4-5, then the mixture was extracted with EtOAc. The extracted organic layer was dried over $Na_2SO_4$ and EtOAc was removed by evaporation. The residue was purified by CC (MeOH/DCM=1:10) and the desired product 9 was obtained as an off white solid (1.067 g, 85% yield).

Step 8: To a stirred solution of 9 (1 equiv.) in methanol, under ice-cooling, was added thionyl chloride (2.5 equiv) dropwise over 15 minutes. After stirring the reaction mixture for 15 minutes at 00° C., the ice-bath was removed and stirring was continued at 40° C. for 4 h, then methanol is distilled and water is added. The mixture is extracted with ethyl acetate and washed with saturated sodium bicarbonate solution, and brine. Drying (over $MgSO_4$) and evaporation of the ethyl acetate and purification by CC (EtOAc/n-hexane) gave the ester 10 in pure form as a white solid (58% yield).

Step 9: A solution of compound 10 (1 equiv) in anhydrous THF was drop-wise added to lithium aluminum hydride (1.5 equiv) in anhydrous THF at 0° C. The reaction mixture was stirred at 0° C. for 2 h. After that, brine was added slowly at 0° C., then the THF was removed by evaporation and the residue extracted with ethyl acetate and water. The extracted organic layer was dried over $Na_2SO_4$ and ethyl acetate was removed by evaporation. The residue was purified by CC (EtOAc/n-hexane) and the desired product 11 was obtained as a white solid (85% yield).

$^1H$ NMR (300 MHz, $CDCl_3$): δ 7.39-7.45 (m, 4H), 7.29 (t, J=2.01 Hz, 1H), 6.92-7.02 (m, 2H), 6.42 (s, 1H), 5.58 (s, NH), 4.76 (d, J=5, 85 Hz, 2H), 4.39-4.53 (m, 2H), 3.52 (q, J=6.96 Hz, 1H), 1.84 (t, J=6.04 Hz, OH), 1.49 (d, J=7.14 Hz, 3H).

Synthesis of Example A46

2-(3-fluoro-4-(hydroxymethyl)phenyl)-N-((1-(4-fluorophenyl)-3-(trifluoromethyl)-1H-pyrazol-5-yl)methyl)propanamide

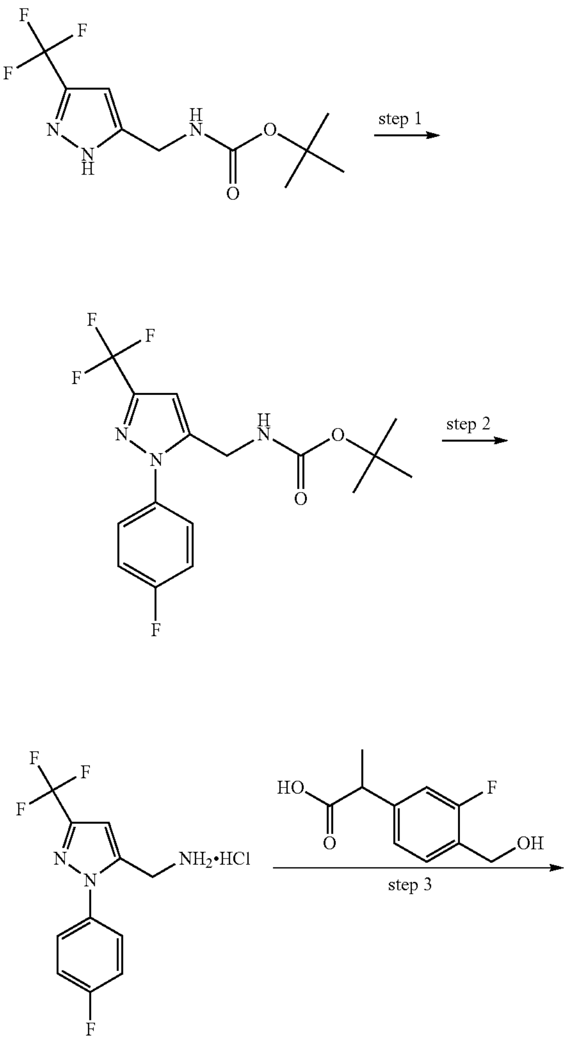

-continued

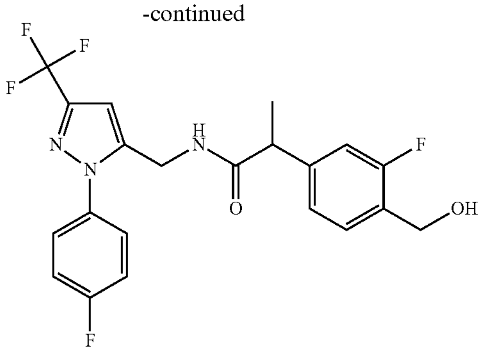

Step 1: To a mixture of tert-butyl (3-(trifluoromethyl)-1H-pyrazol-5-yl)methylcarbamate (501 mg, 1.89 mmol, 1 equiv.), 4-fluorophenylboronic acid (529 mg, 3.78 mmol, 2 equiv.) and copper acetate (517 mg, 2.83 mmol, 1.5 equiv.) in dichloromethane (28 mL) was added pyridine (301 mg, 0.301 mL, 3.78 mmol, 2 equiv) and the mixture was stirred in the presence of air for 2 d at room temperature. The reaction mixture was filtered over silica gel, the filter cake was washed with 250 mL of dichloromethane and the solvent of the filtrate was evaporated to give tert-butyl (1-(4-fluorophenyl)-3-(trifluoromethyl)-1H-pyrazol-5-yl) methylcarbamate (501 mg, 74%).

Step 2: In 9 mL of dioxane, tert-butyl (1-(4-fluorophenyl)-3-(trifluoromethyl)-1H-pyrazol-5-yl)methylcarbamate (501 mg, 1.39 mmol) was dissolved and hydrogen chloride in dioxane (2.27 mL, c=4 mol/L, 9.06 mml, 6.5 equiv.) was added. The reaction mixture was stirred overnight and filtered, the filter cake was washed with ether (2×15 mL) and dried to give (1-(4-fluorophenyl)-3-(trifluoromethyl)-1H-pyrazol-5-yl)methanamine hydrochloride (188 mg, 46%).

Step 3: To a stirred solution of (1-(4-fluorophenyl)-3-(trifluoromethyl)-1H-pyrazol-5-yl)methanamine hydrochloride (101 mg, 0.342 mmol, 1.0 eq) in THF/DMF (1/20, v/v, 2.8 mL) was added 2-(3-fluoro-4-hydroxymethyl)phenyl) propionic acid (68 mg, 0.348 mmol, 1.02 equiv.), HOBt (46 mg. 0.342 mmol, 1 equiv.), TBTU (151 mg, 0.342 mmo, 1 equiv.) and DIPEA (0.232 mL, 176 mg, 1.37 mmol, 4 equiv.) and the mixture was stirred for 3 d at room temperature The reaction mixture was diluted with 20 mL of EtOAc and washed with 20 mL of water. The aqueous phase was extracted with EtOAc (3×20 mL), the combined organic phases were dried over magnesium sulfate, evaporated and the residue was purified by column chromatography (EtOAc/cyclohexane (1:1) as eluent) to give 2-(3-fluoro-4-(hydroxymethyl)phenyl)-N-((1-(4-fluorophenyl)-3-(trifluoromethyl)-1H-pyrazol-5-yl)methyl)propanamide (119 mg, 79%).

Synthesis of Example A50

N-[[2-(3-Chlorophenyl)-5-(trifluoromethyl)-2H-pyrazol-3-yl]-methyl]-2-[4-(hydroxymethyl)-3-methoxy-phenyl]-propionamide

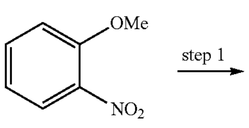

1

-continued

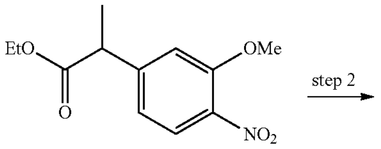

2

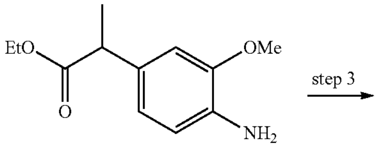

3

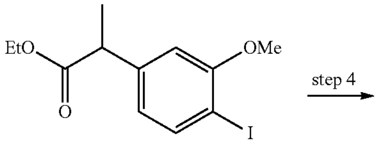

4

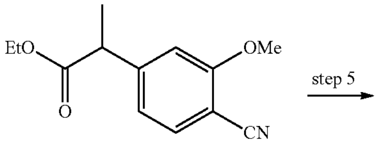

5

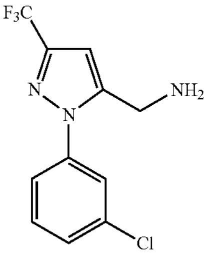

7

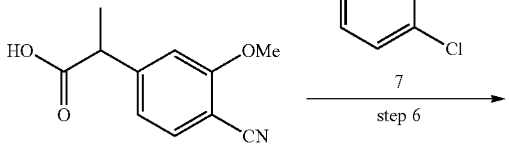

6

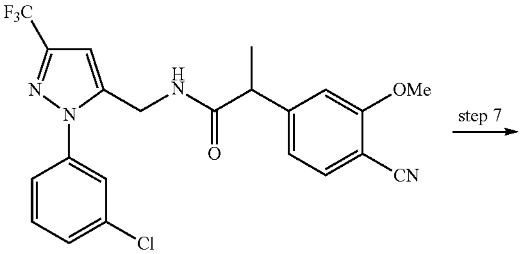

8

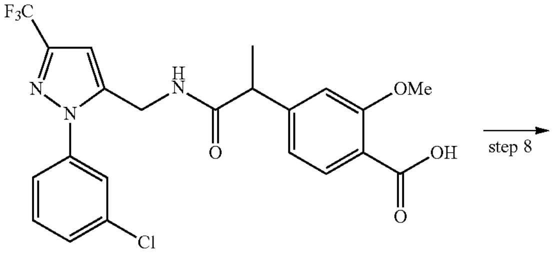

9

-continued

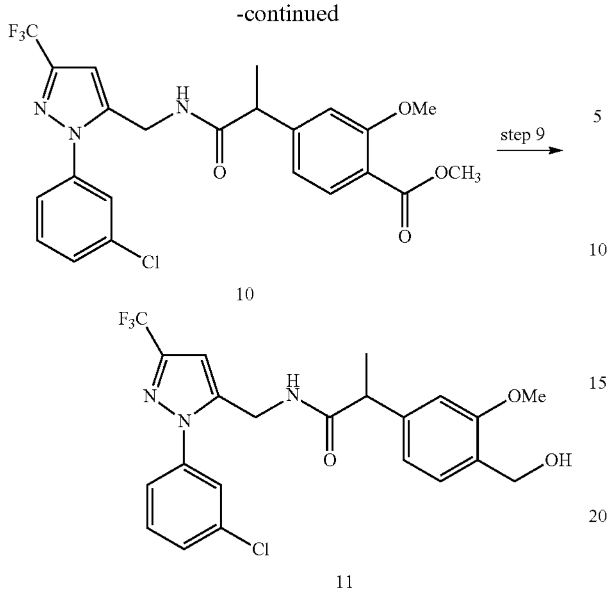

10

11

Step 1: To a stirred solution of 1 (3 g, 19.590 mmol) in DMF were added potassium tert-butoxide (8.792 g, 78.36 mmol) and ethyl 2-chloropropionate (2.5 mL, 19.59 mmol) while maintaining the temperature below −30° C. The reaction mixture was stirred for 5 min at −30° C., then ethyl 2-chloropropionate (0.25 mL, 1.959 mmol) was added to mixture. The reaction mixture was stirred for 10 min at room temperature. The residue was dissolved in EtOAc and washed with water and brine. The organic layer was dried ($MgSO_4$) and filtered. The filtrate removed in vacuo. The crude product was purified by column chromatography. 2 (683 mg) was obtained as 14% yield.

Step 2: To a stirred solution of 2 (683 mg, 2.697 mmol) in tetrahydrofuran and ethanol as co-solvent was added 10% palladium on carbon (70 mg). The mixture was charged with $H_2$ (gas) balloon. The resulting mixture was stirred for 15 h, then filtered using celite. The filtrate removed in vacuo. The crude product was purified by column chromatography. 3 (447 mg) was obtained as 74% yield.

Step 3: To a stirred solution of 3 (447 mg, 2.002 mmol) in MeCN and water were added p-TsOH.$H_2O$ (1.142 g, 6.006 mmol), sodium nitrite (276 mg, 4.004 mmol) and potassium iodide (831 mg, 5.005 mmol). The reaction mixture was stirred for 4 h at room temperature. The mixture dissolved in EtOAc and washed with water and brine. The organic layer was dried ($MgSO_4$) and filtered. The filtrate removed in vacuo. The crude product was purified by column chromatography. 4 (468 mg) was obtained as 70% yield.

Step 4: To a stirred solution of 4 (626 mg, 1.873 mmol) in DMF were added zinc cyanide (227 mg, 1.929 mmol) and $Pd(PPh_3)_4$ (216 mg, 0.1873 mmol). The reaction mixture was stirred for 36 hat 120° C., then cooled to room temperature, diluted with EtOAc. The mixture was filtered using celite pad. The filtrate was dissolved in EtOAc and extracted with $NaHCO_3$. The organic layer was dried ($MgSO_4$) and filtered. The filtrate removed in vacuo. The crude product was purified by column chromatography. 5 (222 mg) was obtained as 51% yield Step 5: To a stirred solution of 5 (222 mg, 0.952 mmol) in co-solvent with THF and water (1:1) were added sodium hydroxide (95 mg, 2.38 mmol). The reaction mixture was stirred for 15 hours at room temperature, then acidified to a pH of 3~4 with AcOH. The residue was dissolved in EtOAc and washed with water and brine. The organic layer was dried ($MgSO_4$) and filtered. The filtrate removed in vacuo. The crude product was purified by column chromatography. 6 (188 mg) was obtained in 96% yield.

Step 6: To a stirred solution of 6 (108 mg, 0.526 mmol) and 7 (160 mg, 0.578 mmol) in acetonitrile were added EDC (151 mg, 0.789 mmol), HOBt (106 mg, 0.789 mmol) and triethylamine (0.18 mL, 1.315 mmol). The reaction mixture was stirred for 15 h at room temperature. The residue dissolved in EtOAc and washed with water and brine. The organic layer was dried ($MgSO_4$) and filtered. The filtrate removed in vacuo. The crude product was purified by column chromatography. 8 (194 mg) was obtained as 80% yield.

Step 7: To a stirred solution of 8 (194 mg, 0.419 mmol) in ethanol (5 mL) were added 4 N NaOH (5 ml). The reaction mixture was stirred for 6 h at 80° C. then cooled to room temperature. The mixture was acidified to a pH of 4~5 by 1 N HCl. The residue was dissolved in EtOAc and the solution washed with water and brine. The organic layer was dried ($MgSO_4$) and filtered. The filtrate removed in vacuo. The crude product was purified by column chromatography. 9 (218 mg) was obtained as 99% yield.

Step 8: To a stirred solution of 9 (218 mg, 0.452 mmol) in methanol were added thionyl chloride (0.08 mL, 1.131 mmol) while the temperature maintaining below 0° C. The reaction mixture was stirred for 24 hours at 35° C., then cooled to room temperature. The solvent was evaporated then the residue was dissolved in EtOAc. The solution was washed with water and brine. The organic layer was dried ($MgSO_4$) and filtered. The solvent of the filtrate was removed in vacuo. The crude product was purified by column chromatography. 10 (145 mg) was obtained as 65% yield.

Step 9: To a stirred solution of 10 (145 mg, 0.292 mmol) in tetrahydrofurane, cooled to 0° C., were added lithium aluminum hydride (17 mg, 0.438 mmol). The resulting reaction mixture was stirred for 2 h at 0° C. Water and 4 N NaOH were added to the mixture for quenching. The residue was dissolved in EtOAc then washed with water. The organic layer was dried ($MgSO_4$) and filtered. The solvent was removed in vacuo. The crude product was purified by column chromatography. 11 (111 mg) was obtained as 81% yield.

$^1H$ NMR (300 MHz, $CDCl_3$) δ 7.42 (m, 3H), 7.27 (m, 2H), 6.78 (dd, 1H, J=7.5 Hz), 6.74 (s, 1H), 6.40 (s, 1H), 5.57 (t, 1H), 4.67 (d, 2H, J=6.21 Hz), 4.44 (m, 2H), 3.87 (s, 3H), 3.53 (q, 1H), 2.24 (t, 1H), 1.50 (d, 3H).

Synthesis of Example A59

1-[[2-(3-Chlorophenyl)-5-(trifluoromethyl)-2H-pyrazol-3-yl]-methyl]-3-[3-fluoro-4-(hydroxymethyl)-phenyl]-urea

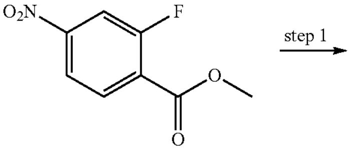

-continued

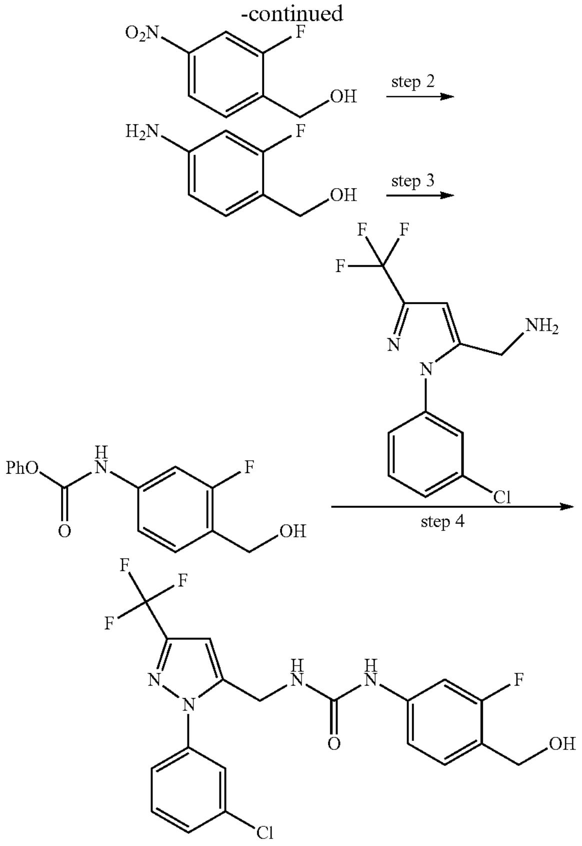

Step 1: To a stirred solution of methyl 2-fluoro-4-nitrobenzoate (10.0 g, 49.7 mmol, 1 eq.) in methanol (100 mL) was added sodium borohydride (9.40 g, 248.7 mmol, 5 eq.) at RT and stirred for 4 h. The methanol was evaporated and the residue was diluted with ethyl acetate (50 mL×2) washed with water (50 mL) and brine (50 mL). The ethyl acetate layer was dried over $Na_2SO_4$, evaporated under vacuum to get (2-fluoro-4-nitrophenyl)methanol (8 g, 94%, off-white solid; TLC system: EtOAc/PE (3:7), $R_f$: 0.30).

Step 2: To a stirred solution of (2-fluoro-4-nitrophenyl) methanol (3.0 g, 1.0 eq.) in EtOAc (30 mL) was added 10% Pd—C and the reaction mixture was stirred under $H_2$ gas balloon at RT for 6 h. The reaction mixture was passed through a celite pad and the solvent evaporated. The residue was purified by neutral alumina column using PE/EtOAc (3:2) as eluent to get (4-amino-2-fluorophenyl)methanol (1.1 g, 48%) as a solid; TLC system: EtOAc/PE (1:1), $R_f$: 0.3).

Step 3: To a stirred solution of (4-amino-2-fluorophenyl) methanol (100 mg, 0.709 mmol, 1 eq.) in acetone (1.0 mL) was added pyridine (0.17 mL, 2.12 mmol, 3 eq.) followed by phenyl chloroformate (0.092 mL, 0.709 mmol, 1 eq.) at 0° C. and stirred at RT for 1 h. The solvent was evaporated and the resulting residue was purified by CC using ethyl acetate/PE (7:13) as eluent to get phenyl 3-fluoro-4-(hydroxymethyl)phenylcarbamate (110 mg, 60%, off-white solid; TLC system: EtOAc/PE (1:1), $R_f$: 0.4).

Step 4: To a stirred solution of (1-(3-chlorophenyl)-3-(trifluoromethyl)-1H-pyrazol-5-yl)methanamine (100 mg, 0.316 mmol, 1.0 eq.) in DCM (2.0 mL) was added TEA (0.07 mL, 0.632 mmol, 3.0 eq) followed by phenyl 3-fluoro-4-(hydroxymethyl)phenylcarbamate (82.4 mg, 0.316 mmol, 1.0 eq.) at RT and stirred for 16 h. After completion of the reaction, a solid precipitate was filtered and washed with DCM (2 mL) followed by n-pentane (5 mL) and dried to get 1-((1-(3-chlorophenyl)-3-(trifluoromethyl)-1H-pyrazol-5-yl)methyl)-3-(3-fluoro-4-(hydroxymethyl)phenyl)urea (compound A59) (80 mg; 47%, white solid; TLC system: EtOAc/PE (3:2); $R_f$: 0.2).

Synthesis of Example A60

1-[[2-(4-Chlorophenyl)-5-(trifluoromethyl)-2H-pyrazol-3-yl]-methyl]-3-[3-fluoro-4-(hydroxymethyl)-phenyl]-urea

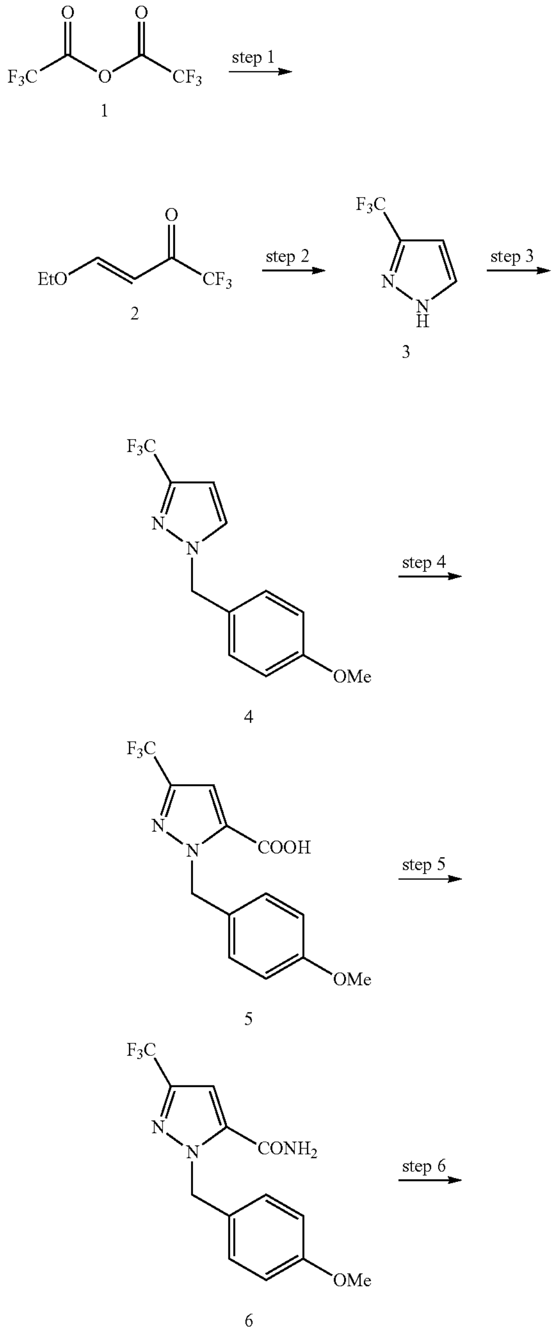

-continued

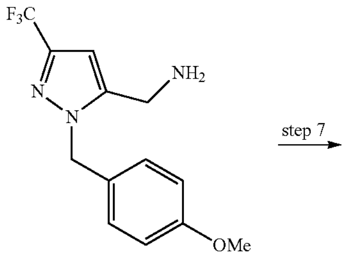

7

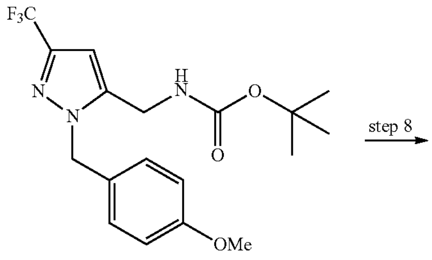

8

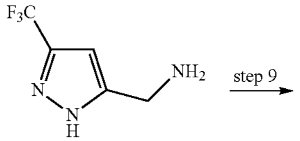

9

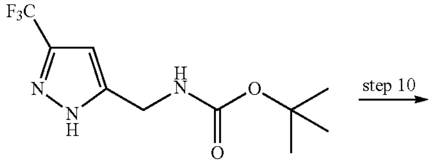

10

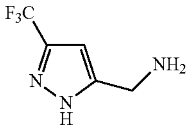

11

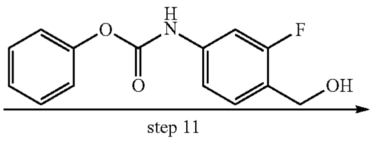

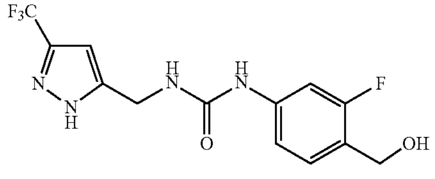

12

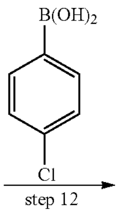

-continued

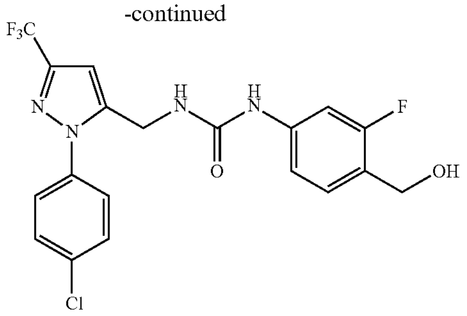

13

Step 1: DMAP (4.25 g, 34 mmol, 0.01 eq) was added to DCM (3 L) and the contents were cooled to −10° C. Trifluoroacetic (triflic) anhydride (765 g, 3.2 mol, 1.05 eq) was added followed by ethyl vinyl ether (250 g, 3.04 mol) drop wise for 45 min at −10° C. Then the overall reaction mixture was initially stirred for 8 h at 0° C. and later for overnight at room temperature. Progress of the reaction was monitored by TLC (10% ethyl acetate/hexane, $R_f$~0.7). On completion of the reaction, reaction contents were treated with saturated $NaHCO_3$ solution (600 mL) and the organic layer was separated. The aqueous layer was extracted with DCM (2×500 mL). The combined organic layer was washed with water (2×1 ltr), dried over sodium sulfate and concentrated under reduced pressure to give the crude product as a brown colored liquid (450 g, crude).

Step 2: Hydrazine dihydrochloride (225 g, 2.14 mol, 1.6 eq) in ethanol (1400 mL) was stirred well. TEA (135.4 g (185.4 mL), 1.34 mol, 1 eq) was added drop wise for 45 min at ambient temperature. Then 2 (225 g, crude) was added drop wise at room temperature and the overall reaction mixture was refluxed overnight. Progress of the reaction was monitored by TLC (20% ethyl acetate/hexane, $R_f$~0.4). On completion of the reaction, ethanol was distilled off completely, residue was taken in ice water (500 mL) and the product extracted with ethyl acetate (2×400 mL). The combined extract was washed with ice water (300 mL), dried over sodium sulfate and concentrated under reduced pressure to yield the required product as a off white solid (175 g, crude).

Step 3: NaH (33.08 g (19.85 mol, 60%), 1.5 eq) was washed with hexane, dry DMF (500 mL) was added drop wise under $N_2$ atmosphere and stirred well. A solution of 3 (75 g, 0.55 mol) in DMF (125 mL) was added drop wise under $N_2$ atmosphere. Then a solution of 4-methoxylbenzyl chloride (86.3 g, 0.55 mol, 1 eq) in DMF (125 mL) was added drop wise and the overall reaction mixture was allowed to stir for 12 h at room temperature. Progress of the reaction was monitored by TLC (10% ethyl acetate/hexane, $R_f$~0.4). On completion of the reaction, reaction contents were poured into ice water (500 mL) and the product was extracted with ethyl acetate (2×400 mL). The ethyl acetate layer was washed with 2N HCl (2×200 ml). Then the contents were dried over sodium sulfate and concentrated under reduced pressure. Obtained crude product was purified by silica gel by column chromatography with 10% ethyl acetate/Hexane to yield the required product as a brown colored liquid (98 g, 70% yield).

Step 4: Diisopropyl amine (28.4 mol, 39.4 mL), 1.2 eq) was taken in THF (500 mL), stirred well and cooled the contents to 0° C. n-BuLi (234.4 mL, 1.5 eq) was added drop wise at 0° C. and the contents were stirred for 1 h at 0° C. Then the mixture was cooled −78° C., a solution of 4 (62 g, 0.24 mol) in THF (200 mL) was added drop wise for 30 min and the contents for were stirred for another h at −78° C. Then dry $CO_2$ gas was bubbled through the reaction mixture for 1.5 h. Progress of the reaction was monitored by TLC (10% ethyl acetate/hexane, $R_f$~0.1). On completion of the reaction, reaction contents were poured into ice water (300 mL) and the aqueous layer was extracted with ethyl acetate (2×200 mL) in basic condition. The aqueous layer was acidified with 20% HCl solution and extracted with ethyl acetate (2×200 mL). The combined organic layer was dried over sodium sulfate and concentrated under reduced pressure to yield the required product as an off white solid (40 g, 55% yield).

Step 5: To a solution of 5 (50 g, 0.16 mol) in DCM (750 mL, 15 times), a catalytic amount of DMF was added and the mixture was cooled to 0° C. Thionyl chloride (99.3 g (61 mL), 0.83 mol, 5 eq) was added drop wise for 30 min at 0° C. The overall reaction mixture was heated to reflux and maintained at this temperature for 2 h. Progress of the reaction was monitored by TLC (10% ethyl acetate/hexane, $R_f$~0.4). On disappearance of the starting material, DCM was distilled off completely. Above prepared acid chloride was dissolved in DCM (500 mL) and added drop wise to aqueous ammonia solution (700 mL) at 0° C. The overall reaction mixture was allowed to stir for 1 h and the progress of the reaction was monitored by TLC (10% ethyl acetate/hexane, $R_f$~0.7). On completion of the reaction, ice cold water (200 mL) was added and the product extracted with ethyl acetate (2×200 mL). The combined organic layer was dried over sodium sulfate and concentrated under reduced pressure to yield the required product as an off white solid (37 g, crude). Crude product obtained was directly used for the next step.

Step 6: Lithium aluminium hydride (LAH) (4.7 g, 0.12 mol, 1 eq) was charged into a flask. THF (250 mL) was added at 0° C. Then a solution of 6 (37 g, 0.12 mol) in THF (120 mL) was added drop wise for 30 min at 0° C. and the reaction mixture was heated to reflux for 5 h. Progress of the reaction was monitored by TLC (50% ethyl acetate/hexane, $R_f$~0.2). As the reaction was not moved completely, LAH (2.3 g) was added again and the mixture was refluxed for another 4 h. After completion of the reaction the reaction contents were slowly added to saturated sodium sulfate solution (1 L) and filtered over celite and the product extracted with ethyl acetate (2×500 mL). Combined extract was dried over sodium sulfate and concentrated under reduced pressure to obtain the crude product as an off white solid (32.5 g, crude). Crude product obtained was directly used for the next step.

Step 7: To a solution of 7 ((80 g, 0.28 mol) in DCM (600 mL) cooled at 0° C., TEA (22.7 g (30.2 mL), 0.026 mol, 0.8 eq) was added drop wise for 10 min. Then Boc anhydride ($Boc_2O$) (61.2 g (62.5 mL), 0.28 mol, 1 eq) was added drop wise for 20-30 min at 0° C. Overall reaction mixture initially stirred for 30 min at 0° C. and stirred for 1 h at room temperature. Progress of the reaction was monitored by TLC (20% ethyl acetate/hexane, $R_f$~0.6). On completion of the reaction, DCM was distilled off completely, and the residue was taken in ice water (500 mL) and the product extracted with ethyl acetate (2×300 mL). Combined extract was dried over sodium sulfate and concentrated under reduced pressure. Crude product obtained was recrystallized from n-hexane (200 mL) to yield the required product as an off white solid (80 g, 74% yield).

Step 8: To a stirred solution of 8 (20 g, 0.052 mol) in toluene (300 mL, 15 times), cooled to 0° C., was added aluminum chloride (17.34 g, 0.129 mol, 2.5 eq) portion wise for 30 min. The reaction mixture was slowly heated to 50-60° C. and allowed to stir for 2 h at the same temperature. Progress of the reaction was monitored by TLC (20% ethyl acetate/hexane, $R_f$~1). On completion of the reaction, reaction contents were treated with diluted HCl, then ice cold water (300 mL) was added and the mixture extracted with ethyl acetate (2×100 mL). The aqueous layer was basified with sodium hydroxide solution and extracted with ethyl acetate and dried over sodium sulfate and concentrated under reduced pressure to give the crude product as a brown colored solid (4.6 g, crude). The crude product obtained was directly used for the next step.

Step 9: 9 (7 g, 42.4 mmol, 1 eq) was given in DCM (7 mL, 10 times) at room temperature, then to that mixture TEA (5.86 mL, 72.4 mmol, 1 eq) was added at room temperature and the mixture stirred for 10 min and cooled to 0-5° C. $Boc_2O$ (9.24 g, 42.4 mmol, 1 eq) was added drop wise to reaction mixture for 30 min and the temperature was maintained for 3 h at 0-5° C. Progress of the reaction was monitored by the TLC (30% ethyl acetate/Hexane). On completion of the reaction, the reaction mixture was brought to ambient temperature for 2 h and the DCM was distilled off, the resulting residue was treated with water (50 mL) and extracted with ethyl acetate (100 mL). The combined organic layer was dried over sodium sulfate, then the solvent was evaporated under vacuum. The obtained crude product was purified with column chromatography to yield the required product as a white colored solid (5 g, Yield 44.48%).

Step 10: To a stirred solution of compound 10 (5 g, 18.8 mmol) in MeOH (36 mL) was added HCl in 2-propanol (5.8 mL, 29.2 mmol) and the mixture was stirred over 48 h at room temperature. The reaction mixture was concentrated in vacuo, diethylether (20 mL) was added and the obtained precipitate filtered out and washed with diethylether (5 mL). After drying the desired product was obtained in 97% yield (3.67 g).

Step 11: To a stirred solution of compound 11 (2.8 g, 13.9 mmol) in DCM (76 mL) was added TEA (7 mL, 41.7 mmol, 3.0 eq) followed by phenyl 3-fluoro-4-(hydroxymethyl) phenylcarbamate (3.63 g, 31.9 mmol, 1.0 eq.) (synthesis described for in example A58) at room temperature and the mixture was stirred for 16 h. After completion of the reaction, a solid precipitate was filtered and washed with DCM (2 mL) followed by n-pentane (5 mL) and dried to get 12 (3.38 g, 73%).

Step 12: 4-Chloro-phenylboronic acid (93 mg, 0.06 mmol), compound 12 (99 mg, 0.3 mmol) and copper(II)-acetate (0.044 mL, 0.45 mmol) were added to DCM (4.5 mL). At room temperature was added pyridine (0.48 mL, 6 mmol) and the mixture was stirred for 48 h. The reaction mixture was concentrated in vacuo, the solid obtained was purified by column chromatography (eluent: cyclohexane/ethyl acetate (1:2)) to afford 1-((1-(4-chlorophenyl)-3-(trifluoromethyl)-1H-pyrazol-5-yl)methyl)-3-(3-fluoro-4-(hydroxymethyl)phenyl)urea (compound A60) (76 mg, 57%).

Examples 58, 61-88 and 92-95 were prepared in a similar manner or may be prepared analogously according to example A60.

Synthesis of Example A89

1-[[2-(2,3-Dichloro-phenyl)-5-(trifluoromethyl)-2H-pyrazol-3-yl]-methyl]-3-[3-fluoro-4-(hydroxymethyl)-phenyl]-urea

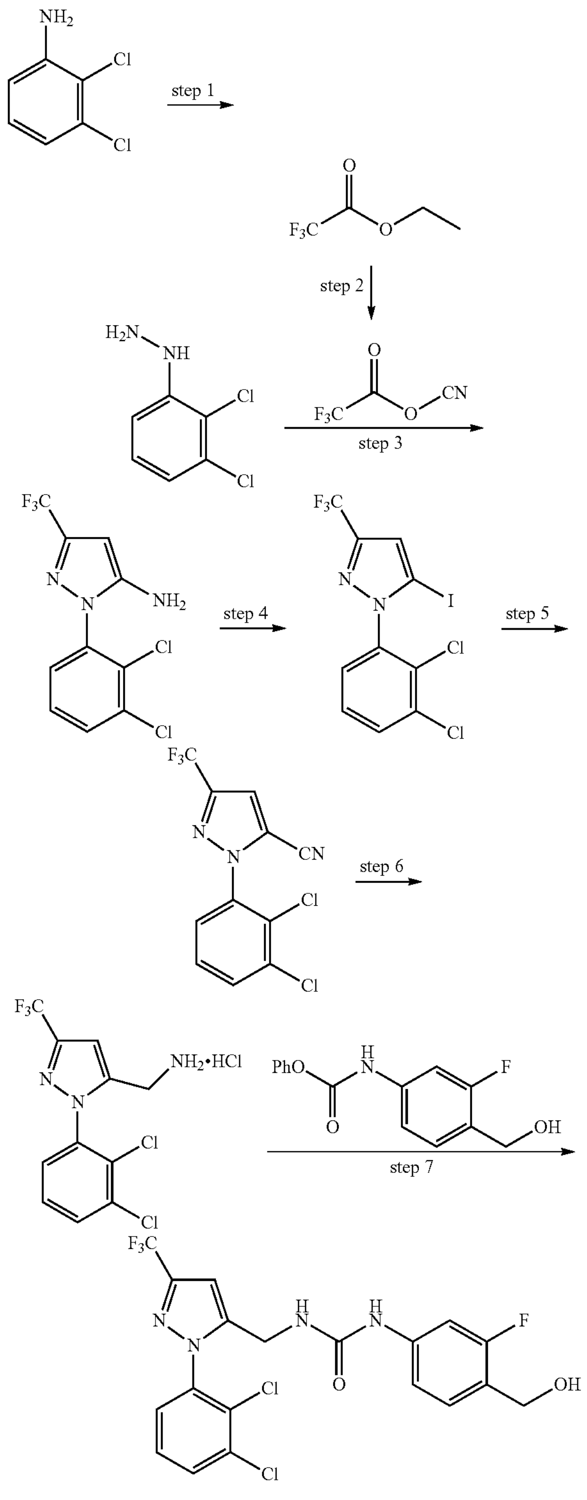

Step 1: To a stirred suspension of 2,3-dichloroaniline (35 g, 216.02 mmol, 1.0 eq.) in conc. HCl (150 mL) was added a solution of $NaNO_2$ (17.9 g, 259.22 mmol, 1.2 eq.) in water (50 mL) dropwise at −5 to 0° C. until the reaction mixture formed a clear solution. The reaction mixture was added dropwise to a stirred solution of $SnCl_2$ (90.1 g, 475.24 mmol, 2.2 eq.) in conc. HCl (300 mL) at −5° C. for 30 min. A solid precipitate obtained was filtered out and washed with excess of ice cold water to get (2,3-dichlorophenyl)hydrazine (45.8 g, 98%, pale yellow solid; TLC system: EtOAc/PE (3:7) $R_f$: 0.55).

Step 2: To a stirred suspension of 60% NaH (33.80 g, 1.408 mol, 2 eq.) in dioxane (700 mL) was added acetonitrile (44.3 mL, 0.845 mol, 1.2 eq.) at 0° C. over a period of 30 min followed by ethyl trifluoroacetate (83.70 mL, 0.704 mol, 1.0 eq.). The reaction mixture was slowly and carefully heated to 100° C. for 3 h. The dioxane was evaporated under reduced pressure and the pH was adjusted to ~6 with 1 N HCl and the mixture extracted with ether (200 mL×4), dried ($MgSO_4$) and the solvent evaporated under vacuum to get 4,4,4-trifluoro-3-oxobutanenitrile (95 g, crude, brown oil).

Step 3: To a stirred suspension of 4,4,4-trifluoro-3-oxobutanenitrile (20 g, 145.98 mmol, 1.0 eq.) in ethanol (200 mL) was added (2,3-dichlorophenyl)hydrazine (47.5 g, 145.98 mmol, 1.0 eq) and refluxed for 3 h. Ethanol was evaporated, the residue diluted with water and extracted with ethyl acetate (300 mL×2), dried ($Na_2SO_4$), and the solvent evaporated under vacuum. The crude product was purified by CC using EtOAc/PE (3:7) as eluent to get 1-(2,3-dichlorophenyl)-3-(trifluoromethyl)-1H-pyrazol-5-amine (17.02 g, 39.65%, yellow solid; TLC system: EtOAc/PE (1:1) $R_f$: 0.6).

Step 4: To a stirred suspension of KI (30.38 g, 186.03 mmol, 3.0 eq.) and isoamylnitrile (26.2 mL, 186.03 mmol, 3.0 eq) in acetonitrile (150 mL) was added 1-(2,3-dichlorophenyl)-3-(trifluoromethyl)-1H-pyrazol-5-amine (18 g, 61.01 mmol, 1.0 eq.) and refluxed for 12 h. Acetonitrile was evaporated, the residue diluted with water and extracted with ethyl acetate (250 mL×2), dried ($Na_2SO_4$), the solvent evaporated under vacuum. The crude product was purified by CC using EtOAc/PE (1:9) to get 1-(2,3-dichlorophenyl)-5-iodo-3-(trifluoromethyl)-1H-pyrazole (11.2 g, crude, yellow oil; TLC system: EtOAc/PE (1:9) $R_f$: 0.6).

Step 5: To a stirred solution of 1-(2,3-dichlorophenyl)-5-iodo-3-(trifluoromethyl)-1H-pyrazole (11.1 g, 27.58 mmol, 1.0 eq) in NMP (50 mL) was added CuCN (2.39 g, 27.58 mmol, 1.0 eq.) and heated to 200° C. for 2 h. The reaction mixture was passed through a celite pad and washed with excess of ethyl acetate. The filtrate was washed with water and the ethyl acetate layer was separated, dried ($Na_2SO_4$), and the solvent evaporated. The resulting residue was purified by CC using ethyl acetate/PE (1:9) to get 1-(2,3-dichlorophenyl)-3-(trifluoromethyl)-1 H-pyrazole-5-carbonitrile (5.02 g, crude, yellow solid).

Step 6: To a stirred solution of 1-(2,3-dichlorophenyl)-3-(trifluoromethyl)-1H-pyrazole-5-carbonitrile (5.02 g, 16.46 mmol, 1.0 eq.) in THF (50 mL) was added $BH_3—S(CH_3)_2$ (3.74 g, 49.38 mmol, 3.0 eq.) at 0° C. and heated to reflux for 1 h. The reaction mixture was cooled to 0° C. and quenched with 1N HCl and basified with 1N solution of NaOH to a pH of ~10 and extracted with ethyl acetate (100 mL×2), dried ($Na_2SO_4$), the solvent evaporated to get a pale yellow oil. The oil was treated with ether HCl to get (1-(2,3-dichlorophenyl)-3-(trifluoromethyl)-1H-pyrazol-5-yl)methanamine hydrochloride (1.15, 27% yield over 3 steps) as a white solid (TLC system: $CHCl_3$/MeOH (9:1), $R_f$: 0.55).

Step 7: To a stirred solution of phenyl 3-fluoro-4-(hydroxymethyl)phenylcarbamate (0.175 g, 0.63 mmol, 1.0 eq) in DCM (5 mL) was added TEA (0.25 mL, 1.9 mmol, 3.0 eq.) followed by compound (1-(2,3-dichlorophenyl)-3-(trifluoromethyl)-1H-pyrazol-5-yl)methanamine hydrochloride (0.218 mg, 0.63 mmol, 1.0 eq.) at RT and stirred for 16 h at RT. The reaction mixture was diluted with water (10 mL) and extracted into DCM (25 mL). The organic layer was washed with brine (10 mL), dried over ($Na_2SO_4$) and the solvent evaporated under vacuum. The resulting residue was purified by CC using EtOAc/PE (1:1) as eluent to get 1-((1-(2,3-dichlorophenyl)-3-(trifluoromethyl)-1H-pyrazol-5-yl)methyl)-3-(3-fluoro-4-(hydroxymethyl)phenyl)urea (70 mg; 23%) as white solid (TLC system: EtOAc, $R_f$: 0.55).

Synthesis of Example A90

1-[[2-(3-Chloro-2-methoxy-phenyl)-5-(trifluoromethyl)-2H-pyrazol-3-yl]-methyl]-3-[3-fluoro-4-(hydroxymethyl)-phenyl]-urea

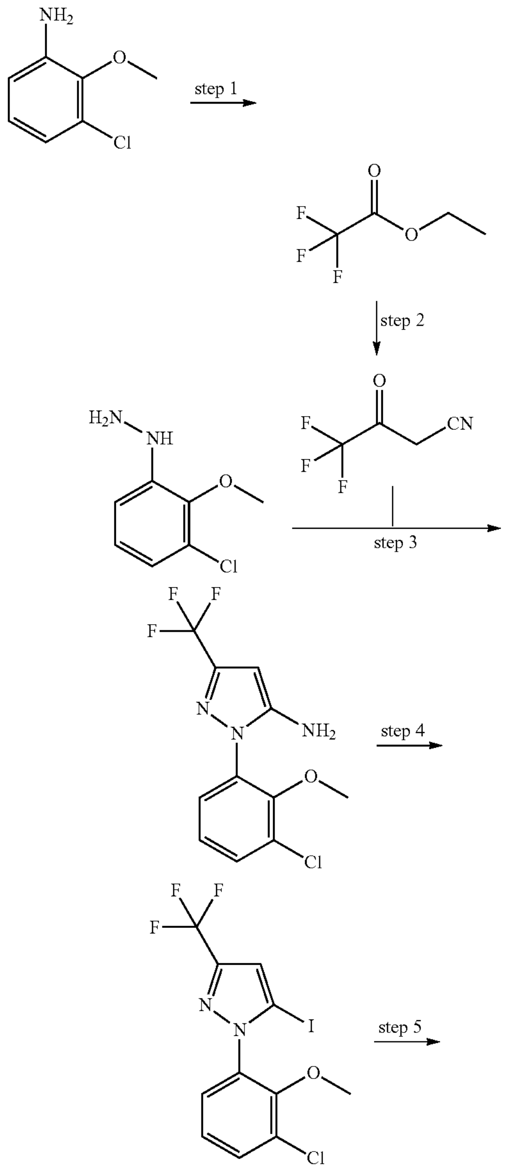

-continued

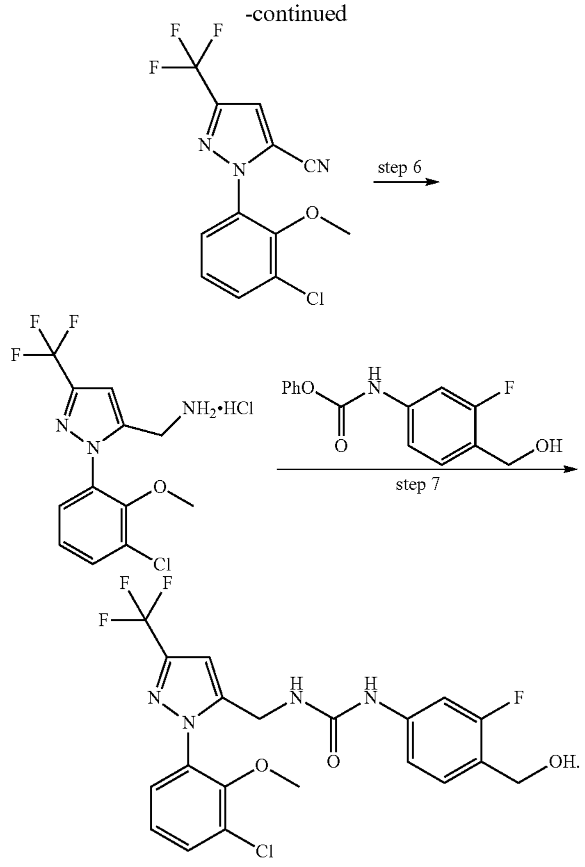

Step 1: To a stirred suspension of 3-chloro-2-methoxyaniline (5 g, 31.7 mmol, 1.0 eq) in conc. HCl (25 mL) was added a solution of $NaNO_2$ (3.28 g, 47.55 mmol, 1.5 eq.) in water (5 mL) dropwise at −5 to 0° C. until the reaction mixture formed a clear solution. The reaction mixture was added drop wise to a stirred solution of $SnCl_2$ (13.24 g, 69.74 mmol, 2.2 eq) in conc. HCl (50 mL) at −5° C. for 30 min. A solid precipitate obtained was filtered out and washed with excess of ice cold water to get (3-chloro-2-methoxyphenyl)hydrazine (6.049 g, 94%, brown solid; TLC system: EtOAc/PE (3:7) $R_f$: 0.4).

Step 2: To a stirred suspension of 60% NaH (33.80 g, 1.408 mol, 2 eq) in dioxane (700 mL) was added acetonitrile (44.3 mL, 0.845 mol, 1.2 eq.) at 0° C. over a period of 30 min followed ethyl trifluoroacetate (83.70 mL, 0.704 mol, 1.0 eq). The reaction mixture was slowly and carefully heated to 100° C. for 3 h. The dioxane was evaporated under reduced pressure and pH was adjusted to ~6 with 1N HCl and extracted with ether (200 mL×4), dried ($MgSO_4$) and evaporated under vacuum to get 4,4,4-trifluoro-3-oxobutanenitrile (95 g, crude, brown oil). The compound was confirmed by matching with the TLC of reference compound.

Step 3: To a stirred solution of 4,4,4-trifluoro-3-oxobutanenitrile (1.64 g, 11.96 mmol, 1.0 eq) in ethanol (15 mL) was added (3-chloro-2-methoxyphenyl)hydrazine (2.5 g, 11.96 mmol, 1.0 eq) and the mixture was refluxed for 3 h. Ethanol was evaporated, the mixture diluted with water and extracted with ethyl acetate (300 mL×2), dried ($Na_2SO_4$), evaporated again under vacuum. The crude product was purified by CC using EtOAc/PE (1:4) as eluent to get 1-(3-chloro-2-methoxyphenyl)-3-(trifluoromethyl)-1H-pyrazol-5-amine (0.84 g, 24%, yellow oil; TLC system: EtOAc/PE (2:3), $R_f$: 0.5).

Step 4: To a stirred suspension of KI (1.36 g, 8.25 mmol, 3.0 eq) and isoamylnitrile (1.1 mL, 8.25 mmol, 3.0 eq) in acetonitrile (20 mL) was added 1-(3-chloro-2-methoxyphenyl)-3-(trifluoromethyl)-1H-pyrazol-5-amine (0.8 g, 2.75 mmol, 1.0 eq) and refluxed for 12 h. Acetonitrile was evaporated, the mixture diluted with water and extracted with ethyl acetate (250 mL×2), dried ($Na_2SO_4$), the solvent evaporated under vacuum. The crude product was purified by CC using EtOAc/PE (1:19) to get 1-(3-chloro-2-methoxyphenyl)-5-iodo-3-(trifluoromethyl)-1H-pyrazole (0.2 g, crude, yellow oil; TLC system: EtOAc/PE (2:3), $R_f$: 0.75).

Step 5: To a stirred solution of 1-(3-chloro-2-methoxyphenyl)-5-iodo-3-(trifluoromethyl)-1H-pyrazole (0.2 g, 0.49 mmol, 1.0 eq) in NMP (5 mL) was added CuCN (0.044 g, 0.49 mmol, 1.0 eq) and heated to 200° C. for 2 h. The reaction mixture was passed through celite pad and washed with excess of ethyl acetate. The filtrate was washed with water and ethyl acetate layer was separated, dried ($Na_2SO_4$), and the solvent evaporated. The resulting residue was purified by CC using ethyl acetate/PE (1:19) to get 1-(3-chloro-2-methoxyphenyl)-3-(trifluoromethyl)-1H-pyrazole-5-carbonitrile (0.05 g, crude, yellow solid; TLC system: EtOAc/PE (1:9) $R_f$: 0.5).

Step 6: To a stirred solution of 1-(3-chloro-2-methoxyphenyl)-3-(trifluoromethyl)-1H-pyrazole-5-carbonitrile (2.03 g, 6.74 mmol, 1.0 eq) in THF (20 mL) was added $BH_3$-DMS (0.512 g, 6.74 mmol, 1.0 eq) at 0° C. and heated to reflux for 3 h. The reaction mixture was cooled to 0° C. and quenched with 1N HCl and basified with 1N solution of NaOH to a pH of ~10 and extracted with ethyl acetate (100 mL×2), dried ($Na_2SO_4$), the solvent evaporated to get a pale yellow oil. The oil was treated with ether and HCl to get (1-(3-chloro-2-methoxyphenyl)-3-(trifluoromethyl)-1H-pyrazol-5-yl)methanamine hydrochloride (0.20, 6% yield over 3 steps) as an off white solid (TLC system: $CHCl_3$/MeOH (9:1), $R_f$ 0.5).

Step 7: To a stirred solution of (1-(3-chloro-2-methoxyphenyl)-3-(trifluoromethyl)-1H-pyrazol-5-yl)methanamine hydrochloride (100 mg, 0.38 mmol, 1.0 eq) in DCM (5 mL) was added TEA (0.16 mL, 1.14 mmol, 3.0 eq) followed by phenyl 3-fluoro-4-(hydroxymethyl)phenylcarbamate (131 mg, 0.38 mmol, 1.0 eq) at RT and stirred for 16 h. The reaction mixture was diluted with water (15 mL), extracted with DCM (2×15 mL). The combined organic layer was washed with brine (15 mL), dried over anhydrous $Na_2SO_4$ and evaporated under vacuum. Crude product was purified by CC to get 1-((1-(3-chloro-2-methoxyphenyl)-3-(trifluoromethyl)-1H-pyrazol-5-yl)methyl)-3-(3-fluoro-4-(hydroxymethyl)phenyl)urea (110 mg; 61%) as off white solid (TLC system: MeOH/$CHCl_3$ (1:9); $R_f$: 0.55).

Synthesis of Example A91

1-[[2-(5-Chloro-2-methoxy-phenyl)-5-(trifluoromethyl)-2H-pyrazol-3-yl]-methyl]-3-[3-fluoro-4-(hydroxymethyl)-phenyl]-urea

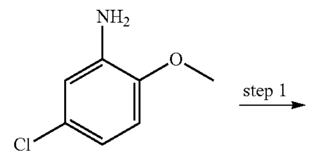

-continued

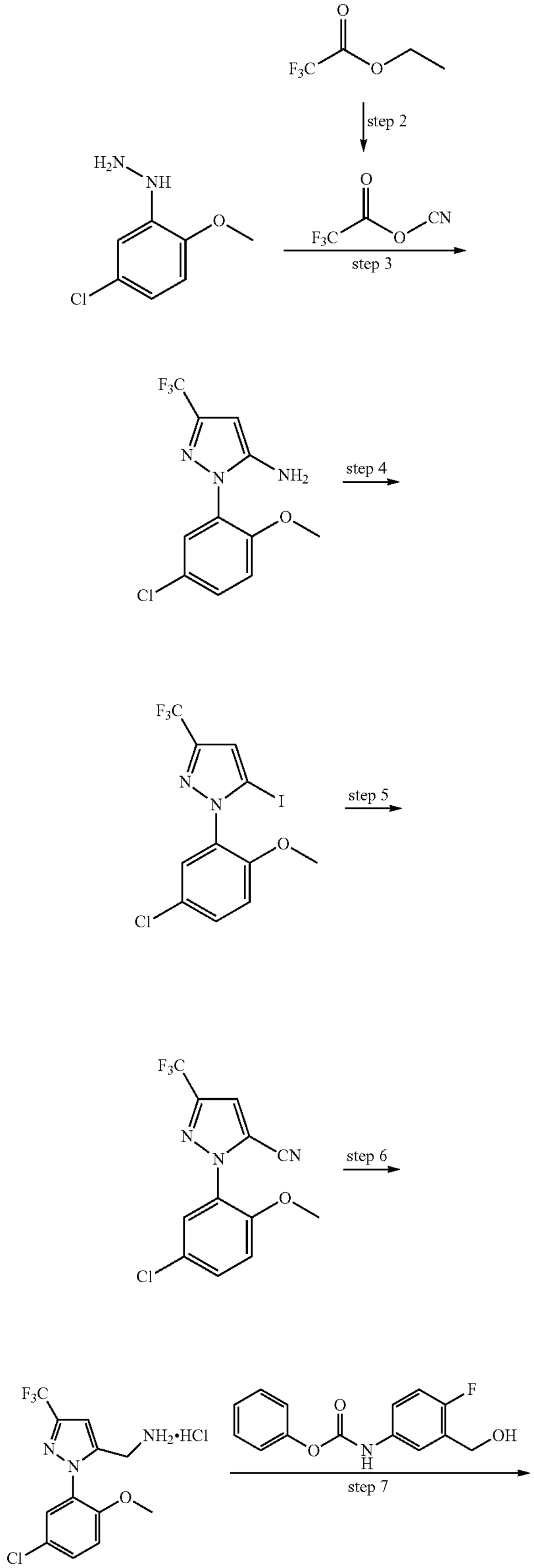

-continued

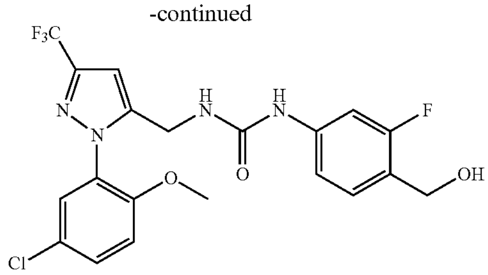

Step 1: To a stirred suspension of 5-chloro-2-methoxyaniline (20.0 g, 126.98 mmol, 1.0 eq) in conc. HCl (250 mL) was added a solution $NaNO_2$ (10.5 g, 152.38 mmol, 1.2 eq) in water (40 mL) dropwise at −5-0° C. until reaction mixture formed a clear solution. The reaction mixture was added dropwise to a stirred solution of $SnCl_2$ (52.90 g, 279.36 mmol, 2.2 eq) in conc. HCl (250 mL) at −5° C. for 30 min. The solid precipitate obtained was filtered out and washed with excess of ice cold water to get (5-chloro-2-methoxyphenyl)hydrazine (25.3 g, 92%, off-white solid; TLC system: EtOAc/PE (3:7) $R_f$: 0.6).

Step 2: As described for example A89, step 2.

Step 3: To a stirred suspension of 4,4,4-trifluoro-3-oxobutanenitrile (25.0 g, 182.44 mmol, 1.0 eq) in ethanol (500 mL) was added get (5-chloro-2-methoxyphenyl)hydrazine (38.13 g, 182.44 mmol, 1.0 eq) and the mixture refluxed for 3 h. Ethanol was evaporated, the residue diluted with water and extracted with ethyl acetate (300 mL×2), dried ($Na_2SO_4$), the solvent evaporated under vacuum. The crude product was purified by CC using EtOAC/PE (2:3) as eluent to get 1-(5-chloro-2-methoxyphenyl)-3-(trifluoromethyl)-1H-pyrazol-5-amine (13.09 g, 25%, yellow solid; TLC system: EtOAc/PE (1:1) $R_f$: 0.6).

Step 4: To a stirred suspension of KI (17.11 g, 103.08 mmol, 3.0 eq) and isoamylnitrile (13.9 mL, 103.8 mmol, 3.0 eq) in acetonitrile (150 mL) was added 1-(5-chloro-2-methoxyphenyl)-3-(trifluoromethyl)-1H-pyrazol-5-amine (10 g, 34.36 mmol, 1.0 eq) and the mixture refluxed for 12 h. Acetonitrile was evaporated, the mixture diluted with water and extracted with ethyl acetate (200 mL×2), dried ($Na_2SO_4$), the solvent evaporated under vacuum. The crude product was purified by CC using EtOAc/PE (1:3) to get 1-(5-chloro-2-methoxyphenyl)-5-iodo-3-(trifluoromethyl)-1H-pyrazole (4.84 g, crude, yellow solid; TLC system: EtOAc/PE (1:4) $R_f$: 0.65).

Step 5: To a stirred solution of 1-(5-chloro-2-methoxyphenyl)-5-iodo-3-(trifluoromethyl)-1H-pyrazole (4.83 g, 12.01 mmol, 1.0 eq) in NMP (20 mL) was added CuCN (1.03 g, 12.01 mmol, 1.0 eq) and the mixture heated to 200° C. for 2 h. The reaction mixture was passed through a celite pad and washed with excess of ethyl acetate. The filtrate was washed with water and the ethyl acetate layer was separated, dried ($Na_2SO_4$), and the solvent evaporated. The resulting residue was purified by CC using ethyl acetate/PE (1:19) to get 1-(5-chloro-2-methoxyphenyl)-3-(trifluoromethyl)-1H-pyrazole-5-carbonitrile (3.85 g, crude, yellow solid; TLC system: EtOAc/PE (1:4) $R_f$: 0.65).

Step 6: To a stirred solution of 1-(5-chloro-2-methoxyphenyl)-3-(trifluoromethyl)-1H-pyrazole-5-carbonitrile (3.09 g, 10.27 mmol, 1.0 eq) in THF (40 mL) was added $BH_3$-DMS (2.30 g, 30.81 mmol, 3.0 eq) at 0° C. and heated to reflux for 1 h. The reaction mixture was cooled to 0° C. and quenched with 1N HCl and basified with 1N solution of NaOH to a pH of ~10 and the mixture extracted with ethyl acetate (100 mL×2), dried ($Na_2SO_4$), the solvent evaporated to get a pale yellow oil. The oil was treated with ether and HCl to get (1-(5-chloro-2-methoxyphenyl)-3-(trifluoromethyl)-1H-pyrazol-5-yl)methanamine hydrochloride (1.3 g, 20% yield over 3 steps) as white solid (TLC system: $CHCl_3$/MeOH (9:1), $R_f$ 0.5).

Step 7: To a stirred solution of phenyl 4-fluoro-3-(hydroxymethyl)phenylcarbamate (0.2 g, 0.76 mmol, 1.0 eq) in DCM (5 mL) was added TEA (0.2306 g, 2.28 mmol, 3.0 eq) followed by (1-(5-chloro-2-m ethoxyphenyl)-3-(trifluoromethyl)-1H-pyrazol-5-yl)methanamine hydrochloride (0.2306 mg, 0.76 mmol, 1.0 eq) at RT and stirred for 16 h at RT. The solvent mixture was evaporated to get a residue, diluted with EtOAC (25 mL), washed with water (20 mL), brine (15 mL), dried over $Na_2SO_4$ and evaporated under vacuum. The resulting residue was purified by preparative HPLC to get 1-((1-(5-chloro-2-methoxyphenyl)-3-(trifluoromethyl)-1H-pyrazol-5-yl)methyl)-3-(3-fluoro-4-(hydroxymethyl)phenyl)urea (0.120 g; 33%) as white solid (TLC system: EtOAc, $R_f$: 0.6).

Synthesis of Example A100

N-[[5-tert-Butyl-2-(3-chlorophenyl)-2H-pyrazol-3-yl]-methyl]-2-[3-fluoro-4-(1-hydroxy-cyclopropyl)-phenyl]-propionamide

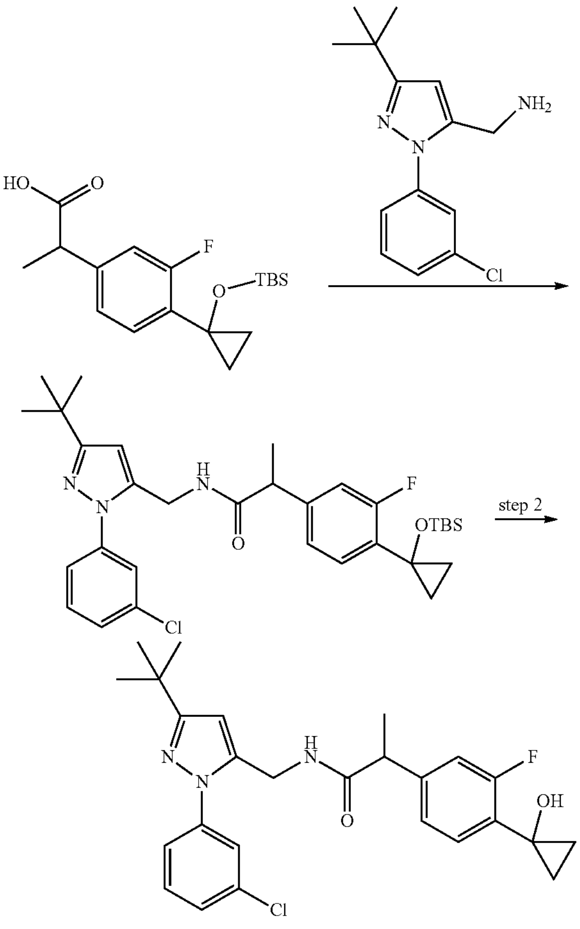

Step 1: To a stirred solution of 2-(4-(1-(tert-butyldimethylsilyloxy)cyclopropyl)-3-fluorophenyl)propanoic acid (135 mg, 0.400 mmol, 1 eq) in THF/DMF (3 mL/0.15 mL) was added DIPEA (0.271 mL, 1.6 mmol, 4 eq) followed by TBTU (131 mg, 0.400 mmol, 1 eq) and HOBt (131 mg, 0.400 mmol, 1 eq) at RT and the mixture was stirred for 3 h, then (3-tert-butyl-1-(3-chlorophenyl)-1H-pyrazol-5-yl) methanamine (175 mg, 0.56 mmol) was added and the mixture stirred for another 36 h. After completion of the reaction the reaction EtOAc was added and the mixture was washed with $H_2O$ (15 mL), dried ($Na_2SO_4$) and the solvent evaporated. The crude product was purified by CC using EtOAc/cyclohexane (1:4) to get N-((3-tert-butyl-1-(3-chlorophenyl)-1H-pyrazol-5-yl)methyl)-2-(4-(1-(tert-butyldimethylsilyloxy)cyclopropyl)-3-fluorophenyl)propanamide (143 mg; 61%).

Step 2: To a stirred solution of N-((3-tert-butyl-1-(3-chlorophenyl)-1H-pyrazol-5-yl)methyl)-2-(4-(1-(tert-butyldimethylsilyloxy)cyclopropyl)-3-fluorophenyl)propanamide (141 mg, 0.240 mmol, 1 eq) in THF (2 mL) was added TBAF (c=1 mol/L in THF, 0.61 mL, 0.61 mmol, 2.6 eq) at room temperature and the mixture was stirred for 5 h after which the solvent was evaporated. The residue was purified by CC using EtOAc/cyclohexane 1:3 as eluent to yield N-((3-tert-butyl-1-(3-chlorophenyl)-1H-pyrazol-5-yl) methyl)-2-(3-fluoro-4-(1-hydroxycyclopropyl)phenyl)propanamide (55 mg, 49%; TLC system: methanol/$CHCl_3$ (1:9) $R_f$: 0.5).

Synthesis of Example A101

N-[[2-(3-Chlorophenyl)-5-(trifluoromethyl)-2H-pyrazol-3-yl]-methyl]-2-[3-fluoro-4-(1-hydroxy-cyclopropyl)-phenyl]-propionamide

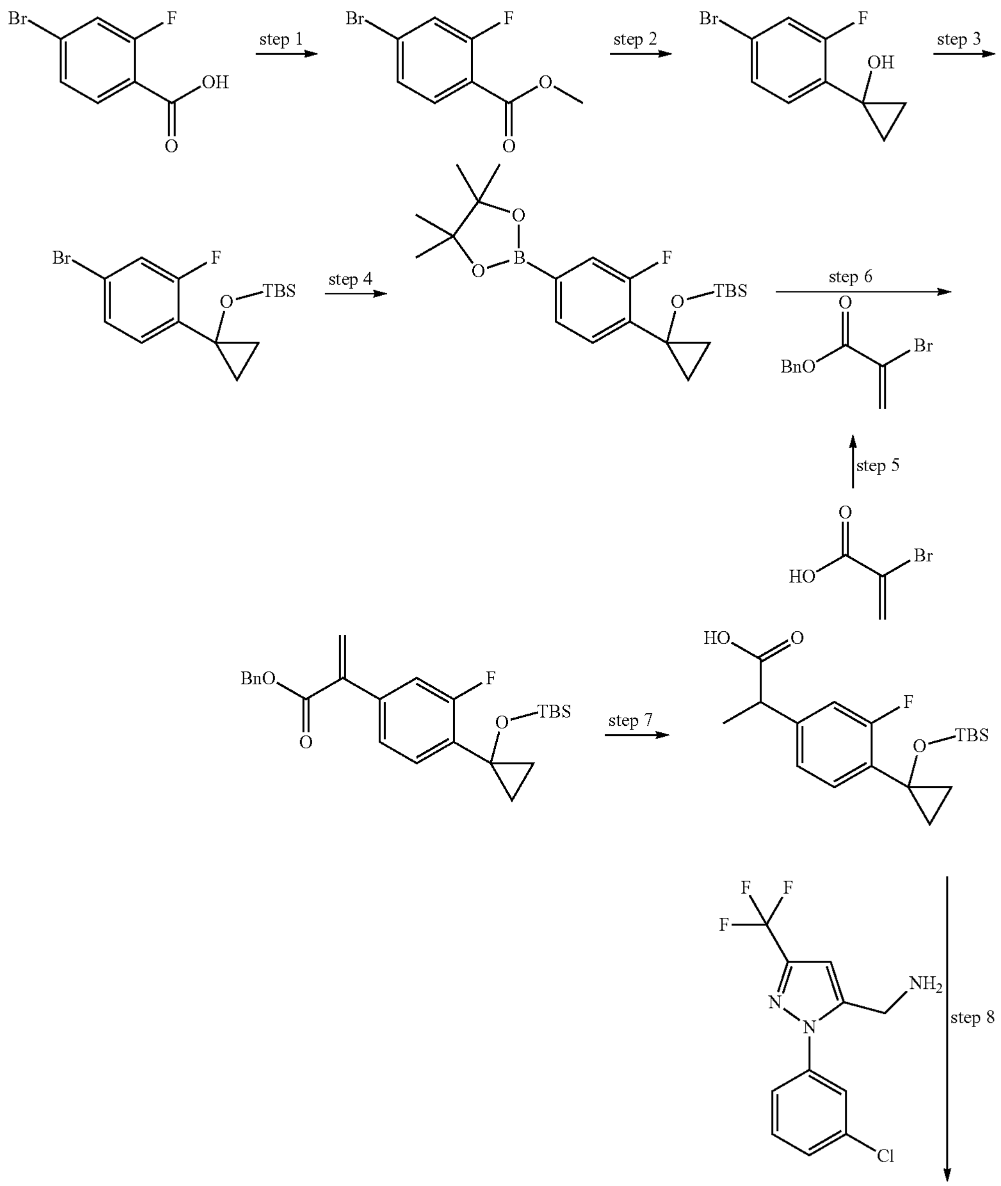

-continued

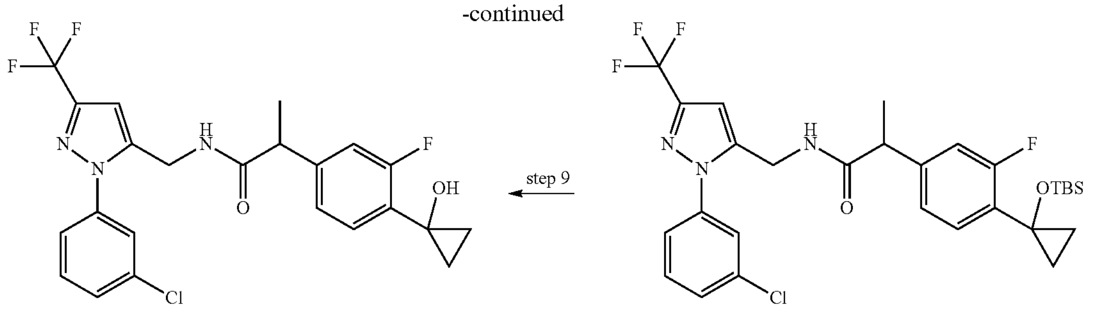

Step 1: To a stirred solution of 4-bromo-2-fluorobenzoic acid (15.0 g, 68.49 mmol, 1 eq) in MeOH (150 mL), $SOCl_2$ (23.09 mL, 136.9 mmol, 2 eq) was added at 0° C. for 15 min and the mixture was stirred at RT for 1.2 h. The MeOH was evaporated and the residue was diluted with ethyl acetate (250 mL), washed with a saturated aqueous solution of $NaHCO_3$, brine (150 mL) and water (150 mL). The ethyl acetate layer was dried over $Na_2SO_4$, evaporated under vacuum to get methyl 4-bromo-2-fluorobenzoate (15 g, 93%) as an off white solid (LC-MS purity, 99%; TLC system: EtOAc/PE (3:7), $R_f$: 0.8).

Step 2: To a stirred solution of $Ti(OiPr)_4$ (44.68 mL, 141.63 mmol, 1 eq) in diethyl ether (250 mL) was added freshly prepared ethyl magnesium iodide (212.44 mL, 424.89 mmol, 3 eq) in diethyl ether (220 mL) at −78° C. for 45 min. The reaction mixture was stirred for 90 min at −78° C., then methyl 4-bromo-2-fluorobenzoate (33.0 g, 141.63 mmol, 1.0 eq) was added and the mixture allowed to stir at RT for 16 h. Saturated aqueous $NH_4Cl$ (30 mL) was added and the mixture passed through celite pad. The ether layer was separated, washed with 1 N HCl (250 mL), brine (500 mL), water (750 mL), dried over $MgSO_4$ and the solvent evaporated. The resulting residue was purified by CC using PE/EtOAc (19:1) as eluent to get 1-(4-bromo-2-fluorophenyl)cyclopropanol (9.01 g, 28%; TLC system: PE/EtOAc (9:1), $R_f$: 0.3).

Step 3: To a stirred solution of 1-(4-bromo-2-fluorophenyl)cyclopropanol (9.01 g, 39.0 mmol, 1 eq) in DCM (100 mL) imidazole (5.33 g, 78 mmol, 2 eq) was added at 0° C. followed by TBDMSCl (7.08 g, 46.8 mmol, 1.2 eq) and the reaction mixture was stirred for 3 h. The reaction mixture was washed with water (100 mL), brine (100 mL), dried over $Na_2SO_4$ and the solvent was evaporated to get (1-(4-bromo-2-fluorophenyl)cyclopropoxy)(tert-butyl)dimethylsilane which was purified by CC using PE as eluent to yield pure (1-(4-bromo-2-fluorophenyl)cyclopropoxy)(tert-butyl) dimethylsilane (9.01 g, 67%; TLC system: PE, $R_f$: 0.8) as a colourless oil.

Step 4: To a stirred and degassed (degassed with Argon) solution of (1-(4-bromo-2-fluorophenyl)cyclopropoxy)(tert-butyl)dimethylsilane (9.87 g, 28.6 mmol, 1 eq), KOAc (8.45 g, 85.8 mmol, 3 eq) and bis-pinacolatodiborane (7.99 g, 31.46 mmol, 1.1 eq) in dioxane (100 mL) was added $Pd(PPh_3)_2Cl_2$ (2.01 g, 2.86 mmol, 0.1 eq) and the mixture heated to 90° C. for 3 h. The dioxane was evaporated and the resulting residue was diluted with PE (30 mL) to filter it through flourosil pad and then evaporated to get crude tert-butyl(1-(2-fluoro-4-(4,4,5,5-tetramethyl-1,3,2-dioxaborolan-2-yl)phenyl)cyclopropoxy)dimethylsilane (10.23 g) as a semi solid (TLC system: PE, $R_f$: 0.3).

Step 5: As described for example A118, step 6.

Step 6: To a stirred and degassed (degassed with Argon) suspension of tert-butyl(1-(2-fluoro-4-(4,4,5,5-tetramethyl-1,3,2-dioxaborolan-2-yl)phenyl)cyclopropoxy)-dimethylsilane (10.23 g, 26.09 mmol, 1 eq), $Cs_2CO_3$ (30.69 g, 78.27 mmol, 3 eq), and benzyl 2-bromoacrylate (9.59 g, 39.14 mmol, 1.5 eq) in DMF (100 mL) was added $Pd(dppf)Cl_2$ (1.06 g, 1.305 mmol, 0.05 eq) and the mixture heated to 90-100° C. for 1 h. The reaction mixture was filtered through celite pad, diluted with water (100 mL) and extracted with ethyl acetate (250 mL). The ethyl acetate layer was washed with water (150 mL), brine (200 mL), dried ($Na_2SO_4$) and the solvent evaporated to get crude benzyl 2-(4-(1-(tert-butyldimethylsilyloxy)-cyclopropyl)-3-fluorophenyl)acrylate (4.14 g) as a yellow oil which was used for the next stage without purification (TLC system: EtOAc/PE (1:49), $R_f$: 0.5).

Step 7: To a stirred solution of crude benzyl 2-(4-(1-(tert-butyldimethylsilyloxy)cyclopropyl)-3-fluorophenyl)acrylate (4.14 g) in EtOAc (30 mL) was added 20% $Pd(OH)_2$ (207 mg, 5% moleq.) and stirred under hydrogen gas balloon at RT for 1 h. The $Pd(OH)_2$ was filtered out, filtrate evaporated and resulting residue was purified by silica gel (neutral, 100-200) column using ethyl acetate/PE (3:17) as eluent to get crude 2-(4-(1-(tert-butyldimethylsilyloxy)cyclopropyl)-3-fluorophenyl)propanoic acid (1.8 g, 64% LC-MS, HPLC purity) as off white solid. The crude product on prep HPLC purification provided (1.23 g, 13% yield over 3 steps). [TLC system: EtOAc/PE (1:5), $R_f$: 0.6].

Step 8: To a stirred solution of 2-(4-(1-(tert-butyldimethylsilyloxy)cyclopropyl)-3-fluorophenyl)propanoic acid (190 mg, 0.56 mmol, 1 eq) in DCM (10 mL) was added DIPEA (0.29 mL, 1.68 mmol, 3 eq) followed by EDC.HCl (128 mg, 0.67 mmol, 1.2 eq) and HOBt (103 mg, 0.67 mmol, 1.2 eq) at RT and stirred for 10 min when (1-(3-chlorophenyl)-3-(trifluoromethyl)-1H-pyrazol-5-yl)methanamine (175 mg, 0.56 mmol) was added and the mixture stirred for 3 h. After completion of the reaction the reaction mixture was washed with $H_2O$ (15 mL), brine (10 mL), dried ($Na_2SO_4$) and the solvents evaporated. The crude product was purified by CC using EtOAc/PE (3:7) to get 2-(4-(1-(tert-butyldimethylsilyloxy)-cyclopropyl)-3-fluorophenyl)-N-((1-(3-chlorophenyl)-3-(trifluoromethyl)-1H-pyrazol-5-yl)methyl)propanamide (103 mg; 31%) as off white solid (TLC system: EtOAc/PE (3:7) $R_f$: 0.5).

Step 9: To a stirred solution of 2-(4-(1-(tert-butyldimethylsilyloxy)cyclopropyl)-3-fluorophenyl)-N-((1-(3-chlorophenyl)-3-(trifluoromethyl)-1H-pyrazol-5-yl)methyl)-propanamide (103 mg, 0.173 mmol, 1 eq) in THF (5 mL) was added TBAF (90 mg, 0.346 mmol, 2 eq) at room temperature and the mixture was stirred for 2 h after which THF was evaporated and the residue was dissolved in ethyl acetate (15 mL), washed with water (10 mL×2), brine (10 mL) and the solvent evaporated. The residue was purified by CC using methanol/$CHCl_3$ (1:9) as eluent to give N-((1-(3-chlorophenyl)-3-(trifluoromethyl)-1H-pyrazol-5-yl)methyl)-2-(3-fluoro-4-(1-hydroxycyclopropyl)phenyl)propanamide (41 mg, 49%) as off white solid (TLC system: methanol/$CHCl_3$ (1:9) $R_f$: 0.5).

Synthesis of Example A105

1-[[5-tert-Butyl-2-(3-chlorophenyl)-2H-pyrazol-3-yl]-methyl]-3-[3-fluoro-4-(1-hydroxy-cyclopropyl)-phenyl]-urea

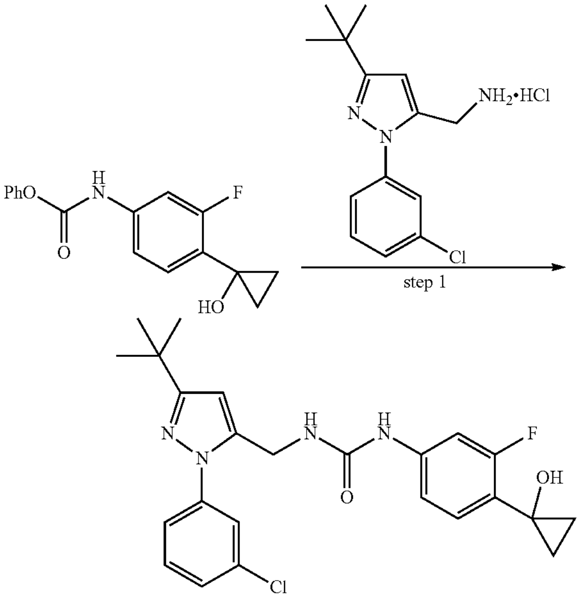

Step 1: To a stirred solution of (3-tert-butyl-1-(3-chlorophenyl)-1H-pyrazol-5-yl)methanamine hydrochloride (synthesis described for example A106) (0.104 mg, 0.348 mmol, 1.0 eq) in MeCN (8 mL) was added TEA (0.193 mL, 1.39 mmol, 4.0 eq) followed by addition of phenyl 3-fluoro-4-(1-hydroxycyclopropyl)phenylcarbamate (0.10 mg, 0.355 mmol, 1.02 eq) at RT and the mixture was stirred at reflux overnight. The solvents were evaporated and the crude product was purified by CC (eluent EtOAc/cyclohexane 1:2) to get 1-((3-tert-butyl-1-(3-chlorophenyl)-1H-pyrazol-5-yl)methyl)-3-(3-fluoro-4-(1-hydroxycyclopropyl)phenyl)urea (104 mg; 65%).

Synthesis of Example A106

1-[[2-(3-Chlorophenyl)-5-(trifluoromethyl)-2H-pyrazol-3-yl]-methyl]-3-[3-fluoro-4-(1-hydroxy-cyclopropyl)-phenyl]-urea

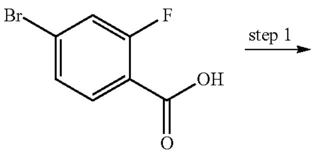

-continued

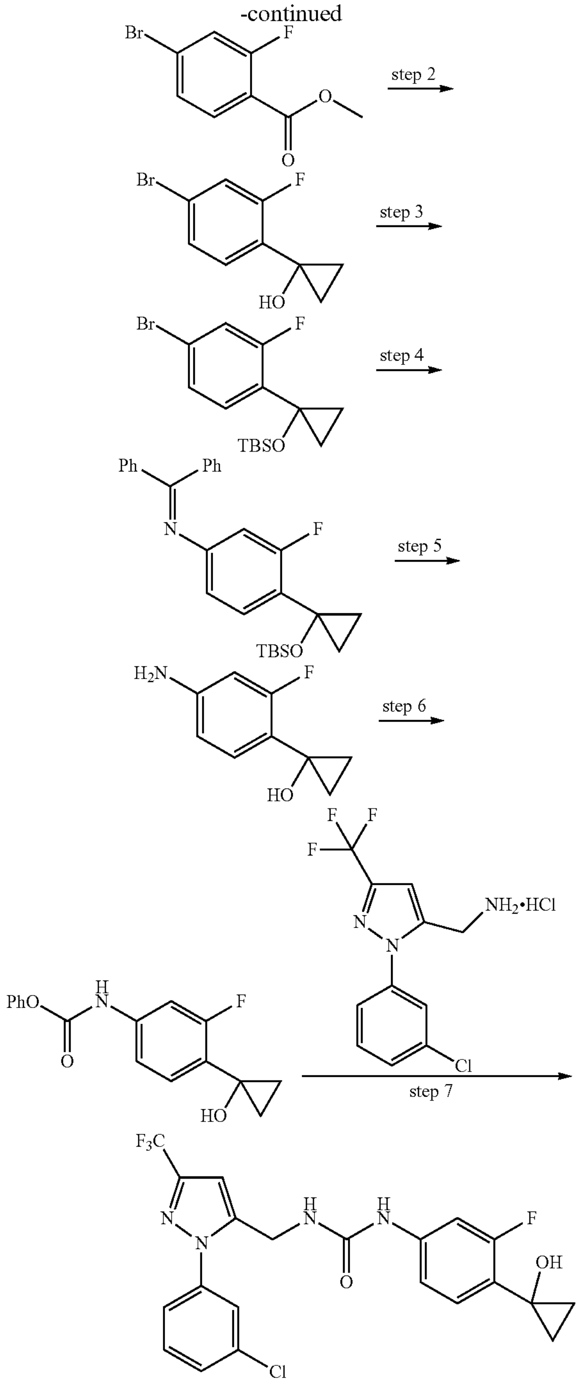

Steps 1-3: as described for the synthesis of example A101

Step 4: To a degassed suspension of (1-(4-bromo-2-fluorophenyl)cyclopropoxy)(tert-butyl)dimethylsilane (4.0 g, 11.59 mmol, 1.0 eq) in toluene (50 mL), was added BINAP (0.261 g, 0.347 mmol, 0.03 eq), benzophenone imine (2.1 g, 11.59 mmol, 1.0 eq) followed by $Cs_2CO_3$ (5.64 g, 17.38 mmol, 1.5 eq) in a sealed tube, then was added $Pd_2(dba)_3$ (0.138 g, 0.15 mmol, 0.013 eq) and the mixture heated to 100° C. for 8 h. The reaction mixture was diluted with EtOAc (120 mL), washed with water (25 mL×2), brine (25 mL) and dried over $Na_2SO_4$ and the solvent was evaporated under vacuum to get 4-(1-(tert-butyldimethylsilyloxy)cyclopropyl)-N-(diphenylmethylene)-3-fluoroaniline (4.8 g) crude product as a yellow oil (TLC system: EtOAc/PE (1:49), $R_f$: 0.75).

Step 5: To a stirred solution of 4-(1-(tert-butyldimethylsilyloxy)cyclopropyl)-N-(diphenylmethylene)-3-fluoroaniline (4.5 mg, 10.11 mmol, 1.0 eq) in THF (10 mL) was added 1N HCl (20 mL) and stirred vigorously for 1 h. The mixture was extracted with EtOAc (20 mL). The aqueous layer was basified with 1N aq. NaOH (30 mL) and extracted with EtOAc (50 mL). The combined organic layers were extracted with brine (20 mL) and dried over $Na_2SO_4$ and the solvent evaporated under vacuum; the resulting residue was purified by CC using EtOAc/PE (1:1) as eluent to get 1-(4-amino-2-fluorophenyl)cyclopropanol (0.7 g, 49%, yellow solid; TLC system: EtOAc/PE (1:1), $R_f$: 0.25).

Step 6: To a stirred solution of 1-(4-amino-2-fluorophenyl)cyclopropanol (0.7 mg, 4.19 mmol, 1.0 eq) in acetone (10 mL) was added pyridine (0.33 mL, 4.19 mmol, 1.0 eq) and phenyl chloroformate (0.5 mL, 4.19 mmol, 1.0 eq) and stirred at 0° C. to RT for 1 h. The solvent was evaporated, the residue diluted with water (10 mL×2), extracted with EtOAc (25 mL), brine (10 mL) and dried over $Na_2SO_4$ and evaporated under vacuum; the resulting residue was purified by CC using EtOAc/PE (1:4 as eluent to get phenyl 3-fluoro-4-(1-hydroxycyclopropyl)phenylcarbamate (0.9 g, 75%, off white solid; TLC system: EtOAc/PE (1:1), $R_f$: 0.6).

Step 7: To a stirred solution of (1-(3-chlorophenyl)-3-(trifluoromethyl)-1H-pyrazol-5-yl)methanamine hydrochloride (0.141 mg, 0.45 mmol, 1.0 eq) in DCM (5 mL) was added TEA (0.137 mg, 1.35 mmol, 3.0 eq) followed by phenyl 3-fluoro-4-(1-hydroxycyclopropyl)-phenylcarbamate (0.130 mg, 0.45 mmol, 1.0 eq) at RT and stirred overnight. The reaction mixture was diluted with DCM (20 mL), washed with water (10 mL), brine (5 mL), dried over anhydrous $Na_2SO_4$ and the solvents evaporated under vacuum. Crude product was purified by CC by using EtOAc/PE (1:1) to get 1-((1-(3-chlorophenyl)-3-(trifluoromethyl)-1H-pyrazol-5-yl)methyl)-3-(3-fluoro-4-(1-hydroxycyclopropyl)-phenyl)urea (0.0912 g; 43%) as pale yellow solid (TLC system: EtOAc/PE (3:1); $R_f$: 0.45).

Synthesis of Example A107

1-[[5-tert-Butyl-2-(3-chlorophenyl)-2H-pyrazol-3-yl]-methyl]-3-[4-(3-hydroxy-oxetan-3-yl)-phenyl]-urea

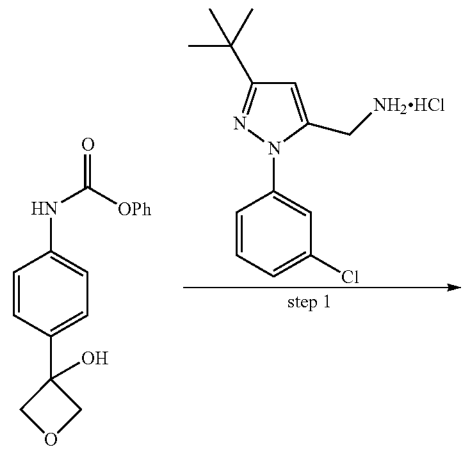

-continued

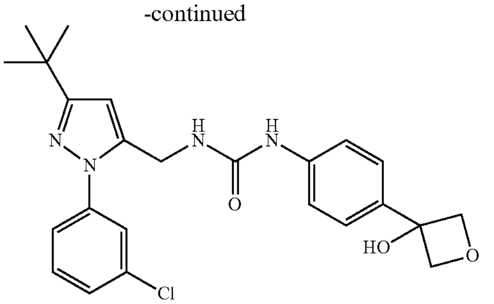

Step 1: To a stirred solution of phenyl 4-(3-hydroxyoxetan-3-yl)phenylcarbamate (synthesis described for example A108) (97 mg, 0.34 mmol, 1.02 eq) and (3-tert-butyl-1-(3-chlorophenyl)-1H-pyrazol-5-yl)methanamine hydrochloride (100 mg, 0.33 mmol, 1.0 eq) in MeCN (8 mL) was added TEA (0.185 mL, 1.33 mmol, 4.0 eq) at RT and the mixture stirred at reflux overnight. The solvents were evaporated and the crude product was purified by CC (EtOAc/cyclohexane 3:2 as eluent) to get 1-((3-tert-butyl-1-(3-chlorophenyl)-1H-pyrazol-5-yl)methyl)-3-(4-(3-hydroxyoxetan-3-yl)phenyl)urea (92 mg; 61%).

Synthesis of Example A108

1-[[2-(3-Chlorophenyl)-5-(trifluoromethyl)-2H-pyrazol-3-yl]-methyl]-3-[4-(3-hydroxy-oxetan-3-yl)-phenyl]-urea

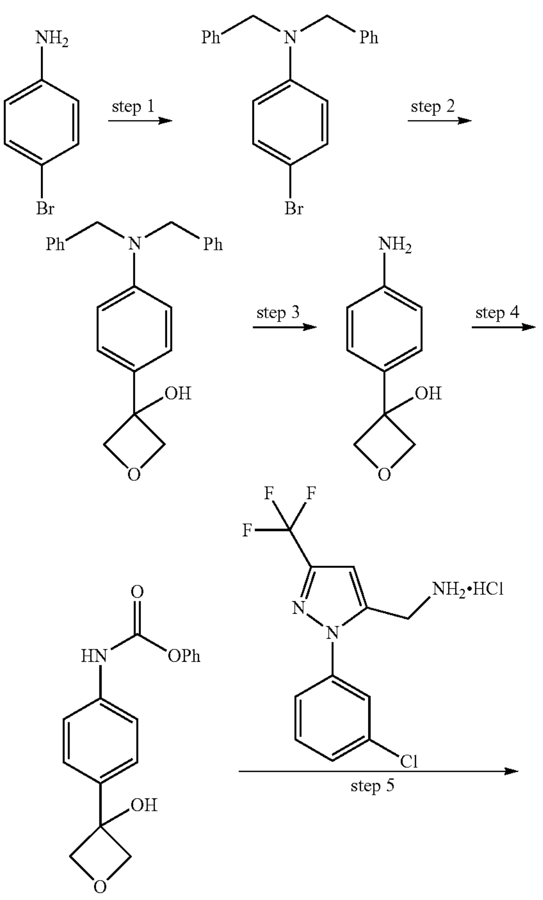

-continued

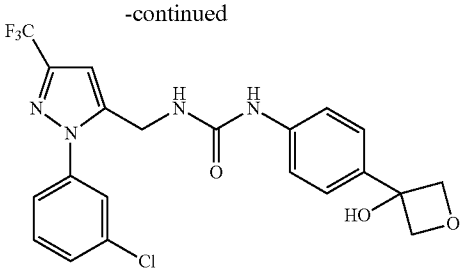

Step 1: To a stirred solution of 4-bromoaniline (500 mg, 2.92 mmol, 1.0 eq) and $K_2CO_3$ (1.21 g, 8.76 mmol, 3.0 eq) in $CH_3CN$ (10 mL) was added benzyl bromide (1.24 g, 7.30 mmol, 2.5 eq) and the mixture stirred for 16 h at 80° C. and cooled to RT. $K_2CO_3$ was filtered out, the filtrate concentrated, the resulting crude product was purified by CC using EtOAc/PE (1:19) to get N,N-dibenzyl-4-bromoaniline (900 mg, 87%; TLC system: EtOAc/PE (3:7), $R_f$: 0.7).

Step 2: To a stirred solution of N,N-dibenzyl-4-bromoaniline (500 mg, 1.42 mmol, 1.0 eq) in dry THF (20 mL), cooled to −78° C., was added n-BuLi (118 g, 1.84 mmol, 1.3 eq) slowly and the mixture stirred at −78° C. for 15 min. Then 3-oxatanone was added (103 g, 1.43 mmol, 1.0 eq) and the temperature was raised to −20° C. The mixture was quenched with sat. $NH_4Cl$ (50 mL), extracted with EtOAC (50 mL×2). The organic layer was washed with brine (50 mL), dried over anhydrous $Na_2SO_4$, concentrated and the resulting crude product was purified by CC using EtOAc/PE (1:4) to get 3-(4-(dibenzylamino)phenyl)oxetan-3-ol (320 mg 65%; TLC system: EtOAc/PE (2:3), $R_f$: 0.3).

Step 3: To a stirred solution of 3-(4-(dibenzylamino) phenyl)oxetan-3-ol (1.5 g, 5.217 mmol, 1.0 eq) in THF (50 mL) and EtOH (50 mL) was added 10% Pd/C (300 mg) and the mixture was stirred in hydrogen atmosphere at 40 psi $H_2$ for 5 h. The mixture was passed through celite, the filtrate concentrated under reduced pressure to get 3-(4-aminophenyl)oxetan-3-ol (1.1 g, 77%; TLC system: EtOAc/PE (7:3), $R_f$: 0.55).

Step 4: To a stirred solution of 3-(4-aminophenyl)oxetan-3-ol (1.19 g, 6.66 mmol, 1.0 eq) in acetone (20 mL) was added pyridine (1.05 g, 13.29 mmol, 2.0 eq) and phenyl chloroformate (1.05 g, 6.68 mmol, 1.1 eq) at 0° C. and the mixture was stirred at 0° C. for 30 min. The solvent was evaporated. The resulting residue was purified by CC using EtOAc/PE (3:7) as eluent to get phenyl 4-(3-hydroxyoxetan-3-yl)phenylcarbamate (1.2 g, 63%) as a white solid (TLC system: EtOAc/PE (7:3), $R_f$: 0.7).

Step 5: To a stirred solution of phenyl 4-(3-hydroxyoxetan-3-yl)phenylcarbamate (100 mg, 0.35 mmol, 1.0 eq) and (1-(3-chlorophenyl)-3-(trifluoromethyl)-1H-pyrazol-5-yl) methanamine hydrochloride (119.3 mg, 0.35 mmol, 1.0 eq) in DCM (10 mL) was added TEA (106 mg, 1.049 mmol, 3.0 eq) at RT and stirred at 40° C. overnight. The mixture was diluted with DCM (30 mL) and washed with water (10 mL), brine (10 mL) and dried over anhydrous $Na_2SO_4$ and concentrated. Crude product was purified by CC using MeOH/ $CHCl_3$ (1:9) to get 1-((1-(3-chlorophenyl)-3-(trifluoromethyl)-1H-pyrazol-5-yl)methyl)-3-(4-(3-hydroxyoxetan-3-yl)phenyl)urea (100 mg; 61%) as a white solid (TLC system: MeOH/$CHCl_3$ (1:9); $R_f$: 0.45).

Synthesis of Example A109

1-[[5-tert-Butyl-2-(3-chlorophenyl)-2H-pyrazol-3-yl]-methyl]-3-[3-fluoro-4-(3-hydroxy-oxetan-3-yl)-phenyl]-urea

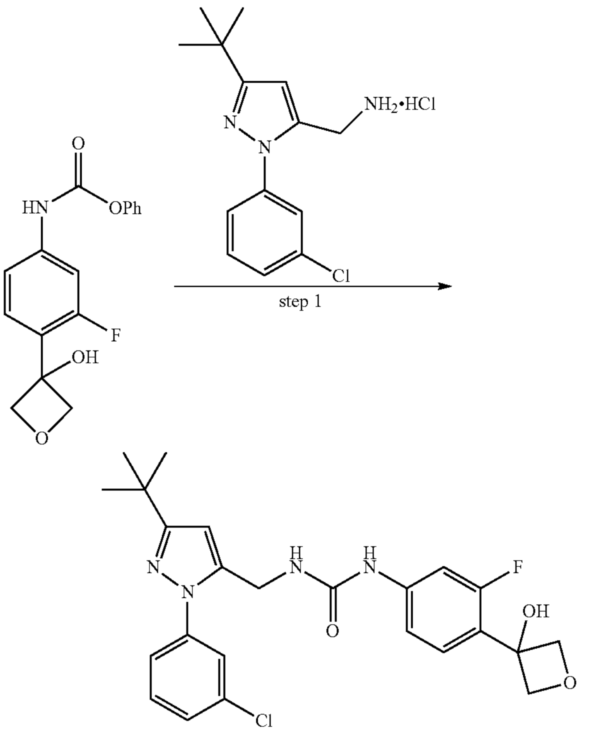

Step 1: To a stirred solution of (3-tert-butyl-1-(3-chlorophenyl)-1H-pyrazol-5-yl)methanamine hydrochloride (96 mg, 0.32 mmol, 1.0 eq) in MeCN (8 mL) was added TEA (0.178 mL, 1.28 mmol, 4.0 eq) followed by phenyl 3-fluoro-4-(3-hydroxyoxetan-3-yl)phenylcarbamate (99 mg, 0.3.3 mmol, 1.02 eq) at RT and stirred at reflux for 16 h. The solvent was evaporated and the crude product was purified by CC (EtOAc/cyclohexane 1:1 as eluent) to get 1-((3-tert-butyl-1-(3-chlorophenyl)-1H-pyrazol-5-yl)methyl)-3-(3-fluoro-4-(3-hydroxyoxetan-3-yl)phenyl)urea (116 mg; 77%).

Synthesis of Example A110

1-[[5-tert-Butyl-2-(3-chlorophenyl)-2H-pyrazol-3-yl]-methyl]-3-[3-fluoro-4-(3-hydroxy-oxetan-3-yl)-phenyl]-urea

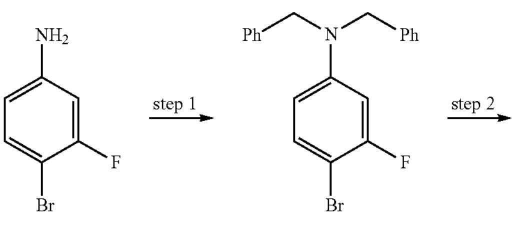

-continued

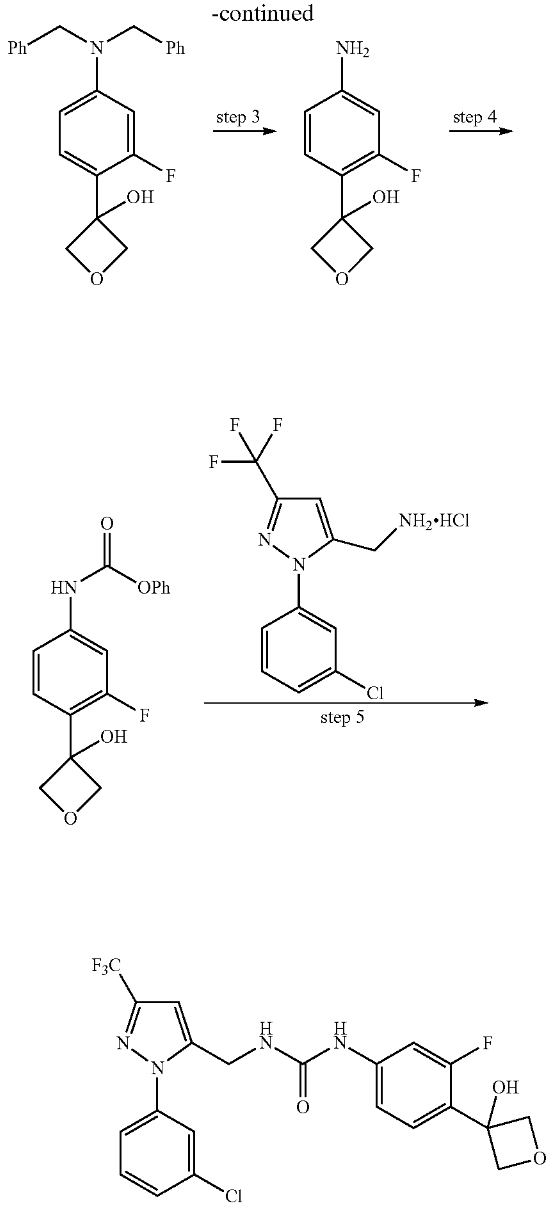

Step 1: To a suspension of 4-bromo-3-fluoroaniline (10.0 g, 52.6 mmol, 1.0 eq) and $K_2CO_3$ (21.7 g, 157.8 mmol, 3.0 eq) in MeCN (10 mL) was added benzyl bromide (19.8 g, 115.8 mmol, 2.2 eq) and the mixture was stirred for 16 h at 80° C. and then filtered through celite pad, and the solvents was evaporated under vacuum and washed with PE (100 mL) to get N,N-dibenzyl-4-bromo-3-fluoroaniline (13.8 g, 55%; TLC system: EtOAc/PE (1:9), $R_f$: 0.6).

Step 2: To a stirred solution of N,N-dibenzyl-4-bromo-3-fluoroaniline (6.8 g, 18.38 mmol, 1.0 eq) in dry THF (150 mL) was cooled to −78° C. was added n-BuLi (1.4 g, 22.6 mmol, 1.2 eq) slowly and the mixture was stirred at −78° C. for 30 min., followed by addition of 3-oxatanone (1.32 g, 18.38 mmol, 1.0 eq) and the temperature was raised to RT. The mixture was quenched with sat. $NH_4Cl$ (20 mL), diluted with water (50 mL) extracted with EtOAC (50 mL×2). The organic layer was washed with brine (25 mL), dried over anhydrous $Na_2SO_4$ and evaporated under vacuum. The resulting crude product was purified by CC using EtOAc/PE (2:3) to get 3-(4-(dibenzylamino)-2-fluorophenyl)oxetan-3-ol (3.0 g, 45%; TLC system: EtOAc/PE (1:1), $R_f$: 0.45).

Step 3: To a stirred solution of 3-(4-(dibenzylamino)-2-fluorophenyl)oxetan-3-ol (2.15 g, 5.92 mmol, 1.0 eq) in THF (125 mL) was added 10% Pd/C (0.230 g) under argon and stirred under hydrogen balloon pressure for 16 h. The mixture was passed through celite, and the filtrate concentrated under vacuum. The resulting crude product was purified by CC using EtOAc/PE (7:3) to get 3-(4-amino-2-fluorophenyl)oxetan-3-ol (0.9 g, 73%; TLC system: EtOAc 100%, $R_f$: 0.5).

Step 4: To a stirred solution of 3-(4-amino-2-fluorophenyl)oxetan-3-ol (0.93 g, 5.08 mmol, 1.0 eq) in acetone (10 mL) was added pyridine (0.82 mL, 10.16 mmol, 2.0 eq) and phenyl chloroformate (0.7 mL, 5.59 mmol, 1.1 eq) at 0° C. and the mixture was stirred at RT for 1 h. The solvents was evaporated and the crude product was extracted with EtOAC (25 mL), diluted with water (15 mL), washed with brine (10 mL), dried over anhydrous $Na_2SO_4$ and evaporated under vacuum. The resulting residue was washed with diethyl ether (25 mL) to get phenyl 3-fluoro-4-(3-hydroxyoxetan-3-yl)phenylcarbamate (0.892 g, 59%) as a off white solid (TLC system: 100% EtOAc, $R_f$: 0.55).

Step 5: To a stirred solution of (1-(3-chlorophenyl)-3-(trifluoromethyl)-1H-pyrazol-5-yl)methanamine hydrochloride (0.206 mg, 0.66 mmol, 1.0 eq) in DCM (5 mL) was added TEA (0.13 g, 1.32 mmol, 2.0 eq) followed by phenyl 3-fluoro-4-(3-hydroxyoxetan-3-yl)phenylcarbamate (0.2 g, 0.66 mmol, 1.0 eq) at RT and stirred for 16 h. The reaction mixture was extracted with DCM (20 mL), washed with water (15 mL), brine (15 mL), dried over anhydrous $Na_2SO_4$ and evaporated under vacuum. Crude product was purified by CC using EtOAc/PE (7:3) to get 1-((1-(3-chlorophenyl)-3-(trifluoromethyl)-1H-pyrazol-5-yl)methyl)-3-(3-fluoro-4-(3-hydroxyoxetan-3-yl)phenyl)urea (0.075 g; 23%) as off white solid (TLC system: EtOAc/PE (1:1); $R_f$: 0.55).

Synthesis of Example A111

N-[[2-(3-Chlorophenyl)-5-(trifluoromethyl)-2H-pyrazol-3-yl]-methyl]-2-[3-fluoro-4-(2-methoxy-ethoxy-methyl)-phenyl]-propionamide

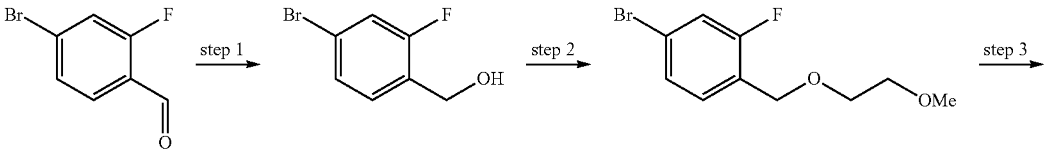

-continued

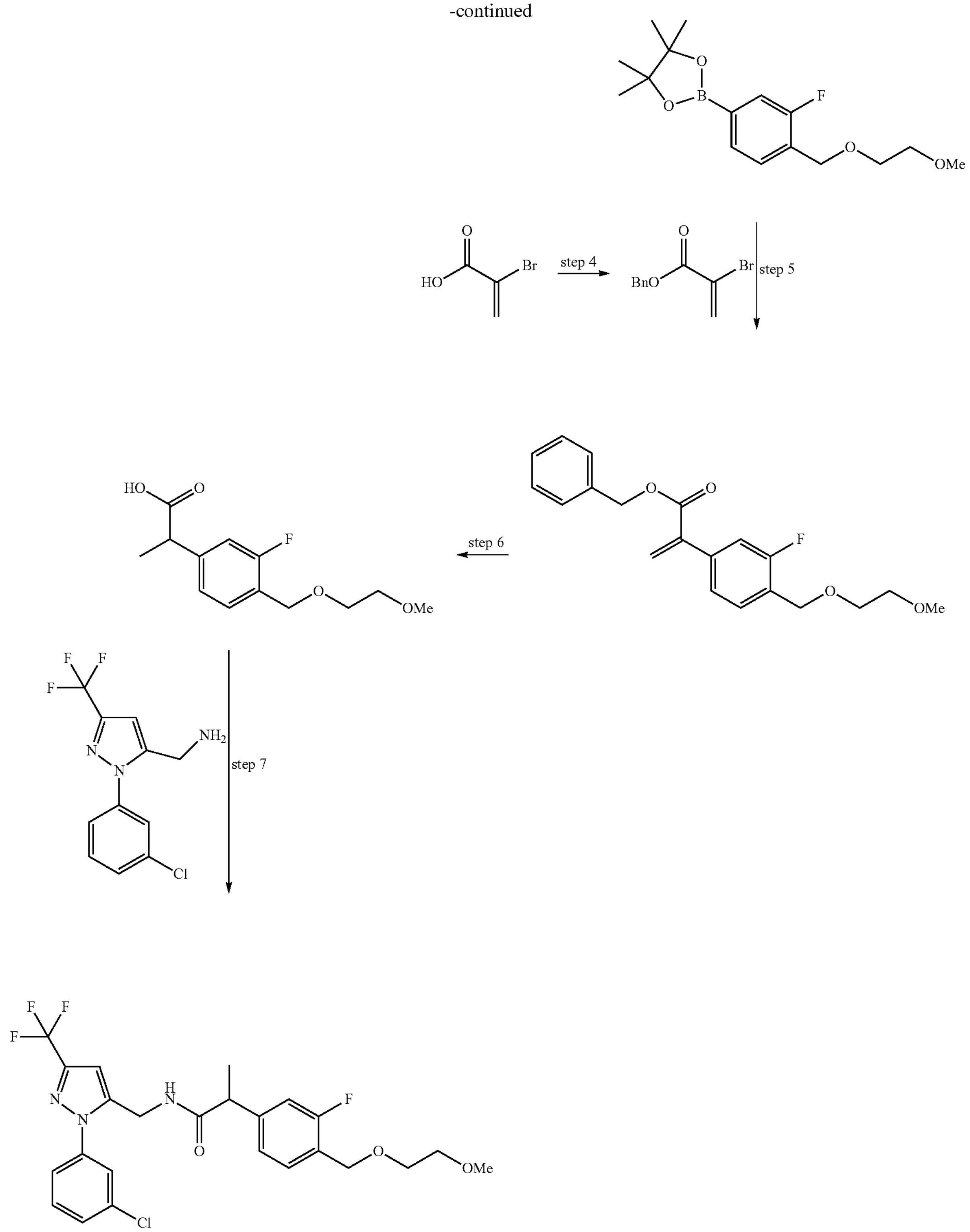

Step 1: as described for example A118, step 3

Step 2: To a stirred solution of (4-bromo-2-fluorophenyl) methanol (10 g, 49.02 mmol) in THF (250 mL) at 0° C., was added 60% NaH (2.93 g, 73.53 mmol) slowly in portions. After addition, the suspension was heated to 50° C. for 30 min, cooled to RT, then was added 1-bromo-2-methoxy ethane (5 mL, 53.92 mmol) and the mixture was stirred at RT for 20 h until complete consumption of (4-bromo-2-fluorophenyl)methanol, as evidenced by TLC analysis. The reaction mixture was diluted with ice cold water (100 mL) and concentrated under reduced pressure. The obtained aqueous residue was extracted with EtOAc (2×150 mL); the combined EtOAc layers were washed with brine solution (50 mL), dried over anhydrous $NaSO_4$, filtered and concentrated. The obtained crude compound was purified by CC using 5% EtOAc in PE as eluent to afford 4-bromo-2-fluoro-1-((2-methoxyethoxy)methyl)benzene (6 g, 47%) as yellow liquid (TLC solvent system: 30% EtOAc-PE; $R_f$: 0.4).

Step 3: A stirred suspension of 4-bromo-2-fluoro-1-((2-methoxyethoxy)methyl)benzene (6.0 g, 22.8 mmol), bispinacolatodiboron (5.8 g, 22.8 mmol), $CH_3COOK$ (6.7 g, 68.4 mmol) in THF (50 mL) was deoxygenated by purging with a stream of Argon for 30 min, and Pd $(PPh_3)_2Cl_2$ (36.5 mg, 0.228 mmol) was added, and purging was continued for further 10 min. The reaction mixture was stirred at 100° C. for 1 h until complete consumption of 4-bromo-2-fluoro-1-((2-methoxyethoxy)methyl)benzene, as evidenced by TLC analysis. The reaction mixture was concentrated and the obtained crude compound was purified by CC using 10% EtOAc in PE as eluent to afford 2-(3-fluoro-4-((2-methoxyethoxy)methyl)phenyl)-4,4,5,5-tetramethyl-1,3,2-dioxaborolane (5 g, 62%) as a pale yellow oil. (TLC solvent system: 30% EtOAc-PE; $R_f$: 0.4).

Step 4: as described for example A118, step 6

Step 5: A suspension of 2-(3-fluoro-4-((2-methoxyethoxy)methyl)phenyl)-4,4,5,5-tetramethyl-1,3,2-dioxaborolane (5 g, 16.129 mmol), $Cs_2CO_3$ (15.7 g, 48.38 mmol) in DMF (50 mL) was deoxygenated by purging Argon for 30 min at RT. Pd(dppf)$Cl_2$ (657 mg, 0.806 mmol) was added and purging was continued. After 10 min, benzyl 2-bromoacrylate (4.6 g, 19.35 mmol) was added and stirred at 100° C. for 1 h until complete consumption of 2-(3-fluoro-4-((2-methoxyethoxy)methyl)phenyl)-4,4,5,5-tetramethyl-1,3,2-dioxaborolane, as evidenced by TLC analysis. The reaction mixture was diluted with ethyl acetate (200 mL), filtered through a celite pad, washed with ethyl acetate (2×25 mL). The filtrate was washed with water (2×100 mL), brine (50 mL), dried over anhydrous $NaSO_4$, filtered and concentrated. The obtained crude compound was purified by CC using 10% ethyl acetate in PE as eluent to afford benzyl 2-(3-fluoro-4-((2-methoxyethoxy)methyl)phenyl)acrylate (1.4 g, 25%) as pale brown oil (TLC solvent system: 30% EtOAc-PE; $R_f$: 0.4).

Step 6: A suspension of benzyl 2-(3-fluoro-4-((2-methoxyethoxy)methyl)phenyl)acrylate (2.8 g, 8.139 mmol), 10% Pd/C (300 mg) in MeOH (20 mL) was hydrogenated (balloon pressure) at RT for 1 h until complete consumption of benzyl 2-(3-fluoro-4-((2-methoxyethoxy)methyl)phenyl)acrylate, as evidenced by TLC analysis. The reaction mixture was filtered through celite pad, washed with MeOH (2×15 mL). The combined filtrate was concentrated and the obtained crude compound was purified by CC using 30% EtOAc in PE as eluent to afford 2-(3-fluoro-4-((2-methoxyethoxy)methyl)phenyl)propanoic acid (1.2 g, 58%) as a colorless oil (TLC solvent system: 30% EtOAc-PE; $R_f$: 0.15).

Step 7: To a stirred DCM (5.0 mL) solution of 2-(3-fluoro-4-((2-methoxyethoxy)methyl)-phenyl)propanoic acid (82.0 mg, 0.321 mmol, 1.0 eq), DIPEA (0.168 mL, 0.961 mmol, 3.0 eq), EDC.HCl (74.0 mg, 0.387 mmol, 1.2 eq) and HOBt (59.0 mg, 0.387 mmol, 1.2 eq) were sequentially added at RT and the mixture stirred for 15 min. (1-(3-chlorophenyl)-3-(trifluoromethyl)-1H-pyrazol-5-yl)methanamine (100 mg, 0.321 mmol, 1 eq) was then added and the mixture stirred for 16 h. On completion of the reaction the mixture was washed with $H_2O$ (20 mL), brine (10 mL), the layers were separated, dried ($Na_2SO_4$) and the solvent evaporated. The crude product was purified by CC using EtOAc/$CHCl_3$ (1:9) to get N-((3-tert-butyl-1-(3-chlorophenyl)-1H-pyrazol-5-yl)methyl)-2-(3-fluoro-4-((2-methoxyethoxy)methyl)phenyl)propanamide (115 mg; 70%, white solid; TLC system: EtOAc/$CHCl_3$ (1:9), $R_f$: 0.5).

Synthesis of Example A117

N-[[5-tert-Butyl-2-(3-chlorophenyl)-2H-pyrazol-3-yl]-methyl]-2-[3-fluoro-4-(2-hydroxy-ethoxy-methyl)-phenyl]-propionamide

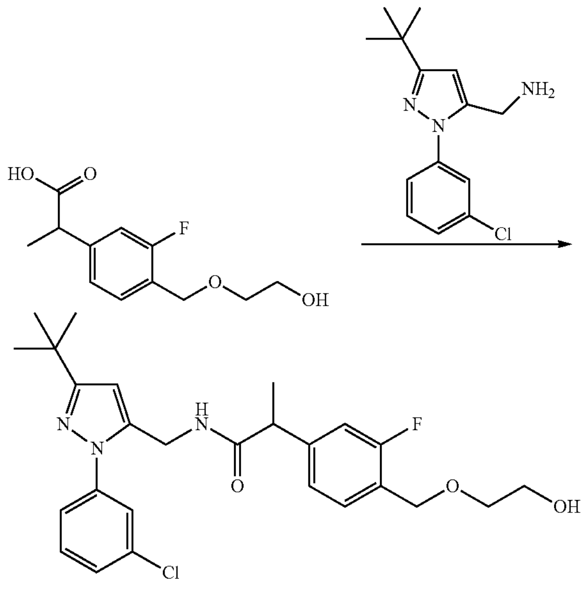

To a stirred THF/DMF (2.0 mL/0.1 mL) solution of 2-(3-fluoro-4-((2-hydroxyethoxy)methyl)phenyl)propanoic acid (synthesis described for example A118) (60.0 mg, 0.25 mmol, 1.0 eq) DIPEA (0.169 mL, 0.13 mmol, 4.0 eq), TBTU (81 mg, 0.25 mmol, 1 eq) and HOBt (33 mg, 0.25 mmol, 1 eq) were sequentially added at RT and the mixture stirred for 15 min. (3-tert-butyl-1-(3-chlorophenyl)-1H-pyrazol-5-yl)methanamine (65 mg, 0.25 mmol, 1 eq) was then added and the mixture stirred for 36 h. After completion of the reaction the solvent was evaporated. The crude product was purified by CC using EtOAc/cyclohexane (1:1) to get N-((3-tert-butyl-1-(3-chlorophenyl)-1H-pyrazol-5-yl)methyl)-2-(3-fluoro-4-((2-hydroxyethoxy)methyl)phenyl)-propanamide (106 mg; 87%).

Synthe
sis of Example A118

N-[[2-(3-Chlorophenyl)-5-(trifluoromethyl)-2H-pyrazol-3-yl]-methyl]-2-[3-fluoro-4-(2-hydroxy-ethoxy-methyl)-phenyl]-propionamide

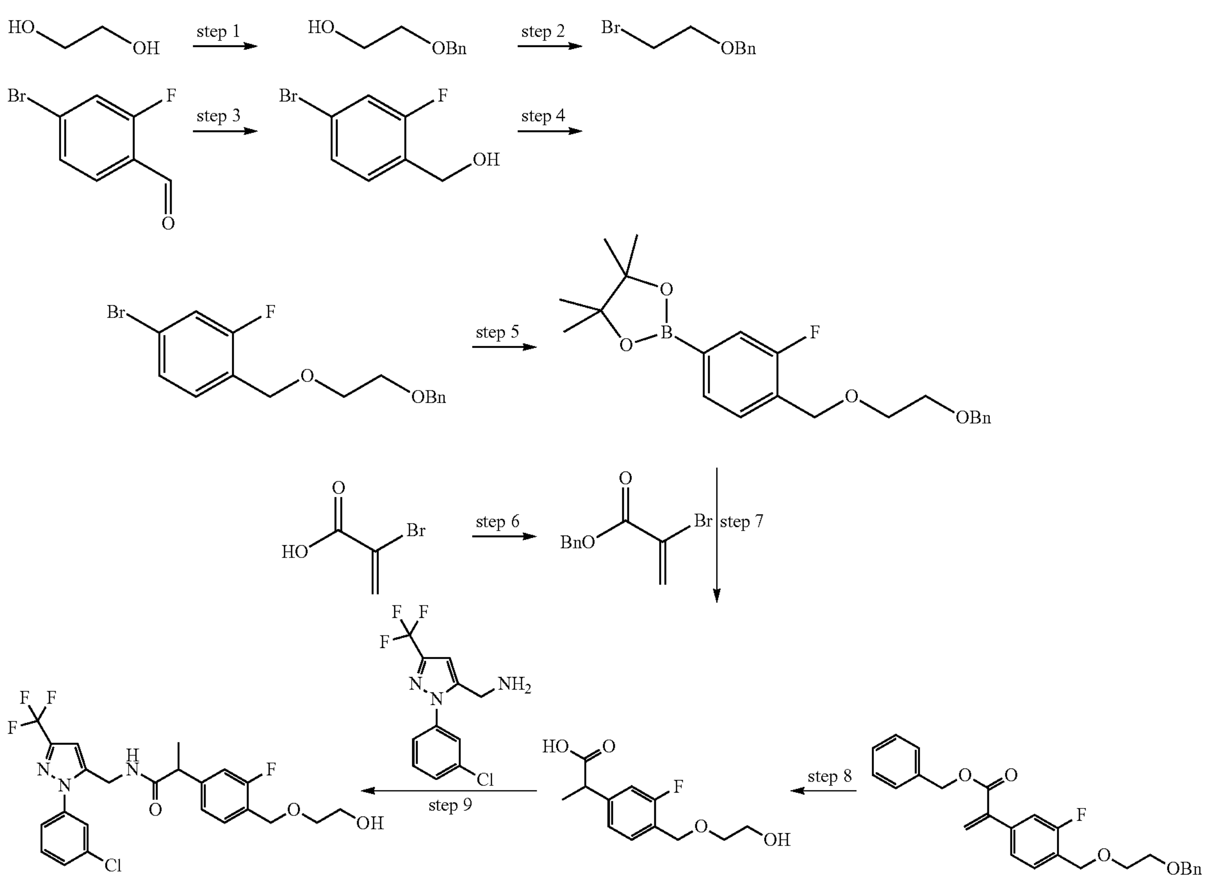

Step 1: To a solution of diethylengylcole (30 g, 483.87 mmol) in THF (300 mL) at 0° C., a 60% suspension of NaH (9.67 g, 241.93 mmol) was slowly added in portions which was followed by the addition of benzyl bromide (28.9 mL, 241.93 mmol) after which the suspension was stirred at RT for 16 h until complete consumption of starting material, as evidenced by TLC analysis. The reaction mixture was then diluted with ice cold water (100 mL), extracted with EtOAc (3×250 mL) and the combined EtOAc layers were washed with brine (50 mL), dried over anhydrous $NaSO_4$, filtered and concentrated. The obtained crude compound was purified by CC using 25% EtOAc in PE as eluent to afford 2-(benzyloxy)ethanol (25 g, 34%) as pale yellow liquid (TLC solvent system: 40% EtOAc in PE; $R_f$: 0.3).

Step 2: To a stirred solution of 2-(benzyloxy)ethanol (17.0 g, 111.84 mmol) and $PPh_3$ (35.0 g, 134.21 mmol) in DCM (170 mL) at −10° C. to −5° C., NBS (23.88 g, 134.21 mmol) was added slowly in portions maintaining the temperature at −10° C. to −5° C. After addition, the reaction mixture was allowed to stir at RT for 1 h until complete consumption starting material, as evidenced by TLC analysis. The reaction mixture was concentrated, the obtained crude compound was purified by CC using 5% EtOAc in PE as eluent to afford ((2-bromoethoxy)methyl)benzene (13.5 g, 56.2%) as pale yellow liquid (TLC solvent system: 30% EtOAc in PE; $R_f$: 0.7).

Step 3: To a stirred solution of 4-Bromo-2-fluoro benzaldehyde (15 g, 79.36 mmol) in MeOH (100 mL) at −5° C. to 0° C. was added $NaBH_4$ (6.0 g, 158.73 mmol) in equal portions and stirred at RT for 1 h until the starting material was completely consumed, as evidenced by TLC analysis. The reaction mixture was then diluted with ice cold water (100 mL) and concentrated under reduced pressure. The residue obtained on concentration was extracted with EtOAc (2×200 mL) and separated. The combined EtOAc layers were washed with brine solution (50 mL), dried over anhydrous $NaSO_4$, filtered and concentrated to afford (4-bromo-2-fluorophenyl)methanol (30 g, 99% (from 2 batches))] as colorless oil (TLC solvent system: 30% EtOAc in PE; $R_f$: 0.3).

Step 4: To a stirred solution of (4-bromo-2-fluorophenyl) methanol (5 g, 24.509 mmol) in DMF (50 mL) at 0° C. NaH (60% suspension in mineral oil, 1.96 g, 49.018 mmol) was added in portions. To the resulting suspension ((2-bromoethoxy)methyl)benzene (6.32 g, 29.41 mmol) was added at 0° C., and the reaction mixture was allowed to stir at RT for 16 h until complete consumption of (4-bromo-2-fluorophenyl) methanol, as evidenced by TLC analysis. The reaction mixture was quenched with MeOH (5 mL), diluted with ice cold water (50 mL) and was extracted with EtOAc (3×100 mL). The combined EtOAc layer was washed with water (50 mL), brine (50 mL), dried over anhydrous $NaSO_4$, filtered and concentrated. The obtained crude compound was purified by CC using 5% EtOAc in PE as eluent to afford 1-((2-(benzyloxy)ethoxy)methyl)-4-bromo-2-fluorobenzene (4.2 g, 51%) as yellow liquid (TLC solvent system: 30% EtOAc in PE; $R_f$: 0.6).

Step 5: A suspension of 1-((2-(benzyloxy)ethoxy) methyl)-4-bromo-2-fluorobenzene (14.0 g, 41.297 mmol), bis-pinacolatodiborone (20.9 g, 82.59 mmol), $CH_3COOK$ (8.09 g, 82.59 mmol) in 1,4-dioxane (50 mL) was deoxygenated by purging with a stream of argon for 30 min to which $Pd(PPh_3)_2Cl_2$ (2.89 g, 4.129 mmol) was added and purging was continued for further 10 min. The reaction mixture was stirred at 100° C. for 30 h until complete consumption of 1-((2-(benzyloxy)ethoxy)methyl)-4-bromo-2-fluorobenzene, as evidenced by TLC analysis. The reaction mixture was concentrated and the obtained crude compound was purified by column chromatography (60-120 mesh florosil) using 5% EtOAc in PE as eluent to afford 2-(4-((2-(benzyloxy)ethoxy)methyl)-3-fluorophenyl)-4,4,5,5-tetramethyl-1,3,2-dioxaborolane (12.5 g, 79%) as a pale yellow oil (TLC solvent system: 30% EtOAc in PE; $R_f$: 0.45).

Step 6: A suspension of 2-bromoacrylic acid (25.0 g, 166.66 mmol), benzyl bromide (21.8.0 mL, 183.32 mmol) and $K_2CO_3$ (46 g, 333.32 mmol) in acetonitrile (250 mL) was stirred at 80° C. for 3 h until complete consumption of 2-bromoacrylic acid, as evidenced by TLC analysis. The reaction mixture was filtered and concentrated. The obtained crude compound was purified by CC using 5% EtOAc in PE as eluent to afford benzyl 2-bromoacrylate (22 g, 53%) as a yellow liquid (TLC solvent system: 5% EtOAc in PE; $R_f$: 0.7).

Step 7: A suspension of 2-(4-((2-(benzyloxy)ethoxy) methyl)-3-fluorophenyl)-4,4,5,5-tetramethyl-1,3,2-dioxaborolane (16 g, 41.45 mmol), $Cs_2CO_3$ (40.5 g, 124.35 mmol) in DMF (150 ml) was deoxygenated by purging argon for 30 min at RT and $Pd(dppf)Cl_2$ (1.69 g, 2.072 mmol) was added and purging continued. After 10 min, benzyl 2-bromoacrylate (15.7 g, 62.17 mmol) was added and stirred at 100° C. for 1 h until complete consumption of 2-(4-((2-(benzyloxy) ethoxy)methyl)-3-fluorophenyl)-4,4,5,5-tetramethyl-1,3,2-dioxaborolane, as evidenced by TLC analysis. The reaction mixture was diluted with ethyl acetate (300 mL), filtered through a Celite and washed with ethyl acetate (2×50 mL). The combined filtrate was washed with water (3×200 mL), brine (50 mL), dried over anhydrous $NaSO_4$, filtered and concentrated. The obtained crude compound was purified by CC using 10% ethyl acetate in PE as eluent to afford benzyl 2-(4-((2-(benzyloxy)ethoxy)methyl)-3-fluorophenyl)acrylate (2.8 g, 16%) as pale brown oil (TLC solvent system: 10% EtOAc in PE; $R_f$: 0.3).

Step 8: A suspension of benzyl 2-(4-((2-(benzyloxy) ethoxy)methyl)-3-fluorophenyl)acrylate (2.2 g, 5.23 mmol), 10% $Pd(OH)_2$ (300 mg) in EtOAc (20 mL) was hydrogenated (balloon pressure) at RT for 2 h until complete consumption of benzyl 2-(4-((2-(benzyloxy)ethoxy) methyl)-3-fluorophenyl)acrylate, as evidenced by TLC analysis. The reaction mixture was filtered through Celite, washed with MeOH (2×15 mL). The combined filtrate was concentrated and the obtained crude compound was purified by dissolving in EtOAc (30 mL) and shaken with aq 10% $NaHCO_3$ solution (12 mL). The EtOAc layer was separated; the aq layer was acidified with aq. citric acid solution (pH~5) and extracted with EtOAc (2×30 mL). The combined EtOAc layer was washed with water (10 mL), brine (10 mL) dried over anhydrous $NaSO_4$, filtered and concentrated to afford 2-(3-fluoro-4-((2-hydroxyethoxy)methyl) phenyl)propanoic acid (450 mg, 36%) as colorless oil (TLC solvent system: 100% EtOAc; $R_f$: 0.15).

Step 9: To a stirred DCM (5.0 mL) solution of 2-(3-fluoro-4-((2-hydroxyethoxy)methyl)-phenyl)propanoic (116.0 mg, 0.481 mmol, 1.0 eq) DIPEA (0.34 mL, 1.924 mmol, 4.0 eq), EDC.HCl (76.5 mg, 0.4 mmol, 1.2 eq) and HOBt (61.0 mg, 0.4 mmol, 1.2 eq) were sequentially added at RT and stirred for 15 min. (1-(3-chlorophenyl)-3-(trifluoromethyl)-1H-pyrazol-5-yl)methanamine (150 mg, 0.481 mmol, 1 eq) was then added and the RM stirred for 3 h. After completion of the reaction the RM was washed with $H_2O$ (20 mL), brine (10 mL), separated, dried ($Na_2SO_4$) and evaporated. The crude product was purified CC using EtOAc/PE (55:45) to get N-((1-(3-chlorophenyl)-3-(trifluoromethyl)-1H-pyrazol-5-yl)methyl)-2-(3-fluoro-4-((2-hydroxyethoxy)methyl)phenyl)propanamide (85 mg; 35%, pale yellow semi solid; TLC system: EtOAc/PE (4:1) $R_f$: 0.3).

Synthesis of Example A124

N-((3-tert-butyl-1-(4-fluorophenyl)-1H-pyrazol-5-yl) methyl)-2-(3-fluoro-4-((2-hydroxyethoxy)methyl) phenyl)propanamide

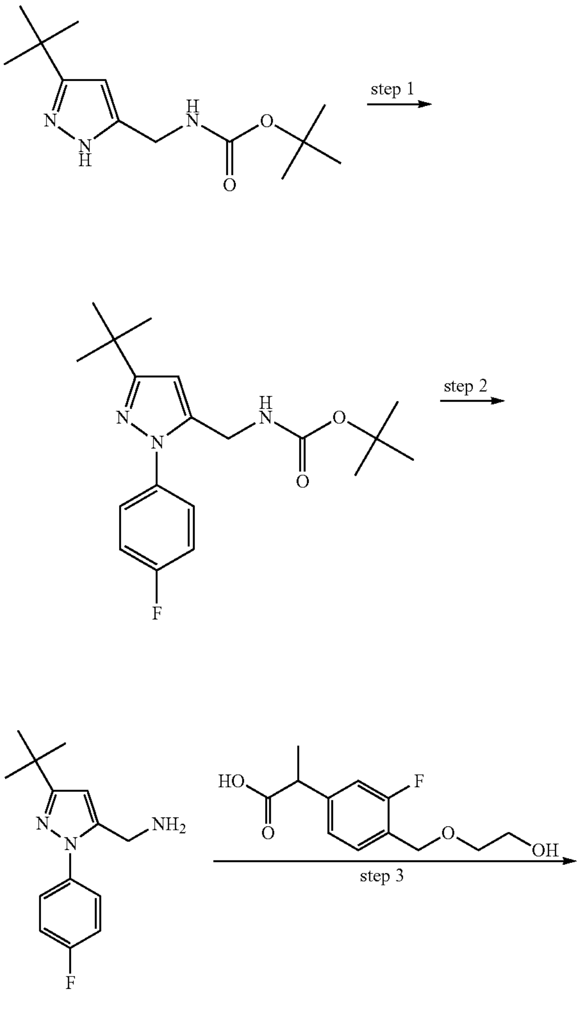

-continued

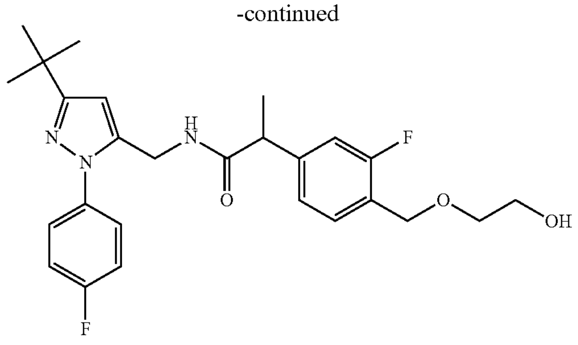

Step 1: To a mixture of tert-butyl (3-tert-butyl-1H-pyrazol-5-yl)methylcarbamate (501 mg, 1.98 mmol, 1 equiv.), 4-fluorophenylboronic acid (554 mg, 3.96 mmol, 2 equiv.) and copper acetate (541 mg, 2.97 mmol, 1.5 equiv.) in dichloromethane (30 mL) was added pyridine (315 mg, 0.315 mL, 3.96 mmol, 2 equiv) and the mixture was stirred in the presence of air for 2 d at room temperature. The reaction mixture was filtered over silica gel, the filter cake was washed with dichloromethane (250 mL) and the solvent of the filtrate was evaporated to give tert-butyl (3-tert-butyl-1-(4-fluorophenyl)-1H-pyrazol-5-yl)methylcarbamate (232 mg, 34%).

Step 2: In 3 mL of dichloromethane, tert-butyl (3-tert-butyl-1-(4-fluorophenyl)-1H-pyrazol-5-yl)methylcarbamate (232 mg, 0.668 mmol, 1 equiv.) was dissolved and trifluoroacetic acid (0.496 mg, 0.331 ml, 6.5 equiv.) was added. The reaction mixture was stirred overnight at room temperature, extracted with aqueous sodium carbonate (c=1 mol/L), dried over magnesium sulfate and evaporated to give (3-tert-butyl-1-(4-fluorophenyl)-1H-pyrazol-5-yl) methanamine (127 mg) which was used without further purification.

Step 3: To a stirred solution of (3-tert-butyl-1-(4-fluorophenyl)-1H-pyrazol-5-yl)methanamine (60 mg, 0.25 mmol, 1.0 eq) in THF/DMF (1120, v/v, 2 mL) was added 2-(3-fluoro-4-((2-hydroxyethoxy)methyl)phenyl)propanoic acid (61 mg, 0.25 mmol, 1 equiv.), HOBt (35 mg. 0.25 mmol, 1 equiv.), TBTU (80 mg, 0.25 mmo, 1 equiv.) and DIPEA (0.168 mL, 127 mg, 1.01 mmol, 4 equiv.) and the mixture was stirred for 3 d at room temperature. The reaction mixture was evaporated and the residue was purified by column chromatography (EtOAc/cyclohexane (1:2) as eluent) to give N-((3-tert-butyl-1-(4-fluorophenyl)-1H-pyrazol-5-yl) methyl)-2-(3-fluoro-4-((2-hydroxyethoxy)methyl)phenyl) propanamide (93 mg, 78%).

Synthesis of Example A125

N-((3-tert-butyl-1-(3-(trifluoromethoxy)phenyl)-1H-pyrazol-5-yl)methyl)-2-(3-fluoro-4-((2-hydroxyethoxy)methyl)phenyl)propanamide

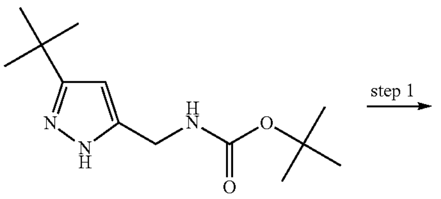

-continued

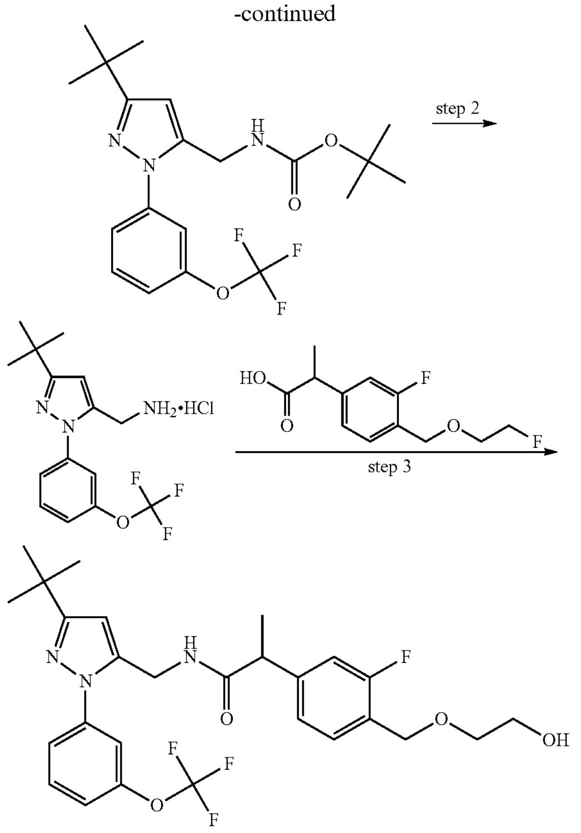

Step 1: To a mixture tert-butyl (3-tert-butyl-1H-pyrazol-5-yl)methylcarbamate (501 mg, 1.98 mmol, 1 equiv.), 3-(trifluoromethoxy)-phenylboronic acid (814 mg, 3.96 mmol, 2 equiv.) and copper acetate (541 mg, 2.97 mmol, 1.5 equiv.) in dichloromethane (30 mL) was added pyridine (315 mg, 0.315 mL, 3.96 mmol, 2 equiv.) and the mixture was stirred in the presence of air for 2 d at room temperature. The reaction mixture was filtered over silica gel, the filter cake was washed with dichloromethane (250 mL) and the solvent of the filtrate was evaporated to give tert-butyl (3-tert-butyl-1-(3-(trifluoromethoxy)phenyl)-1H-pyrazol-5-yl)methylcarbamate (294 mg, 36%).

Step 2: In 4.7 mL of dioxane, tert-butyl (3-tert-butyl-1-(3-(trifluoromethoxy)phenyl)-1H-pyrazol-5-yl)methylcarbamate (294 mg, 0.711 mmol, 1 equiv.) was dissolved and hydrogen chloride in dioxane (1.16 mL, c=4 mol/L, 4.62 mmo, 6.5 equiv.) was added. The reaction mixture was stirred overnight at room temperature: The suspension was evaporated and the product was precipitated in ether/pentane (7 mL, 1/2.5, v/v). The precipitate was filtered out, washed with n-pentane (2x5 mL) and dried to (3-tert-butyl-1-(3-(trifluoromethoxy)phenyl)-1H-pyrazol-5-yl)methanamine hydrochloride (119 mg, 48%).

Step 3: To a stirred solution of (3-tert-butyl-1-(3-(trifluoromethoxy)phenyl)-1H-pyrazol-5-yl)methanamine hydrochloride (119 mg, 0.351 mmol, 1 eq) in THF/DMF (1/20, v/v, 3 mL) was added 2-(3-fluoro-4-((2-hydroxyethoxy) methyl)phenyl)propanoic acid (84 mg, 0.35 mmol, 1 equiv.), HOBt (49 mg. 0.35 mmol, 1 equiv.), TBTU (112 mg, 0.351 mmo, 1 equiv.) and DIPEA (0.234 mL, 178 mg, 1.40 mmol, 4 equiv.) and the mixture was stirred for at room temperature overnight. The reaction mixture was evaporated and the residue was purified by column chromatography (EtOAc/cyclohexane (1:2) as eluent) to give N-((3-tert-butyl-1-(3-

(trifluoromethoxy)phenyl)-1H-pyrazol-5-yl)methyl)-2-(3-fluoro-4-((2-hydroxyethoxy)methyl)phenyl)propanamide (137 mg, 73%).

Synthesis of Example A126

N-((1-(3,5-difluorophenyl)-3-(trifluoromethyl)-1H-pyrazol-5-yl)methyl)-2-(3-fluoro-4-((2-hydroxy-ethoxy)methyl)phenyl)propanamide

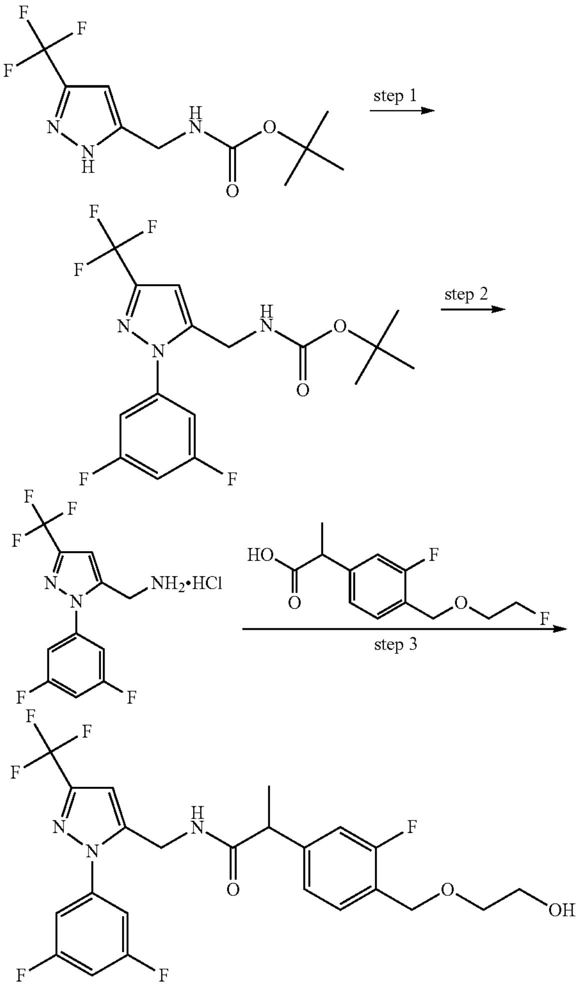

Step 1: To a mixture tert-butyl (3-(trifluoromethyl)-1H-pyrazol-5-yl)methylcarbamate (251 mg, 0.946 mmol, 1 equiv.), 3,5-difluorophenylboronic acid (299 mg, 1.89 mmol, 2 equiv.) and copper acetate (258 mg, 1.49 mmol, 1.5 equiv.) in dichloromethane (14 mL) was added pyridine (151 mg, 0.151 mL, 1.89 mmol, 2 equiv) and the mixture was stirred in the presence of air for 2 d at room temperature. The reaction mixture was filtered over silica gel, the filter cake was washed with dichloromethane (250 mL) and the solvent of the filtrate was evaporated to give tert-butyl (1-(3,5-difluorophenyl)-3-(trifluoromethyl)-1H-pyrazol-5-yl)methylcarbamate (214 mg, 60%).

Step 2: In 4 mL of dioxane, tert-butyl (1-(3,5-difluorophenyl)-3-(trifluoromethyl)-1H-pyrazol-5-yl)methylcarbamate (214 mg, 0.567 mmol, 1 equiv.) was dissolved and hydrogen chloride in dioxane (0.923 mL, c=4 mol/L, 3.69 mmo, 6.5 equiv.) was added. The reaction mixture was stirred overnight at room temperature, the precipitate was filtered out, washed with dioxane (2×15 m L) and dried to give (1-(3,5-difluorophenyl)-3-(trifluoromethyl)-1H-pyrazol-5-yl)methanamine hydrochloride (139 mg, 78%).

Step 3: To a stirred solution of (1-(3,5-difluorophenyl)-3-(trifluoromethyl)-1H-pyrazol-5-yl)methanamine hydrochloride (16 mg, 0.050 mmol, 1.0 eq) in THF/DMF (1/20, v/v, 0.5 mL) was added 2-(3-fluoro-4-((2-hydroxyethoxy)methyl)phenyl)propanoic acid (11 mg, 0.050 mmol, 1 equiv.), HOBt (7 mg. 0.05 mmol, 1 equiv.), TBTU (16 mg, 0.050 mmo, 1 equiv.) and DIPEA (0.033 mL, 25 mg, 0.20 mmol, 4 equiv.) and the mixture was stirred for at room temperature overnight. The solvent of the reaction mixture was evaporated and the residue was purified by column chromatography (EtOAc/cyclohexane (1:1) as eluent) to give N-((1-(3,5-difluorophenyl)-3-(trifluoromethyl)-1H-pyrazol-5-yl)methyl)-2-(3-fluoro-4-((2-hydroxyethoxy)methyl)phenyl)propanamide (23 mg, 92%).

Synthesis of Example A127

1-[[2-(3-Chlorophenyl)-5-(trifluoromethyl)-2H-pyrazol-3-yl]-methyl]-3-[3-fluoro-4-(2-hydroxy-ethoxy-methyl)-phenyl]-urea

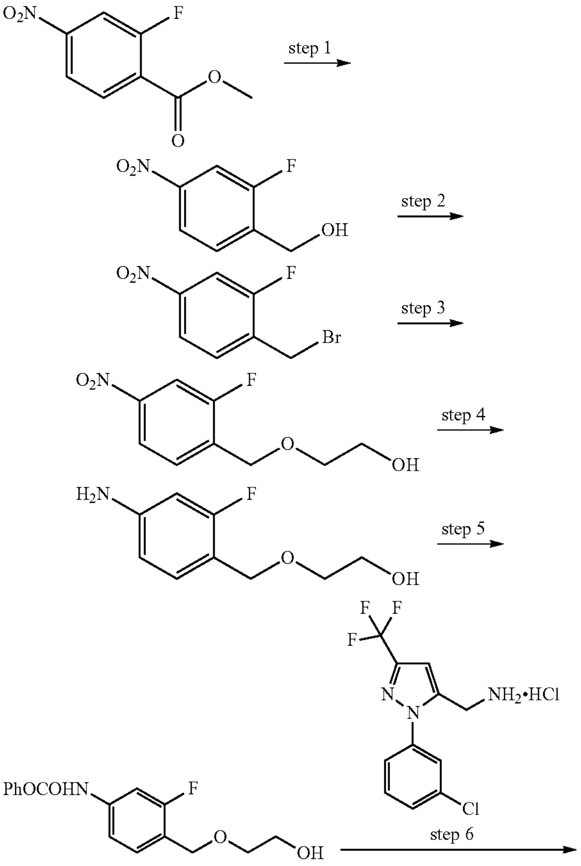

-continued

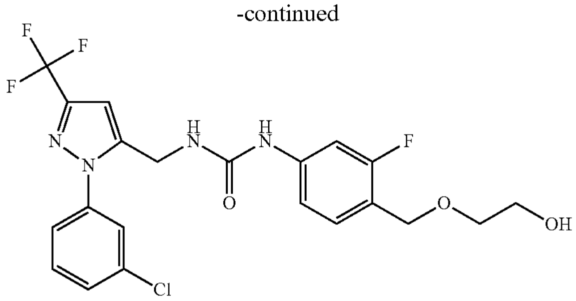

Step 1: as described for example A59, step 1

Step 2: To a cooled (0° C.) and stirred solution of DCM (100 mL) containing (2-fluoro-4-nitrophenyl)methanol (9 g, 52.6 mmol, 1 eq), triphenylphosphine (16.5 g, 63.1 mmol, 1.2 eq) was added followed by addition of NBS (11.24 g, 63.1 mmol, 1.2 eq), the mixture was allowed to warm to RT and stirred for 2 h. The DCM was evaporated under reduced pressure and the residue was purified by CC using PE/EtOAc (9:1) as eluent to get 1-(bromomethyl)-2-fluoro-4-nitrobenzene (10.50 g, 85%; TLC system: PE/EtOAc (7:3), $R_f$: 0.6).

Step 3: To a cooled (0° C.) suspension of 60% NaH (1.39 g, 57.8 mmol, 1.5 eq) in ethylene glycol (90 mL) 1-(bromomethyl)-2-fluoro-4-nitrobenzene (9.0 g, 38.6 mmol, 1 eq) was added and the mixture was stirred at RT for 16 h. The reaction mixture was diluted with water (100 mL) and extracted with EtOAc (30 mL×2). The ethyl acetate layers were collected and dried ($Na_2SO_4$) and evaporated under vacuum. The residue was purified by CC using PE/EtOAc (7:3) as eluent to get 2-(2-fluoro-4-nitrobenzyloxy)ethanol (5 g, 67%, oil; TLC system: PE/EtOAc (3:2), $R_f$: 0.3).

Step 4: To a stirred THF (50 mL) solution of 2-(2-fluoro-4-nitrobenzyloxy)ethanol (5.0 g, 1.0 eq) 10% Pd/C was added and reaction mixture stirred under $H_2$ gas balloon at for 16 h. The reaction mixture was passed through celite pad and the solvent evaporated. The residue was purified by CC using PE/EtOAc (3:2) as eluent to get 2-(4-amino-2-fluorobenzyloxy)ethanol (3.0 g, 60%, solid; TLC system: EtOAc/PE (3:2), $R_f$: 0.3).

Step 5: To a stirred solution of 2-(4-amino-2-fluorobenzyloxy)ethanol (2.5 g, 13.5 mmol, 1 eq) in acetone (25 mL) pyridine (3.26 mL, 40.5 mmol, 3 eq) was added followed by phenyl chloroformate (1.7 mL, 13.5 mmol, 1 eq) at 0° C. and the mixture was stirred at RT for 1 h. The solvent was evaporated and resulting residue was purified by CC using ethyl acetate/PE (7:13) as eluent to get 2-(4-(benzoyloxyamino)-2-fluorobenzyloxy)ethanol (2.8 g, 70%, white solid; TLC system: EtOAc/PE (1:1), $R_f$: 0.4).

Step 6: To a stirred solution of (1-(3-chlorophenyl)-3-(trifluoromethyl)-1H-pyrazol-5-yl)methanamine hydrochloride (102 mg, 0.327 mmol, 1.0 eq) in DCM (2.0 mL) was added $Et_3N$ (0.09 mL, 0.654 mmol, 2.0 eq) followed by 2-(4-(benzoyloxyamino)-2-fluorobenzyloxy)ethanol (100 mg, 0.327 mmol, 1.0 eq) at RT and stirred for 16 h. The reaction mixture washed with water (2 mL) and the solvent evaporated to get 1-((1-(3-chlorophenyl)-3-(trifluoromethyl)-1H-pyrazol-5-yl)methyl)-3-(3-fluoro-4-((2-hydroxyethoxy)-methyl)phenyl)urea (80 mg; 50%, off-white solid; TLC system: EtOAc/PE (3:2), $R_f$: 0.2).

Synthesis of Example A128

1-[[2-(3-Chlorophenyl)-5-(trifluoromethyl)-2H-pyrazol-3-yl]-methyl]-3-[3-fluoro-4-(2-methoxy-ethoxy-methyl)-phenyl]-urea

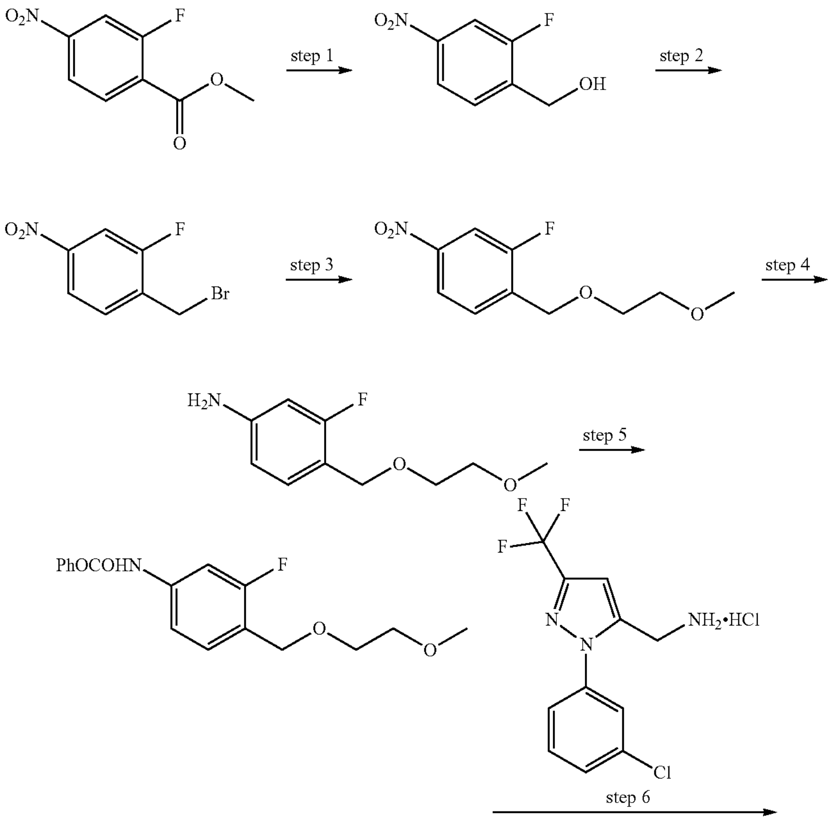

-continued

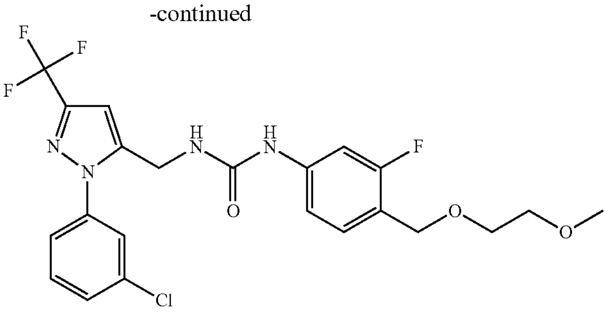

Step 1: as described for example A59, step 1

Step 2: as described for example A127, step 2

Step 3: To a suspension of $K_2CO_3$ (8.8 g, 64.0 mmol, 1.5 eq) in methoxyethanol (100 mL) was added 1-(bromomethyl)-2-fluoro-4-nitrobenzene (10.0 g, 42.0 mmol, 1 eq) and the mixture was stirred at RT for 5 h. The reaction mixture was diluted with water (100 mL) and extracted with EtOAc (30 mL×2). The ethyl acetate layers were collected and dried ($Na_2SO_4$) and evaporated under vacuum. The residue was purified by CC using PE/EtOAc (17:3) as eluant to get 2-fluoro-1-((2-methoxyethoxy)methyl)-4-nitrobenzene (4 g, 40%) as oil (TLC system: PE/EtOAc (7:3), $R_f$: 0.5).

Step 4: To a stirred solution of 2-fluoro-1-((2-methoxyethoxy)methyl)-4-nitrobenzene (4.0 g, 1.0 eq) in THF (50 mL) was added 10% Pd—C and the reaction mixture was stirred under $H_2$ gas balloon at for 16 h. The reaction mixture was passed through celite pad and the solvent evaporated to get 3-fluoro-4-((2-methoxyethoxy)methyl)aniline (2.50 g, 72%) as solid (TLC system: EtOAc/PE (1:1), $R_f$: 0.3).

Step 5: To a stirred solution of 3-fluoro-4-((2-methoxyethoxy)methyl)aniline (2.5 g, 13.0 mmol, 1 eq) in acetone (25 mL) was added pyridine (3.15 mL, 39.0 mmol, 3 eq) followed by phenyl chloroformate (1.64 mL, 13.0 mmol, 1 eq) at 0° C. and the mixture was stirred at RT for 1 h. The solvent was evaporated and resulting residue was purified by CC using ethyl acetate/PE (3:7) as eluent to get O-benzoyl-N-(3-fluoro-4-((2-methoxyethoxy)methyl)phenyl)-hydroxylamine as white solid (TLC system: EtOAc/PE (1:1), $R_f$: 0.4).

Step 6: To a stirred solution of (1-(3-chlorophenyl)-3-(trifluoromethyl)-1H-pyrazol-5-yl)methanamine hydrochloride (80 mg, 0.256 mmol, 1.0 eq) in DCM (2.0 mL) was added TEA (0.07 mL, 0.512 mmol, 2.0 eq) followed by O-benzoyl-N-(3-fluoro-4-((2-methoxyethoxy)methyl)phenyl)hydroxylamine (80.1 mg, 0.256 mmol, 1.0 eq) at RT and the mixture was stirred for 16 h. The separated solid was filtered, washed with DCM (2 mL) to get 1-((1-(3-chlorophenyl)-3-(trifluoromethyl)-1H-pyrazol-5-yl)methyl)-3-(3-fluoro-4-((2-methoxy-ethoxy)methyl)phenyl)urea (70 mg; 55%, white solid) (TLC system: EtOAc/PE (3:2); $R_f$: 0.2)

Synthesis of Example A1 29

1-[[5-tert-Butyl-2-(3-chlorophenyl)-2H-pyrazol-3-yl]-methyl]-3-[3-fluoro-4-(2-hydroxy-ethoxy-methyl)-phenyl]-urea

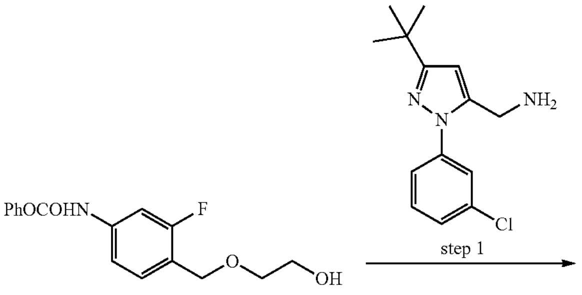

-continued

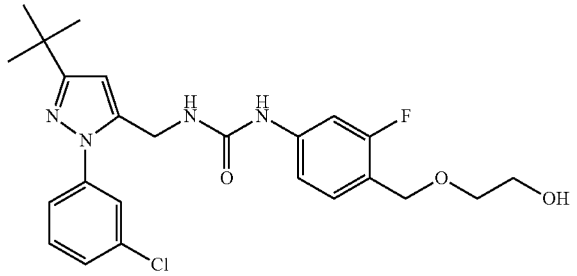

Step 1: To a stirred solution of ((3-tert-butyl-1-(3-chlorophenyl)-1H-pyrazol-5-yl)methanamine (108 mg, 0.409 mmol, 1.0 eq) in MeCN (7 mL) was added TEA (0.266 mL, 0.1:64 mmol, 4.0 eq) followed by 2-(4-(benzoyloxyamino)-2-fluorobenzyloxy)ethanol (133 mg, 0.438 mmol, 1.07 eq) at reflux and stirred for 16 h. The solvent was evaporated and the residue was purified by CC (EtOAc/hexane 2:1) to get 1-((3-tert-butyl-1-(3-chlorophenyl)-1H-pyrazol-5-yl) methyl)-3-(3-fluoro-4-((2-hydroxyethoxy)methyl)phenyl) urea (96 mg; 49%).

Synthesis of Example A133

1-[[2-(2,3-Dichloro-phenyl)-5-(trifluoromethyl)-2H-pyrazol-3-yl]-methyl]-3-[3-fluoro-4-(2-hydroxy-ethoxy-methyl)-phenyl]-urea

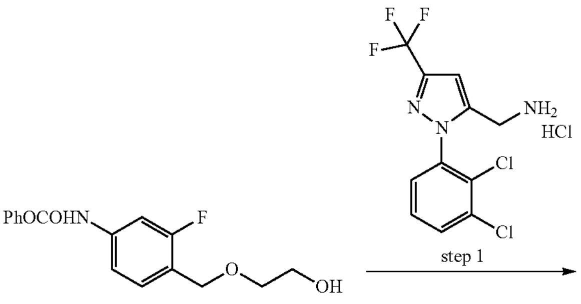

-continued

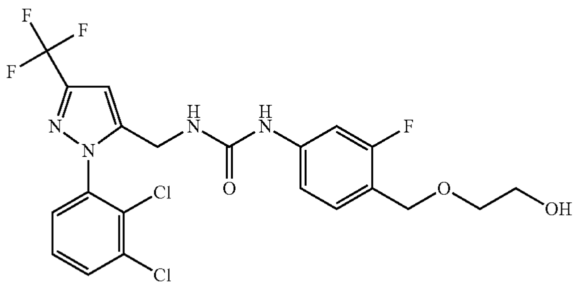

Step 1: To a stirred solution (1-(2,3-dichlorophenyl)-3-(trifluoromethyl)-1H-pyrazol-5-yl)methanamine hydrochloride (101 mg, 0.291 mmol, 1.0 eq) in MeCN (7 mL) was added TEA (0.266 mL, 0.164 mmol, 4.0 eq) followed by 2-(4-(benzoyloxyamino)-2-fluorobenzyloxy)ethanol (90 mg, 0.297 mmol, 1.07 eq) at reflux and the mixture was stirred for 16 h. The solvent was evaporated and the residue was purified by CC (EtOAc/cyclohexane 2:1) to get 1-((1-(2,3-dichlorophenyl)-3-(trifluoromethyl)-1H-pyrazol-5-yl)methyl)-3-(3-fluoro-4-((2-hydroxyethoxy)methyl)phenyl)urea (101 mg; 67%).

Synthesis of Example A134

1-((3-tert-butyl-1-(4-fluorophenyl)-1H-pyrazol-5-yl)methyl)-3-(3-fluoro-4-((2-hydroxyethoxy)methyl)phenyl)urea

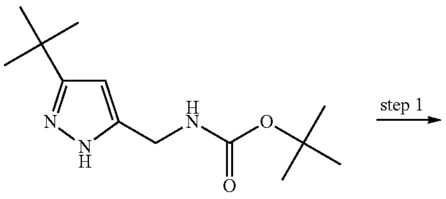

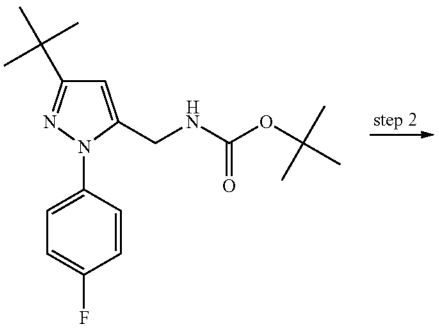

-continued

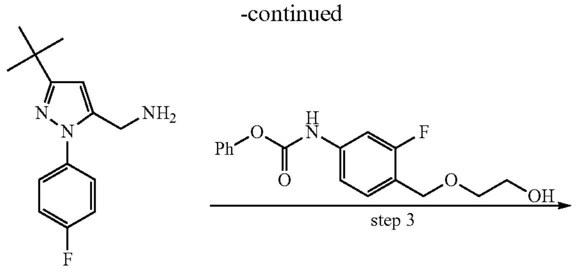

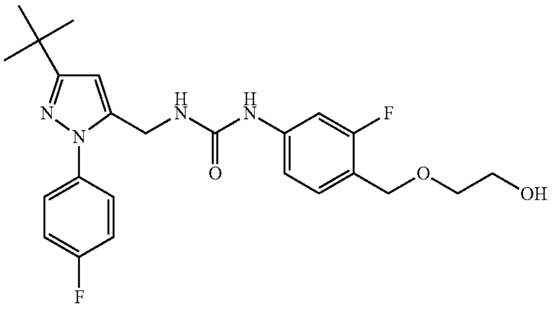

Step 1: To a mixture of tert-butyl (3-tert-butyl-1H-pyrazol-5-yl)methylcarbamate (501 mg, 1.98 mmol, 1 equiv.), 4-fluorophenylboronic acid (554 mg, 3.96 mmol, 2 equiv.) and copper acetate (541 mg, 2.97 mmol, 1.5 equiv.) in dichloromethane (30 mL) was added pyridine (315 mg, 0.315 mL, 3.96 mmol, 2 equiv) and the mixture was stirred in the presence of air for 2 d at room temperature. The reaction mixture was filtered over silica gel, the filter cake was washed with dichloromethane (250 mL) and the solvent of the filtrate was evaporated to give tert-butyl (3-tert-butyl-1-(4-fluorophenyl)-1H-pyrazol-5-yl)methylcarbamate (232 mg, 34%).

Step 2: In 3 mL of dichloromethane, tert-butyl (3-tert-butyl-1-(4-fluorophenyl)-1H-pyrazol-5-yl)methylcarbamate (232 mg, 0.668 mmol, 1 equiv.) was dissolved and trifluoroacetic acid (0.496 mg, 0.331 mml, 6.5 equiv.) was added. The reaction mixture was stirred overnight at room temperature, extracted with aqueous sodium carbonate (c=1 mol/L), dried over magnesium sulfate and evaporated to give (3-tert-butyl-1-(4-fluorophenyl)-1H-pyrazol-5-yl)methanamine (127 mg) which was used without further purification.

Step 3: To a stirred solution of (3-tert-butyl-1-(4-fluorophenyl)-1H-pyrazol-5-yl)methanamine (60 mg, 0.247 mmol, 1.0 eq) in acetonitrile (6 mL) was added TEA (0.136 mL, 99 mg, 0.986 mmol, 4.0 eq) followed by phenyl 3-fluoro-4-((2-hydroxyethoxy)methyl)-phenylcarbamate (76 mg, 0.252 mmol, 1.02 eq.) and stirred at reflux for 16 h. The solvent of the reaction mixture was evaporated and the residue was purified by column chromatography (EtOAc/cyclohexane (1:2)) to get 1-((3-tert-butyl-1-(4-fluorophenyl)-1H-pyrazol-5-yl)methyl)-3-(3-fluoro-4-((2-hydroxyethoxy)methyl)phenyl)urea (83 mg, 73%).

Synthesis of Example A135

1-((1-(3-ethoxy-5-methylphenyl)-3-(trifluoromethyl)-1H-pyrazol-5-yl)methyl)-3-(3-fluoro-4-((2-hydroxyethoxy)methyl)phenyl)urea

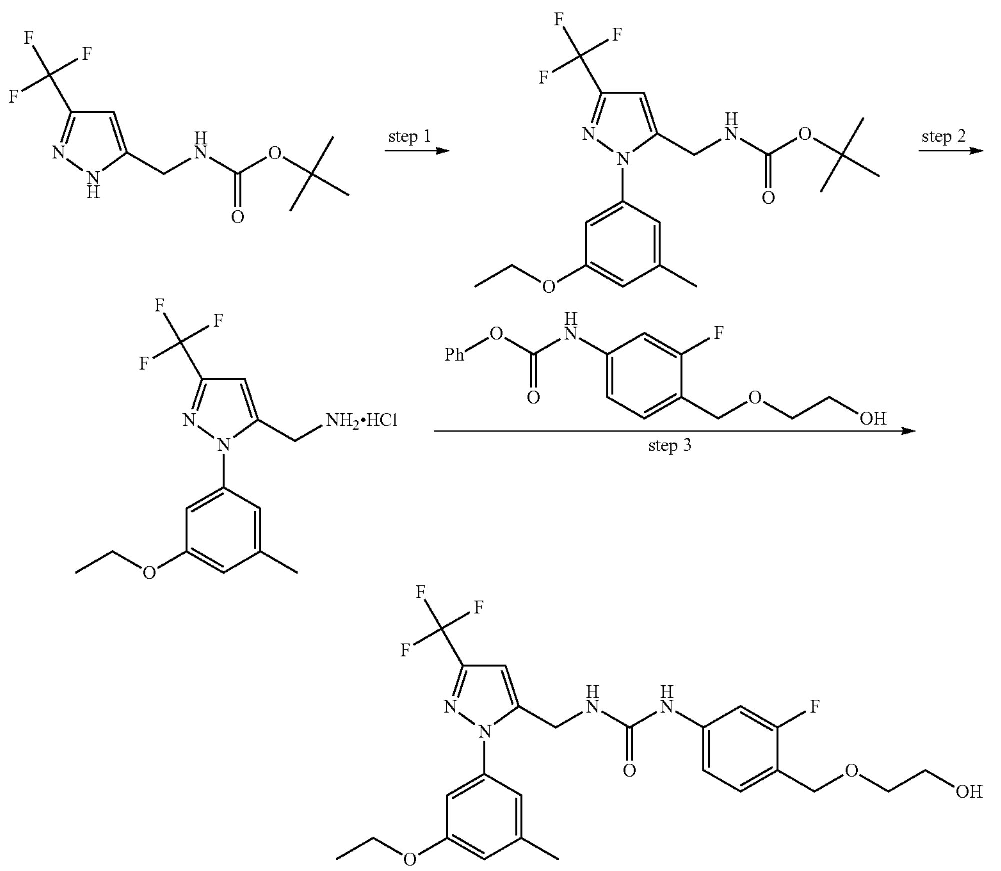

Step 1: To a mixture of dioxane, tert-butyl (3-(trifluoromethyl)-)-1H-pyrazol-5-yl)methylcarbamate (251 mg, 0.947 mmol, 1 equiv.), 3-ethoxy-5-methylphenylboronic acid (341 mg, 1.89 mmol, 2 equiv.) and copper acetate (259 mg, 1.42 mmol, 1.5 equiv.) in dichloromethane was added pyridine (151 mg, 0.151 mL, 1.89 mmol, 2 equiv) and the mixture was stirred for 2 d at room temperature. The reaction mixture was filtered over silica gel, the filter cake was washed with 250 mL of dichloromethane and the filtrate was evaporated to give tert-butyl (1-(3-ethoxy-5-methylphenyl)-3-(trifluoromethyl)-1H-pyrazol-5-yl)methylcarbamate (354 mg, 94%).

Step 2: In 6 mL of dioxane, tert-butyl (1-(3-ethoxy-5-methylphenyl)-3-(trifluoromethyl)-1H-pyrazol-5-yl)methylcarbamate (354 mg, 0.886 mmol) was dissolved and hydrogen chloride in dioxane (1.44 mL, c=4 mol/L, 5.76 mml, 6.5 equiv.) was added. The reaction mixture was stirred overnight and filtered, the filter cake was washed with dioxane (2×15 mL) and dried to give (1-(3-ethoxy-5-methylphenyl)-3-(trifluoromethyl)-1H-pyrazol-5-yl)methanamine hydrochloride (211 mg, 71%).

Step 3: To a stirred solution of (1-(3-ethoxy-5-methylphenyl)-3-(trifluoromethyl)-1H-pyrazol-5-yl)methanamine hydrochloride (100 mg, 0.300 mmol, 1.0 eq) in acetonitrile (7 mL) was added TEA (0.166 mL, 1.20 mmol, 4.0 eq) followed by phenyl 3-fluoro-4-((2-hydroxyethoxy)methyl)-phenylcarbamate (93 mg, 0.306 mmol, 1.02 eq) and stirred at reflux for 16 h. The solvent of the reaction mixture was evaporated and the residue was purified by column chromatography (EtOAc/cyclohexane (1:1)) to get 1-((1-(3-ethoxy-5-methyl phenyl)-3-(trifluoromethyl)-1H-pyrazol-5-yl) methyl)-3-(3-fluoro-4-((2-hydroxyethoxy)methyl)phenyl) urea (60 mg, 39%).

Synthesis of Example A140

1-[[5-tert-Butyl-2-(3-chlorophenyl)-2H-pyrazol-3-yl]-methyl]-3-[3-fluoro-4-(2-hydroxy-ethyl)-phenyl]-urea

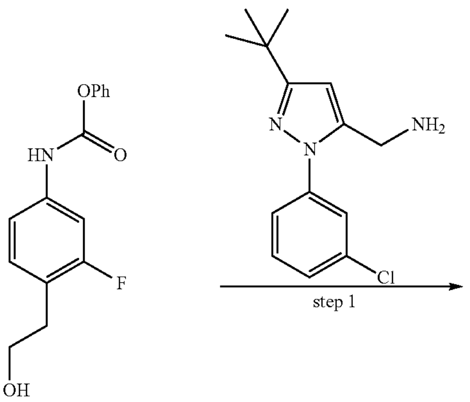

-continued

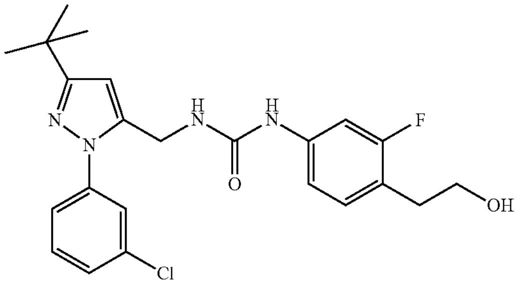

Step 1: To a stirred solution of (3-tert-butyl-1-(3-chlorophenyl)-1H-pyrazol-5-yl)methanamine (synthesis described for example A141) (102 mg, 0.387 mmo, 1.0 eq) in MeCN (9 mL) was added TEA (0.214 mL, 1.55 mmol, 4.0 eq) followed by phenyl 3-fluoro-4-(2-hydroxyethyl)phenylcarbamate (108 mg, 0.395 mmol, 1.02 eq) and the mixture was stirred for 16 h at reflux. The reaction mixture was concentrated under vacuum and the residue purified by CC using EtOAc/hexane (2:1) as eluent to get 1-((3-tert-butyl-1-(3-chlorophenyl)-1H-pyrazol-5-yl)methyl)-3-(3-fluoro-4-(2-hydroxyethyl)phenyl)urea (159 mg; 92%, white solid).

Synthesis of Example A138

N-[[2-(3-Chlorophenyl)-5-(trifluoromethyl)-2H-pyrazol-3-yl]-methyl]-2-[3-fluoro-4-(2-hydroxy-ethyl)-phenyl]-propionamide

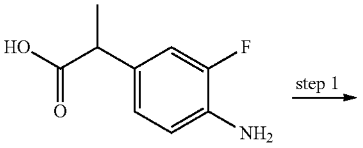

1

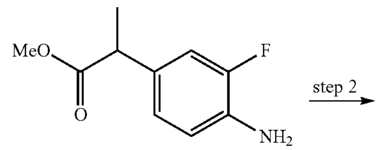

2

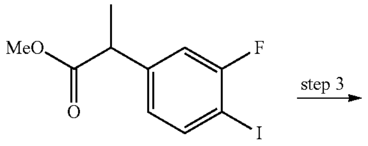

3

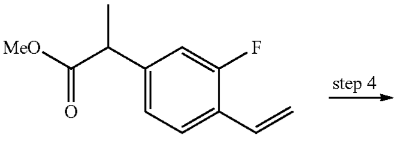

4

-continued

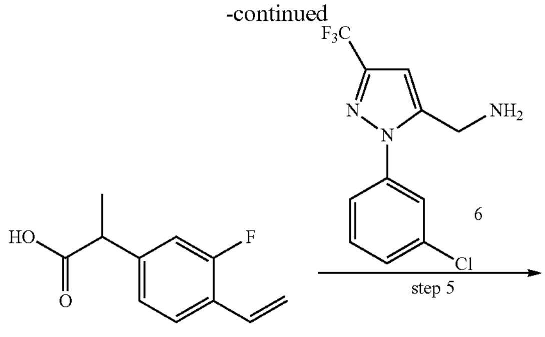

5

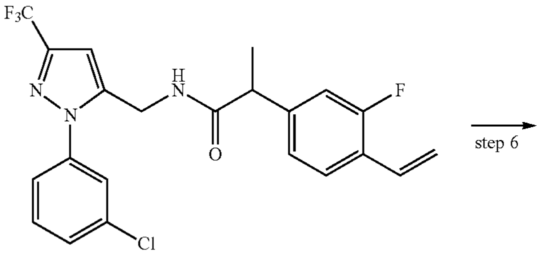

7

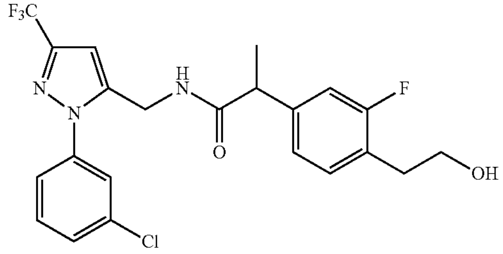

8

Step 1: To a stirred solution of 1 (2.5 g, 13.7 mmol) in 25 mL of methanol, under ice-cooling, was added thionyl chloride (1.5 mL, 20.5 mmol) dropwise over 10 minutes. After stirring the reaction mixture for 2 h, methanol is distilled out and 30 mL of water is added. The separated ester is extracted with ethyl acetate and washed with 15 mL of saturated sodium bicarbonate solution, and brine. Drying ($Mg_2SO_4$) and evaporation of the ethyl acetate and purification by CC yielded (2.23 g) as yellow oil by 83% yield.

Step 2: To a solution of p-TsOH.$H_2O$ (6.45 g, 34 mmol) in MeCN (20 mL) was added 2 (11.3 mmol). The resulting suspension was cooled to 10-15° C. and to this was added, gradually, a solution of $NaNO_2$ (1.56 g, 22.6 mmol) and KI (4.69 g, 28.3 mmol) in $H_2O$. The reaction mixture was stirred for 10 min then allowed to come to 20° C. and stirred until the starting material was consumed. To the reaction mixture was then added $H_2O$ (50 mL), $NaHCO_3$ (1 M; until pH=9-10) and $Na_2S_2O_3$ (2M, 10 mL). The precipitated aromatic iodide as filtered out and the mixture extracted with EtOAc and purified by column chromatography to yield 3 (1.43 g) as yellow oil by 42% yield.

Step 3: A 100-mL round-bottom flask containing $Pd(PPh_3)_4$ (0.231 mmol), LiCl (5.56 mmol) and DMF (15.00 mL) was purged with nitrogen gas several times. To the flask were then added 3 (4.63 mmol) and tributyl(vinyl)tin (5.56 mmol). The reaction mixture was stirred at room temperature for 15 h. The reaction mixture was then treated with 10 mL of saturated $CsF_2$ solution and allowed to stir for 30 min at ambient temperature, filtered through Celite and silica gel, and diluted with 50 mL (3 times) of EtOAc. The organic layer was washed with water, dried ($Mg_2SO_4$) and concentrated in vacuo. The residue was purified by CC using EtOAc/n-hexane as solvent system to give the desired product 4 as yellow oil by 83% yield (800 mg).

Step 4: To a solution of 4 (800 mg, 3.84 mmol) in THF (5 mL) was added a 10 mL mixture solvents of THF and $H_2O$ (1:1), and $LiOH.H_2O$ (403 mg, 9.61 mmol). The reaction mixture was stirred at room temperature for 2 h. To the reaction mixture was then added $H_2O$ (50 mL), the mixture was cooled, and acidified by diluted HCl to a pH of 1-2. The mixture is extracted with ethyl acetate. The organic layer was washed with water, dried ($Mg_2SO_4$) and concentrated in vacuo. 5 (748 mg) was obtained as yellow oil by 99% yield. The product was carried on to next step without further purification Step 5: A solution of the carboxylic acid 5 (748 mg, 3.85 mmol) in DCM was cooled in an ice-bath and EDC (1.05 equiv), HOBt (1.05 equiv), TEA (3 equiv), and 6 (1 equiv) were added consecutively. The reaction mixture was stirred overnight at room temperature. Water was added to the reaction mixture and it was extracted with DCM. The combined organic extracts were washed successively with saturated $NaHCO_3$ solution (30 mL), 0.5 N HCl (30 mL), and then water (30 mL), and dried over $Mg_2SO_4$. Evaporation of the solvent followed by CC purification afforded 7 (1.04 g) as off white solid by 60% yield.

Step 6: Compound 7 (259 mg, 0.59 mmol) in 2M $BH_3.SMe_2$ in THF (0.53 mL) was stirred for 1 h at 0° C., then 1 h at ambient temperature. A solution of 1N NaOH (1.6 mL) was added to the reaction mixture at 0° C., then a solution of 30% $H_2O_2$ (1.2 mL) was added. The mixture was stirred 30 min at 0° C., then 30 min at ambient temperature. Ethyl acetate (30 mL) was added, the organic layer was separated, washed with water (30 mL), saturated $NaCO_3$ (30 mL), saturated NaCl (30 mL) and dried over $Na_2SO_4$. After evaporation of the solvent in vacuo, the crude product was purified by CC to afford 8 (131 mg) as a white solid by 47% yield.

$^1H$ NMR (300 MHz, $CDCl_3$): δ 7.37-7.45 (m, 3H), 7.29 (t, J=2.01 Hz, 1H), 7.21 (d, J=7.68 Hz, 1H), 6.91-6.95 (m, 2H), 6.41 (s, 1H), 5.57 (s, NH), 4.45-4.48 (dd, $J_1$=5.67 Hz, $J_2$=2.67 Hz, 2H), 3.50 (t, J=7.32 Hz, 1H), 2.90 (t, J=6.96 Hz, 1H), 1.84 (t, J=6.78 Hz, 2H), 1.48 (d, J=7.14 Hz, 3H).

Synthesis of Example A141

1-[[2-(3-Chlorophenyl)-5-(trifluoromethyl)-2H-pyrazol-3-yl]-methyl]-3-[3-fluoro-4-(2-hydroxy-ethyl)-phenyl]-urea

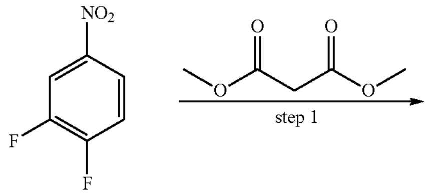

-continued

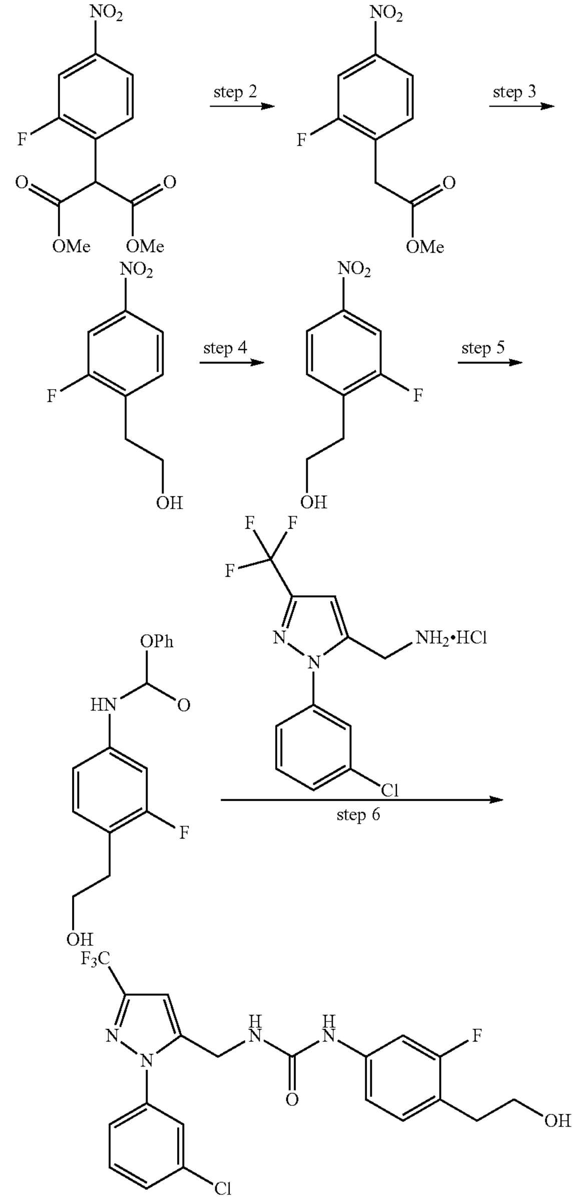

Step 1: To a stirred solution of dimethyl malonate (6.22 g, 47.1 mmol, 1.5 eq) in DMF (30 mL) was added $K_2CO_3$ (8.70 g, 63 mmol, 2.0 eq) and heated to 50° C. for 30 min when 1,2-difluoro-4-nitrobenzene (5.0 g, 31.4 mmol, 1.0 eq) was added and the reaction mixture was stirred for 5 h at 50° C. The reaction mixture was cooled to RT, filtered to remove $K_2CO_3$, and the DMF was evaporated under vacuum. The residue was diluted with EtOAc (100 mL), washed with water, brine, dried over $Na_2SO_4$ and evaporated to get dimethyl 2-(2-fluoro-4-nitrophenyl)malonate (6.5 g, 76%) as a solid (TLC system: EtOAc/PE (3:7), $R_f$: 0.50).

Step 2: To a stirred solution of dimethyl 2-(2-fluoro-4-nitrophenyl)malonate (5.0 g, 18.5 mmol, 1.0 eq) in DMSO (30 mL) was added NaCl (1.07 g, 18.5 mmol, 1.0 eq) and water (0.5 mL) and stirred at 120° C. for 3 h. The reaction mixture was diluted with water (100 mL), extracted with EtOAc (50 mL×2), washed with brine, dried over $Na_2SO_4$ and the solvent evaporated. The crude residue was purified by CC using PE/EtOAc (19:1) to get methyl 2-(2-fluoro-4- nitrophenyl)acetate (2.5 g, 64%) as a viscous oil (TLC system: EtOAc/PE (1:4), $R_f$: 0.55).

Step 3: To a stirred solution of methyl 2-(2-fluoro-4-nitrophenyl)acetate (3.0 g, 14.0 mmol, 1.0 eq) in methanol (30 mL) was added $NaBH_4$ (2.08 g, 36.3 mmol, 4.0 eg) at 0° C. and stirred at 70° C. for 16 h, then the methanol was evaporated and the residue was diluted with water (30 mL), the pH adjusted to being neutral with 2N HCl and the mixture extracted with EtOAc (50 mL×3). The organic layer was separated, washed with brine, dried over $Na_2SO_4$ and the solvent evaporated to yield 2-(2-fluoro-4-nitrophenyl) ethanol (2.0 g, 77%) as a viscous oil (TLC system: EtOAc/PE (3:7), $R_f$: 0.3).

Step 4: To a stirred solution of 2-(2-fluoro-4-nitrophenyl) ethanol (200 mg, 0.94 mmol, 1.0 eq) in ethanol (10 mL) was added 10% Pd/C (50 mg) and the mixture was stirred under a $H_2$ gas balloon at RT for 5 h. The reaction mixture was passed through a celite bed and the solvent of the filtrate evaporated to get 2-(4-amino-2-fluorophenyl)ethanol (130 mg, 75%) as a viscous oil (TLC system: EtOAc/PE (1:1), $R_f$: 0.2).

Step 5: To a stirred solution of 2-(4-amino-2-fluorophenyl)ethanol (1.3 g, 8.38 mmol, 1.0 eq) in acetone (50 mL) was added pyridine (1.32 g, 16.7 mmol, 2.0 eq) and phenyl chloroformate (1.45 g, 9.23 mmol, 1.1 eq) at 0° C. and the mixture was stirred at RT for 2 h. The solvent was evaporated, the residue diluted with EtOAc (50 mL), washed with water (100 mL) followed by brine and the solvent evaporated. The resulting residue was purified by CC using EtOAc/PE (1:4) to get phenyl 3-fluoro-4-(2-hydroxyethyl) phenylcarbamate (1.5 g, 65%, white solid). (TLC system: EtOAc/PE (1:1), $R_f$: 0.3).

Step 6: To a stirred solution of (1-(3-chlorophenyl)-3-(trifluoromethyl)-1H-pyrazol-5-yl)methanamine hydrochloride (227 mg, 0.73 mmol, 1.0 eq) in THF (10 mL) was added TEA (147 mg, 1.45 mmol, 2.0 eq) followed by phenyl 3-fluoro-4-(2-hydroxyethyl)phenylcarbamate (200 mg, 0.73 mmol, 1.0 eq) at RT and the mixture was stirred for 16 h. The reaction mixture was concentrated under vacuum and the residue purified by CC using neutral alumina and EtOAc/PE (3:2) as eluent), followed by preparative HPLC to get 1-((1-(3-chlorophenyl)-3-(trifluoromethyl)-1H-pyrazol-5-yl)methyl)-3-(3-fluoro-4-(2-hydroxyethyl)phenyl)urea (150 mg; 45%, white solid; TLC system: EtOAc/PE (3:2); $R_f$: 0.2).

Synthesis of Example A151

1-[[2-(3-Chlorophenyl)-5-(trifluoromethyl)-2H-pyrazol-3-yl]-methyl]-3-[4-(1,2-dihydroxy-ethyl)-3-fluoro-phenyl]-urea

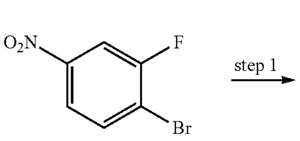

1

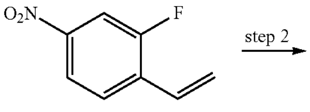

2

-continued

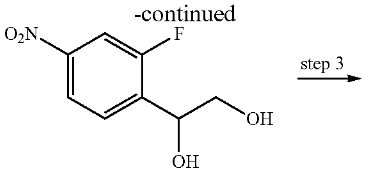

3

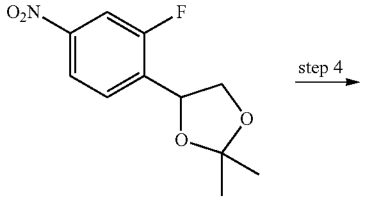

4

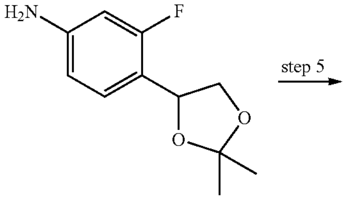

5

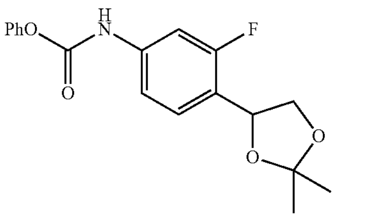

6

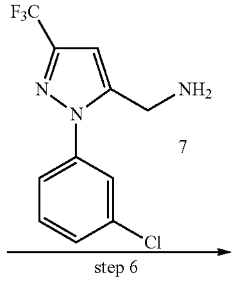

7

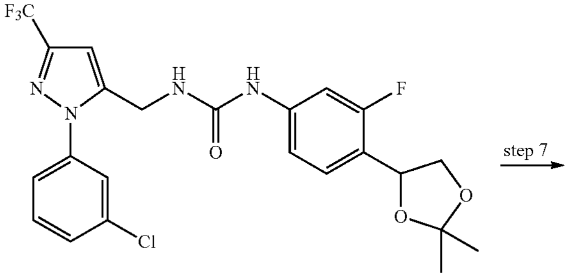

8

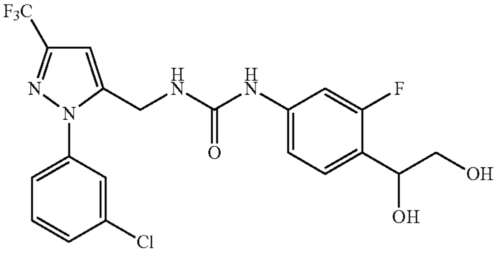

9

Step 1: To a stirred solution of 1 (1 g, 4.54 mmol) in anhydrous THF was added lithium chloride (962 mg, 22.7 mmol), $Pd(PPh_3)_4$ (524 mg, 0.454 mmol) and tributylvinyl tin (1.59 mL, 5.45 mmol) at room temperature. The reaction mixture was stirred overnight under reflux. The reaction mixture was cooled to room temperature until the reaction was finished. The reaction mixture was filtered on Celite bed, and then the solvent of the filtrate was reduced in vacco. The residue was extracted with EtOAc and washed with water and brine. The organic layer was dried over $MgSO_4$ and filtered. The solvent of the filtrate was removed under low pressure. The crude product was purified by column chromatography to produce 2 (285 mg) with 38% yield.

Step 2: To a stirred solution of 2 (285 mg, 1.70 mmol) in water and acetone as co-solvent was added 0.5% $OsO_4$ in $H_2O$ and 50% NMO in $H_2O$. The reaction mixture was stirred overnight at room temperature. The reaction mixture was diluted with DCM and washed with water and brine. The organic layer was dried over $MgSO_4$ and filtered. The solvent of the filtrate was removed under low pressure. The crude product was purified by column chromatography to afford 3 (262 mg, 76%).

Step 3: To a stirred solution of 3 (262 mg, 1.30 mmol) in DCM was added p-TsOH.$H_2O$ (247 mg, 1.30 mmol) and 2,2-dimethoxypropane (0.32 mL, 2.60 mmol). The reaction mixture was stirred for 2 h at room temperature. The mixture dissolved in DCM and washed with water and brine. The organic layer was dried over $MgSO_4$ and filtered. The solvent of the filtrate was removed under low pressure. The crude product was purified by column chromatography to produce 4 (262 mg, 83%).

Step 4: Starting material 4 (262 mg, 1.09 mmol) was dissolved in MeOH. Pd/C (26 mg) was added to it. The resulting mixture was stirred at room temperature for 2 h under $H_2$. TLC showed complete consumption of starting material. The mixture was filtered through celite bed and the filtrate was concentrated under reduced pressure to afford desired compound 5 (227 mg, 99%).

Step 5: Compound 5 (227 mg, 1.07 mmol) was dissolved in MeCN. The reaction mixture was added to pyridine (0.09 mL, 1.18 mmol) and phenyl chloroformate (0.15 mL, 1.18 mmol) and stirred at room temperature for 3 h. TLC showed complete consumption of starting material. The reaction mixture was diluted with water and extracted with EtOAc. The organic part was washed with water and brine. The organic layer was dried over $MgSO_4$ and concentrated under reduced pressure. The crude product was purified by column chromatography to give pure compound 6 (403 mg, 99%).

Step 6: To a solution of compound 6 (150 mg, 0.45 mmol) in DMF was added DMAP (55 mg, 0.45 mmol) and amine 7 (125 mg, 0.45 mmol) at room temperature. The reaction mixture was heated to 50° C. overnight (about 12-15 h). TLC showed complete consumption of starting material. The reaction mixture was diluted with water and extracted with EtOAc. The organic part was washed with water and brine. The organic layer was dried over $MgSO_4$ and concentrated under reduced pressure. The crude product was purified by CC to produce pure compound 8 (213 mg, 92%).

Step 7: To a stirred solution of 8 (78 mg, 0.20 mmol) in water was added conc. HCl (0.1 mL). The resulting reaction mixture was stirred at ambient temperature for 3 h. TLC showed complete consumption of starting material. The reaction mixture was diluted with water and extracted with EtOAc. The organic part was washed with water and brine. The organic layer was dried over $MgSO_4$ and concentrated under reduced pressure. The crude product was purified by column chromatography to afford desired compound 9 (55 mg, 76%).

$^1H$ NMR (300 MHz, DMSO-$d_6$): δ 8.86 (s, 1H, Ar—NH), 7.76 (s, 1H, Ar—H), 7.63 (m, 3H, Ar—H), 7.36~7.27 (m, 2H, Ar—H), 6.99 (dd, 1H, $J_1$=8.40 Hz, $J_2$=2.40 Hz, Ar—H), 6.80 (m, 2H, Ar—H and $ArCH_2$—NH), 5.25 (d, 1H, J=4.20 Hz, Ar—CH), 4.74 (m, 2H, R—$CH_2$—O), 4.41 (d, 2H, J=5.40 Hz, Ar—$CH_2$).

Synthesis of Example A152

1-[[5-tert-Butyl-2-(3-chlorophenyl)-2H-pyrazol-3-yl]-methyl]-3-[3-fluoro-4-[2-hydroxy-1-(hydroxymethyl)-ethyl]-phenyl]-urea

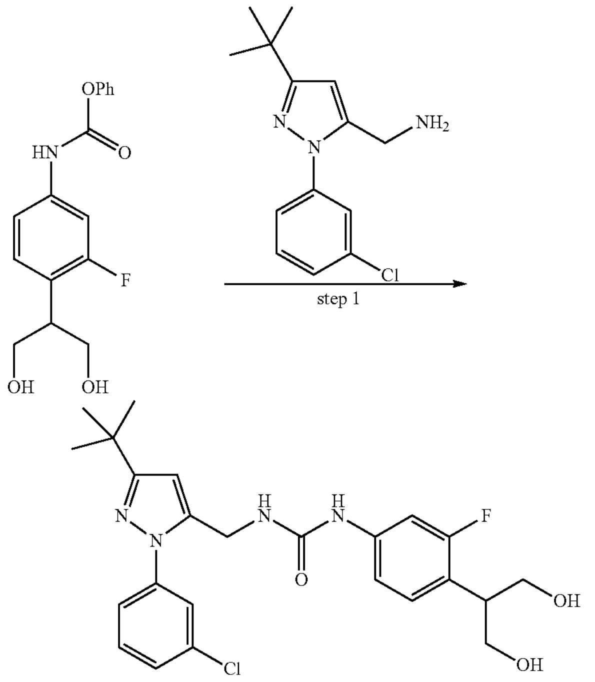

Step 1: To a stirred solution of (3-tert-butyl-1-(3-chlorophenyl)-1H-pyrazol-5-yl)methanamine (synthesis described for example A153) (102 mg, 0.387 mmol, 1.0 eq) in MeCN (9 mL) was added TEA (0.2145 mL, 1.55 mmol, 4.0 eq) followed by phenyl 4-(1,3-dihydroxypropan-2-yl)-3-fluorophenylcarbamate (120 mg, 0.395 mmol, 1.02 eq) at RT and the mixture was stirred at reflux for 16 h. The solvent was evaporated and the crude product was purified by CC using EtOAc as eluent to get 1-((3-tert-butyl-1-(3-chlorophenyl)-1H-pyrazol-5-yl)methyl)-3-(4-(1,3-dihydroxypropan-2-yl)-3-fluorophenyl)urea (162 mg; 88%).

Synthesis of Example A153

1-[[2-(3-Chlorophenyl)-5-(trifluoromethyl)-2H-pyrazol-3-yl]-methyl]-3-[3-fluoro-4-[2-hydroxy-1-(hydroxymethyl)-ethyl]-phenyl]-urea

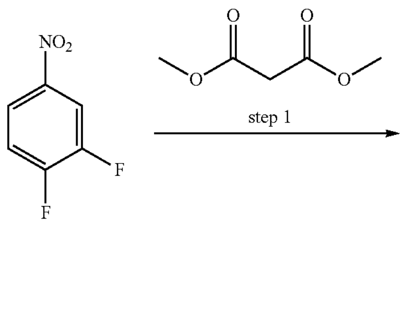

-continued

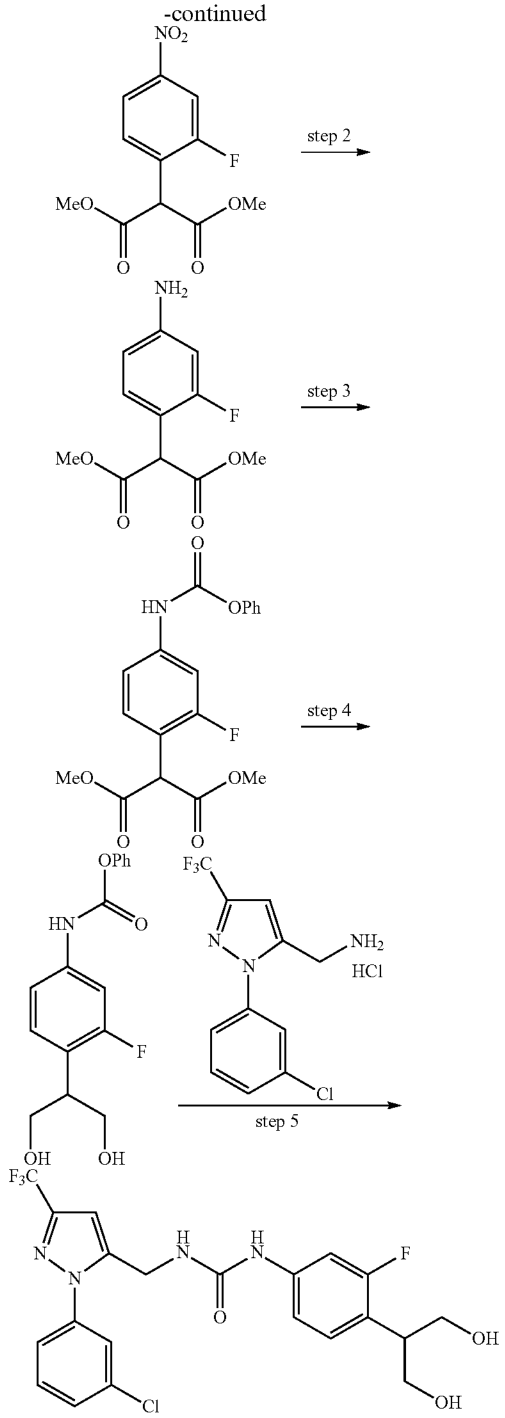

Step 1: as described for example A141, step 1

Step 2: To a stirred ethanol solution (40 mL) of dimethyl 2-(2-fluoro-4-nitrophenyl)malonate (4.0 g, 14.76 mmol, 1.0 eq) 10% Pd—C (400 mg) was added and the mixture was stirred under a $H_2$ gas balloon at RT for 2 h, then the mixture was passed through a celite bed and the solvent of the filtrate was evaporated to get dimethyl 2-(4-amino-2-fluorophenyl) malonate (3.2 g, 87%, solid; TLC system: EtOAc/PE (3:7), $R_f$: 0.3).

Step 3: To a stirred solution of dimethyl 2-(4-amino-2-fluorophenyl)malonate (3.0 g, 12.448 mmol, 1.0 eq) in acetone (30 mL) was added pyridine (3.0 mL, 37.344 mmol, 3.0 eq) and phenyl chloroformate (1.89 mL, 14.937 mmol, 1.2 eq) at 0° C. and the mixture was stirred at RT for 1 h. The solvent was evaporated, the residue diluted with EtOAc (50 mL), washed with water (100 mL), brine (20 mL) and the solvent evaporated. The resulting residue was purified by CC using EtOAc/PE (1:4) as eluent to get dimethyl 2-(2-fluoro-4-(phenoxycarbonylamino)phenyl)malonate (3.5 g, 78%, white solid; TLC system: EtOAc/PE (3:7), $R_f$: 0.5).

Step 4: To a stirred solution of dimethyl 2-(2-fluoro-4-(phenoxycarbonylamino)phenyl)malonate (3.0 g, 8.31 mmol, 1.0 eq) in ethanol (15 mL) and THF (15 mL) was added $NaBH_4$ (621 mg, 16.62 mmol, 2.0 eq) followed by lithium chloride (705 g, 16.62 mmol, 2.0 eq) at 0° C. and the mixture was stirred at 0° C. for 5 h. The solvent was evaporated and the residue diluted with water (30 mL) and extracted with EtOAc (2x50 mL). The organic layer was separated, washed with brine, dried over $Na_2SO_4$ and evaporated. The residue was purified by CC using MeOH/DCM (1:19) as eluent to get phenyl 4-(1,3-dihydroxypropan-2-yl)-3-fluorophenylcarbamate (482 mg, 19%, white solid; TLC system: MeOH/DCM (1:9), $R_f$: 0.6)

Step 5: To a stirred solution of (1-(3-chlorophenyl)-3-(trifluoromethyl)-1H-pyrazol-5-yl)methanamine hydrochloride (153 mg, 0.4918 mmol, 1.0 eq) in DMF (5 mL) was added TEA (0.205 mL, 1.4754 mmol, 3.0 eq) followed by phenyl 4-(1,3-dihydroxypropan-2-yl)-3-fluorophenylcarbamate (150 mg, 0.4918 mmol, 1.0 eq) at RT and the mixture stirred for 16 h. The reaction mixture was diluted with water (10 mL) and extracted with ethyl acetate (15 mL). The organic layer was washed with water (10 mL) and brine (5 mL), dried over anhydrous $Na_2SO_4$, and evaporated under vacuum. The crude product was purified by neutral alumina column chromatography using MeOH/$CHCl_3$ (1:19) as eluent to get 1-((1-(3-chlorophenyl)-3-(trifluoromethyl)-1H-pyrazol-5-yl)methyl)-3-(4-(1,3-dihydroxypropan-2-yl)-3-fluorophenyl)urea (85.5 mg; 36%) as off white solid; TLC system: MeOH/$CHCl_3$ (1:9); $R_f$: 0.5).

Synthesis of Example A154

1-[[2-(3-Chlorophenyl)-5-(trifluoromethyl)-2H-pyrazol-3-yl]-methyl]-3-[3-fluoro-4-[2-hydroxy-1-(hydroxymethyl)-1-methyl-ethyl]-phenyl]-urea

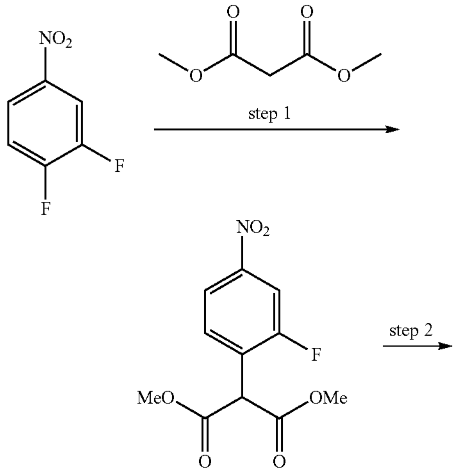

-continued

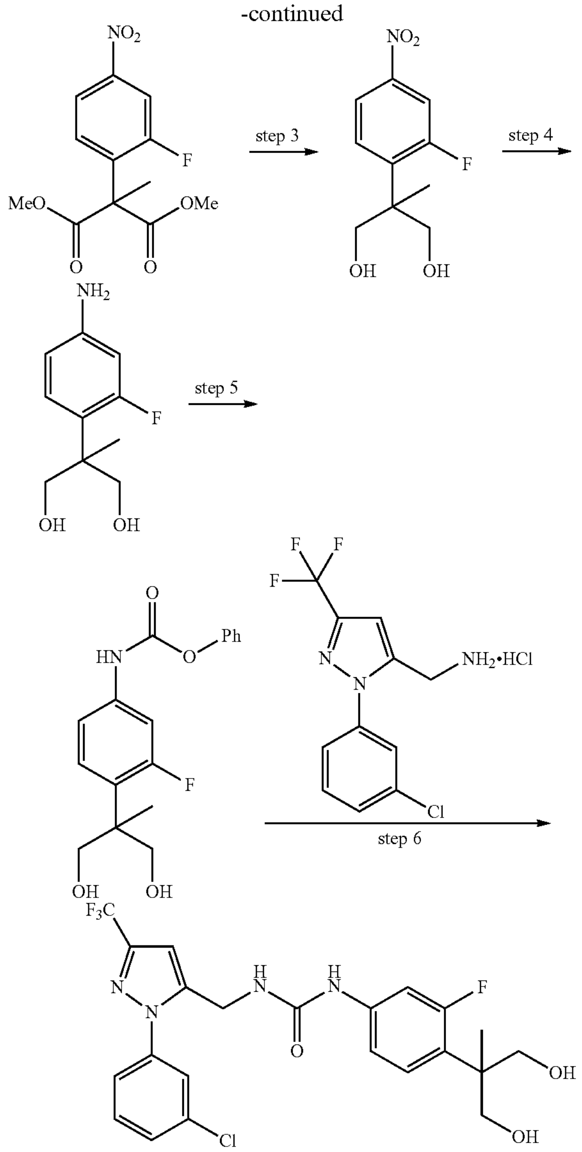

Step 1: as described for example A141, step 1

Step 2: To a stirred solution of dimethyl 2-(2-fluoro-4-nitrophenyl)malonate (200 mg, 0.73 mmol, 1.0 eq) and $K_2CO_3$ (204 mg 1.47 mmol 2.0 eq) in DMF (5 mL), was added methyl iodide (210 mg, 1.47 mmol 2.0 eq) at RT and the mixture was stirred at RT for 6 h. $K_2CO_3$ was filtered out and the filtrate concentrated under vacuum. The residue was diluted with water (50 mL) and extracted with EtOAc (20 mL). The organic layer was separated washed with brine solution, dried over anhydrous $Na_2SO_4$ and the solvent evaporated to get dimethyl 2-(2-fluoro-4-nitrophenyl)-2-methylmalonate (150 mg, 71%; TLC system: EtOAc/PE (1:9), $R_f$: 0.4).

Step 3: To a stirred solution of dimethyl 2-(2-fluoro-4-nitrophenyl)-2-methylmalonate (1.0 g, 3.50 mmol, 1.0 eq) in methanol (20 mL) was added $NaBH_4$ (0.67 gm, 17.63 mmol, 5.0 eq) at 0° C. and stirred at RT for 16 h. The mixture was diluted with water (20 mL), extracted with ethyl acetate (20 mL). The organic layer was washed with brine, dried over anhydrous $Na_2SO_4$, and the solvent was vaporated under reduced pressure. The crude product obtained was purified by CC using EtOAc/PE (2:3) to get 2-(2-fluoro-4-nitrophenyl)-2-methylpropane-1,3-diol (400 mg, 50%; TLC system: EtOAc/PE (1:1), $R_f$: 0.3).

Step 4: To a stirred solution of 2-(2-fluoro-4-nitrophenyl)-2-methylpropane-1,3-diol (100 mg, 0.34 mmol, 1.0 eq) in ethanol was added 10% Pd/C (30 mg) and the mixture was stirred under hydrogen gas balloon atmosphere for 3 h at RT. The reaction mixture was filtered through celite pad and filtrate concentrated under vacuum to get 2-(4-amino-2-fluorophenyl)-2-methylpropane-1,3-diol (65 mg, 76%; TLC system: EtOAc/PE (1:1), $R_f$: 0.4).

Step 5: To a stirred solution of 2-(4-amino-2-fluorophenyl)-2-methylpropane-1,3-diol (1.5 g, 7.53 mmol, 1.0 eq) in acetone (50 mL) was added pyridine (1.2 g, 15.18 mmol, 2.0 eq) and phenyl chloroformate (1.3 g, 8.28 mmol, 1.1 eq) at 0° C. and the mixture was stirred at RT for 1 h. The acetone was evaporated, and the resulting residue was diluted with EtOAc (50 mL), washed with water (100 mL), brine (20 mL) and the solvent evaporated. The crude product was purified by silica CC using EtOAc/PE (3:2) as eluent to get phenyl 4-(1,3-dihydroxy-2-methylpropan-2-yl)-3-fluorophenylcarbamate (1.7 g, 71%) as a white solid (TLC system: EtOAc/PE (7:3), $R_f$: 0.55).

Step 6: To a stirred solution of (1-(3-chlorophenyl)-3-(trifluoromethyl)-1H-pyrazol-5-yl)methanamine hydrochloride (195 mg, 0.62 mmol, 1.0 eq) in DMF (10 mL) was added TEA (190 mg, 1.24 mml, 2.0 eq) followed by phenyl 4-(1,3-dihydroxy-2-methylpropan-2-yl)-3-fluorophenylcarbamate (200 mg, 0.62 mmol, 1.0 eq) at RT and the mixture was stirred for 16 h at 50° C. The reaction mixture was concentrated under vacuum and the residue purified by neutral alumina column chromatography using MeOH/$CHCl_3$ (0.5:9.5) as eluent to get 1-((1-(3-chlorophenyl)-3-(trifluoromethyl)-1H-pyrazol-5-yl)methyl)-3-(4-(1,3-dihydroxy-2-methylpropan-2-yl)-3-fluorophenyl)urea (170 mg; 54%) as a white solid (TLC system: MeOH/$CHCl_3$ (1:9); $R_f$: 0.45).

Synthesis of Example A155

1-[[2-(3-Chlorophenyl)-5-(trifluoromethyl)-2H-pyrazol-3-yl]-methyl]-3-[4-[2-hydroxy-1-(hydroxymethyl)-1-methyl-ethyl]-phenyl]-urea

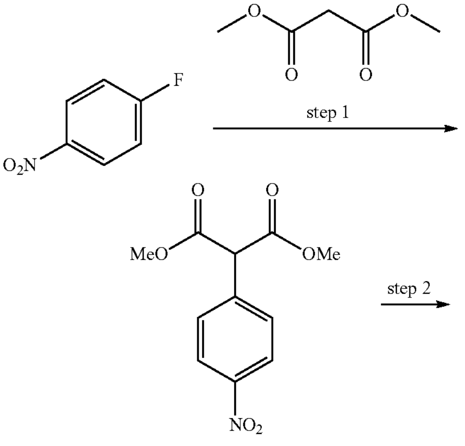

-continued

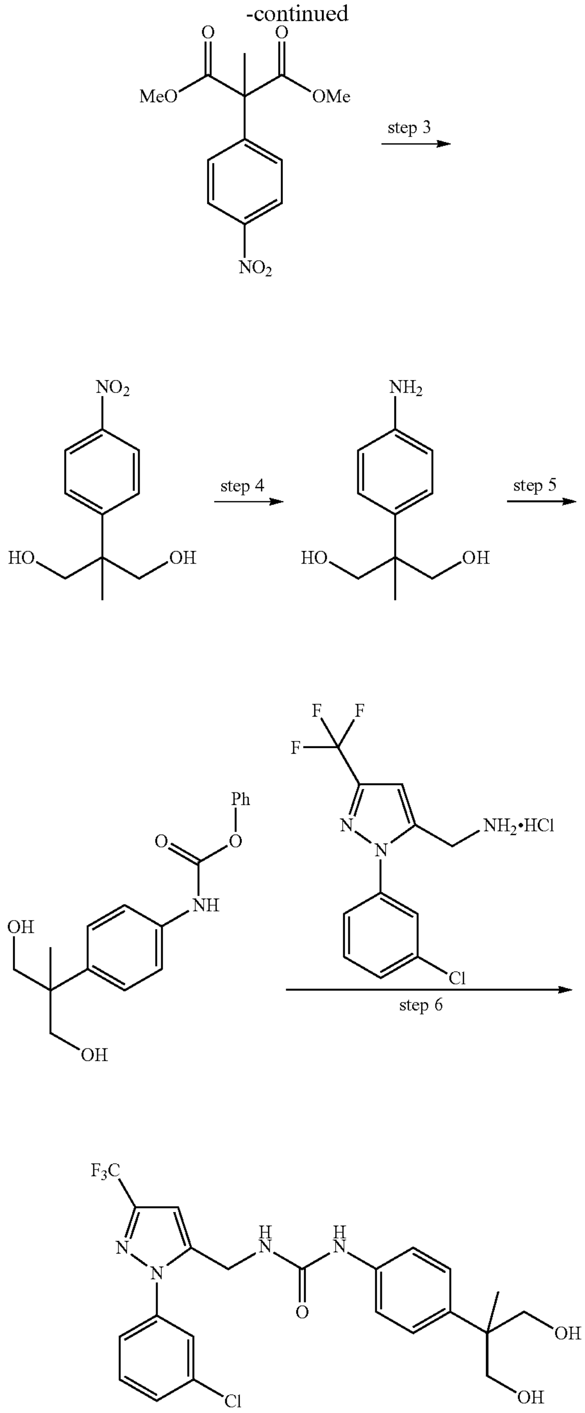

Step 1: To a suspension of dimethyl malonate (9.77 mL, 85.07 mmol, 1.2 eq) in DMF (100 mL) and $K_2CO_3$ (29.36 g, 212.76 mmol, 3.0 eq) was added 1-fluoro-4-nitrobenzene (7.51 mL, 70.91 mmol, 1.0 eq) at RT and the mixture was stirred for 16 h at 70° C. The reaction mixture was cooled to RT and diluted with water (200 mL) and extracted with ethyl acetate (2×100 mL). The ethyl acetate layers were collected, washed with cold water (2×50 mL), brine (50 mL), dried over sodium sulfate and evaporated under vacuum. The crude product was washed with n-pentane (50 mL) to get dimethyl 2-(4-nitrophenyl)malonate 14 g, 78%) as pale yellow solid (TLC system: EtOAc/PE (3:7), $R_f$: 0.50).

Step 2: To a stirred solution of dimethyl 2-(4-nitrophenyl) malonate (10 g, 39.52 mmol, 1.0 eq) and $K_2CO_3$ (10.9 g 79.05 mmol 2.0 eq) in DMF (40 mL), was added methyl iodide (4.94 mL, 79.05 mmol 2.0 eq) at 0° C. and the mixture stirred at RT for 18 h. $K_2CO_3$ was filtered out and the filtrate concentrated under vacuum. The residue was diluted with water (80 mL) and extracted with EtOAc (2×80 mL). The organic layer was separated washed with brine solution, dried over anhydrous $Na_2SO_4$ and the solvent evaporated to get dimethyl 2-methyl-2-(4-nitrophenyl)malonate (7 g, 66%; TLC system: EtOAc/PE (3:7), $R_f$: 0.5.)

Step 3: To a stirred solution of dimethyl 2-methyl-2-(4-nitrophenyl)malonate (5 g, 18.72 mmol, 1.0 eq) in methanol (50 mL) was added $NaBH_4$ (2.12 g, 56.17 mmol, 3.0 eq) at 0° C. and stirred at RT for 16 h. The solvent was evaporated and the residue was diluted with water (50 mL). The product was extracted with EtOAc (2×60 mL). The combined organic layer was washed with brine (20 mL), dried over anhydrous $Na_2SO_4$, evaporated under reduced pressure. The crude product obtained was purified by CC using EtOAc/PE (1:1) to get 2-methyl-2-(4-nitrophenyl)propane-1,3-diol (1.6 g 40%; TLC system: EtOAc/PE (1:1), R, 0.2).

Step 4: To a stirred solution of 2-methyl-2-(4-nitrophenyl) propane-1,3-diol (1.2 g, 5.68 mmol, 1.0 eq) in ethanol (30 mL) was added 10% Pd/C (300 mg) and the mixture was stirred under hydrogen gas balloon atmosphere for 5 h at RT. The reaction mixture was filtered through celite pad and filtrate concentrated under vacuum to get 2-(4-aminophenyl)-2-methylpropane-1,3-diol (1 g, 97%; TLC system: chloroform/MeOH (9:1); $R_f$: 0.3).

Step 5: To a stirred solution of 2-(4-aminophenyl)-2-methylpropane-1,3-diol (1 g, 5.52 mmol, 1.0 eq) in sat. aq. $NaHCO_3$ (4 mL), water (2 mL) and THF (4 mL) was added phenyl chloroformate (0.76 mL, 6.08 mmol, 1.1 eq) at 0° C. and the mixture was stirred at 0° C. for 0.5 h. The mixture was diluted with water (10 mL) and extracted with EtOAc (2×30 mL). The combined organic layer was washed with brine (10 mL) and the solvent evaporated. The crude product was purified by CC using chloroform/MeOH (95:5) as eluent to get phenyl 4-(1,3-dihydroxy-2-methylpropan-2-yl) phenylcarbamate (1.1 g, 60%) as a white solid (TLC system: chloroform-MeOH; 9:1; $R_f$: 0.4).

Step 6: To a stirred solution of (1-(3-chlorophenyl)-3-(trifluoromethyl)-1H-pyrazol-5-yl)methanamine hydrochloride (103 mg, 0.33 mmol, 1.0 eq) in DMF (5 mL) was added TEA (0.092 mL, 0.66 mmol, 2.0 eq) followed by phenyl 4-(1,3-dihydroxy-2-methylpropan-2-yl)phenylcarbamate (100 mg, 0.33 mmol, 1.0 eq) at 0° C. and the mixture was stirred for 16 h at RT. The reaction mixture was concentrated under vacuum and the residue purified by neutral alumina column chromatography using MeOH/$CHCl_3$ (0.5:9.5) as eluent to get 1-((1-(3-chlorophenyl)-3-(trifluoromethyl)-1H-pyrazol-5-yl)methyl)-3-(4-(1,3-dihydroxy-2-methylpropan-2-yl)phenyl)urea (105 mg; 65%) as a white solid (TLC system: MeOH/$CHCl_3$ (1:9), $R_f$: 0.3).

Synthesis of Example A156

1-[[5-tert-Butyl-2-(3-chlorophenyl)-2H-pyrazol-3-yl]-methyl]-3-[3-fluoro-4-[2-hydroxy-1-(hydroxymethyl)-1-methyl-ethyl]-phenyl]-urea

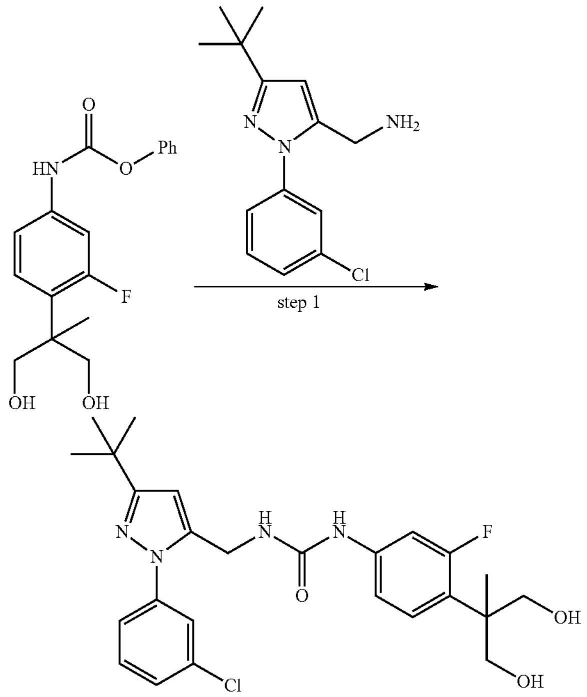

Step 1: To a stirred solution of (1-(3-chlorophenyl)-3-(trifluoromethyl)-1H-pyrazol-5-yl)methanamine (synthesis described for example A154) (80 mg, 0.31 mmol, 1.0 eq) in MeCN (7 mL) was added TEA (0.17 mL, 1.2 mmol, 4 eq) followed by phenyl 4-(1,3-dihydroxy-2-methylpropan-2-yl)-3-fluorophenylcarbamate (99 mg, 0.31 mmol, 1.0 eq) at RT and the mixture stirred for 16 h at reflux. The reaction mixture was concentrated under vacuum and residue purified by CC using EtOAc/n-hexane (4:1) as eluent to get 1-((3-tert-butyl-1-(3-chlorophenyl)-1H-pyrazol-5-yl)methyl)-3-(4-(1,3-dihydroxy-2-methylpropan-2-yl)-3-fluorophenyl)urea (112 mg; 75%).

Synthesis of Example A157

1-[[5-tert-Butyl-2-(3-chlorophenyl)-2H-pyrazol-3-yl]-methyl]-3-[4-[2-hydroxy-1-(hydroxymethyl)-1-methyl-ethyl]-phenyl]-urea

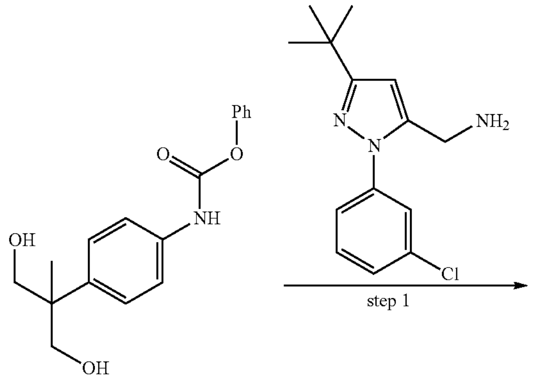

-continued

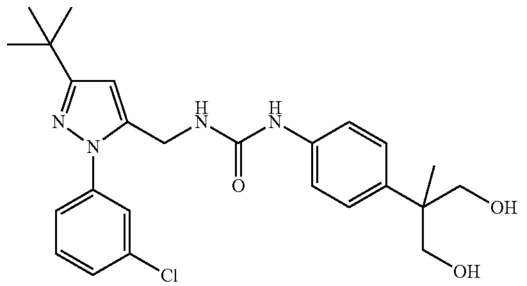

Step 1: To a stirred solution of (3-tert-butyl-1-(3-chlorophenyl)-1H-pyrazol-5-yl)methanamine (80 mg, 0.31 mmol, 1.0 eq) in MeCN (7 mL) was added TEA (0.17 mL, 1.2 mmol, 4 eq) followed by phenyl 4-(1,3-dihydroxy-2-methylpropan-2-yl)phenylcarbamate (94 mg, 0.31 mmol, 1 eq) and the mixture was stirred for 16 h at reflux. The reaction mixture was concentrated under vacuum and the residue was purified by CC using EtOAc/n-hexane 1:1 as eluent to get 1-((3-tert-butyl-1-(3-chlorophenyl)-1H-pyrazol-5-yl)methyl)-3-(4-(1,3-dihydroxy-2-methylpropan-2-yl)phenyl)urea (106 mg; 73%).

Synthesis of Example A158

1-[[2-(3-Chlorophenyl)-5-(trifluoromethyl)-2H-pyrazol-3-yl]-methyl]-3-[4-[1,2-dihydroxy-1-(hydroxymethyl)-ethyl]-phenyl]-urea

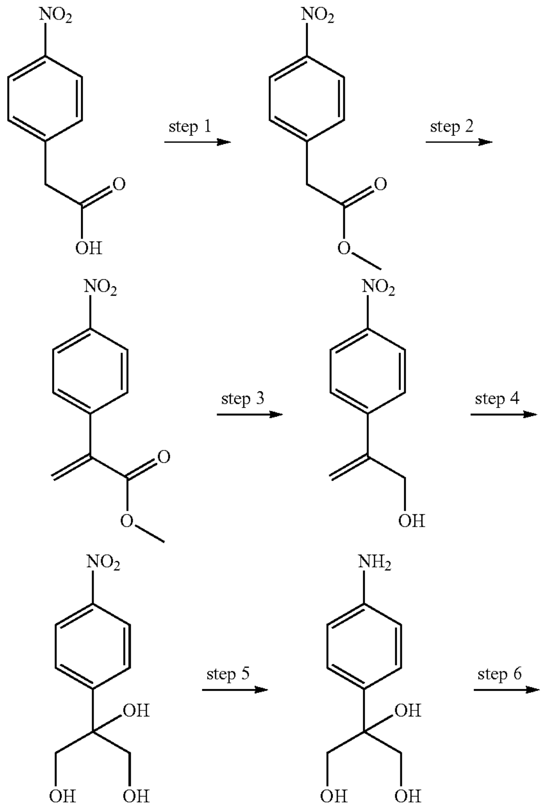

-continued

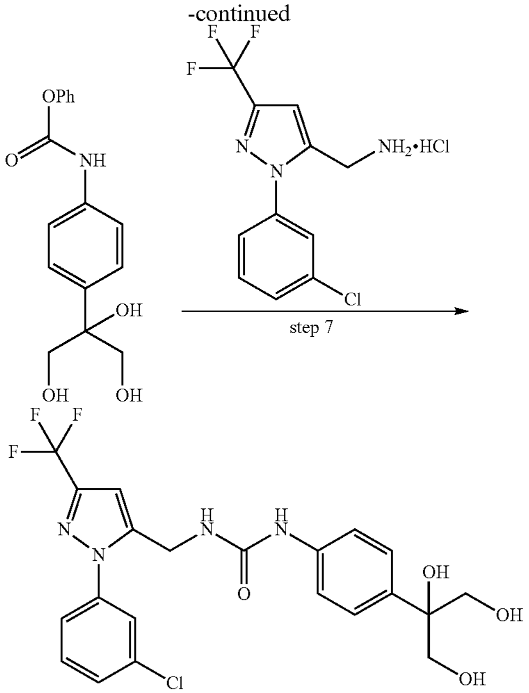

Step 1: To a stirred MeOH (100 mL) solution of 2-(4-nitrophenyl)acetic acid (10.0 g, 55.202 mmol, 1.0 eq) $SOCl_2$ (6.7 mL, 110.045 mmol, 2.0 eq) was added at 0° C. for 10 min and the mixture was stirred at RT for 2 h, then excess of $SOCl_2$ was removed under vacuum and the residue was dissolved in EtOAC (50 mL), washed with water, sat. (aq) $NaHCO_3$, dried ($Na_2SO_4$) and the solvent was evaporated to get methyl 2-(4-nitrophenyl)acetate (10.5 g, 98%, solid; TLC system: EtOAc/PE (3:7), $R_f$: 0.60).

Step 2: To a stirred solution of methyl 2-(4-nitrophenyl) acetate (8.0 g, 40.994 mmol, 1.0 eq) in DMSO (40 mL) was added tetramethyldiaminomethane (8.38 mL, 61.491 mmol, 1.5 eq) followed by acetic anhydride (12.78 mL, 135.17 mmol, 3.3 eq) at RT and the mixture was stirred for 2 h. The reaction mixture was diluted with water (40 mL), extracted with ether (80 mL×2) and the solvent evaporated. The crude product was purified by CC using EtOAc/PE (1:9) as eluent) to get methyl 2-(4-nitrophenyl)acrylate (4.0 g, 47%, solid; TLC system: EtOAc/PE (3:7), $R_f$: 0.60).

Step 3: To a stirred solution of methyl 2-(4-nitrophenyl) acrylate (4.0 g, 19.323 mmol, 1.0 eq) in ether (40 mL) was added DIBALH (20% solution in toluene) (40 mL, 57.97 mmol, 3.0 eq) at −78° C., then the mixture was allowed to warm to 0° C. over a period of 2 h, then the mixture was quenched with water (1.0 mL), NaOH solution (15%) (3 mL), extracted with ether (20 mL×2), washed with water (20 mL), brine (20 mL), dried ($MgSO_4$) and the solvent evaporated. The resulting residue was purified by CC using EtOAc/PE (3:7) as eluent to get 2-(4-nitrophenyl)prop-2-en-1-ol (1.5 g, 43%, oil); TLC system: EtOAc/PE (1:1), $R_f$: 0.4).

Step 4: To a stirred acetone (8.0 mL) solution containing water (2.0 mL) 2-(4-nitrophenyl)prop-2-en-1-ol (1.5 g, 8.379 mmol, 1.0 eq), osmium tetraoxide (2.5% solution in 2-methyl-2-propanol) (1.4 mL, 0.141 mmol, 0.017 eq) and NMO (50% aq. Solution) (4 mL, 16.73 mmol, 2 eq) were added at 0° C. and the mixture was stirred for 1 h at RT, then saturated $NaHCO_3$ solution in water (3 mL) was added and the mixture was extracted with ethyl acetate (30 mL), washed with water (5 mL), brine (5 mL), dried ($Na_2SO_4$) and the solvent evaporated. The resulting residue was purified by CC using $MeOH/CHCl_3$ (1:19) as eluent to get 2-(4-nitrophenyl)propane-1,2,3-triol (1.1 g, 61%, solid; TLC system: $MeOH/CHCl_3$ (1:9), $R_f$: 0.5).

Step 5: To a stirred solution of 2-(4-nitrophenyl)propane-1,2,3-triol (1.1 g, 5.164 mmol, 1.0 eq) in ethanol (25 mL) was added 10% Pd/C (200 mg) and the mixture was stirred under a $H_2$ gas balloon at RT for 1 h. The reaction mixture was passed through a celite bed and the solvent of the filtrate was evaporated to get 2-(4-aminophenyl)propane-1,2,3-triol (900 mg, 95%, solid; TLC system: $MeOH/CHCl_3$ (1:9), $R_f$: 0.3).

Step 6: To a stirred solution of 2-(4-aminophenyl)propane-1,2,3-triol (900 mg, 4.918 mmol, 1.0 eq) in $THF/H_2O$/sat. $NaHCO_3$ (4 mL: 2 mL: 4 mL) was added phenyl chloroformate (0.68 mL, 5.367 mmol, 1.1 eq) at 0° C. and the mixture was stirred at RT for 0.5 h, then the THF was evaporated, the residue was diluted with EtOAc (20 mL), washed with water (20 mL) followed by brine and the solvent evaporated. The resulting residue was purified by CC using $MeOH/CHCl_3$ (1:19) as eluent to get phenyl 4-(1,2,3-trihydroxypropane-2-yl)phenylcarbamate (900 mg, 60%, white solid; TLC system: $MeOH/CHCl_3$ (1:9), $R_f$: 0.4).

Step 7: To a stirred THF (10 mL) solution of (1-(3-chlorophenyl)-3-(trifluoromethyl)-1H-pyrazol-5-yl)methanamine hydrochloride (102 mg, 0.33 mmol, 1.0 eq), TEA (0.1 mL, 0.66 mmol, 2.0 eq) followed by compound phenyl 4-(1,2,3-trihydroxypropan-2-yl)phenylcarbamate (100 mg, 0.33 mmol, 1.0 eq) was added at RT and the mixture stirred for 16 h, then it was concentrated under vacuum and the residue was purified by CC using $MeOH/CHCl_3$ (3:17) as eluent to get 1-((1-(3-chlorophenyl)-3-(trifluoromethyl)-1H-pyrazol-5-yl)methyl)-3-(4-(1,2,3-trihydroxypropan-2-yl) phenyl)urea (120 mg; 75%, white solid; TLC system: $MeOH/CHCl_3$ (1:4); $R_f$: 0.3).

Synthesis of Example A159

1-[[5-tert-Butyl-2-(3-chlorophenyl)-2H-pyrazol-3-yl]-methyl]-3-[4-[1,2-dihydroxy-1-(hydroxymethyl)-ethyl]-phenyl]-urea

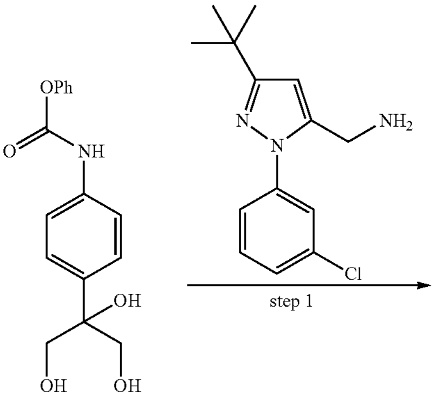

-continued

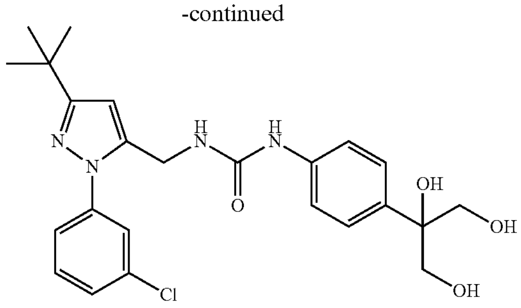

Step 1: To a stirred MeCN (9 mL) solution of (3-tert-butyl-1-(3-chlorophenyl)-1H-pyrazol-5-yl)methanamine (102 mg, 0.387 mmol, 1.0 eq), TEA (0.214 mL, 1.55 mmol, 4.0 eq) followed by phenyl 4-(1,2,3-trihydroxypropan-2-yl)phenylcarbamate (119 mg, 0.395 mmol, 1.02 eq) was added at RT and the mixture was stirred for 16 h at reflux, then it was concentrated under vacuum and the residue purified by CC using EtOAc as eluent to get 1-((3-tert-butyl-1-(3-chlorophenyl)-1H-pyrazol-5-yl)methyl)-3-(4-(1,2,3-trihydroxypropan-2-yl)phenyl)urea (122 mg; 67%).

TABLE 1

Mass Spectrometric Data for Example Compounds of Formula (Q)

| Example Compound | [M + H] |
|---|---|
| A1 | 448.3 |
| A2 | 460.2 |
| A3 | 446.0 |
| A4 | 462.4 |
| A5 | 480.0 |
| A6 | 465.9 |
| A7 | 477.9 |
| A8 | 461.2 |
| A9 | 491.9 |
| A10 | 459.9 |
| A11 | 435.2 |
| A12 | 447.1 |
| A13 | 443.3 |
| A14 | 455.3 |
| A15 | 441.0 |
| A16 | 441.0 |
| A17 | 475.2 |
| A18 | 486.9 |
| A19 | 461.1 |
| A20 | 473.0 |
| A21 | 457.1 |
| A22 | 490.9 |
| A23 | 484.9 |
| A24 | 491.4 |
| A25 | 503.2 |
| A27 | 413.3 |
| A28 | 425.1 |
| A29 | 430.3 |
| A30 | 442.3 |
| A31 | 428.4 |
| A32 | 444.5 |
| A33 | 456.2 |
| A34 | 456.0 |
| A35 | 456.0 |
| A36 | 472.8 |
| A37 | 427.9 |
| A38 | 439.8 |
| A39 | 446.0 |
| A40 | 457.9 |
| A41 | 462.3 |
| A42 | 474.2 |
| A43 | 451.9 |
| A44 | 463.9 |
| A45 | 428.0 |
| A47 | 478.0 |
| A48 | 489.9 |

TABLE 1-continued

Mass Spectrometric Data for Example Compounds of Formula (Q)

| Example Compound | [M + H] |
|---|---|
| A49 | 456.4 |
| A50 | 468.4 |
| A51 | 461.3 |
| A52 | 474.1 |
| A53 | 414.9 |
| A54 | 414.9 |
| A55 | 461.5 |
| A56 | 411.1 |
| A57 | 433.2 |
| A58 | 409.1 |
| A59 | 443.1 |
| A60 | 443.1 |
| A61 | 427.1 |
| A62 | 426.9 |
| A63 | 427.1 |
| A64 | 444.9 |
| A65 | 461.1 |
| A66 | 445.1 |
| A67 | 438.9 |
| A68 | 439.1 |
| A69 | 423.1 |
| A70 | 423.1 |
| A71 | 423.1 |
| A72 | 437.2 |
| A73 | 437.2 |
| A74 | 437.2 |
| A75 | 437.2 |
| A76 | 441.1 |
| A77 | 441.1 |
| A78 | 457.1 |
| A79 | 467.2 |
| A80 | 441.1 |
| A81 | 448.1 |
| A82 | 451.2 |
| A83 | 459.1 |
| A84 | 453.2 |
| A85 | 434.1 |
| A86 | 452.2 |
| A87 | 453.2 |
| A88 | 467.2 |
| A89 | 477.1 |
| A90 | 473.1 |
| A91 | 473.1 |
| A92 | 453.2 |
| A93 | 467.2 |
| A94 | 453.2 |
| A95 | 457.1 |
| A96 | 447.9 |
| A97 | 459.8 |
| A98 | 458.4 |
| A99 | 470.4 |
| A100 | 470.2 |
| A101 | 482.0 |
| A102 | 466.0 |
| A103 | 478.0 |
| A104 | 483.9 |
| A105 | 457.2 |
| A106 | 469.1 |
| A107 | 455.2 |
| A108 | 467.1 |
| A109 | 473.2 |
| A110 | 485.1 |
| A111 | 513.9 |
| A112 | 532.1 |
| A113 | 486.1 |
| A114 | 496.2 |
| A115 | 508.2 |
| A116 | 472.2 |
| A117 | 488.2 |
| A118 | 499.9 |
| A119 | 500.1 |
| A120 | 500.1 |
| A121 | 518.2 |
| A122 | 484.2 |
| A123 | 480.2 |
| A127 | 487.1 |

TABLE 1-continued

| Mass Spectrometric Data for Example Compounds of Formula (Q) | |
|---|---|
| Example Compound | [M + H] |
| A128 | 501.1 |
| A129 | 475.1 |
| A130 | 505.1 |
| A131 | 470.5 |
| A132 | 456.0 |
| A133 | 459.0 |
| A136 | 454.1 |
| A137 | 477.9 |
| A138 | 470.3 |
| A139 | 458.5 |
| A140 | 445.1 |
| A141 | 457.0 |
| A145 | 474.5 |
| A146 | 468.3 |
| A147 | 456.4 |
| A148 | 486.3 |
| A150 | 461.4 |
| A151 | 473.5 |
| A152 | 475.0 |
| A153 | 487.2 |
| A154 | 501.0 |
| A155 | 483.0 |
| A156 | 489.2 |
| A157 | 471.2 |
| A158 | 484.9 |
| A159 | 473.0 |

Synthesis of Example B5

N-[[2-(3-Chlorophenyl)-5-(trifluoromethyl)-2H-pyrazol-3-yl]-methyl]-2-[4-(methanesulfonamido-methyl)-phenyl]-propionamide

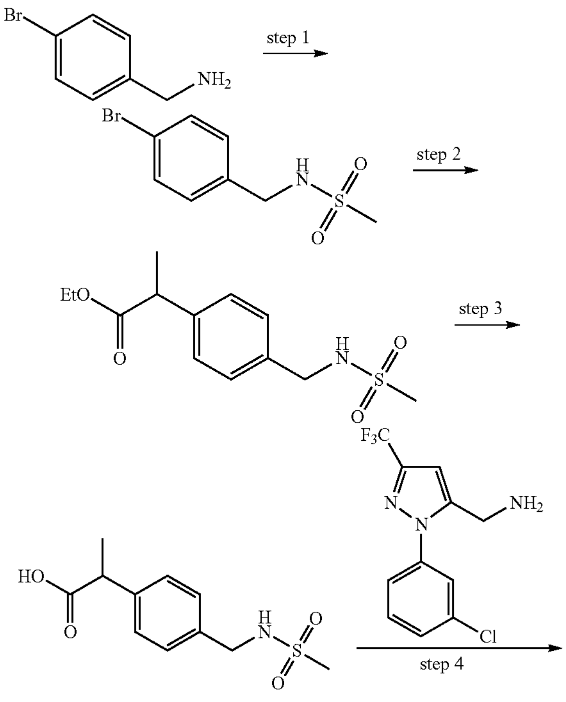

-continued

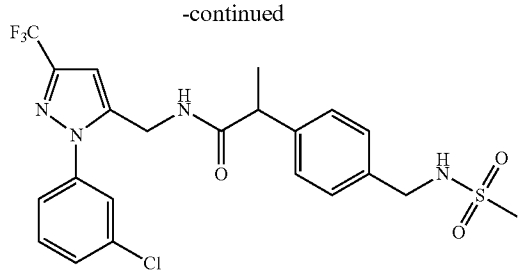

Step 1: To a stirred solution of (4-bromophenyl)methanamine (500 mg, 2.687 mmol) in pyridine were added methanesulfonyl chloride (0.4 mL, 5.106 mmol) at 0° C. The reaction mixture was stirred for 1 h, then diluted with dichloromethane. The mixture was washed with water. The organic layer was dried ($MgSO_4$) and filtered. The solvent removed in vacuo. The crude product was purified by CC. N-(4-bromobenzyl)methanesulfonamide (675 mg) was obtained (95% yield).

Step 2: To a stirred solution of N-(4-bromobenzyl)methanesulfonamide (675 mg, 2.555 mmol) in DMF were added ethyl 2-chloropropionate (0.42 mL), manganese (280 mg) and (2,2'-bipyridine)nickel(II)-dibromide ($NiBr_2$bipy) (67 mg, 0.17885 mmol). TFA (1-2 drops) was added. The reaction mixture was stirred for 36 h at 60° C. After cooling down to room temperature, the mixture was hydrolyzed by 1N HCl and extracted with diethyl ether. The organic layer was dried ($MgSO_4$) and filtered. The solvent was removed in vacuo. The crude product was purified by CC. Ethyl 2-(4-(methylsulfonamidoethyl)phenyl)propanoate (325 mg) was obtained.

Step 3: To a stirred solution of ethyl 2-(4-(methylsulfonamidoethyl)phenyl)propanoate (325 mg, 1.139 mmol) in a co-solvent of THF and water (1:1) was added sodium hydroxide (114 mg, 2.8475 mmol). The reaction mixture was refluxed for 16 h, then cooled to room temperature, acidified to pH 3-4 with AcOH. The residue dissolved in EtOAc and washed with water and brine. The organic layer was dried ($MgSO_4$) and filtered. The solvent removed in vacuo. The crude product was purified by CC. 2-(4-(methylsulfonamidomethyl)phenyl)propanoic acid (74 mg) was obtained in 25% yield.

Step 4: To a stirred solution of 2-(4-(methylsulfonamidomethyl)phenyl)propanoic acid (37 mg, 0.144 mmol) and (1-(3-chlorophenyl)-3-(trifluoromethyl)-1H-pyrazol-5-yl)methanamine (44 mg, 0.158 mmol) in acetonitrile were added EDC (41 mg, 0.216 mmol), HOBt (29 mg, 0.216 mmol) and triethylamine (0.05 mL, 0.36 mmol). The reaction mixture was stirred for 15 h at room temperature. The residue dissolved in EtOAc and washed with water and brine. The organic layer was dried ($MgSO_4$) and filtered. The solvent was removed in vacuo. The crude product was purified by CC. Example compound B5 (62 mg) was obtained in 84% yield.

$^1$H NMR (300 MHz, $CDCl_3$): δ 7.35 (m, 8H), 6.35 (s, 1H), 5.56 (t, 1H), 4.5 (m, 3H), 4.32 (d, 2H), 3.53 (q, 1H), 2.94 (s, 3H), 1.50 (d, 3H).

Synthesis of Example B17

N-[[2-(3-Chlorophenyl)-5-(trifluoromethyl)-2H-pyrazol-3-yl]-methyl]-2-[4-[[(ethylsulfonyl)amino]-methyl]-3-fluoro-phenyl]-propionamide

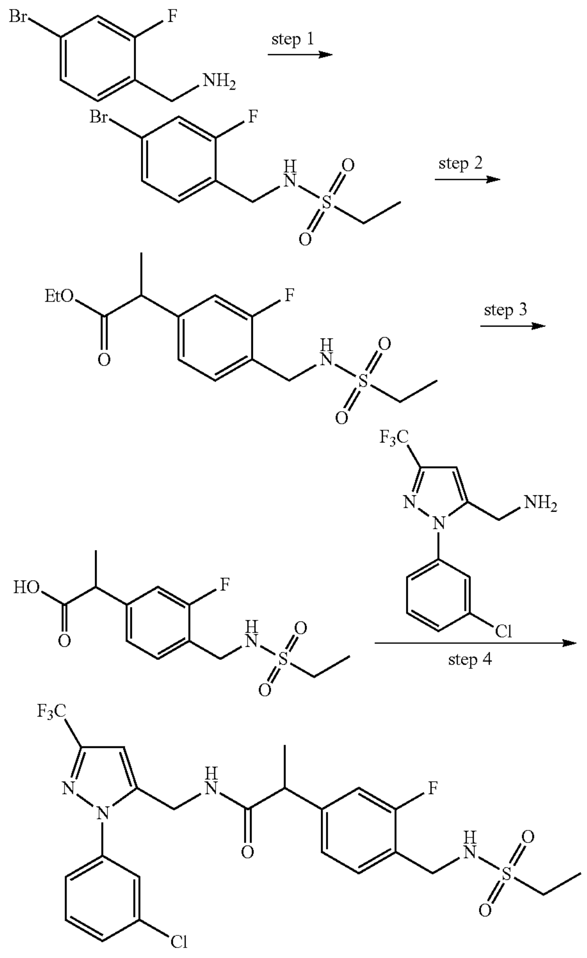

Step 1: 4-Bromo-2-fluorobenzylamine (924 mg, 4.53 mmol) was dissolved in pyridine and ethane sulfonyl chloride (0.82 mL, 8.60 mmol) was added to the solution at 0° C. The mixture was stirred for 1 h at 0° C. Then, the mixture was quenched with 1N HCl and extracted with ethyl acetate (EtOAc). Drying ($MgSO_4$) and evaporation of the ethyl acetate followed and the residue was purified by CC (eluent EtOAc/n-hexane) to yield N-(4-bromo-2-fluorobenzyl)ethanesulfonamide in pure form (1.06 g, 79%).

Step 2: To a solution of N-(4-bromo-2-fluorobenzyl) ethanesulfonamide (305 mg, 1.03 mmol) in DMF, manganese (113 mg, 2.06 mmol), $NiBr_2$bipy (27 mg, 0.07 mmol), ethyl-2-chloro propionate (0.17 ml, 1.34 mmol) was added, followed by addition of TFA (0.002 ml, 0.028 mmol). The mixture was stirred for 1 day at 65° C. The reaction mixture was quenched by conc. HCl (7-drops) and then extracted with diethyl ether, dried ($MgSO_4$) and the solvent was evaporated in vacuo. The residue was purified by CC (EtOAc/n-hexane). Ethyl 2-(4-(ethylsulfonamidomethyl)-3-fluorophenyl)propanoate in pure form (65 mg, 20%) was obtained.

Step 3: To a solution of ethyl 2-(4-(ethylsulfonamidomethyl)-3-fluorophenyl)propanoate (305 mg, 1.03 mmol) in DMF, manganese (113 mg, 2.06 mmol), $NiBr_2$bipy (27 mg, 0.07 mmol), ethyl-2-chloro propionate (0.17 mL, 1.34 mmol) was added, followed by addition of TFA (0.002 mL, 0.028 mmol). The mixture was stirred for 1 day at 65° C. The reaction mixture was quenched by conc. HCl (7-drops) and then extracted with diethyl ether, dried ($MgSO_4$) and the solvent was evaporated in vacuo. The residue was purified by CC (EtOAc/n-hexane). 2-(4-(ethyl-sulfonamidomethyl)-3-fluorophenyl)propanoic acid in pure form (65 mg, 20%) was obtained.

Step 4: 2-(4-(ethyl-sulfonamidomethyl)-3-fluorophenyl) propanoic acid (60 mg, 0.207 mmol) and (1-(3-chlorophenyl)-3-(trifluoromethyl)-1H-pyrazol-5-yl)methanamine (63 mg, 0.228 mmol) were dissolved and mixed in 1,4-dioxane followed by addition of HOBt (42 mg, 0.310 mmol) and EDC (60 mg, 0.313 mmol) and TEA (0.07 mL, 0.518 mmol). The reaction mixture was stirred for overnight and then quenched by water and extracted with EtOAc. Drying ($MgSO_4$) and evaporation of the ethyl acetate followed and the residue was purified by CC (EtOAc/n-hexane) to give the example B17 in pure form (104 mg, 92%).

$^1$H-NMR ($CD_3OD$): δ 7.50 (m, 5H, Ar), 7.05 (m, 2H, Ar), 6.57 (s, 1H, Ar), 4.43 (m, 2H, Ar—$CH_2$), 4.27 (s, 2H, Ar—$CH_2$), 3.58 (q, 1H, J=7.14 Hz, amide 1H), 2.97 (q, 2H, J=7.32 Hz, ethanesulfonylamide 2H), 1.36 (d, 3H, J=7.14 Hz, amide 3H), 1.27 (t, 3H, J=7.32 Hz, ethanesulfonylamide 3H).

Synthesis of Example B22

2-[3-Chloro-4-(methanesulfonamido-methyl)-phenyl]-N-[[2-(3-chlorophenyl)-5-(trifluoromethyl)-2H-pyrazol-3-yl]-methyl]-propionamide

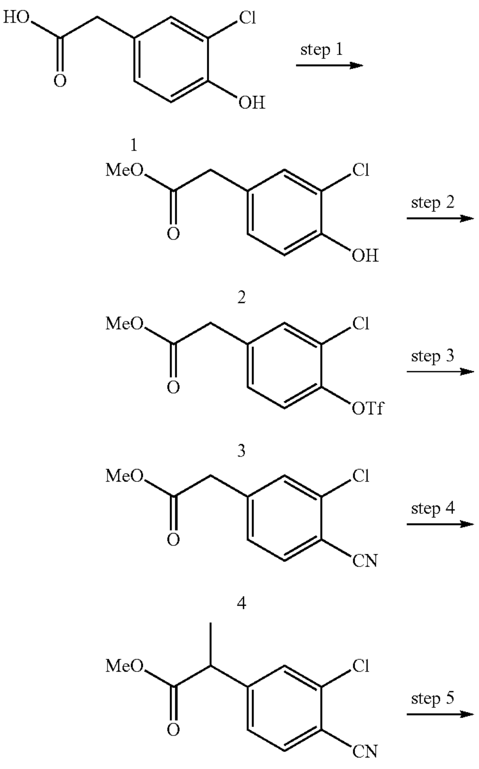

1

2

3

4

5

-continued

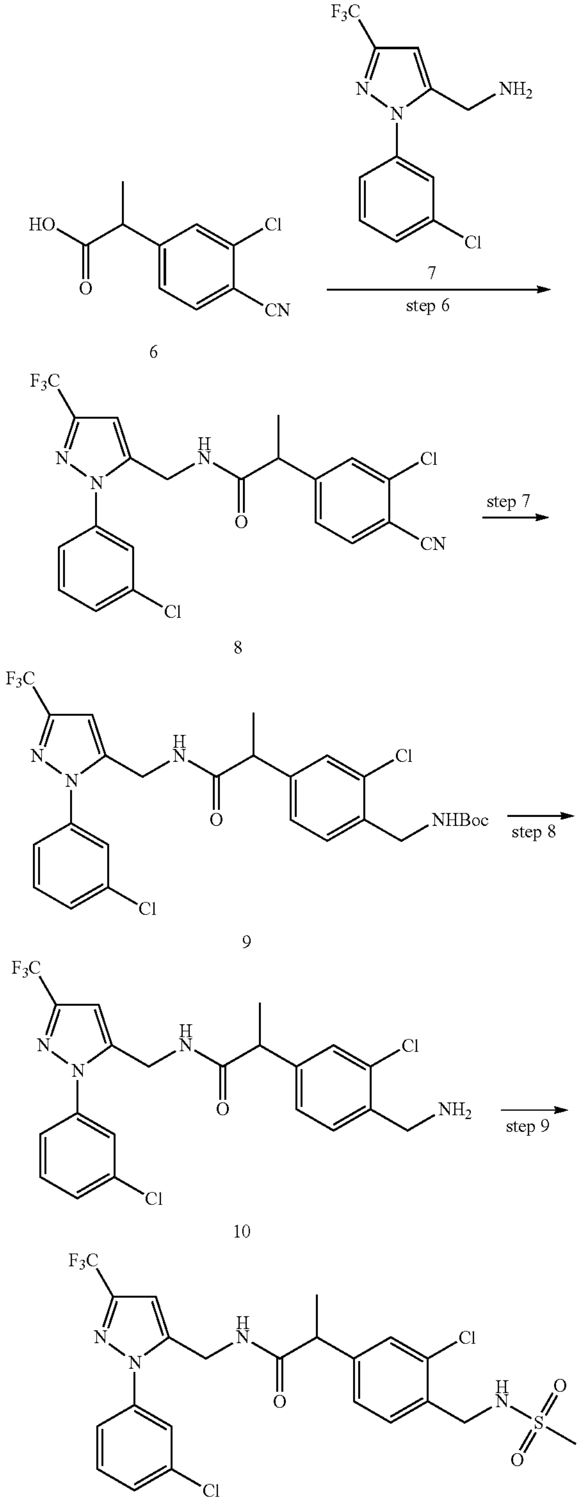

7

6

8

9

10

11

Step 1: To a stirred solution of 1 (3 g, 16.078 mmol) in methanol (35 mL) was added sulfuric acid (0.3 mL). The reaction mixture was refluxed for 15 h and cooled to room temperature. The solvent was evaporated. The residue was dissolved in EtOAc and extracted with a sat. solution of $NaHCO_3$. The organic layer was dried ($MgSO_4$) and filtered. The solvent was removed in vacuo. The crude product was purified by CC. 2 (3.557 g) was obtained in 99% yield.

Step 2: To a stirred solution of 2 (3.557 g, 17.73 mmol) and TEA (2.5 mL, 17.73 mmol) in dichloromethane, triflic anhydride (3 mL, 17.73 mmol) is added dropwise at 0° C. The reaction mixture was stirred for 2 h. The residue was extracted with $CH_2Cl_2$ and washed with water and brine. The organic layer was dried ($MgSO_4$) and filtered. The solvent was removed in vacuo. The crude product was purified by CC. 3 (5.15 g) was obtained in 87% yield.

Step 3: To a stirred solution of 3 (4.419 g, 13.283 mmol) in DMF were added zinc(II) cyanide (1.6 g, 13.681 mmol) and $Pd(PPh_3)_4$ (1.5 g, 1.3283 mmol). The reaction mixture was stirred for 34 hours at 80° C., then cooled to room temperature and diluted with EtOAc. The mixture was filtered using a celite pad. The filtrate was diluted with EtOAc and extracted with a sat. solution of $NaHCO_3$. The organic layer was dried ($MgSO_4$) and filtered. The solvent was removed in vacuo. The crude product was purified by column chromatography. 4 (1.044 g) was obtained in 37% yield.

Step 4: To a stirred solution of 4 (931 mg, 4.441 mmol) in DMF were added sodium hydride (60 wt.-% in mineral oil, 178 mg, 4.441 mmol) and iodomethane (0.3 ml, 4.441 mmol) at 0° C. The reaction mixture was stirred for 1 hour at 0° C., then diluted with water. The residue dissolved in EtOAc and washed with water and brine. The organic layer was dried ($MgSO_4$) and filtered. The solvent was removed in vacuo. The crude product was purified by column chromatography. 5 (642 mg) was obtained in 65% yield.

Step 5: To a stirred solution of 5 (642 mg, 2.870 mmol) in a co-solvent of THF and water (1:1) was added sodium hydroxide (287 mg, 7.175 mmol). The reaction mixture was stirred for 15 hours at room temperature, then acidified to pH 3-4 with AcOH. The residue was dissolved in EtOAc and washed with water and brine. The organic layer was dried ($MgSO_4$) and filtered. The solvent was removed in vacuo. The crude product was purified by column chromatography. 6 (665 mg) was obtained in 99% yield.

Step 6: To a stirred solution of 6 (224 mg, 1.069 mmol) and 7 (324 mg, 1.175 mmol) in acetonitrile were added EDC (307 mg, 1.064 mmol), HOBt (217 mg, 1.064 mmol) and triethylamine (0.4 mL, 2.673 mmol). The reaction mixture was stirred for 15 hours at room temperature. The mixture was diluted with EtOAc and washed with water and brine. The organic layer was dried ($MgSO_4$) and filtered. The solvent was removed in vacuo. The crude product was purified by column chromatography. 8 (366 mg) was obtained in 78% yield.

Step 7: To a stirred solution of 8 (366 mg, 1.460 mmol) in methanol, cooled to 0° C., were added $Boc_2O$ (342 mg, 1.566 mmol) and $NiCl_2.6H_2O$ (19 mg, 0.0783 mmol). $NaBH_4$ (207 mg, 5.481 mmol) was then added in small portions. The reaction was exothermic and effervescent. The resulting reaction mixture was allowed to warm to room temperature and left to stir for 1 hour. Diethylenetriamine (DETA) (0.09 mL, 0.783 mmol) was added to the mixture. The mixture was stirred for 1 hour. The solvent was evaporated. The residue dissolved in EtOAc and extracted with a sat. solution of $NaHCO_3$. The organic layer was dried ($MgSO_4$) and filtered. The solvent was removed in vacuo. The crude product was purified by column chromatography. 9 (227 mg) was obtained in 50% yield.

Step 8: To a stirred solution of 9 (227 mg, 0.397 mmol) in dichloromethane (4 mL), cooled to 0° C., were added trifluoroacetic acid (2 mL). The resulting reaction mixture was stirred for 1 hour at 0° C. and 1 hour at room temperature, then basified to pH 8-9 with aq. $NaHCO_3$. The mixture was filtered using a celite pad. The filtrate was dissolved in dichloromethane and extracted with a sat. solution of $NaHCO_3$. The organic layer was dried ($MgSO_4$) and filtered. The solvent was removed in vacuo. The crude product was purified by column chromatography. 10 (116 mg) was obtained in 62% yield.

Step 9: To a stirred solution of 10 (116 mg, 0.246 mmol) in pyridine, cooled to 0° C., was added methanesulfonyl chloride (116 mg). The resulting reaction mixture was stirred for 15 hours at room temperature. The mixture dissolved in dichloromethane and washed with 1N HCl. The organic layer was dried ($MgSO_4$) and filtered. The solvent was removed in vacuo. The crude product was purified by column chromatography. 11 (108 mg) was obtained as 80% yield.

$^1H$ NMR (300 MHz, $CDCl_3$): δ 7.43 (m, 4H), 7.29 (m, 3H), 7.15 (dd, 1H, J=7.86 Hz), 6.43 (s, 1H), 5.63 (t, 1H), 4.76 (t, 1H), 4.48 (d, 2H), 4.40 (d, 2H), 3.48 (q, 1H, J=7.14 Hz), 2.90 (s, 3H), 1.47 (d, 3H, J=7.14 Hz).

Synthesis of Example B28

1-[[5-tert-Butyl-2-(3-chlorophenyl)-2H-pyrazol-3-yl]-methyl]-3-[4-(methanesulfonamido-methyl)-phenyl]-urea

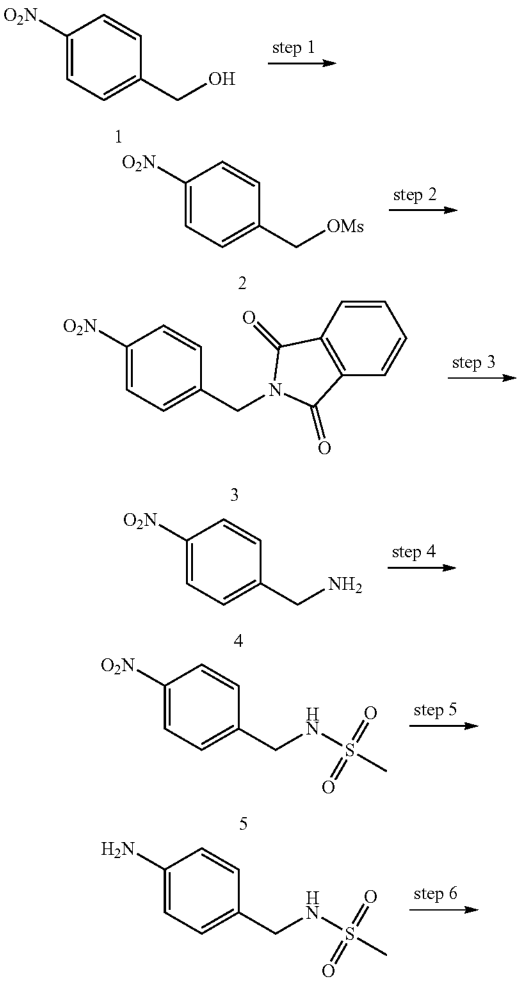

1

2

3

4

5

6

-continued

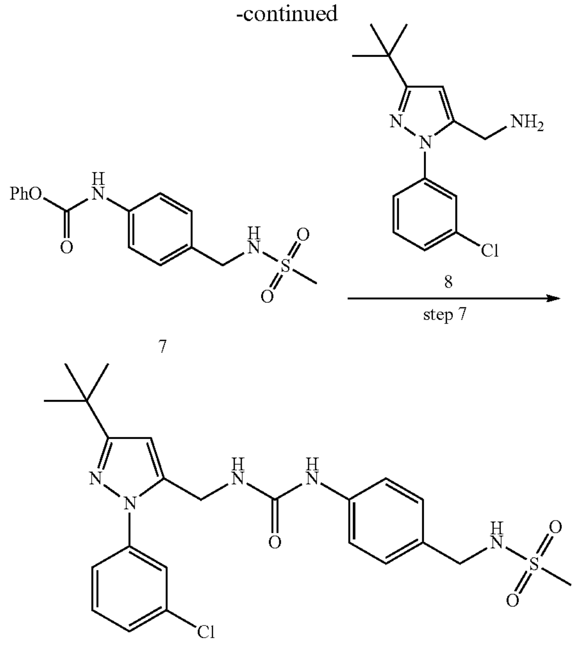

7

8

9

Step 1: To a stirred solution of 1 (299 mg, 1.952 mmol) in dichloromethane was added triethylamine (0.3 ml, 2.147 mmol). Methanesulfonyl chloride (0.18 ml, 2.343 mmol) is added dropwise at 0° C. The reaction mixture was heated to 80° C. and stirred for 4 hours, then cooled to room temperature, and diluted with dichloromethane. The mixture was washed with water. The organic layer was dried ($MgSO_4$) and filtered. The solvent was removed in vacuo. The crude product was purified by column chromatography. 2 (333 mg) was obtained in 74% yield.

Step 2: To a stirred solution of 2 (333 mg, 1.440 mmol) in DMF was added potassium phthalimide (293 mg, 1.584 mmol). The reaction mixture was stirred for 16 hours. The mixture was dissolved in EtOAc, washed with water and brine. The organic layer was dried ($MgSO_4$) and filtered. The solvent removed in vacuo. The crude product was purified by column chromatography. 3 (535 mg) was obtained as a crude product.

Step 3: To a stirred solution of 3 (218 mg, 0.772 mmol) in THF were added hydrazine monohydrate (246 mg, 3.089 mmol) and p-toluenesulfonic acid monohydrate (15 mg, 0.0772 mmol). The reaction mixture was stirred for 4 hours at 80° C., then cooled to room temperature, and diluted with EtOAc. The mixture was washed with water and brine. The organic layer was dried ($MgSO_4$) and filtered. The solvent was removed in vacuo. The crude product was purified by column chromatography. 4 (46 mg) was obtained in 39% yield.

Step 4: To a stirred solution of 4 (46 mg, 0.302 mmol) in pyridine, cooled to 0° C., was added methanesulfonyl chloride (46 mg). The resulting reaction mixture was stirred for 1 hour at room temperature. The mixture dissolved in dichloromethane and washed with 1 N HCl. The organic layer was dried ($MgSO_4$) and filtered. The solvent was removed in vacuo. The crude product was purified by column chromatography. 5 (43 mg) was obtained in 62% yield.

Step 5: To a stirred solution of 5 (43 mg, 0.188 mmol) in EtOAc was added 10% palladium on carbon (5 mg). The mixture was charged with a $H_2$ (gas) balloon. The resulting mixture was stirred for 3 hours, then filtered over celite. The solvent was removed in vacuo. The crude product was purified by column chromatography. 6 (41 mg) was obtained in 99% yield.

Step 6: To a stirred solution of 6 (41 mg, 0.204 mmol) in tetrahydrofuran and acetonitrile as co-solvent were added phenylchloroformate (34 mg, 0.2142 mmol) and pyridine (0.02 mL, 0.2448 mmol). The reaction mixture was stirred for 3 hours at room temperature. The mixture was diluted with EtOAc and washed with water and brine. The organic layer was dried ($MgSO_4$) and filtered. The solvent was removed in vacuo. The crude product was purified by column chromatography. 7 (54 mg) was obtained in 83% yield.

Step 7: To a stirred solution of 7 (28 mg, 0.087 mmol) and 8 (23 mg, 0.087 mmol) in acetonitrile was added DMAP (11 mg, 0.087 mmol). The reaction mixture was stirred for 15 hours at 50° C. The mixture was diluted with EtOAc and washed with water and brine. The organic layer was dried ($MgSO_4$) and filtered. The solvent was removed in vacuo. The crude product was purified by column chromatography. 9 (example compound B28) (32 mg) was obtained in 75% yield.

$^1H$ NMR (400 MHz, $CDCl_3$): δ 7.43 (s, 1H), 7.30 (m, 2H), 7.12 (q, 4H), 6.89 (s, 1H), 6.24 (s, 1H), 5.28 (d, 1H), 4.92 (t, 1H), 4.39 (d, 2H), 4.15 (d, 2H), 4.09 (q, 1H), 2.85 (s, 3H), 1.28 (s, 9H).

Synthesis of Example B29

N-[[2-(3-Chlorophenyl)-5-(trifluoromethyl)-2H-pyrazol-3-yl]-methyl]-2-[3-fluoro-4-[(methyl-methylsulfonyl-amino)-methyl]-phenyl]-propionamide

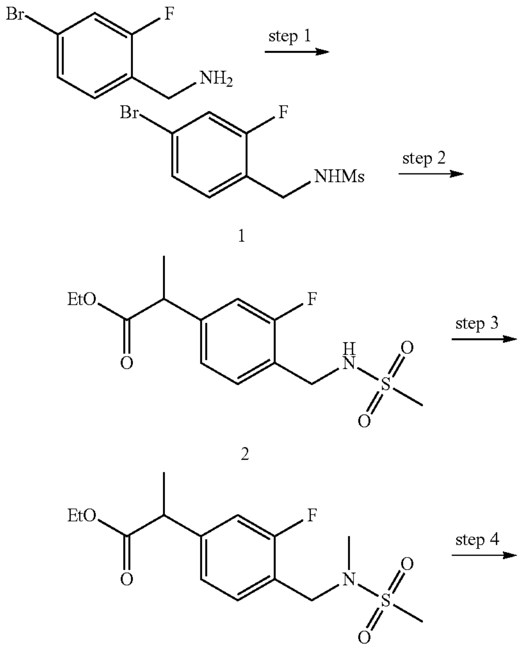

1
2
3

-continued

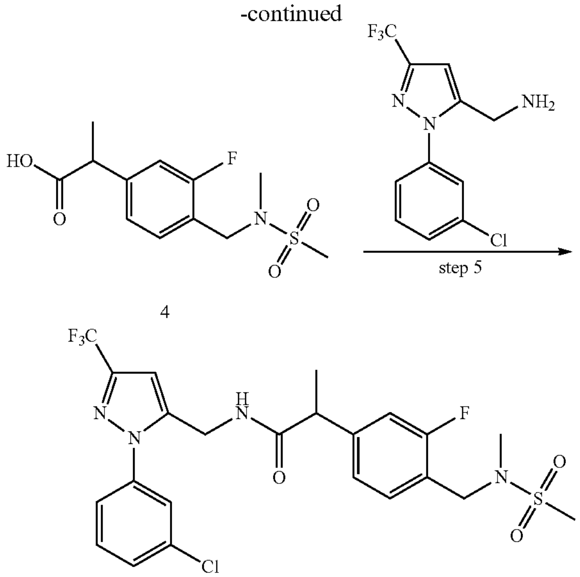

4

Step 1: Commercially available (4-bromo-2-fluorophenyl)methanamine is stirred in pyridine and methanesulfonyl chloride (1.9 eq.) is added drop-wise at 0° C. The reaction mixture is stirred at room-temperature for 1 h. The reaction is quenched with 1 N HCl and extracted with EtOAc. The organic layer is dried over by $MgSO_4$ and the solvent evaporated. The crude product is purified by column chromatography and 1 obtained.

Step 2: Compound 1 is dissolved in anhydrous DMF and charged with $N_2$. Commercially available rthyl-2-chloro propionate (1.3 eq.) is added dropwise and manganese (2 eq.), $NiBr_2$bipy (0.1 equiv.) are added followed by TFA (0.026 eq.). The reaction mixture is refluxed overnight. The reaction mixture is warmed to ambient temperature. The reaction is quenched with 1 N HCl and the organic layer is extracted with diethyl ether. The extracted organic layer is dried over $MgSO_4$, and concentrated into compound 2 that is used in the next step without further purification.

Step 3: Crude compound 2 is stirred in acetone at 0° C., and $K_2O_3$ (1.5 eq.) is added. Methyl iodide (3 eq.) is added drop-wise and the reaction mixture is refluxed. After 15 h, the reaction mixture is quenched with water and extracted with EtOAc. The organic layer is dried over $MgSO_4$ and concentrated. The crude product is purified by column chromatography and obtained as desired product 3.

Step 4: To a solution of compound 3 in THF and water (1:1) was added NaOH (2.5 equiv.) and the resulting mixture was stirred at room temperature. After 15 hours, the reaction mixture was acidified with AcOH acid to a pH of 2-3. The mixture is extracted with DCM and water. The organic layer was washed with water, dried ($MgSO_4$) and concentrated in vacuo. The product was purified by column chromatography and the desired product 4 was obtained.

Step 5: To a solution of the carboxylic acid (4) in 1,4-dioxane was added EDC (1.5 eq.), HOBt (1.5 eq.), and (1-(3-chlorophenyl)-3-(trifluoromethyl)-1H-pyrazol-5-yl) methanamine (1 eq.) and dropwise TEA (2.5 eq.). The reaction mixture was stirred overnight at room temperature. Water was added to the reaction mixture and the mixture was extracted with ethyl acetate. The extracted organic layer was dried over $MgSO_4$. Evaporation of the solvent followed by column chromatographic purification (EtOAc/n-hexane) afforded example compound B29.

$^1H$ NMR (300 MHz, $CDCl_3$): δ 7.41-7.32 (m, 5H, Ar—H), 6.99-6.95 (m, 3H, Ar—H), 6.06 (s, 1H, Ar—H), 5.643 (bs, 1H, Ar—NH), 4.46 (d, 2H, J=6.00 Hz, pyrazole-α-H), 3.88 (s, 2H, Ar-α-H), 3.49 (q, 1H, J=7.50 Hz, Ar-α-H), 2.48 (s, 3H, methansulfonyl-$CH_3$), 1.47 (d, 3H, J=6.00 Hz, Ar-α-$CH_3$)

Synthesis of Example B31

1-[[5-tert-Butyl-2-(3-chlorophenyl)-2H-pyrazol-3-yl]-methyl]-3-[3-fluoro-4-(methanesulfonamido-methyl)-phenyl]-urea

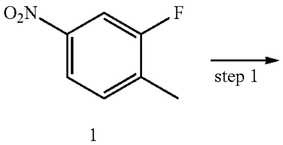

1

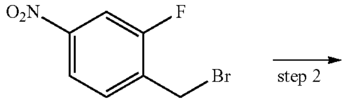

2

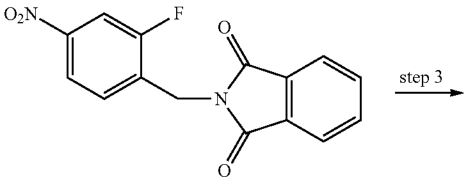

3

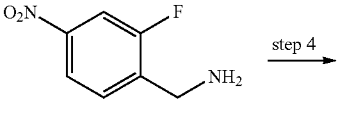

4

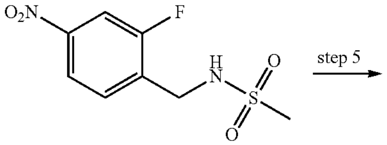

5

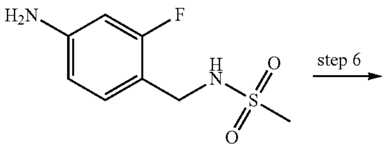

6

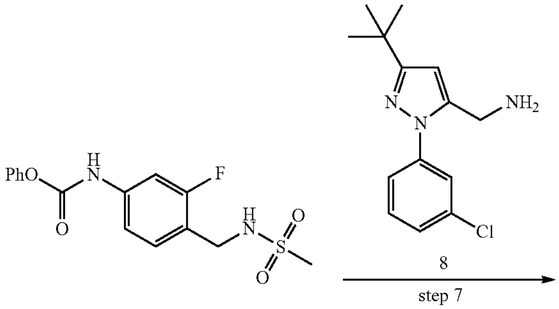

8

7

-continued

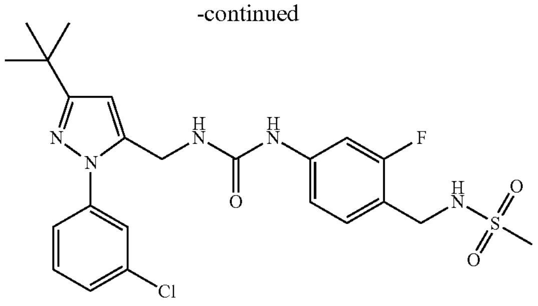

9

Step 1: To a stirred solution of 1 (1.993 g, 12.847 mmol) in carbon tetrachloride were added benzoyl peroxide (497 mg, 1.2847 mmol) and N-bromosuccinimide (2.972 g, 16.701 mmol). The reaction mixture was refluxed for 18 h, then cooled to room temperature. The mixture was diluted with EtOAc, then washed with water and brine. The organic layer was dried ($MgSO_4$) and filtered. The solvent was removed in vacuo. The crude product was purified by column chromatography. 2 (780 mg) was obtained in 26% yield.

Step 2: To a stirred solution of 2 (780 mg, 3.333 mmol) in DMF was added potassium phthalimide (1.235 g, 6.666 mmol). The reaction mixture was stirred for 18 h. The mixture was dissolved in EtOAc, washed with water and brine. The organic layer was dried ($MgSO_4$) and filtered. The solvent was removed in vacuo. The crude product was purified by column chromatography. 3 (1.034 g) was obtained as crude product.

Step 3: To a stirred solution of 3 (1.034 g, 3.444 mmol) in THF were added hydrazine monohydrate (1.104 g, 13.776 mmol) and p-toluenesulfonic acid monohydrate (66 mg, 0.3444 mmol). The reaction mixture was refluxed for 6 hours, then cooled to room temperature, and diluted with EtOAc. The mixture was washed with water and brine. The organic layer was dried ($MgSO_4$) and filtered. The solvent was removed in vacuo. The crude product was purified by column chromatography. 4 (329 mg) was obtained in 56% yield.

Step 4: To a stirred solution of 4 (131 mg, 0.770 mmol) in pyridine, cooled to 0° C., was added methanesulfonyl chloride (131 mg). The resulting reaction mixture was stirred for 1 hour at room temperature. The mixture was diluted with dichloromethane and washed with 1N HCl. The organic layer was dried ($MgSO_4$) and filtered. The solvent was removed in vacuo. The crude product was purified by column chromatography. 5 (173 mg) was obtained in 91% yield.

Step 5: To a stirred solution of 5 (187 mg, 0.753 mmol) in tetrahydrofuran and ethanol as co-solvent were added 10% palladium on carbon (20 mg). The mixture was charged with $H_2$ (gas) balloon. The resulting mixture was stirred for 15 hours, then filtered using celite. The solvent was removed in vacuo. The crude product was purified by column chromatography. 6 (135 mg) was obtained in 82% yield.

Step 6: To a stirred solution of 6 (135 mg, 0.618 mmol) in tetrahydrofuran and acetonitrile as co-solvent were added phenylchloroformate (0.08 mL, 0.6489 mmol) and pyridine (0.06 mL, 0.7416 mmol). The reaction mixture was stirred for 1 hour at room temperature. The mixture was diluted with EtOAc and washed with water and brine. The organic layer was dried ($MgSO_4$) and filtered. The solvent was removed in vacuo. The crude product was purified by column chromatography. 7 (140 mg) was obtained in 67% yield.

Step 7: To a stirred solution of 7 (46 mg, 0.136 mmol) and 8 (36 mg, 0.136 mmol) in acetonitrile was added DMAP (17 mg, 0.136 mmol). The reaction mixture was stirred for 15 hours at 50° C. The mixture was diluted with EtOAc and washed with water and brine. The organic layer was dried ($MgSO_4$) and filtered. The solvent was removed in vacuo. The crude product was purified by column chromatography. 9 (72 mg) was obtained in 99% yield.

$^1$H NMR (300 MHz, DMSO-$d_6$): δ 8.84 (s, 1H), 7.60 (s, 1H), 7.45 (m, 4H), 7.26 (t, 1H), 7.01 (dd, 1H), 6.76 (t, 1H), 6.32 (s, 1H), 4.40 (d, 2H), 4.09 (d, 2H), 2.85 (s, 3H), 1.27 (s, 9H).

Synthesis of Example B35

1-[[2-(3-Chlorophenyl)-5-(trifluoromethyl)-2H-pyrazol-3-yl]-methyl]-3-[4-[(sulfamoylamino)-methyl]-phenyl]-urea

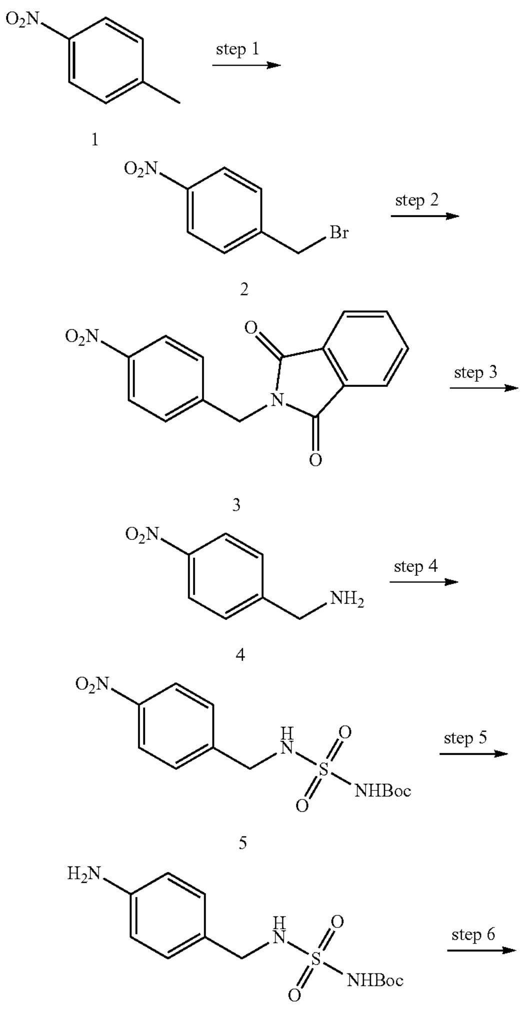

1

2

3

4

5

6

-continued

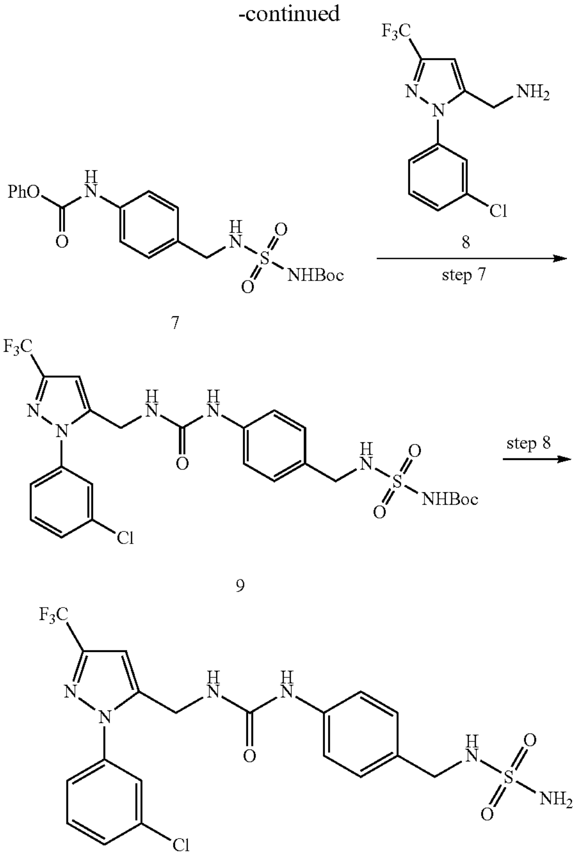

7

9

10

Step 1: NBS (1.51 g, 8.509 mmol) was added to a solution of 4-nitro-toluene 1 (1.2 g, 7.735 mmol) in carbon tetrachloride. 70% Benzoyl peroxide (120 mg) was added to the mixture at room temperature. The mixture was refluxed. After 24 h, the mixture was extracted with ethyl acetate (EtOAc). Drying ($MgSO_4$) and evaporation of the ethyl acetate followed and the residue was purified by column chromatography (EtOAc/n-hexane) to give the compound 2 in pure form in 61% yield.

Step 2: To a solution of compound 2 (1.1 g, 4.69 mmol) in DMF, potassium phthalimide (1.9 g, 10.314 mmol) was added. The mixture was stirred overnight and then extracted with EtOAc and washed by brine. Drying ($MgSO_4$) and evaporation of the ethyl acetate followed and the residue was purified by column chromatography (EtOAc/n-hexane) to give the compound 3 in pure form in 99% yield.

Step 3: To a solution of compound 3 (1.6 g, 5.33 mmol) in THF, hydrazine monohydrate (4 eq) was added. The mixture was refluxed for 6 hours and cooled to RT. The mixture was treated with potassium bicarbonate to a pH of 12~13. The mixture was extracted with EtOAc and washed by brine. Drying ($MgSO_4$) and evaporation of the ethyl acetate followed and the residue was purified by column chromatography (EtOAc/n-hexane) to give the compound 4 in pure form in 65% yield (592 mg).

Step 4: Chlorosulfonyl isocyanate (0.063 mL) and t-BuOH (0.07 mL) were mixed in DCM. After 10 minutes, a solution of compound 4 (100 mg, 0.657 mmol) in DCM was added at 50° C. After stirring for 30 min. the mixture was cooled to room temperature and then TEA (0.11 mL) was added and the mixture was stirred for 3 hours and then extracted with EtOAc and washed by brine. Drying ($MgSO_4$) and evaporation of the ethyl acetate followed and the residue was purified by column chromatography (EtOAc/n-hexane) to give the compound 5 in pure form in 51% yield (112 mg).

Step 5: 10% Palladium on carbon (7 mg) was added to a solution of compound 5 (65 mg) in ethanol and THF and the mixture was charged with $H_2$ (g). After stirring the reaction mixture for 6 h, the mixture was filtered using Celite and the solvent evaporated in vacuo to give the compound 6 in pure form in 58% yield (98 mg).

Step 6: Compound 6 (86 mg, 0.285 mmol) was dissolved in THF/acetonitrile. Pyridine (0.03 mL, 0.342 mmol) was added and then it addition of phenylchloroformate (0.04 ml, 0.300 mmol) at 0° C. followed. The mixture was stirred at 0° C. for 30 min and heated up to room temperature and then it was stirred for 30 min. After that, it was extracted with EtOAc and washed by brine. Drying ($MgSO_4$) and evaporation of the ethyl acetate followed and the residue was purified by column chromatography (EtOAc/n-hexane) to give the compound 7 in pure form in 49% yield (59 mg).

Step 7: Compound 7 (58 mg, 0.138 mmol) was dissolved in MeCN. Compound 8 (38 mg, 0.138 mmol) and DMAP (16 mg) were added to the solution. The reaction mixture was stirred overnight at 50° C. The mixture was extracted with EtOAc and washed by brine. Drying ($MgSO_4$) and evaporation of the ethyl acetate followed and the residue was purified by column chromatography (EtOAc/n-hexane) to give the compound 9 in pure form in 50% yield (60 mg).

Step 8: To a solution of compound 9 (80 mg, 0.133 mmol) in DCM (6 mL), TFA (2 mL) is added at 0° C. The mixture was stirred for 30 min and stirred for 2 hr more at room temperature. The mixture was neutralized with sodium bicarbonate to a pH of 7-8 and then extracted with EtOAc and washed by brine. Drying ($MgSO_4$) and evaporation of the ethyl acetate followed and the residue was purified by column chromatography (EtOAc/n-hexane) to give the compound 10 in pure form in 75% yield (50 mg).

$^1$H-NMR ($CD_3OD$): 7.64 (m, 1H, Ar), 7.55 (m, 3H, Ar), 7.28 (m, 4H, Ar), 6.75 (s, 1H, Ar), 4.47 (s, 2H, $CH_2NH$), 4.09 (s, 2H, $CH_2NH$).

Synthesis of Example B40

1-[4-(Aminomethyl)-3-fluoro-phenyl]-3-[[5-tert-butyl-2-(3-chlorophenyl)-2H-pyrazol-3-yl]-methyl]-urea

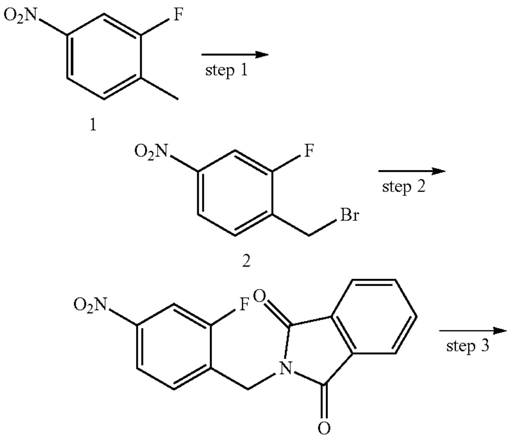

1

2

3

-continued

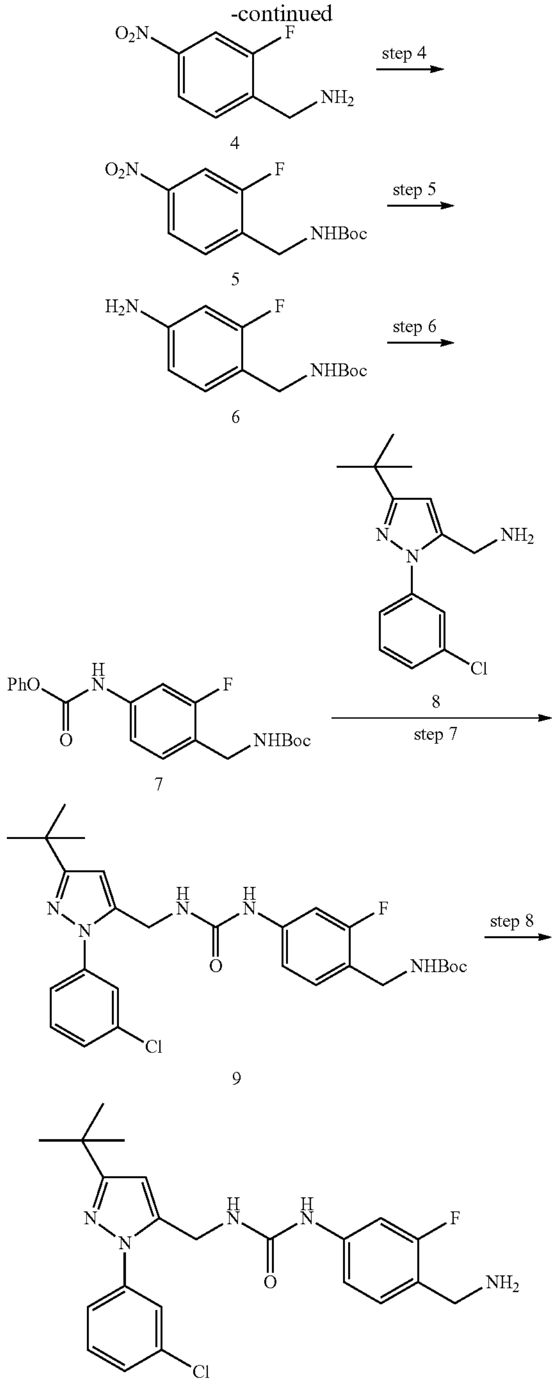

4

5

6

8

7

9

10

Steps 1-3 are performed as described for the synthesis of example B31

Step 4: Compound 4 (100 mg, 0.588 mmol) was dissolved in DCM. At 0° C., $Boc_2O$ (154 mg, 0.705 mmol) was added to the solution. After stirring for 30 min, the mixture was heated to room temperature and then TEA (0.13 ml) was added and the mixture was stirred overnight. And then it was extracted with EtOAc and washed by brine. Drying ($MgSO_4$) and evaporation of the ethyl acetate followed and the residue was purified by column chromatography (EtOAc/n-hexane) to give the compound 5 in pure form in 86% yield (136 mg).

Step 5: 10% Palladium on carbon (20 mg) was added to a solution of compound 5 (136 mg) in ethanol and THF and the mixture was charged with $H_2$ (g). After stirring the reaction mixture for 6 h, the mixture was filtered using Celite and the solvent was evaporated in vacuo. Compound 6 was obtained in 85% (103 mg).

Step 6: Compound 6 (103 mg, 0.429 mmol) was dissolved in THF/MeCN. Pyridine (0.04 mL, 0.515 mmol) was added and then addition of phenylchloroformate (0.06 mL, 0.450 mmol) at 0° C. was followed. The mixture was stirred at 0° C. for 30 min and heated up to room temperature and then it was stirred for another 30 min. After that, it was extracted with EtOAc and washed by brine. Drying ($MgSO_4$) and evaporation of the ethyl acetate followed and the residue was purified by column chromatography (EtOAc/n-hexane) to give the compound 7 in pure form in 75% yield (116 mg).

Step 7: Compound 7 (70 mg, 0.194 mmol) was dissolved in MeCN. Compound 8 (52 mg, 0.137 mmol) and DMAP (24 mg) were added to the solution. The reaction mixture was stirred overnight at 50° C. The mixture was extracted with EtOAc and washed by brine. Drying ($MgSO_4$) and evaporation of the ethyl acetate followed and the residue was purified by column chromatography (EtOAc/n-hexane) to give the compound 9 in pure form in 97% yield (100 mg).

Step 8: To a solution of compound 9 (100 mg, 0.189 mmol) in DCM (6 mL), TFA (2 mL) is added at 0° C. and the mixture was stirred for 30 min and stirred for 2 h more at room temperature. The mixture was neutralized with sodium bicarbonate to a pH of 7-8 and then extracted with EtOAc and washed by brine. Drying ($MgSO_4$) and evaporation of the ethyl acetate followed and the residue was purified by column chromatography (EtOAc/n-hexane) to give the compound 10 in pure form in 74% yield (60 mg).

$^1$H-NMR (300 MHz, DMSO-d6): δ 9.00 (s, 1H, urea), 7.60 (s, 1H, Ar), 7.47 (m, 4H, Ar, urea), 7.33 (m, 1H, Ar), 7.07 (m, 1H, Ar), 6.94 (m, 1H, Ar), 6.31 (s, 1H, Ar), 4.39 (m, 2H, Ar—$CH_2$), 3.88 (s, 2H, Ar—$CH_2$), 1.26 (s, 9H, t-butyl 9H).

Synthesis of Example B46

1-[[5-tert-Butyl-2-(3-chlorophenyl)-2H-pyrazol-3-yl]-methyl]-3-[3-fluoro-4-[(sulfamoylamino)-methyl]-phenyl]-urea

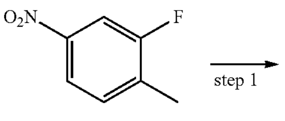

1

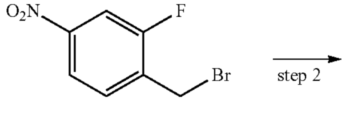

2

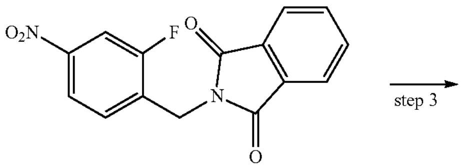

3

-continued

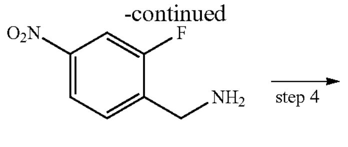

4

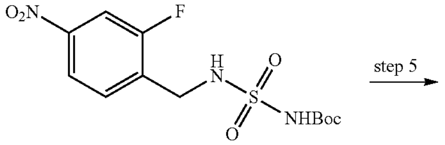

5

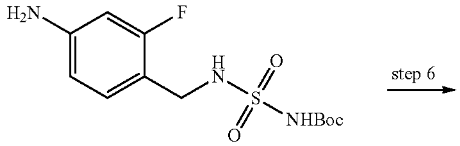

6

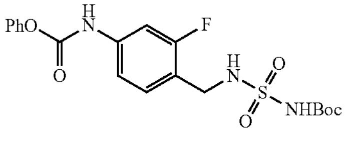

7

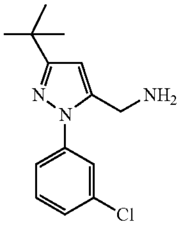

8

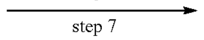

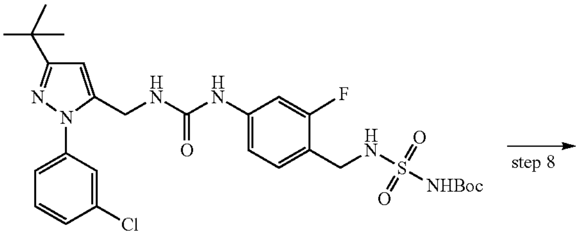

9

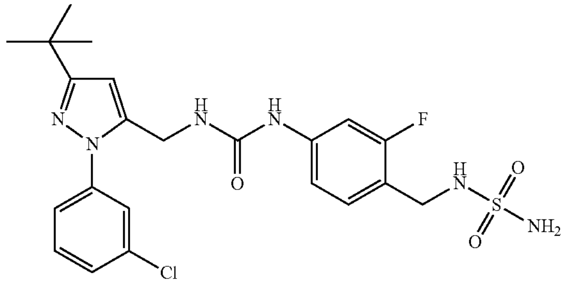

10

Steps 1-3 are performed as described for the synthesis of example B31

Step 4: Chlorosulfonyl isocyanate (0.1 mL) and t-BuOH (0.12 mL) were mixed in DCM. After 10 minutes, a solution of compound 4 (200 mg, 1.176 mmol) in DCM was added at 50° C. After stirring for 30 min. the mixture was cooled to room temperature and then TEA (0.11 mL) was added and the mixture was stirred for 3 hours and then extracted with EtOAc and washed by brine. Drying ($MgSO_4$) and evaporation of the ethyl acetate followed and the residue was purified by column chromatography (EtOAc/n-hexane) to give the compound 5 in pure form in 23% yield (139 mg).

Step 5: 10% Palladium on carbon (42 mg) was added to a solution of compound 5 (135 mg) in ethanol and THF and the mixture was charged with $H_2$ (g). After stirring the reaction mixture for 6 h, the mixture was filtered using Celite and the solvent evaporated in vacuo to give the compound 6 in pure form in 99% yield (127 mg).

Step 6: Compound 6 (127 mg, 0.398 mmol) was dissolved in THF/acetonitrile. Pyridine (0.04 ml, 0.478 mmol) was added and then addition of phenylchloroformate (0.05 mL, 0.418 mmol) at 0° C. followed. The mixture was stirred at 0° C. for 30 min and heated up to room temperature and then it was stirred for 30 min. After that, it was extracted with EtOAc and washed by brine.

Drying ($MgSO_4$) and evaporation of the ethyl acetate followed and the residue was purified by column chromatography (EtOAc/n-hexane) to give the compound 7 in pure form in 91% yield (160 mg).

Step 7: Compound 7 (50 mg, 0.114 mmol) was dissolved in MeCN. Compound 8 (30 mg, 0.114 mmol) and DMAP (14 mg) were added to the solution. The reaction mixture was stirred overnight at 50° C. The mixture was extracted with EtOAc and washed by brine. Drying ($MgSO_4$) and evaporation of the ethyl acetate followed and the residue was purified by column chromatography (EtOAc/n-hexane) to give the compound 9 in pure form in 65% yield (45 mg).

Step 8: To a solution of compound 9 (45 mg, 0.074 mmol) in DCM (6 mL), TFA (2 mL) is added at 0° C. The mixture was stirred for 30 min and stirred for 2 h more at room temperature. The mixture was neutralized with sodium bicarbonate to a pH of 7-8 and then extracted with EtOAc and washed by brine. Drying ($MgSO_4$) and evaporation of the ethyl acetate followed and the residue was purified by column chromatography (EtOAc/n-hexane) to give the compound 10 in pure form in 74% yield (28 mg).

$^1$H-NMR (300 MHz, $CD_3OD$): δ 7.48 (m, 4H, Ar), 7.33 (m, 2H, Ar), 6.96 (m, 1H, Ar), 6.36 (s, 1H, Ar), 4.41 (s, 2H), 4.17 (s, 2H), 1.32 (s, 9H, t-butyl 9H).

Synthesis of Example B63

N-[[5-tert-Butyl-2-(3-chlorophenyl)-2H-pyrazol-3-yl]-methyl]-2-[3-fluoro-4-(methylamino-methyl)-phenyl]-propionamide

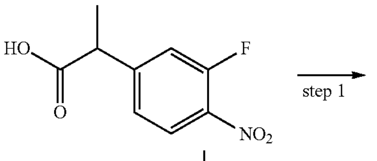

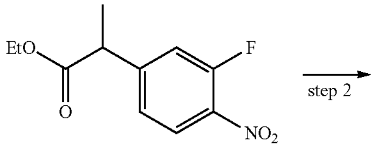

1

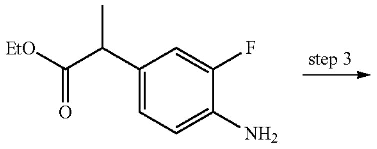

2

-continued

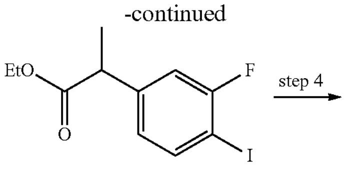

3

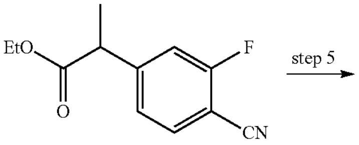

4

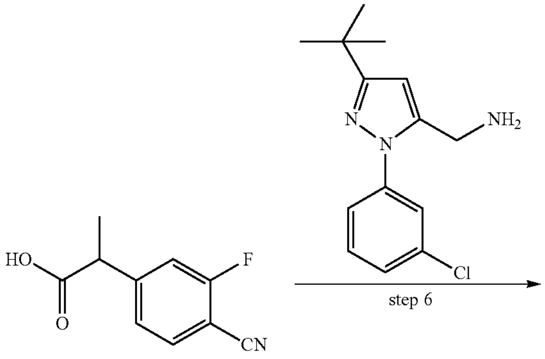

5

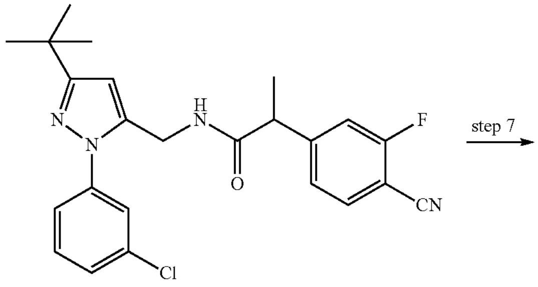

6

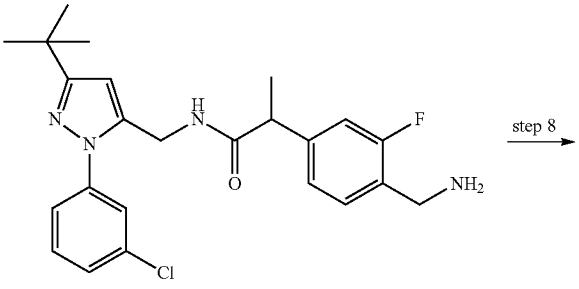

7

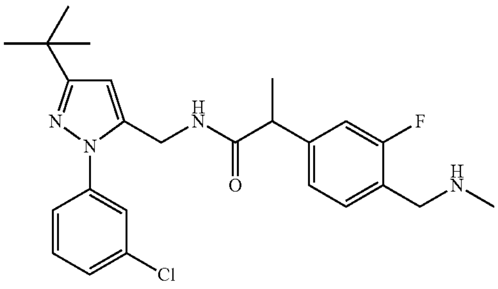

8

Step 1: To a stirred solution of 2-(3-Fluoro-4-nitro-phenyl)-propionic acid in methanol was added sulfuric acid (0.3 mL). The reaction mixture was refluxed for 15 h and cooled to room temperature. The solvent was evaporated. The residue was dissolved in EtOAc and extracted with a sat. solution of $NaHCO_3$. The organic layer was dried ($MgSO_4$) and filtered. The solvent was removed in vacuo. The crude product was purified by CC. 1 was obtained.

Step 2: 10% Palladium on carbon was added to a solution of ethyl ester (1) in ethanol and THF and the mixture was charged with $H_2$ (g). After stirring the reaction mixture for 6 h, the mixture was filtered using Celite and purified by column chromatography to obtain 2.

Step 3: A solution of p-TsOH.$H_2O$ (3 equiv.) in $CH_3CN$ was added to a solution of 2 (1 eq.) in $CH_3CN$. The resulting suspension was cooled to 10-15° C. and to this was added, gradually, a solution of $NaNO_2$ (2 eq.) and KI (2.5 eq.) in $H_2O$. The reaction mixture was stirred for 10 min then allowed to come to 20° C. and stirred until the starting material was consumed. After 4 hours, water, $NaHCO_3$ (until pH=9-10) was added and extracted with ethyl acetate. The organic layer was washed with water, dried ($MgSO_4$) and concentrated in vacuo. The residue was purified by CC to give 3.

Step 4: Compound 3, $Pd_2(dba)_3$, dppf, Zn powder, $Zn(CN)_2$ were placed in round flask charged with $N_2$ and DMA (0.02 equiv.) was added dropwise by syringe. The reaction mixture was stirred at 120° C. for 15 hours and cooled to room temperature followed by extraction with EtOAc and washing with a 2N $NH_4OH$ solution. The organic layer was washed with water, dried ($Na_2SO_4$) and concentrated in vacuo. The residue was purified on CC to give the desired product 4.

Step 5: To a solution of compound 4 in THF and water (1:1) is added NaOH (2.5 equiv.) and the mixture stirred at room temperature. After 15 hours, the reaction mixture is acidified by AcOH until pH=2-3. The mixture is extracted with DCM and water. The organic layer is washed with water, dried ($MgSO_4$) and concentrated in vacuo. The product is purified by CC (eluent DCM:MeOH 10:1) and the desired product 5 obtained.

Step 6: EDC (1.5 equiv), HOBt (1.5 equiv), and (3-tert-butyl-1-(3-chlorophenyl)-1H-pyrazol-5-yl)methanamine (1 eq.) are added to a solution of (5) and then added drop-wise is TEA (2.5 mL). The reaction mixture is stirred overnight at room temperature. The reaction is quenched with water and extracted with ethyl acetate. The extracted organic layer is dried over $MgSO_4$. After evaporation of the solvent, the residue is purified by column chromatographic purification (eluent EtOAc:n-hexane) and 6 is obtained.

Step 7: Nickel(II) chloride hexahydrate (1 eq.) and compound 6 are stirred in anhydrous ethanol during 15 minute for activation. Sodium borohydride (7 eq.) is added the mixture stirred for 2 h. Celite was added to the reaction and it was filtered by using a celite packed filter, and washing with ethanol was perform. The residue is purified after concentration to obtain 7.

Step 8: Sodium methoxide (1M in methanol) was added to a solution of compound 7 in methanol followed by the addition of paraformaldehyde (5 eq.). The reaction mixture was refluxed for 1.5 h then cooled to 0° C. with an ice bath. Sodium borohydride (6 equiv.) was added with caution. The mixture was refluxed again for 1 h and cooled down. The mixture was extracted with DCM and washed with water. After evaporating the solvent, the mixture was purified by column chromatography (DCM:MeOH=4:1) to obtain example compound B63.

$^1H$ NMR (300 MHz, $CDCl_3$): δ 7.41-7.32 (m, 5H, Ar—H), 6.99-6.95 (m, 3H, Ar—H), 6.06 (s, 1H, Ar—H), 5.643 (bs, 1H, Ar—NH), 4.46 (d, 2H, J=6.00 Hz, pyrazole-α-H), 3.88 (s, 2H, Ar-α-H), 3.49 (q, 1H, J=7.50 Hz, Ar-α-H), 2.48 (s, 3H, methansulfonyl-$CH_3$), 1.47 (d, 3H, J=6.00 Hz, Ar-α-$CH_3$), 1.33 (s, 9H, t-butyl).

Synthesis of Example B64

N-[[5-tert-Butyl-2-(3-chlorophenyl)-2H-pyrazol-3-yl]-methyl]-2-[4-(dimethylaminomethyl)-3-fluoro-phenyl]-propionamide

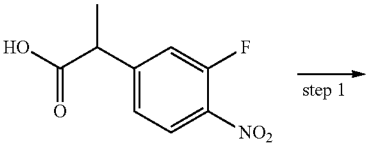

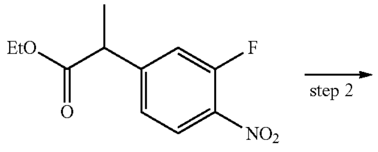

1

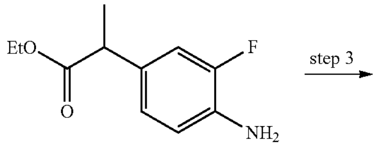

2

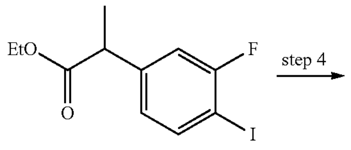

3

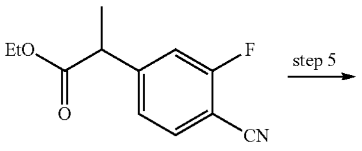

4

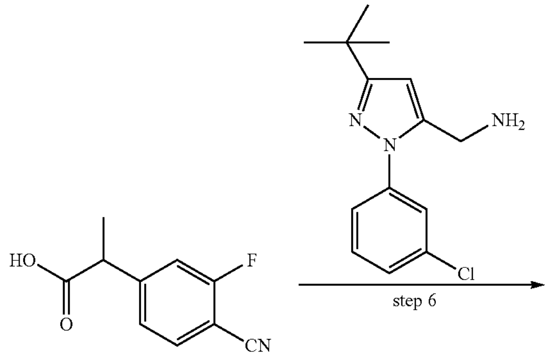

5

-continued

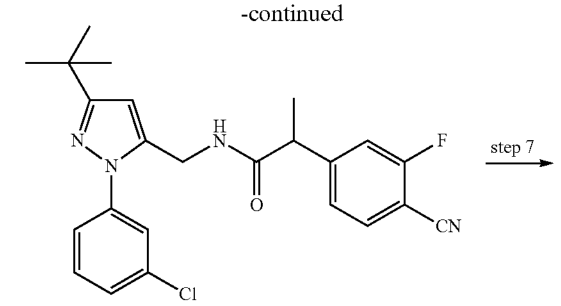

6

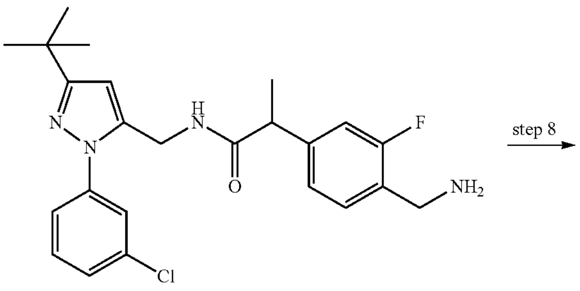

7

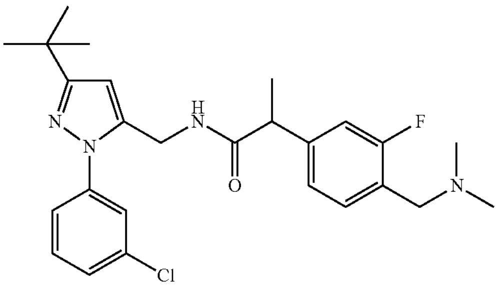

8

Steps 1-7 are performed as described for the synthesis of example B63

Step 8: Sodium cyanoborohydrid is added to a solution of compound 7 and paraformaldehyde in acetic acid. The reaction mixture is stirred at room temperature for 15 hours and poured on ice. Sodium bicarbonate was used to adjust the pH to 9. The mixture was extracted with EtOAc and dried over sodium sulfate. After evaporating solvent, the mixture is purified by column chromatography to obtain the desired product example compound B64.

$^1$H NMR (400 MHz, $CDCl_3$): δ 7.38 (s, 1H, Ar—H), 7.35-7.27 (m, 3H, Ar—H), 7.21 (d, 1H, Ar—H), 6.95 (m, 2H, Ar—H), 6.01 (s, 1H, Ar—H), 5.48 (bs, 1H, Ar—NH), 4.46 (d, 2H, J=600 Hz, pyrazole-α-H), 3.68 (s, 2H, Ar-α-H), 3.49 (q, 1H, J=7.50 Hz, Ar-α-H), 2.30 (s, 6H, methansulfonyl-$CH_3$ and N—$CH_3$), 1.47 (d, 3H, J=600 Hz, Ar-α-$CH_3$), 1.33 (s, 9H, t-butyl).

Synthesis of Example B86

1-[4-(Methanesulfonamido-methyl)-3-methoxy-phenyl]-3-[[2-(m-tolyl)-5-(trifluoromethyl)-2H-pyrazol-3-yl]-methyl]-urea

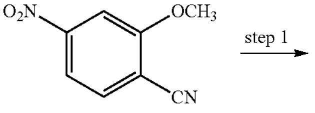

1

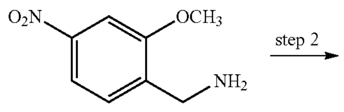

2

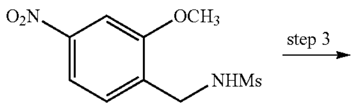

3

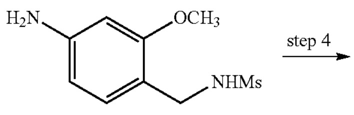

4

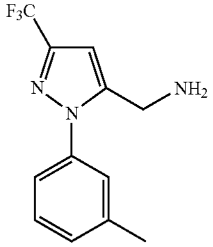

6

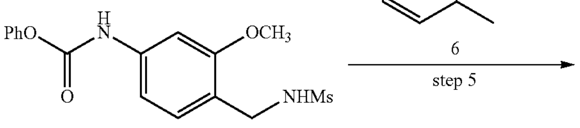

5

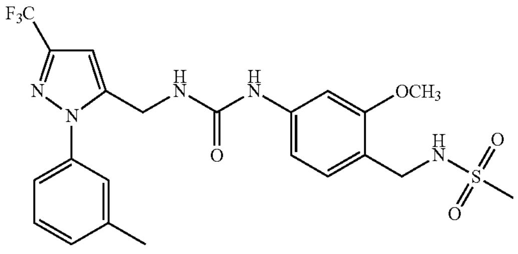

7

Step 1: To a stirred solution of 1 (300 mg, 1.683 mmol) in THF were added borane methyl sulfide complex (2M in THF) (1.4 mL, 2.83 mmol) at room temperature. The reaction mixture was stirred for 16 h at 66° C., then cooled to room temperature. The residue was diluted with EtOAc and washed with water and brine. The organic layer was dried ($MgSO_4$) and filtered. The solvent was removed in vacuo. The crude product was purified by column chromatography. 2 (270 mg) was obtained as 68% yield.

Step 2: To a stirred solution of 2 (190 mg, 1.04 mmol) in pyridine was added methanesulfonyl chloride at 0° C. The reaction mixture was stirred for 1 h at room temperature. The mixture was quenched by 1N HCl. The residue was diluted with DCM and washed with water and brine. The organic layer was dried ($MgSO_4$) and filtered. The solvent was removed in vacuo. The crude product was purified by column chromatography. 3 (205 mg) was obtained as 76% yield.

Step 3: To a stirred solution of 3 (205 mg, 0.79 mmol) in tetrahydrofuran and ethanol as co-solvent was added 10% palladium on carbon (21 mg). The mixture was charged with $H_2$ (gas) balloon. The resulting mixture was stirred for 16 h, then filtered using celite. The filtrate removed in vacuo. The filtrate removed in vacuo. The crude product was purified by column chromatography. 4 (190 mg) was obtained as 99% yield.

Step 4: To a stirred solution of 4 (190 mg, 0.83 mmol) in THF (6 mL) and $CH_3CN$ (8 mL) as co-solvent were added phenyl chloroformate (0.11 mL, 0.866 mmol) and pyridine (0.08 mL, 0.99 mmol). The reaction mixture was stirred for 3 h at room temperature. The residue was dissolved in EtOAc and washed with water and brine. The organic layer was dried ($MgSO_4$) and filtered. The solvent was removed in vacuo. The crude product was purified by column chromatography. 5 (238 mg) was obtained as 82% yield.

Step 5: To a stirred solution of 5 (79 mg, 0.225 mmol) in MeCN and 6 (57 mg, 0.225 mmol) were added DMAP (28 mg, 0.225 mmol). The reaction mixture was stirred for 16 hours at 50° C. The residue dissolved in EtOAc and washed with water and brine. The organic layer was dried ($MgSO_4$) and filtered. The solvent was removed in vacuo. The crude product was purified by column chromatography. 7 (104 mg) was obtained as 90% yield.

$^1H$ NMR (300 MHz, DMSO) δ7.42 (m, 4H, Ar), 7.17 (m, 2H, Ar), 6.83 (d, J=9.87 Hz, 1H, Ar), 6.77 (s, 1H, Ar), 4.38 (d, 2H, J=5.67 Hz, $CH_2$), 4.03 (d, 2H, J=6.06 Hz, $CH_2$), 3.74 (s, 3H, methoxy), 2.81 (s, 3H, mesyl), 2.40 (s, 3H, Ar—$CH_3$).

Synthesis of Example B95

N-[[2-(3-Chlorophenyl)-5-cyclopropyl-2H-pyrazol-3-yl]-methyl]-2-[3-fluoro-4-[(sulfamoylamino)-methyl]-phenyl]-propionamide

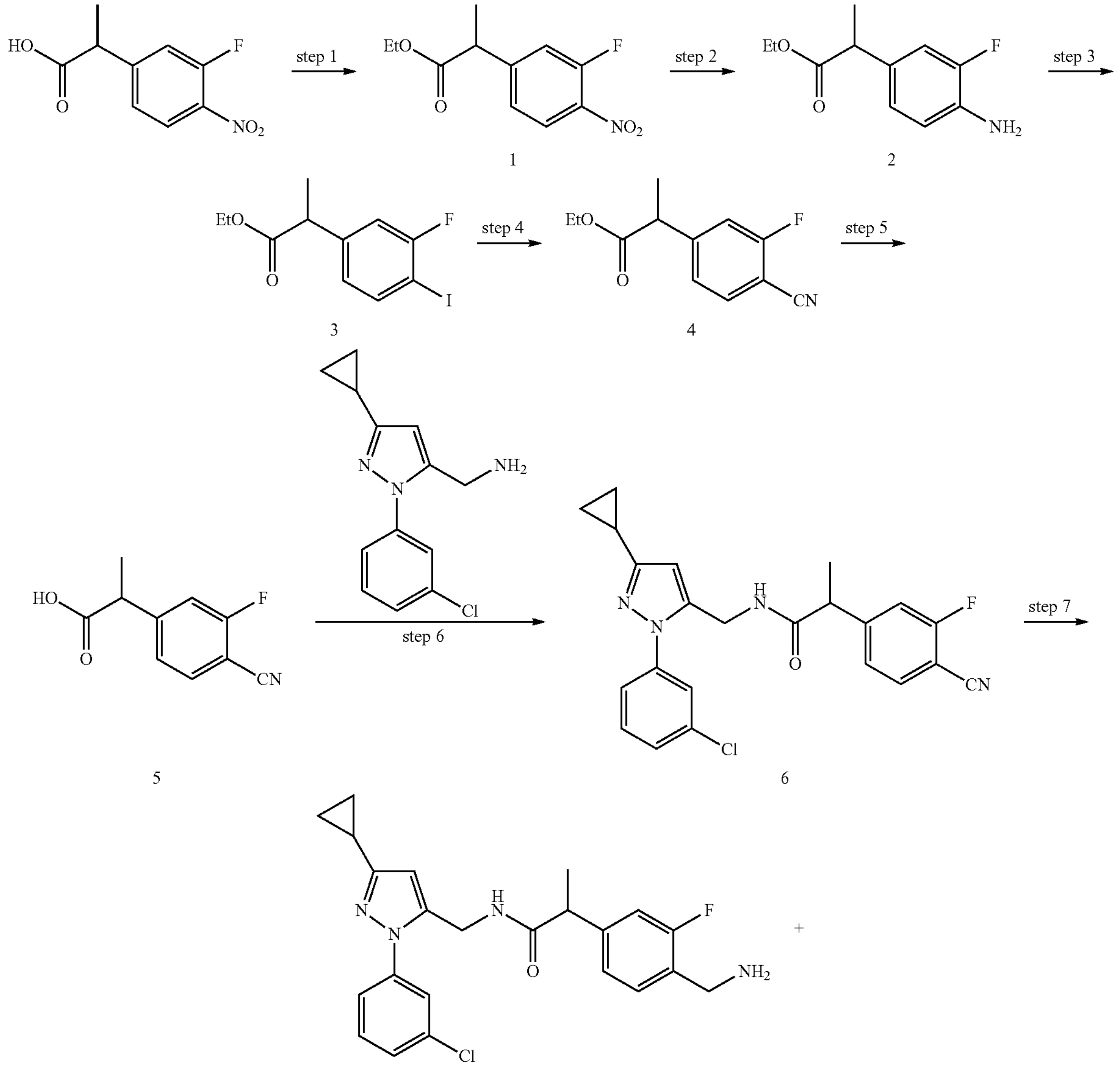

7

-continued

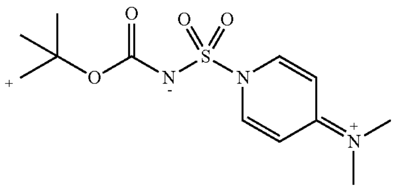

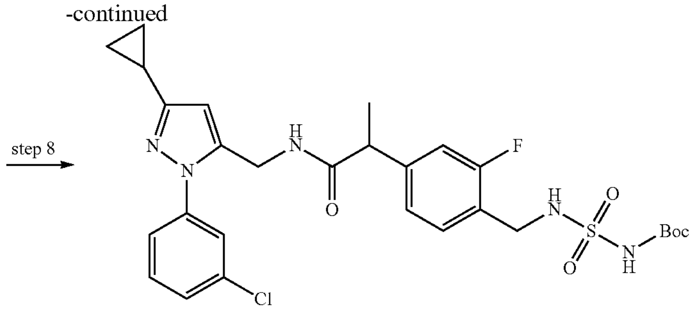

8

9 step 10 step 9

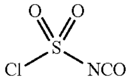

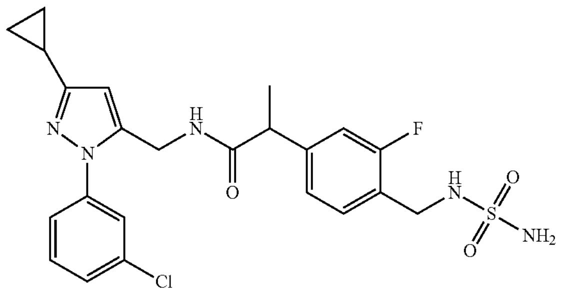

10

Steps 1-5 are performed as described for the synthesis of example B63

Step 6: EDC (1.5 equiv), HOBt (1.5 equiv), and (1-(3-chlorophenyl)-3-cyclopropyl-1H-pyrazol-5-yl)methanamine (1 eq.) are added to a solution of (5) and then added drop-wise is TEA (2.5 mL). The reaction mixture is stirred overnight at room temperature. The reaction is quenched with water and extracted with ethyl acetate. The extracted organic layer is dried over $MgSO_4$. After evaporation of the solvent, the residue is purified by column chromatographic purification (eluent EtOAc/n-hexane) and 6 is obtained.

Step 7: Nickel(II) chloride hexahydrate (1 eq.) and compound 6 are stirred in anhydrous ethanol during 15 minute for activation. Sodium borohydride (7 eq.) is added the mixture stirred for 2 hours. Celite was added to the reaction and it was filtered by using a celite packed filter, and washing with ethanol was performed. The residue is purified after concentration to obtain 7.

Step 8: Compound 7 and compound 8 are dissolved in DCM. TEA (0.1 eq.) is added dropwise. The reaction mixture is stirred for 15 h at room temperature and quenched with water. The organic layer is extracted with DCM and concentrated. After purification by CC, compound 9 is obtained.

Step 9: TFA (12 mL) is added to a solution of compound 9 in a solution of DCM and the reaction mixture is stirred for 4 h at room temperature. Water is added to the mixture and the separated mixture is extracted with DCM. The residue is purified after concentration by CC and compound 10 (example B95) is obtained.

$^1$H NMR (400 MHz, $CDCl_3$) δ 7.41-7.33 (m, 5H, Ar—H), 6.94 (m, 2H, Ar—H), 5.39 (s, 1H, Ar—H), 5.39 (bs, 1H, α-NH), 4.43 (bs, 1H, Ar-α-NH), 4.46 (2, 2H, Ar-α-$CH_2$), 4.41 (m, 2H, J=600 Hz, α-$CH_2$), 4.32 (d, 2H, α-$CH_2$), 3.47 (m, 1H), 2.38 (s, 3H, Ar—$CH_3$), 1.44 (d, 3H, J=600 Hz, α-$CH_3$), 0.93 (m, 2H, cyclopropyl-$CH_2$), 0.68 (m, 2H, cyclopropyl-$CH_2$).

Step 10: 1 eq. of CSI (Chlorosulfonyl isocyanate) is added dropwise to a cold solution of tert-butyl alcohol (1 eq.) in anhydrous DCM. Then DMAP (2 eq.) is added. The mixture is stirred for 3 h at room temperature. The organic layer is extracted with DCM and washed with water. After column chromatography, a colorless powder (compound 8) is obtained.

Synthesis of Example B97

N-[[2-(3-Chlorophenyl)-5-(trifluoromethyl)-2H-pyrazol-3-yl]-methyl]-2-[3-fluoro-4-[(sulfamoylamino)-methyl]-phenyl]-propionamide

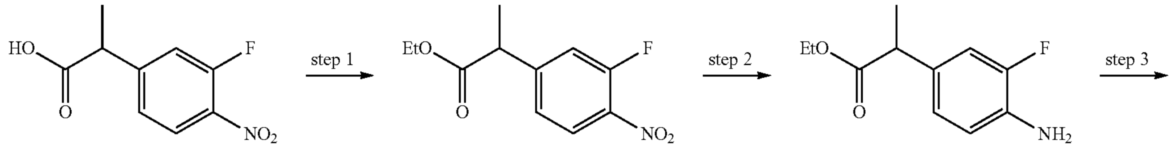

1

2

-continued
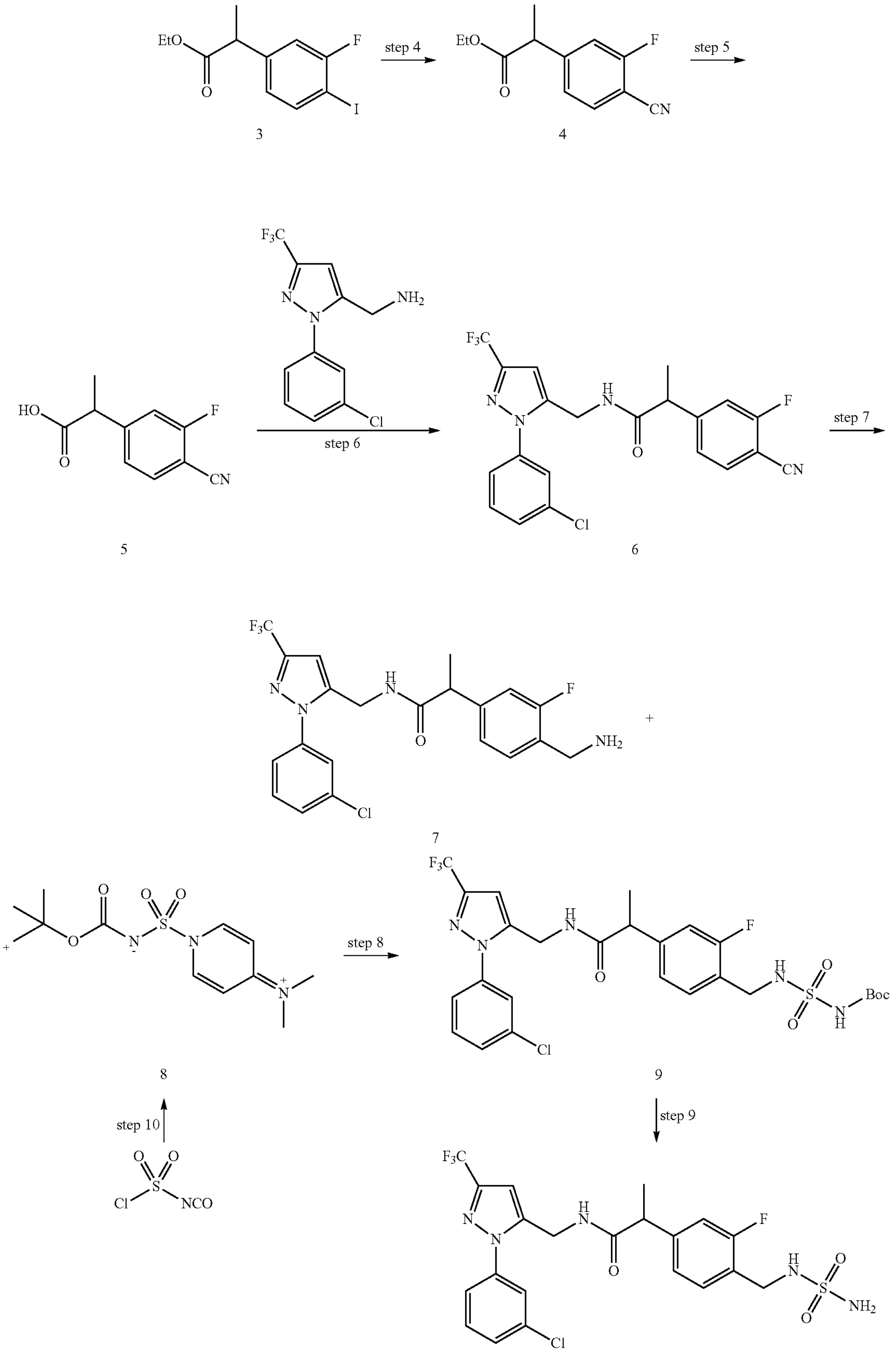
3 4 5 6 7 8 9 10

Steps 1-5 are performed as described for the synthesis of example B95

Step 6: EDC (1.5 equiv), HOBt (1.5 equiv), and (1-(3-chlorophenyl)-3-(trifluoromethyl)-1H-pyrazol-5-yl)methanamine (1 eq.) are added to a solution of (5) and then added drop-wise is TEA (2.5 mL). The reaction mixture is stirred overnight at room temperature. The reaction is quenched with water and extracted with ethyl acetate. The extracted organic layer is dried over $MgSO_4$. After evaporation of the solvent, the residue is purified by column chromatographic purification (eluent EtOAc/n-hexane) and 6 is obtained.

Steps 7-10 are performed as described for the synthesis of example B95 NMR characterization of example B97 (compound 10):

$^1$H NMR (400 MHz, $CDCl_3$): δ 7.41-7.33 (m, 5H, Ar—H), 6.94 (m, 2H, Ar—H), 6.40 (s, 1H, Ar—H), 5.59 (bs, 1H, α-NH), 4.64 (bs, 1H, Ar-α-NH), 4.46 (s, 2H, Ar-α-$CH_2$), 4.32 (d, 2H, J=8.00 Hz, α-$CH_2$), 4.09 (q, 1H, α-CH), 1.44 (d, 3H, J=600 Hz, α-$CH_3$)

TABLE 2

Mass Spectrometric Data for Example Compounds of Formula (R)

| Example compound | [M + H] |
|---|---|
| B1 | 533.2 |
| B2 | 550.8 |
| B3 | 538.9 |
| B4 | 489.9 |
| B5 | 515.4 |
| B6 | 503.6 |
| B7 | 517.0 |
| B8 | 567.0 |
| B9 | 505.1 |
| B10 | 523.0 |
| B11 | 520.5 |
| B12 | 532.4 |
| B13 | 538.0 |
| B14 | 438.2 |
| B15 | 529.2 |
| B16 | 535.6 |
| B17 | 547.5 |
| B18 | 533.4 |
| B19 | 535.0 |
| B20 | 521.6 |
| B21 | 505.2 |
| B22 | 549.9 |
| B23 | 519.0 |
| B24 | 470.0 |
| B25 | 458.1 |
| B26 | 507.2 |
| B27 | 538.1 |
| B28 | 490.6 |
| B29 | 547.5 |
| B30 | 535.6 |
| B31 | 508.6 |
| B32 | 526.0 |
| B33 | 484.2 |
| B34 | 472.5 |
| B35 | 503.6 |
| B36 | 491.5 |
| B37 | 503.0 |
| B38 | 470.0 |
| B39 | 442.2 |
| B40 | 430.6 |
| B41 | 521.4 |
| B42 | 455.3 |
| B43 | 555.0 |
| B44 | 485.9 |
| B45 | 474.0 |

TABLE 2-continued

Mass Spectrometric Data for Example Compounds of Formula (R)

| Example compound | [M + H] |
|---|---|
| B46 | 509.7 |
| B47 | 442.5 |
| B48 | 504.0 |
| B49 | 521.9 |
| B50 | 492.6 |
| B51 | 526.8 |
| B52 | 520.6 |
| B53 | 492.0 |
| B54 | 542.1 |
| B55 | 554.0 |
| B56 | 475.0 |
| B57 | 505.1 |
| B58 | 515.0 |
| B59 | 493.1 |
| B60 | 504.9 |
| B61 | 493.3 |
| B62 | 522.9 |
| B63 | 457.7 |
| B64 | 471.5 |
| B65 | 483.6 |
| B66 | 497.4 |
| B67 | 485.6 |
| B68 | 513.2 |
| B69 | 511.0 |
| B70 | 539.4 |
| B71 | 517.0 |
| B72 | 510.1 |
| B73 | 528.1 |
| B74 | 492.9 |
| B75 | 475.3 |
| B76 | 545.5 |
| B77 | 486.9 |
| B78 | 521.6 |
| B79 | 511.0 |
| B80 | 529.1 |
| B81 | 502.4 |
| B82 | 541.1 |
| B83 | 510.0 |
| B84 | 516.7 |
| B85 | 504.6 |
| B86 | 511.9 |
| B87 | 500.1 |
| B88 | 501.2 |
| B89 | 481.9 |
| B90 | 470.2 |
| B91 | 495.9 |
| B92 | 484.1 |
| B93 | 522.7 |
| B94 | 542.0 |
| B95 | 506.5 |
| B96 | 540.6 |
| B97 | 534.5 |
| B98 | 533.9 |
| B99 | 478.1 |
| B100 | 510.2 |
| B101 | 484.1 |
| B102 | 516.8 |
| B103 | 504.6 |
| B106 | 529.3 |
| B107 | 517.6 |

Synthesis of Example C1

N-[[2-(3-Chlorophenyl)-5-(trifluoromethyl)-2H-pyrazol-3-yl]-methyl]-2-[4-(1,1-dioxo-[1,2]thiazolidin-2-yl)-3-fluoro-phenyl]-propionamide

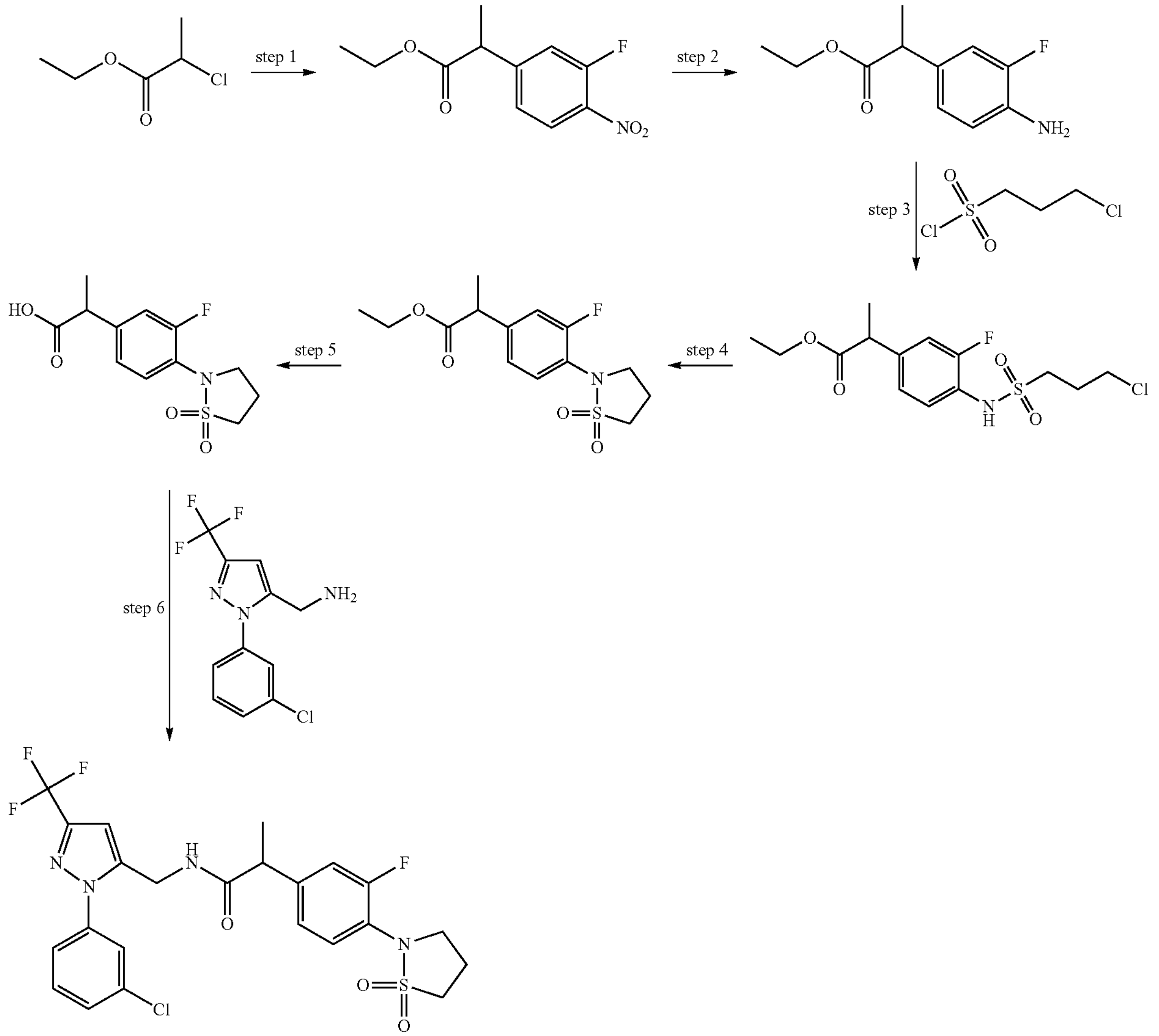

Step 1: Under a nitrogen atmosphere, potassium tert. butyloxide (8.2 g, 73 mmol) was slurried in DMF and cooled to −45° C. A mixture of o-fluoronitrobenzene (3.88 mL, 36.6 mmol) and ethyl-2-chloropropionate (4.66 mL, 36.6 mmol) was added while maintaining this temperature and the mixture was stirred for 15 min. The reaction mixture was adjusted with HCl (16%) to pH=4 and diluted with water (250 mL). The aqueous phase was repeatedly extracted with ethyl acetate (3×100 mL), the combined organic phases are washed with water (3×100 mL) and brine (1×100 mL) and dried over magnesium sulfate. After concentration in vacuo ethyl 2-(3-fluoro-4-nitrophenyl)propanoate was obtained (8.47 g, 96%).

Step 2: A suspension of ethyl 2-(3-fluoro-4-nitrophenyl) propanoate (8.3 g, 34.41 mmol) and Pd/C (10% Pd) in EtOH (170 mL) was hydrogenated for 1 h under a hydrogen atmosphere (2.5 bar, 22 SC). The suspension was removed by filtration, concentrated under vacuum and purified by column chromatography (SiO$_2$, ethyl acetate/hexane 1:5) to obtain ethyl 2-(4-amino-3-fluorophenyl)propanoate (6.4 g, 77%).

Step 3: Chloropropanesulfonyl chloride (0.576 mL, 4.73 mmol) was added to a solution of ethyl 2-(4-amino-3-fluorophenyl)propanoate (1 g, 4.735 mmol) and pyridine (0.382 mL, 4.735 mmol) in DCM (18 mL) at 0° C. The reaction mixture was stirred for 1 h, after it was partitioned between DCM (10 mL) and 1N hydrochloric acid (10 mL). The organic phase was separated and dried over magnesium sulfate, filtered and concentrated in vacuo to afford ethyl 2-(4-(3-chloropropylsulfonamido)-3-fluorophenyl)propanoate as an oil (1.5 g).

Step 4: Potassium carbonate (881 mg, 6.39 mmol) and ethyl 2-(4-(3-chloropropylsulfonamido)-3-fluorophenyl) propanoate (1.5 g, 4.264 mmol) were dissolved in DMF (9 mL) at room temperature under an atmosphere of nitrogen. The reaction mixture was stirred for 24 h after which time it was partitioned between diethyl ether (50 mL) and water (50 mL). The organic phases were washed with 1 N HCl (30 mL) and water (30 mL) and dried over magnesium sulfate. After filtration and concentration in vacuo 2-[4-(1,1-dioxo-[1,2]thiazolidin-2-yl)-3-fluoro-phenyl]-propionic acid ethyl ester was obtained (598 mg, 44%).

Step 5: 2-[4-(1,1-Dioxo-[1,2]thiazolidin-2-yl)-3-fluoro-phenyl]-propionic acid ethyl ester (448 mg, 1.42 mmol) was dissolved in a 2:1 mix of THF/water (2.8 mL+1.4 mL) and stirred for 15 min. 3 equivalents of LiOH (98 mg, 4.26 mmol), which is also dissolved in a 2:1 THF/water mix (1 mL+0.5 mL), are added to this solution. The reaction mixture was stirred overnight under reflux. While cooling, the aqueous phase is set to pH 1 using 4 N aq. HCl and repeatedly extracted with ethyl acetate (3×10 mL). The combined organic phases are dried over magnesium sulfate and concentrated under reduced pressure to afford 2-[4-(1,1-dioxo-[1,2]thiazolidin-2-yl)-3-fluoro-phenyl]-propionic acid (350 mg, 86%).

Step 6: To a solution of 2-[4-(1,1-Dioxo-[1,2]thiazolidin-2-yl)-3-fluoro-phenyl]-propionic acid (50 mg, 0.174 mmol) in THF (1.3 mL) was added 1-hydroxybenzotriazole (23 mg, 0.174 mmol), O-(1H-benzotriazol-1-yl)-N,N,N',N'-tetramethyluroniumtetrafluoroborate (56 mg, 0.174 mmol), n-ethyldiisopropylamine (0.059 mL, 0.348 mmol) and (1-(3-chlorophenyl)-3-(trifluoromethyl)-1H-pyrazol-5-yl)methanamine (47 mg, 0.174 mmol). The reaction mixture was stirred for 48 h at room temperature. The reaction mixture was concentrated in vacuo and purified by column chromatography (eluent: ethyl acetate/cyclohexan (2:1)) to give pure N-[[2-(3-chlorophenyl)-5-(trifluoromethyl)-2H-pyrazol-3-yl]-methyl]-2-[4-(1,1-dioxo-[1,2]thiazolidin-2-yl)-3-fluoro-phenyl]-propionamide (example compound C1) (68 mg, 72%).

Synthesis of Example C2

N-[[5-tert-Butyl-2-(3-chloro-4-fluoro-phenyl)-2H-pyrazol-3-yl]-methyl]-2-[4-(1,1-dioxo-[1,2]thiazolidin-2-yl)-3-fluoro-phenyl]-propionamid

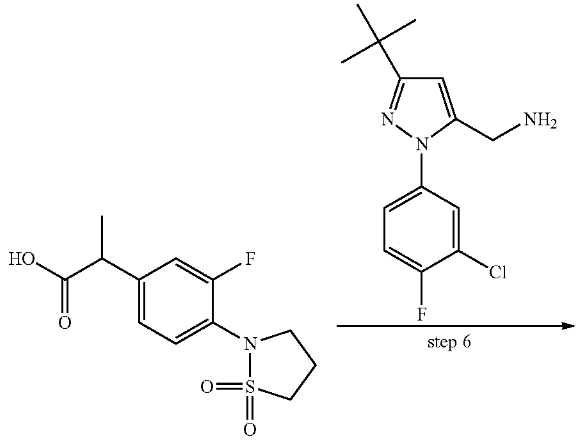

-continued

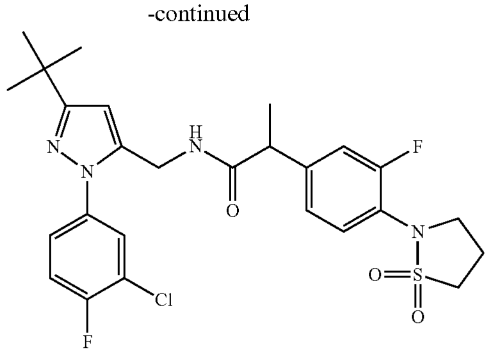

Steps 1-5: were carried out as described for example compound C1

Step 6: To a solution of 2-[4-(1,1-dioxo-[1,2]thiazolidin-2-yl)-3-fluoro-phenyl]-propionic acid (50 mg, 0.174 mmol) in THF (1.3 mL) was added 1-hydroxybenzotriazole (23 mg, 0.174 mmol), O-(1H-benzotriazol-1-yl)-N,N,N',N'-tetramethyluroniumtetrafluoroborate (56 mg, 0.174 mmol), n-ethyldiisopropylamine (0.059 mL, 0.348 mmol) and (3-tert-butyl-1-(3-chloro-4-fluorophenyl)-1H-pyrazol-5-yl)methanamine (81 mg, 0.174 mmol). The reaction mixture was stirred for 48 h at room temperature. The reaction mixture was concentrated in vacuo and purified by column chromatography (eluent: ethyl acetate/cyclohexan (2:1)) to give pure example compound C2 (75 mg, 78%).

Example compound 3 was prepared analogously according to example C1.

Synthesis of Example C6

1-[[2-(3-Chlorophenyl)-5-(trifluoromethyl)-2H-pyrazol-3-yl]-methyl]-3-[3-fluoro-4-(3-hydroxy-azetidin-1-yl)-phenyl]-urea

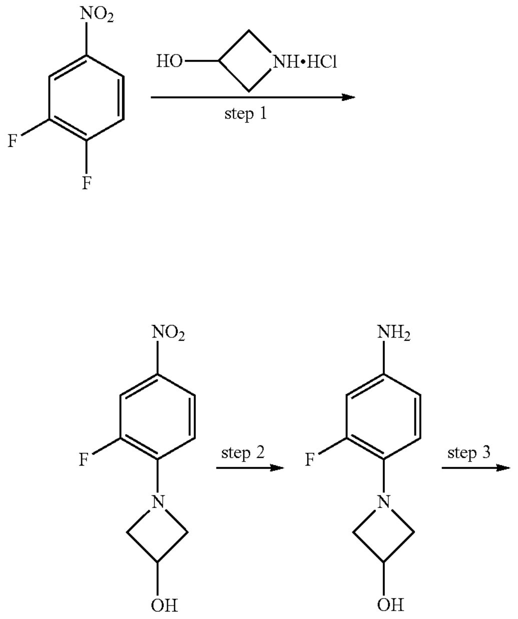

-continued

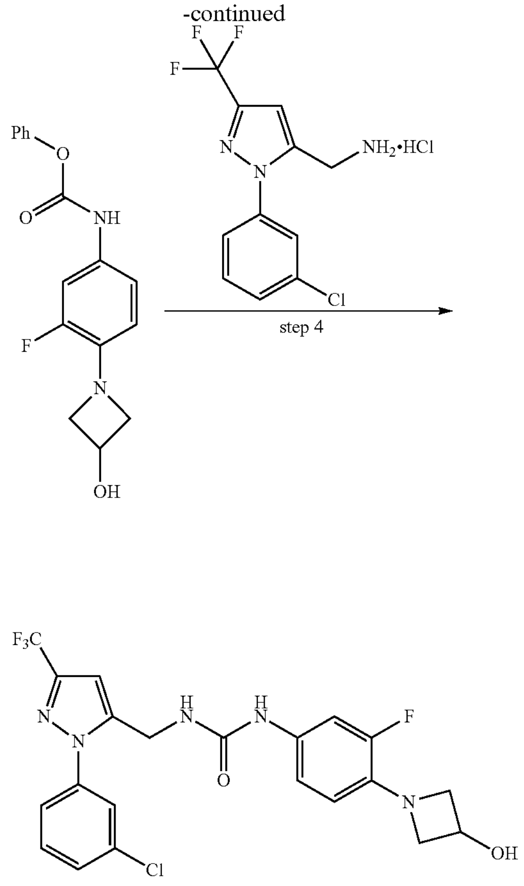

Step 1: To a stirred solution of 1,2-difluoro-4-nitrobenzene (200 mg, 1.25 mmol, 1 eq) in THF (5 mL) was added TEA (0.26 mL, 1.88 mmol, 1.5 eq) and 3-hydroxyazetidine-.HCl (205 mg, 1.88 mmol, 1.5 eq) at RT and refluxed for 24 h. THF was evaporated and the residue was washed with water (10 mL) to obtain 1-(2-fluoro-4-nitrophenyl)azetidin-3-ol (200 mg, 75%) as a solid (TLC: EtOAc/PE (3:7), $R_f$: 0.30).

Step 2: To a stirred solution of 1-(2-fluoro-4-nitrophenyl)azetidin-3-ol (160 mg, 0.75 mmol, 1.0 eq) in ethanol (10 mL) was added 10% Pd—C (20 mg) and stirred under $H_2$ gas balloon at RT for 5 h. The reaction mixture was passed through celite and concentrated to obtain 1-(4-amino-2-fluorophenyl)azetidin-3-ol (110 mg, 80.0%, viscous oil) (TLC: EtOAc/PE (1:1), $R_f$: 0.1).

Step 3: To a stirred solution of 1-(4-amino-2-fluorophenyl)azetidin-3-ol (1.8 g, 9.94 mmol, 1.0 eq) in acetone (50 mL) was added pyridine (1.57 g, 19.87 mmol, 2.0 eq) and phenyl chloroformate (1.71 g, 10.89 mmol, 1.1 eq) and stirred at RT for 2 h. The reaction mixture was evaporated, diluted with EtOAc (100 mL), washed with water (100 mL) followed by brine and evaporated. The residue obtained was purified by CC (eluent: EtOAc/PE (1:4)) to obtain phenyl 3-fluoro-4-(3-hydroxyazetidine-1-yl)phenylcarbamate (2.3 g, 76%, brown solid) (TLC: EtOAc/PE (1:1), $R_f$: 0.45).

Step 4: To a stirred solution of (1-(3-chlorophenyl)-3-(trifluoromethyl)-1H-pyrazol-5-yl)methanamine hydrochloride (103 mg, 0.33 mmol, 1.0 eq) in DCM (10 mL) was added TEA (0.10 mL, 0.66 mmol, 2.0 eq) followed by phenyl 3-fluoro-4-(3-hydroxyazetidin-1-yl)phenylcarbamate (100 mg, 0.33 mmol, 1.0 eq) at RT and stirred for 48 h. The reaction mixture was diluted with water (5 mL) and extracted with DCM (20 mL), washed with brine, dried over $Na_2SO_4$ and evaporated. The residue was purified by CC using 1.0% MeOH in EtOAc as eluent to obtain 1-((1-(3-chlorophenyl)-3-(trifluoromethyl)-1H-pyrazol-5-yl)methyl)-3-(3-fluoro-4-(3-hydroxyazetidin-1-yl)phenyl)urea (100 mg; 63%, light brown solid) (TLC: EtOAc/PE 3:2; $R_f$: 0.3).

Synthesis of Example C7

1-[[5-tert-Butyl-2-(3-chlorophenyl)-2H-pyrazol-3-yl]-methyl]-3-[3-fluoro-4-(3-hydroxy-azetidin-1-yl)-phenyl]-urea

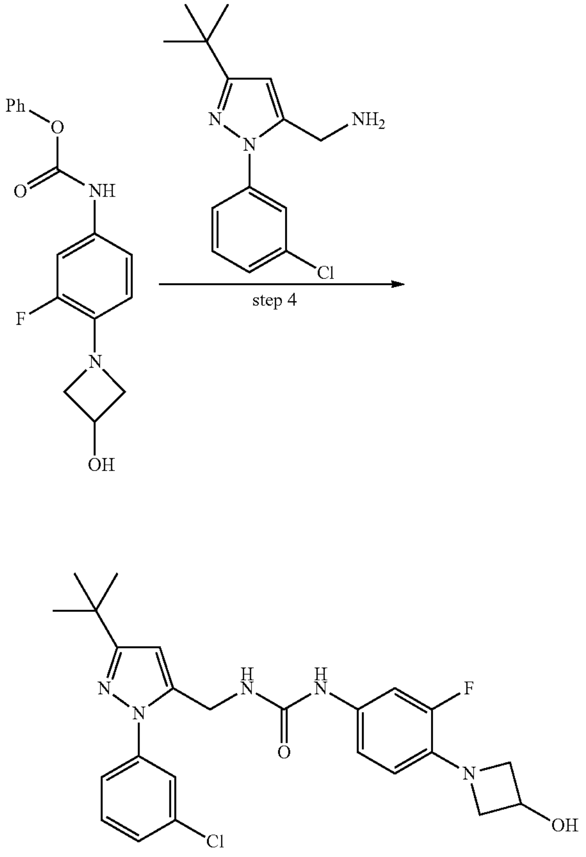

Steps 1-3: were carried out as described for example compound C6

Step 4: To a stirred solution of (3-tert-butyl-1-(3-chlorophenyl)-1H-pyrazol-5-yl)methanamine (106 mg, 0.398 mmol, 1.0 eq) in acetonitrile (9 mL) was added TEA (0.22 mL, 1.6 mmol, 4.0 eq) followed by phenyl 3-fluoro-4-(3-hydroxyazetidin-1-yl)phenylcarbamate (122 mg, 0.406 mmol, 1.02 eq) and the mixture was stirred at reflux for 16 h. The reaction mixture was evaporated and the residue was purified by CC (EtOAc/n-hexane 2:1 as eluent) to obtain 1-((3-tert-butyl-1-(3-chlorophenyl)-1H-pyrazol-5-yl)methyl)-3-(3-fluoro-4-(3-hydroxyazetidin-1-yl)phenyl)urea (183 mg; 97%).

Example compounds C8-C9 were prepared in a similar manner according to C6.

Synthesis of Example C10

1-((1-(3,4-difluorophenyl)-3-(trifluoromethyl)-1H-pyrazol-5-yl)methyl)-3-(3-fluoro-4-(3-hydroxyazetidin-1-yl)phenyl)urea

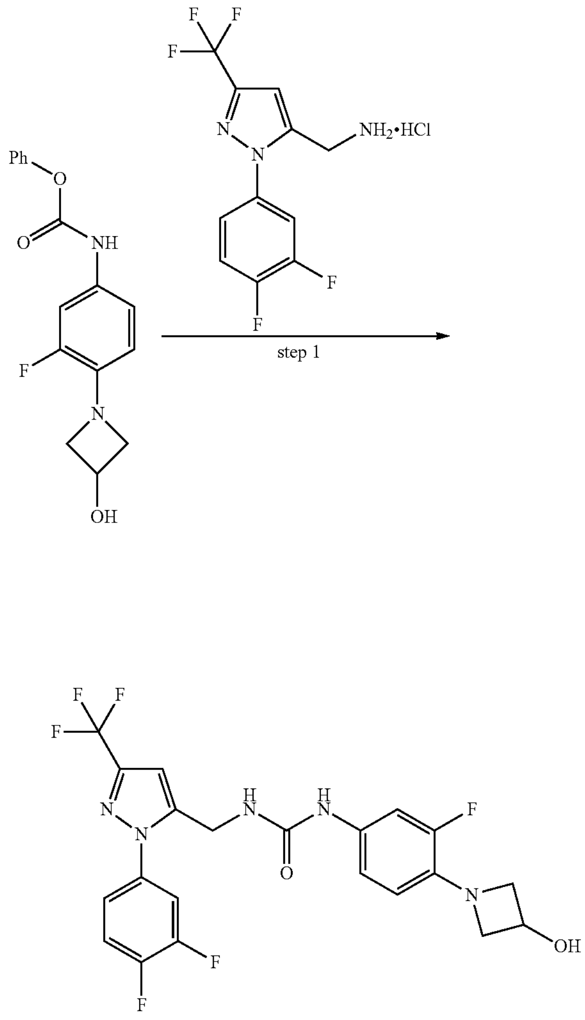

Step 1: To a stirred solution of ((1-(3,4-difluorophenyl)-3-(trifluoromethyl)-1H-pyrazol-5-yl)methanamine hydrochloride (75 mg, 0.239 mmol, 1.0 eq) in acetonitrile (5.5 mL) was added TEA (0.13 mL, 0.96 mmol, 4.0 eq.) followed by phenyl 3-fluoro-4-(3-hydroxyazetidin-1-yl)phenylcarbamate (73 mg, 0.244 mmol, 1.02 eq) and stirred at reflux for 16 h. The solvent of the reaction mixture was evaporated and the residue was purified by column chromatography (EtOAc/cyclohexane (4:1) as eluent) to get 1-((1-(3,4-difluorophenyl)-3-(trifluoromethyl)-1H-pyrazol-5-yl)methyl)-3-(3-fluoro-4-(3-hydroxyazetidin-1-yl)phenyl)urea (102 mg, 88%).

Synthesis of Example C11

1-((3-tert-butyl-1-(3,4-difluorophenyl)-1H-pyrazol-5-yl)methyl)-3-(3-fluoro-4-(3-hydroxyazetidin-1-yl)phenyl)urea

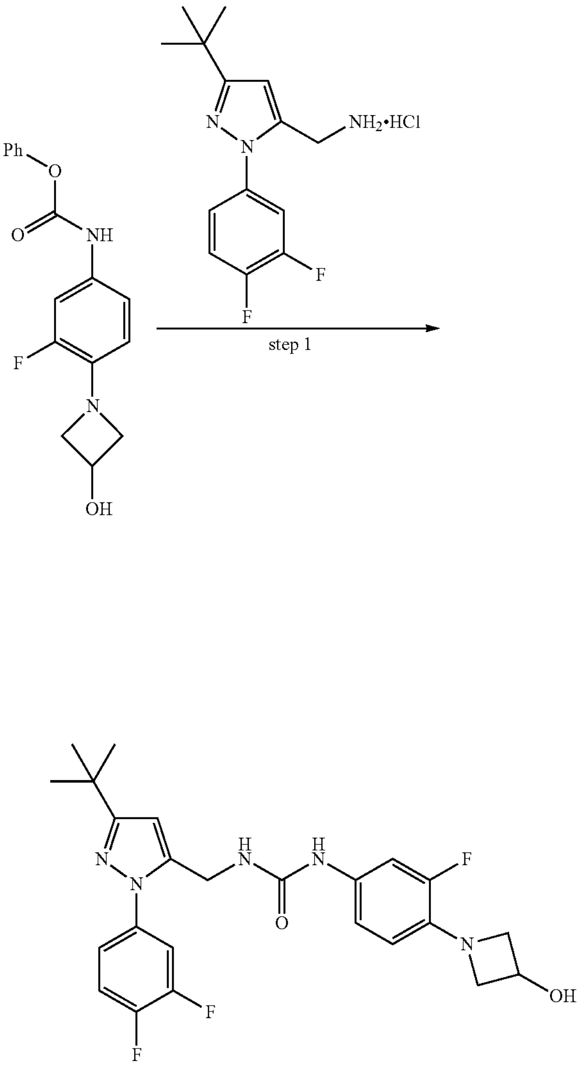

Step 1: To a stirred solution of (3-tert-butyl-1-(3,4-difluorophenyl)-1H-pyrazol-5-yl)methanamine hydrochloride (85 mg, 0.282 mmol, 1.0 eq) in acetonitrile (6.7 mL) was added TEA (0.16 mL, 1.1 mmol, 4.0 eq) followed by phenyl 3-fluoro-4-(3-hydroxyazetidin-1-yl)phenylcarbamate (86 mg, 0.287 mmol, 1.02 eq) and stirred at reflux for 16 h. The solvent of the reaction mixture was evaporated and the residue was purified by column chromatography (EtOAc/cyclohexane (1:2) as eluent) to get 1-((3-tert-butyl-1-(3,4-difluorophenyl)-1H-pyrazol-5-yl)methyl)-3-(3-fluoro-4-(3-hydroxyazetidin-1-yl)phenyl)urea (62 mg, 46%).

Synthesis of Example C12

1-(3-fluoro-4-(3-hydroxyazetidin-1-yl)phenyl)-3-((1-m-tolyl-3-(trifluoromethyl)-1H-pyrazol-5-yl)methyl)urea

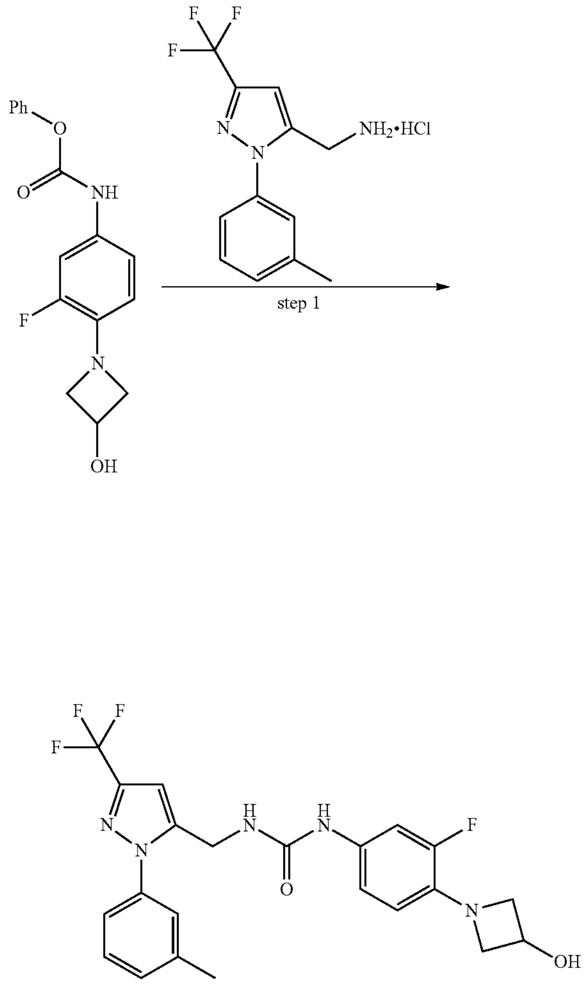

Step 1: To a stirred solution of (1-m-tolyl-3-(trifluoromethyl)-1H-pyrazol-5-yl)methanamine hydrochloride (75 mg, 0.257 mmol, 1.0 eq) in acetonitrile (6 mL) was added TEA (0.14 mL, 1.0 mmol, 4.0 eq) followed by phenyl 3-fluoro-4-(3-hydroxyazetidin-1-yl)phenylcarbamate (78 mg, 0.262 mmol, 1.02 eq) and stirred at reflux for 16 h. The solvent of the reaction mixture was evaporated and the residue was purified by column chromatography (EtOAc/cyclohexane (4:1) as eluent) to get 1-(3-fluoro-4-(3-hydroxyazetidin-1-yl)phenyl)-3-((1-m-tolyl-3-(trifluoromethyl)-1H-pyrazol-5-yl)methyl)urea (71 mg, 71%).

Synthesis of C13

1-((3-cyclopropyl-1-(3,4-difluorophenyl)-1H-pyrazol-5-yl)methyl)-3-(3-fluoro-4-(3-hydroxyazetidin-1-yl)phenyl)urea

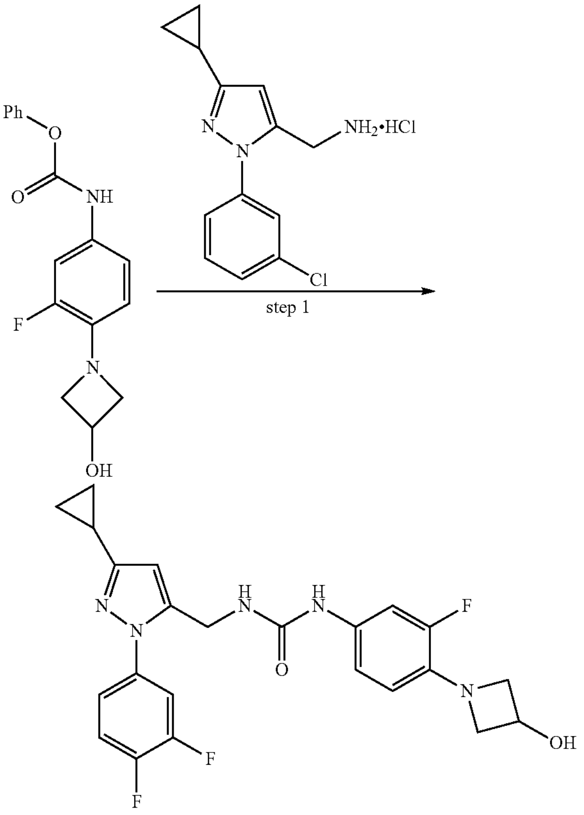

Step 1: To a stirred solution of (1-(3-chlorophenyl)-3-cyclopropyl-1H-pyrazol-5-yl)methanamine hydrochloride (101 mg, 0.408 mmol, 1.0 eq) in acetonitrile (9.5 mL) was added TEA (0.23 mL, 1.6 mmol, 4.0 eq) followed by phenyl 3-fluoro-4-(3-hydroxyazetidin-1-yl)phenylcarbamate (124 mg, 0.416 mmol, 1.02 eq) and stirred at reflux for 16 h. The solvent of the reaction mixture was evaporated and the residue was purified by column chromatography (EtOAc/cyclohexane (1:1) as eluent). The collected fractions were evaporated, the residue was treated with ether and filtered. The filter cake was dried to give 1-((3-cyclopropyl-1-(3,4-difluorophenyl)-1H-pyrazol-5-yl)methyl)-3-(3-fluoro-4-(3-hydroxyazetidin-1-yl)phenyl)urea

TABLE 4

Mass Spectrometric Data for Example Compounds of Formula (S)

| Example Compound | [M + H] |
|---|---|
| C1 | 545.2 |
| C2 | 551.3 |
| C3 | 547.1 |
| C4 | 466.2 |
| C5 | 498.0 |
| C6 | 484.0 |
| C7 | 472.1 |
| C8 | 489.0 |
| C9 | 468.1 |

Synthesis of Example D1

N-[[5-tert-Butyl-2-(3-chlorophenyl)-2H-pyrazol-3-yl]-methyl]-2-(3-fluoro-4-methylsulfonyl-phenyl)-propionamide

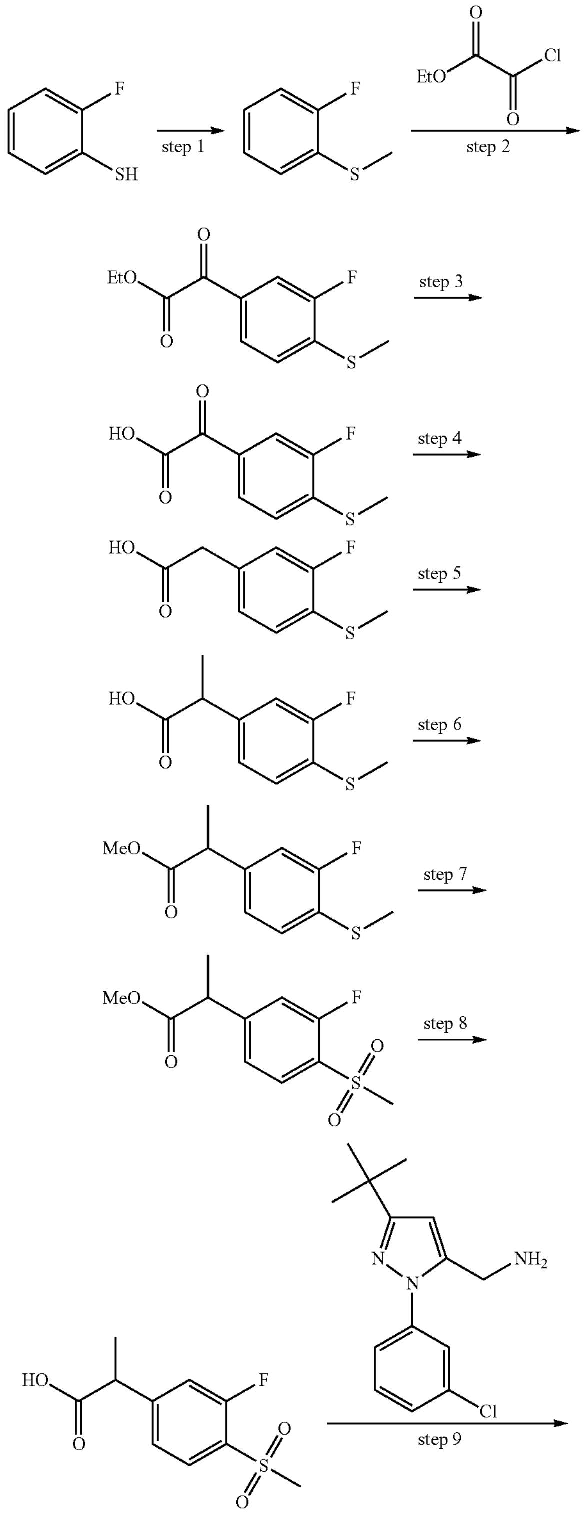

-continued

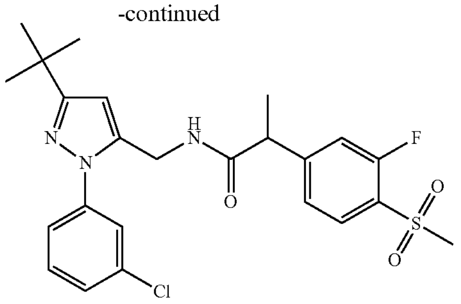

Step 1: To 2-fluorobenzenethiol (4.8 g (3.6 mL), 0.03 mol), sodium hydroxide (1.8 g) was added at room temperature. Dimethyl sulfide (4.7 g, 1 eq) was neutralized with potassium carbonate and added to the above contents at room temperature. The overall reaction mixture was stirred for 3 h at room temperature. Progress of the reaction was monitored by TLC (5% ethyl acetate/hexane, $R_f$~0.8). On completion of the reaction, cold water was added to the contents and the compound extracted with ethyl acetate (2×50 mL). Combined extract was dried over sodium sulfate and concentrated under reduced pressure to (2-fluorophenyl)(methyl)sulfane as a pale blue colored liquid (5 g, crude). The crude product obtained was directly used for the next step.

Step 2: To a solution of $AlCl_3$ (9.2 g, 0.06 mol, 2 eq) in chloroform (50 mL) cooled at 0° C., ethyl (chlorocarbonyl) formate (7.3 g, 0.05 mol, 1.6 eq) was added drop wise and the reaction mixture was stirred for 30-45 min at the same temperature. (2-fluorophenyl)(methyl)sulfane (5 g, crude) was added at 0° C. and the reaction mixture was stirred for 4 h at room temperature. Progress of the reaction was monitored by TLC (5% ethyl acetate in n-hexane, $R_f$~0.5). On completion of the reaction, crushed ice was added and the mixture was stirred for some time. The organic layer was separated and the aqueous layer was extracted with DCM (2×50 mL). The combined extract was washed with $NaHCO_3$ solution, dried over sodium sulfate and concentrated under reduced pressure to yield ethyl 2-(3-fluoro-4-(methylthio)phenyl)-2-oxoacetate as an yellow colored liquid (5.5 g).

Step 3: To a solution of ethyl 2-(3-fluoro-4-(methylthio)phenyl)-2-oxoacetate (5.5 g, 0.02 mol) in toluene (55 mL, 10 times), 3 M sodium hydroxide solution (9.09 mL) was added at 50° C. and the reaction mixture was stirred for 3 h at the same temperature. Progress of the reaction was monitored by TLC (30% ethyl acetate/hexane, $R_f$~0.1). On completion of the reaction, the contents were cooled to 0° C., the mixture was acidified with diluted HCl and the solid precipitated was filtered. The crude product 2-(3-fluoro-4-(methylthio)phenyl)-2-oxoacetic acid obtained as an yellow colored solid (4.5 g, crude) was directly used for the next step.

Step 4: 2-(3-Fluoro-4-(methylthio)phenyl)-2-oxoacetic acid (4.5 g, crude) was added to hydrazine hydrate (5.1 mL, 5 eq) at −50° C. The contents were heated to 80° C., KOH (2.7 g, 2.3 eq) was added and the overall reaction mixture was stirred for 12 h at 100° C. Progress of the reaction was monitored by TLC (50% ethyl acetate/hexane, $R_f$~0.8). On completion of the reaction, to the contents was added water and ethyl acetate and the layers were separated. The aqueous layer was acidified with diluted HCl at 0-5° C., the precipitate was filtered and dried to yield 2-(3-fluoro-4-(methylthio)phenyl)acetic acid as a white colored solid (3 g, 71%).

Step 5: 2-(3-Fluoro-4-(methylthio)phenyl)acetic acid (3 g, 0.01 mol) was dissolved in dry THF (60 mL) and the mixture was cooled to −78° C. Lithium bis(trimethylsilyl) amide (45 mL, 3 eq) was added at −78° C. and the mixture was stirred for 1 h at the same temperature. Methyl iodide (0.93 mL, 1 eq) was added at −78° C., the mixture was allowed to come to room temperature and stirred for 3 h at the same temperature. Progress of the reaction was monitored by TLC (50% ethyl acetate/hexane, $R_f$~0.5). Although the reaction had not been completed the mixture was worked-up. The reaction contents were quenched with saturated ammonium chloride solution at 0° C. The contents were acidified with diluted HCl, the organic layer was separated and the aqueous layer was extracted with ethyl acetate (2×50 mL). the combined extract was dried over sodium sulfate, concentrated under reduced pressure and the crude product obtained was purified by column chromatography (10% ethyl acetate/hexane) to yield 2-(3-fluoro-4-(methylthio)phenyl)propanoic acid as an yellow solid (1 g, 31%).

Step 6: To a solution of 2-(3-fluoro-4-(methylthio)phenyl) propanoic acid (1 g, 0.009 mol) in acetone (10 mL), potassium carbonate (0.63 g) was added at room temperature. DMS (0.58 g, 1 eq) was neutralized with potassium carbonate and filtered. The filtered DMS was added to the above contents and the overall reaction mixture was stirred for 2 h at room temperature. Progress of the reaction was monitored by TLC (20% ethyl acetate/hexane, $R_f$~0.9). On completion of the reaction, the mixture was filtered and the filtrate was concentrated under reduced pressure. The residue obtained was taken in water and the compound extracted with ethyl acetate (2×25 mL). The combined extract was dried over sodium sulfate, concentrated under reduced pressure and the crude product obtained as brown colored liquid (1 g) was directly used for the next step.

Step 7: Formic acid (6.5 mL, 1 eq) was added to methyl 2-(3-fluoro-4-(methylthio)phenyl)propanoate (1 g, crude) and the mixture cooled to 0° C. Hydrogen peroxide (1.4 mL, 3 eq) was added drop wise at 0° C. and the reaction mixture was stirred overnight at room temperature. Progress of the reaction was monitored by TLC (20% ethyl acetate/hexane, $R_f$~0.4). On completion of the reaction, the contents were cooled to 0° C., water was added and the mixture was extracted with ethyl acetate (2×25 mL). The combined extract was washed with $NaHCO_3$ solution, dried over sodium sulfate and concentrated under reduced pressure to yield methyl 2-(3-fluoro-4-(methylsulfonyl)phenyl)propanoate as colorless thick liquid (1 g, crude). The crude product obtained was directly used for the next step.

Step 8: To a solution of methyl 2-(3-fluoro-4-(methylsulfonyl)phenyl)propanoate (2.1 g, 0.008 mol) in methanol (21 mL, 10 times), a solution of sodium hydroxide (0.32 g, 1 eq) in water (3 mL) was added at 0° C. The contents were allowed to come to room temperature and the mixture was stirred for 2 h. Progress of the reaction was monitored by TLC (50% ethyl acetate/hexane, $R_f$~0.1). On completion of the reaction, methanol was distilled off completely and the residue obtained was taken in water. The contents were acidified to a pH of 4 with diluted HCl, the precipitate was filtered and dried to yield 2-(3-fluoro-4-(methylsulfonyl) phenyl)propanoic acid as a white colored solid (1.7 g, 85%).

Step 9: To a solution of (3-tert-butyl-1-(3-chloro-4-fluorophenyl)-1H-pyrazol-5-yl)methanamine (49 mg, 0.189 mmol) in DCM (1.3 mL) at room temperature and under nitrogen atmosphere was added 1-chloro-N,N,2-trimethyl-1-propenylamine (48 μL, 0.369 mmol), After 1 h of stirring were added 2-(3-fluoro-4-(methylsulfonyl)phenyl)propanoic acid (93 mg, 0.378 mmol) and N-ethyldiisopropylamine (0.11 mL, 0.662 mmol). The reaction mixture was stirred overnight at room temperature, washed with $NaHCO_3$ solution (2×10 mL), dried over sodium sulfate and concentrated under reduced pressure. The obtained crude product was purified by column chromatography (eluent: ethyl acetate/cyclohexane (2:1)) to give pure N-[[5-tert-butyl-2-(3-chlorophenyl)-2H-pyrazol-3-yl]-methyl]-2-(3-fluoro-4-methylsulfonyl-phenyl)-propionamide (example compound D1) (66 mg, 71%).

Synthesis of Example D2

N-[[2-(3-Chlorophenyl)-5-(trifluoromethyl)-2H-pyrazol-3-yl]-methyl]-2-(3-fluoro-4-methylsulfonyl-phenyl)-propionamide

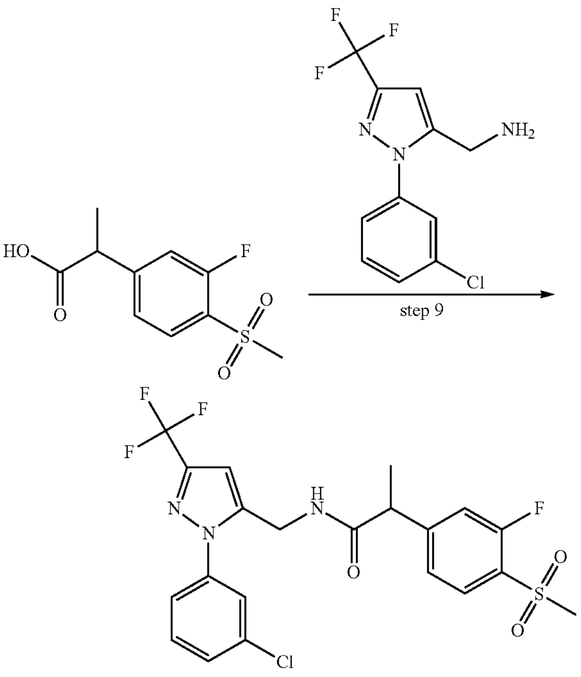

Steps 1-8: as described for example D1

Step 9: To a solution of 2-(3-fluoro-4-(methylsulfonyl) phenyl)propanoic acid (60 mg, 0.244 mmol) in THF (1.9 mL) was added 1-hydroxybenzotriazole (32 mg, 0.244 mmol), O-(1H-benzotriazol-1-yl)-N,N,N',N'-tetramethyluronium tetrafluoroborate (78 mg, 0.244 mmol), N-ethyldiisopropylamine (0.083 mL, 0.488 mmol) and (1-(3-chlorophenyl)-3-(trifluoromethyl)-1H-pyrazol-5-yl)methanamine (67 mg, 0.244 mmol). The solution was stirred for 48 h at room temperature. The reaction mixture was concentrated in vacuo and purified by column chromatography (ethyl acetate/cyclohexane (2:1)) to give pure N-[[2-(3-chlorophenyl)-5-(trifluoromethyl)-2H-pyrazol-3-yl]-methyl]-2-(3-fluoro-4-methylsulfonyl-phenyl)-propionamide (example compound D2) (93 mg, 76%).

Example compounds D3 and D4 were prepared in a similar manner.

Synthesis of Example D5

2-(3-Chloro-4-methylsulfonyl-phenyl)-N-[[2-(3-chlorophenyl)-5-(trifluoromethyl)-2H-pyrazol-3-yl]-methyl]-propionamide

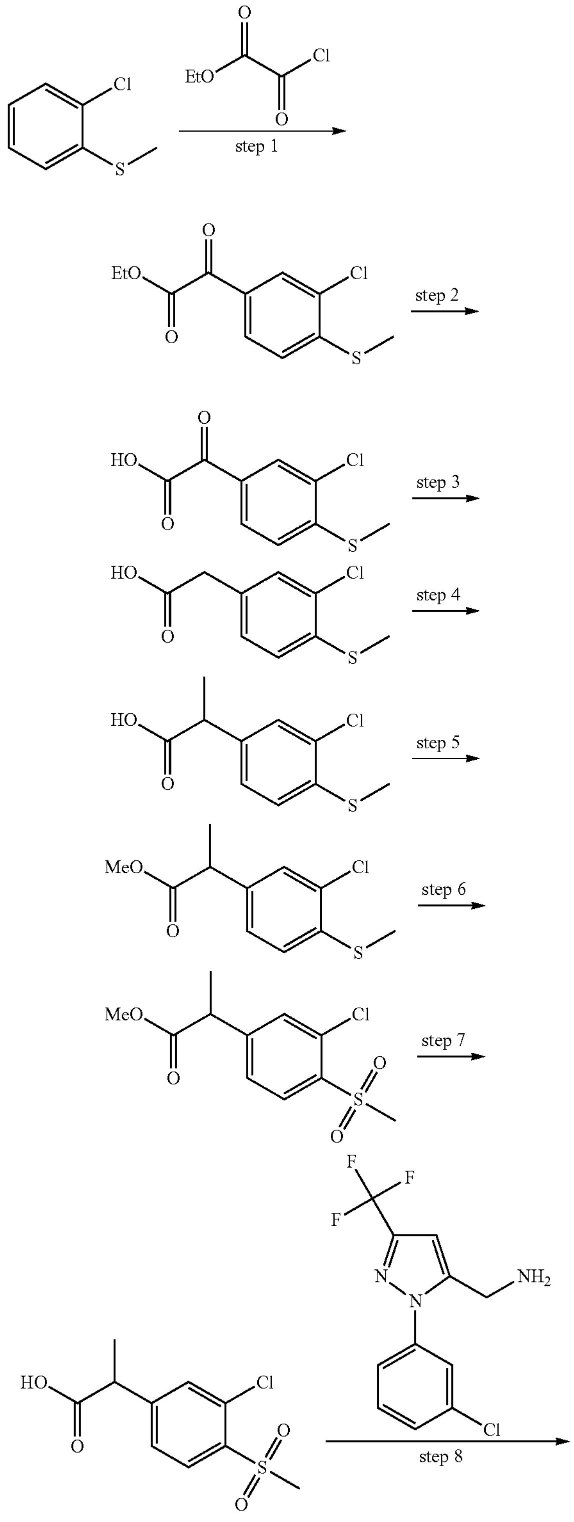

-continued

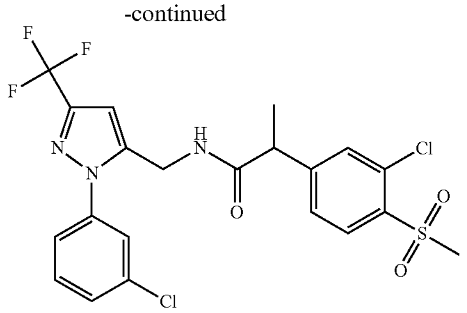

Step 1: To a well stirred solution of $AlCl_3$ (16.58 g, 2 eq) in chloroform (100 mL), ethyl (chlorocarbonyl)formate (10.02 g (8.35 mL), 1.6 eq) was added at 0° C. and the contents were allowed to stir for 30 min. Then (2-chlorophenyl)(methyl)sulfane (10 g (8.33 mL), 0.06 mol) was added at 0° C. and the overall reaction mass was allowed to stir for 3-4 h at room temperature. Progress of the reaction was monitored by TLC (5% ethyl acetate/hexane, $R_f$~0.3). On completion of the reaction, crushed ice was added and the contents were allowed to stir for 10 min. The organic layer was separated and the aqueous layer was extracted with DCM (2×100 mL). The combined extract was dried over sodium sulfate and concentrated under reduced pressure to yield ethyl 2-(3-chloro-4-(methylthio)phenyl)-2-oxoacetate as a pale yellow colored liquid (12 g, 73%).

Step 2: A solution of ethyl 2-(3-chloro-4-(methylthio)phenyl)-2-oxoacetate (12 g, 0.49 mol) in toluene (120 mL, 10 times) was heated to 50° C. 3M NaOH solution (2.23 g, 1.2 eq) was added drop wise at 50° C. and the contents were allowed to reflux for 3 h at 60° C. Progress of the reaction was monitored by TLC (50% ethyl acetate/hexane, $R_f$~0.1). On completion of the reaction, toluene was distilled off and the residue obtained was taken in ice cold water. Then the contents were acidified with diluted HCl at 0° C. and allowed to stir for 1 h at room temperature. The precipitate was filtered and dried to yield 2-(3-chloro-4-(methylthio)phenyl)-2-oxoacetic acid as an yellow colored solid (10 g, 93%).

Step 3: To hydrazine hydrate (10 g, 5 eq) cooled at −50° C., 2-(3-chloro-4-(methylthio)phenyl)-2-oxoacetic acid (10 g, 0.04 mol) was added. The contents were initially warmed to room temperature and slowly heated to 80° C. Then KOH (5.59 g, 2.3 eq) was added portion wise at 80° C. and the overall reaction mass was allowed to reflux for 12-16 h at the same temperature. Progress of the reaction was monitored by TLC (50% ethyl acetate/hexane, $R_f$~0.4). On completion of the reaction, the reaction contents were diluted with a mixture of water and ethyl acetate. The organic layer was separated and the aqueous layer was extracted with ethyl acetate (2×100 mL). Then the aqueous layer was acidified with diluted HCl and allowed to stir for 1 h at room temperature. The precipitate was filtered and dried to yield 2-(3-chloro-4-(methylthio)phenyl)acetic acid as a white colored solid (8 g, 85%).

Step 4: 2-(3-chloro-4-(methylthio)phenyl)acetic acid (2 g, 0.009 mol) was taken in THF (20 mL, 10 times) and cooled to −78° C. Lithium bis(trimethylsilyl)amide (27.77 mL, 3 eq) was added drop wise at −78° C. and allowed to stir for 2 h at the same temperature. Then methyl iodide (1.31 g, 1 eq) was added drop wise at −78° C. and the overall reaction mass was allowed to stir for 3 h at the same temperature. Progress of the reaction was monitored by TLC (50% ethyl acetate/hexane, $R_f$~0.2). As the reaction was not completed, reaction mass was warmed to room temperature and allowed to stir for 10 h. Again TLC was monitored and still the reaction was not completed. Then the reaction contents were quenched with saturated ammonium chloride solution and acidified with diluted HCl. THF layer was separated and the aqueous layer was extracted with ethyl acetate (2×50 mL). The combined extract was dried over sodium sulfate, concentrated under reduced pressure and the crude product obtained was purified by column chromatography (10% ethyl acetate/n-hexane) to yield 2-(3-chloro-4-(methylthio) phenyl)propanoic acid as a pale yellow colored solid (1.2 g, 53%).

Step 5: To a solution of 2-(3-chloro-4-(methylthio)phenyl)propanoic acid (3.5 g, 0.015 mol) in acetone (35 mL), potassium carbonate (2.06 g, 0.01 mol, 1 eq) was added at room temperature. DMS (1.91 g, 1 eq) was neutralized with potassium carbonate and filtered. The filtered DMS was added to the above contents and the overall reaction mixture was stirred for 2 h at room temperature. Progress of the reaction was monitored by TLC (50% ethyl acetate/hexane, $R_f$~0.9). On completion of the reaction, filtered the contents and the filtrate was concentrated under reduced pressure. The residue obtained was taken in water and the compound extracted with ethyl acetate (2×100 mL). The combined extract was dried over sodium sulfate, concentrated under reduced pressure and the crude product obtained as brown colored liquid (3.5 g) was directly used for the next step.

Step 6: Formic acid (20.8 mL, 1 eq) was added to methyl 2-(3-chloro-4-(methylthio)phenyl)propanoate (3.2 g, crude) and cooled to 0° C. Hydrogen peroxide (4.48 mL, 3 eq) was added drop wise at 0° C. and the reaction mass was stirred for overnight at room temperature. Progress of the reaction was monitored by TLC (30% ethyl acetate/hexane, $R_f$~0.3). On completion of the reaction, the contents were cooled to 0° C., water was added and the mixture was extracted with ethyl acetate (2×100 mL). The combined extract was washed with $NaHCO_3$ solution, dried over sodium sulfate and concentrated under reduced pressure to obtain methyl 2-(3-chloro-4-(methylsulfonyl)phenyl)propanoate as a colorless thick liquid (3.2 g, crude). Crude product obtained was directly used for the next step.

Step 7: To a solution of methyl 2-(3-chloro-4-(methylsulfonyl)phenyl)propanoate (3.2 g, crude) in methanol (32 mL, 10 times), a solution of sodium hydroxide (0.46 g, 1 eq) in water (5 mL) was added at 0° C. The contents were warmed to room temperature and allowed to stir for 2 h.

Progress of the reaction was monitored by TLC (50% ethyl acetate/hexane, $R_f$~0.1). On completion of the reaction, methanol was distilled off completely and the residue obtained was taken in water. The contents were acidified to a pH of 4 and diluted with HCl at 0° C., the precipitate was filtered and dried to yield 2-(3-chloro-4-(methylsulfonyl) phenyl)propanoic acid as a white colored solid (2.7 g, 88%).

Step 8: To a solution of 2-(3-chloro-4-(methylsulfonyl) phenyl)propanoic acid (60 mg, 0.229 mmol) in THF (1.9 mL) was added 1-hydroxybenzotriazole (30 mg, 0.229 mmol), O-(1H-benzotriazol-1-yl)-N,N,N',N'-tetramethyluronium tetrafluoroborate (74 mg, 0.229 mmol), N-ethyldiisopropylamine (0.078 mL, 0.458 mmol) and (1-(3-chlorophenyl)-3-(trifluoromethyl)-1H-pyrazol-5-yl)methanamine (63 mg, 0.229 mmol). The solution was stirred for 48 h at room temperature. The reaction mixture was concentrated in vacuo and purified by column chromatography (eluent: ethyl acetate/cyclohexane (1:2)) to give 2-(3-chloro-4-methylsulfonyl-phenyl)-N-[[2-(3-chlorophenyl)-5-(trifluoromethyl)-2H-pyrazol-3-yl]-methyl]-propionamide (example compound D5) (100 mg, 84%).

Synthesis of Example D6

N-[[2-(3-Chlorophenyl)-5-(trifluoromethyl)-2H-pyrazol-3-yl]-methyl]-2-[3-fluoro-4-(methylsulfonyl-methyl)-phenyl]-propionamide

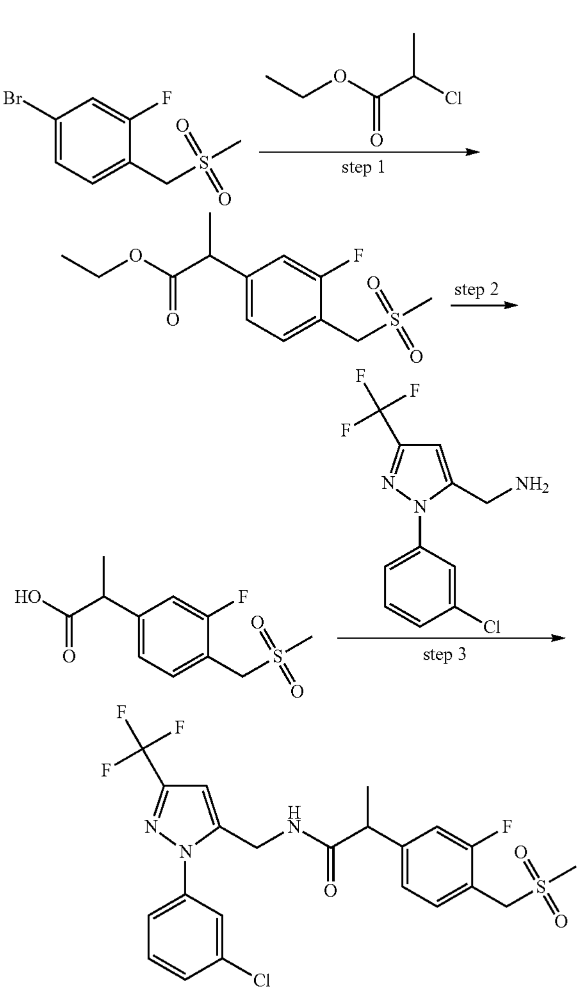

Step 1: To a stirred solution of 4-bromo-2-fluoro-1-(methylsulfonylmethyl)benzene (2 g, 7.487 mmol) in dimethylformamide (11 mL) were added ethyl 2-chloropropionate (1.24 mL, 9.733 mmol), manganese (822 mg, 14.974 mmol) and (2,2'-bipyridine)nickel(II)-dibromide (196 mg, 0.524 mmol). Trifluoroacetic acid (4 drops) was added. The reaction mixture was stirred overnight at 60° C. After cooling down to room temperature, the mixture was hydrolyzed by 1N HCl (30 mL) and extracted with ethyl acetate (3×50 mL). The organic layer was dried over magnesium sulfate and filtered. The solvent was removed in vacuo. The crude product was purified by CC (eluent: ethyl acetate/cyclohexane (1:1)) to give ethyl 2-(3-fluoro-4-(methylsulfonylmethyl)phenyl)propanoate (966 mg, 45%).

Step 2: To a stirred solution of ethyl 2-(3-fluoro-4-(methylsulfonylmethyl)phenyl)propanoate (950 mg, 3.295 mmol) in co-solvent with tetrahydrofuran and water (1:1) were added lithium hydroxide (236 mg, 9.885 mmol). The reaction mixture was refluxed for overnight, then cooled to room temperature, diluted with water (25 mL) and diethyl ether (25 mL). After phase separation the aqueous layer was acidified by HCl to a pH=3 and extracted with DCM (3×50 mL). The organic layer was dried over magnesium sulfate and filtered. The solvent of the filtrate was removed in vacuo to give 2-(3-fluoro-4-(methylsulfonylmethyl)-phenyl)propanoic acid (846 mg, 99%).

Step 3: To a stirred solution of 2-(3-fluoro-4-(methylsulfonylmethyl)phenyl)propanoic acid (68 mg, 0.231 mmol) and (1-(3-chlorophenyl)-3-(trifluoromethyl)-1H-pyrazol-5-yl)methanamine (60 mg, 0.231 mmol) in THF (1.8 mL) were added O-(1H-Benzotriazol-1-yl)-N,N,N',N'-tetramethyluronium tetrafluorborat (73 mg, 0.231 mmol), 1-hydroxybenzotriazole (30 mg, 0.231 mmol) and N-ethyldiisopropylamine (0.078 mL, 0.462 mmol). The reaction mixture was stirred for 48 h at room temperature, concentrated in vacuo and the residue was purified by CC (eluent: ethyl acetate/cyclohexane (3:2)) to give N-[[2-(3-Chlorophenyl)-5-(trifluoromethyl)-2H-pyrazol-3-yl]-methyl]-2-[3-fluoro-4-(methylsulfonyl-methyl)-phenyl]-propionamide (83 mg, 69%).

Example compound D10 was prepared analogously according to D6

Synthesis of Example D7

N-[[5-tert-Butyl-2-(3-chlorophenyl)-2H-pyrazol-3-yl]-methyl]-2-[3-fluoro-4-(methylsulfonyl-methyl)-phenyl]-propionamide

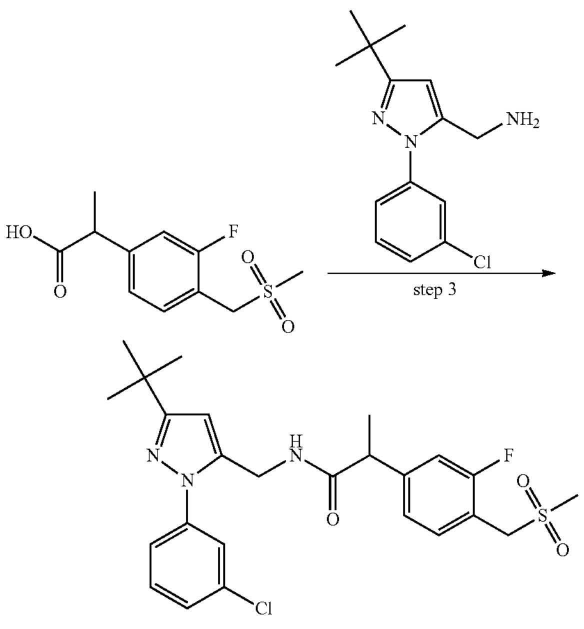

Steps 1-2: were carried out as described for example compound D6

Step 3: To a stirred solution of 2-(3-fluoro-4-(methylsulfonylmethyl)phenyl)propanoic acid (60 mg, 0.231 mmol) and (3-tert-butyl-1-(3-chlorophenyl)-1H-pyrazol-5-yl)methanamine (60 mg, 0.231 mmol) in THF (1.8 mL) were added O-(1H-benzotriazol-1-yl)-N,N,N',N'-tetramethyluronium tetrafluorborat (73 mg, 0.231 mmol), 1-hydroxybenzotriazole (30 mg, 0.231 mmol) and N-ethyldiisopropylamine (0.078 mL, 0.462 mmol). The reaction mixture was stirred for 48 h at room temperature, concentrated in vacuo and the residue was purified by CC (eluent: ethyl acetate/cyclohexane (3:2)) to give N-[[5-tert-butyl-2-(3-chlorophenyl)-2H-pyrazol-3-yl]-methyl]-2-[3-fluoro-4-(methylsulfonyl-methyl)-phenyl]-propionamide (94 mg, 80%).

Example compounds D8, D9, D11, D13, D16-D21, D23 and 24 were prepared in a similar manner or may be prepared analogously according to D7.

Synthesis of Example D12

2-[3-Fluoro-4-(methylsulfonyl-methyl)-phenyl]-N-[[2-(4-fluorophenyl)-5-(trifluoromethyl)-2H-pyrazol-3-yl]-methyl]-propionamide

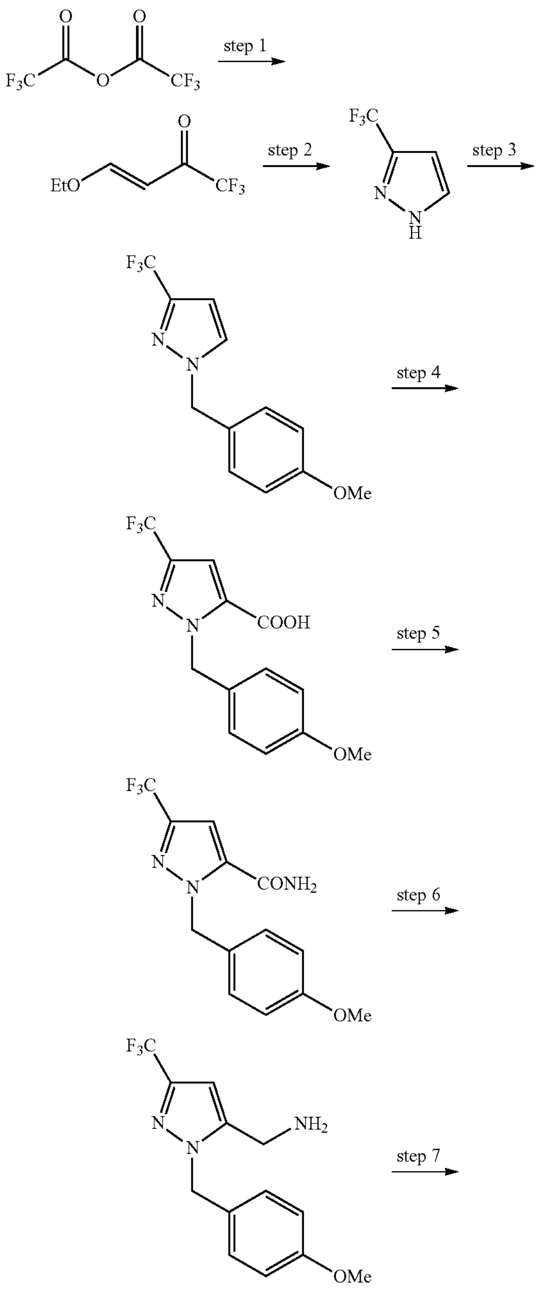

-continued

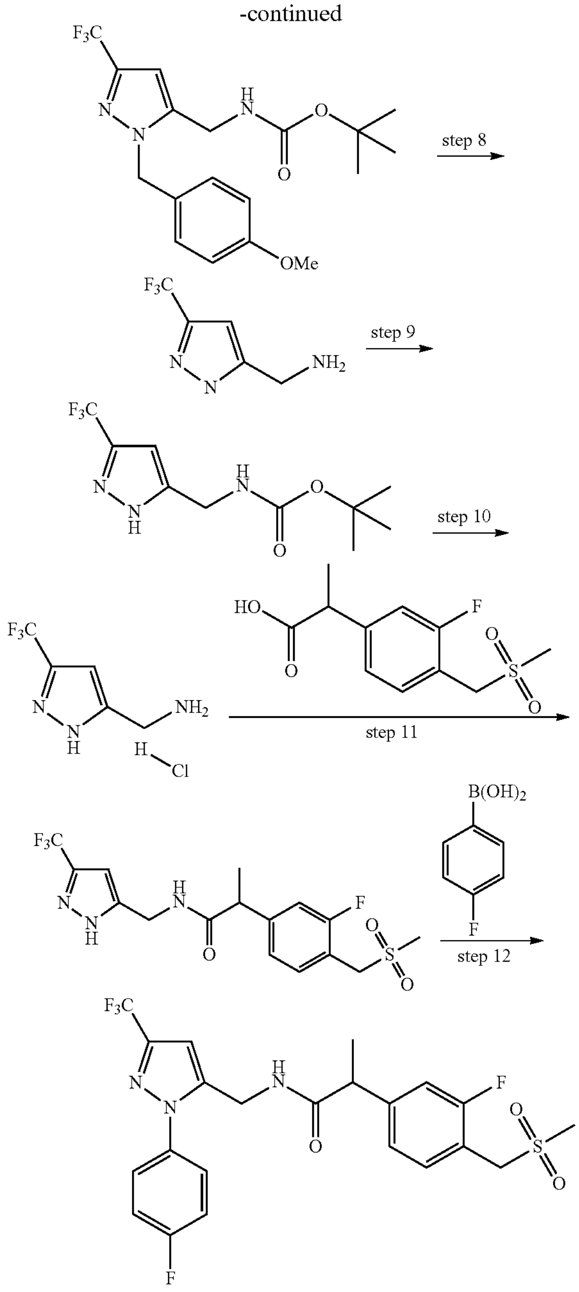

Step 1: DMAP (4.25 g, 34 mmol) was added to DCM (3 L) and the contents were cooled to −10° C. Trifluoroacetic anhydride (765 g, 3.2 mol) was added followed by ethyl vinyl ether (250 g, 3.04 mol) which was added drop wise for 45 min at −10° C. Then the overall reaction mixture was stirred for 8 h at 0° C. and later overnight at room temperature. Progress of the reaction was monitored by TLC (10% ethyl acetate/hexane, $R_f$~0.7). On completion of the reaction, the reaction contents were treated with saturated $NaHCO_3$ solution (600 mL) and the organic layer was separated. The aqueous layer was extracted with DCM (2×500 mL). The combined organic layer was washed with water (2×1 L), dried over sodium sulfate and concentrated under reduced pressure to give (E)-4-ethoxy-1,1,1-trifluorobut-3-en-2-one as a brown colored liquid (450 g, crude).

Step 2: Hydrazine dihydrochloride (225 g, 2.14 mol) in ethanol (1400 mL) was stirred well. TEA (185.4 mL, 1.34 mol) was added drop wise for 45 min at ambient temperature. Then (E)-4-ethoxy-1,1,1-trifluorobut-3-en-2-one (225 g, crude) was added drop wise at room temperature and the overall reaction mixture was refluxed overnight. Progress of the reaction was monitored by TLC (20% ethyl acetate/hexane, $R_f$~0.4). On completion of the reaction, ethanol was distilled off completely, residue was taken in ice water (500 mL) and the product extracted with ethyl acetate (2×400 mL). Combined extract was washed with ice water (300 mL), dried over sodium sulfate and concentrated under reduced pressure to yield 3-(trifluoromethyl)-1H-pyrazole as a off white solid (175 g, crude).

Step 3: NaH (33.08 g (19.85 mol, 60%) was washed with n-hexane, then dry DMF (500 mL) was added drop wise under $N_2$ atmosphere and the mixture was stirred well. A solution of 3-(trifluoromethyl)-1H-pyrazole (75 g, 0.55 mol) in DMF (125 mL) was added drop wise under $N_2$ atmosphere. Then a solution of 4-methoxylbenzyl chloride (86.3 g, 0.55 mol) in DMF (125 mL) was added drop wise and the overall reaction mixture was allowed to stir for 12 h at room temperature. Progress of the reaction was monitored by TLC (10% ethyl acetate/hexane, $R_f$~0.4). On completion of the reaction, the reaction contents were poured into ice water (500 mL) and the product was extracted with ethyl acetate (2×400 mL). The ethyl acetate layer was washed with 2N HCl (2×200 ml). Then the contents were dried over sodium sulfate and concentrated under reduced pressure. The obtained crude product was purified by CC with 10% ethyl acetate/n-hexane to yield 1-(4-methoxybenzyl)-3-(trifluoromethyl)-1H-pyrazole as a brown colored liquid (98 g, 70%).

Step 4: Diisopropyl amine (28.4 mol, 39.4 mL) was taken in THF (500 mL), stirred well and cooled to 0° C. n-BuLi (234.4 mL) was added drop wise at 0° C. and the mixture was stirred for 1 h at 0° C. Then the contents were cooled to −78° C., a solution of 1-(4-methoxybenzyl)-3-(trifluoromethyl)-1H-pyrazole (62 g, 0.24 mol) in THF (200 mL) was added drop wise for 30 min and the contents were stirred for another h at −78° C. Then dry $CO_2$ gas was bubbled through the reaction mixture for 1.5 h. Progress of the reaction was monitored by TLC (10% ethyl acetate/hexane, $R_f$~0.1). On completion of the reaction, the reaction contents were poured into ice water (300 mL) and the aqueous layer was extracted with ethyl acetate (2×200 mL) in basic condition. The aqueous layer was acidified with 20% HCl solution and extracted with ethyl acetate (2×200 mL). The combined organic layer was dried over sodium sulfate and concentrated under reduced pressure to yield 1-(4-methoxybenzyl)-3-(trifluoromethyl)-1H-pyrazole-5-carboxylic acid as an off white solid (40 g, 55%).

Step 5: To a solution of 1-(4-methoxybenzyl)-3-(trifluoromethyl)-1H-pyrazole-5-carboxylic acid (50 g, 0.16 mol) in DCM (750 mL), a catalytic amount of DMF was added and the mixture was cooled to 0° C. Thionyl chloride (61 mL, 0.83 mol) was added drop wise for 30 min at 0° C. The overall reaction mixture was heated to reflux and maintained for 2 h. Progress of the reaction was monitored by TLC (10% ethyl acetate/hexane, $R_f$~0.4). On disappearance of the starting material, DCM was distilled off completely. Above prepared acid chloride was dissolved in DCM (500 mL) and added drop wise to aqueous ammonia solution (700 mL) at 0° C. The overall reaction mixture was allowed to stir for 1 h and the progress of the reaction was monitored by TLC (10% ethyl acetate/hexane, $R_f$~0.7). On completion of the reaction, ice cold water (200 mL) was added and the product was extracted with ethyl acetate (2×200 mL). The combined organic layer was dried over sodium sulfate and concentrated under reduced pressure to yield 1-(4-methoxybenzyl)-3-(trifluoromethyl)-1H-pyrazole-5-carboxamide as an off white solid (37 g, crude). Crude product obtained was directly used for the next step.

Step 6: LAH (4.7 g, 0.12 mol) was charged into a flask. THF (250 mL) was added at 0° C. Then a solution of 1-(4-methoxybenzyl)-3-(trifluoromethyl)-1H-pyrazole-5-carboxamide (37 g, 0.12 mol) in THF (120 mL) was added drop wise for 30 min at 0° C. and reaction mixture was heated to reflux for 5 h. Progress of the reaction was monitored by TLC (50% ethyl acetate/hexane, $R_f$~0.2). As the reaction was not completed, LAH (2.3 g) was added again and the mixture was refluxed for another 4 h. After completion of the reaction, the reaction contents were slowly added to saturated sodium sulfate (1 L) solution and filtered over celite and the product was extracted with ethyl acetate (2×500 mL). The combined extract was dried over sodium sulfate and concentrated under reduced pressure to obtain the crude (1-(4-methoxybenzyl)-3-(trifluoromethyl)-1H-pyrazol-5-yl)methanamine as an off white solid (32.5 g, crude). The crude product obtained was directly used for the next step.

Step 7: To a solution of (1-(4-methoxybenzyl)-3-(trifluoromethyl)-1H-pyrazol-5-yl)methanamine (80 g, 0.28 mol) in DCM (600 mL) cooled at 0° C., TEA (30.2 mL, 0.026 mol) was added drop wise for 10 min. Then Boc anhydride (62.5 mL, 0.28 mol) was added drop wise for 20-30 min at 0° C. The overall reaction mixture was stirred for 30 min at 0° C. and stirred for 1 h at room temperature. Progress of the reaction was monitored by TLC (20% ethyl acetate/hexane, $R_f$~0.6). On completion of the reaction, DCM was distilled off completely, the residue was taken in ice water (500 mL) and the product extracted with ethyl acetate (2×300 mL). The combined extract was dried over sodium sulfate and concentrated under reduced pressure. The crude product obtained was recrystallized from n-hexane (200 mL) to yield tert-butyl (1-(4-methoxybenzyl)-3-(trifluoromethyl)-1H-pyrazol-5-yl)methylcarbamate as an off white solid (80 g, 74%).

Step 8: To a stirred solution of tert-butyl (1-(4-methoxybenzyl)-3-(trifluoromethyl)-1H-pyrazol-5-yl)methylcarbamate (20 g, 0.052 mol) in toluene (300 mL) cooled to 0° C. was added aluminum chloride (17.34 g, 0.129 mol) portion wise for 30 min. The reaction mixture was slowly heated to 50-60° C. and allowed to stir for 2 h at the same temperature. Progress of the reaction was monitored by TLC (20% ethyl acetate/hexane, $R_f$~0.1). On completion of the reaction, the reaction contents were treated with diluted HCl, ice cold water (300 mL) was added and the mixture was extracted with ethyl acetate (2×100 mL). The aqueous layer was basified with sodium hydroxide solution and extracted with ethyl acetate and dried over sodium sulfate and concentrated under reduced pressure to give (3-(trifluoromethyl)-1H-pyrazol-5-yl)methanamine as a brown colored solid (4.6 g, crude). The crude product obtained was used directly for the next step.

Step 9: (3-(Trifluoromethyl)-1H-pyrazol-5-yl)methanamine (7 g, 42.4 mmol) was dissolved in DCM (7 mL) at room temperature, then to that TEA (5.86 mL, 72.4 mmol) was added at room temperature and the mixture was stirred for 10 min and tooled to 0-5° C. $(Boc)_2O$ (9.24 g, 42.4 mmol) was added drop wise to reaction mixture for 30 min and maintained for 3 h at 0-5° C. Progress of the reaction was monitored by the TLC (30% ethyl acetate/n-hexane). On completion of the reaction, the reaction mixture was brought to room temperature for 2 h and the DCM was distilled off, the residue obtained was treated with water (50 mL) and extracted with ethyl acetate (100 mL). The combined organic layer was dried over sodium sulfate, and the solvent evaporated under vacuum. The resulting crude product was purified with CC to yield tert-butyl (3-(trifluoromethyl)-1H-pyrazol-5-yl)methylcarbamate as a white colored solid (5 g, 44%).

Step 10: To a stirred solution of tert-butyl (3-(trifluoromethyl)-1H-pyrazol-5-yl)methylcarbamate (5 g, 18.8 mmol) in MeOH (36 mL) was added HCl in 2-propanol (5.8 mL, 29.2 mmol) and the mixture was stirred for 48 h at room temperature. The reaction mixture was concentrated in vacuo, diethylether (20 mL) was added and the resulting precipitate filtered out and washed with diethylether (5 mL). After drying (3-(trifluoromethyl)-1H-pyrazol-5-yl)methanamine hydrochloride was obtained (3.67 g, 97%).

Step 11: To a stirred solution of (3-(trifluoromethyl)-1H-pyrazol-5-yl)methanamine hydrochloride (194 mg, 0.96 mmol) and 2-(3-fluoro-4-(methylsulfonylmethyl)phenyl)propanoic acid (250 mg, 0.96 mmol) in THF (7.4 mL) were added O-(1H-benzotriazol-1-yl)-N,N,N',N'-tetramethyluronium tetrafluorborat (308 mg, 0.96 mmol), 1-hydroxybenzotriazole (135 mg, 0.96 mmol) and N-ethyldiisopropylamine (0.491 mL, 2.881 mmol). The reaction mixture was stirred for overnight at room temperature, concentrated in vacuo, purified by CC (eluent: ethyl acetate/cyclohexane (9:1)) to give 2-(3-fluoro-4-(methylsulfonylmethyl)phenyl)-N-((3-(trifluoromethyl)-1H-pyrazol-5-yl)methyl)propanamide (335 mg, 86%).

Step 12: 4-Fluorophenylboronic acid (41 mg, 0.295 mmol), 2-(3-fluoro-4-(methylsulfonylmethyl)phenyl)-N-((3-(trifluoromethyl)-1H-pyrazol-5-yl)methyl)propanamide (60 mg, 0.147 mmol) and copper(II)-acetate (0.021 mL, 0.221 mmol) were added to DCM (2.2 mL). At room temperature was added pyridine (0.238 mL, 2.946 mmol) and the mixture was stirred for overnight. The reaction mixture was concentrated in vacuo, the solid obtained was purified by CC (eluent: cyclohexane/ethyl acetate (1:2)) to afford 2-[3-fluoro-4-(methylsulfonyl-methyl)-phenyl]-N-[[2-(4-fluorophenyl)-5-(trifluoromethyl)-2H-pyrazol-3-yl]-methyl]-propionamide (55 mg, 75%).

Example compounds D14, D15, D22 and D25 were prepared in a similar manner or may be prepared analogously according to D12.

Synthesis of Example D26

1-[[2-(3-Chlorophenyl)-5-cyclopropyl-2H-pyrazol-3-yl]-methyl]-3-[3-fluoro-4-(2-methylsulfonyl-ethyl)-phenyl]-urea

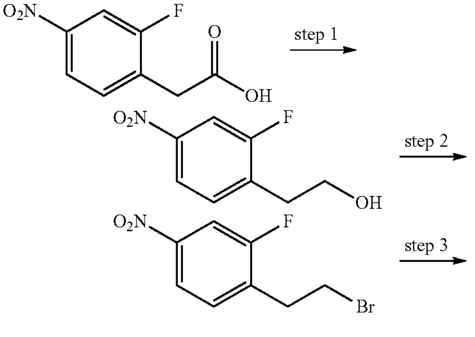

-continued

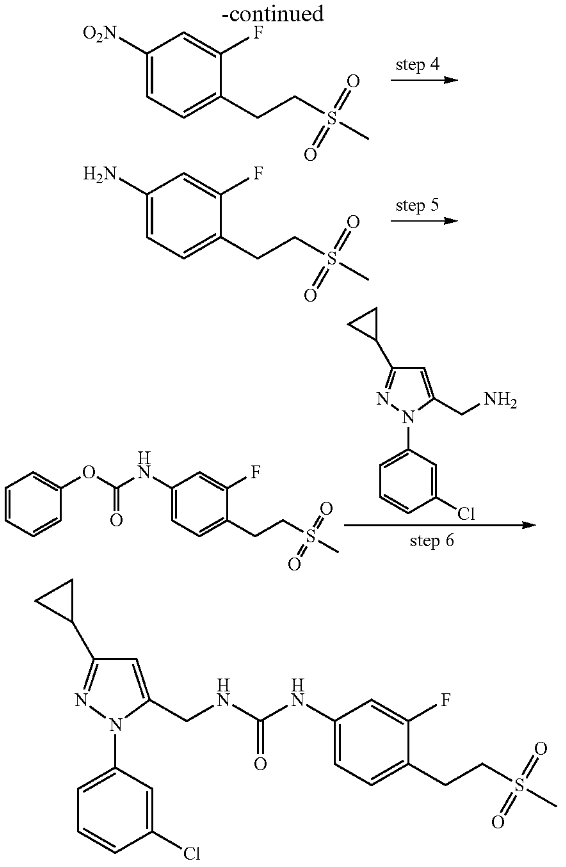

Step 1: To a stirred solution of 2-(2-fluoro-4-nitrophenyl) acetic acid (1 g, 5.02 mmol) in tetrahydrofuran (10 mL) was added $BH_3.S(CH_3)_2$ (7.5 mL, 7.53 mmol) at 0° C. The reaction mixture was allowed to stir at room temperature for 10 h. Then reaction mixture was cooled to 0° C. and the excess of borane was quenched with methanol (10 mL). The reaction mixture was concentrated under reduced pressure to obtain a crude compound which was purified by CC (eluent: ethyl acetate/n-hexane (1:1)) to give 2-(2-fluoro-4-nitrophenyl)ethanol (0.89 g, 95%).

Step 2: 2-(2-Fluoro-4-nitrophenyl)ethanol (0.89 g, 4.8 mmol) was added to a stirred solution of 48% aqueous hydrobromic acid (0.77 g, 9.62 mmol) and concentrated sulfuric acid (0.25 mL) under cooling. The reaction mixture was heated to 100° C. for 3 h. The reaction mixture was diluted with water (25 mL) and was extracted with ethyl acetate (3×25 mL). The combined organic layer was washed with brine (25 mL) and dried over anhydrous magnesium sulfate and concentrated under reduced pressure to afford the crude compound. The crude product was purified by CC (eluent: 5% ethyl acetate in n-hexane) to afford 1-(2-bromoethyl)-2-fluoro-4-nitrobenzene (1 g, 85%).

Step 3: To a stirred solution of 1-(2-bromoethyl)-2-fluoro-4-nitrobenzene (1 g, 4.03 mmol) in isopropanol (15 mL) was added sodium methane sulfinate (2.05 g, 20.16 mmol) at room temperature. The reaction mixture was heated to 70° C. for 10 h. The reaction mixture was cooled to room temperature and was concentrated under reduced pressure to obtain a crude compound which was filtered out and the residue was washed with water (2×5 mL) to obtain pure 2-fluoro-1-(2-(methylsulfonyl)ethyl)-4-nitrobenzene (700 mg, 70%).

Step 4: 2-Fluoro-1-(2-(methylsulfonyl)ethyl)-4-nitrobenzene (700 mg, 2.83 mmol) was dissolved in ethyl acetate (7 mL), and to the solution was added (10%) Pd/C (70 mg) under argon atmosphere which was subjected to hydrogenation in a Parr apparatus and the reaction was continued to stir for 2 h. The reaction mixture was filtered through celite and was washed thoroughly with ethyl acetate and was concentrated under reduced pressure to obtain 3-fluoro-4-(2-(methylsulfonyl)ethyl)aniline (590 mg, 96%).

Step 5: To a stirred solution of 3-fluoro-4-(2-(methylsulfonyl)ethyl)aniline (200 mg, 0.92 mmol) in acetone/DMF (3 mL+1.27 mL), pyridine (0.222 mL, 2.76 mmol) was added dropwise phenyl chloroformate (0.152 mL, 1.197 mmol) at 0° C. and the mixture was stirred at room temperature for 1 h. The acetone was evaporated and the residue was diluted with DCM (30 mL). The mixture was washed with saturated $NaHCO_3$ solution (15 mL) and the organic layer extracted with DCM (2×20 mL). The combined organic layer was dried over magnesium sulfate and concentrated in vacuo to give pure phenyl 3-fluoro-4-(2-(methylsulfonyl)ethyl)phenylcarbamate (260 mg, 84%).

Step 6: To a stirred solution of phenyl 3-fluoro-4-(2-(methylsulfonyl)ethyl)phenylcarbamate (90 mg, 0.267 mmol) and (1-(3-chlorophenyl)-3-cyclopropyl-1H-pyrazol-5-yl)methanamine (70 mg, 0.286 mmol) in THF (4 mL) was added N-ethyldiisopropylamine (0.087 mL, 0.507 mmol) and stirred for 1 h in a microwave (150° C., 7 bar). The reaction mixture was concentrated in vacuo and purified by CC (eluent: ethyl acetate/cyclohexane (2:1)) to give 1-[[2-(3-chlorophenyl)-5-cyclopropyl-2H-pyrazol-3-yl]-methyl]-3-[3-fluoro-4-(2-methylsulfonyl-ethyl)-phenyl]-urea (30 mg, 23%).

Example compounds D27-D33 were prepared in a similar manner or may be prepared analogously according to D26.

TABLE 5

Mass Spectrometric Data for Example Compounds of Formula (T)

| Example Compound | [M + H] |
|---|---|
| D1 | 492.0 |
| D2 | 504.3 |
| D3 | 488.1 |
| D4 | 522.1 |
| D5 | 520.2 |
| D6 | 518.2 |
| D7 | 506.3 |
| D8 | 524.0 |
| D9 | 490.2 |
| D10 | 502.1 |
| D12 | 502.1 |
| D14 | 520.1 |
| D15 | 520.1 |
| D26 | 491.1 |
| D27 | 519.1 |
| D28 | 537.0 |
| D29 | 507.2 |
| D30 | 491.2 |
| D31 | 509.2 |
| D32 | 499.1 |
| D33 | 527.2 |

Synthesis of Example E4

4-[1-[[2-(3-Chlorphenyl)-5-(trifluormethyl)-2H-pyrazol-3-yl]-methyl-carbamoyl]-ethyl]-2-fluoro-benzamide

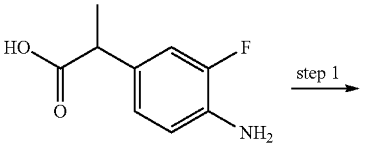

1

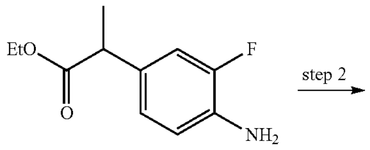

2

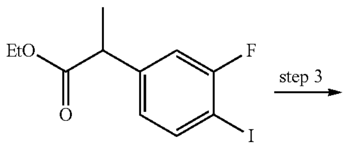

3

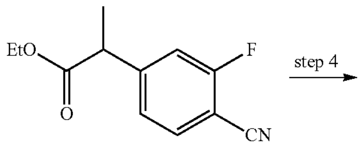

4

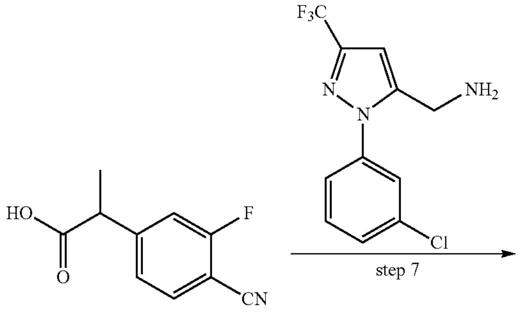

5

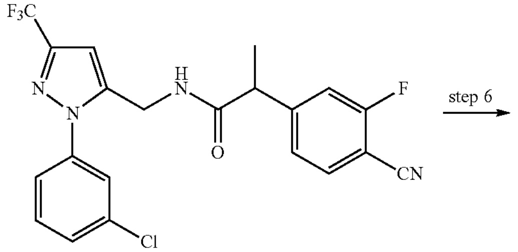

6

-continued

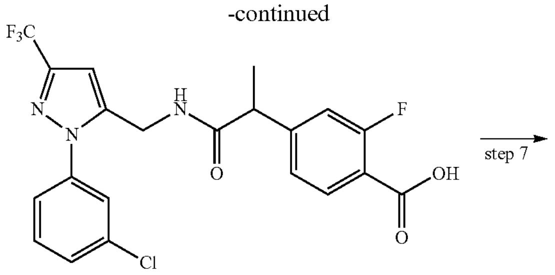

7

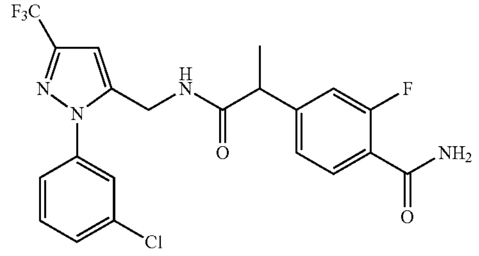

8

Step 1: To a solution of 2-(4-Amino-3-fluorophenyl) propionic acid (1) (1 g, 5.459 mmol) in EtOH was added $SOCl_2$ (0.6 ml, 8.189 mmol) at 0° C. The mixture was stirred for 2 hours at room temperature and then $SOCl_2$ was removed under reduced pressure. The residue was diluted with EtOAc and washed with a saturated $NaHCO_3$ solution. The resulting mixture was dried over $MgSO_4$ and concentrated. The residue was purified by column chromatography to afford the pure compound 2 (1 g, 87%).

Step 2: To a solution of compound 2 (1 g, 4.734 mmol) in water and $H_2SO_4$ (0.5 ml) was added $NaNO_2$ (490 mg, 7.101 mmol), KI (2358 mg, 14.202 mmol) at 0° C. The reaction mixture was stirred overnight at room temperature and then treated with saturated $NaHSO_3$ solution and eluted with EtOAc. The organic layer was washed with water, dried over $MgSO_4$ and concentrated. The residue was purified by column chromatography to afford the pure compound 3 (1.15 g, 75%).

Step 3: To a solution of starting material 3 (1.15 g, 3.570 mmol) in DMF was added $Zn(CN)_2$ (629 mg, 5.355 mmol) and $Pd(PPh_3)_4$ (825 mg, 0.714 mmol). The reaction mixture was refluxed for 8 hours and then cooled to room temperature. The mixture was filtered through a plug of Celite and concentrated. The residue was diluted with EtOAc and washed with 10% HCl solution. The organic layer was dried over $MgSO_4$ and concentrated. The residue was purified by column chromatography to afford the pure compound 4 (520 mg, 66%).

Step 4: To a solution compound 4 (520 mg, 2.351 mmol) in THF and water was added LiOH monohydrate (148 mg, 3.526 mmol). The reaction mixture was stirred for 2 hours at 40° C. and then acidified with 10% HCl solution. The mixture was extracted with EtOAc. The organic layer dried over $MgSO_4$ and concentrated under reduced pressure to afford desired compound 5 (440 mg, 97%).

Step 5: To a solution of compound 5 (440 mg, 2.278 mmol) in acetonitrile was added HOBt (462 mg, 3.417 mmol), EDC (655 mg, 3.417 mmol) and (1-(3-chlorophenyl)-3-(trifluoromethyl)-1H-pyrazol-5-yl)methanamine (659 mg, 2.392 mmol). The reaction mixture was stirred overnight at room temperature. The mixture was added water and extracted with EtOAc. The organic layer was dried over $MgSO_4$ and concentrated under reduced pressure. The crude product was purified by column chromatography to give pure compound 6 (870 mg, 85%).

Step 6: To a solution compound 6 (870 mg, 1.930 mmol) in EtOH was added 2N NaOH (9.7 ml, 19.300 mmol). The reaction mixture was stirred overnight at 100° C. and then was cooled to room temperature. The mixture was acidified with 10% HCl solution and extracted with EtOAc. The organic layer was dried over $MgSO_4$ and concentrated under reduced pressure. The crude product was purified by column chromatography to give pure compound 7 (550 mg, 61%).

Step 7: To 7 (150 mg, 0.319 mmol) in DCM was added $SOCl_2$ (0.12 ml, 1.597 mmol). The reaction mixture was refluxed for 2 hours and then $SOCl_2$ was removed under reduced pressure. The residue was dissolved in 1,4-dioxane and a solution of $NH_3$ (0.5 M) in 1,4-dioxane (3.2 ml, 1.595 mmol) was added. The reaction mixture was stirred at room temperature for 2 hours and then diluted with EtOAc and washed with water. The organic layer was dried over $MgSO_4$, filtered and concentrated. The crude product was purified by column chromatography to give pure compound 8 (70 mg, 47%).

Synthesis of Example E6

4-[[[2-(3-Chlorophenyl)-5-(trifluoromethyl)-2H-pyrazol-3-yl]-methyl-carbamoyl]amino]-2-fluoro-benzamide

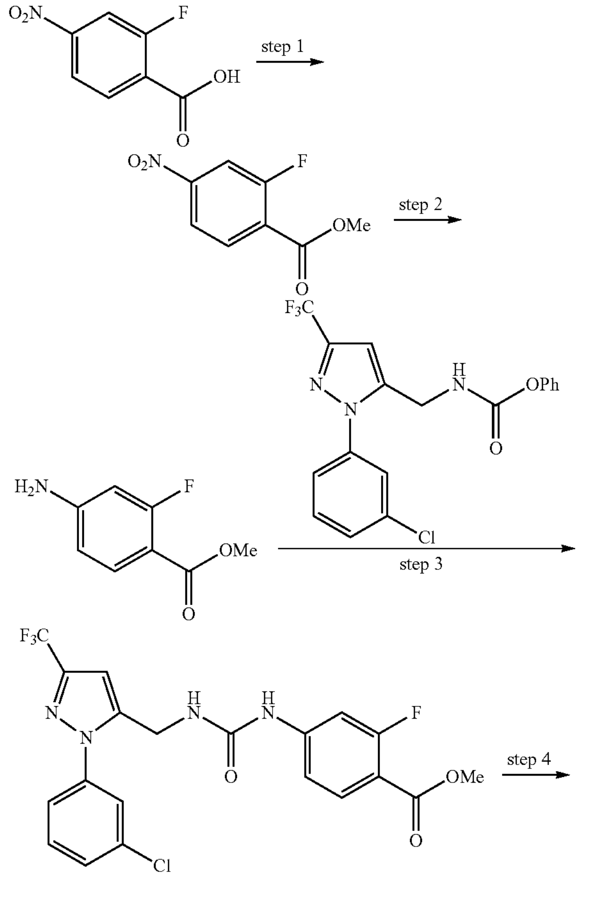

-continued

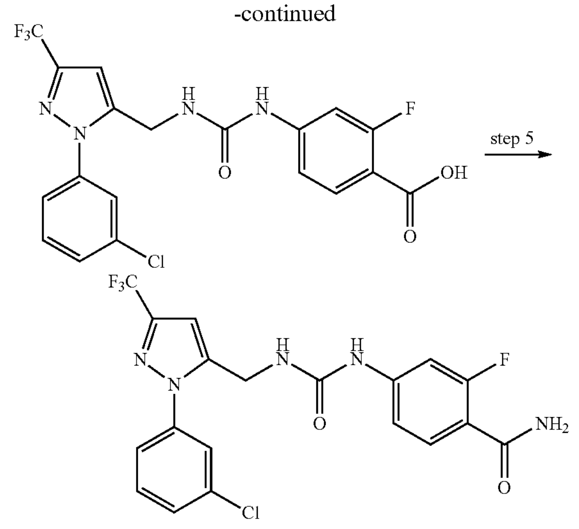

Step 1: To a solution of 2-fluoro-4-nitrobenzoic acid (1 g, 5.402 mmol) in MeOH was added $H_2SO_4$ (2.9 ml). The reaction mixture was refluxed overnight, and then cooled to room temperature and concentrated. The residue was diluted with EtOAc and washed with a saturated $NaHCO_3$ solution. The organic layer was dried over $MgSO_4$ and concentrated. The crude product was purified by column chromatography to afford the pure compound methyl 2-fluoro-4-nitrobenzoate (1.05 g, 98%).

Step 2: Methyl 2-fluoro-4-nitrobenzoate (1.05 g, 5.273 mmol) was dissolved in MeOH. Pd/C (105 mg) was added to the resulting mixture. The reaction mixture was stirred at room temperature for 2 hours under $H_2$. The mixture was filtered through Celite and the filtrate was concentrated under reduced pressure. The crude product was purified by column chromatography to give pure compound methyl 4-amino-2-fluorobenzoate (870 mg, 98%).

Step 3: To a solution of methyl 4-amino-2-fluorobenzoate (870 mg, 5.143 mmol) in acetonitrile was added DMAP (691 mg, 5.657 mmol) and phenyl (1-(3-chlorophenyl)-3-(trifluoromethyl)-1H-pyrazol-5-yl)methylcarbamate (2036 mg, 5.143 mmol) at room temperature. The reaction mixture was refluxed overnight and then cooled to room temperature. The mixture was added water and extracted with EtOAC. The organic layer was dried over $MgSO_4$ and concentrated. The crude product was purified by column chromatography to give pure methyl 4-(3-((1-(3-chlorophenyl)-3-(trifluoromethyl)-1H-pyrazol-5-yl)methyl)ureido)-2-fluorobenzoate (1.3 g, 54%).

Step 4: To a solution of methyl 4-(3-((1-(3-chlorophenyl)-3-(trifluoromethyl)-1H-pyrazol-5-yl)methyl)ureido)-2-fluorobenzoate (1.3 g, 2.761 mmol) in THF and water was added LiOH monohydrate (174 mg, 4.142 mmol). The reaction mixture was stirred for 2 hours at 40° C. and then acidified with a 10% HCl solution. The mixture was extracted with EtOAc. The organic layer dried over $MgSO_4$ and concentrated under reduced pressure to afford desired compound 4-(3-((1-(3-chlorophenyl)-3-(trifluoromethyl)-1H-pyrazol-5-yl)methyl)ureido)-2-fluorobenzoic acid (1.1 g, 87%).

Step 5: To a solution of compound 4-(3-((1-(3-chlorophenyl)-3-(trifluoromethyl)-1H-pyrazol-5-yl)methyl)ureido)-2-fluorobenzoic acid (100 mg, 0.219 mmol) in DMF was added HBTU (125 mg, 0.329 mmol), DIPEA (0.11 ml, 0.657 mmol) and $NH_3$ (0.5M solution in 1,4-dioxane; 1.3 ml, 0.657 mmol). The reaction mixture was stirred for 2 hours at room temperature. The mixture was added water and extracted with EtOAc. The organic layer was dried over $MgSO_4$ and concentrated under reduced pressure. The crude product was purified by column chromatography to give pure example compound E6 (60 mg, 60%).

$^1H$ NMR (300 MHz, DMSO-$d_6$): δ 9.13 (br.s, NH), 7.76 (m, 1H, Ar), 7.61 (m, 4H, Ar), 7.47 (m, 2H, Ar, NH), 7.39 (br.s, NH), 7.07 (dd, 1H, J=8.61, 2.04 Hz, Ar), 6.91 (t, NH, J=5.49 Hz, Ar—$CH_2NH$), 6.85 (s, 1H, pyrazole-H), 4.44 (d, 2H, J=5.49 Hz, Ar—$CH_2$).

Synthesis of Example E9

4-[[[2-(3-Chlorophenyl)-5-(trifluoromethyl)-2H-pyrazol-3-yl]-methyl-carbamoyl]amino]-2-fluoro-N-methyl-benzamide

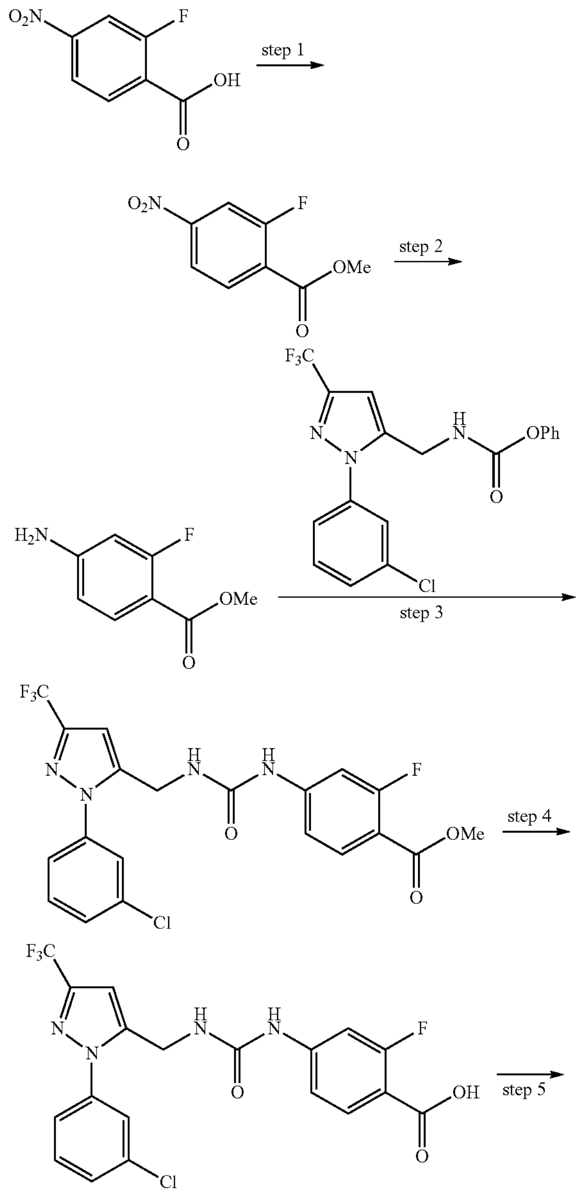

-continued

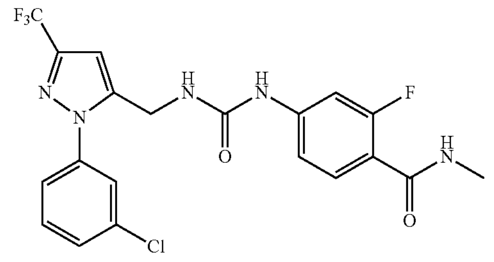

Steps 1-4: as described for example compound E6

Step 5: To a solution of compound 4-(3-((1-(3-chlorophenyl)-3-(trifluoromethyl)-1H-pyrazol-5-yl)methyl)ureido)-2-fluorobenzoic acid (150 mg, 0.328 mmol) in DMF was added HBTU (187 mg, 0.492 mmol), DIPEA (0.11 ml, 0.657 mmol) and methylamine (2M solution in THF; 0.33 ml, 0.657 mmol). The reaction mixture was stirred for 2 hours at room temperature. The mixture was added water and extracted with EtOAc. The organic layer was dried over $MgSO_4$ and concentrated under reduced pressure. The crude product was purified by column chromatography to give pure compound example compound E9 (130 mg, 84%).

$^1H$ NMR (300 MHz, DMSO-$d_6$): δ 9.10 (br.s, NH), 7.93 (m, NH), 7.75 (m, 1H, Ar), 7.52 (m, 5H, Ar), 7.06 (m, 1H, Ar), 6.89 (m, NH), 6.83 (s, 1H, pyrazole-H), 4.42 (d, 2H, J=5.67 Hz, Ar—$CH_2$), 2.73 (d, 3H, J=4.56 Hz, $CONHCH_3$).

Synthesis of Example E13

4-[[[2-(3-Chlorophenyl)-5-(trifluoromethyl)-2H-pyrazol-3-yl]-methyl-carbamoyl]amino]-2-fluoro-N,N-dimethyl-benzamide

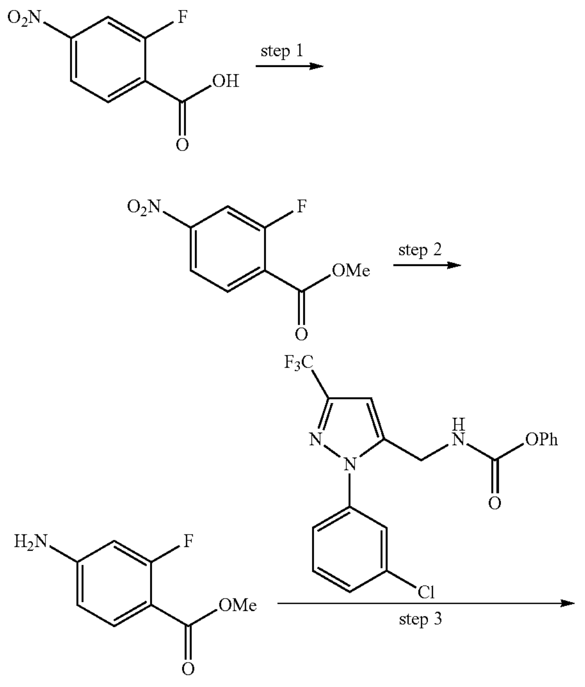

-continued

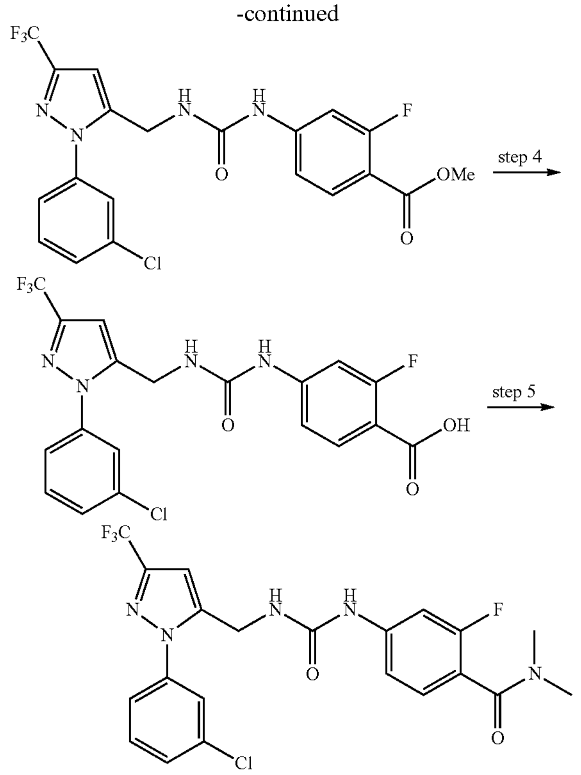

Steps 1-4: as described for example compound E6

Step 5: To a solution of compound 4-(3-((1-(3-chlorophenyl)-3-(trifluoromethyl)-1H-pyrazol-5-yl)methyl)ureido)-2-fluorobenzoic acid (150 mg, 0.328 mmol) in DMF was added HBTU (187 mg, 0.492 mmol), DIPEA (0.11 ml, 0.657 mmol) and dimethylamine (2M solution in THF; 0.33 ml, 0.657 mmol). The reaction mixture was stirred for 2 hours at room temperature. The mixture was added water and extracted with EtOAc. The organic layer was dried over $MgSO_4$ and concentrated under reduced pressure. The crude product was purified by column chromatography to give pure example compound E13 (110 mg, 69%)

$^1$H NMR (300 MHz, $CD_3OD$): δ 7.64 (m, 1H, Ar), 7.55 (m, 3H, Ar), 7.45 (m, 1H, Ar), 7.25 (m, 1H, Ar), 7.08 (m, 1H, Ar), 6.76 (s, 1H, pyrazole-H), 4.48 (m, 2H, Ar—$CH_2$), 3.09 (s, 3H, $CON(CH_3)_2$), 2.96 (d, 3H, J=1.50 Hz, $CON(CH_3)_2$).

Synthesis of Example E18

4-[[[2-(3-Chlorophenyl)-5-(trifluoromethyl)-2H-pyrazol-3-yl]-methyl-carbamoyl]amino]-2-fluoro-N-(2-hydroxy-ethyl)-benzamide

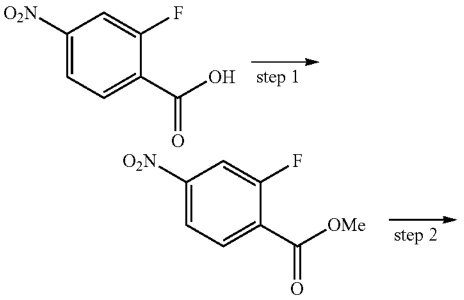

-continued

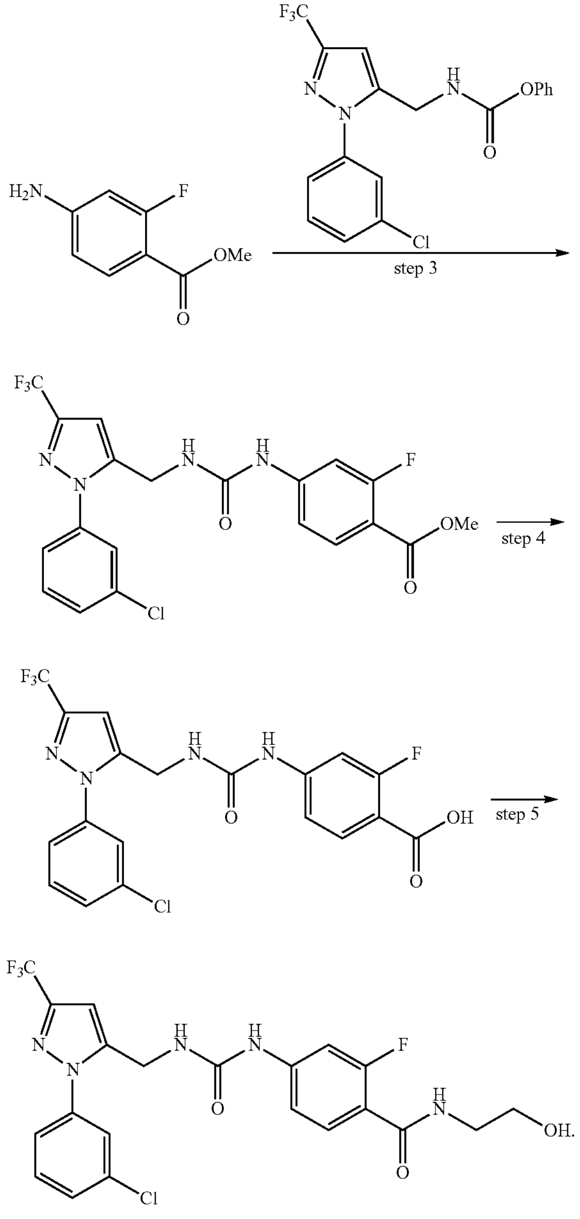

Steps 1-4: as described for example compound E6

Step 5: To a solution of 4-(3-((1-(3-chlorophenyl)-3-(trifluoromethyl)-1H-pyrazol-5-yl)methyl)ureido)-2-fluorobenzoic acid (150 mg, 0.328 mmol) in DMF was added HBTU (187 mg, 0.492 mmol), DIPEA (0.11 ml, 0.657 mmol) and ethanol amine (0.021 ml, 0.344 mmol). The reaction mixture was stirred for 2 hours at room temperature. The mixture was added water and extracted with EtOAc. The organic layer was dried over $MgSO_4$ and concentrated under reduced pressure. The crude product was purified by column chromatography to give pure compound example compound E18 (115 mg, 70%)

$^1$H NMR (300 MHz, DMSO-$d_6$): δ 9.12 (br.s, NH), 7.86 (m, NH), 7.75 (m, 1H, Ar), 7.53 (m, 5H, Ar), 7.07 (m, 1H, Ar), 6.90 (m, NH), 6.84 (s, 1H, pyrazole-H), 4.73 (t, 1H, J=5.70 Hz, ethanol-OH), 4.42 (d, 2H, J=5.70 Hz, Ar—$CH_2$), 3.43 (m, 2H, ethanol-$CH_2$), 3.33 (m, 2H, ethanol-$CH_2$).

Synthesis of Example E45

4-[1-[[2-(3-Chlorophenyl)-5-(trifluoromethyl)-2H-pyrazol-3-yl]-methyl-carbamoyl]-ethyl]-2-fluoro-N-(4-fluorophenyl)-benzamide

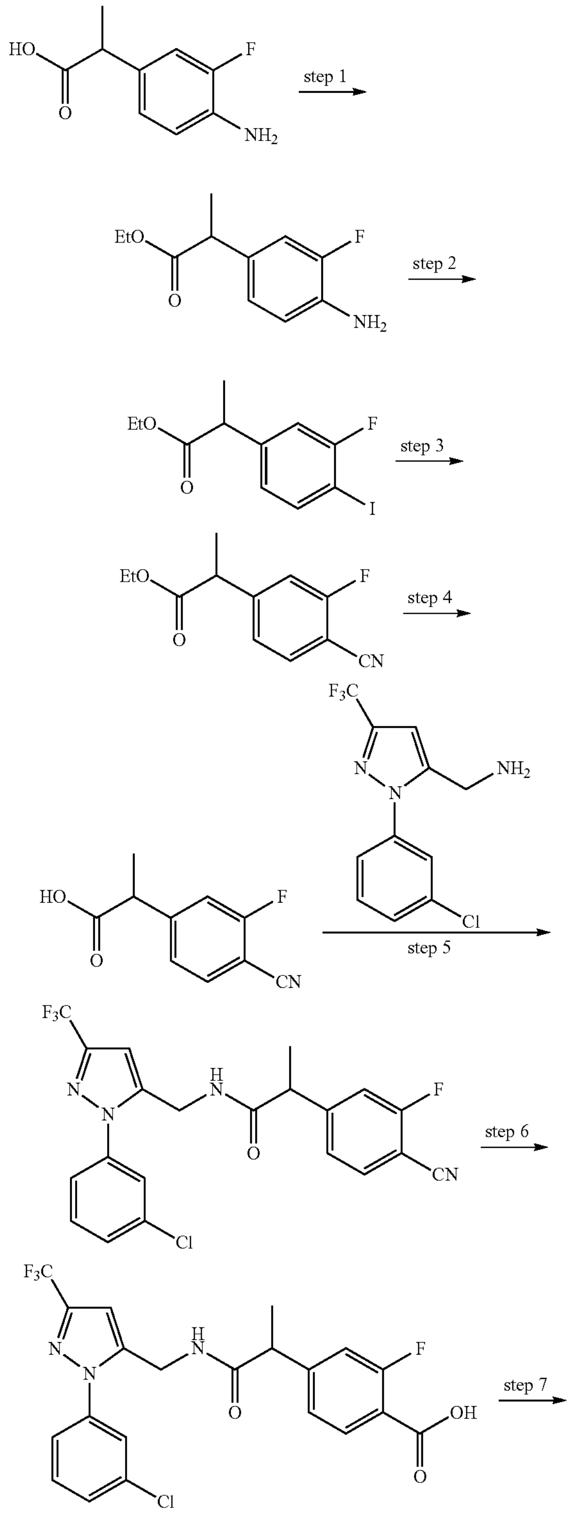

-continued

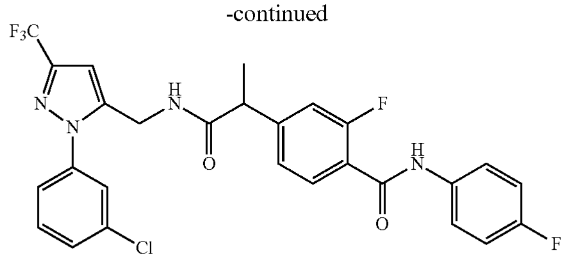

Step 1: To a solution of 2-(4-Amino-3-fluorophenyl) propionic acid (1 g, 5.459 mmol) in EtOH was added $SOCl_2$ (0.6 ml, 8.189 mmol) at 0° C. The mixture was stirred for 2 hours at room temperature and then $SOCl_2$ was removed under reduced pressure. The residue was diluted with EtOAc and washed with a saturated $NaHCO_3$ solution. The resulting mixture was dried over $MgSO_4$ and concentrated. The residue was purified by column chromatography to afford ethyl 2-(4-amino-3-fluorophenyl)propanoate (1 g, 87%).

Step 2: To a solution of ethyl 2-(4-amino-3-fluorophenyl) propanoate (1 g, 4.734 mmol) in water and $H_2SO_4$ (0.5 ml) was added $NaNO_2$ (490 mg, 7.101 mmol), KI (2358 mg, 14.202 mmol) at 0° C. The reaction mixture was stirred overnight at room temperature and then treated with saturated $NaHSCO_3$ solution and eluted with EtOAc. The organic layer was washed with water, dried over $MgSO_4$ and concentrated. The residue was purified by column chromatography to afford ethyl 2-(3-fluoro-4-iodophenyl)propanoate (1.15 g, 75%).

Step 3: To a solution of ethyl 2-(3-fluoro-4-iodophenyl) propanoate (1.15 g, 3.570 mmol) in DMF was added $Zn(CN)_2$ (629 mg, 5.355 mmol) and $Pd(PPh_3)_4$ (825 mg, 0.714 mmol). The reaction mixture was refluxed for 8 hours and then cooled to room temperature. The mixture was filtered through a plug of Celite and concentrated. The residue was diluted with EtOAc and washed with 10% HCl solution. The organic layer was dried over $MgSO_4$ washed and concentrated. The residue was purified by column chromatography to afford the pure compound ethyl 2-(4-cyano-3-fluorophenyl)propanoate (520 mg, 66%).

Step 4: To a solution of ethyl 2-(4-cyano-3-fluorophenyl) propanoate (520 mg, 2.351 mmol) in THF and water was added LiOH monohydrate (148 mg, 3.526 mmmol). The reaction mixture was stirred for 2 hours at 40° C. and then acidified with 10% HCl solution. The mixture was extracted with EtOAc. The organic layer dried over $MgSO_4$ and concentrated under reduced pressure to afford desired compound 2-(4-cyano-3-fluorophenyl)propanoic acid (440 mg, 97%).

Step 5: To a solution of 2-(4-cyano-3-fluorophenyl)propanoic acid (440 mg, 2.278 mmol) in acetonitrile was added HOBt (462 mg, 3.417 mmol), EDC (655 mg, 3.417 mmol) and (1-(3-chlorophenyl)-3-(trifluoromethyl)-1H-pyrazol-5-yl)methanamine (659 mg, 2.392 mmol). The reaction mixture was stirred overnight at room temperature. The mixture was added water and extracted with EtOAc. The organic layer was dried over $MgSO_4$ and concentrated under reduced pressure. The crude product was purified by column chromatography to give pure compound N-((1-(3-chlorophenyl)-3-(trifluoromethyl)-1H-pyrazol-5-yl)methyl)-2-(4-cyano-3-fluorophenyl)propanamide (870 mg, 85%).

Step 6: To a solution compound N-((1-(3-chlorophenyl)-3-(trifluoromethyl)-1H-pyrazol-5-yl)methyl)-2-(4-cyano-3-fluorophenyl)propanamide (870 mg, 1.930 mmol) in EtOH was added 2N NaOH (9.7 ml, 19.300 mmol). The reaction mixture was stirred overnight at 100° C. and then was cooled to room temperature. The mixture was acidified with 10% HCl solution and extracted with EtOAc. The organic layer was dried over $MgSO_4$ and concentrated under reduced pressure. The crude product was purified by column chromatography to give pure compound 4-(1-((1-(3-chlorophenyl)-3-(trifluoromethyl)-1H-pyrazol-5-yl)methylamino)-1-oxopropan-2-yl)-2-fluorobenzoic acid (550 mg, 61%).

Step 7: To 4-(1-((1-(3-chlorophenyl)-3-(trifluoromethyl)-1H-pyrazol-5-yl)methylamino)-1-oxopropan-2-yl)-2-fluorobenzoic acid (150 mg, 0.319 mmol) in acetonitrile was added $SOCl_2$ (0.12 ml, 1.597 mmol). The reaction mixture was refluxed for 2 hours and then $SOCl_2$ was removed under reduced pressure. The residue was dissolved in acetonitrile and it was added to the solution 4-fluoroaniline (0.032 ml, 0.335 mmol) and TEA (0.067 ml, 0.479 mmol) in acetonitrile. The reaction mixture was stirred at room temperature for 2 hours and then diluted with acetonitrile and washed with water. The organic layer was dried over $MgSO_4$ and was then concentrated. The crude product was purified by column chromatography to give example compound E41 (80 mg, 45%).

$^1H$ NMR (300 MHz, Acetone-$d_6$): δ 9.41 (br.s, NH), 7.72 (m, 8H, Ar), 7.19 (m, 4H, Ar), 6.71 (s, 1H, pyrazole-H), 4.57 (m, 2H, Ar—$CH_2$), 3.78 (quartet, 1H, J=6.93 Hz, amide-CH), 1.42 (d, 3H, J=7.14 Hz, amide-$CH_3$).

Synthesis of Example E59

2-Chloro-4-[[[2-(3-chlorophenyl)-5-(trifluoromethyl)-2H-pyrazol-3-yl]-methyl-carbamoyl]amino]-benzoic acid methyl ester

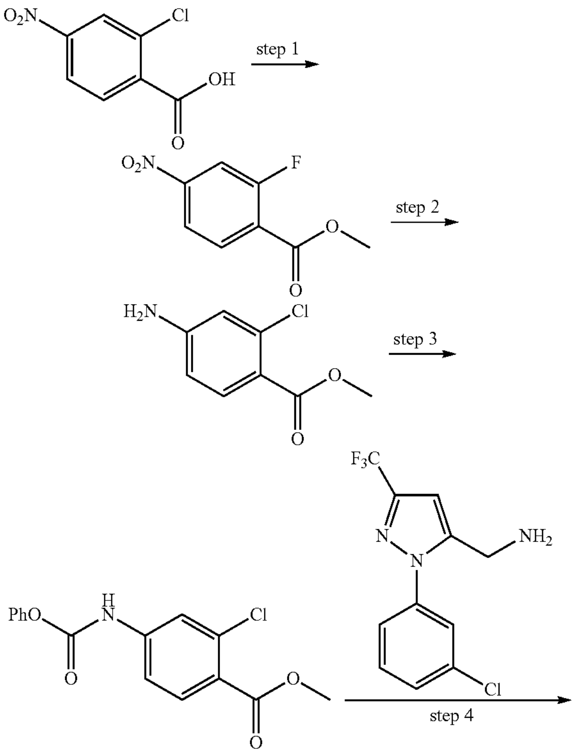

-continued

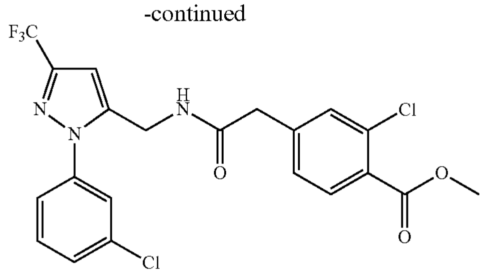

Step 1: To a stirred solution of 2-Chloro-4-nitrobenzoic acid (500 mg, 2.48 mmol) in methanol was added sulfuric acid in catalytic amounts. The mixture was heated to reflux overnight. TLC showed complete consumption of starting material. The reaction mixture was slowly cooled room temperature and neutralized with sodium bicarbonate. The mixture was extracted with EtOAc and washed with water and brine. The extract was dried over $MgSO_4$ and concentrated under reduced pressure. The crude product was purified by column chromatography to afford pure compound methyl 2-chloro-4-nitrobenzoate 468 mg).

Step 2: To a stirred solution of methyl 2-chloro-4-nitrobenzoate (468 mg, 2.17 mmol) in ethanol was added Sn(II) chloride and heated to reflux for 1.5 h. TLC showed complete consumption of starting material. The reaction mixture was cooled to room temperature. The solvent was removed in vacuo and extracted with EtOAc. The organic layer was washed with water and brine. The extract was dried over $MgSO_4$ and concentrated under reduced pressure to give desired product methyl 4-amino-2-chlorobenzoate (407 mg).

Step 3: Methyl 4-amino-2-chlorobenzoate (407 mg, 2.2 mmol) was dissolved in acetonitrile. To the reaction mixture was added pyridine (0.3 ml, 2.4 mmol) and phenyl chloroformate (0.21 ml, 2.6 mmol) and the mixture was stirred at room temperature for 1 h under $N_2$. TLC showed complete consumption of starting material. The reaction mixture was diluted with water and extracted with EtOAc. The organic layer was washed with water and brine. The organic layer was dried over $MgSO_4$ and concentrated under reduced pressure. The crude product was purified by column chromatography to give pure compound methyl 2-chloro-4-(phenoxycarbonylamino)benzoate (713 mg).

Step 4: To a solution of methyl 2-chloro-4-(phenoxycarbonylamino)benzoate (80 mg, 0.26 mmol) in DMF was added DMAP (32 mg, 0.26 mmol) and (1-(3-chlorophenyl)-3-(trifluoromethyl)-1H-pyrazol-5-yl)methanamine (74 mg, 0.27 mmol) at room temperature. The reaction mixture was heated to 50° C. overnight. TLC showed complete consumption of starting material. The reaction mixture was diluted with water and extracted with EtOAc. The organic layer was washed with water and brine. The organic layer was dried over $MgSO_4$ and concentrated under reduced pressure. The crude product was purified by column chromatography to give pure example compound E59 (77 mg).

$^1H$ NMR (300 MHz, CDCl3): 7.84 (d, 1H, J=8.61 Hz, Ar), 7.52 (s, 1H, Ar), 7.47-7.45 (m, 3H, Ar), 7.40-7.38 (m, 1H, Ar), 7.30 (d, 1H, J=2.19 Hz, Ar), 6.68 (s, 1H, pyrazole), 6.57 (s, 1H, NH), 5.06 (bs, s, 1H), 4.55 (d, 2H, J=5.31 Hz, —CH2), 3.90 (s, 3H, methoxy).

Synthesis of Example E61

1-((1-(3-chlorophenyl)-3-(trifluoromethyl)-1H-pyrazol-5-yl)methyl)-3-(3-fluoro-4-formylphenyl)urea

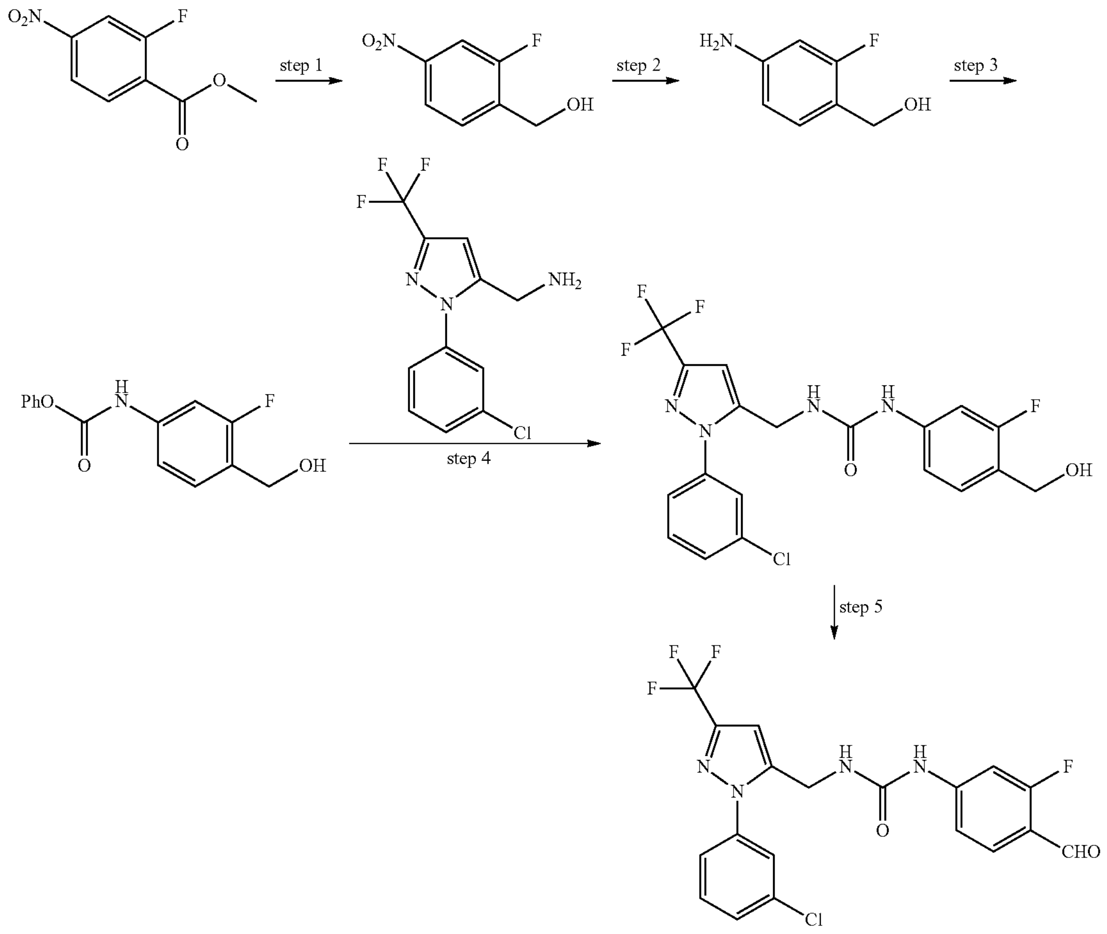

Step 1: To a stirred solution of methyl 2-fluoro-4-nitrobenzoate (10.0 g, 49.7 mmol, 1 eq.) in methanol (100 mL) was added sodium borohydride (9.40 g, 248.7 mmol, 5 eq.) at RT and stirred for 4 h. The methanol was evaporated and the residue was diluted with ethyl acetate (50 mL×2) washed with washed with water (50 mL) and brine (50 mL). The ethyl acetate layer was dried over $Na_2SO_4$, evaporated under vacuum to get (2-fluoro-4-nitrophenyl)methanol (8 g, 94%, off-white solid; TLC system: EtOAc/PE (3:7), $R_f$: 0.30).

Step 2: To a stirred solution of (2-fluoro-4-nitrophenyl) methanol (3.0 g, 1.0 eq.) in EtOAc (30 mL) was added 10% Pd—C and the reaction mixture was stirred under $H_2$ gas balloon at RT for 6 h. The reaction mixture was passed through a celite pad and the solvent evaporated. The residue was purified by neutral alumina column using PE/EtOAc (3:2) as eluent to get (4-amino-2-fluorophenyl)methanol (1.1 g, 48%) as a solid; TLC system: EtOAc/PE (1:1), $R_f$: 0.3).

Step 3: To a stirred solution of (4-amino-2-fluorophenyl) methanol (100 mg, 0.709 mmol, 1 eq.) in acetone (1.0 mL) was added pyridine (0.17 mL, 2.12 mmol, 3 eq.) followed by phenyl chloroformate (0.092 mL, 0.709 mmol, 1 eq.) at 0° C. and stirred at RT for 1 h. The solvent was evaporated and the residue obtained was purified by CC using ethyl acetate/PE (7:13) as eluent to get phenyl 3-fluoro-4-(hydroxymethyl)phenylcarbamate (110 mg, 60%, off-white solid; TLC system: EtOAc/PE (1:1), $R_f$: 0.4).

Step 4: To a stirred solution of (1-(3-chlorophenyl)-3-(trifluoromethyl)-1H-pyrazol-5-yl)methanamine (100 mg, 0.316 mmol, 1.0 eq.) in DCM (2.0 mL) was added $Et_3N$ (0.07 mL, 0.632 mmol, 3.0 eq) followed by phenyl 3-fluoro-4-(hydroxymethyl)phenylcarbamate (82.4 mg, 0.316 mmol, 1.0 eq.) at RT and stirred for 16 h. After completion of the reaction, a solid precipitate was filtered and washed with DCM (2 mL) followed by n-pentane (5 mL) and dried to get 1-((1-(3-chlorophenyl)-3-(trifluoromethyl)-1H-pyrazol-5-yl)methyl)-3-(3-fluoro-4-(hydroxymethyl)phenyl)urea (compound A59) (80 mg; 47%, white solid; TLC system: EtOAc/PE (3:2); $R_f$: 0.2).

Step 5: To a stirred solution of 1-((1-(3-chlorophenyl)-3-(trifluoromethyl)-1H-pyrazol-5-yl)methyl)-3-(3-fluoro-4-(hydroxymethyl)phenyl)urea (240 mg, 0.54 mmol, 1.0 eq) in DCM (10 mL) and cooled to 0° C. was added Dess-Martin periodinane (345 mg, 0.813 mmol, 1.5 eq) slowly portion wise at 0° C. and stirred for 1 h at 0° C., and then stirred for 30 min. at RT. DCM was evaporated and EtOAC (50 mL) was added. The mixture was washed with water (20 mL), brine (20 mL), dried over anhydrous $Na_2SO_4$ and evaporated under vacuum. The crude product was purified by CC using EtOAc/PE (2:3) to yield compound 1-((1-(3-chlorophenyl)-3-(trifluoromethyl)-1H-pyrazol-5-yl)methyl)-3-(3-fluoro-4-formylphenyl)urea (120 mg; 48%) as an yellow solid (TLC: EtOAc/PE (1:1); $R_f$: 0.5).

Synthesis of Example E62

4-(3-((1-(3-chlorophenyl)-3-(trifluoromethyl)-1H-pyrazol-5-yl)methyl)ureido)-2-fluorobenzoic acid

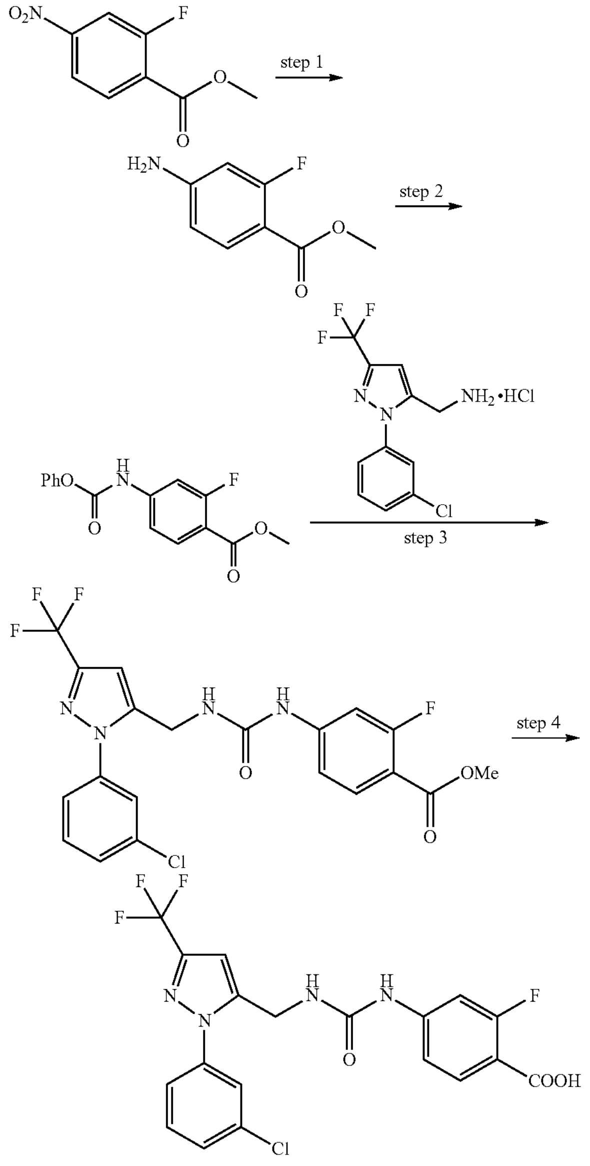

Step 1: To a stirred solution of methyl 2-fluoro-4-nitrobenzoate (1 g, 4.9 mmol, 1.0 eq) in EtOH (15 mL) was added 10% Pd/C (300 mg) and stirred under hydrogen gas balloon pressure. The reaction mixture was passed through celite, washed with EtOAC, the filtrate was concentrated to obtain methyl 4-amino-2-fluorobenzoate (800 mg; 95%) as a pale yellow solid (TLC: EtOAc/PE (2:3); $R_f$: 0.2).

Step 2: To a stirred solution of methyl 4-amino-2-fluorobenzoate (800 mg, 4.6 mmol, 1.0 eq) in acetone (10 mL) was added phenyl chloroformate (0.6 mL, 4.6 mmol, 1.0 eq) and followed by pyridine (1.1 mL, 13.8 mmol, 3.0 eq) at 0° C. and stirred at RT for 1 h. The acetone in the RM was evaporated and diluted with water (50 mL) extracted with EtOAC (2×100 mL). The organic layer was washed with water (50 mL), brine (50 mL), dried over anhydrous $Na_2SO_4$ and evaporated under vacuum. The crude product was washed with n-pentane to yield methyl 2-fluoro-4-(phenoxycarbonylamino)benzoate (1.2 g, 89.6%) as white solid (TLC: EtOAc/PE (2:3); $R_f$: 0.3).

Step 3: To a stirred solution of (1-(3-chlorophenyl)-3-(trifluoromethyl)-1H-pyrazol-5-yl)methanamine hydrochloride (321 mg, 1.03 mmol, 1.0 eq) in DCM (10 mL) was added TEA (0.28 mL, 0.26 mmol, 2.0 eq) followed by methyl 2-fluoro-4-(phenoxycarbonylamino)benzoate (300 mg, 1.03 mmol, 1.0 eq) at RT and stirred for 16 h. Then the reaction mixture was evaporated, diluted with water (50 mL) and extracted with ethyl acetate (2×70 mL). The combined organic layer was washed with brine (50 mL), dried over anhydrous $Na_2SO_4$ and evaporated under vacuum. The crude product was purified CC using EtOAc/PE (2:3) as eluent to obtain methyl 4-(3-((1-(3-chlorophenyl)-3-(trifluoromethyl)-1H-pyrazol-5-yl)methyl)ureido)-2-fluorobenzoate (300 mg; 63%) as a white solid (TLC: EtOAc/PE (1:1); $R_f$: 0.3).

Step 4: To a stirred solution of methyl 4-(3-((1-(3-chlorophenyl)-3-(trifluoromethyl)-1H-pyrazol-5-yl)methyl) ureido)-2-fluorobenzoate (120 mg, 0.25 mmol, 1.0 eq) in THF (10 mL) was added LiOH (21.4 mg, 0.51 mmol, 2.0 eq) dissolved in $H_2O$ (2 mL) at RT and stirred for 6 h at 45° C. The reaction mixture was concentrated, diluted with water (20 mL), brine (20 mL), the pH was adjusted to 4 with HCl (1N), and extracted with ethyl acetate (30 mL). The organic layer was washed with water (20 mL) brine (20 mL), dried over anhydrous $Na_2SO_4$ and evaporated under vacuum. The crude product was purified by CC using EtOAc/PE (7:3) to obtain 4-(3-((1-(3-chlorophenyl)-3-(trifluoromethyl)-1H-pyrazol-5-yl)methyl)ureido)-2-fluorobenzoic acid (100 mg; 85%) as a yellow solid (TLC: EtOAc/PE (7:3); $R_f$: 0.2).

TABLE 6

Mass Spectrometric Data for compounds of Formula (U)

| Example Compound | [M + H] |
|---|---|
| E1 | 465.9 |
| E2 | 478.0 |
| E3 | 484.0 |
| E4 | 457.5 |
| E5 | 444.4 |
| E6 | 456.2 |
| E7 | 456.5 |
| E8 | 458.3 |
| E9 | 470.2 |
| E10 | 471.5 |
| E11 | 483.3 |
| E12 | 472.5 |
| E13 | 484.2 |
| E14 | 514.6 |
| E15 | 526.3 |
| E16 | 539.4 |
| E17 | 527.5 |
| E18 | 500.4 |
| E19 | 525.1 |
| E20 | 566.4 |
| E21 | 554.6 |
| E22 | 540.0 |
| E23 | 553.1 |
| E24 | 541.5 |
| E25 | 501.6 |
| E26 | 513.0 |
| E27 | 515.5 |
| E28 | 527.0 |
| E29 | 533.5 |
| E30 | 536.0 |
| E31 | 550.0 |
| E32 | 561.9 |
| E33 | 560.4 |

TABLE 6-continued

| Mass Spectrometric Data for compounds of Formula (U) | |
|---|---|
| Example Compound | [M + H] |
| E34 | 549.9 |
| E35 | 568.0 |
| E36 | 531.4 |
| E37 | 519.5 |
| E38 | 549.2 |
| E39 | 537.5 |
| E40 | 533.4 |
| E41 | 545.5 |
| E42 | 533.4 |
| E43 | 545.0 |
| E44 | 551.5 |
| E45 | 563.4 |
| E46 | 579.8 |
| E47 | 583.5 |
| E48 | 613.4 |
| E49 | 601.6 |
| E50 | 569.5 |
| E51 | 581.4 |
| E52 | 552.6 |
| E53 | 540.6 |
| E54 | 473.9 |
| E55 | 461.8 |
| E56 | 457.6 |
| E57 | 471.4 |
| E58 | 483.4 |
| E59 | 487.8 |
| E60 | 475.9 |
| E61 | 441.1 |
| E62 | 457.1 |

Pharmacological Data

The affinity of the compounds according to the invention for the vanilloid receptor 1 (VR1/TRPV1 receptor) was determined as described hereinbefore (pharmacological methods I and II respectively). The compounds according to the invention of the above-indicated formula (I) display outstanding affinity to the VR1/TRPV1 receptor (Tables 7 through 12).

In the following tables the abbreviations have the following meanings:

Cap=capsaicin
AG=agonist
pAG=partial agonist
pH=after pH stimulus
NADA=N-arachidonoyl dopamine
NE=no effect
FTm=formalin test carried out on mice The value after the "@" symbol indicates the concentration at which the inhibition (as a percentage) was respectively determined.

TABLE 7

| Compound according to Example | $K_i$ (rat) [nM] Cap | $K_i$ (human being) [nM] Cap | $IC_{50}$ (human being) hVR1 [nM], pH | $K_i$ (rat) [nM] NADA | $K_i$ (human being) [nM] NADA | $IC_{50}$ (human being) [nM], 45° C. | FTm |
|---|---|---|---|---|---|---|---|
| 1 | 25% @ 5 µM | NE | NE | | | | |
| 2 | 25% @ 5 µM | NE | NE | | | | |
| 3 | 14% @ 5 µM | 12% @ 5 µM | NE | | | | |
| 4 | 20% @ 5 µM | 9% @ 5 µM | NE | | | | |
| 5 | 76% @ 1 µM | 50.2 | 36% @ 10 µM | | 4.99 | 282 | |
| 6 | 14.5 | 27.7 | 13% @ 10 µM | | | | |
| 7 | 0.35 | 21.6 | NE | | | | |
| 12 | 5.9 | 8 | 40% @ 10 µM | | | | |
| 13 | 25.9 (15) | 75.2 (49) | | | | | |
| 14 | 7.2 | 3.7 | 25% @ 10 µM | | | | |
| 15 | 2.5 | 2.1 | 14% @ 5 µM | | | | |
| 16 | 0.2 | 0.3 | NE | 0.03 | 0.04 | 35% @ 0.625 µM | |
| 17 | 0.1 | 0.1 | 37% @ 10 µM | | | | |
| 18 | | 0.5 | 31% @ 10 µM | | 0.22 | 7.0 | |
| 19 | 819 | 44% @ 1 µM | NE | | | | |
| 20 | 2834 | 55% @ 1 µM | NE | | | | |
| 21 | 1.2 | 0.3 | 179 | | 0.12 | 27.0 | |
| 22 | 42.7 | 31.7 | 42% @ 10 µM | | | | |
| 23 | 0.4 | 0.3 | 47.1 | | | 16.13 | |
| 24 | 0.4 | 0.3 | 39.2 | | | | |
| 25 | 5.1 | 26.5 | 2,585 | | | | |
| 26 | 0.1 | 0.1 | 8.0 | | 0.1 | 8.05 | |
| 27 | 1.2 | 2.2 | NE | | 0.12 | | |
| 28 | | 0.4 | 16 | | | 665 | |
| 29 | | 1.2 | 42% @ 10 µM | | 0.08 | 34% @ 2 µM | |
| 30 | | 6.3 | | | | | |
| 33 | | 4.0 | | | | | |
| 39 | | 7.2 | | | | | |
| 40 | | 0.8 | | | | | |
| 41 | | 85 | | | | | |
| 47 | | 17 | | | | | |
| 49 | | AG | AG | | AG | AG | |
| 55 | | 114 | NE | | | | |
| 56 | | AG | AG | | AG | AG | |
| 61 | | AG | | | | | |
| 73 | | AG | | | | | |
| 74 | 85 | 51.8 | | 49 | | 12% @ 2.5 µM | 1 po FTm 13% |
| 117 | | 56 | | | | | |
| 118 | | AG | | | | | |

TABLE 7-continued

| Compound according to Example | $K_i$ (rat) [nM] Cap | $K_i$ (human being) [nM] Cap | $IC_{50}$ (human being) hVR1 [nM], pH | $K_i$ (rat) [nM] NADA | $K_i$ (human being) [nM] NADA | $IC_{50}$ (human being) [nM], 45° C. | FTm |
|---|---|---|---|---|---|---|---|
| 119 | | 107 | | | | | |
| 120 | | 6% @ 1 μM | | | | | |
| 122 | | AG | | | | | |
| 123 | | 44% @ 5 μM | | | | | |
| 125 | | AG | | | | | |
| 126 | | 31.4 | | | | | |
| 127 | | 58.1 | | | | | |
| 128 | | 16.3 | | | | | |
| 129 | | 63.6 | | | | | |
| 130 | | 112 | | | | | |
| 131 | | 58% @ 5 μM | | | | | |
| 132 | | 34% @ 5 μM | | | | | |
| 133 | | 12% @ 5 μM | | | | | |
| 134 | | 2.5 | | | | 546 | |
| 135 | | 24% @ 5 μM | | | | | |
| 137 | | 65.1 | | | | | |
| 139 | | AG | | | | | |
| 141 | 25.5 | 13.6 | | | | 28% @ 2.5 μM | |
| 142 | | AG | | | | | |
| 143 | | 56% @ 1 μM | | | | | |
| 144 | | AG | | | | | |
| 147 | | 26 | | | | | |

TABLE 8

Vanilloid Receptor Affinity of Compounds of formula (Q):

| Example Compound | (f) Ki (human being) [nM] Cap | Example Compound | (f) Ki (human being) [nM] Cap |
|---|---|---|---|
| A1 | 12 | A53 | 18 |
| A2 | 33 | A54 | 6 |
| A3 | 6 | A55 | 3 |
| A4 | 2 | A56 | 2 |
| A5 | AG | A57 | 2 |
| A6 | 14 | A58 | 6 |
| A7 | 26 | A59 | 7 |
| A8 | 55 | A60 | 10 |
| A9 | 7 | A61 | 26 |
| A10 | 1 | A62 | 30 |
| A11 | AG | A63 | 9 |
| A12 | 8 | A64 | 26 |
| A13 | AG | A65 | 6 |
| A14 | 25 | A66 | 9 |
| A15 | AG | A67 | 43 |
| A16 | AG | A68 | 13 |
| A17 | AG | A69 | 45 |
| A18 | 68 | A70 | 9 |
| A19 | 13 | A71 | 42 |
| A20 | 37 | A72 | 14 |
| A21 | 7 | A73 | 27 |
| A22 | 40 | A74 | 44 |
| A23 | 35 | A75 | 19 |
| A24 | AG | A76 | 41 |
| A25 | 65 | A77 | 19 |
| A29 | 1 | A78 | 11 |
| A30 | 21 | A79 | 20 |
| A31 | 3 | A80 | 7 |
| A32 | AG | A81 | 21 |
| A33 | 2 | A82 | 2 |
| A34 | 37 | A83 | 12 |
| A35 | 1 | A84 | 53 |
| A36 | 0.3 | A85 | 53% @ 5 μM |
| A37 | AG | A86 | 25 |
| A38 | 11 | A87 | 63 |
| A39 | AG | A88 | 86 |
| A40 | 27 | A89 | 45 |
| A41 | AG | A90 | 27 |
| A42 | 3 | A91 | 51 |
| A43 | 21 | A92 | 19 |
| A44 | 0.2 | A93 | 18 |
| A45 | 1 | A94 | 30 |

TABLE 8-continued

Vanilloid Receptor Affinity of Compounds of formula (Q):

| Example Compound | (f) Ki (human being) [nM] Cap | Example Compound | (f) Ki (human being) [nM] Cap |
|---|---|---|---|
| A47 | AG | A95 | 13 |
| A48 | AG | A96 | 2 |
| A49 | AG | A97 | 11 |
| A50 | 1 | A98 | AG |
| A51 | AG | A99 | 6 |
| A52 | 40 | A100 | 0.7 |
| A101 | 4 | A158 | 13% @ 5 μM |
| A102 | 15 | A159 | 24% @ 5 μM |
| A103 | 22 | A27 | 1 |
| A104 | 12 | A28 | 22 |
| A105 | 19 | | |
| A106 | 31 | | |
| A107 | 45 | | |
| A108 | 48 | | |
| A109 | 43 | | |
| A110 | 48 | | |
| A111 | 38 | | |
| A112 | 79 | | |
| A113 | 63 | | |
| A114 | 46 | | |
| A115 | 3 | | |
| A116 | 18 | | |
| A117 | 9 | | |
| A118 | 27 | | |
| A119 | 57 | | |
| A120 | 5 | | |
| A121 | 20 | | |
| A122 | 45 | | |
| A123 | 24 | | |
| A127 | 40 | | |
| A128 | 67 | | |
| A129 | 43 | | |
| A130 | 47 | | |
| A131 | 56 | | |
| A132 | 48% @ 5 μM | | |
| A133 | 12 | | |
| A136 | 40 | | |
| A137 | 0.6 | | |
| A138 | 8 | | |
| A139 | AG | | |
| A140 | AG | | |
| A141 | 26 | | |

TABLE 8-continued

Vanilloid Receptor Affinity of Compounds of formula (Q):

| Example Compound | (f) Ki (human being) [nM] Cap | Example Compound | (f) Ki (human being) [nM] Cap |
|---|---|---|---|
| A145 | AG | | |
| A146 | 13 | | |
| A147 | AG | | |
| A148 | 4 | | |
| A150 | 19 | | |
| A151 | 62 | | |
| A152 | 39% @ 5 μM | | |
| A153 | 50% @ 5 μM | | |
| A154 | 117 | | |
| A155 | 26% @ 5 μM | | |
| A156 | 84 | | |
| A157 | 35% @ 5 μM | | |

TABLE 9

Vanilloid Receptor Affinity of Compounds of Formula (R)

| Compound according to Example | (f) Ki (human being) [nM] Cap |
|---|---|
| B1 | 5 |
| B2 | 2.4 |
| B3 | 3 |
| B4 | 61 |
| B5 | 9 |
| B6 | 7 |
| B7 | 7 |
| B8 | 1 |
| B9 | 6 |
| B10 | 6 |
| B11 | 9 |
| B12 | 41 |
| B13 | 1 |
| B14 | 64 |
| B15 | 6 |
| B16 | 2 |
| B17 | 3 |
| B18 | 13 |
| B19 | 6 |
| B20 | 52 |
| B21 | 30 |
| B22 | 3 |
| B23 | 13 |
| B24 | 55 |
| B25 | 45 |
| B26 | 12 |
| B27 | 8 |
| B28 | 11 |
| B29 | 59 |
| B30 | 39 |
| B31 | 9 |
| B32 | 2 |
| B33 | 38% @ 5 μM |
| B34 | 15 |
| B35 | 9 |
| B36 | 6 |
| B37 | 46 |
| B38 | 18% @ 5 μM |
| B39 | 37% @ 5 μM |
| B40 | 92 |
| B41 | 74 |
| B42 | 46 |
| B43 | 1 |
| B44 | 44 |
| B45 | 31 |
| B46 | 9 |
| B47 | AG |
| B48 | 40 |
| B49 | 11 |
| B50 | 15 |

TABLE 9-continued

Vanilloid Receptor Affinity of Compounds of Formula (R)

| Compound according to Example | (f) Ki (human being) [nM] Cap |
|---|---|
| B51 | 15 |
| B52 | 9 |
| B53 | 33 |
| B54 | 8 |
| B55 | 27 |
| B56 | 56 |
| B57 | 58 |
| B58 | 16 |
| B59 | 16 |
| B60 | 25 |
| B61 | 8 |
| B62 | 36 |
| B63 | 30 |
| B64 | 45 |
| B65 | 36% @ 5 μM |
| B66 | 29 |
| B67 | AG |
| B68 | 4 |
| B69 | 30 |
| B70 | 14 |
| B71 | 41 |
| B72 | 13 |
| B73 | 3 |
| B74 | 37 |
| B75 | 19 |
| B76 | 12 |
| B77 | 44 |
| B78 | 21 |
| B79 | 2 |
| B80 | 2 |
| B81 | 33 |
| B82 | 0.8 |
| B83 | 3 |
| B84 | 53 |
| B85 | 16 |
| B86 | 93 |
| B87 | 15 |
| B88 | 29 |
| B89 | 24 |
| B90 | 12 |
| B91 | 57 |
| B92 | 67 |
| B93 | 4 |
| B94 | 0.9 |
| B95 | 22 |
| B96 | 0.9 |
| B97 | 1 |
| B98 | 3 |
| B99 | 43% @ 5 μM |
| B100 | 17% @ 5 μM |
| B101 | 43% @ 5 μM |
| B102 | 1 |
| B103 | 0.7 |

TABLE 10

Vanilloid Receptor Affinity of Compounds of Formula (S)

| Compound according to Example | (f) Ki (human being) [nM] Cap |
|---|---|
| C1 | 49 |
| C2 | 50 |
| C3 | 54% @ 5 μM |
| C4 | 13% @ 5 μM |
| C5 | 44 |
| C6 | 43 |
| C7 | 15 |

TABLE 10-continued

Vanilloid Receptor Affinity of Compounds of Formula (S)

| Compound according to Example | (f) Ki (human being) [nM] Cap |
|---|---|
| C8 | 53% @ 5 μM |
| C9 | 50% @ 5 μM |

TABLE 11

Vanilloid Receptor Affinity of Compounds of Formula (T)

| Compound according to Example | (f) Ki (human being) [nM] Cap |
|---|---|
| D1 | AG |
| D2 | 73 |
| D3 | 55% @ 5 μM |
| D4 | 41 |
| D5 | 7 |
| D6 | 38 |
| D7 | 27 |
| D8 | 48 |
| D9 | 30 |
| D10 | 75 |
| D26 | 42 |
| D27 | 40 |
| D28 | 32 |
| D29 | 13 |
| D31 | 15 |
| D33 | 4 |

TABLE 12

Vanilloid Receptor Affinity of Compounds of Formula (U)

| Compound according to Example | (f) Ki (human being) [nM] Cap |
|---|---|
| E1 | 24 |
| E2 | 35 |
| E3 | 62 |
| E4 | 8 |
| E5 | AG |
| E6 | 58 |
| E7 | 66 |
| E8 | AG |
| E9 | 29 |
| E10 | AG |
| E11 | 11 |
| E12 | 62 |
| E13 | 28% @ 5 μM |
| E14 | 38% @ 5 μM |
| E15 | NE |
| E16 | 32% @ 5 μM |
| E17 | 42% @ 5 μM |
| E18 | 37 |
| E19 | 41 |
| E20 | AG |
| E21 | AG |
| E22 | 49% @ 5 μM |
| E23 | 24.8% @ 5 μM |
| E24 | AG |
| E25 | AG |
| E26 | 25.00 |
| E27 | 2.00 |
| E28 | 37% @ 5 μM |
| E29 | 5 |
| E30 | 3 |
| E31 | AG |
| E32 | 48 |
| E33 | 6 |

TABLE 12-continued

Vanilloid Receptor Affinity of Compounds of Formula (U)

| Compound according to Example | (f) Ki (human being) [nM] Cap |
|---|---|
| E34 | 0.5 |
| E35 | 2 |
| E36 | 14.00 |
| E37 | 5 |
| E38 | 3 |
| E39 | 2 |
| E40 | 4.0 |
| E41 | 60% @ 5 μM |
| E42 | 1.00 |
| E43 | 0.8 |
| E44 | 1 |
| E45 | 0.3 |
| E46 | 2 |
| E47 | 3.00 |
| E48 | 27 |
| E49 | 3 |
| E50 | 12 |
| E51 | 49 |
| E52 | 59 |
| E53 | AG |
| E54 | 20% @ 5 μM |
| E55 | 28% @ 5 μM |
| E56 | 52% @ 5 μM |
| E57 | AG |
| E58 | AG |
| E59 | 63 |
| E60 | 19 |
| E61 | 23 |
| E62 | NE |

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

The invention claimed is:

1. A compound corresponding to formula (Q)

(Q)

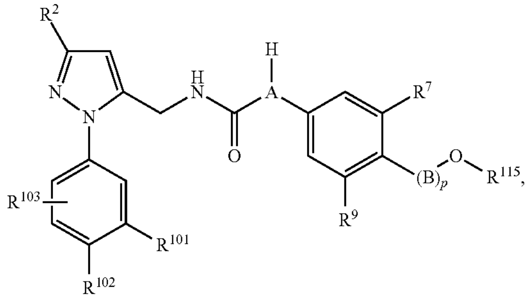

wherein $R^{101}$, $R^{102}$ and $R^{103}$ are each independently selected from the group consisting of H, F, Cl, Br, $CFH_2$, $CF_2H$, $CF_3$, CN, $CH_2$—OH, $CH_2CH_2$—OH, $CH_2$—$OCH_3$, $CH_2CH_2$—$OCH_3$, $OCFH_2$, $OCF_2H$, $OCF_3$, OH, $NH_2$, a $C_{1-4}$ alkyl, an O—$C_{1-4}$ alkyl, a NH—$C_{1-4}$ alkyl, and a $N(C_{1-4}\ alkyl)_2$, wherein the $C_{1-4}$ alkyl is in each case unsubstituted;

$R^2$ represents $CF_3$, an unsubstituted $C_{1-4}$ alkyl or an unsubstituted $C_{3-6}$ cycloalkyl;

$R^7$ and $R^9$ are each independently selected from the group consisting of H, F, Cl, Br, $CFH_2$, $CF_2H$, $CF_3$, CN, OH, $OCF_3$, a $C_{1-4}$ alkyl, and an O—$C_{1-4}$ alkyl, wherein the $C_{1-4}$ alkyl is in each case unsubstituted;

A denotes N, CH or $C(CH_3)$;

p denotes 0 or 1;

$R^{115}$ represents H or a $C_{1-6}$alkyl, which is unsubstituted or mono-, di- or trisubstituted with 1, 2 or 3 substituents independently selected from the group consisting of OH and $OCH_3$;

B denotes $C(R^{116a})(R^{116b})$, wherein $R^{116a}$ is selected from the group consisting of H, $CH_3$, $CH_2OH$ and OH, and $R^{116b}$ is selected from the group consisting of H, $CH_3$ and $CH_2OH$, with the proviso that $R^{116a}$ is not OH, when $R^{115}$ represents H; or $R^{116a}$ and $R^{116b}$ together with the carbon atom connecting them form an unsubstituted $C_{3-6}$ cycloalkyl or an unsubstituted 3 to 6 membered heterocyclyl, wherein at least one ring member of the heterocyclyl is selected from the group consisting of O, S, N, NH and N($C_{1-4}$ alkyl); or B denotes $C(R^{116c})(R^{116d})$—$C(R^{117a})(R^{117b})$, wherein $R_{116c}$ is selected from the group consisting of H, $CH_3$, $CH_2OH$ and OH, and $R^{116d}$ is selected from the group consisting of H, $CH_3$ and $CH_2OH$; or $R^{116c}$ and $R^{116d}$ together with the carbon atom connecting them form an unsubstituted $C_{3-6}$ cycloalkyl or an unsubstituted 3 to 6 membered heterocyclyl, wherein at least one ring member of the heterocyclyl is selected from the group consisting of O, S, N, NH and N($C_{1-4}$ alkyl);

$R^{117a}$ is selected from the group consisting of H, $CH_3$, $CH_2OH$ and OH, and $R^{117b}$ is selected from the group consisting of H, $CH_3$ and $CH_2OH$, with the proviso that $R^{117a}$ is not OH, when $R^{115}$ represents H; or $R^{117a}$ and $R^{117b}$ together with the carbon atom connecting them form an unsubstituted $C_{3-6}$ cycloalkyl or an unsubstituted 3 to 6 membered heterocyclyl, wherein at least one ring member of the heterocyclyl is selected from the group consisting of O, S, N, NH and N($C_{1-4}$ alkyl);

in the form of a free compound or a physiologically acceptable salt thereof, and if appropriate, in the form of an individual stereoisomer or a mixture of stereoisomers.

2. A compound according to claim 1, wherein $R^2$ represents $CF_3$, tert.-butyl or cyclopropyl;

$R^{101}$, $R^{102}$ and $R^{103}$ are each independently selected from the group consisting of H, F, Cl, Br, $CFH_2$, $CF_2H$, $CF_3$, CN, $CH_2$—OH, $CH_2$—$OCH_3$, $OCF_3$, OH, $CH_3$, $CH_2CH_3$, $CH(CH_3)_2$, O—$CH_3$, O—$CH_2CH_3$, $NH_2$, $NH(CH_3)$, and $N(CH_3)_2$;

$R^7$ and $R^9$ are each independently selected from the group consisting of H, F, Cl, Br, $CF_3$, CN, OH, $OCF_3$, $CH_3$, $CH_2CH_3$, $CH(CH_3)_2$, O—$CH_3$, and O—$CH_2CH_3$; and A denotes N or $C(CH_3)$.

3. A compound according to claim 1, wherein at least one of $R^{101}$, $R^{102}$ and $R^{103}$ is not H, and at least one of $R^7$ and $R^9$ is not H.

4. A compound according to claim 1, wherein the partial structure (QS1)

(QS1)

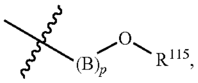

represents (a) partial structure (PQ1)

(PQ1)

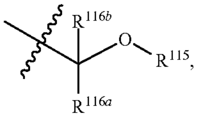

wherein $R^{115}$ represents H, $CH_2OH$, $CH_2CH_2OH$, $CH(OH)CH_2OH$, or $CH(OCH_3)CH_2OH$;

$R^{116a}$ is selected from the group consisting of H, $CH_3$, and OH, and $R^{116b}$ is selected from the group consisting of H, and $CH_3$, with the proviso that $R^{116a}$ is not OH, when $R^{115}$ represents H; or $R^{116a}$ and $R^{116b}$ together with the carbon atom connecting them form an unsubstituted moiety selected from the group consisting of cyclopropyl, cyclobutyl, oxiranyl and oxetanyl; or (b) partial structure (PQ2)

(PQ2)

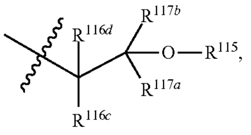

wherein $R^{115}$ represents H, $CH_3$, $CH_2OH$, $CH_2OCH_3$, $CH_2CH_3$, $CH(OH)CH_3$, $CH_2CH_2OH$, $CH(OH)CH_2OH$, $CH(OCH_3)CH_2OH$, $CH(OH)CH_2OCH_3$, or $CH_2CH_2OCH_3$;

$R^{116c}$ is selected from the group consisting of H, $CH_3$, and $CH_2OH$, and $R^{116d}$ is selected from the group consisting of H, $CH_3$ and $CH_2OH$;

$R^{117a}$ is selected from the group consisting of H, $CH_3$, $CH_2OH$ and OH, and $R^{117b}$ is selected from the group consisting of H, $CH_3$ and $CH_2OH$, with the proviso that $R^{117a}$ is not OH, when $R^{115}$ represents H;

or, if p is 0, (c) partial structure (PQ3)

(PQ3)

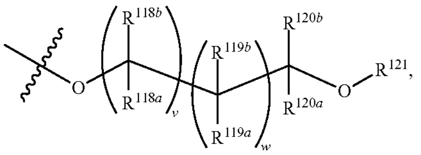

wherein v denotes 0 or 1;

w denotes 0 or 1;

$R^{118a}$ is selected from the group consisting of H and OH, and $R^{118b}$ is selected from the group consisting of H and $CH_3$;

$R^{119a}$ is selected from the group consisting of H and OH, and $R^{119b}$ is selected from the group consisting of H and $CH_3$;

$R^{120a}$ is selected from the group consisting of H and OH, and $R^{120b}$ is selected from the group consisting of H and $CH_3$;

$R^{121}$ represents H or $CH_3$;

with the proviso that $R^{120a}$ is not OH, when $R^{121}$ represents H.

5. A compound according to claim 1, wherein partial structure (QS1)

(QS1)

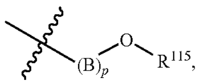

represents (a) partial structure (PQ1)

(PQ1)

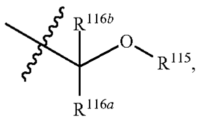

wherein $R^{115}$ represents H, $CH_2OH$, or $CH_2CH_2OH$;

$R^{116a}$ is selected from the group consisting of H, $CH_3$, and OH, and $R^{116b}$ is selected from the group consisting of H, and $CH_3$, with the proviso that $R^{116a}$ is not OH, when $R^{115}$ represents H; or $R^{116a}$ and $R^{116b}$ together with the carbon atom connecting them form an unsubstituted $C_{3-6}$ cycloalkyl selected from the group consisting of cyclopropyl and cyclobutyl or an unsubstituted 3 to 6 membered heterocyclyl selected from the group consisting of oxiranyl and oxetanyl; or (b) partial structure (PQ2)

(PQ2)

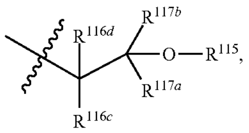

wherein $R^{115}$ represents H, $CH_2OH$, $CH_2CH_2OH$, or CH(OH)$CH_2OH$;

$R^{116c}$ is selected from the group consisting of H, $CH_3$, and $CH_2OH$, and $R^{116d}$ is selected from the group consisting of H, $CH_3$ and $CH_2OH$;

$R^{117a}$ is selected from the group consisting of H, $CH_3$, $CH_2OH$ and OH, and $R^{117b}$ is selected from the group consisting of H, $CH_3$ and $CH_2OH$;

with the proviso that $R^{117a}$ is not OH, when $R^{115}$ represents H;

or, if p is 0, (c) partial structure (PQ3)

(PQ3)

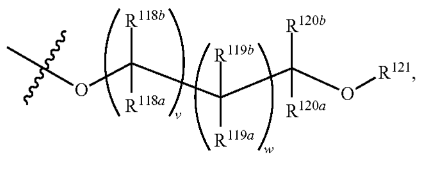

wherein v denotes 0 or 1;

w denotes 0 or 1;

$R^{118a}$ is selected from the group consisting of H and OH, and $R^{118b}$ is selected from the group consisting of H and $CH_3$;

$R^{119a}$ is selected from the group consisting of H and OH, and $R^{119b}$ is selected from the group consisting of H and $CH_3$;

$R^{120a}$ is selected from the group consisting of H and OH, and $R^{120b}$ is selected from the group consisting of H and $CH_3$;

$R^{121}$ represents H or $CH_3$, with the proviso that $R^{120a}$ is not OH, when $R^{121}$ represents H.

6. A compound according to claim 1, wherein partial structure (QS1)

(QS1)

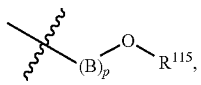

represents (a) partial structure (PQ1-1)

(PQ1-1)

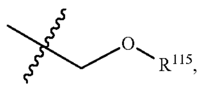

wherein $R^{115}$ represents H, $CH_2OH$, or $CH_2CH_2OH$; or (b) partial structure (PQ2-1)

(PQ2-1)

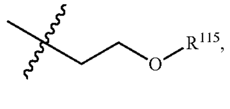

wherein $R^{115}$ represents H, $CH_2OH$, or $CH_2CH_2OH$; or, if p is 0,
(c) partial structure (PQ3-1)

(PQ3-1)

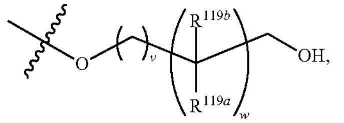

wherein
v denotes 0 or 1;
w denotes 0 or 1;
$R^{119a}$ is selected from the group consisting of H and OH, and
$R^{119b}$ is selected from the group consisting of H and $CH_3$.

7. A compound according to claim 1, wherein partial structure (QS1)

(QS1)

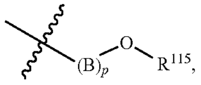

represents
(a) partial structure (PQ1-2) or partial structure (PQ1-3)

(PQ1-2)

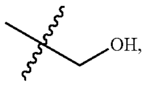

(PQ1-3)

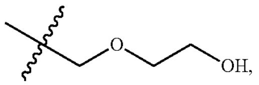

(b) partial structure (PQ2-1)

(PQ2-1)

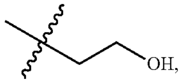

or, if p is 0,
(c) partial structure (PQ3-2)

(PQ3-2)

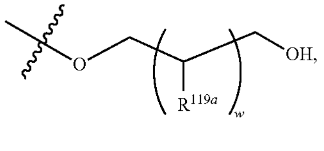

wherein
w denotes 1, and $R^{119a}$ represents OH; or
w denotes 0.

8. A compound according to claim 1, wherein
$R^{101}$, $R^{102}$ and $R^{103}$ are each independently selected from the group consisting of H, F, Cl, Br, $CFH_2$, $CF_2H$, $CF_3$, CN, $CH_2$—OH, $CH_2$—$OCH_3$, $OCF_3$, OH, $CH_3$, $CH_2CH_3$, $CH(CH_3)_2$, O—$CH_3$, O—$CH_2CH_3$, $NH_2$, $NH(CH_3)$, and $N(CH_3)_2$;
$R^2$ represents $CF_3$, tert.-butyl or cyclopropyl;
$R^7$ and $R^9$ are each independently selected from the group consisting of H, F, Cl, Br, $CF_3$, CN, OH, $OCF_3$, $CH_3$, $CH_2CH_3$, $CH(CH_3)_2$, O—$CH_3$, and O—$CH_2CH_3$;
A denotes N, CH or $C(CH_3)$, and
partial structure (QS1)

(QS1)

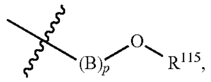

represents
(a) $CH_2OH$ or $CH_2O$—$CH_2CH_2OH$,
(b) $CH_2CH_2OH$, or
(c) O—$CH_2CH_2OH$ or O—CH—CH(OH)—$CH_2OH$.

9. A compound according to claim 1, selected from the group consisting of:
A1 N-[[5-tert-Butyl-2-(3-chlorophenyl)-2H-pyrazol-3-yl]-methyl]-2-(3,5-difluoro-4-methoxy-phenyl)-acetamide;
A2 N-[[2-(3-Chlorophenyl)-5-(trifluoromethyl)-2H-pyrazol-3-yl]-methyl]-2-(3,5-difluoro-4-methoxy-phenyl)-acetamide;
A3 N-[[2-(3-Chlorophenyl)-5-cyclopropyl-2H-pyrazol-3-yl]-methyl]-2-(3,5-difluoro-4-methoxy-phenyl)-propionamide;
A4 N-[[5-tert-Butyl-2-(3-chlorophenyl)-2H-pyrazol-3-yl]-methyl]-2-(3,5-difluoro-4-methoxy-phenyl)-propionamide;
A5 N-[[5-tert-Butyl-2-(3-chloro-4-fluoro-phenyl)-2H-pyrazol-3-yl]-methyl]-2-(3,5-difluoro-4-methoxy-phenyl)-propionamide;
A6 N-[[5-tert-Butyl-2-(3-chloro-4-fluoro-phenyl)-2H-pyrazol-3-yl]-methyl]-2-(3,5-difluoro-4-methoxy-phenyl)-acetamide;
A7 N-[[2-(3-Chloro-4-fluoro-phenyl)-5-(trifluoromethyl)-2H-pyrazol-3-yl]-methyl]-2-(3,5-difluoro-4-methoxy-phenyl)-acetamide;
A8 1-[[2-(3-Chlorophenyl)-5-(trifluoromethyl)-2H-pyrazol-3-yl]-methyl]-3-(3,5-difluoro-4-methoxy-phenyl)-urea;
A9 N-[[2-(3-Chloro-4-fluoro-phenyl)-5-(trifluoromethyl)-2H-pyrazol-3-yl]-methyl]-2-(3,5-difluoro-4-methoxy-phenyl)-propionamide;
A10 N-[[2-(3-Chlorophenyl)-5-(trifluoromethyl)-2H-pyrazol-3-yl]-methyl]-2-(3,5-difluoro-4-hydroxy-phenyl)-propionamide;
A11 1-[[5-tert-Butyl-2-(3-chlorophenyl)-2H-pyrazol-3-yl]-methyl]-3-(3,5-difluoro-4-hydroxy-phenyl)-urea;
A12 1-[[2-(3-Chlorophenyl)-5-(trifluoromethyl)-2H-pyrazol-3-yl]-methyl]-3-(3,5-difluoro-4-hydroxy-phenyl)-urea;
A13 1-[[5-tert-Butyl-2-(3-chlorophenyl)-2H-pyrazol-3-yl]-methyl]-3-(3,4-dimethoxyphenyl)-urea;
A14 1-[[2-(3-Chlorophenyl)-5-(trifluoromethyl)-2H-pyrazol-3-yl]-methyl]-3-(3,4-dimethoxyphenyl)-urea;
A15 1-[[2-(3-Chlorophenyl)-5-(trifluoromethyl)-2H-pyrazol-3-yl]-methyl]-3-(4-hydroxy-3-methoxy-phenyl)-urea;

A16 1-[[2-(3-Chlorophenyl)-5-(trifluoromethyl)-2H-pyrazol-3-yl]-methyl]-3-(3-hydroxy-4-methoxy-phenyl)-urea;

A17 1-[[5-tert-Butyl-2-(3-chlorophenyl)-2H-pyrazol-3-yl]-methyl]-3-[3-fluoro-4-(2-methoxy-ethoxy)-phenyl]-urea;

A18 1-[[2-(3-Chlorophenyl)-5-(trifluoromethyl)-2H-pyrazol-3-yl]-methyl]-3-[3-fluoro-4-(2-methoxy-ethoxy)-phenyl]-urea;

A19 1-[[5-tert-Butyl-2-(3-chlorophenyl)-2H-pyrazol-3-yl]-methyl]-3-[3-fluoro-4-(2-hydroxy-ethoxy)-phenyl]-urea;

A20 1-[[2-(3-Chlorophenyl)-5-(trifluoromethyl)-2H-pyrazol-3-yl]-methyl]-3-[3-fluoro-4-(2-hydroxy-ethoxy)-phenyl]-urea;

A21 1-[3-Fluoro-4-(2-hydroxy-ethoxy)-phenyl]-3-[[2-(3-fluorophenyl)-5-(trifluoromethyl)-2H-pyrazol-3-yl]-methyl]-urea;

A22 1-[[2-(3-Chloro-4-fluoro-phenyl)-5-(trifluoromethyl)-2H-pyrazol-3-yl]-methyl]-3-[3-fluoro-4-(2-hydroxy-ethoxy)-phenyl]-urea;

A23 1-[[2-(3-Chlorophenyl)-5-(trifluoromethyl)-2H-pyrazol-3-yl]-methyl]-3-[4-(2,3-dihydroxy-propoxy)-phenyl]-urea;

A24 1-[[5-tert-Butyl-2-(3-chlorophenyl)-2H-pyrazol-3-yl]-methyl]-3-[4-(2,3-dihydroxy-propoxy)-3-fluoro-phenyl]-urea;

A25 1-[[2-(3-Chlorophenyl)-5-(trifluoromethyl)-2H-pyrazol-3-yl]-methyl]-3-[4-(2,3-dihydroxy-propoxy)-3-fluoro-phenyl]-urea;

A26 1-[4-(2,3-Dihydroxy-propoxy)-phenyl]-3-[[2-(3-fluorophenyl)-5-(trifluoromethyl)-2H-pyrazol-3-yl]-methyl]-urea;

A27 1-[[5-tert-Butyl-2-(3-chlorophenyl)-2H-pyrazol-3-yl]-methyl]-3-[4-(hydroxymethyl)-phenyl]-urea;

A28 1-[[2-(3-Chlorophenyl)-5-(trifluoromethyl)-2H-pyrazol-3-yl]-methyl]-3-[4-(hydroxymethyl)-phenyl]-urea;

A29 N-[[5-tert-Butyl-2-(3-chlorophenyl)-2H-pyrazol-3-yl]-methyl]-2-[3-fluoro-4-(hydroxymethyl)-phenyl]-acetamide;

A30 N-[[2-(3-Chlorophenyl)-5-(trifluoromethyl)-2H-pyrazol-3-yl]-methyl]-2-[3-fluoro-4-(hydroxymethyl)-phenyl]-acetamide A31 N-[[2-(3-Chlorophenyl)-5-cyclopropyl-2H-pyrazol-3-yl]-methyl]-2-[3-fluoro-4-(hydroxymethyl)-phenyl]-propionamide;

A32 N-[[5-tert-Butyl-2-(3-chlorophenyl)-2H-pyrazol-3-yl]-methyl]-2-[3-fluoro-4-(hydroxymethyl)-phenyl]-propionamide;

A33 N-[[2-(3-Chlorophenyl)-5-(trifluoromethyl)-2H-pyrazol-3-yl]-methyl]-2-[3-fluoro-4-(hydroxymethyl)-phenyl]-propionamide;

A34 (2S)—N-[[2-(3-Chlorophenyl)-5-(trifluoromethyl)-2H-pyrazol-3-yl]-methyl]-2-[3-fluoro-4-(hydroxymethyl)-phenyl]-propionamide;

A35 (2R)—N-[[2-(3-Chlorophenyl)-5-(trifluoromethyl)-2H-pyrazol-3-yl]-methyl]-2-[3-fluoro-4-(hydroxymethyl)-phenyl]-propionamide;

A36 2-[3-Chloro-4-(hydroxymethyl)-phenyl]-N-[[2-(3-chlorophenyl)-5-(trifluoromethyl)-2H-pyrazol-3-yl]-methyl]-propionamide;

A37 N-[[5-tert-Butyl-2-(3-fluorophenyl)-2H-pyrazol-3-yl]-methyl]-2-[3-fluoro-4-(hydroxymethyl)-phenyl]-propionamide;

A38 2-[3-Fluoro-4-(hydroxymethyl)-phenyl]-N-[[2-(3-fluorophenyl)-5-(trifluoromethyl)-2H-pyrazol-3-yl]-methyl]-propionamide;

A39 N-[[5-tert-Butyl-2-(3,4-difluoro-phenyl)-2H-pyrazol-3-yl]-methyl]-2-[3-fluoro-4-(hydroxymethyl)-phenyl]-propionamide;

A40 N-[[2-(3,4-Difluoro-phenyl)-5-(trifluoromethyl)-2H-pyrazol-3-yl]-methyl]-2-[3-fluoro-4-(hydroxymethyl)-phenyl]-propionamide;

A41 N-[[5-tert-Butyl-2-(3-chloro-4-fluoro-phenyl)-2H-pyrazol-3-yl]-methyl]-2-[3-fluoro-4-(hydroxymethyl)-phenyl]-propionamide;

A42 N-[[2-(3-Chloro-4-fluoro-phenyl)-5-(trifluoromethyl)-2H-pyrazol-3-yl]-methyl]-2-[3-fluoro-4-(hydroxymethyl)-phenyl]-propionamide;

A43 2-[3-Fluoro-4-(hydroxymethyl)-phenyl]-N-[[2-(3-methoxyphenyl)-5-(trifluoromethyl)-2H-pyrazol-3-yl]-methyl]-propionamide;

A44 2-[3-Fluoro-4-(hydroxymethyl)-phenyl]-N-[[2-(3-isopropyl-phenyl)-5-(trifluoromethyl)-2H-pyrazol-3-yl]-methyl]-propionamide;

A45 N-[[5-tert-Butyl-2-(4-fluorophenyl)-2H-pyrazol-3-yl]-methyl]-2-[3-fluoro-4-(hydroxymethyl)-phenyl]-propionamide;

A46 2-[3-Fluoro-4-(hydroxymethyl)-phenyl]-N-[[2-(4-fluorophenyl)-5-(trifluoromethyl)-2H-pyrazol-3-yl]-methyl]-propionamide;

A47 N-[[5-tert-Butyl-2-[3-(trifluoromethyl)phenyl]-2H-pyrazol-3-yl]-methyl]-2-[3-fluoro-4-(hydroxymethyl)-phenyl]-propionamide;

A48 2-[3-Fluoro-4-(hydroxymethyl)-phenyl]-N-[[5-(trifluoromethyl)-2-[3-(trifluoromethyl)phenyl]-2H-pyrazol-3-yl]-methyl]-propionamide;

A49 N-[[5-tert-Butyl-2-(3-chlorophenyl)-2H-pyrazol-3-yl]-methyl]-2-[4-(hydroxymethyl)-3-methoxy-phenyl]-propionamide;

A50 N-[[2-(3-Chlorophenyl)-5-(trifluoromethyl)-2H-pyrazol-3-yl]-methyl]-2-[4-(hydroxymethyl)-3-methoxy-phenyl]-propionamide;

A51 N-[[5-tert-Butyl-2-(3-chlorophenyl)-2H-pyrazol-3-yl]-methyl]-2-[3-chloro-4-(hydroxymethyl)-phenyl]-propionamide;

A52 N-[[2-(3-Chlorophenyl)-5-(trifluoromethyl)-2H-pyrazol-3-yl]-methyl]-2-[3,5-difluoro-4-(hydroxymethyl)-phenyl]-propionamide;

A53 1-[[2-(3-Chlorophenyl)-5-cyclopropyl-2H-pyrazol-3-yl]-methyl]-3-[3-fluoro-4-(hydroxymethyl)-phenyl]-urea;

A54 1-[[5-tert-Butyl-2-(3-fluorophenyl)-2H-pyrazol-3-yl]-methyl]-3-[3-fluoro-4-(hydroxymethyl)-phenyl]-urea;

A55 1-[[5-tert-Butyl-2-(3-chlorophenyl)-2H-pyrazol-3-yl]-methyl]-3-[3-fluoro-4-(hydroxymethyl)-phenyl]-urea;

A56 1-[[5-tert-Butyl-2-(m-tolyl)-2H-pyrazol-3-yl]-methyl]-3-[3-fluoro-4-(hydroxymethyl)-phenyl]-urea;

A57 1-[[5-tert-Butyl-2-(3,4-difluoro-phenyl)-2H-pyrazol-3-yl]-methyl]-3-[3-fluoro-4-(hydroxymethyl)-phenyl]-urea;

A58 1-[3-Fluoro-4-(hydroxymethyl)-phenyl]-3-[[2-phenyl-5-(trifluoromethyl)-2H-pyrazol-3-yl]-methyl]-urea;

A59 1-[[2-(3-Chlorophenyl)-5-(trifluoromethyl)-2H-pyrazol-3-yl]-methyl]-3-[3-fluoro-4-(hydroxymethyl)-phenyl]-urea;

A60 1-[[2-(4-Chlorophenyl)-5-(trifluoromethyl)-2H-pyrazol-3-yl]-methyl]-3-[3-fluoro-4-(hydroxymethyl)-phenyl]-urea;

A61 1-[3-Fluoro-4-(hydroxymethyl)-phenyl]-3-[[2-(2-fluorophenyl)-5-(trifluoromethyl)-2H-pyrazol-3-yl]-methyl]-urea;

A62 1-[3-Fluoro-4-(hydroxymethyl)-phenyl]-3-[[2-(3-fluorophenyl)-5-(trifluoromethyl)-2H-pyrazol-3-yl]-methyl]-urea;

A63 1-[3-Fluoro-4-(hydroxymethyl)-phenyl]-3-[[2-(4-fluorophenyl)-5-(trifluoromethyl)-2H-pyrazol-3-yl]-methyl]-urea;

A64 1-[[2-(3,4-Difluoro-phenyl)-5-(trifluoromethyl)-2H-pyrazol-3-yl]-methyl]-3-[3-fluoro-4-(hydroxymethyl)-phenyl]-urea;

A65 1-[[2-(3-Chloro-4-fluoro-phenyl)-5-(trifluoromethyl)-2H-pyrazol-3-yl]-methyl]-3-[3-fluoro-4-(hydroxymethyl)-phenyl]-urea;

A66 1-[[2-(3,5-Difluoro-phenyl)-5-(trifluoromethyl)-2H-pyrazol-3-yl]-methyl]-3-[3-fluoro-4-(hydroxymethyl)-phenyl]-urea;

A67 1-[3-Fluoro-4-(hydroxymethyl)-phenyl]-3-[[2-(3-methoxyphenyl)-5-(trifluoromethyl)-2H-pyrazol-3-yl]-methyl]-urea;

A68 1-[3-Fluoro-4-(hydroxymethyl)-phenyl]-3-[[2-(4-methoxyphenyl)-5-(trifluoromethyl)-2H-pyrazol-3-yl]-methyl]-urea;

A69 1-[3-Fluoro-4-(hydroxymethyl)-phenyl]-3-[[2-(o-tolyl)-5-(trifluoromethyl)-2H-pyrazol-3-yl]-methyl]-urea;

A70 1-[3-Fluoro-4-(hydroxymethyl)-phenyl]-3-[[2-(m-tolyl)-5-(trifluoromethyl)-2H-pyrazol-3-yl]-methyl]-urea;

A71 1-[3-Fluoro-4-(hydroxymethyl)-phenyl]-3-[[2-(p-tolyl)-5-(trifluoromethyl)-2H-pyrazol-3-yl]-methyl]-urea;

A72 1-[[2-(2,3-Dimethyl-phenyl)-5-(trifluoromethyl)-2H-pyrazol-3-yl]-methyl]-3-[3-fluoro-4-(hydroxymethyl)-phenyl]-urea;

A73 1-[[2-(3,5-Dimethyl-phenyl)-5-(trifluoromethyl)-2H-pyrazol-3-yl]-methyl]-3-[3-fluoro-4-(hydroxymethyl)-phenyl]-urea;

A74 1-[[2-(2,5-Dimethyl-phenyl)-5-(trifluoromethyl)-2H-pyrazol-3-yl]-methyl]-3-[3-fluoro-4-(hydroxymethyl)-phenyl]-urea;

A75 1-[[2-(3,4-Dimethyl-phenyl)-5-(trifluoromethyl)-2H-pyrazol-3-yl]-methyl]-3-[3-fluoro-4-(hydroxymethyl)-phenyl]-urea;

A76 1-[3-Fluoro-4-(hydroxymethyl)-phenyl]-3-[[2-(2-fluoro-3-methyl-phenyl)-5-(trifluoromethyl)-2H-pyrazol-3-yl]-methyl]-urea;

A77 1-[3-Fluoro-4-(hydroxymethyl)-phenyl]-3-[[2-(3-fluoro-5-methyl-phenyl)-5-(trifluoromethyl)-2H-pyrazol-3-yl]-methyl]-urea;

A78 1-[[2-(4-Chloro-3-methyl-phenyl)-5-(trifluoromethyl)-2H-pyrazol-3-yl]-methyl]-3-[3-fluoro-4-(hydroxymethyl)-phenyl]-urea;

A79 1-[[2-(4-Ethoxy-3-methyl-phenyl)-5-(trifluoromethyl)-2H-pyrazol-3-yl]-methyl]-3-[3-fluoro-4-(hydroxymethyl)-phenyl]-urea;

A80 1-[3-Fluoro-4-(hydroxymethyl)-phenyl]-3-[[2-(4-fluoro-3-methyl-phenyl)-5-(trifluoromethyl)-2H-pyrazol-3-yl]-methyl]-urea;

A81 1-[[2-(4-Cyano-3-methyl-phenyl)-5-(trifluoromethyl)-2H-pyrazol-3-yl]-methyl]-3-[3-fluoro-4-(hydroxymethyl)-phenyl]-urea;

A82 1-[3-Fluoro-4-(hydroxymethyl)-phenyl]-3-[[2-(3-isopropyl-phenyl)-5-(trifluoromethyl)-2H-pyrazol-3-yl]-methyl]-urea;

A83 1-[[2-[3-(Difluoro-methyl)-phenyl]-5-(trifluoromethyl)-2H-pyrazol-3-yl]-methyl]-3-[3-fluoro-4-(hydroxymethyl)-phenyl]-urea;

A84 1-[3-Fluoro-4-(hydroxymethyl)-phenyl]-3-[[2-[3-(methoxymethyl)-phenyl]-5-(trifluoromethyl)-2H-pyrazol-3-yl]-methyl]-urea;

A85 1-[[2-(3-Cyano-phenyl)-5-(trifluoromethyl)-2H-pyrazol-3-yl]-methyl]-3-[3-fluoro-4-(hydroxymethyl)-phenyl]-urea;

A86 1-[[2-(3-Dimethylamino-phenyl)-5-(trifluoromethyl)-2H-pyrazol-3-yl]-methyl]-3-[3-fluoro-4-(hydroxymethyl)-phenyl]-urea;

A87 1-[3-Fluoro-4-(hydroxymethyl)-phenyl]-3-[[2-(4-methoxy-3-methyl-phenyl)-5-(trifluoromethyl)-2H-pyrazol-3-yl]-methyl]-urea;

A88 1-[[2-(2-Ethoxy-5-methyl-phenyl)-5-(trifluoromethyl)-2H-pyrazol-3-yl]-methyl]-3-[3-fluoro-4-(hydroxymethyl)-phenyl]-urea;

A89 1-[[2-(2,3-Dichloro-phenyl)-5-(trifluoromethyl)-2H-pyrazol-3-yl]-methyl]-3-[3-fluoro-4-(hydroxymethyl)-phenyl]-urea;

A90 1-[[2-(3-Chloro-2-methoxy-phenyl)-5-(trifluoromethyl)-2H-pyrazol-3-yl]-methyl]-3-[3-fluoro-4-(hydroxymethyl)-phenyl]-urea;

A91 1-[[2-(5-Chloro-2-methoxy-phenyl)-5-(trifluoromethyl)-2H-pyrazol-3-yl]-methyl]-3-[3-fluoro-4-(hydroxymethyl)-phenyl]-urea;

A92 1-[3-Fluoro-4-(hydroxymethyl)-phenyl]-3-[[2-(3-methoxy-5-methyl-phenyl)-5-(trifluoromethyl)-2H-pyrazol-3-yl]-methyl]-urea;

A93 1-[[2-(3-Ethoxy-5-methyl-phenyl)-5-(trifluoromethyl)-2H-pyrazol-3-yl]-methyl]-3-[3-fluoro-4-(hydroxymethyl)-phenyl]-urea;

A94 1-[3-Fluoro-4-(hydroxymethyl)-phenyl]-3-[[2-(2-methoxy-3-methyl-phenyl)-5-(trifluoromethyl)-2H-pyrazol-3-yl]-methyl]-urea;

A95 1-[3-Fluoro-4-(hydroxymethyl)-phenyl]-3-[[2-(3-fluoro-4-methoxy-phenyl)-5-(trifluoromethyl)-2H-pyrazol-3-yl]-methyl]-urea;

A96 1-[[5-tert-Butyl-2-(3-chlorophenyl)-2H-pyrazol-3-yl]-methyl]-3-[3-chloro-4-(hydroxymethyl)-phenyl]-urea;

A97 1-[3-Chloro-4-(hydroxymethyl)-phenyl]-3-[[2-(3-chlorophenyl)-5-(trifluoromethyl)-2H-pyrazol-3-yl]-methyl]-urea;

A98 N-[[5-tert-Butyl-2-(3-chlorophenyl)-2H-pyrazol-3-yl]-methyl]-2-[3-fluoro-4-(1-hydroxy-ethyl)-phenyl]-propionamide;

A99 N-[[2-(3-Chlorophenyl)-5-(trifluoromethyl)-2H-pyrazol-3-yl]-methyl]-2-[3-fluoro-4-(1-hydroxy-ethyl)-phenyl]-propionamide;

A100 N-[[5-tert-Butyl-2-(3-chlorophenyl)-2H-pyrazol-3-yl]-methyl]-2-[3-fluoro-4-(1-hydroxy-cyclopropyl)-phenyl]-propionamide;

A101 N-[[2-(3-Chlorophenyl)-5-(trifluoromethyl)-2H-pyrazol-3-yl]-methyl]-2-[3-fluoro-4-(1-hydroxy-cyclopropyl)-phenyl]-propionamide;

A102 2-[3-Fluoro-4-(1-hydroxy-cyclopropyl)-phenyl]-N-[[2-(3-fluorophenyl)-5-(trifluoromethyl)-2H-pyrazol-3-yl]-methyl]-propionamide;

A103 2-[3-Fluoro-4-(1-hydroxy-cyclopropyl)-phenyl]-N-[[2-(3-methoxyphenyl)-5-(trifluoromethyl)-2H-pyrazol-3-yl]-methyl]-propionamide;

A104 N-[[2-(3,4-Difluoro-phenyl)-5-(trifluoromethyl)-2H-pyrazol-3-yl]-methyl]-2-[3-fluoro-4-(1-hydroxy-cyclopropyl)-phenyl]-propionamide;

A105 1-[[5-tert-Butyl-2-(3-chlorophenyl)-2H-pyrazol-3-yl]-methyl]-3-[3-fluoro-4-(1-hydroxy-cyclopropyl)-phenyl]-urea;

A106 1-[[2-(3-Chlorophenyl)-5-(trifluoromethyl)-2H-pyrazol-3-yl]-methyl]-3-[3-fluoro-4-(1-hydroxy-cyclopropyl)-phenyl]-urea;

A107 1-[[5-tert-Butyl-2-(3-chlorophenyl)-2H-pyrazol-3-yl]-methyl]-3-[4-(3-hydroxy-oxetan-3-yl)-phenyl]-urea;

A108 1-[[2-(3-Chlorophenyl)-5-(trifluoromethyl)-2H-pyrazol-3-yl]-methyl]-3-[4-(3-hydroxy-oxetan-3-yl)-phenyl]-urea;

A109 1-[[5-tert-Butyl-2-(3-chlorophenyl)-2H-pyrazol-3-yl]-methyl]-3-[3-fluoro-4-(3-hydroxy-oxetan-3-yl)-phenyl]-urea;

A110 1-[[2-(3-Chlorophenyl)-5-(trifluoromethyl)-2H-pyrazol-3-yl]-methyl]-3-[3-fluoro-4-(3-hydroxy-oxetan-3-yl)-phenyl]-urea;

A111 N-[[2-(3-Chlorophenyl)-5-(trifluoromethyl)-2H-pyrazol-3-yl]-methyl]-2-[3-fluoro-4-(2-methoxy-ethoxy-methyl)-phenyl]-propionamide;

A112 N-[[2-(3-Chloro-4-fluoro-phenyl)-5-(trifluoromethyl)-2H-pyrazol-3-yl]-methyl]-2-[3-fluoro-4-(2-methoxy-ethoxy-methyl)-phenyl]-propionamide;

A113 N-[[2-(3-Chlorophenyl)-5-(trifluoromethyl)-2H-pyrazol-3-yl]-methyl]-2-[3-fluoro-4-(2-hydroxy-ethoxy-methyl)-phenyl]-acetamide;

A114 2-[3-Fluoro-4-(2-hydroxy-ethoxy-methyl)-phenyl]-N-[[2-(3-methoxyphenyl)-5-(trifluoromethyl)-2H-pyrazol-3-yl]-methyl]-propionamide;

A115 2-[3-Fluoro-4-(2-hydroxy-ethoxy-methyl)-phenyl]-N-[[2-(3-isopropyl-phenyl)-5-(trifluoromethyl)-2H-pyrazol-3-yl]-methyl]-propionamide;

A116 N-[[5-tert-Butyl-2-(3-fluorophenyl)-2H-pyrazol-3-yl]-methyl]-2-[3-fluoro-4-(2-hydroxy-ethoxy-methyl)-phenyl]-propionamide;

A117 N-[[5-tert-Butyl-2-(3-chlorophenyl)-2H-pyrazol-3-yl]-methyl]-2-[3-fluoro-4-(2-hydroxy-ethoxy-methyl)-phenyl]-propionamide;

A118 N-[[2-(3-Chlorophenyl)-5-(trifluoromethyl)-2H-pyrazol-3-yl]-methyl]-2-[3-fluoro-4-(2-hydroxy-ethoxy-methyl)-phenyl]-propionamide;

A119 (2S)—N-[[2-(3-Chlorophenyl)-5-(trifluoromethyl)-2H-pyrazol-3-yl]-methyl]-2-[3-fluoro-4-(2-hydroxy-ethoxy-methyl)-phenyl]-propionamide;

A120 (2R)—N-[[2-(3-Chlorophenyl)-5-(trifluoromethyl)-2H-pyrazol-3-yl]-methyl]-2-[3-fluoro-4-(2-hydroxy-ethoxy-methyl)-phenyl]-propionamide;

A121 N-[[2-(3-Chloro-4-fluoro-phenyl)-5-(trifluoromethyl)-2H-pyrazol-3-yl]-methyl]-2-[3-fluoro-4-(2-hydroxy-ethoxy-methyl)-phenyl]-propionamide;

A122 2-[3-Fluoro-4-(2-hydroxy-ethoxy-methyl)-phenyl]-N-[[2-(3-fluorophenyl)-5-(trifluoromethyl)-2H-pyrazol-3-yl]-methyl]-propionamide;

A123 2-[3-Fluoro-4-(2-hydroxy-ethoxy-methyl)-phenyl]-N-[[2-(m-tolyl)-5-(trifluoromethyl)-2H-pyrazol-3-yl]-methyl]-propionamide;

A124 N-[[5-tert-Butyl-2-(4-fluorophenyl)-2H-pyrazol-3-yl]-methyl]-2-[3-fluoro-4-(2-hydroxy-ethoxy-methyl)-phenyl]-propionamide;

A125 N-[[5-tert-Butyl-2-[3-(trifluoromethyloxy)-phenyl]-2H-pyrazol-3-yl]-methyl]-2-[3-fluoro-4-(2-hydroxy-ethoxy-methyl)-phenyl]-propionamide;

A126 N-[[2-(3,5-Difluoro-phenyl)-5-(trifluoromethyl)-2H-pyrazol-3-yl]-methyl]-2-[3-fluoro-4-(2-hydroxy-ethoxy-methyl)-phenyl]-propionamide;

A127 1-[[2-(3-Chlorophenyl)-5-(trifluoromethyl)-2H-pyrazol-3-yl]-methyl]-3-[3-fluoro-4-(2-hydroxy-ethoxy-methyl)-phenyl]-urea;

A128 1-[[2-(3-Chlorophenyl)-5-(trifluoromethyl)-2H-pyrazol-3-yl]-methyl]-3-[3-fluoro-4-(2-methoxy-ethoxy-methyl)-phenyl]-urea;

A129 1-[[5-tert-Butyl-2-(3-chlorophenyl)-2H-pyrazol-3-yl]-methyl]-3-[3-fluoro-4-(2-hydroxy-ethoxy-methyl)-phenyl]-urea;

A130 1-[[2-(3-Chloro-4-fluoro-phenyl)-5-(trifluoromethyl)-2H-pyrazol-3-yl]-methyl]-3-[3-fluoro-4-(2-hydroxy-ethoxy-methyl)-phenyl]-urea;

A131 1-[3-Fluoro-4-(2-hydroxy-ethoxy-methyl)-phenyl]-3-[[2-(3-fluorophenyl)-5-(trifluoromethyl)-2H-pyrazol-3-yl]-methyl]-urea;

A132 1-[[2-(3,4-Difluoro-phenyl)-5-(trifluoromethyl)-2H-pyrazol-3-yl]-methyl]-3-[3-fluoro-4-(2-hydroxy-ethoxy-methyl)-phenyl]-urea;

A133 1-[[2-(2,3-Dichloro-phenyl)-5-(trifluoromethyl)-2H-pyrazol-3-yl]-methyl]-3-[3-fluoro-4-(2-hydroxy-ethoxy-methyl)-phenyl]-urea;

A134 1-[[5-tert-Butyl-2-(4-fluorophenyl)-2H-pyrazol-3-yl]-methyl]-3-[3-fluoro-4-(2-hydroxy-ethoxy-methyl)-phenyl]-urea;

A135 1-[[2-(3-Ethoxy-5-methyl-phenyl)-5-(trifluoromethyl)-2H-pyrazol-3-yl]-methyl]-3-[3-fluoro-4-(2-hydroxy-ethoxy-methyl)-phenyl]-urea;

A136 2-[3-Fluoro-4-(2-hydroxy-ethyl)-phenyl]-N-[[2-(3-fluorophenyl)-5-(trifluoromethyl)-2H-pyrazol-3-yl]-methyl]-propionamide;

A137 2-[3-Fluoro-4-(2-hydroxy-ethyl)-phenyl]-N-[[2-(3-isopropyl-phenyl)-5-(trifluoromethyl)-2H-pyrazol-3-yl]-methyl]-propionamide;

A138 N-[[2-(3-Chlorophenyl)-5-(trifluoromethyl)-2H-pyrazol-3-yl]-methyl]-2-[3-fluoro-4-(2-hydroxy-ethyl)-phenyl]-propionamide;

A139 N-[[5-tert-Butyl-2-(3-chlorophenyl)-2H-pyrazol-3-yl]-methyl]-2-[3-fluoro-4-(2-hydroxy-ethyl)-phenyl]-propionamide;

A140 1-[[5-tert-Butyl-2-(3-chlorophenyl)-2H-pyrazol-3-yl]-methyl]-3-[3-fluoro-4-(2-hydroxy-ethyl)-phenyl]-urea;

A141 1-[[2-(3-Chlorophenyl)-5-(trifluoromethyl)-2H-pyrazol-3-yl]-methyl]-3-[3-fluoro-4-(2-hydroxy-ethyl)-phenyl]-urea;

A142 1-[3-Fluoro-4-(2-hydroxy-ethyl)-phenyl]-3-[[2-(3-fluorophenyl)-5-(trifluoromethyl)-2H-pyrazol-3-yl]-methyl]-urea;

A143 1-[3-Fluoro-4-(2-hydroxy-ethyl)-phenyl]-3-[[2-(3-methoxyphenyl)-5-(trifluoromethyl)-2H-pyrazol-3-yl]-methyl]-urea;

A144 1-[3-Fluoro-4-(2-hydroxy-ethyl)-phenyl]-3-[[2-(m-tolyl)-5-(trifluoromethyl)-2H-pyrazol-3-yl]-methyl]-urea;

A145 N-[[5-tert-Butyl-2-(3-chlorophenyl)-2H-pyrazol-3-yl]-methyl]-2-[4-(1,2-dihydroxy-ethyl)-3-fluoro-phenyl]-propionamide;

A146 N-[[2-(3-Chlorophenyl)-5-(trifluoromethyl)-2H-pyrazol-3-yl]-methyl]-2-[4-(1,2-dihydroxy-ethyl)-phenyl]-propionamide;

A147 N-[[5-tert-Butyl-2-(3-chlorophenyl)-2H-pyrazol-3-yl]-methyl]-2-[4-(1,2-dihydroxy-ethyl)-phenyl]-propionamide;

A148 N-[[2-(3-Chlorophenyl)-5-(trifluoromethyl)-2H-pyrazol-3-yl]-methyl]-2-[4-(1,2-dihydroxy-ethyl)-3-fluoro-phenyl]-propionamide;

A149 2-[4-(1,2-Dihydroxy-ethyl)-3-fluoro-phenyl]-N-[[2-(3-fluorophenyl)-5-(trifluoromethyl)-2H-pyrazol-3-yl]-methyl]-propionamide;

A150 1-[[5-tert-Butyl-2-(3-chlorophenyl)-2H-pyrazol-3-yl]-methyl]-3-[4-(1,2-dihydroxy-ethyl)-3-fluoro-phenyl]-urea;

A151 1-[[2-(3-Chlorophenyl)-5-(trifluoromethyl)-2H-pyrazol-3-yl]-methyl]-3-[4-(1,2-dihydroxy-ethyl)-3-fluoro-phenyl]-urea;

A152 1-[[5-tert-Butyl-2-(3-chlorophenyl)-2H-pyrazol-3-yl]-methyl]-3-[3-fluoro-4-[2-hydroxy-1-(hydroxymethyl)-ethyl]-phenyl]-urea;

A153 1-[[2-(3-Chlorophenyl)-5-(trifluoromethyl)-2H-pyrazol-3-yl]-methyl]-3-[3-fluoro-4-[2-hydroxy-1-(hydroxymethyl)-ethyl]-phenyl]-urea;

A154 1-[[2-(3-Chlorophenyl)-5-(trifluoromethyl)-2H-pyrazol-3-yl]-methyl]-3-[3-fluoro-4-[2-hydroxy-1-(hydroxymethyl)-1-methyl-ethyl]-phenyl]-urea;

A155 1-[[2-(3-Chlorophenyl)-5-(trifluoromethyl)-2H-pyrazol-3-yl]-methyl]-3-[4-[2-hydroxy-1-(hydroxymethyl)-1-methyl-ethyl]-phenyl]-urea;

A156 1-[[5-tert-Butyl-2-(3-chlorophenyl)-2H-pyrazol-3-yl]-methyl]-3-[3-fluoro-4-[2-hydroxy-1-(hydroxymethyl)-1-methyl-ethyl]-phenyl]-urea;

A157 1-[[5-tert-Butyl-2-(3-chlorophenyl)-2H-pyrazol-3-yl]-methyl]-3-[4-[2-hydroxy-1-(hydroxymethyl)-1-methyl-ethyl]-phenyl]-urea;

A158 1-[[2-(3-Chlorophenyl)-5-(trifluoromethyl)-2H-pyrazol-3-yl]-methyl]-3-[4-[1,2-dihydroxy-1-(hydroxymethyl)-ethyl]-phenyl]-urea; and A159 1-[[5-tert-Butyl-2-(3-chlorophenyl)-2H-pyrazol-3-yl]-methyl]-3-[4-[1,2-dihydroxy-1-(hydroxymethyl)-ethyl]-phenyl]-urea;

in the form of a free compound or a physiologically acceptable salt thereof, and if applicable, in the form of an individual stereoisomer or a mixture of stereoisomers.

10. A pharmaceutical composition comprising a compound according to claim 1 and at least one pharmaceutically acceptable carrier or auxiliary substance.

11. A method of treating in inhibiting a disease or disorder selected from the group consisting of pain; hyperalgesia; allodynia; causalgia; migraine; depression; nervous affection; axonal injuries; neurodegenerative diseases; cognitive dysfunctions; epilepsy; respiratory diseases; coughs; urinary incontinence; overactive bladder; disorders and injuries of the gastrointestinal tract; duodenal ulcers; gastric ulcers; irritable bowel syndrome; strokes; eye irritations; skin irritations; neurotic skin diseases; allergic skin diseases; psoriasis; vitiligo; herpes simplex; inflammations; diarrhea; pruritus; osteoporosis; arthritis; osteoarthritis; rheumatic diseases; eating disorders; medication dependency; misuse of medication; withdrawal symptoms in medication dependency; development of tolerance to medication; drug dependency; misuse of drugs; withdrawal symptoms in drug dependency; alcohol dependency; misuse of alcohol and withdrawal symptoms in alcohol dependency; or for effecting diuresis; antinatriuresis; influencing the cardiovascular system; increasing vigilance; treatment of wounds or burns; treatment of severed nerves; increasing libido; modulating movement activity; effecting anxiolysis; local anaesthesia or inhibiting undesirable side effects triggered by the administration of a vanilloid receptor 1 agonist, in a subject in need thereof, said method comprising administering to said subject a pharmacologically effective amount of a compound according to claim 1.

12. A method as claimed in claim 11, wherein said disease or disorder is pain selected from the group consisting of acute pain, chronic pain, neuropathic pain, visceral pain and joint pain; a neurodegenerative disease selected from the group consisting of multiple sclerosis, Alzheimer's disease, Parkinson's disease and Huntington's disease; a cognitive deficiency state; a respiratory disease selected from the group consisting of asthma, bronchitis and pulmonary inflammation; an inflammation of the intestine, the eyes, the bladder, the skin or the nasal mucous membrane; an eating disorder selected from the group consisting of bulimia, cachexia, anorexia and obesity; or development of tolerance to natural or synthetic opioids; or for inhibiting undesirable side effects selected from the group consisting of hyperthermia, hypertension and bronchoconstriction triggered by administration of a vanilloid receptor 1 agonist selected from the group consisting of capsaicin, resiniferatoxin, olvanil, arvanil, SDZ-249665, SDZ-249482, nuvanil and capsavanil.

* * * * *